US011937817B2

(12) United States Patent
Shelton, IV et al.

(10) Patent No.: US 11,937,817 B2
(45) Date of Patent: Mar. 26, 2024

(54) SURGICAL INSTRUMENTS WITH ASYMMETRIC JAW ARRANGEMENTS AND SEPARATE CLOSURE AND FIRING SYSTEMS

(71) Applicant: Cilag GmbH International, Zug (CH)

(72) Inventors: Frederick E. Shelton, IV, Hillsboro, OH (US); Jason L. Harris, Lebanon, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/854,758

(22) Filed: Jun. 30, 2022

(65) Prior Publication Data
US 2022/0346792 A1  Nov. 3, 2022

Related U.S. Application Data

(63) Continuation of application No. 16/281,658, filed on Feb. 21, 2019, now Pat. No. 11,589,865.
(Continued)

(51) Int. Cl.
*A61B 17/072* (2006.01)
*A61B 17/00* (2006.01)
*A61B 17/29* (2006.01)

(52) U.S. Cl.
CPC ............ *A61B 17/07207* (2013.01); *A61B 2017/00398* (2013.01); *A61B 2017/0046* (2013.01); *A61B 2017/00734* (2013.01); *A61B 2017/07228* (2013.01); *A61B 2017/07257* (2013.01); *A61B 2017/07271* (2013.01); *A61B 2017/07278* (2013.01); *A61B 2017/07285* (2013.01); *A61B 2017/2927* (2013.01);
(Continued)

(58) Field of Classification Search
None
See application file for complete search history.

(56) References Cited

U.S. PATENT DOCUMENTS 1,853,416 A    4/1932   Hall
2,222,125 A   11/1940   Stehlik
(Continued)

FOREIGN PATENT DOCUMENTS

AU    2015201140 A1    3/2015
CA       2795323 A1    5/2014
(Continued)

OTHER PUBLICATIONS

US 10,504,709 B2, 12/2019, Karancsi et al. (withdrawn)
(Continued)

*Primary Examiner* — Tanzim Imam
(74) *Attorney, Agent, or Firm* — Troutman Pepper Hamilton Sanders LLP

(57) ABSTRACT

A method for controlling a powered surgical stapler that includes an end effector with jaws that are movable between an open and a closed position and a firing member that is movable between a starting position and an ending position within the end effector. The jaws and firing member are controlled by separate rotary systems and the end effector includes a firing member lockout system that prevents axial movement of the firing member unless the surgical staple cartridge is in ready to fire condition.

18 Claims, 206 Drawing Sheets

Related U.S. Application Data

(60) Provisional application No. 62/807,319, filed on Feb. 19, 2019, provisional application No. 62/807,310, filed on Feb. 19, 2019, provisional application No. 62/807,309, filed on Feb. 19, 2019, provisional application No. 62/650,887, filed on Mar. 30, 2018, provisional application No. 62/649,300, filed on Mar. 28, 2018, provisional application No. 62/649,333, filed on Mar. 28, 2018, provisional application No. 62/649,302, filed on Mar. 28, 2018, provisional application No. 62/649,313, filed on Mar. 28, 2018, provisional application No. 62/649,294, filed on Mar. 28, 2018, provisional application No. 62/649,307, filed on Mar. 28, 2018, provisional application No. 62/649,310, filed on Mar. 28, 2018, provisional application No. 62/649,309, filed on Mar. 28, 2018, provisional application No. 62/649,291, filed on Mar. 28, 2018, provisional application No. 62/649,327, filed on Mar. 28, 2018, provisional application No. 62/649,323, filed on Mar. 28, 2018, provisional application No. 62/649,315, filed on Mar. 28, 2018, provisional application No. 62/649,320, filed on Mar. 28, 2018, provisional application No. 62/649,296, filed on Mar. 28, 2018.

(52) U.S. Cl.
CPC ............... *A61B 2017/2933* (2013.01); *A61B 2017/2939* (2013.01); *A61B 2017/2946* (2013.01)

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |
| 4,202,722 A | 5/1980 | Paquin |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,849,752 A | 7/1989 | Bryant |
| D303,787 S | 10/1989 | Messenger et al. |
| 4,892,244 A | 1/1990 | Fox et al. |
| 4,976,173 A | 12/1990 | Yang |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |

(56) References Cited

U.S. PATENT DOCUMENTS

| | | |
|---|---|---|
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |

(56) References Cited

U.S. PATENT DOCUMENTS

| | | |
|---|---|---|
| 7,407,074 B2 | 8/2008 | Ortiz et al. |
| 7,408,439 B2 | 8/2008 | Wang et al. |
| 7,422,136 B1 | 9/2008 | Marczyk |
| 7,422,139 B2 | 9/2008 | Shelton, IV et al. |
| 7,423,972 B2 | 9/2008 | Shaham et al. |
| D579,876 S | 11/2008 | Novotney et al. |
| 7,457,804 B2 | 11/2008 | Uber et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,951,148 B2 | 5/2011 | McClurken |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |

(56) References Cited

U.S. PATENT DOCUMENTS

| | | |
|---|---|---|
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,876,857 B2 | 11/2014 | Burbank |
| 8,882,662 B2 | 11/2014 | Charles |
| 8,886,790 B2 | 11/2014 | Harrang et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,936,614 B2 | 1/2015 | Allen, IV |
| 8,945,095 B2 | 2/2015 | Blumenkranz et al. |
| 8,945,163 B2 | 2/2015 | Voegele et al. |

(56) References Cited

U.S. PATENT DOCUMENTS

| | | |
|---|---|---|
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,429 B2 | 2/2016 | St. Pierre et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |

(56) References Cited

U.S. PATENT DOCUMENTS

| | | |
|---|---|---|
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,563 B2 | 9/2017 | Shikhman et al. |
| 9,753,135 B2 | 9/2017 | Bosch |
| 9,753,568 B2 | 9/2017 | McMillen |

(56) References Cited

U.S. PATENT DOCUMENTS

| | | |
|---|---|---|
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |

(56) References Cited

U.S. PATENT DOCUMENTS

| | | |
|---|---|---|
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |

(56) References Cited

U.S. PATENT DOCUMENTS

| | | |
|---|---|---|
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,964 B2 | 3/2020 | Weinberg et al. |

(56) References Cited

U.S. PATENT DOCUMENTS

| | | |
|---|---|---|
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |

(56) References Cited

U.S. PATENT DOCUMENTS

| | | |
|---|---|---|
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,567 B2 | 2/2021 | Shelton, IV et al. |
| 10,912,580 B2 | 2/2021 | Green et al. |
| 10,912,619 B2 | 2/2021 | Jarc et al. |
| 10,916,415 B2 | 2/2021 | Karancsi et al. |
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,705 B2 | 3/2021 | Muhsin et al. |
| 10,932,772 B2 | 3/2021 | Shelton, IV et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,950,982 B2 | 3/2021 | Regnier et al. |
| 10,952,708 B2 | 3/2021 | Scheib et al. |
| 10,954,935 B2 | 3/2021 | O'Shea et al. |
| 10,959,727 B2 | 3/2021 | Hunter et al. |
| 10,959,729 B2 | 3/2021 | Ehrenfels et al. |
| 10,959,744 B2 | 3/2021 | Shelton, IV et al. |
| 10,959,788 B2 | 3/2021 | Grover et al. |
| 10,960,150 B2 | 3/2021 | Zergiebel et al. |
| 10,966,791 B2 | 4/2021 | Harris et al. |
| 10,966,798 B2 | 4/2021 | Tesar et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,973,682 B2 | 4/2021 | Vezzu et al. |
| 10,980,536 B2 | 4/2021 | Weaner et al. |
| 10,980,537 B2 | 4/2021 | Shelton, IV et al. |
| 10,980,560 B2 | 4/2021 | Shelton, IV et al. |
| 10,980,610 B2 | 4/2021 | Rosenberg et al. |
| 10,987,102 B2 | 4/2021 | Gonzalez et al. |
| 10,987,178 B2 | 4/2021 | Shelton, IV et al. |
| 10,992,698 B2 | 4/2021 | Patel et al. |
| 10,993,715 B2 | 5/2021 | Shelton, IV et al. |
| 10,998,098 B2 | 5/2021 | Greene et al. |
| 11,000,276 B2 | 5/2021 | Shelton, IV et al. |
| 11,000,278 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,563 B2 | 5/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,197 B2 | 6/2021 | Shelton, IV et al. |
| 11,045,591 B2 | 6/2021 | Shelton, IV et al. |
| 11,051,817 B2 | 7/2021 | Shelton, IV et al. |
| 11,051,836 B2 | 7/2021 | Shelton, IV et al. |
| 11,051,873 B2 | 7/2021 | Wiener et al. |
| 11,051,876 B2 | 7/2021 | Shelton, IV et al. |
| 11,056,244 B2 | 7/2021 | Shelton, IV et al. |
| 11,058,423 B2 | 7/2021 | Shelton, IV et al. |
| 11,058,498 B2 | 7/2021 | Shelton, IV et al. |
| 11,058,501 B2 | 7/2021 | Tokarchuk et al. |
| 11,064,997 B2 | 7/2021 | Shelton, IV et al. |
| 11,069,012 B2 | 7/2021 | Shelton, IV et al. |
| 11,071,560 B2 | 7/2021 | Deck et al. |
| 11,071,595 B2 | 7/2021 | Johnson et al. |
| 11,076,921 B2 | 8/2021 | Shelton, IV et al. |
| 11,083,458 B2 | 8/2021 | Harris et al. |
| 11,090,047 B2 | 8/2021 | Shelton, IV et al. |
| 11,090,048 B2 | 8/2021 | Fanelli et al. |
| 11,090,075 B2 | 8/2021 | Hunter et al. |
| 11,096,688 B2 | 8/2021 | Shelton, IV et al. |
| 11,096,693 B2 | 8/2021 | Shelton, IV et al. |
| 11,100,631 B2 | 8/2021 | Yates et al. |
| 11,103,268 B2 | 8/2021 | Shelton, IV et al. |
| 11,109,866 B2 | 9/2021 | Shelton, IV et al. |
| 11,109,878 B2 | 9/2021 | Shelton, IV et al. |
| 11,114,195 B2 | 9/2021 | Shelton, IV et al. |
| 11,116,485 B2 | 9/2021 | Scheib et al. |
| 11,123,070 B2 | 9/2021 | Shelton, IV et al. |
| 11,129,611 B2 | 9/2021 | Shelton, IV et al. |
| 11,129,634 B2 | 9/2021 | Scheib et al. |
| 11,129,636 B2 | 9/2021 | Shelton, IV et al. |
| 11,129,669 B2 | 9/2021 | Stulen et al. |
| 11,129,670 B2 | 9/2021 | Shelton, IV et al. |
| 11,132,462 B2 | 9/2021 | Shelton, IV et al. |
| 11,134,942 B2 | 10/2021 | Harris et al. |
| 11,141,160 B2 | 10/2021 | Shelton, IV et al. |
| 11,141,213 B2 | 10/2021 | Yates et al. |
| 11,147,607 B2 | 10/2021 | Yates et al. |
| 11,160,551 B2 | 11/2021 | Shelton, IV et al. |
| 11,160,605 B2 | 11/2021 | Shelton, IV et al. |
| 11,166,716 B2 | 11/2021 | Shelton, IV et al. |
| 11,166,772 B2 | 11/2021 | Shelton, IV et al. |
| 11,179,150 B2 | 11/2021 | Yates et al. |
| 11,179,151 B2 | 11/2021 | Shelton, IV et al. |
| 11,179,155 B2 | 11/2021 | Shelton, IV et al. |
| 11,179,175 B2 | 11/2021 | Houser et al. |
| 11,179,204 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,570 B2 | 12/2021 | Shelton, IV et al. |
| 11,207,065 B2 | 12/2021 | Harris et al. |
| 11,207,067 B2 | 12/2021 | Shelton, IV et al. |
| 11,207,090 B2 | 12/2021 | Shelton, IV et al. |
| 11,213,293 B2 | 1/2022 | Worthington et al. |
| 11,213,294 B2 | 1/2022 | Shelton, IV et al. |
| 11,213,359 B2 | 1/2022 | Shelton, IV et al. |
| 11,218,822 B2 | 1/2022 | Morgan et al. |
| 11,219,453 B2 | 1/2022 | Shelton, IV et al. |
| 11,224,426 B2 | 1/2022 | Shelton, IV et al. |
| 11,229,436 B2 | 1/2022 | Shelton, IV et al. |
| 11,229,471 B2 | 1/2022 | Shelton, IV et al. |
| 11,234,756 B2 | 2/2022 | Shelton, IV et al. |
| 11,241,230 B2 | 2/2022 | Shelton, IV et al. |
| 11,253,256 B2 | 2/2022 | Harris et al. |
| 11,253,315 B2 | 2/2022 | Yates et al. |
| 11,257,589 B2 | 2/2022 | Shelton, IV et al. |
| 11,259,806 B2 | 3/2022 | Shelton, IV et al. |
| 11,259,807 B2 | 3/2022 | Shelton, IV et al. |
| 11,259,830 B2 | 3/2022 | Nott et al. |

(56) References Cited

U.S. PATENT DOCUMENTS

| | | |
|---|---|---|
| 11,266,409 B2 | 3/2022 | Huitema et al. |
| 11,266,468 B2 | 3/2022 | Shelton, IV et al. |
| 11,272,931 B2 | 3/2022 | Boudreaux et al. |
| 11,273,001 B2 | 3/2022 | Shelton, IV et al. |
| 11,278,280 B2 | 3/2022 | Shelton, IV et al. |
| 11,278,281 B2 | 3/2022 | Shelton, IV et al. |
| 11,284,890 B2 | 3/2022 | Nalagatla et al. |
| 11,284,936 B2 | 3/2022 | Shelton, IV et al. |
| 11,291,440 B2 | 4/2022 | Harris et al. |
| 11,291,441 B2 | 4/2022 | Giordano et al. |
| 11,291,444 B2 | 4/2022 | Boudreaux et al. |
| 11,291,445 B2 | 4/2022 | Shelton, IV et al. |
| 11,291,465 B2 | 4/2022 | Parihar et al. |
| 11,291,495 B2 | 4/2022 | Yates et al. |
| 11,291,510 B2 | 4/2022 | Shelton, IV et al. |
| 11,298,128 B2 | 4/2022 | Messerly et al. |
| 11,298,129 B2 | 4/2022 | Bakos et al. |
| 11,298,130 B2 | 4/2022 | Bakos et al. |
| 11,298,148 B2 | 4/2022 | Jayme et al. |
| 11,304,699 B2 | 4/2022 | Shelton, IV et al. |
| 11,304,720 B2 | 4/2022 | Kimball et al. |
| 11,304,745 B2 | 4/2022 | Shelton, IV et al. |
| 11,304,763 B2 | 4/2022 | Shelton, IV et al. |
| 11,308,075 B2 | 4/2022 | Shelton, IV et al. |
| 11,311,306 B2 | 4/2022 | Shelton, IV et al. |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,317,919 B2 | 5/2022 | Shelton, IV et al. |
| 11,317,937 B2 | 5/2022 | Nott et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,746 B2 | 5/2022 | Boudreaux |
| 11,344,326 B2 | 5/2022 | Faller et al. |
| 11,350,959 B2 | 6/2022 | Messerly et al. |
| 11,350,978 B2 | 6/2022 | Henderson et al. |
| 11,357,503 B2 | 6/2022 | Bakos et al. |
| 11,364,075 B2 | 6/2022 | Yates et al. |
| 11,369,377 B2 | 6/2022 | Boudreaux et al. |
| 11,376,002 B2 | 7/2022 | Shelton, IV et al. |
| 11,382,697 B2 | 7/2022 | Shelton, IV et al. |
| 11,389,164 B2 | 7/2022 | Yates et al. |
| 11,389,188 B2 | 7/2022 | Gee et al. |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0169584 A1 | 11/2002 | Fu et al. |
| 2003/0009111 A1 | 1/2003 | Cory et al. |
| 2003/0018329 A1 | 1/2003 | Hooven |
| 2003/0046109 A1 | 3/2003 | Uchikubo |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0100867 A1 | 5/2005 | Hilscher et al. |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0222631 A1 | 10/2005 | Dalal et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0184160 A1 | 8/2006 | Ozaki et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0234708 A1 | 9/2008 | Houser et al. |
| 2008/0235052 A1 | 9/2008 | Node-Langlois et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |

(56) References Cited

U.S. PATENT DOCUMENTS

| | | |
|---|---|---|
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1 | 2/2011 | Ma |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0237883 A1 | 9/2011 | Chun |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0144284 A1 | 6/2013 | Behnke, II et al. |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0197531 A1 | 8/2013 | Boukhny et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |

(56) References Cited

U.S. PATENT DOCUMENTS

| | | |
|---|---|---|
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William et al. |
| 2014/0121669 A1 | 5/2014 | Claus |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276749 A1 | 9/2014 | Johnson |
| 2014/0287393 A1 | 9/2014 | Kumar et al. |
| 2014/0303660 A1 | 10/2014 | Boyden et al. |
| 2014/0303990 A1 | 10/2014 | Schoenefeld et al. |
| 2014/0305987 A1* | 10/2014 | Parihar ............ A61B 17/1155 227/175.2 |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0057675 A1 | 2/2015 | Akeel et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0202014 A1 | 7/2015 | Kim et al. |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282821 A1 | 10/2015 | Look et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |
| 2016/0066913 A1 | 3/2016 | Swayze et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |
| 2016/0166256 A1* | 6/2016 | Baxter, III ........ A61B 17/07207 227/176.1 |
| 2016/0174998 A1 | 6/2016 | Lal et al. |
| 2016/0175025 A1 | 6/2016 | Strobl |
| 2016/0180045 A1 | 6/2016 | Syed |
| 2016/0184054 A1 | 6/2016 | Lowe |
| 2016/0192960 A1 | 7/2016 | Bueno et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0270861 A1 | 9/2016 | Guru et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | McHenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |

(56) References Cited

U.S. PATENT DOCUMENTS

| | | |
|---|---|---|
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0173262 A1 | 6/2017 | Veltz |
| 2017/0177807 A1 | 6/2017 | Fabian |
| 2017/0196583 A1 | 7/2017 | Sugiyama |
| 2017/0202595 A1 | 7/2017 | Shelton, IV |
| 2017/0202608 A1 | 7/2017 | Shelton, IV et al. |
| 2017/0215944 A1 | 8/2017 | Keffeler |
| 2017/0224332 A1 | 8/2017 | Hunter et al. |
| 2017/0224428 A1 | 8/2017 | Kopp |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281186 A1 | 10/2017 | Shelton, IV et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0337043 A1 | 11/2017 | Brincat et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0065248 A1 | 3/2018 | Barral et al. |
| 2018/0078170 A1 | 3/2018 | Panescu et al. |
| 2018/0098816 A1 | 4/2018 | Govari et al. |
| 2018/0108438 A1 | 4/2018 | Ryan et al. |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0132895 A1 | 5/2018 | Silver |
| 2018/0144243 A1 | 5/2018 | Hsieh et al. |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0177383 A1 | 6/2018 | Noonan et al. |
| 2018/0182475 A1 | 6/2018 | Cossler et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0315492 A1 | 11/2018 | Bishop et al. |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0353186 A1 | 12/2018 | Mozdzierz et al. |
| 2018/0357383 A1 | 12/2018 | Allen et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0099221 A1 | 4/2019 | Schmidt et al. |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125358 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |

(56) References Cited

U.S. PATENT DOCUMENTS

| | | |
|---|---|---|
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0163875 A1 | 5/2019 | Allen et al. |
| 2019/0167296 A1 | 6/2019 | Tsubuku et al. |
| 2019/0192157 A1 | 6/2019 | Scott et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200997 A1 | 7/2019 | Shelton, IV et al. |
| 2019/0201021 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201075 A1 | 7/2019 | Shelton, IV et al. |
| 2019/0201080 A1 | 7/2019 | Messerly et al. |
| 2019/0201083 A1 | 7/2019 | Shelton, IV et al. |
| 2019/0201085 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201102 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201130 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206003 A1 | 7/2019 | Harris et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274713 A1 | 9/2019 | Scoggins et al. |
| 2019/0274714 A1 | 9/2019 | Cuti et al. |
| 2019/0274718 A1 | 9/2019 | Denzinger et al. |
| 2019/0274719 A1 | 9/2019 | Stulen |
| 2019/0274749 A1 | 9/2019 | Brady et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298464 A1 | 10/2019 | Abbott |
| 2019/0307520 A1 | 10/2019 | Peine et al. |
| 2019/0311802 A1 | 10/2019 | Kokubo et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054321 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |

(56) References Cited

U.S. PATENT DOCUMENTS

| | | |
|---|---|---|
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0237372 A1 | 7/2020 | Park |
| 2020/0261078 A1 | 8/2020 | Bakos et al. |
| 2020/0261086 A1 | 8/2020 | Zeiner et al. |
| 2020/0261087 A1 | 8/2020 | Timm et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0348662 A1 | 11/2020 | Cella et al. |
| 2020/0405304 A1 | 12/2020 | Mozdzierz et al. |
| 2020/0405375 A1 | 12/2020 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzadi et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0160438 A1 | 5/2022 | Shelton, IV et al. |
| 2022/0175374 A1 | 6/2022 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2037167 A1 | 7/1980 |
| GB | 2509523 A | 7/2014 |
| JP | S5373315 A | 6/1978 |
| JP | 2001029353 A | 2/2001 |
| JP | 2007123394 A | 5/2007 |
| JP | 2010057642 A | 3/2010 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015129395 A1 | 9/2015 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018116247 A1 | 6/2018 |

(56) References Cited

FOREIGN PATENT DOCUMENTS

| WO | WO-2018152141 A1 | 8/2018 |
|---|---|---|
| WO | WO-2018176414 A1 | 10/2018 |

OTHER PUBLICATIONS

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.
Slocinski et al., "Distance measure for impedance spectra for quantified evaluations," Lecture Notes on Impedance Spectroscopy, vol. 3, Taylor and Francis Group (Jul. 2012)—Book Not Attached.
Zoccali, Bruno, "A Method for Approximating Component Temperatures at Altitude Conditions Based on CFD Analysis at Sea Level Conditions," (white paper), www.tdmginc.com, Dec. 6, 2018 (9 pages).
Flores et al., "Large-scale Offloading in the Internet of Things," 2017 IEEE International Conference on Pervasive Computing and Communications Workshops (PERCOM Workshops), IEEE, pp. 479-484, Mar. 13, 2017.
Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.
Yuyi Mao et al., "A Survey on Mobile Edge Computing: The Communication Perspective," IEEE Communications Surveys & Tutorials, pp. 2322-2358, Jun. 13, 2017.
Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.
Benkmann et al., "Concept of iterative optimization of minimally invasive surgery," 2017 22nd International Conference on Methods and Models in Automation and Robotics (MMAR), IEEE pp. 443-446, Aug. 28, 2017.
Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.
Miksch et al., "Utilizing temporal data abstraction for data validation and therapy planning for artificially ventilated newborn infants," Artificial Intelligence in Medicine, vol. 8, No. 6, pp. 543-576 (1996).
Horn et al., "Effective data validation of high-frequency data: Time-point-time-interval-, and trend-based methods," Computers in Biology and Medic, New York, NY, vol. 27, No. 5, pp. 389-409 (1997).
Stacey et al., "Temporal abstraction in intelligent clinical data analysis: A survey," Artificial Intelligence in Medicine, vol. 39, No. 1, pp. 1-24 (2006).
Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.
Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].
Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.
Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.
Phumzile Malindi, "5. QoS in Telemedicine," "Telemedicine," Jun. 20, 2011, IntechOpen, pp. 119-138.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.
Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.
Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.
Altenberg et al., "Genes of Glycolysis are Ubiquitously Overexpressed in 24 Cancer Classes," Genomics, vol. 84, pp. 1014-1020 (2004).
Takahashi et al., "Automatic smoke evacuation in laparoscopic surgery: a simplified method for objective evaluation," Surgical Endoscopy, vol. 27, No. 8, pp. 2980-2987, Feb. 23, 2013.
Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).
Marshall Brain, How Microcontrollers Work, 2006, retrieved from the internet <https://web.archive.org/web/20060221235221/http://electronics.howstuffworks.com/microcontroller.htm/printable> (Year: 2006).
CRC Press, "The Measurement, Instrumentation and Sensors Handbook," 1999, Section VII, Chapter 41, Peter O'Shea, "Phase Measurement," pp. 1303-1321, ISBN 0-8493-2145-X.
Jiang, "'Sound of Silence' : a secure indoor wireless ultrasonic communication system," Article, 2014, pp. 46-50, Snapshots of Doctoral Research at University College Cork, School of Engineering—Electrical & Electronic Engineering, UCC, Cork, Ireland.
Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.
Salamon, "AI Detects Polyps Better Than Colonoscopists" Online Article, Jun. 3, 2018, Medscape Medical News, Digestive Disease Week (DDW) 2018: Presentation 133.
Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.
Dottorato, "Analysis and Design of the Rectangular Microstrip Patch Antennas for TM0n0 operating mode, " Article, Oct. 8, 2010, pp. 1-9, Microwave Journal.
Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.
Hsiao-Wei Tang, "*ARCM*", Video, Sep. 2012, YouTube, 5 screenshots, Retrieved from internet: <https://www.youtube.com/watch?v=UldQaxb3fRw&feature=youtu.be>.
Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.
Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

(56) References Cited

OTHER PUBLICATIONS

"ATM-MPLS Network Interworking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1755-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.
"Surgical instrumentation: the true cost of instrument trays and a potential strategy for optimization"; Mhlaba et al.; Sep. 23, 2015 (Year: 2015).
Nabil Simaan et al, "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.
Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].
Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.
Screen captures from YouTube video clip entitled "Four ways to use the Lego Brick Separator Tool, " 2 pages, uploaded on May 29, 2014 by user "Sarah Lewis". Retrieved from internet: https://www.youtube.com/watch?v=ucKiRD6U1LU (Year: 2014).
Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.
Lalys, et al., "Automatic knowledge-based recognition of low-level tasks in ophthalmological procedures", Int J CARS, vol. 8, No. 1, pp. 1-49, Apr. 19, 2012.

\* cited by examiner

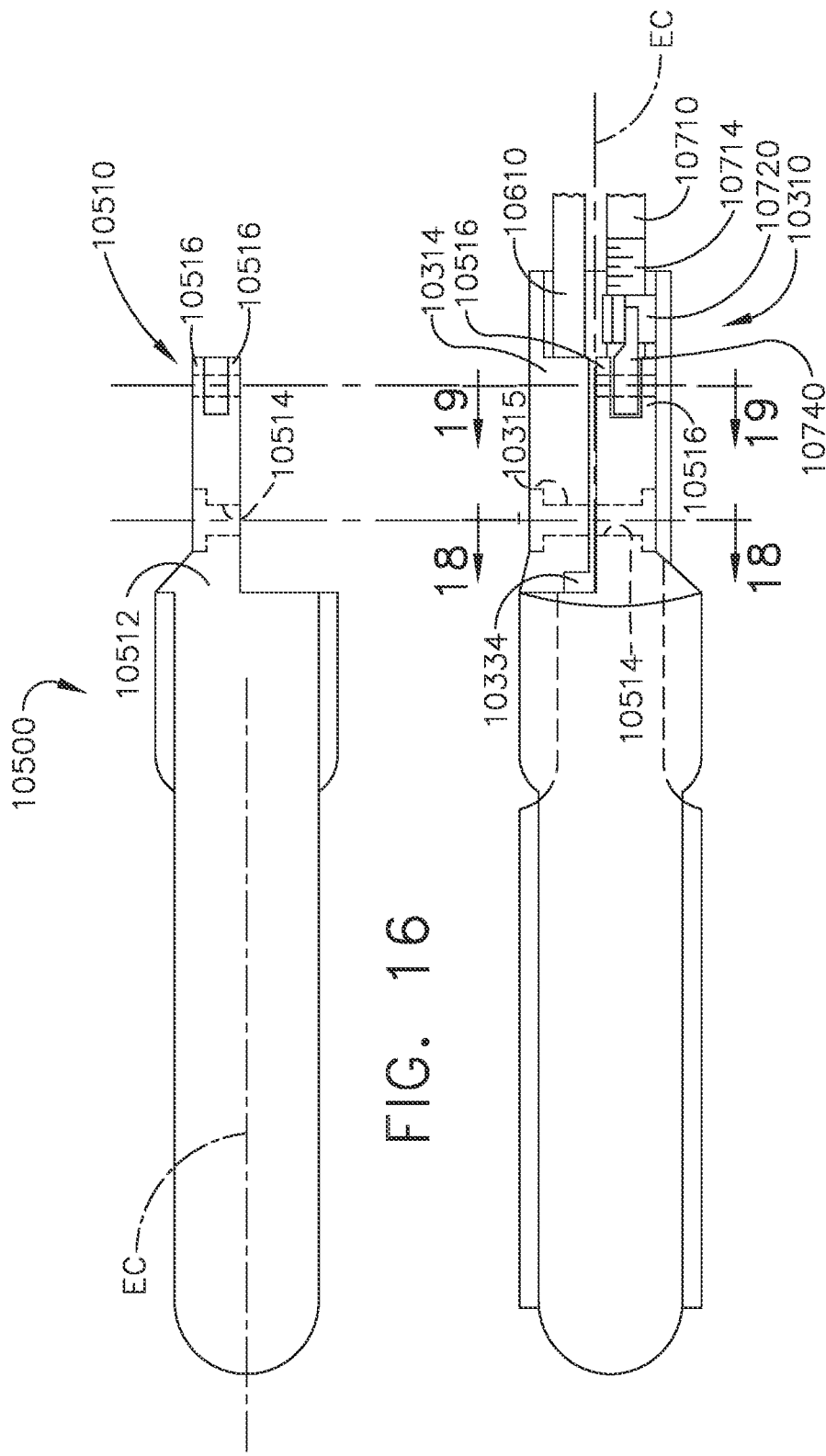

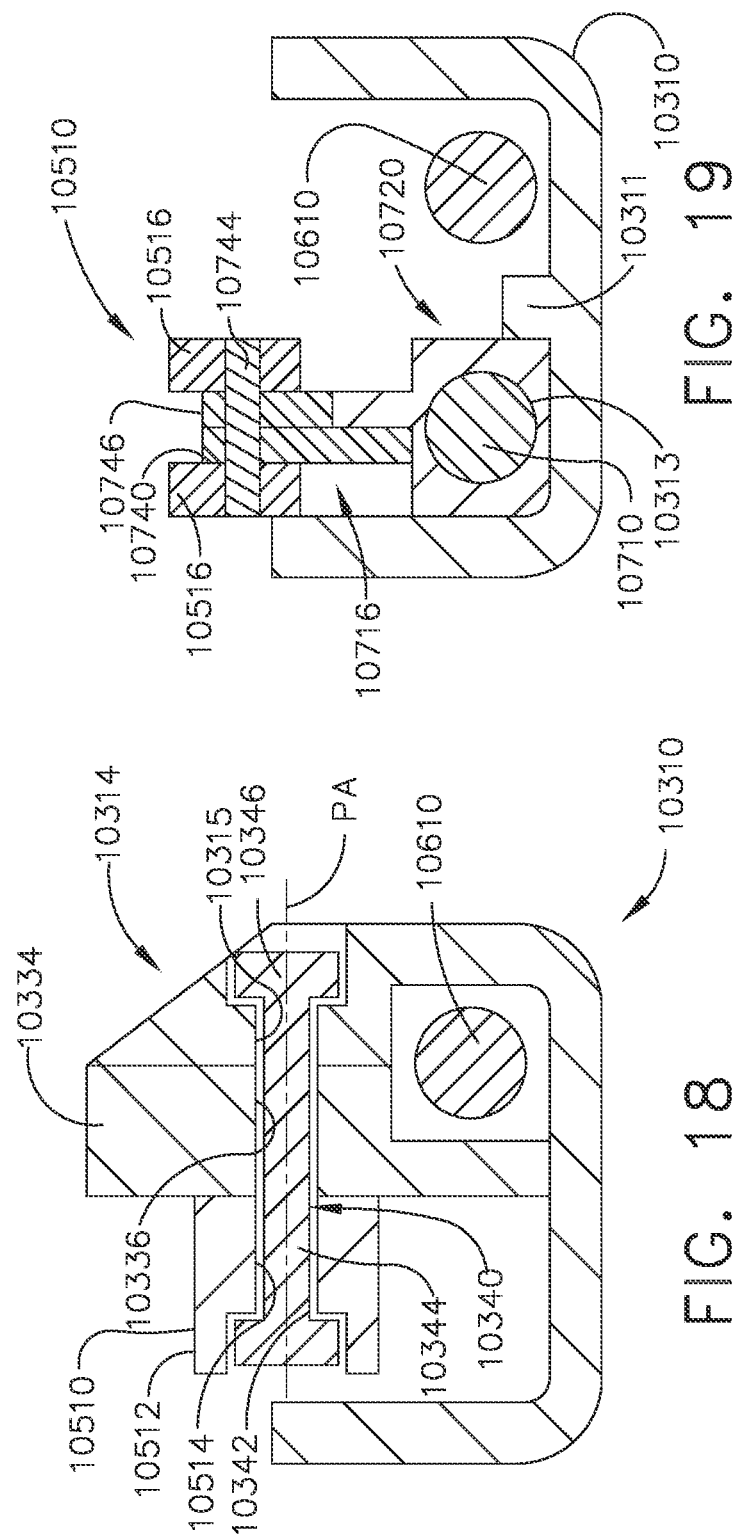

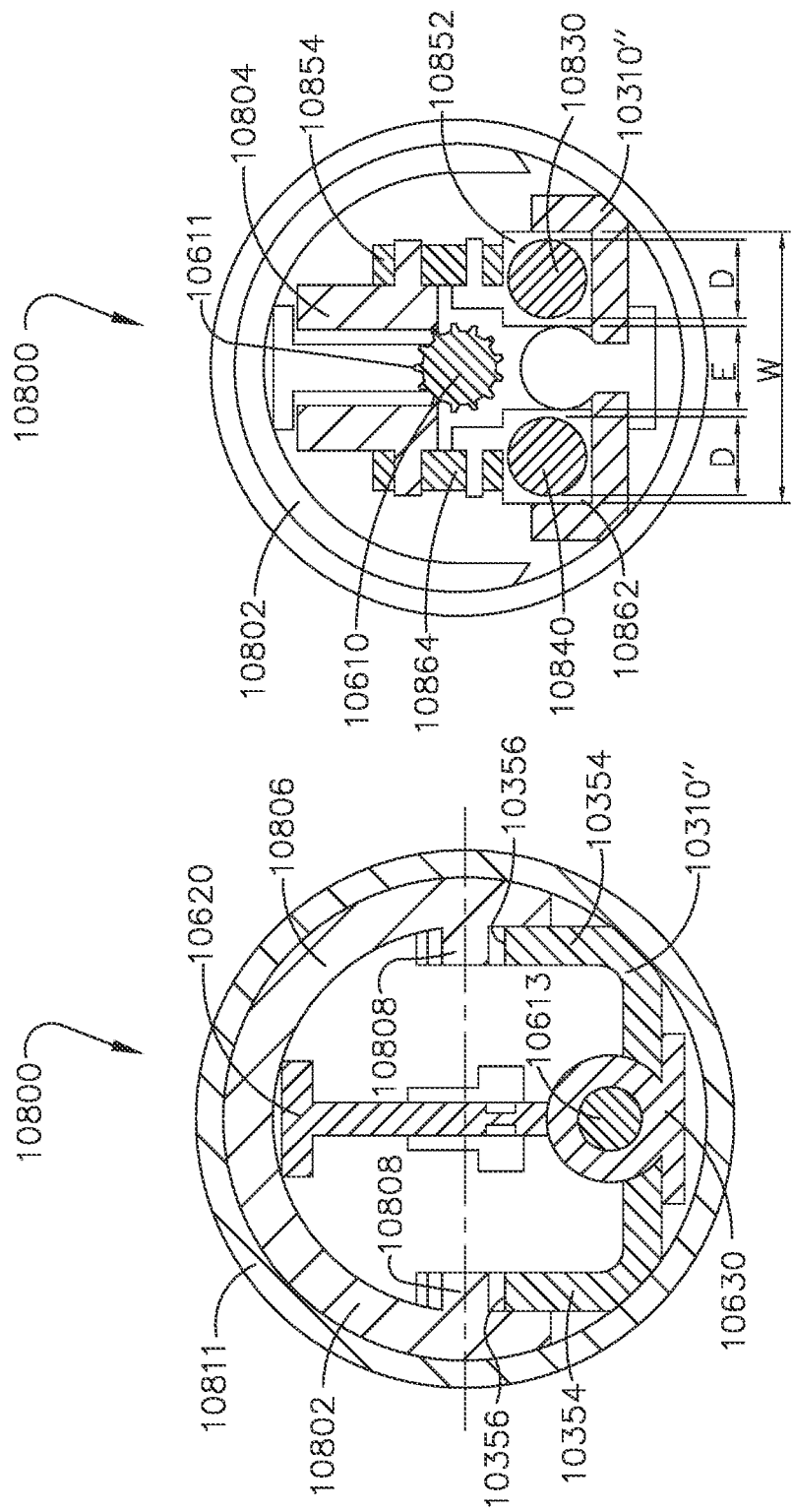

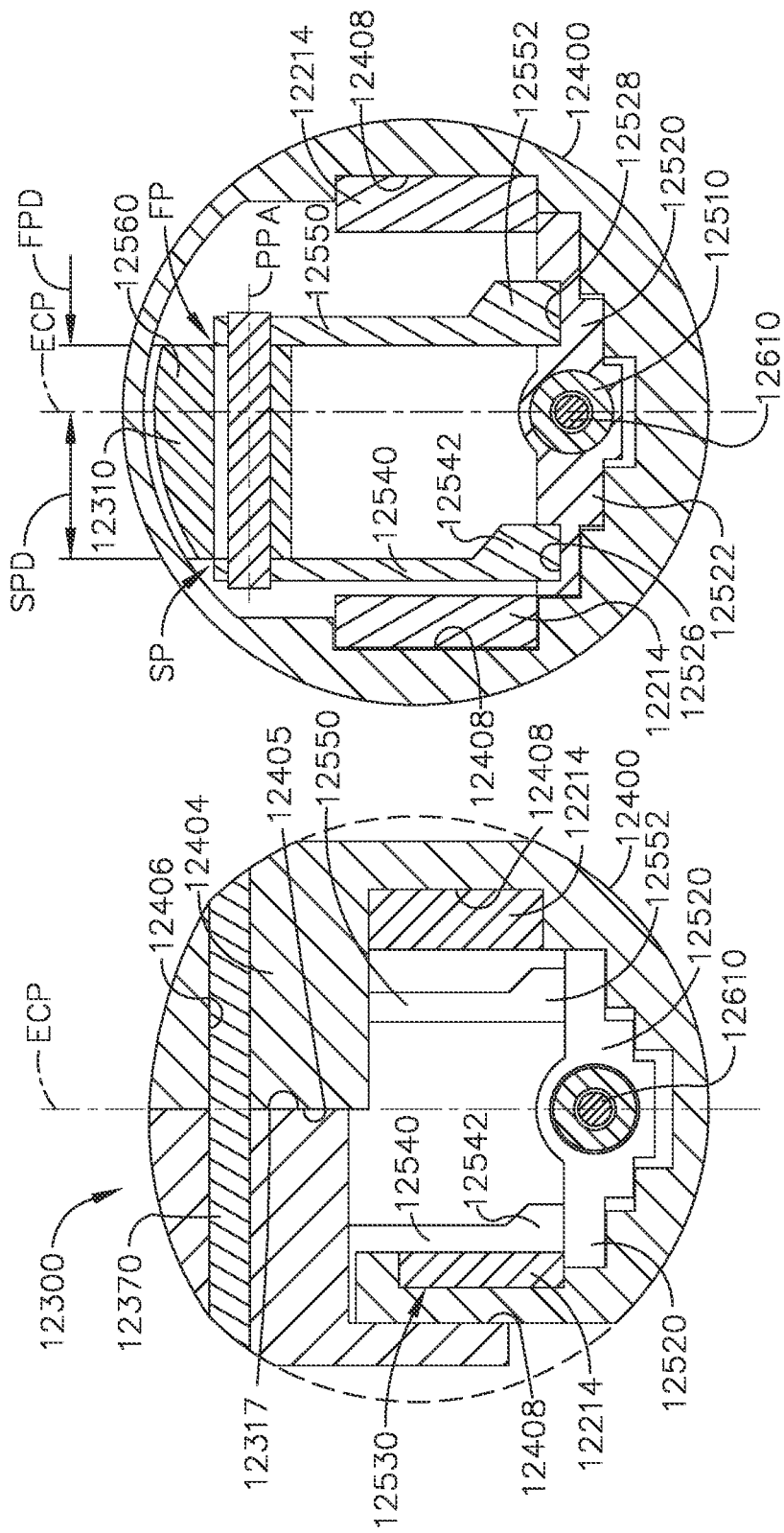

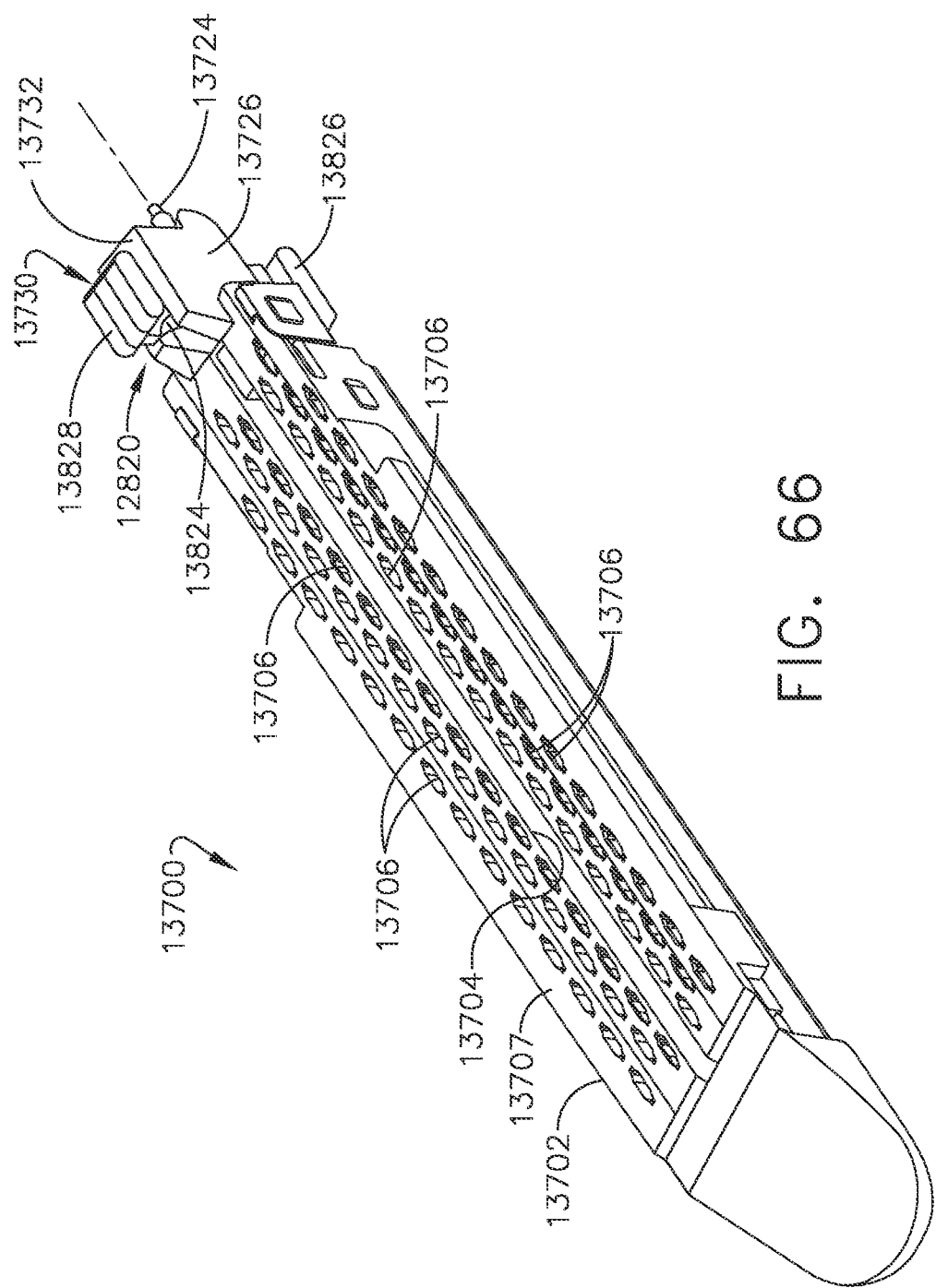

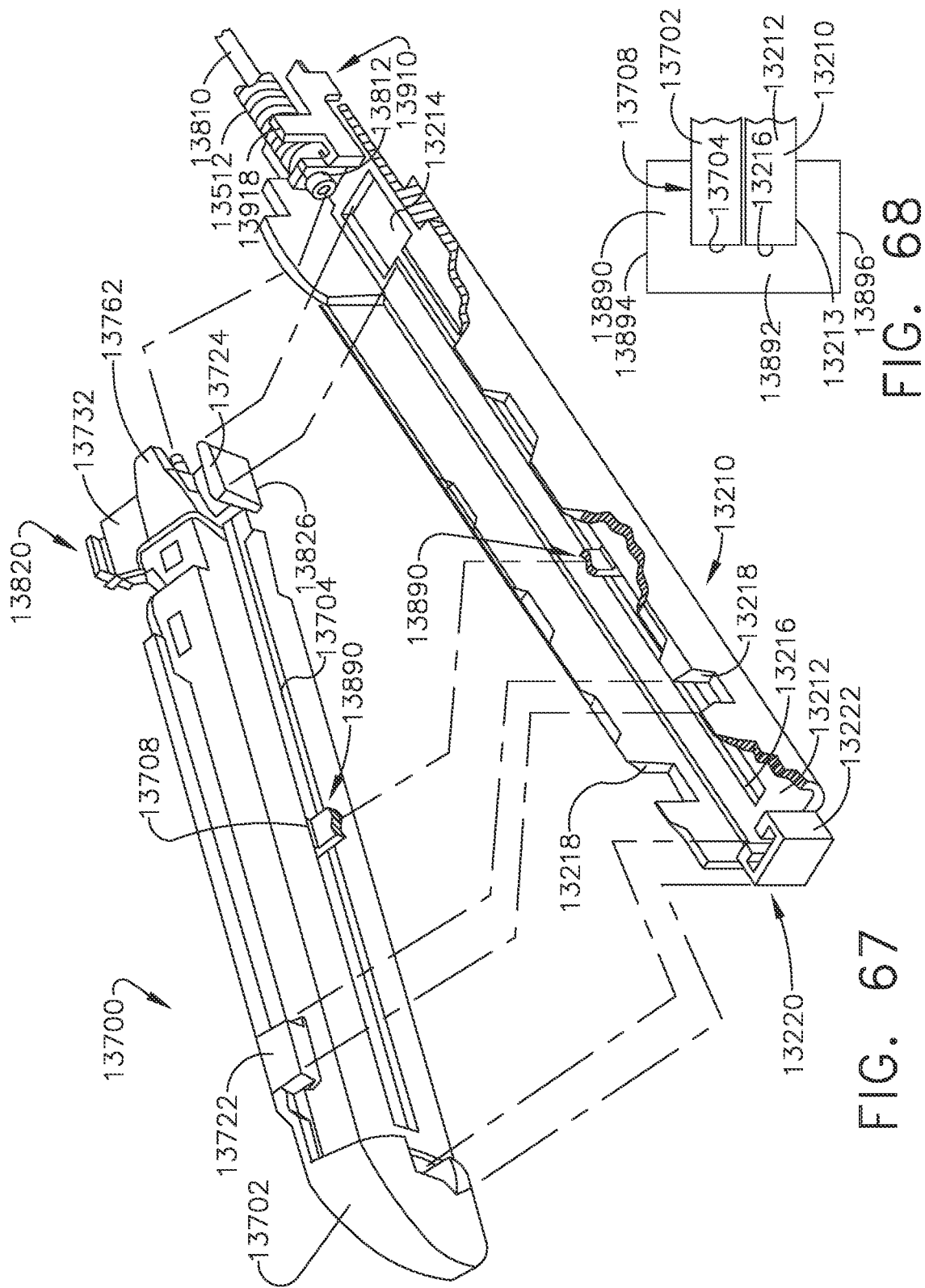

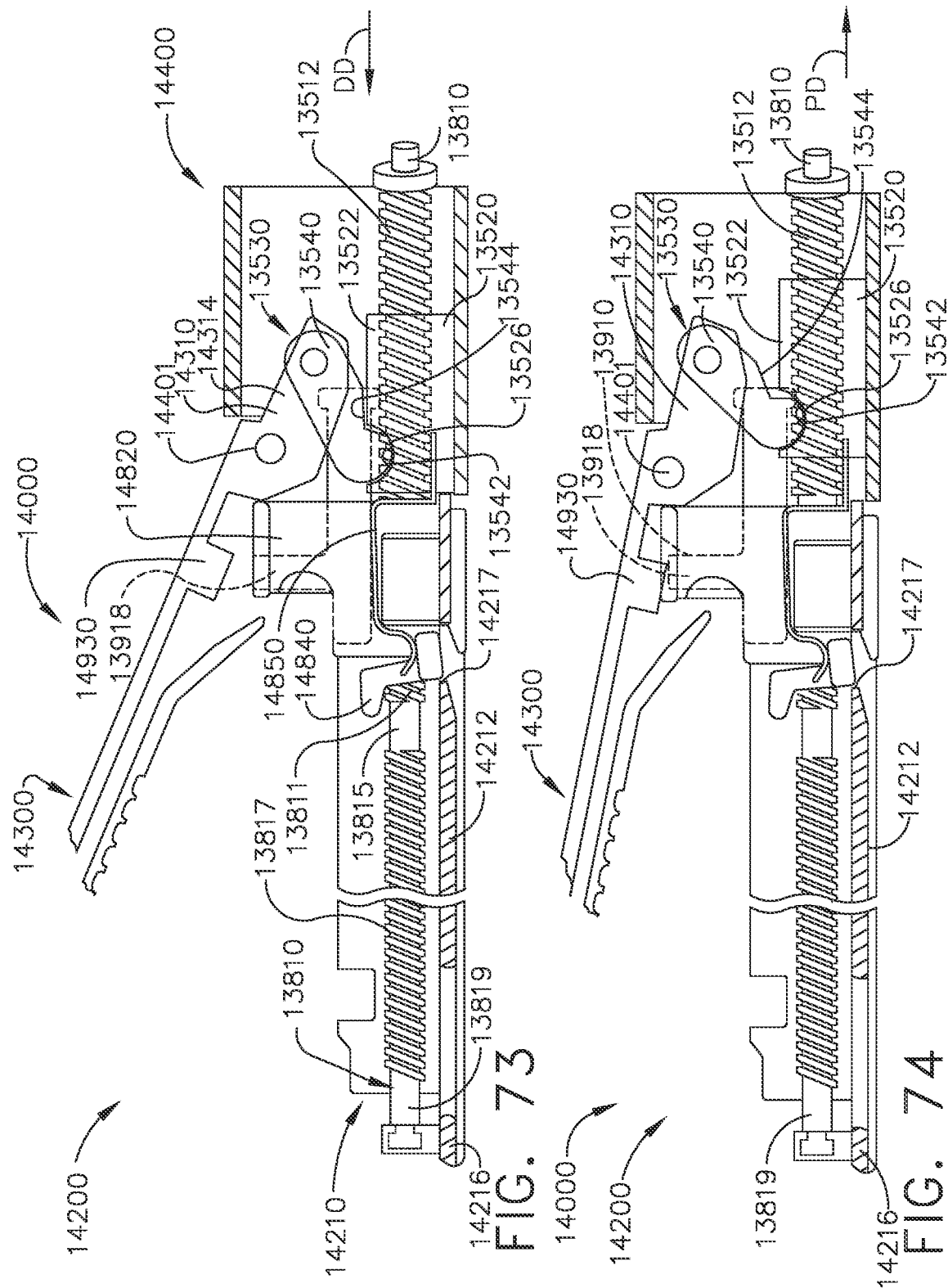

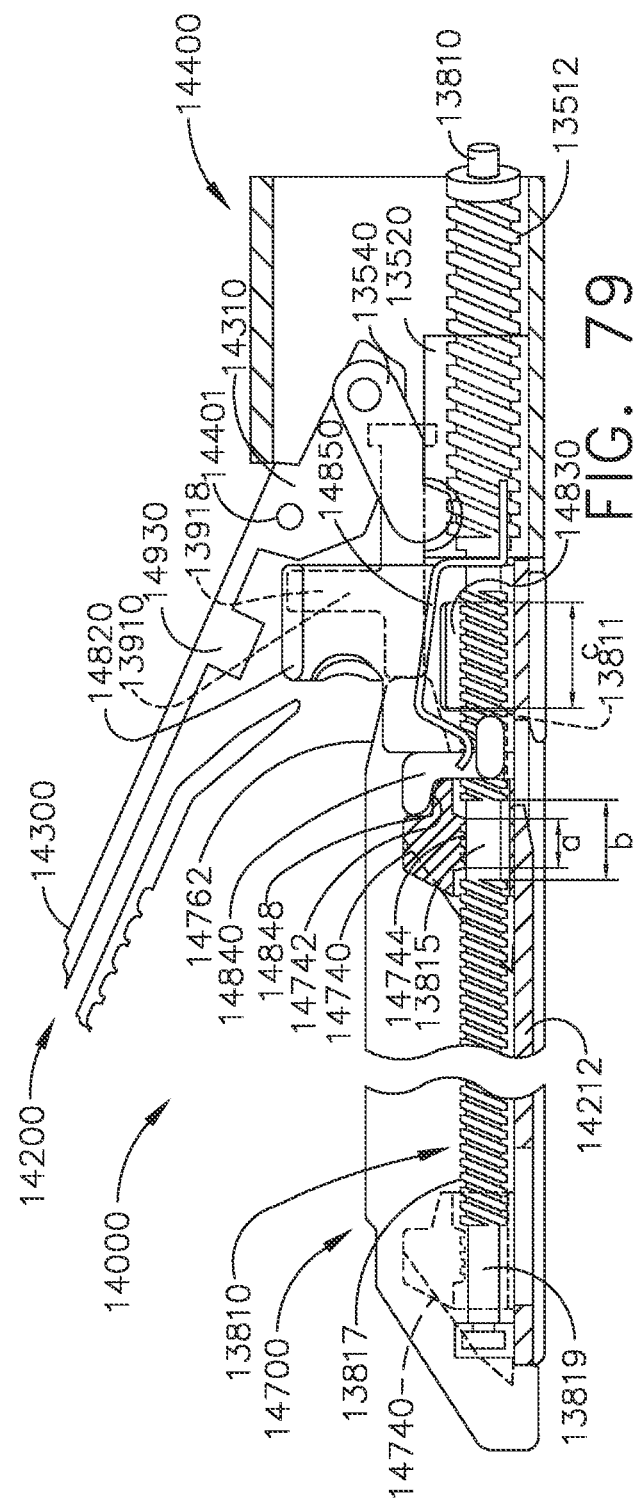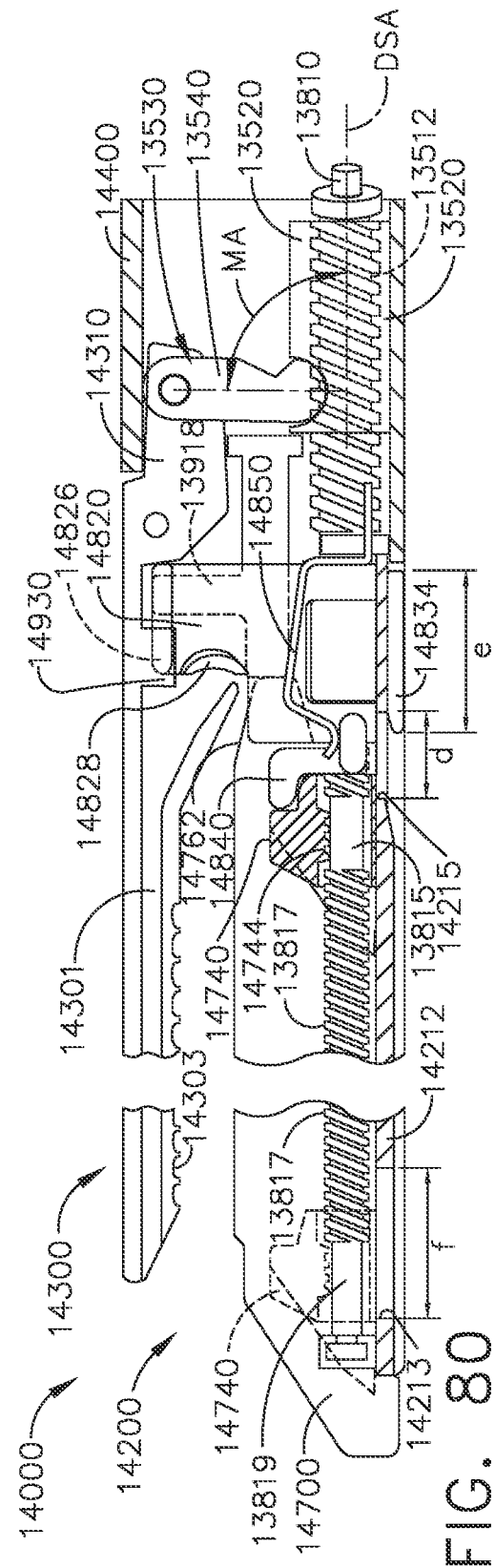

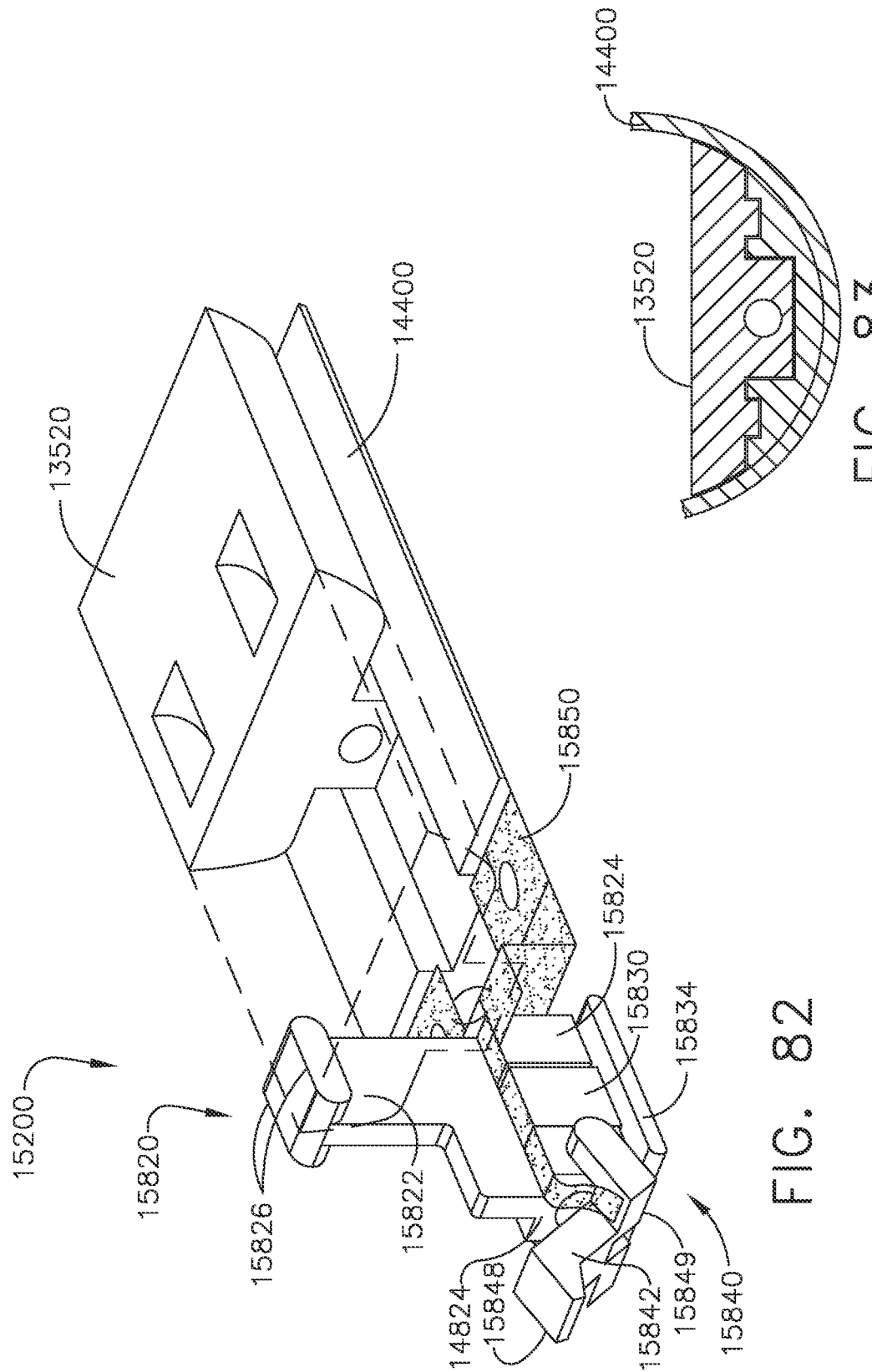

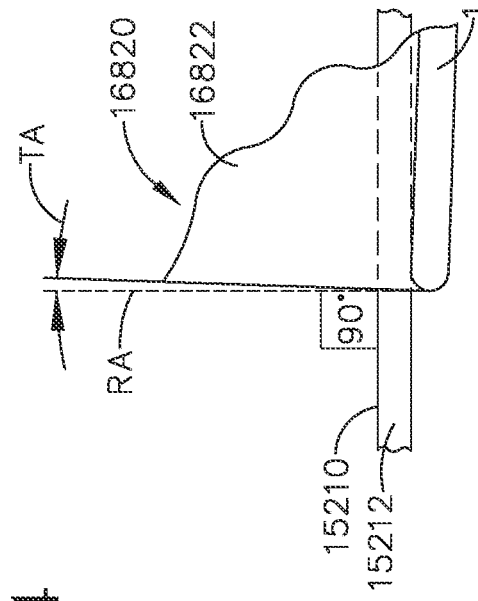
FIG. 92
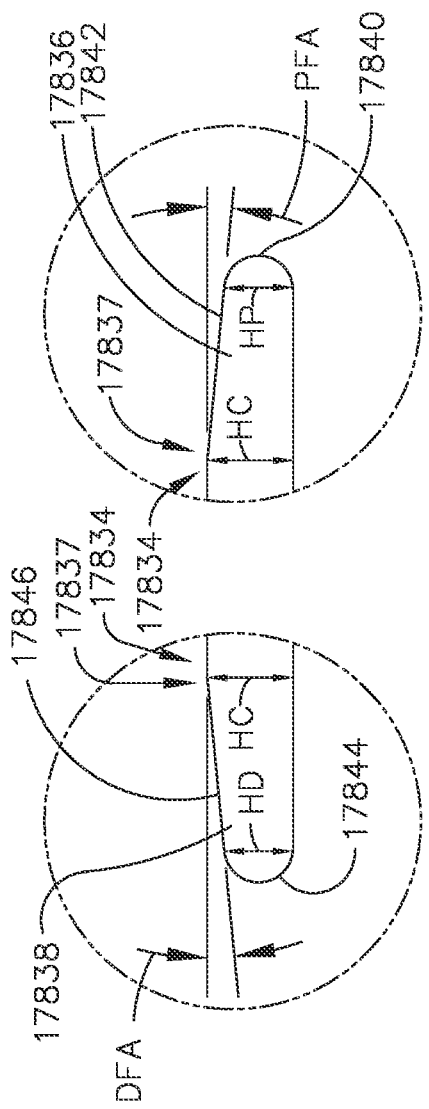
FIG. 94
FIG. 95

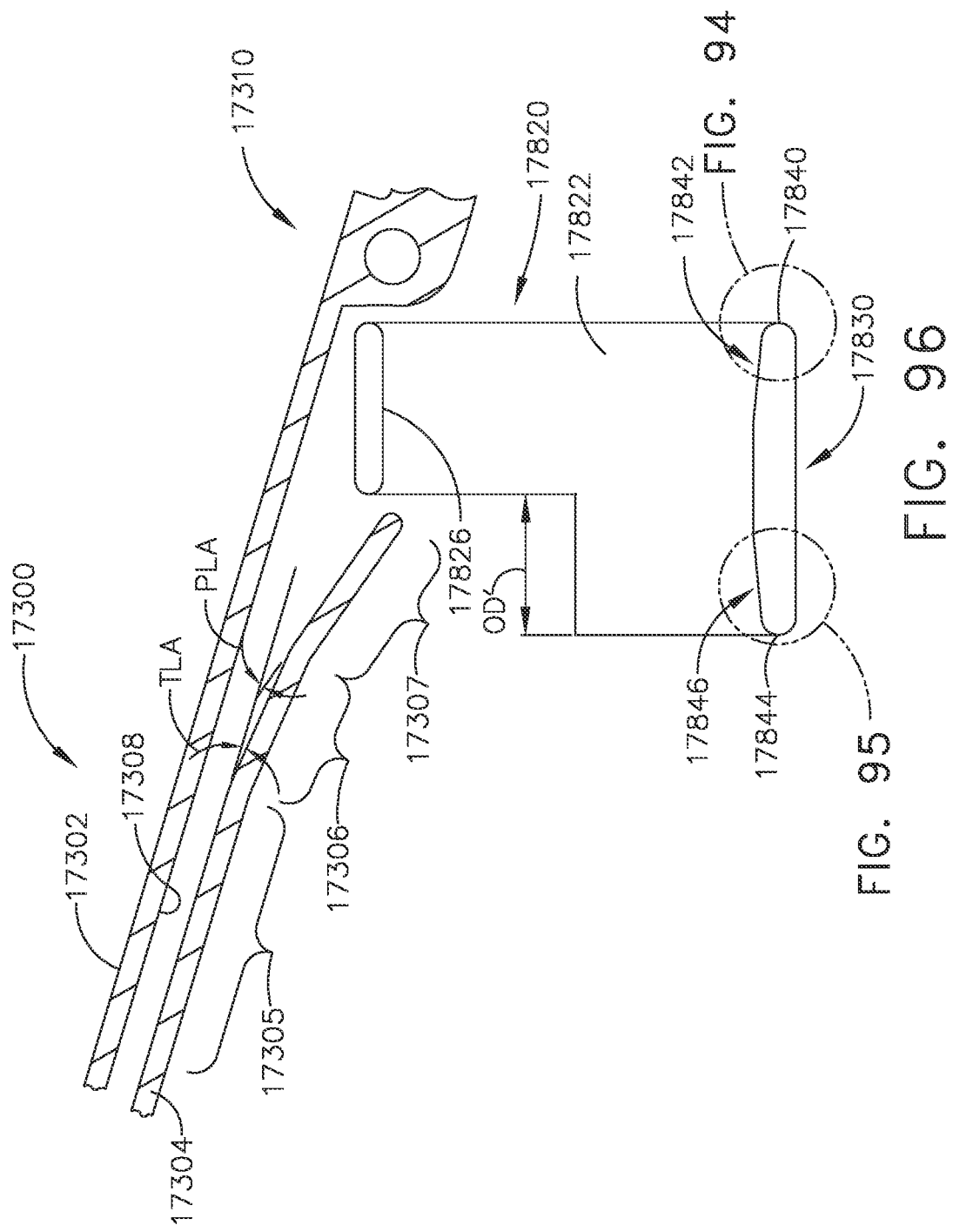

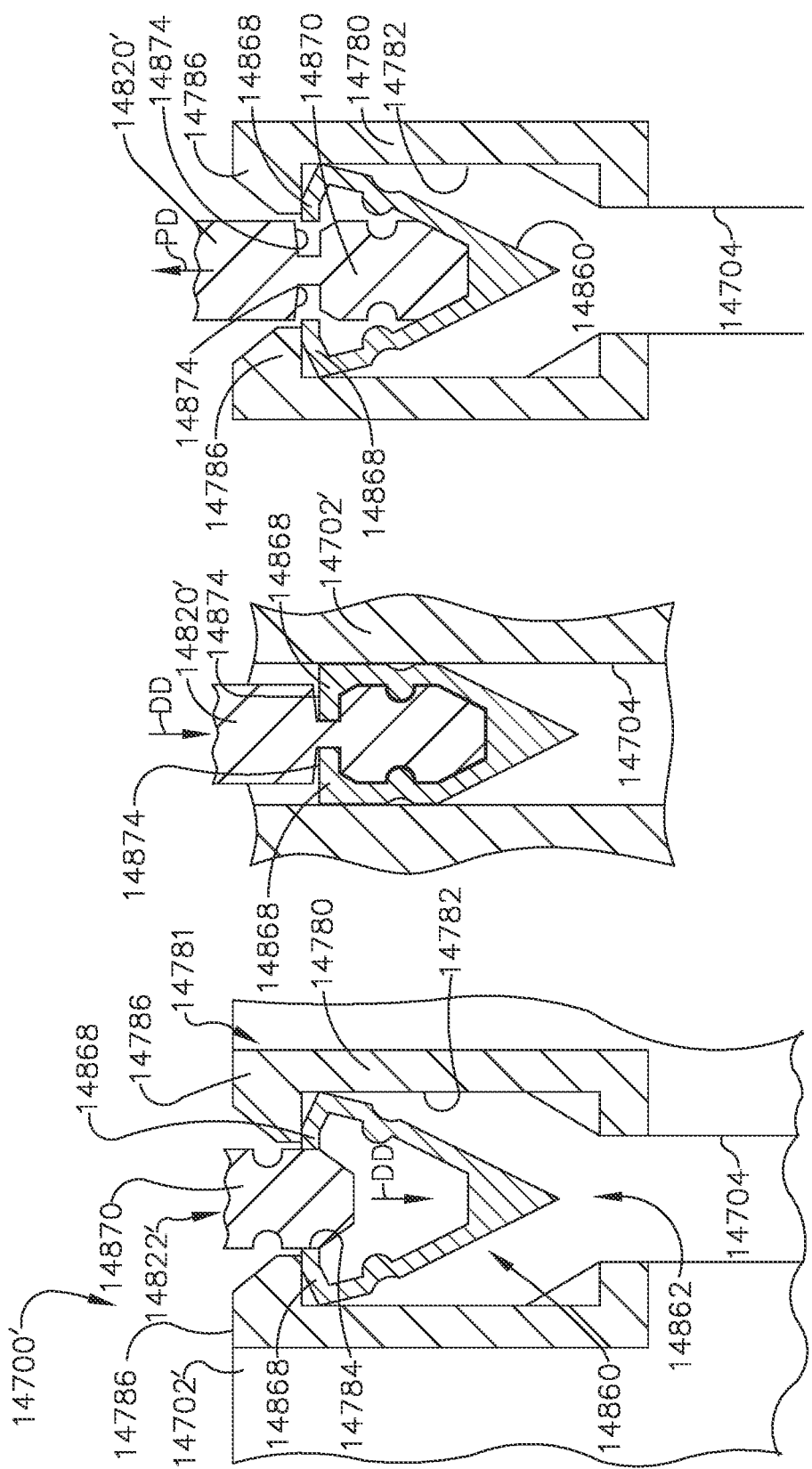

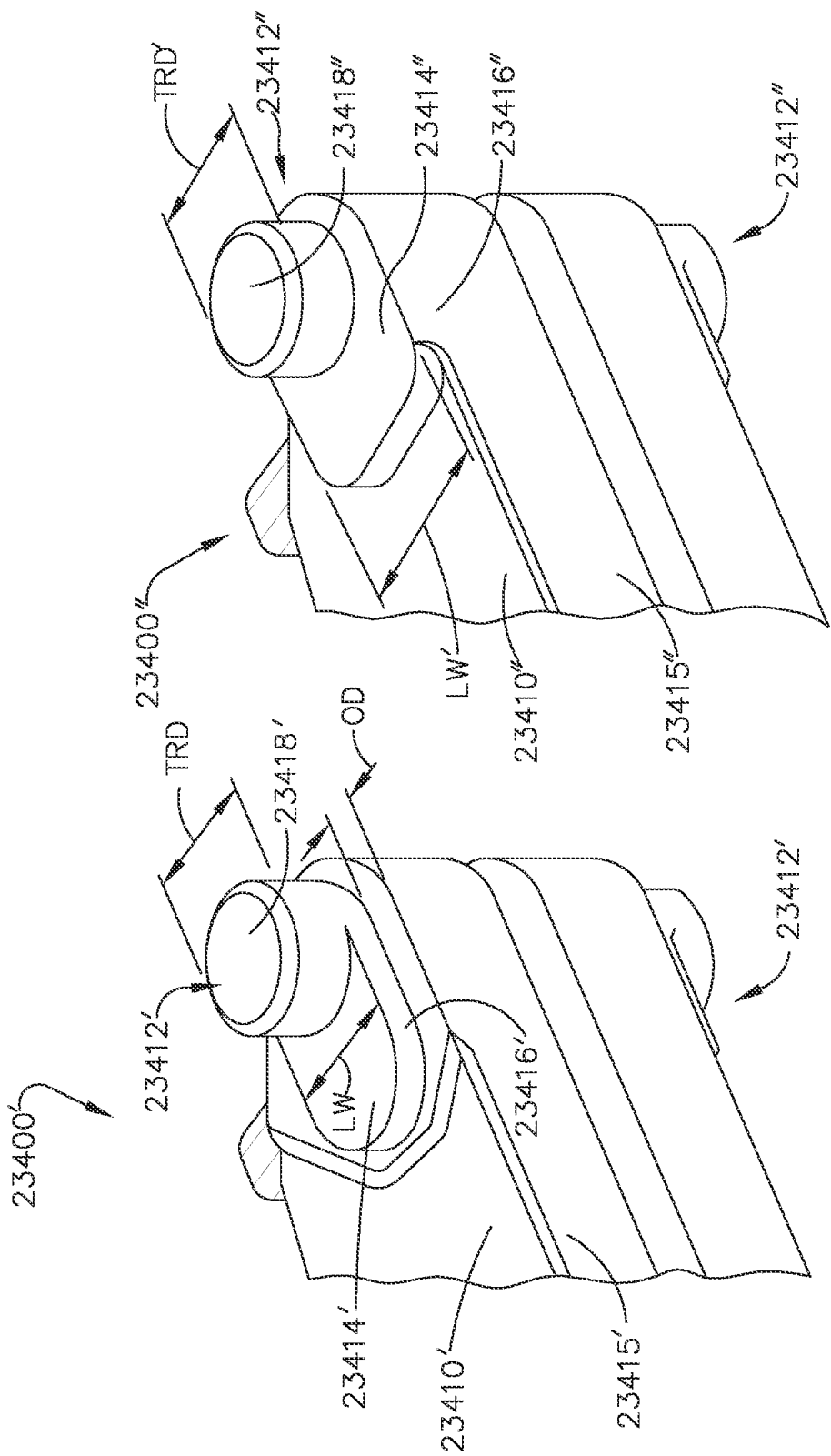

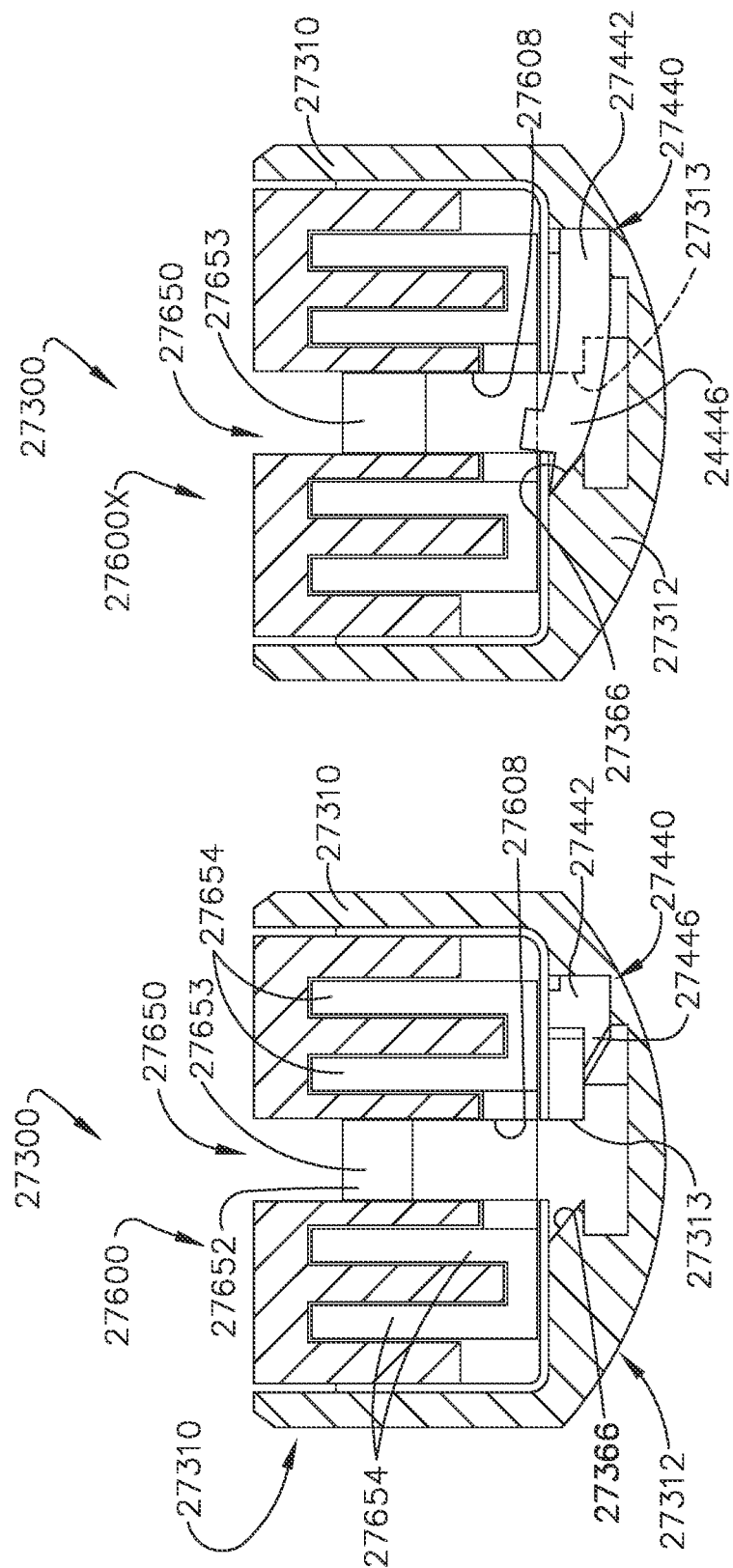

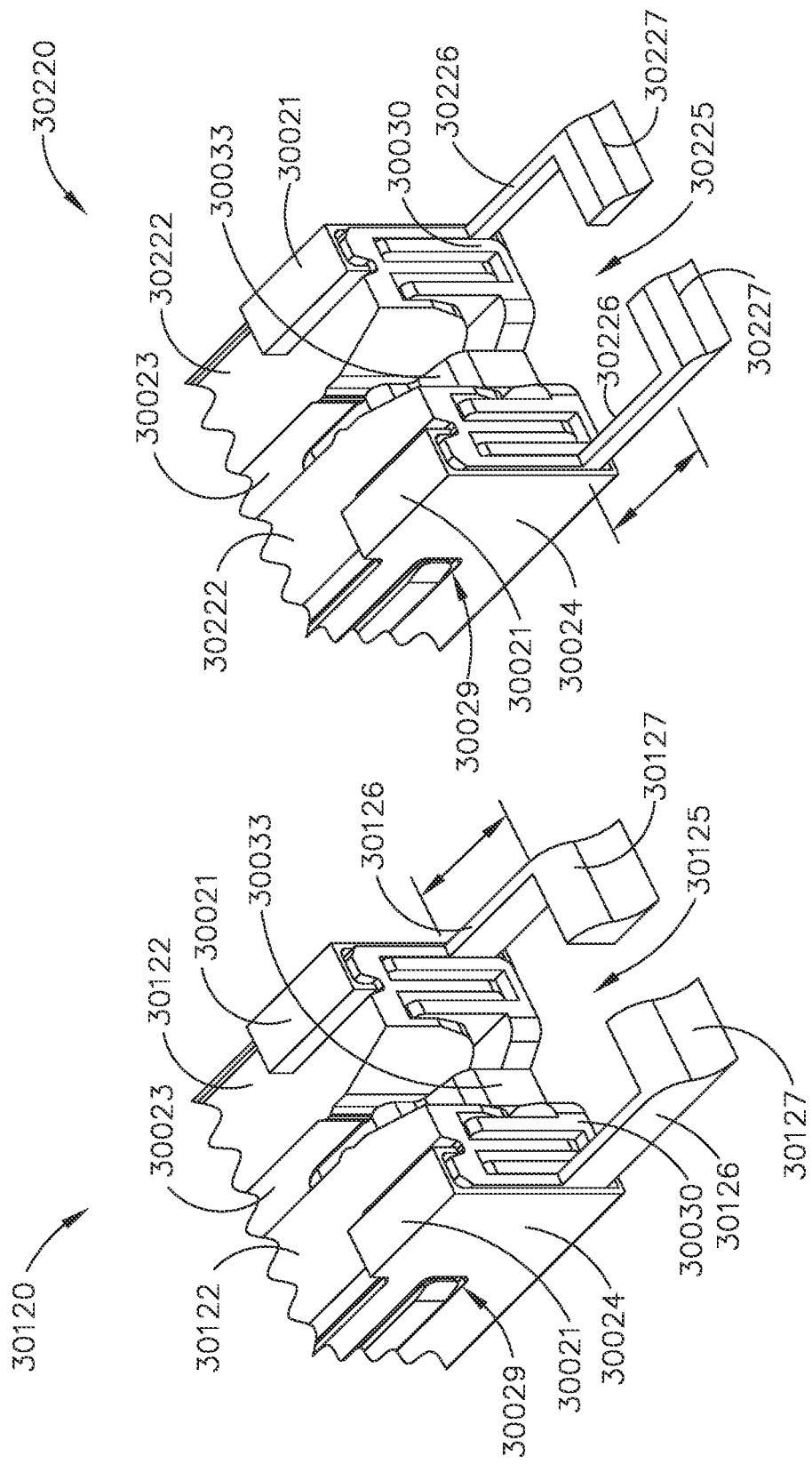

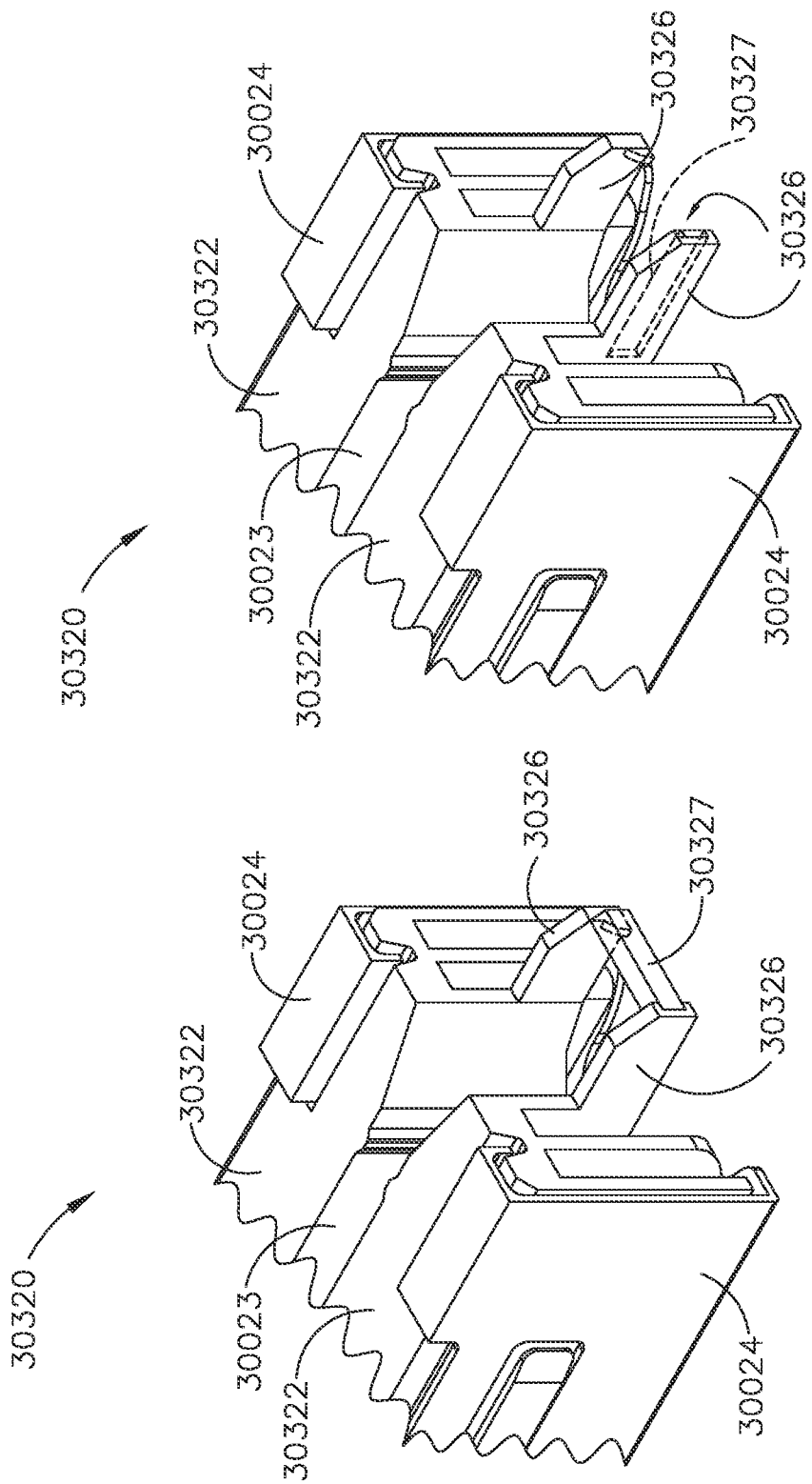

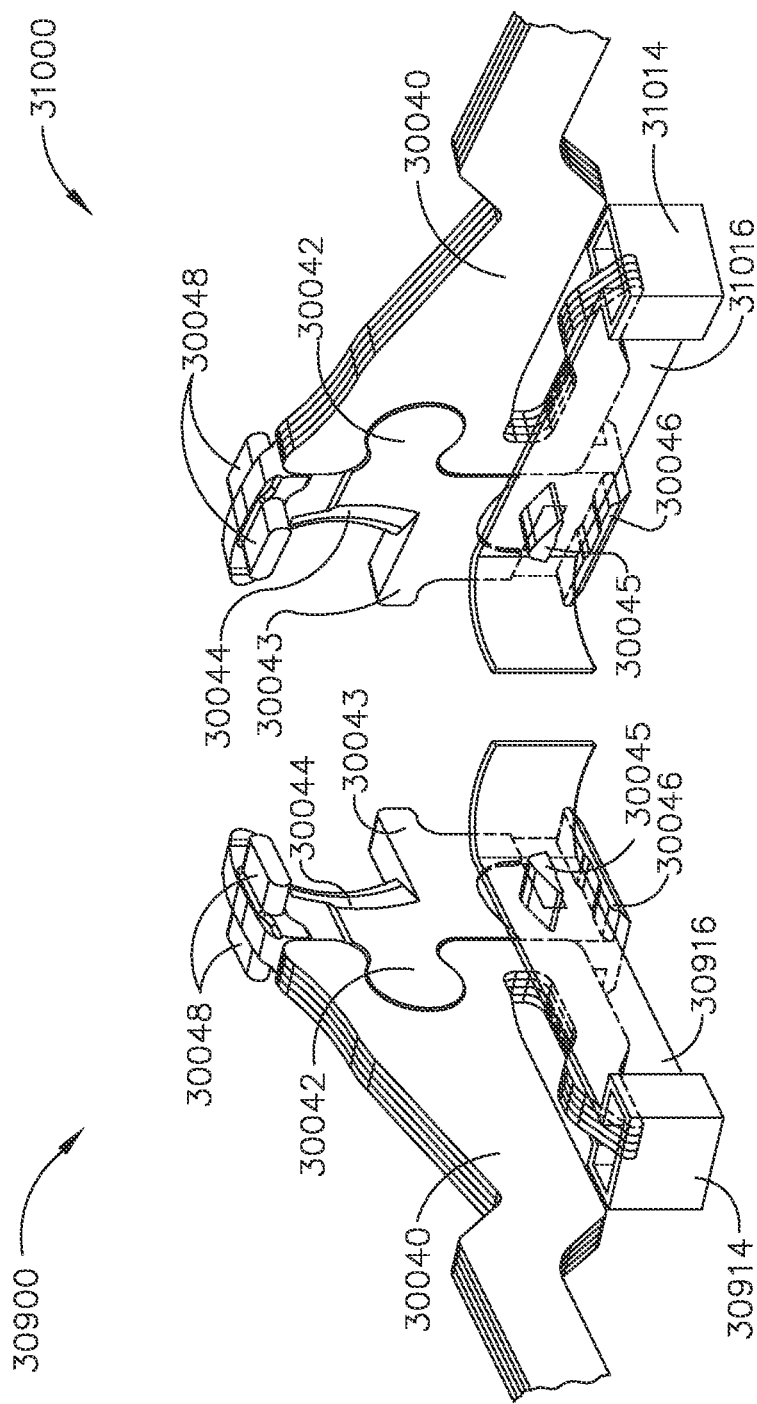

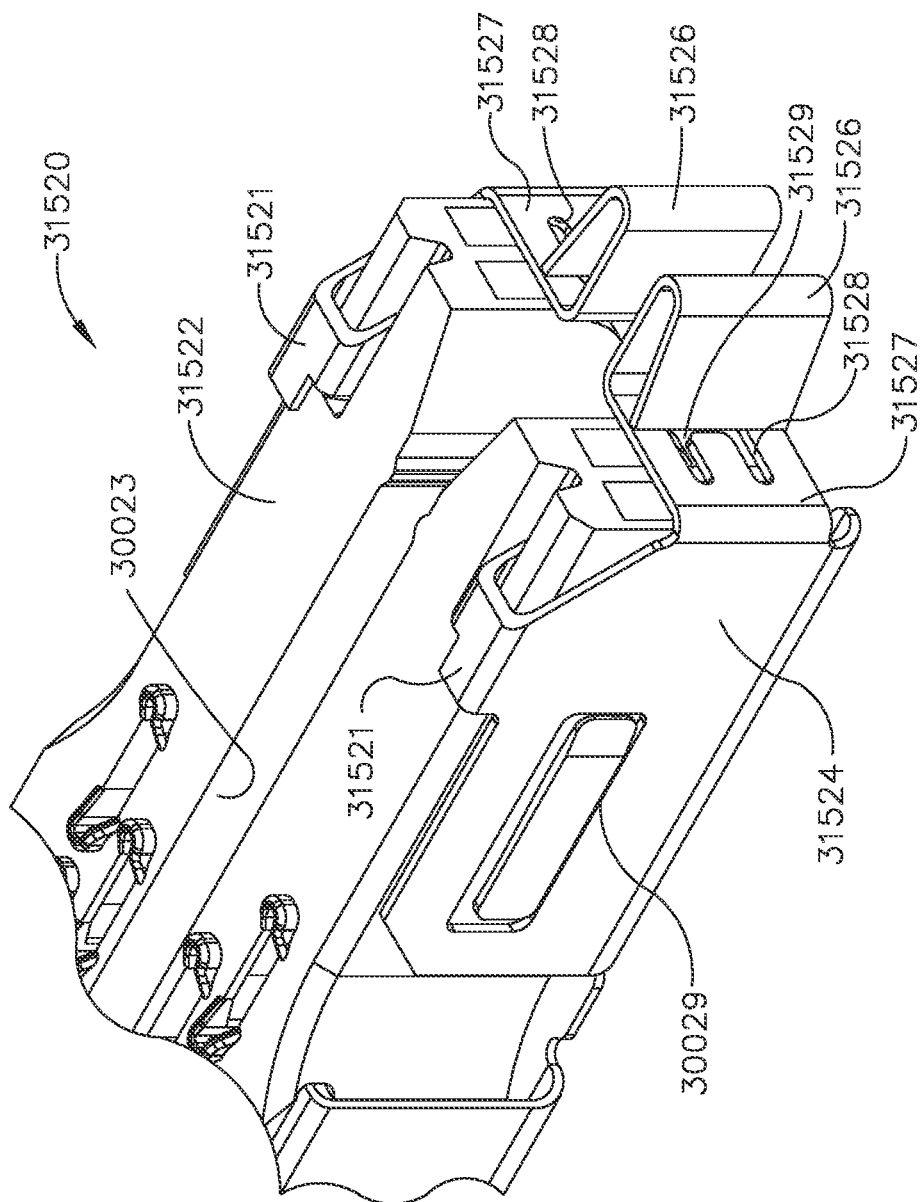
FIG. 2279A

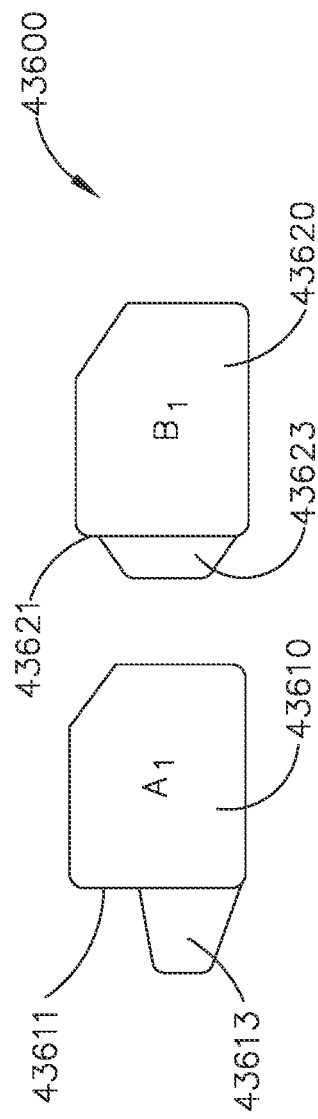
FIG. 289
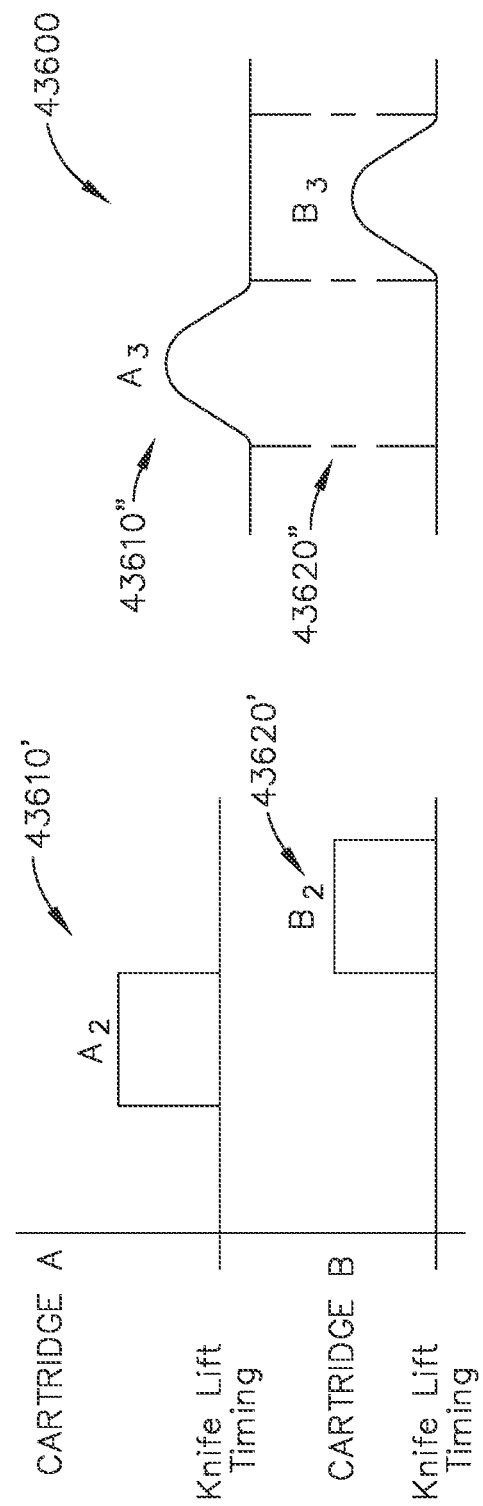
FIG. 291
FIG. 290

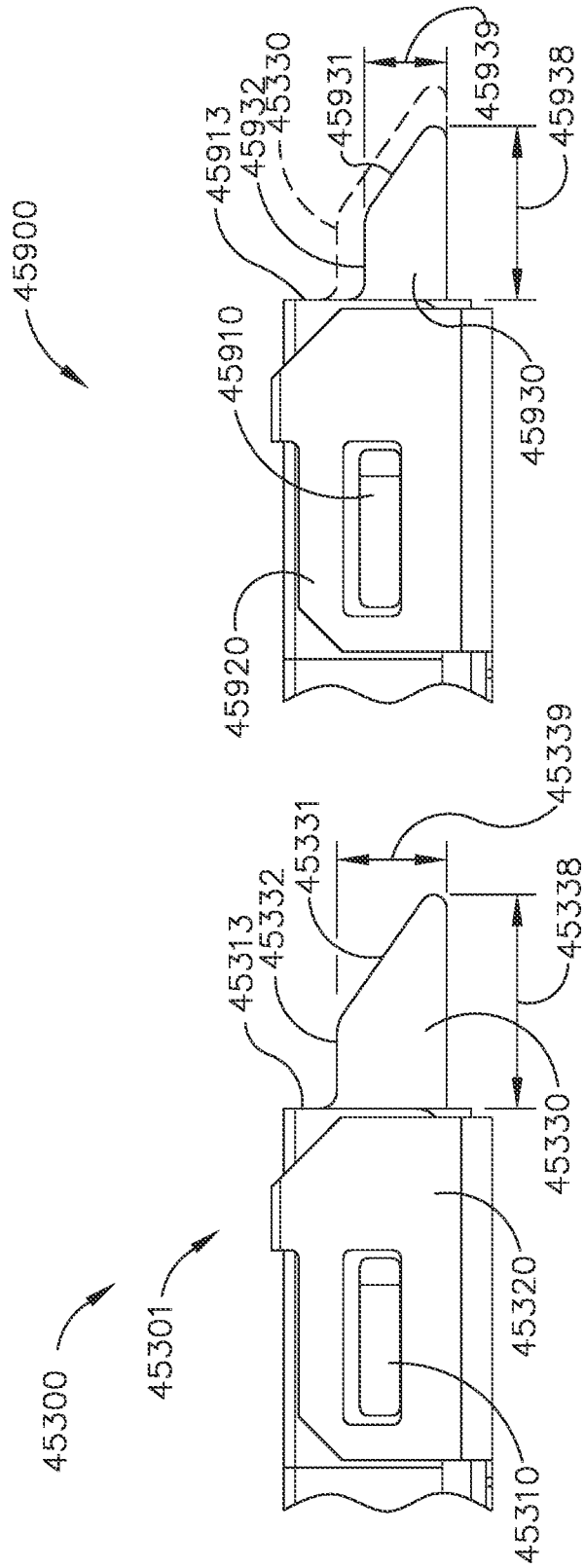

SURGICAL INSTRUMENTS WITH ASYMMETRIC JAW ARRANGEMENTS AND SEPARATE CLOSURE AND FIRING SYSTEMS

CROSS-REFERENCE TO RELATED APPLICATIONS

This application is a continuation application claiming priority under 35 U.S.C. § 120 to U.S. patent application Ser. No. 16/281,658, entitled METHODS FOR CONTROLLING A POWERED SURGICAL STAPLER THAT HAS SEPARATE ROTARY CLOSURE AND FIRING SYSTEMS, filed Feb. 21, 2019, now U.S. Patent Application Publication No. 2019/0298350, which claims the benefit of U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS, filed Feb. 19, 2019, of U.S. Provisional Patent Application Ser. No. 62/807,319, entitled SURGICAL STAPLING DEVICES WITH IMPROVED LOCKOUT SYSTEMS, filed Feb. 19, 2019, and of U.S. Provisional Patent Application Ser. No. 62/807,309, entitled SURGICAL STAPLING DEVICES WITH IMPROVED ROTARY DRIVEN CLOSURE SYSTEMS, filed Feb. 19, 2019, the disclosures of which are incorporated by reference herein in their entireties. This application claims the benefit of U.S. Provisional Patent Application Ser. No. 62/650,887, entitled SURGICAL SYSTEMS WITH OPTIMIZED SENSING CAPABILITIES, filed Mar. 30, 2018, the disclosure of which is incorporated by reference herein in its entirety. This application claims the benefit of U.S. Provisional Patent Application Ser. No. 62/649,302, entitled INTERACTIVE SURGICAL SYSTEMS WITH ENCRYPTED COMMUNICATION CAPABILITIES, filed Mar. 28, 2018, of U.S. Provisional Patent Application Ser. No. 62/649,294, entitled DATA STRIPPING METHOD TO INTERROGATE PATIENT RECORDS AND CREATE ANONYMIZED RECORD, filed Mar. 28, 2018, of U.S. Provisional Patent Application Ser. No. 62/649,300, entitled SURGICAL HUB SITUATIONAL AWARENESS, filed Mar. 28, 2018, of U.S. Provisional Patent Application Ser. No. 62/649,309, entitled SURGICAL HUB SPATIAL AWARENESS TO DETERMINE DEVICES IN OPERATING THEATER, filed Mar. 28, 2018, of U.S. Provisional Patent Application Ser. No. 62/649,310, entitled COMPUTER IMPLEMENTED INTERACTIVE SURGICAL SYSTEMS, filed Mar. 28, 2018, of U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT, filed Mar. 28, 2018, of U.S. Provisional Patent Application Ser. No. 62/649,296, entitled ADAPTIVE CONTROL PROGRAM UPDATES FOR SURGICAL DEVICES, filed Mar. 28, 2018, of U.S. Provisional Patent Application Ser. No. 62/649,333, entitled CLOUD-BASED MEDICAL ANALYTICS FOR CUSTOMIZATION AND RECOMMENDATIONS TO A USER, filed Mar. 28, 2018, of U.S. Provisional Patent Application Ser. No. 62/649,327, entitled CLOUD-BASED MEDICAL ANALYTICS FOR SECURITY AND AUTHENTICATION TRENDS AND REACTIVE MEASURES, filed Mar. 28, 2018, of U.S. Provisional Patent Application Ser. No. 62/649,315, entitled DATA HANDLING AND PRIORITIZATION IN A CLOUD ANALYTICS NETWORK, filed Mar. 28, 2018, of U.S. Provisional Patent Application Ser. No. 62/649,313, entitled CLOUD INTERFACE FOR COUPLED SURGICAL DEVICES, filed Mar. 28, 2018, of U.S. Provisional Patent Application Ser. No. 62/649,320, entitled DRIVE ARRANGEMENTS FOR ROBOT-ASSISTED SURGICAL PLATFORMS, filed Mar. 28, 2018, of U.S. Provisional patent application Ser. No. 62/649,307, entitled AUTOMATIC TOOL ADJUSTMENTS FOR ROBOT-ASSISTED SURGICAL PLATFORMS, filed Mar. 28, 2018, and of U.S. Provisional patent application Ser. No. 62/649,323, entitled SENSING ARRANGEMENTS FOR ROBOT-ASSISTED SURGICAL PLATFORMS, filed Mar. 28, 2018, the disclosures of which are incorporated by reference herein in their entireties.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 16 is a top view of an anvil of the end effector of FIG. 14;

FIG. 17 is another top view of the anvil of FIG. 16 attached to an elongate channel of the end effector of FIG. 14;

FIG. 18 is a cross-sectional view of the anvil and end effector of FIG. 17 taken along line 18-18 in FIG. 17;

FIG. 19 is another cross-sectional view of the anvil and end effector of FIG. 17 taken along line 19-19 in FIG. 17;

FIG. 26 is a cross-sectional end view of the rotary powered surgical end effector of FIG. 24;

FIG. 27 is another cross-sectional end view of the rotary powered surgical end effector of FIG. 24;

FIG. 60 is a cross-sectional end view of the surgical end effector of FIG. 59 taken along line 60-60 in FIG. 59;

FIG. 61 is a cross-sectional end view of the surgical end effector of FIG. 59 taken along line 61-61 in FIG. 59;

FIG. 66 is a perspective view of the surgical staple cartridge of FIG. 65;

FIG. 67 is partial perspective assembly view of an elongate channel portion of the surgical end effector of FIG. 65 and a bottom perspective view of the surgical staple cartridge of FIG. 66;

FIG. 68 is a side elevational view of a clip of the surgical staple cartridge of FIG. 67 in engagement with a portion of the elongate channel of FIG. 67 when the staple cartridge has been operably installed in the elongate channel;

FIG. 73 is a partial cross-sectional side view of another surgical end effector with an anvil thereof in an open position and prior to installation of a surgical staple cartridge therein;

FIG. 74 is another partial cross-sectional side view of the surgical end effector of FIG. 73 after the anvil has started to close;

FIG. 79 is a cross-sectional side view of the surgical end effector of FIG. 73 with a surgical staple cartridge installed therein and the anvil thereof in an open position;

FIG. 80 is another cross-sectional side view of the surgical end effector of FIG. 73, with the anvil thereof in a closed position;

FIG. 82 is a perspective view of a portion of a firing member and a closure system of the surgical end effector of FIG. 81;

FIG. 83 is a cross-sectional end view of a portion of an elongate channel and closure shuttle of the surgical end effector of FIG. 81;

FIG. 92 is a side view of a portion of the firing member of FIG. 90 in relation to a portion of an elongate channel of a surgical end effector;

FIG. 94 is a partial side elevational view of a portion of a proximal segment of a flange assembly of the firing member of FIG. 93;

FIG. 95 is a partial side elevational view of a portion of a distal segment of the flange assembly of FIG. 94;

FIG. 96 is a side elevational view of the firing member of FIG. 93 in relation to an anvil of a surgical end effector with the anvil in an open position and shown in cross-section;

FIG. 119 is a perspective view of a distal end of the surgical staple cartridge of FIG. 112, with a portion omitted to expose the camming assembly thereof in an ending position and the tissue cutting member thereof in a stored position;

FIG. 120 is another perspective view of the surgical staple cartridge of FIG. 119;

FIG. 121 is a partial side elevational view of a surgical end effector during installation of a surgical staple cartridge therein with portions of the end effector and cartridge omitted for clarity;

FIG. 122 is another partial side elevational view of the surgical end effector and staple cartridge of FIG. 121 with a firing member of the end effector in operable engagement with a camming assembly of the cartridge prior to commencement of a firing process;

FIG. 123 is another partial side elevational view of the surgical end effector and staple cartridge of FIG. 121 after completion of the firing process and during retraction of the firing member in a proximal direction;

FIG. 124 is a perspective view of another surgical staple cartridge and a portion of a firing member of a powered surgical end effector;

FIG. 125 is another perspective view of a portion of the firing member of FIG. 124 and a removable blade structure of the surgical staple cartridge of FIG. 124;

FIG. 126 is a perspective view of the removable blade structure of FIG. 125;

FIG. 127 is a partial cross-sectional top view showing the positions of the blade structure of the staple cartridge and firing member of FIG. 124 during the initial installation of the surgical staple cartridge;

FIG. 128 is another top cross-sectional view of a portion of the surgical staple cartridge and firing member of FIG. 124 during the distal advancement of the firing member through the staple cartridge;

FIG. 129 is another top cross-sectional view of a portion of the surgical staple cartridge and firing member of FIG. 124 during the retraction of the firing member back to a starting position;

FIG. 130 is a perspective view of another removable blade structure;

Figure 131:
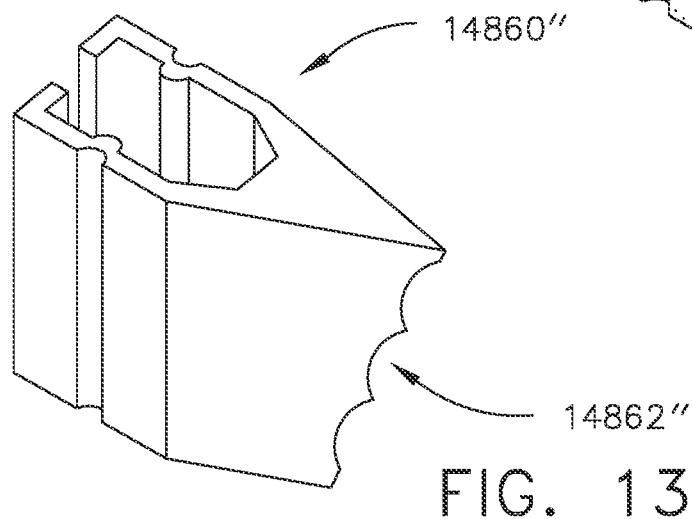
Figure 132:
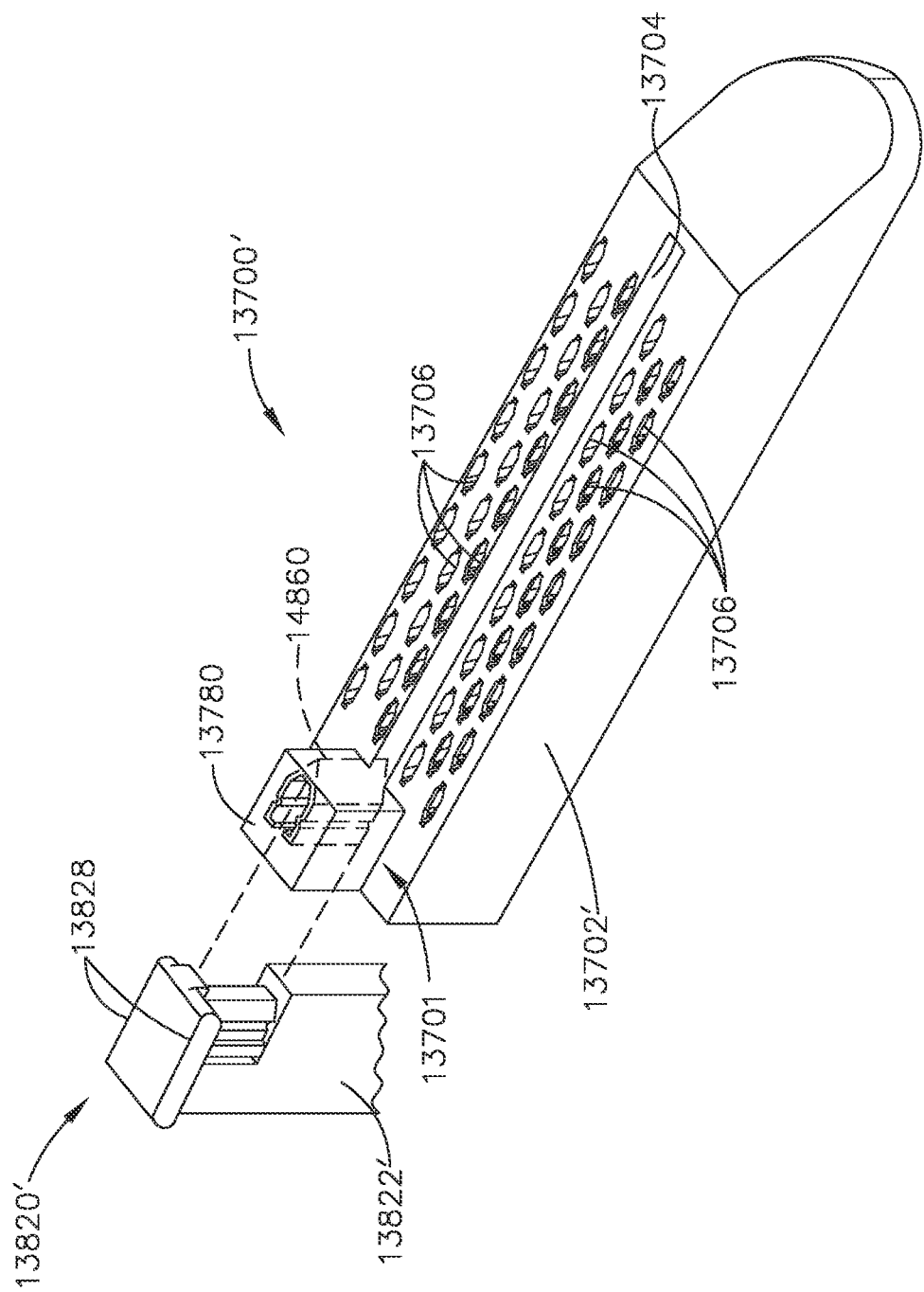
Figure 133:
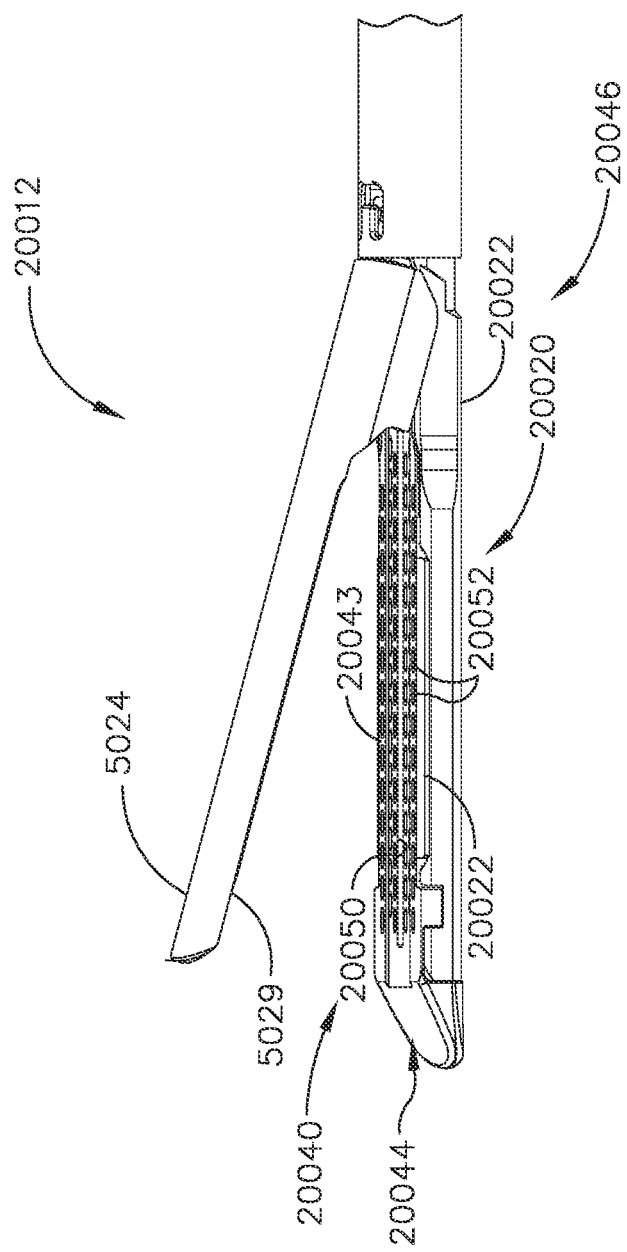
Figure 134:
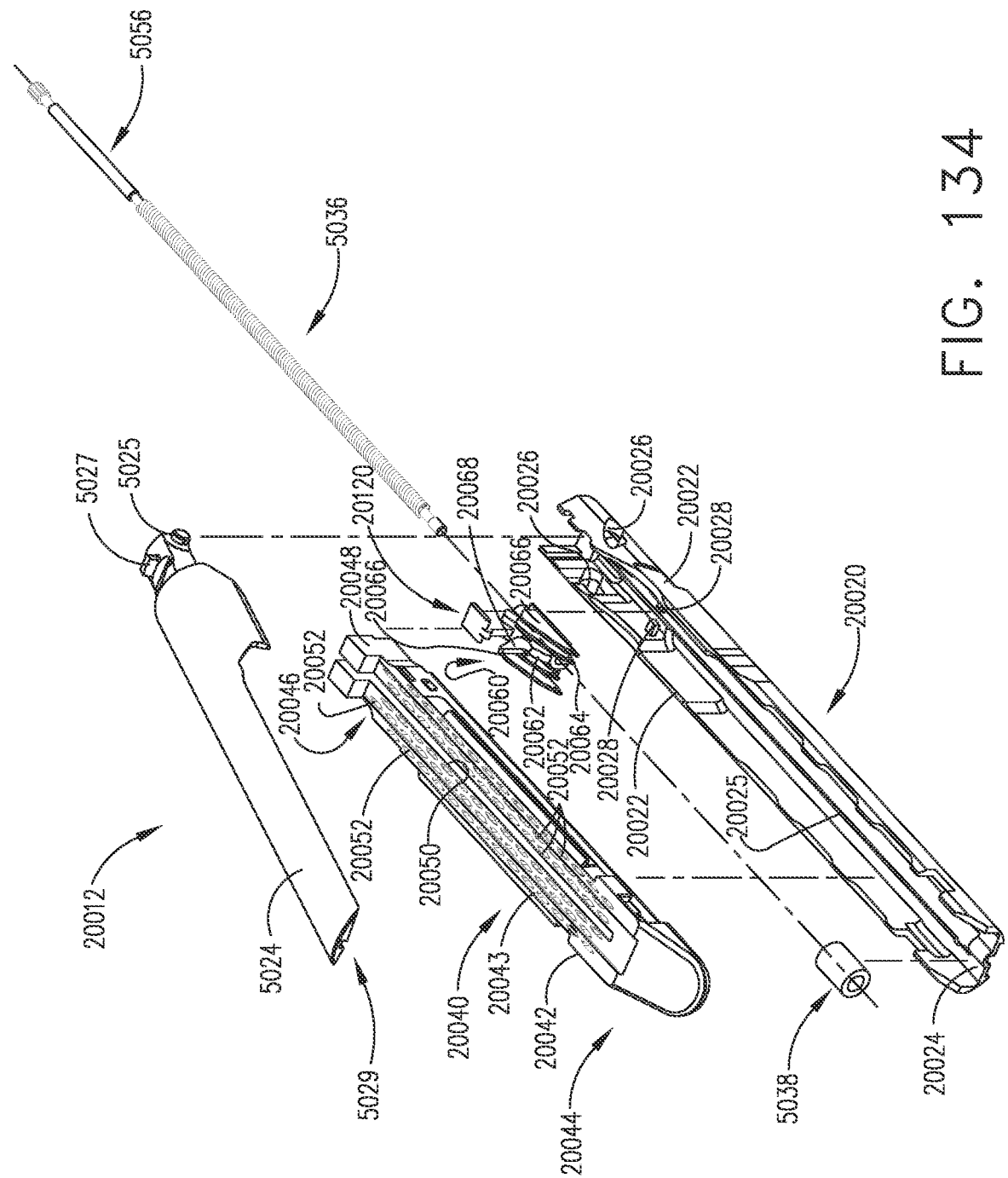
Figure 135:
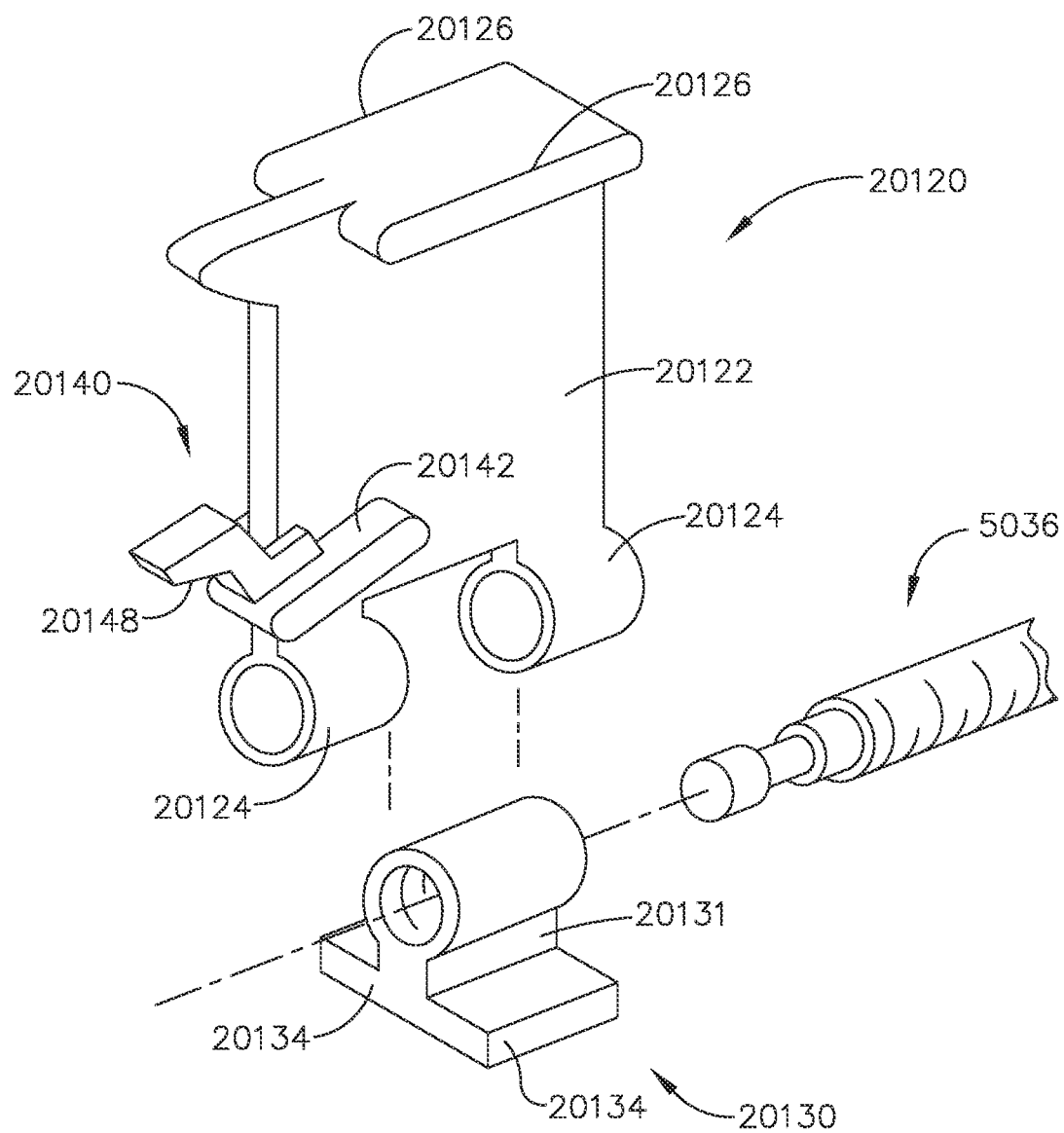
Figure 136:
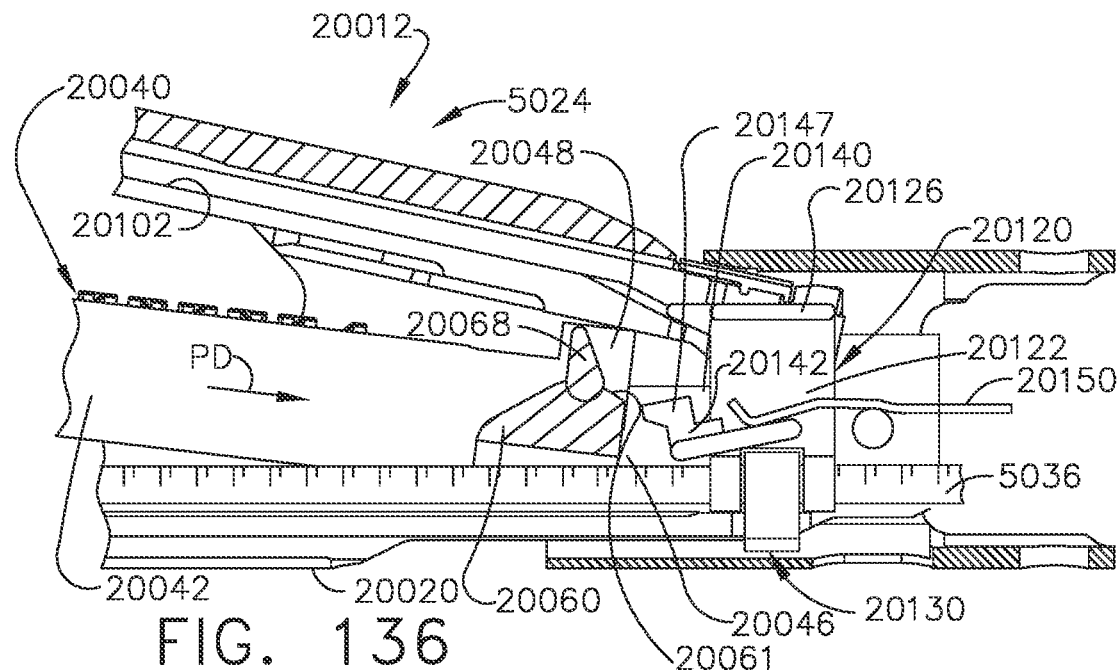
Figure 137:
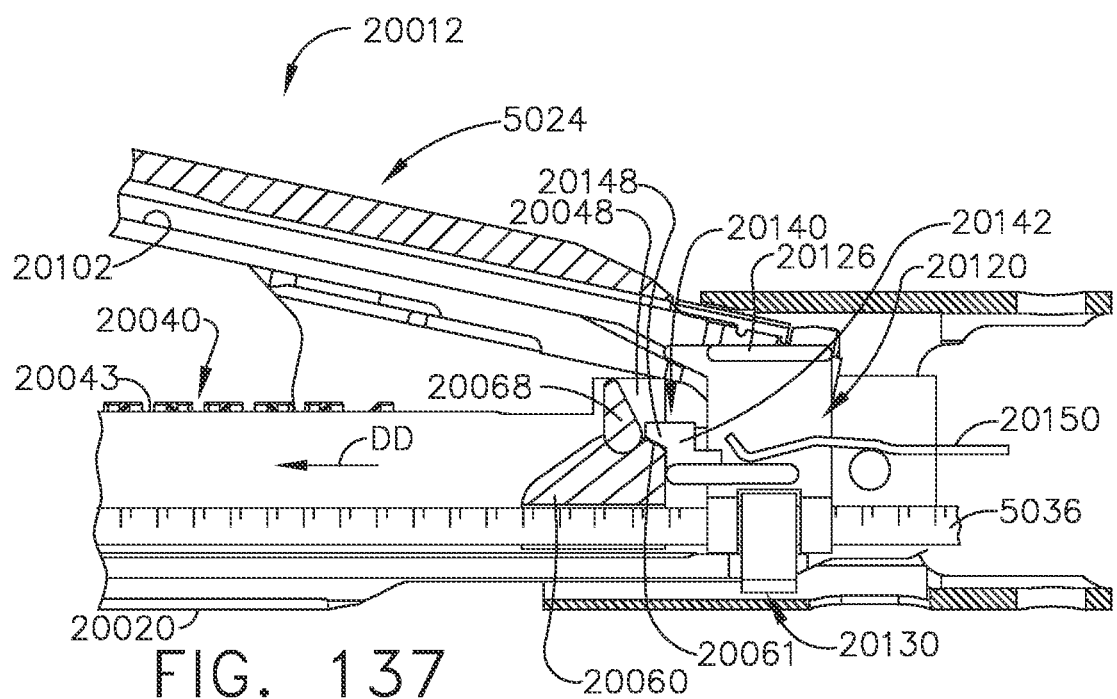
Figure 138:
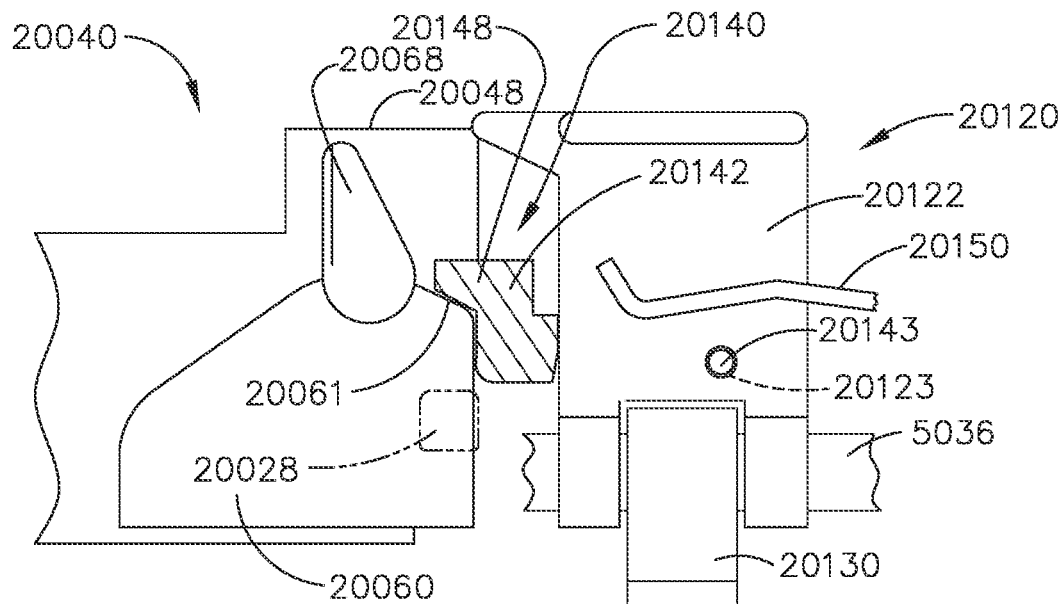
Figure 139:
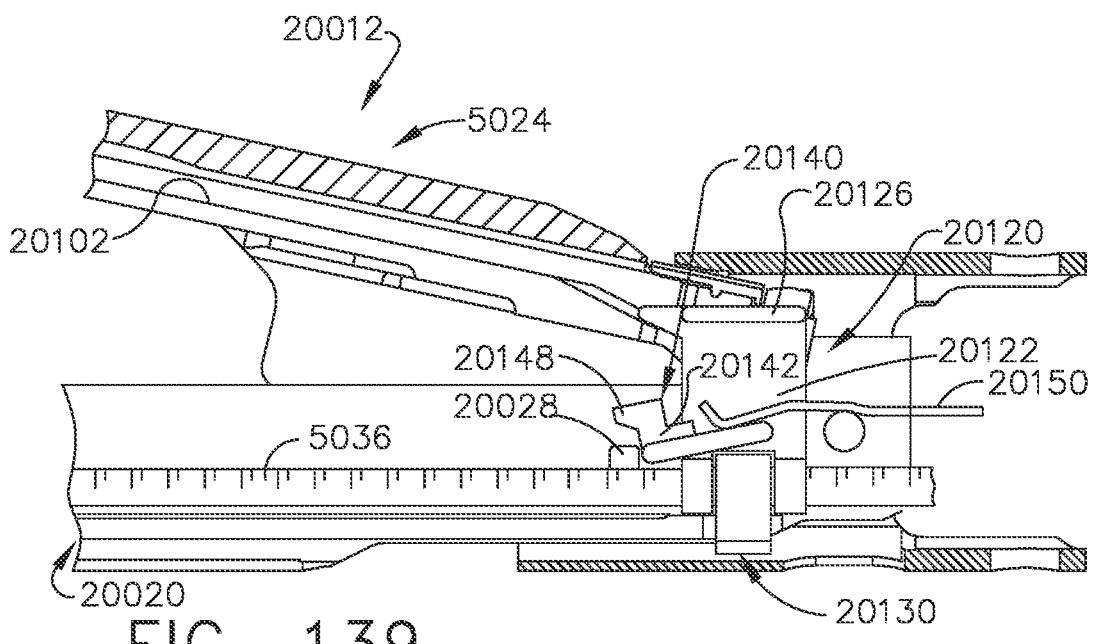
Figure 140:
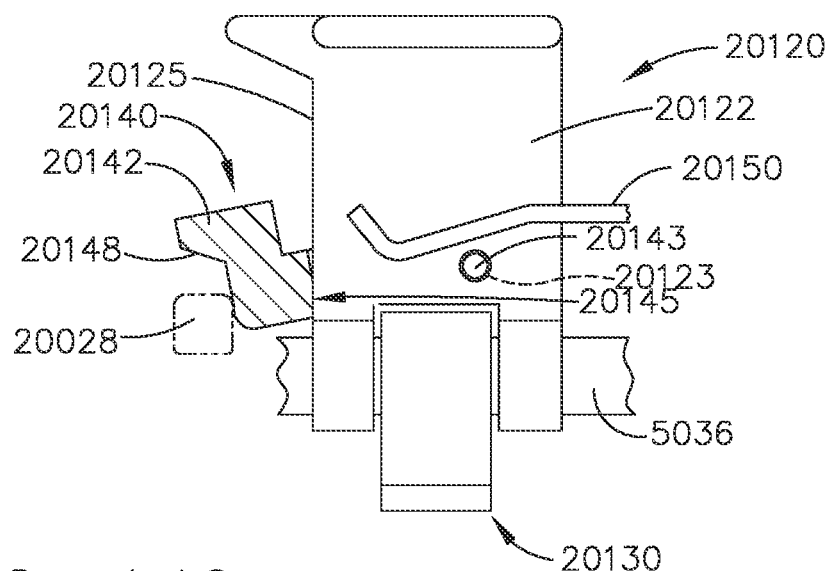
Figure 141:
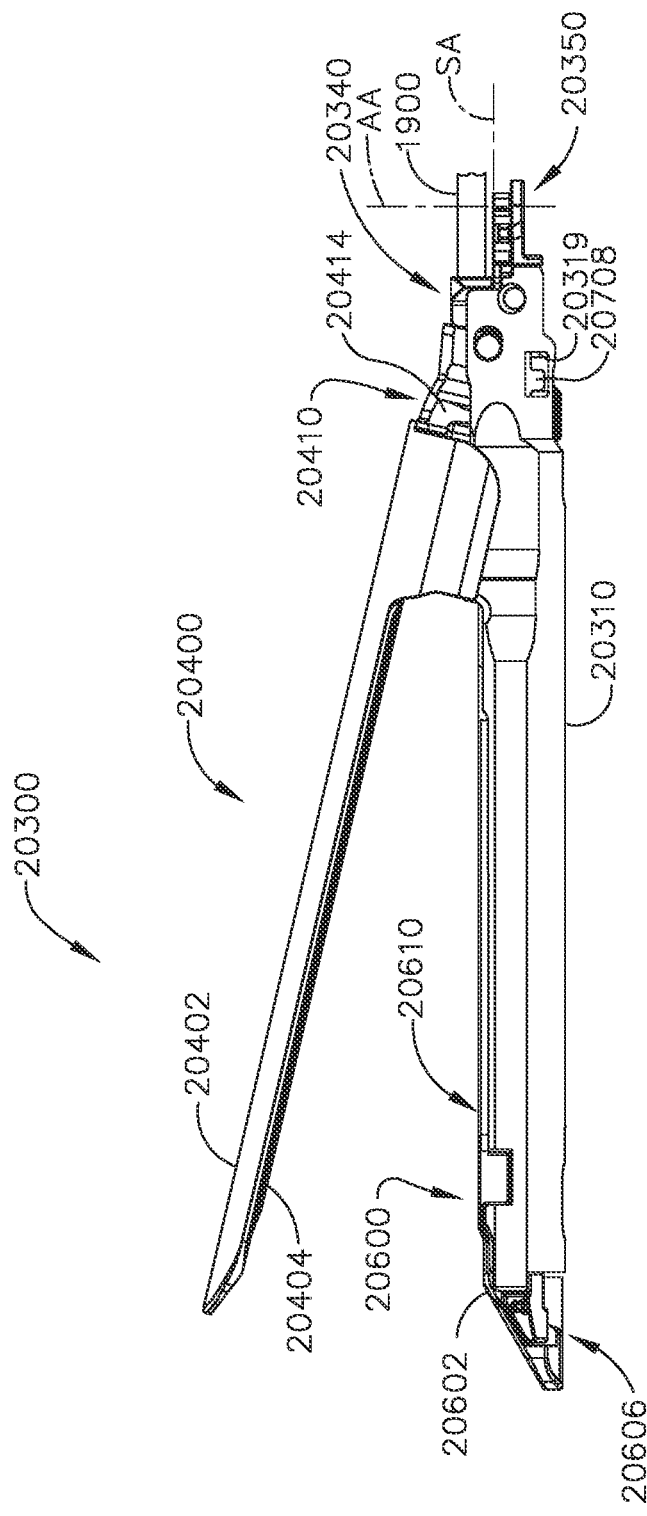
Figure 142:
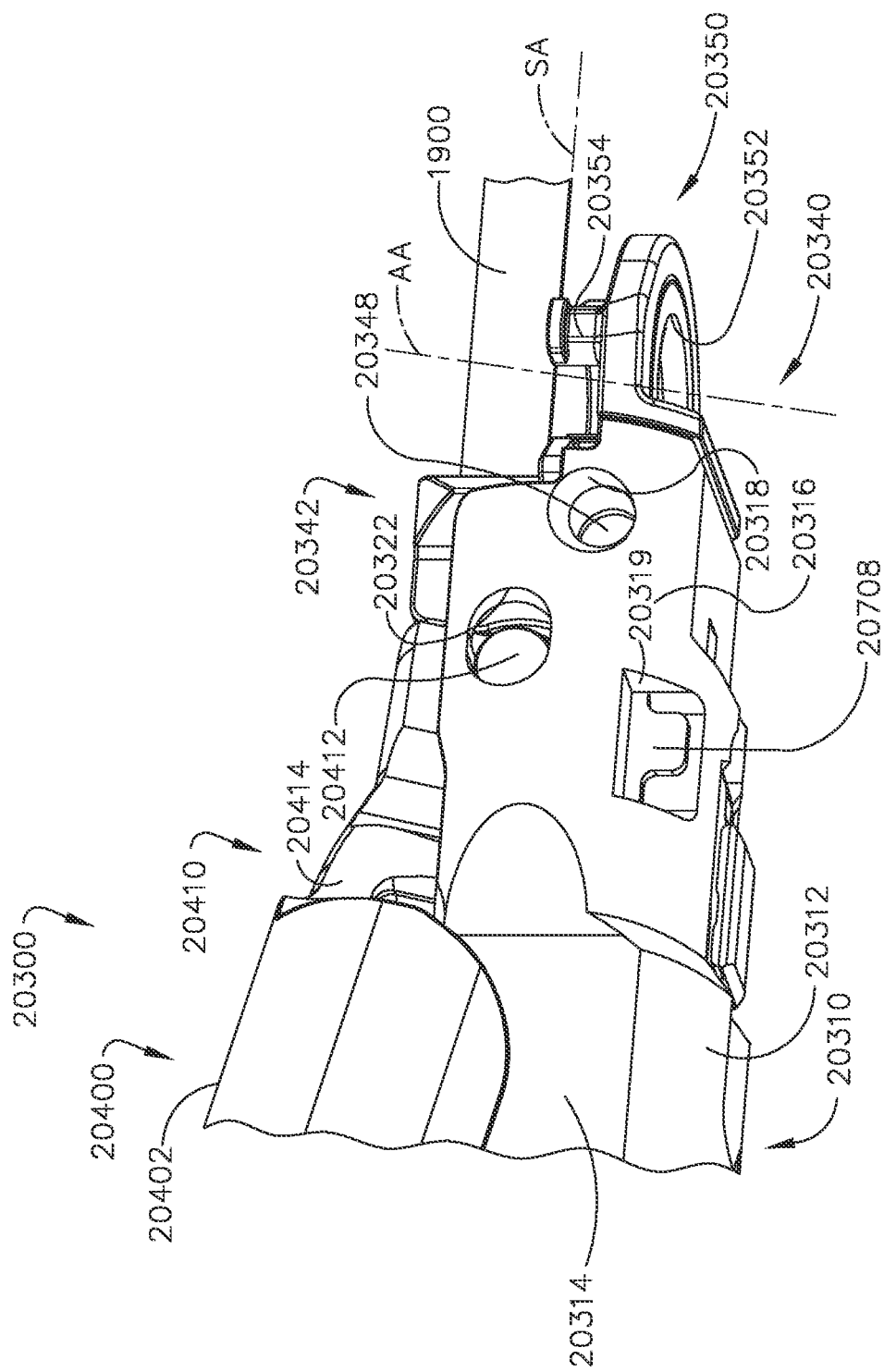
Figure 143:
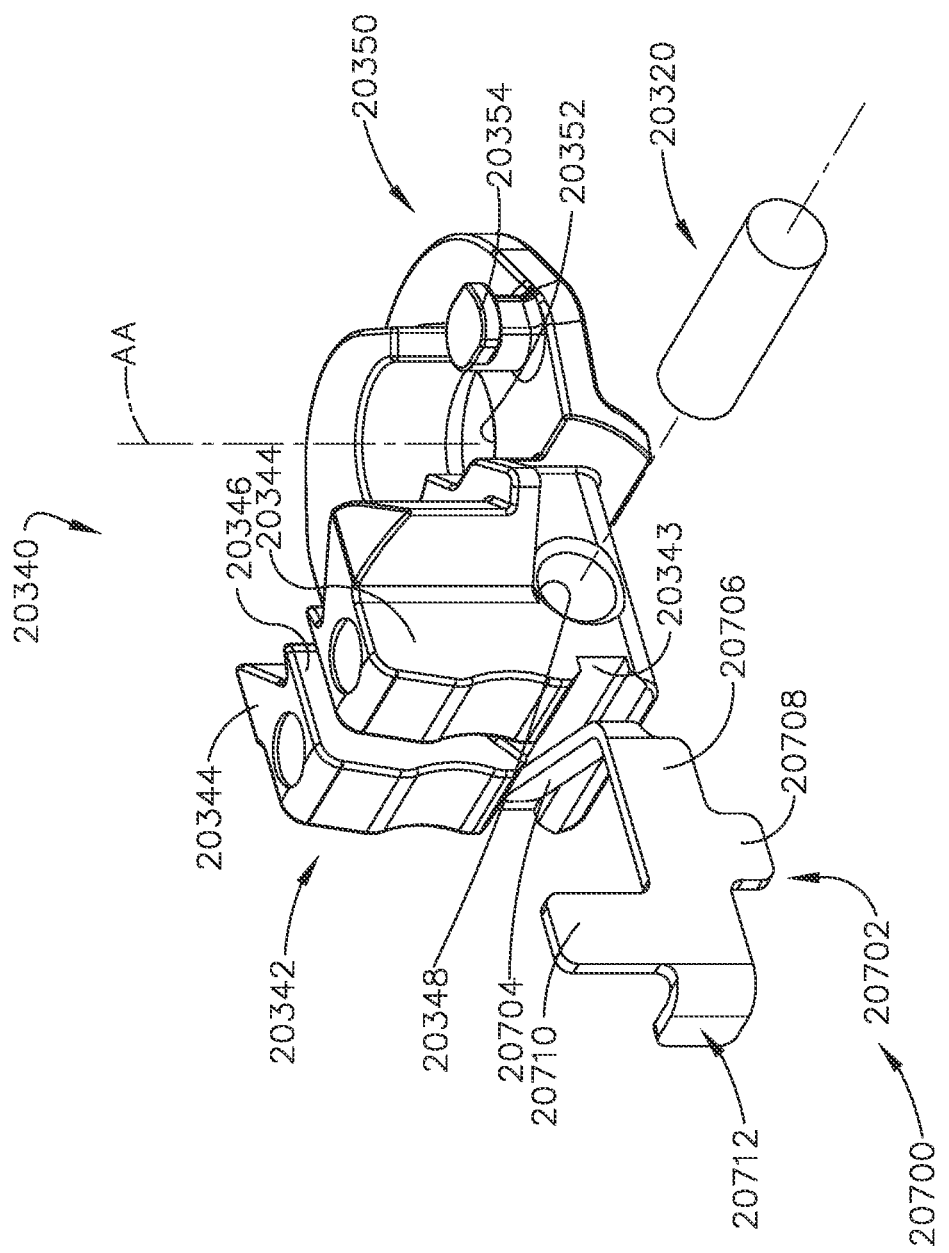
Figure 144:
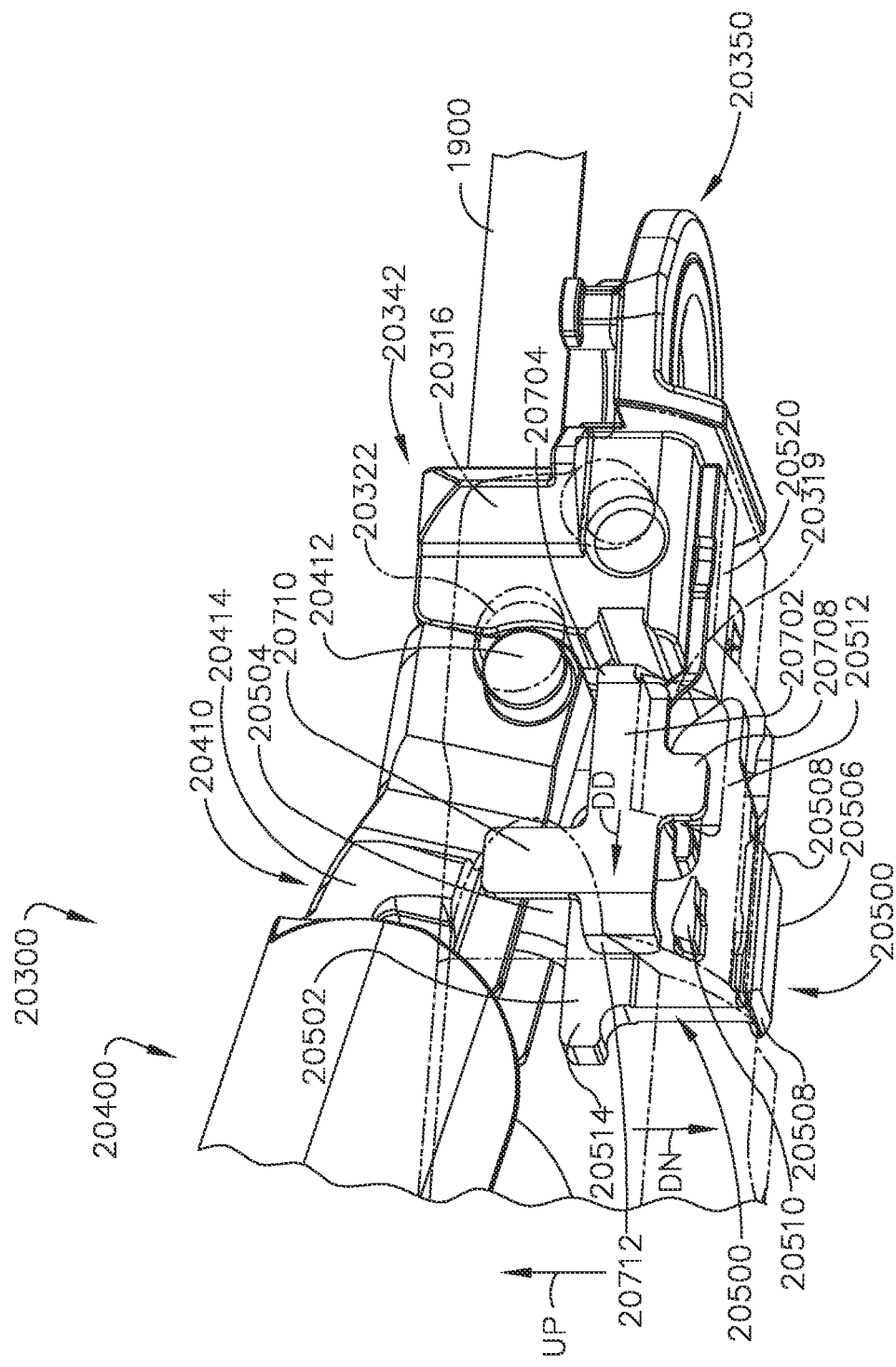
Figure 145:
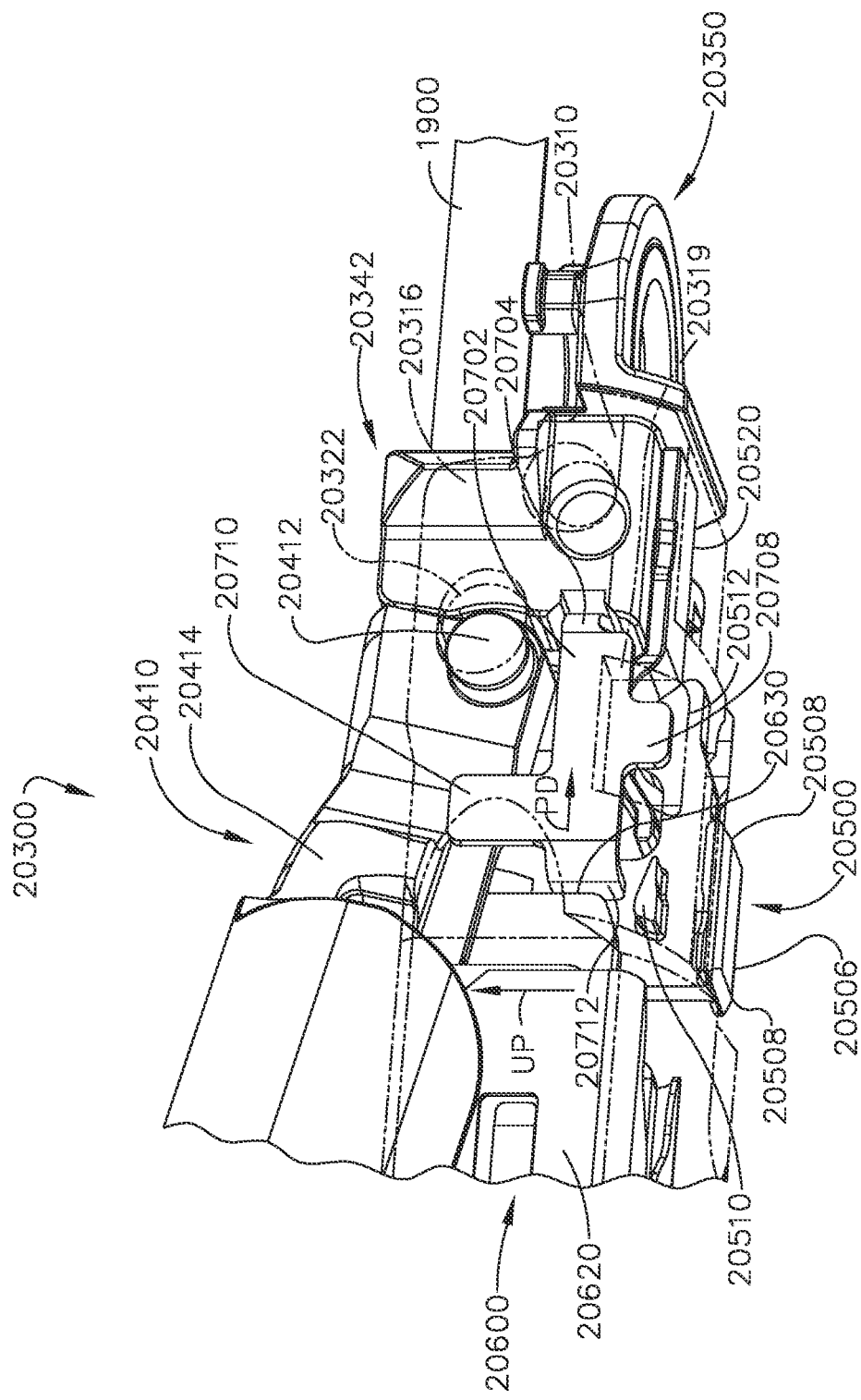
Figure 146:
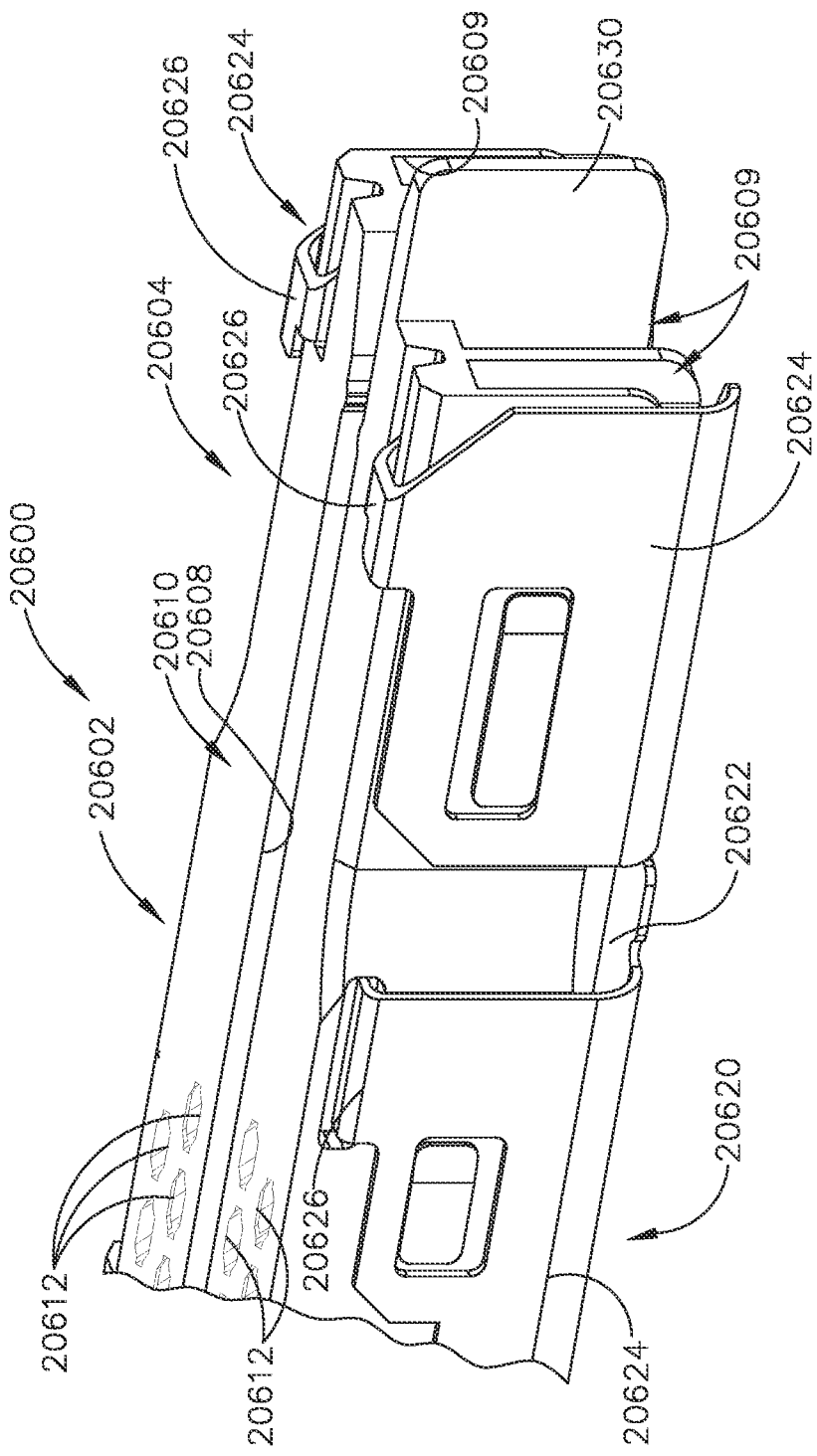
Figure 147:
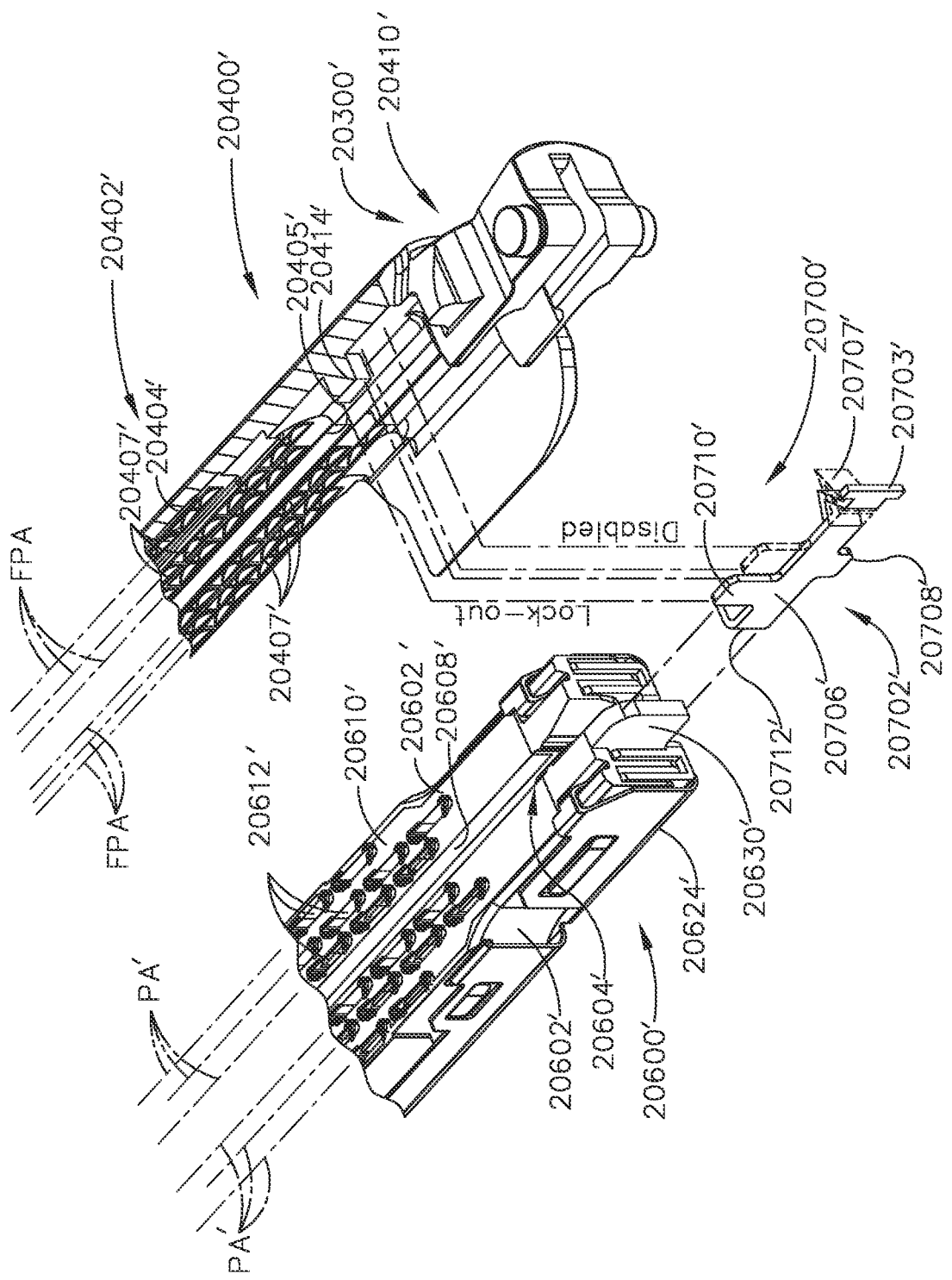
Figure 148:
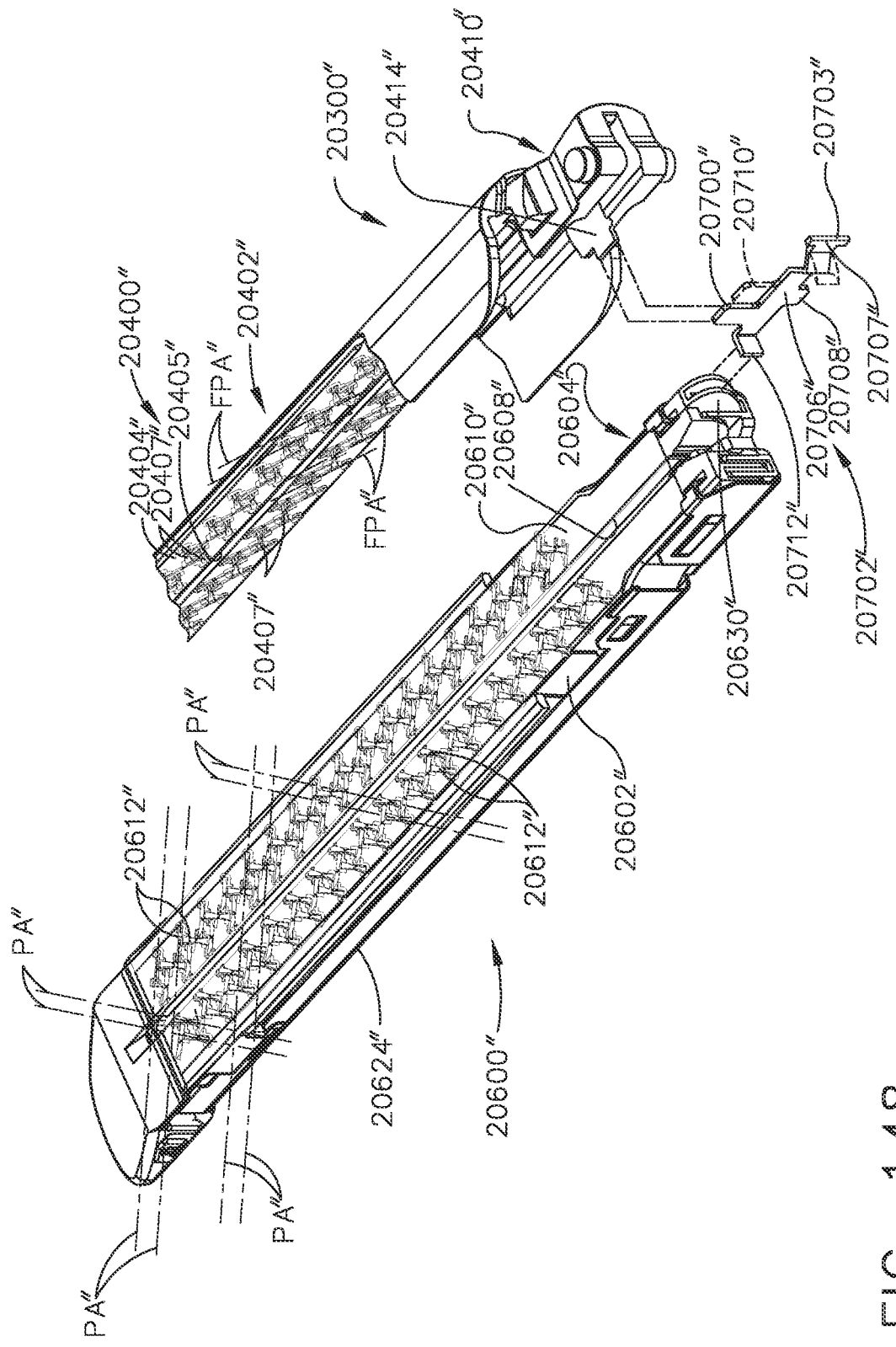
Figure 149:
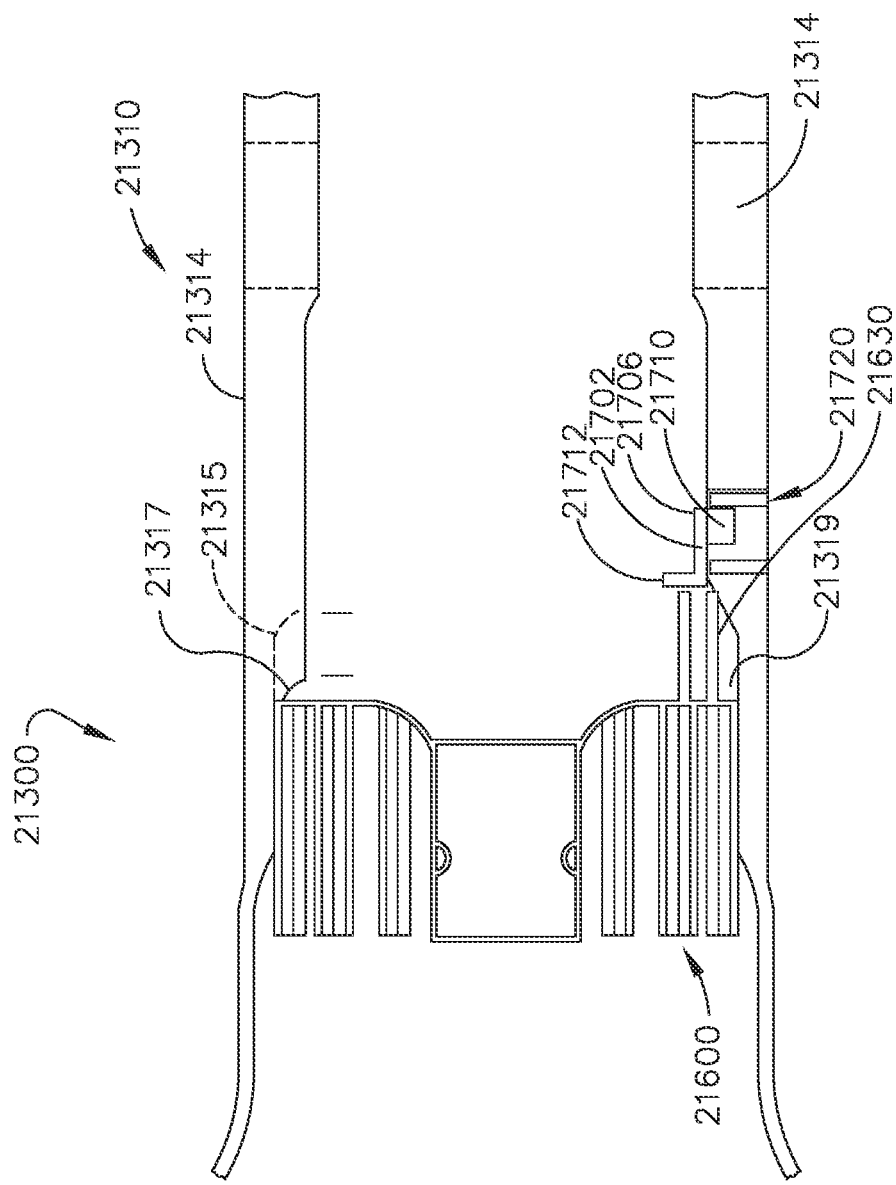
Figure 150:
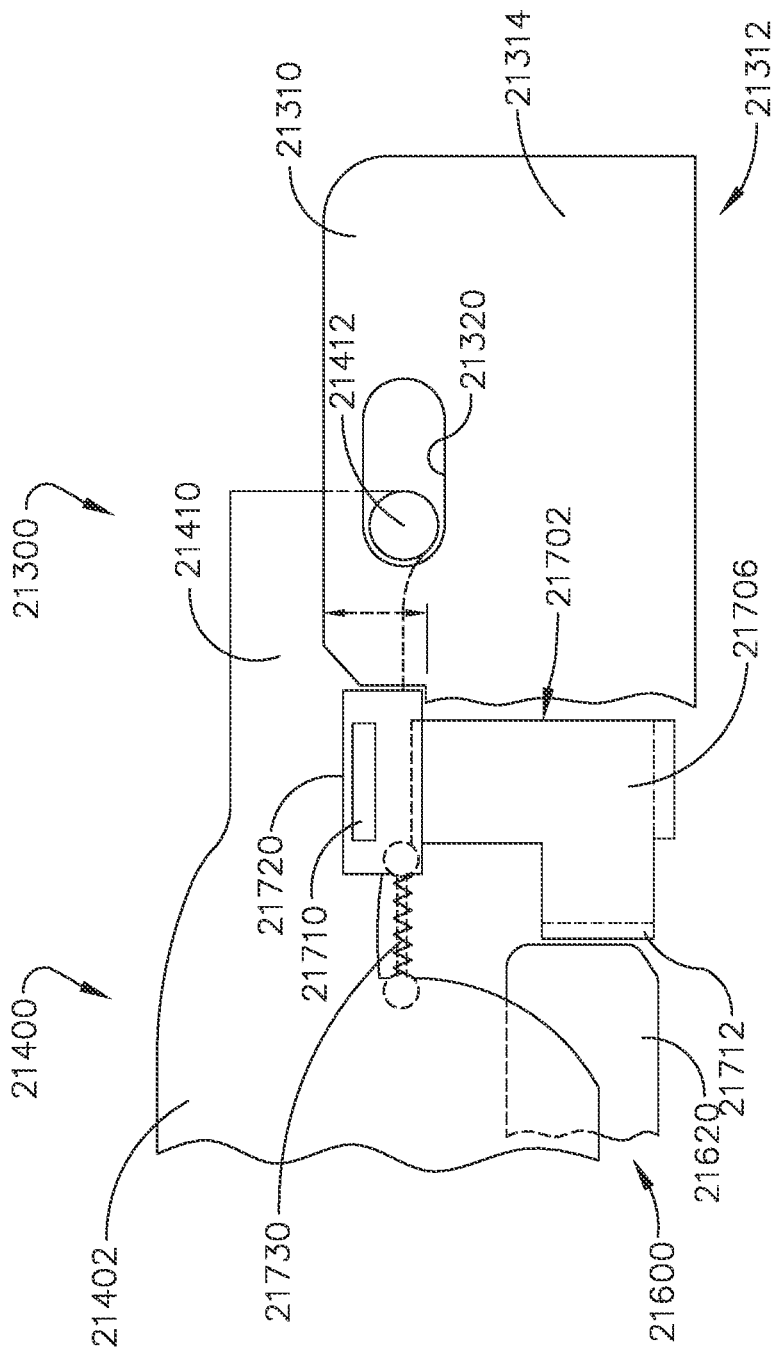
Figures 151, 152:
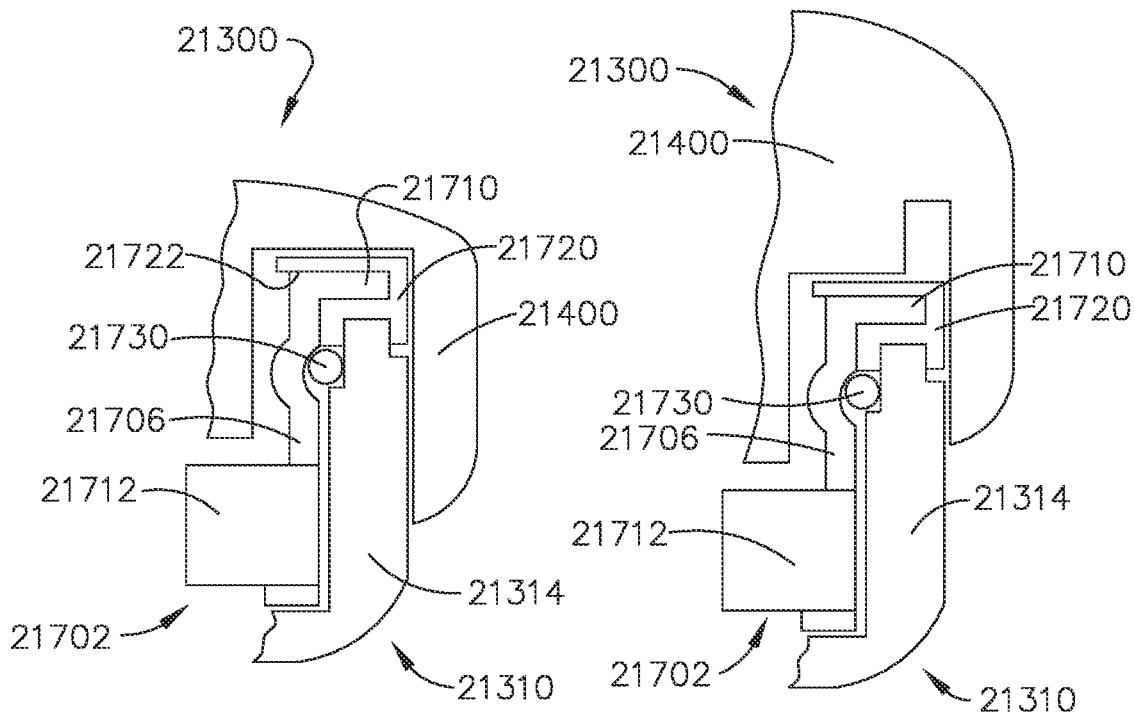
Figure 153:
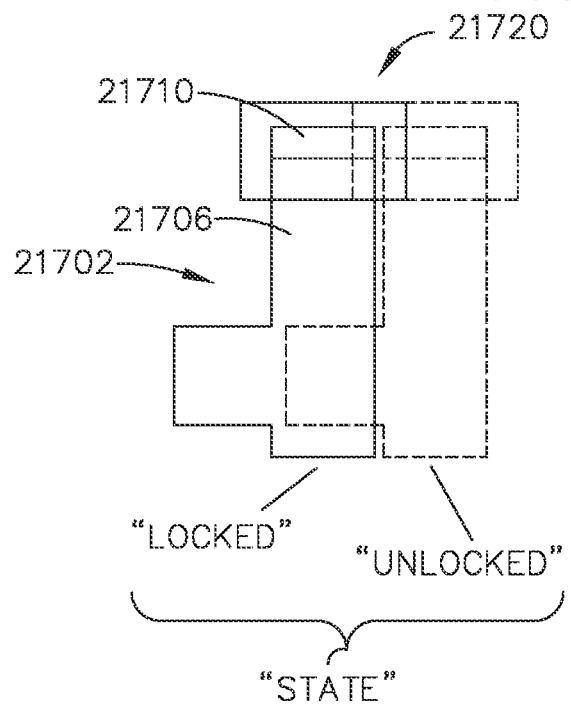
Figure 154:
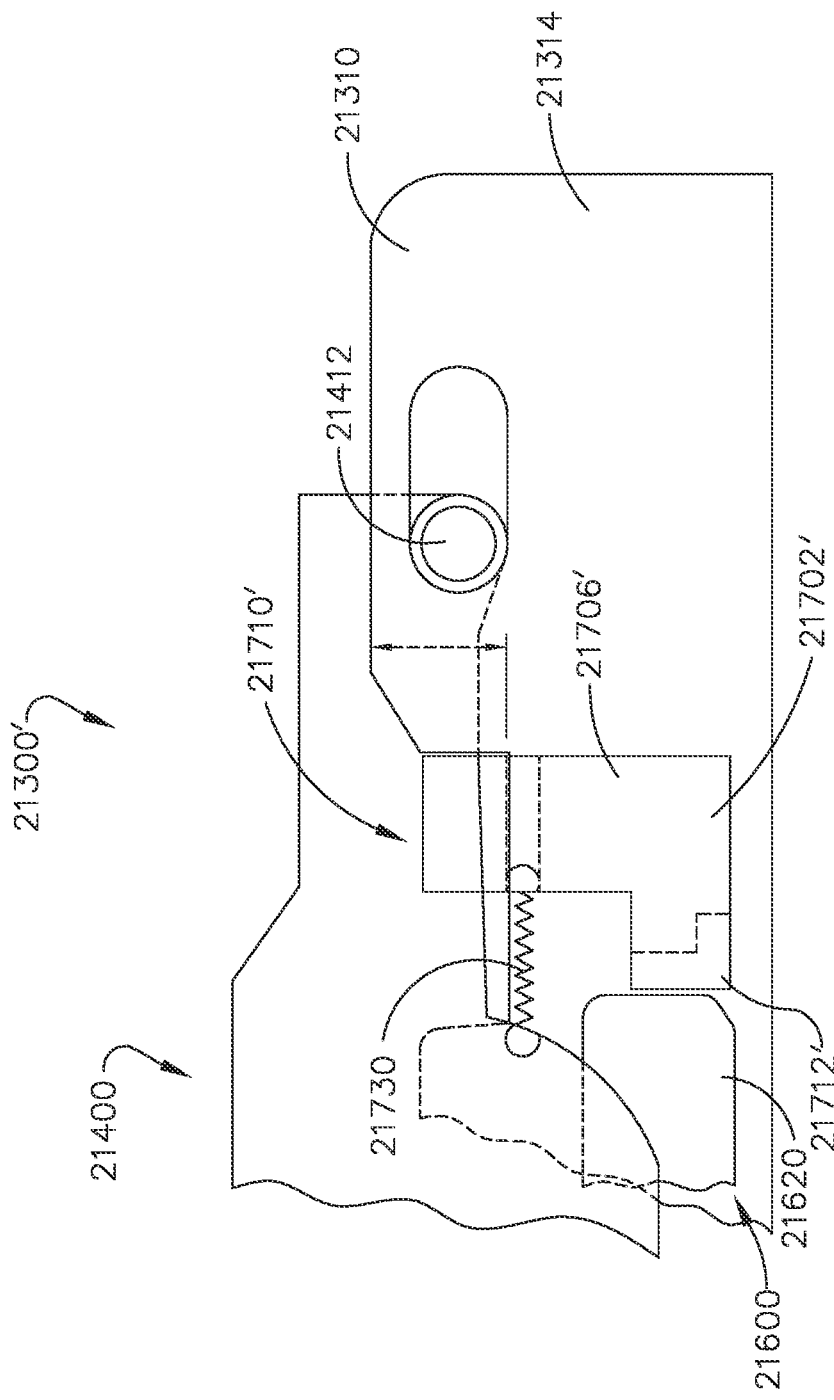
Figure 155:
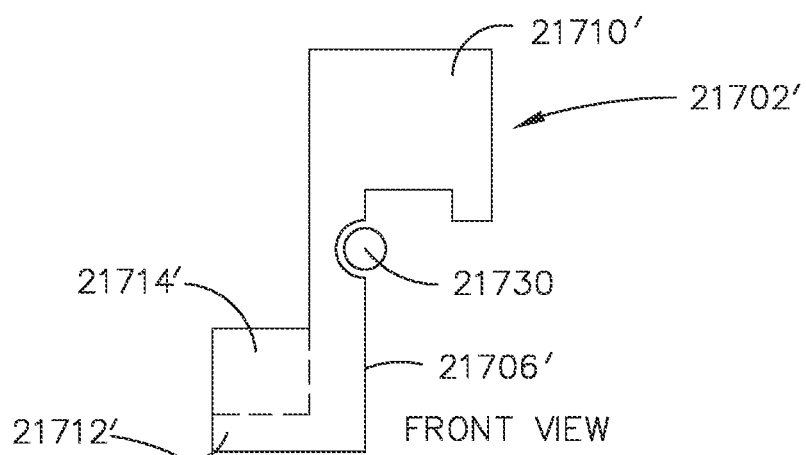
Figure 156:
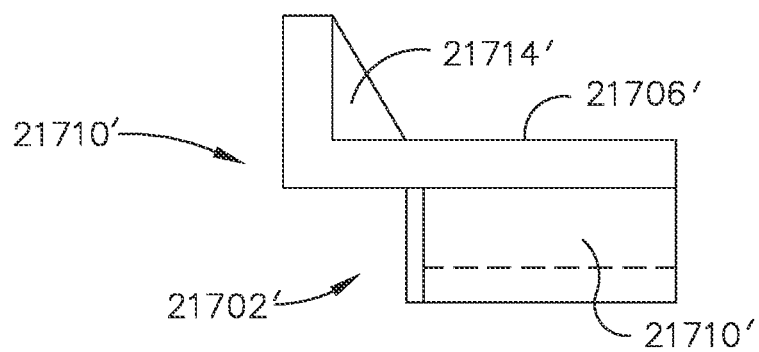
Figure 160:
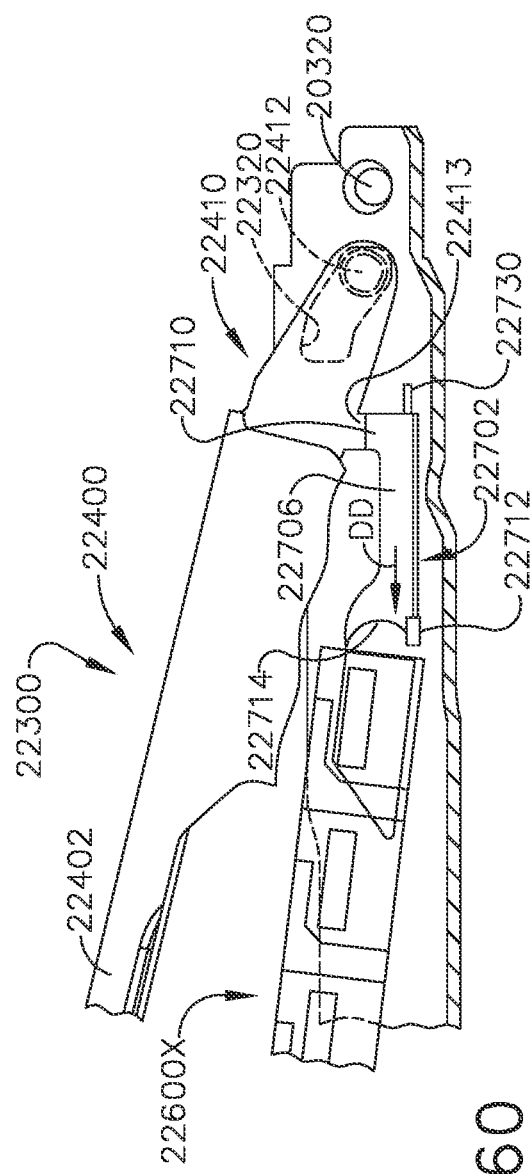
Figure 157:
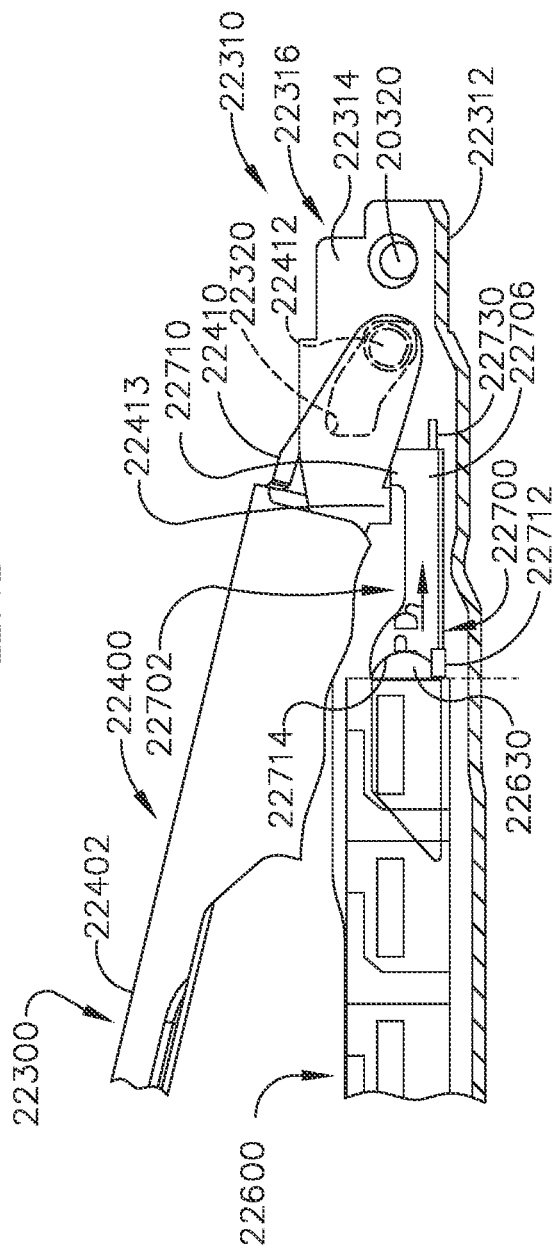
Figure 158:
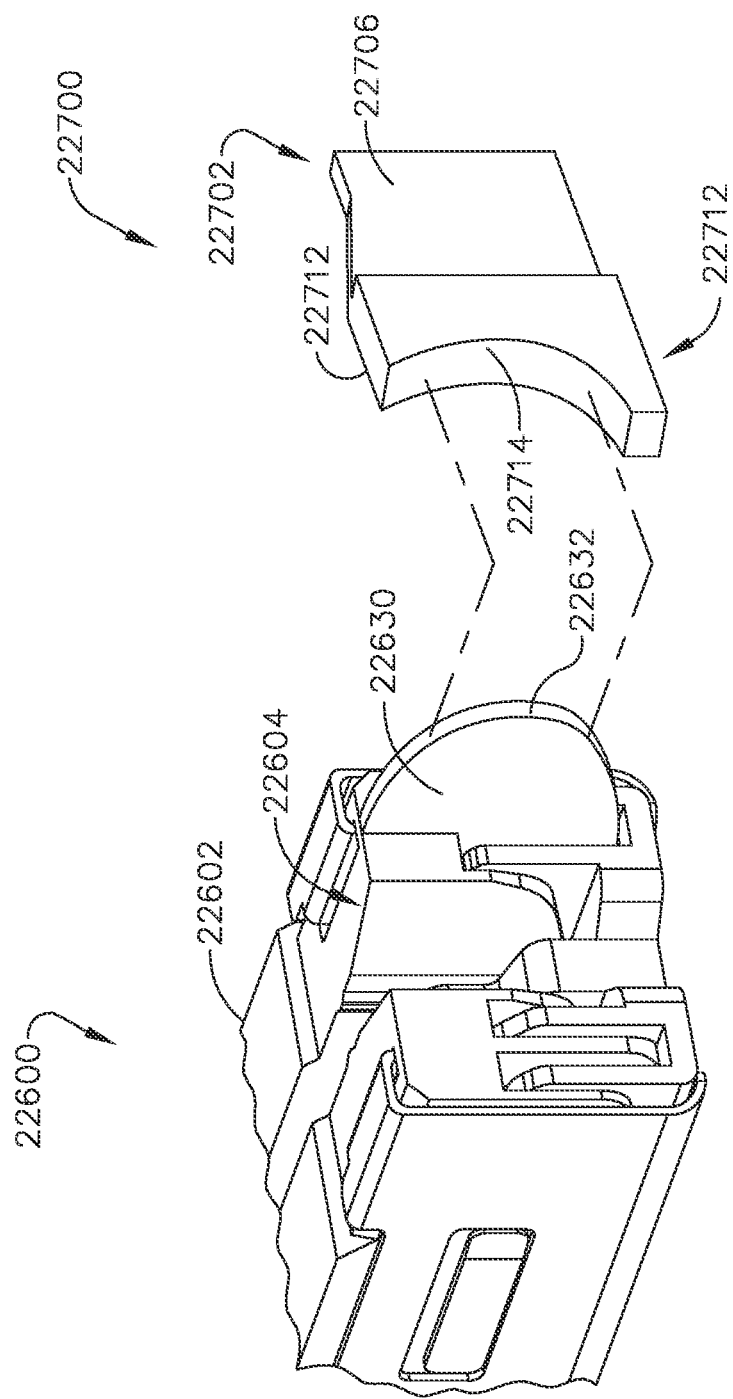
Figure 159:
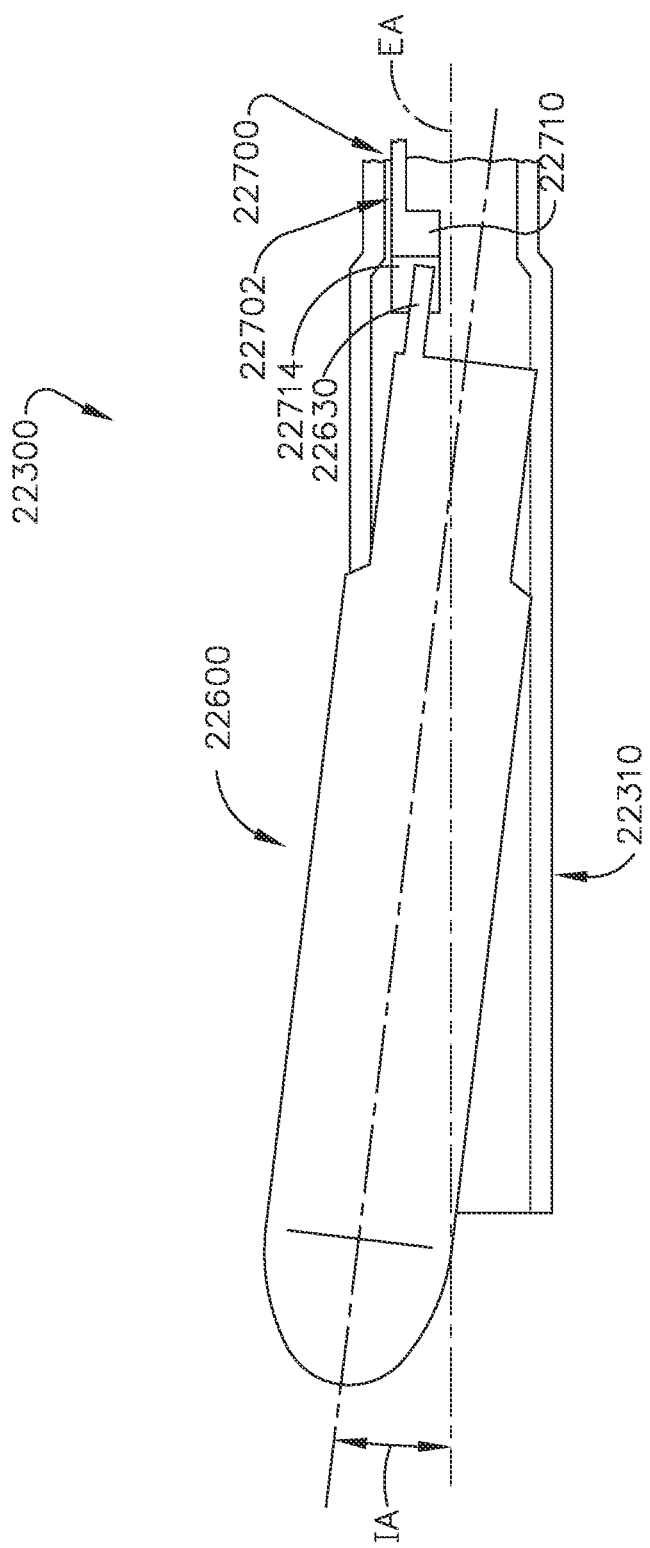
Figure 161:
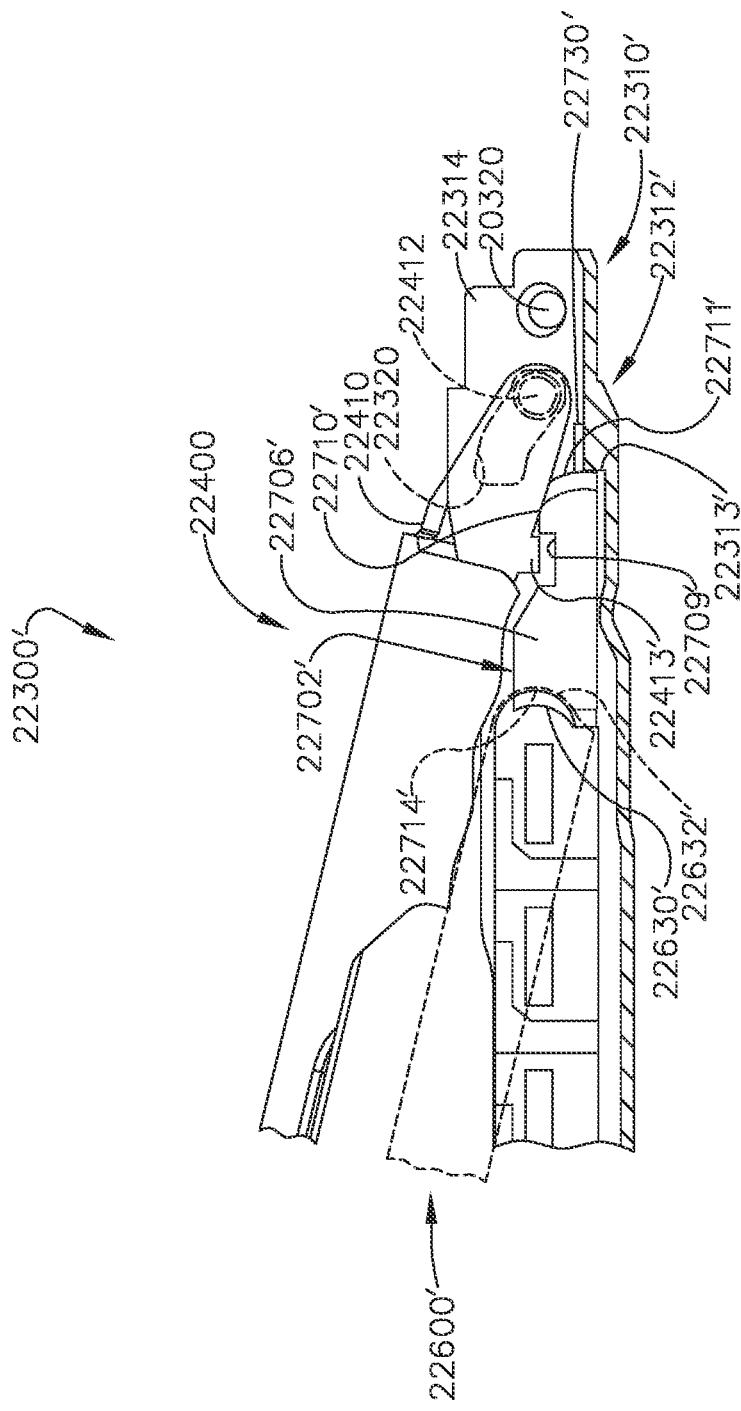
Figure 162:
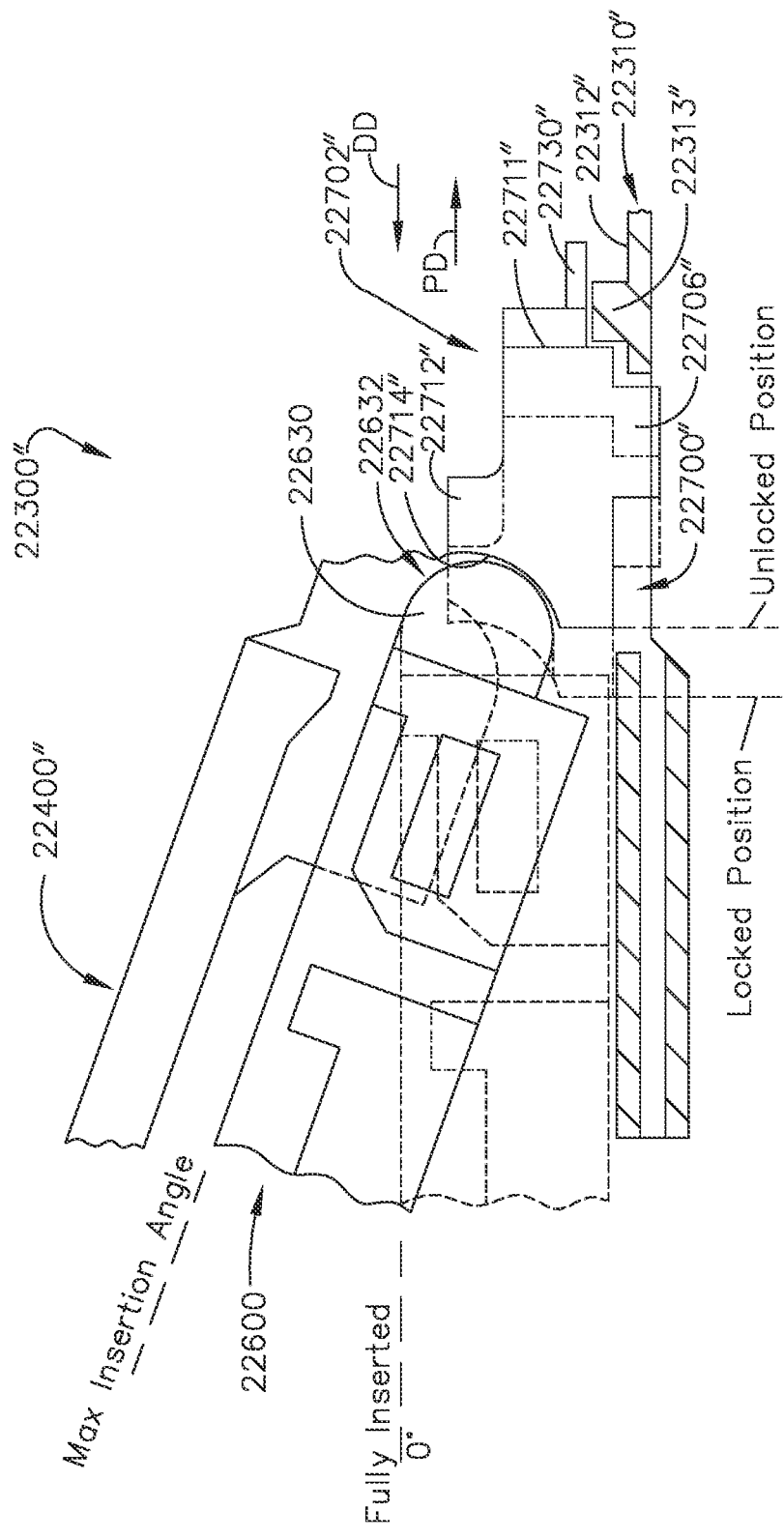
Figure 163:
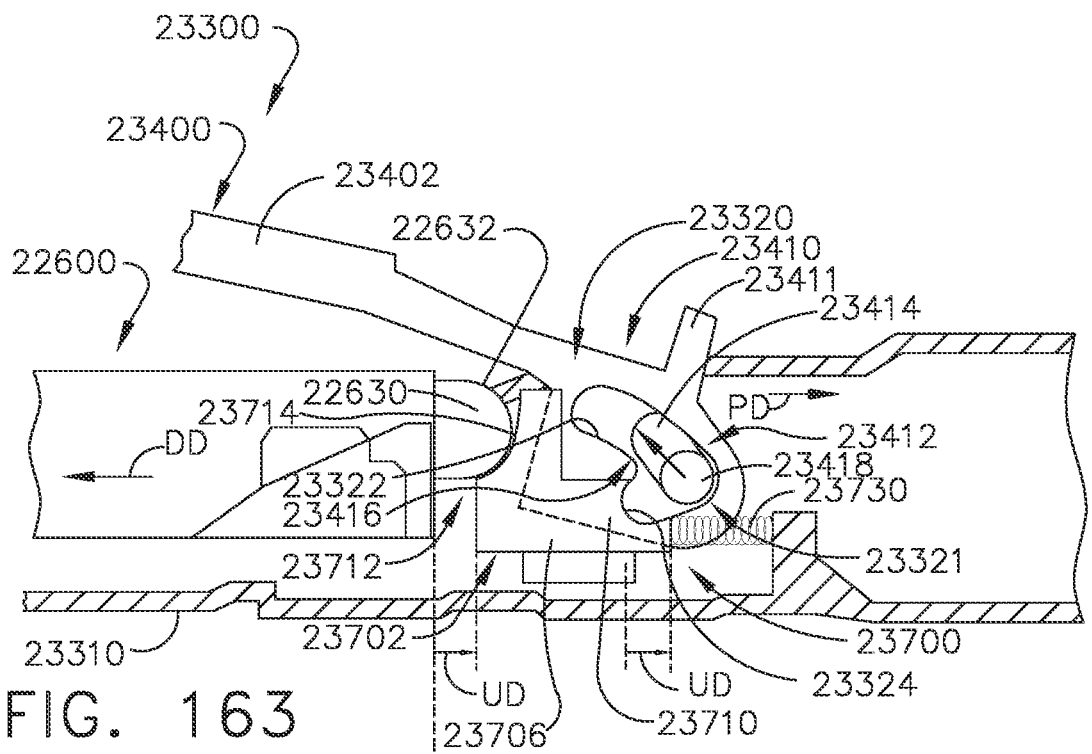
Figure 164:
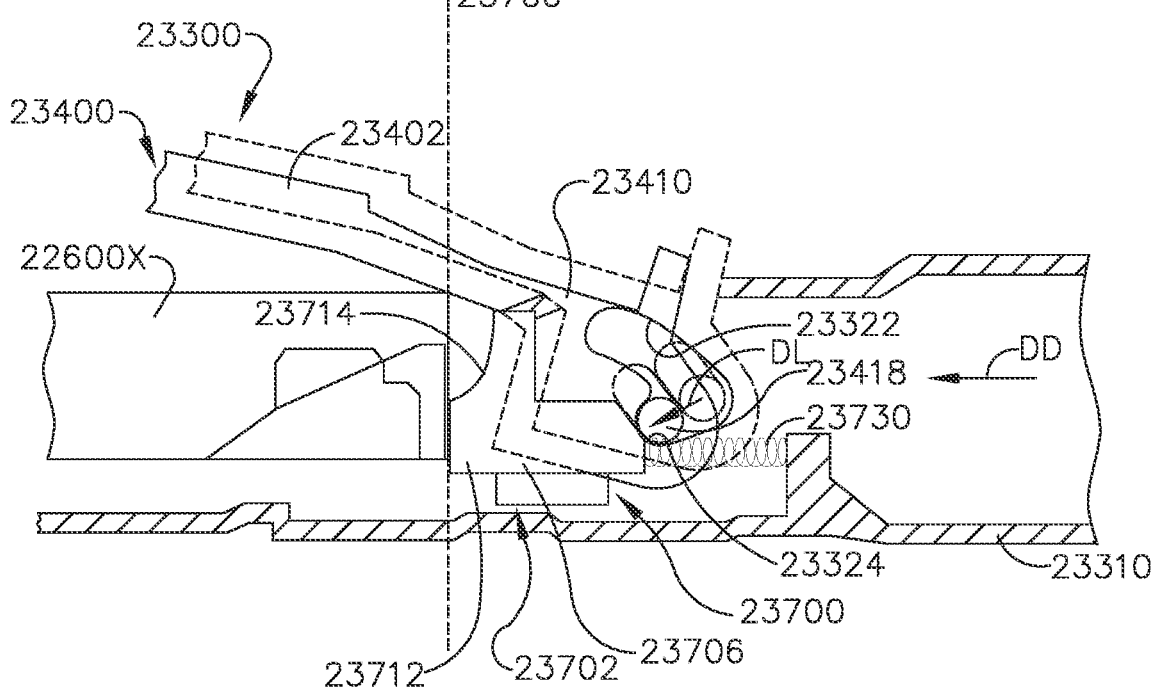
Figure 173:
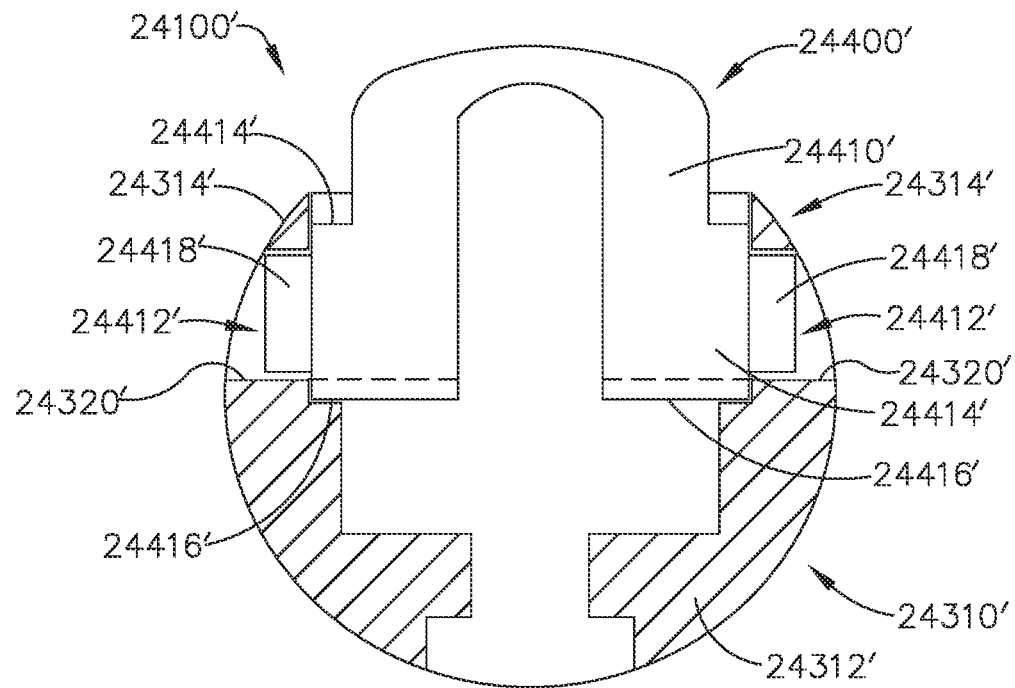
Figure 167:
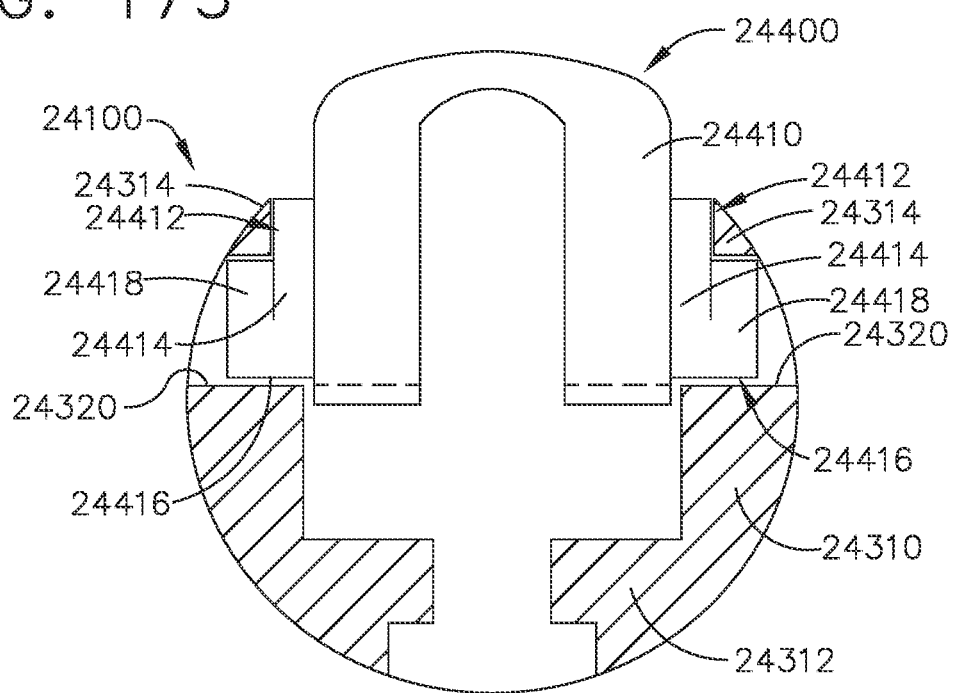
Figure 168:
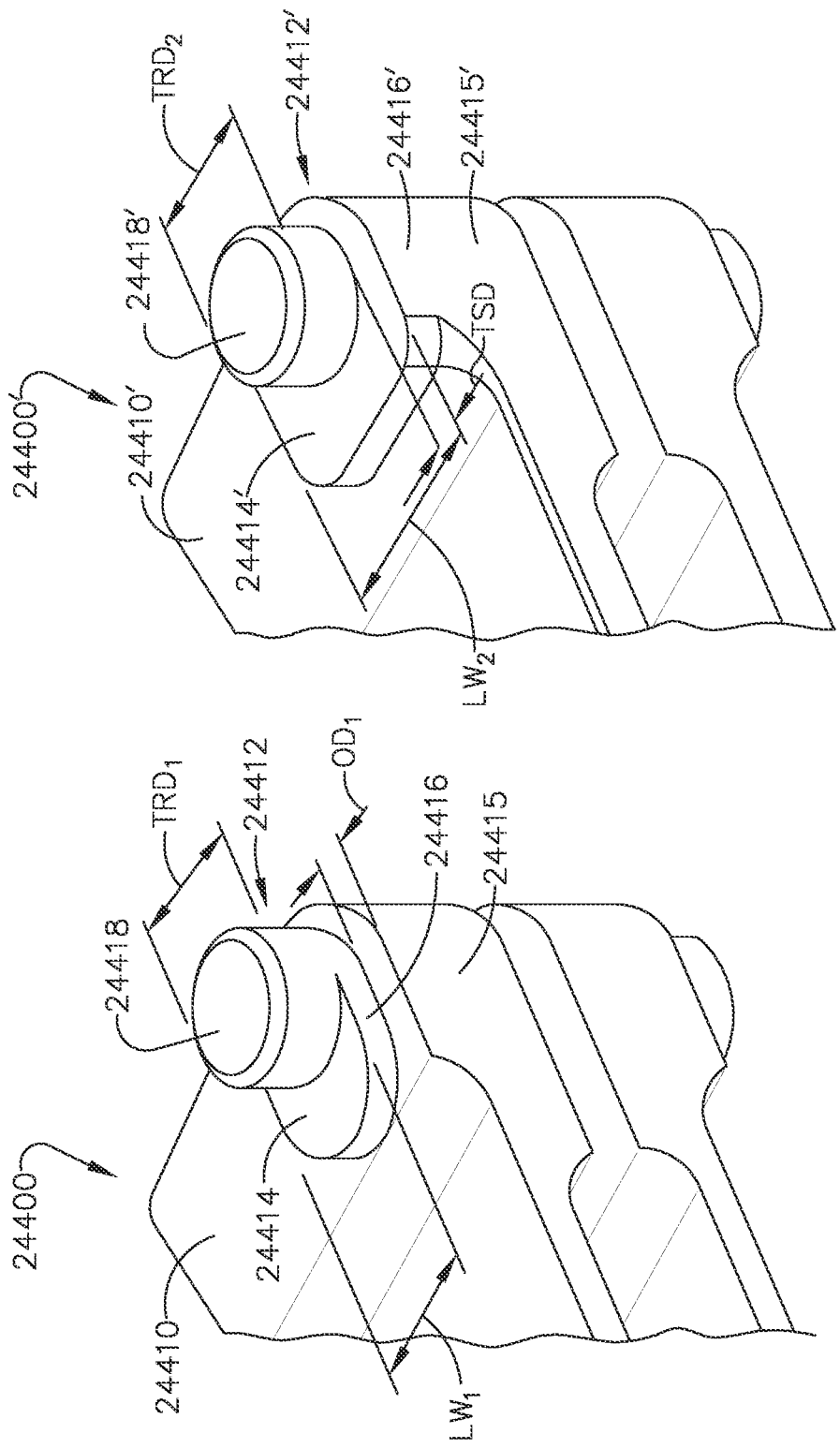
Figure 169:
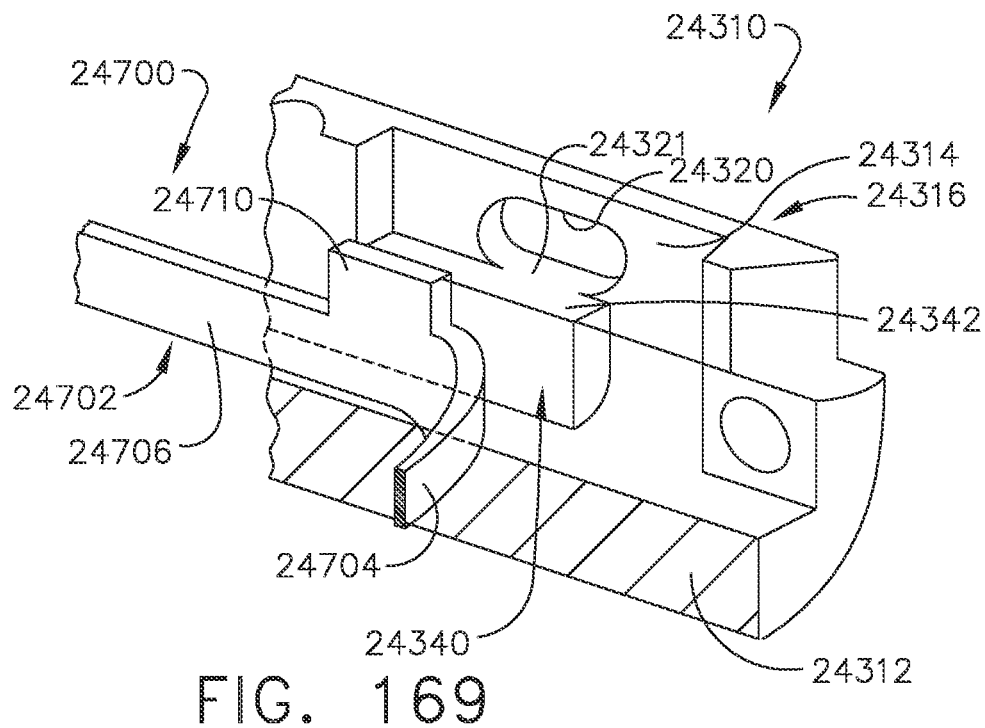
Figure 171:
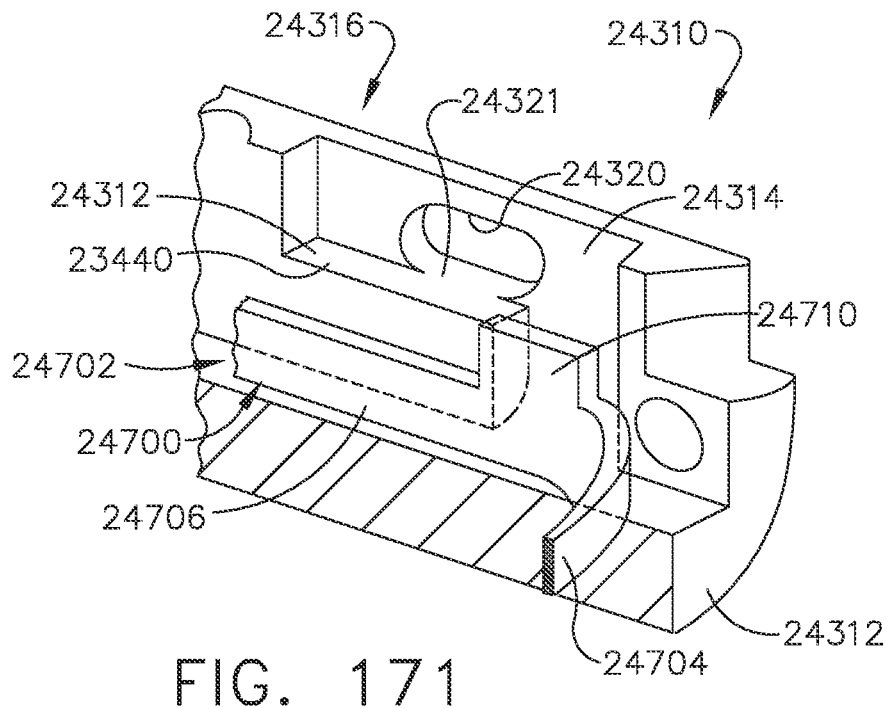
Figure 170:
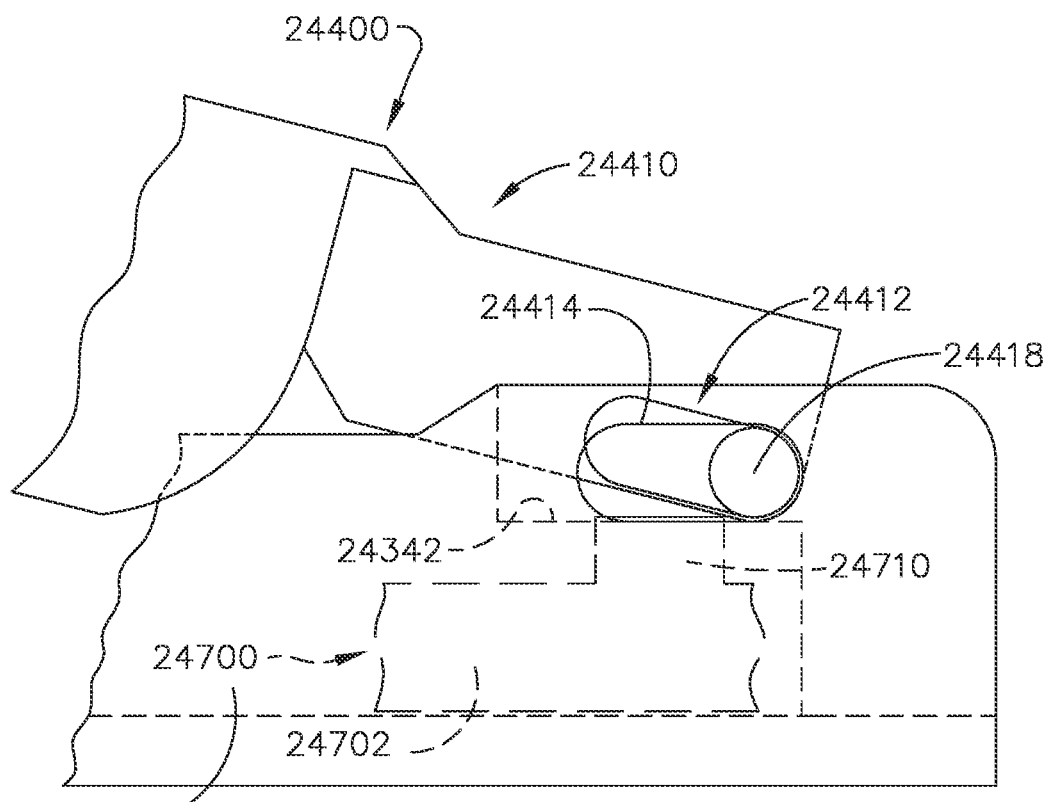
Figure 172:
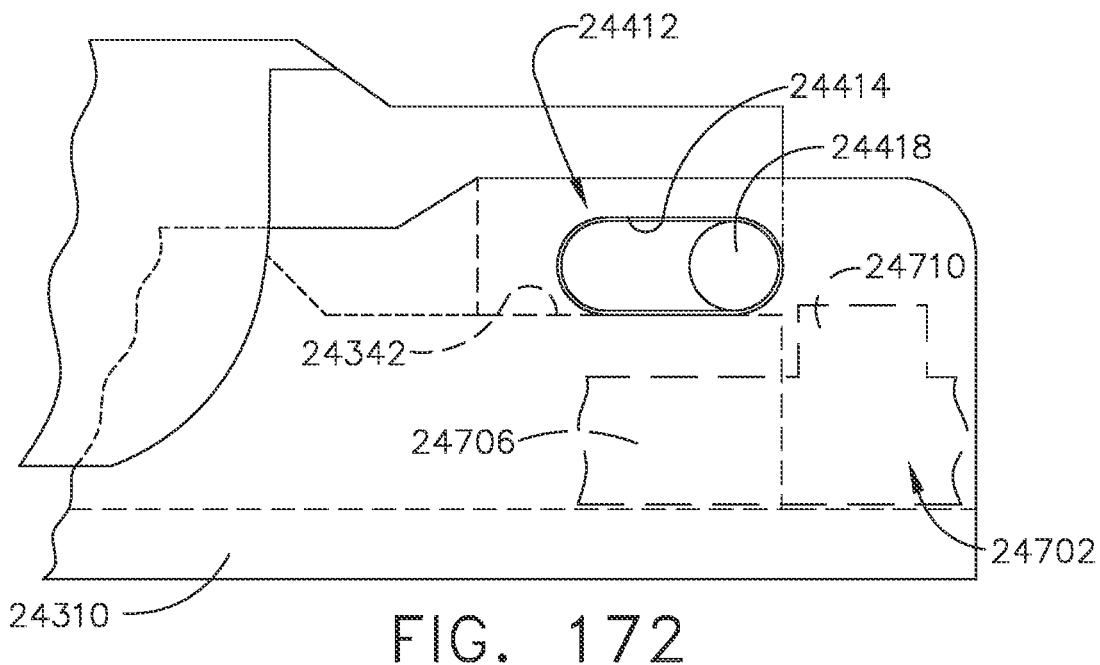
Figure 175:
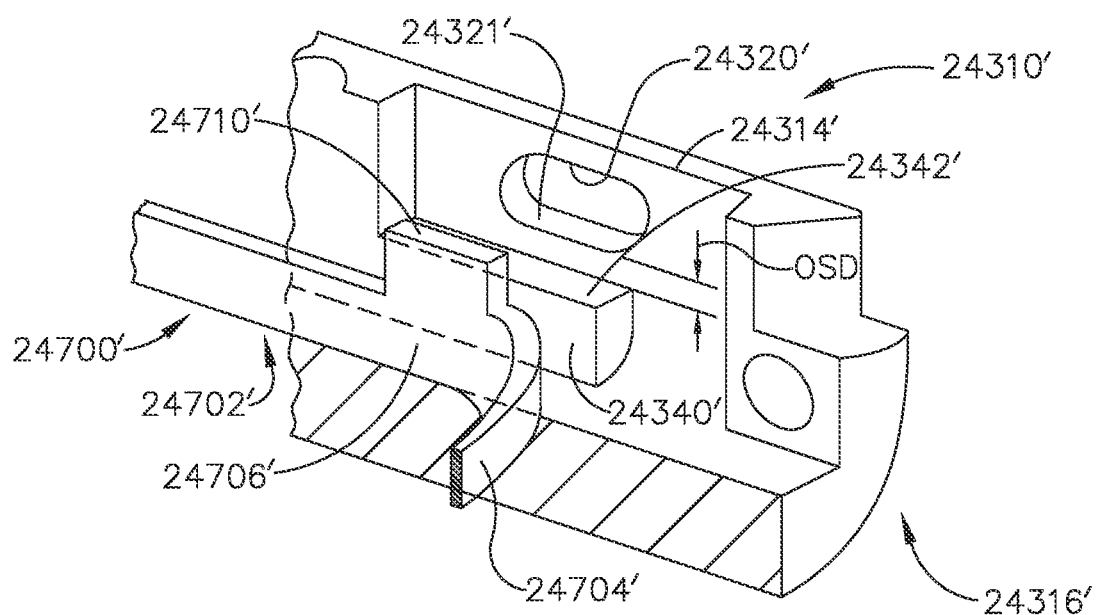
Figure 176:
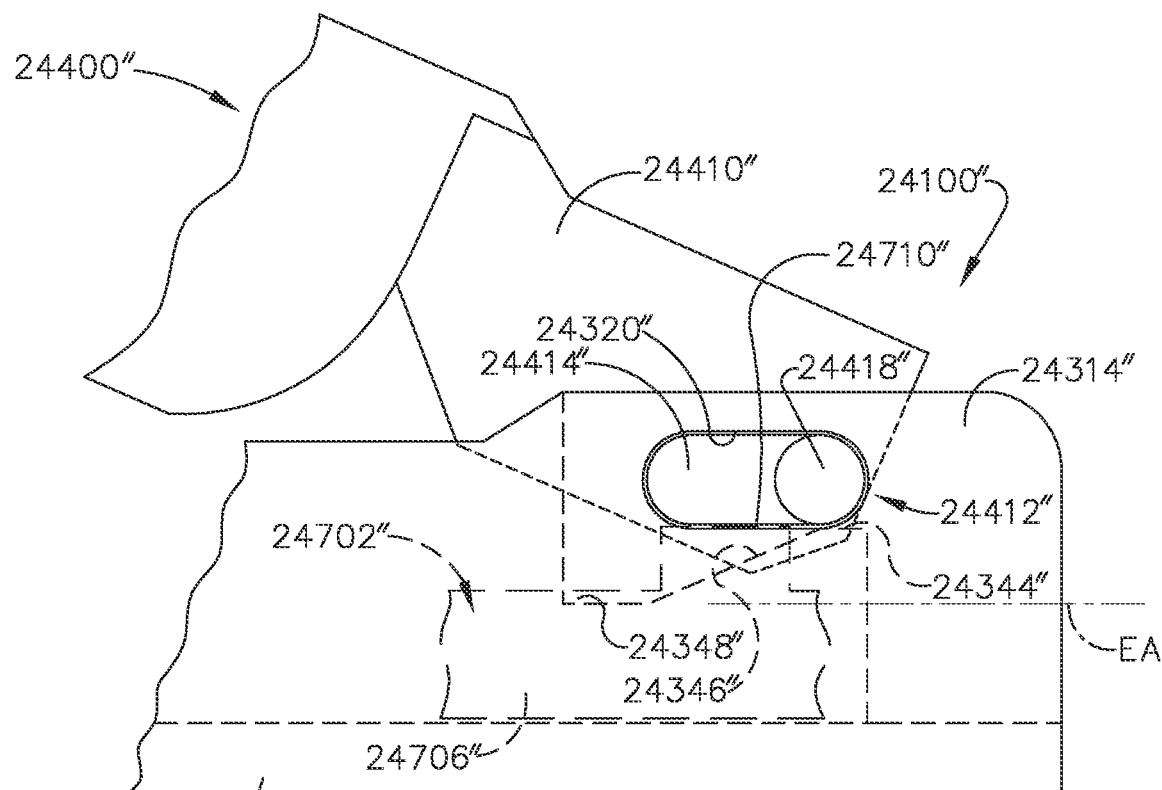
Figure 181:
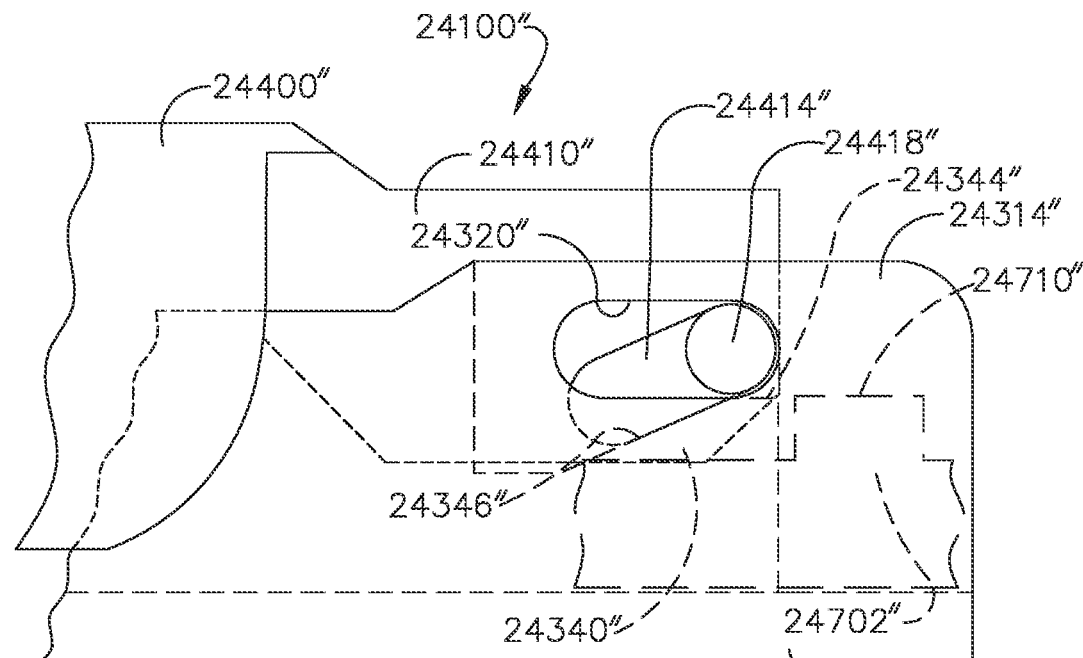
Figure 177:
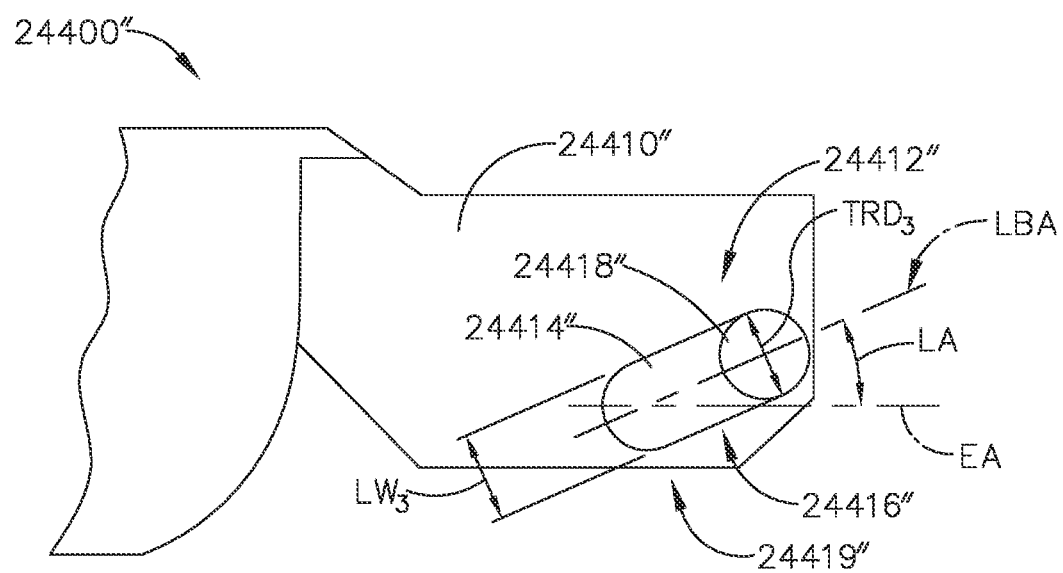
Figures 178, 182:
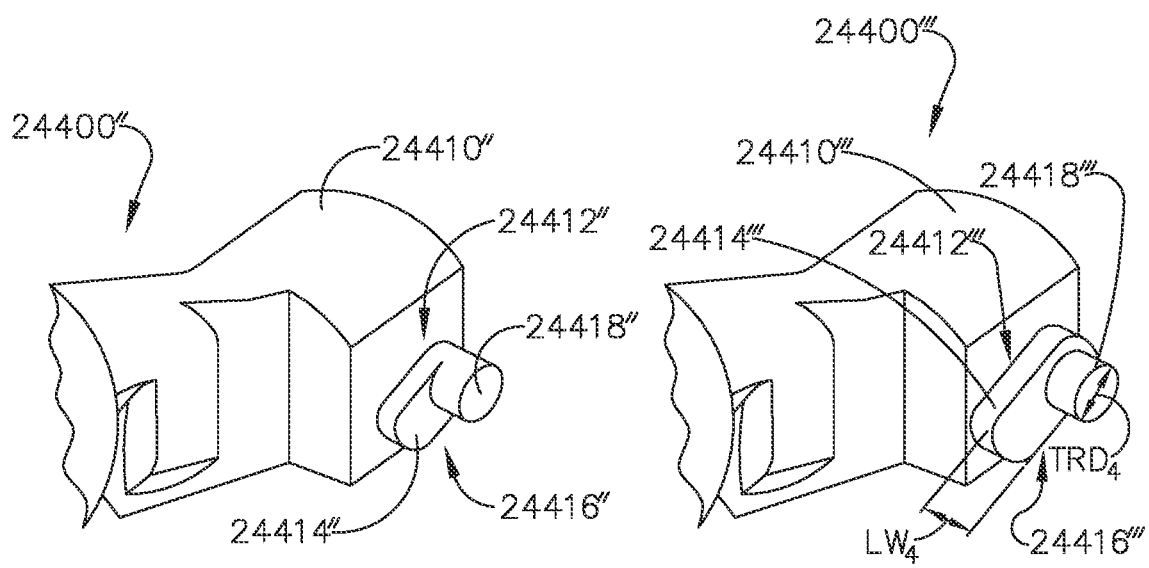
Figure 179:
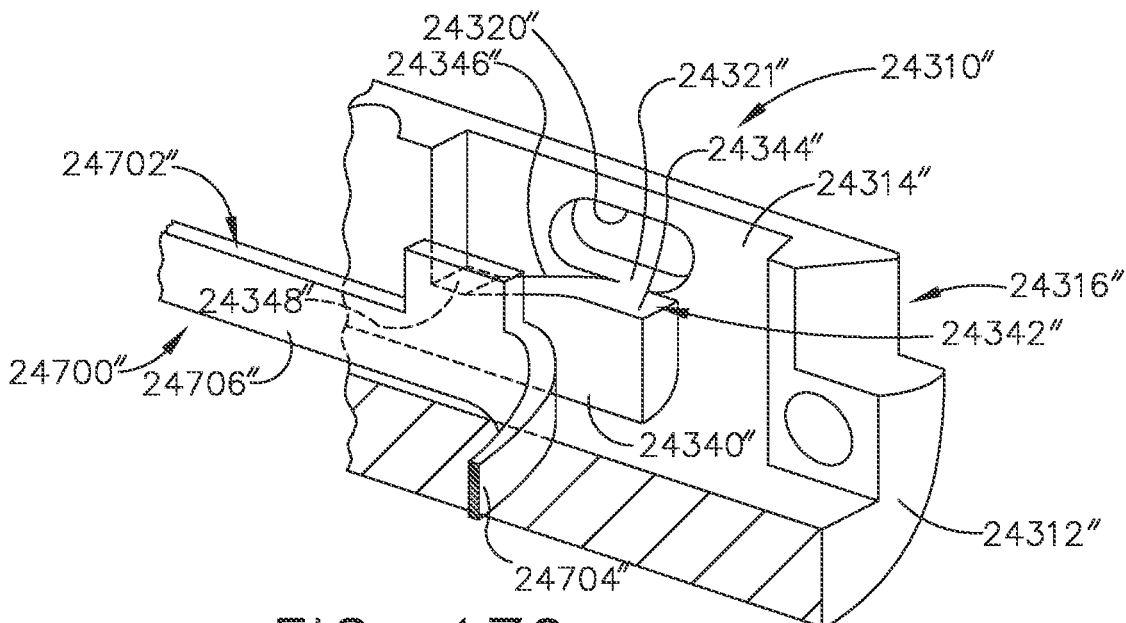
Figure 180:
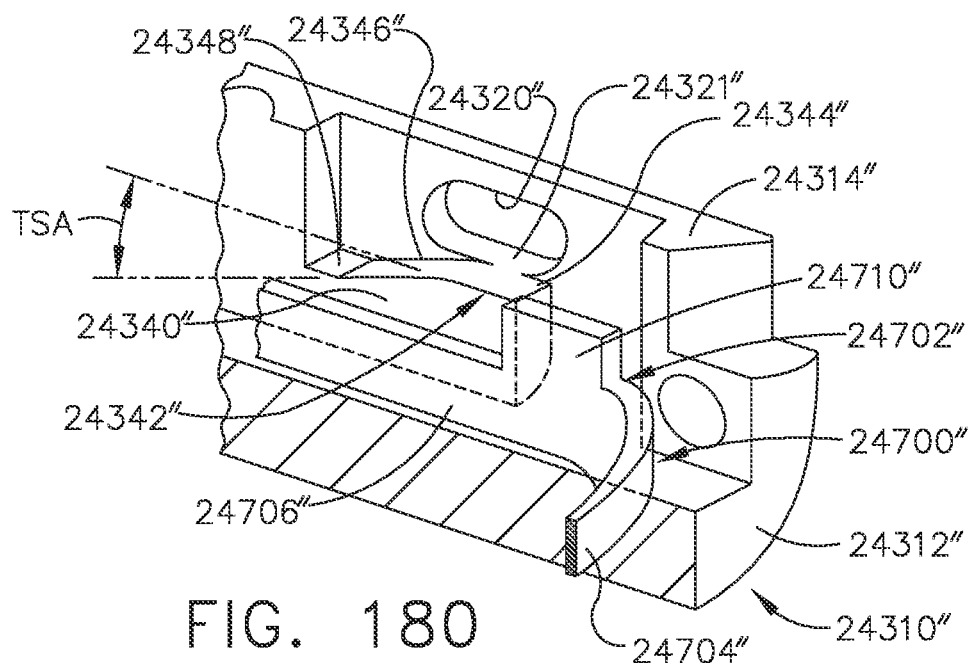
Figure 183:
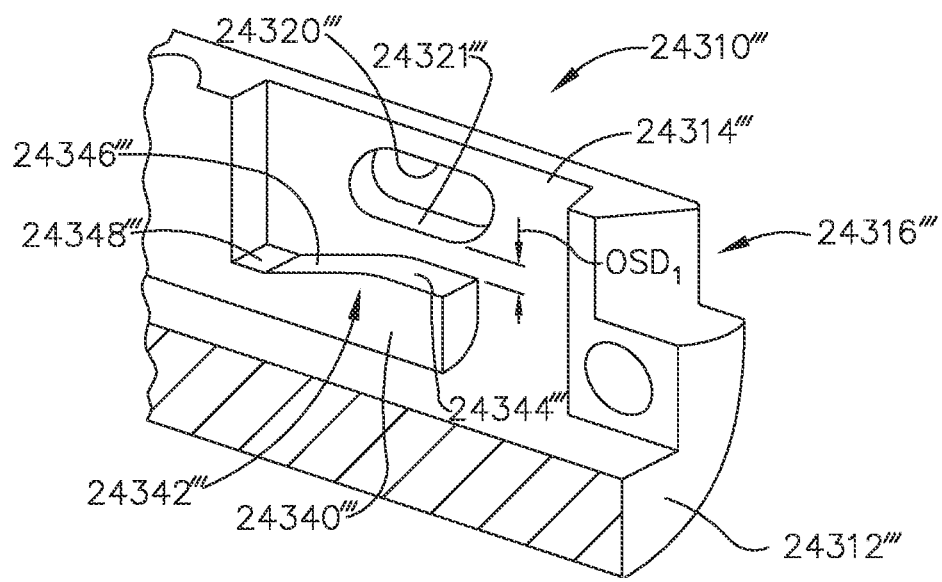
Figure 184:
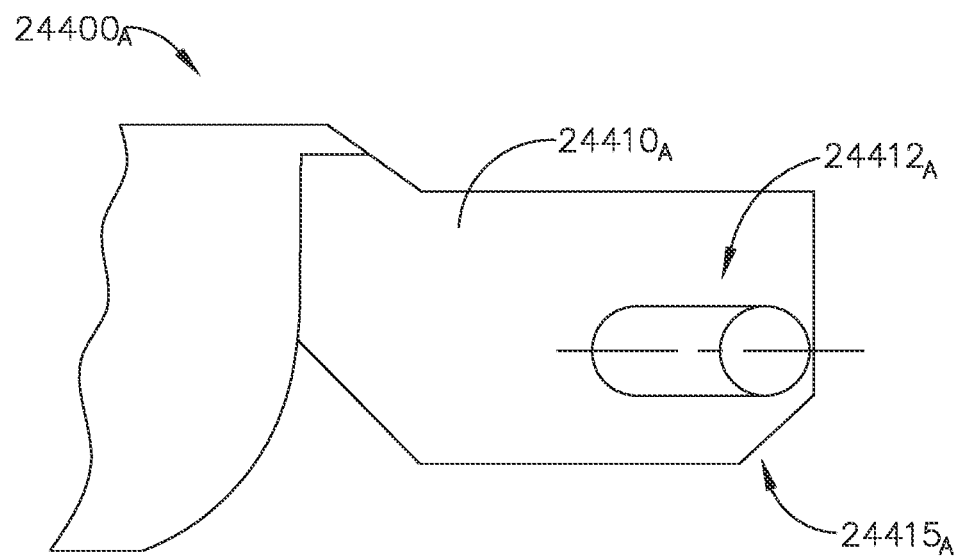
Figures 185, 186:
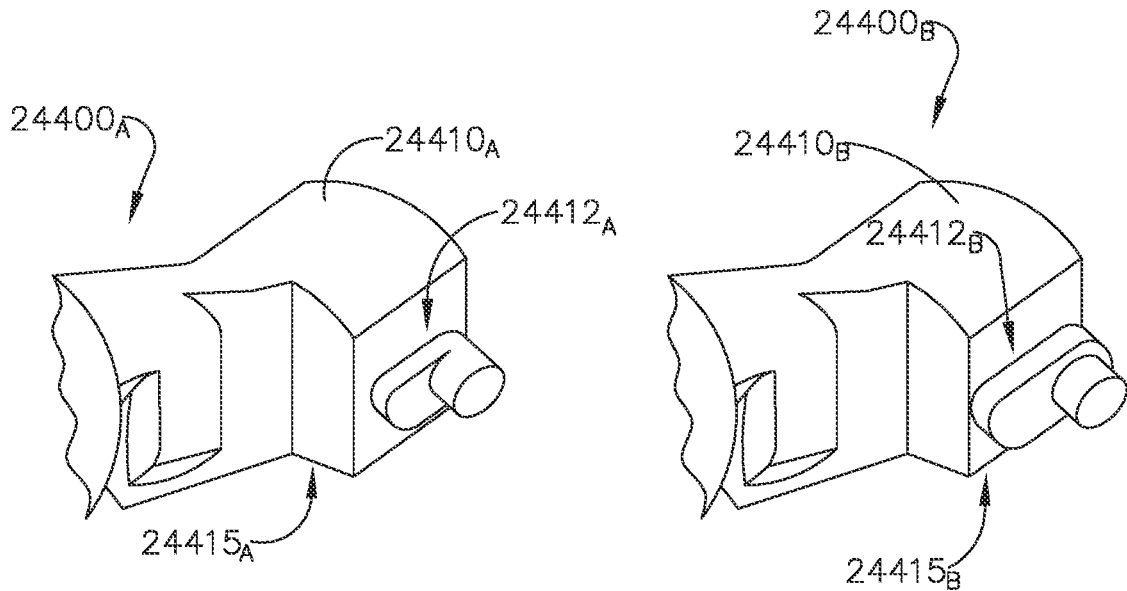
Figure 187:
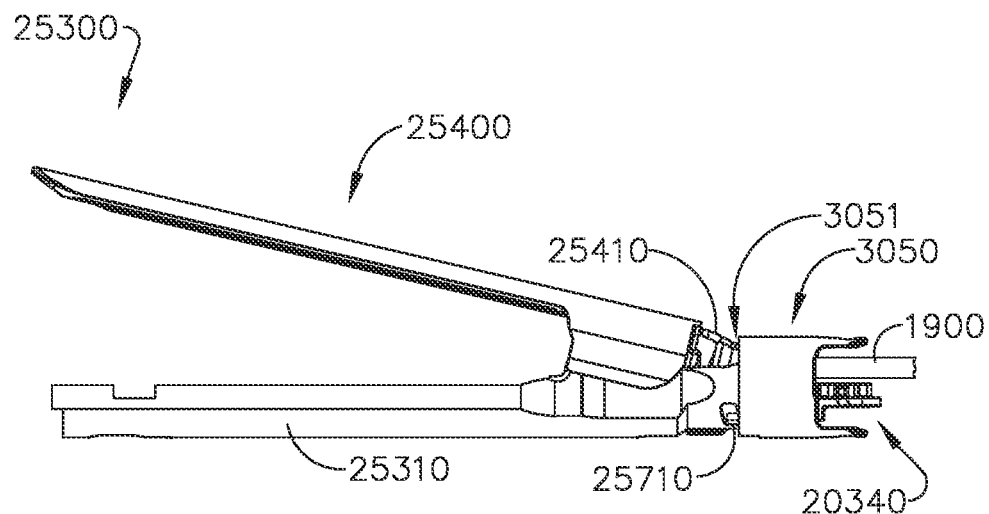
Figure 188:
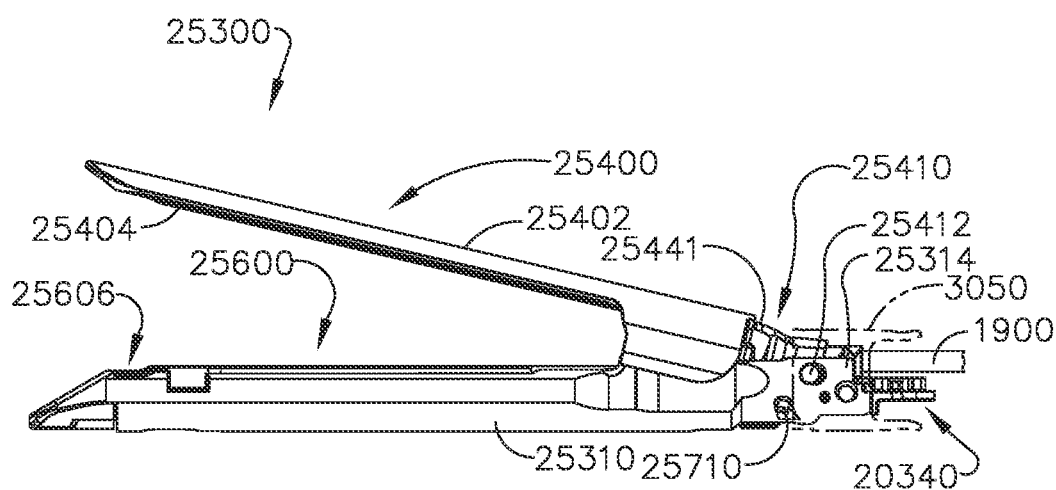
Figure 189:
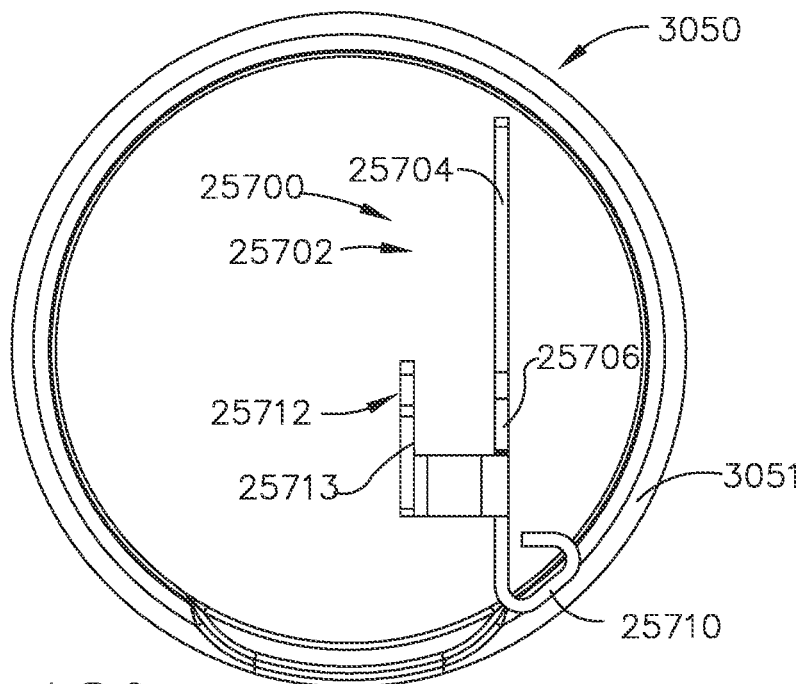
Figure 190:
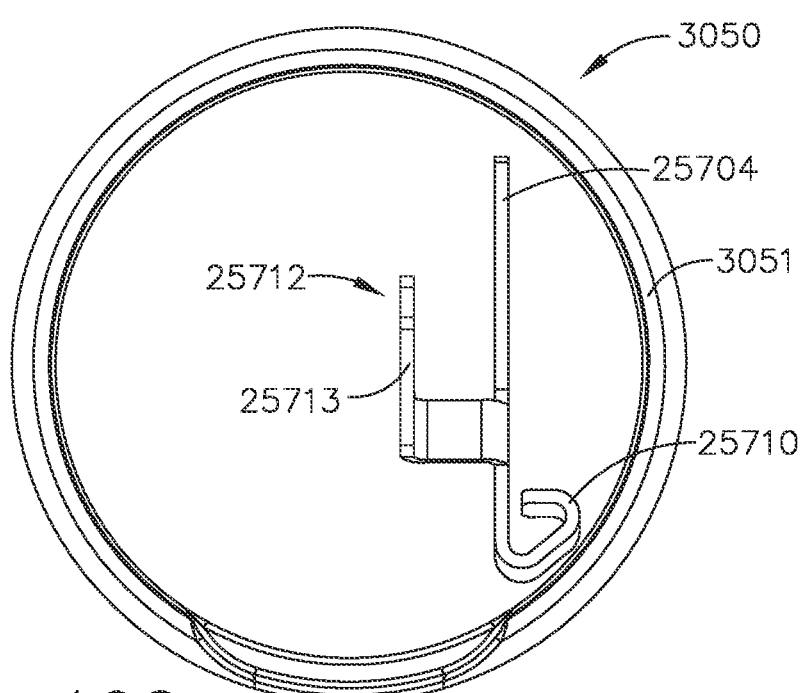
Figure 191:
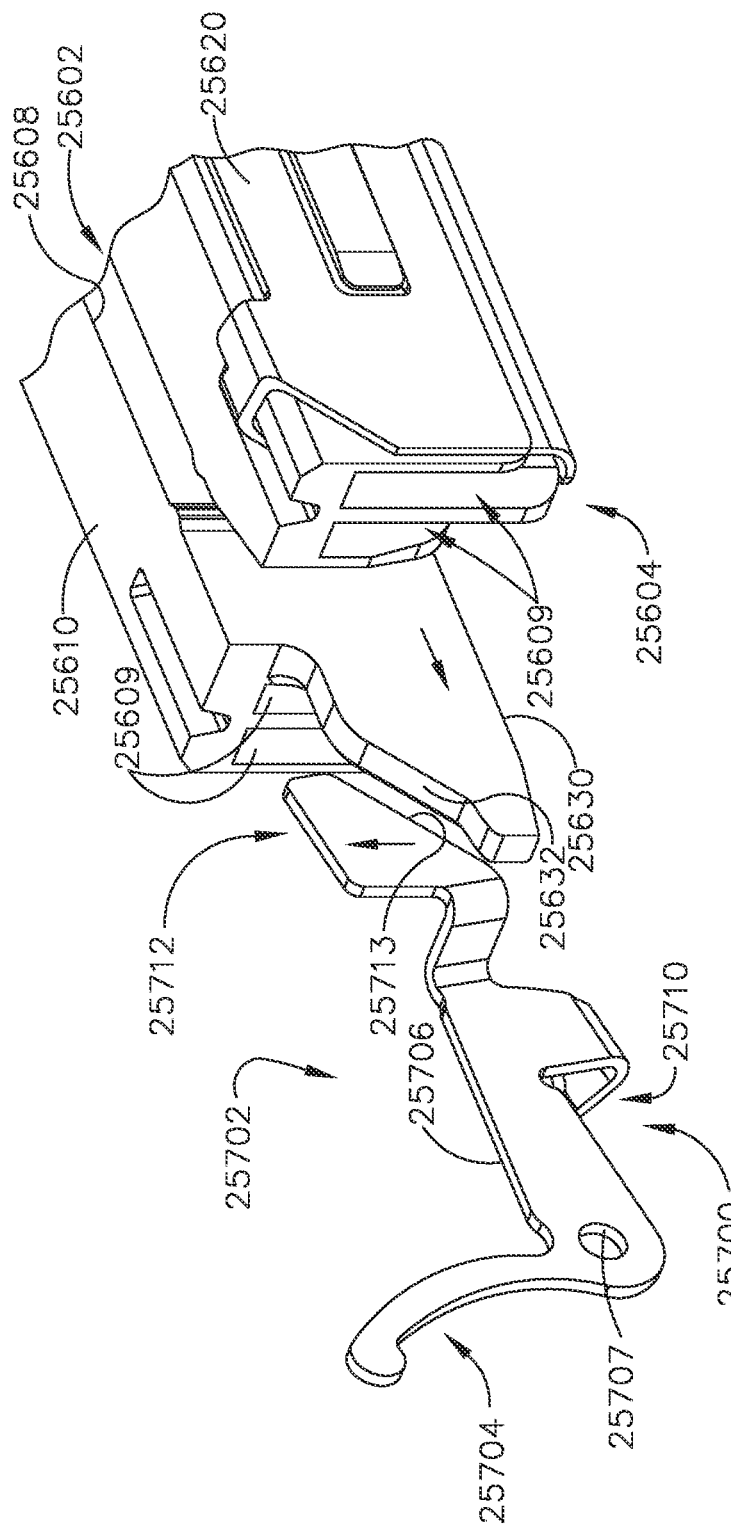
Figure 192:
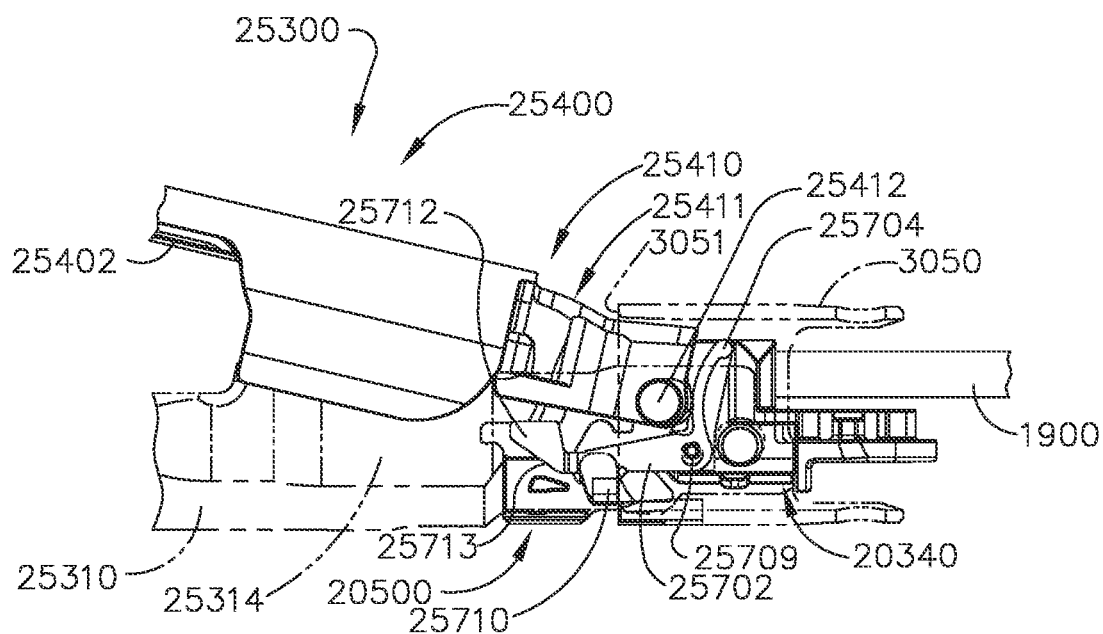
Figure 193:
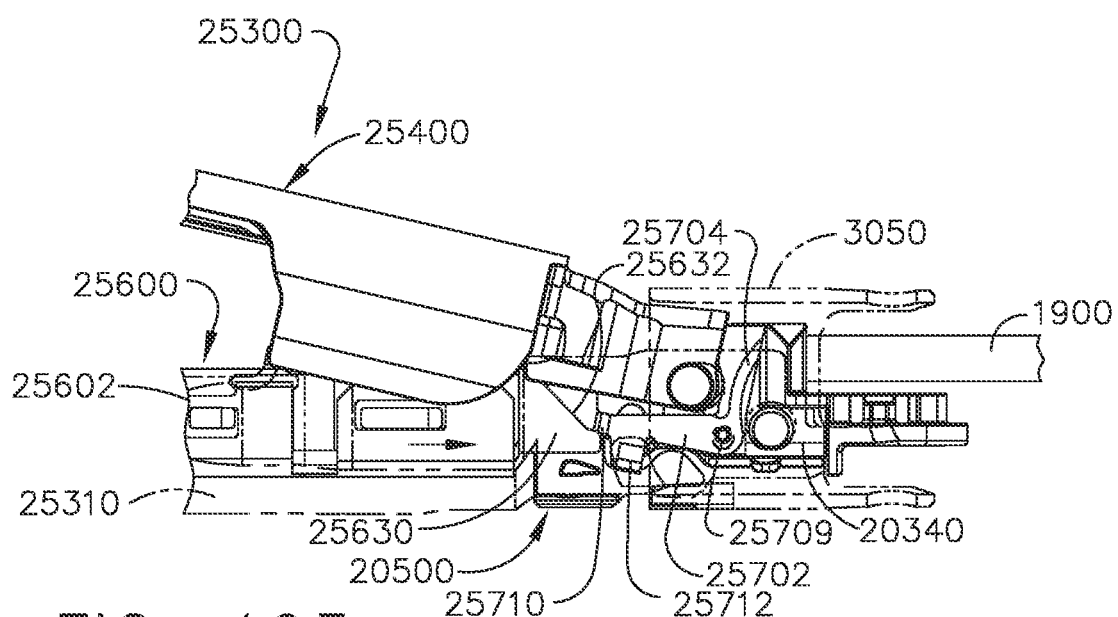
Figure 194:
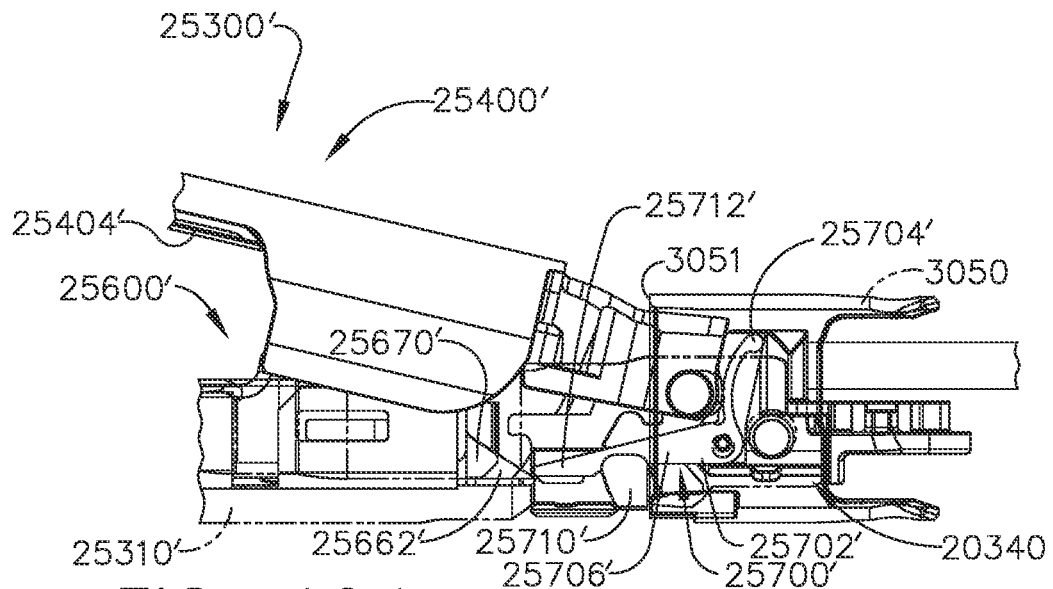
Figure 195:
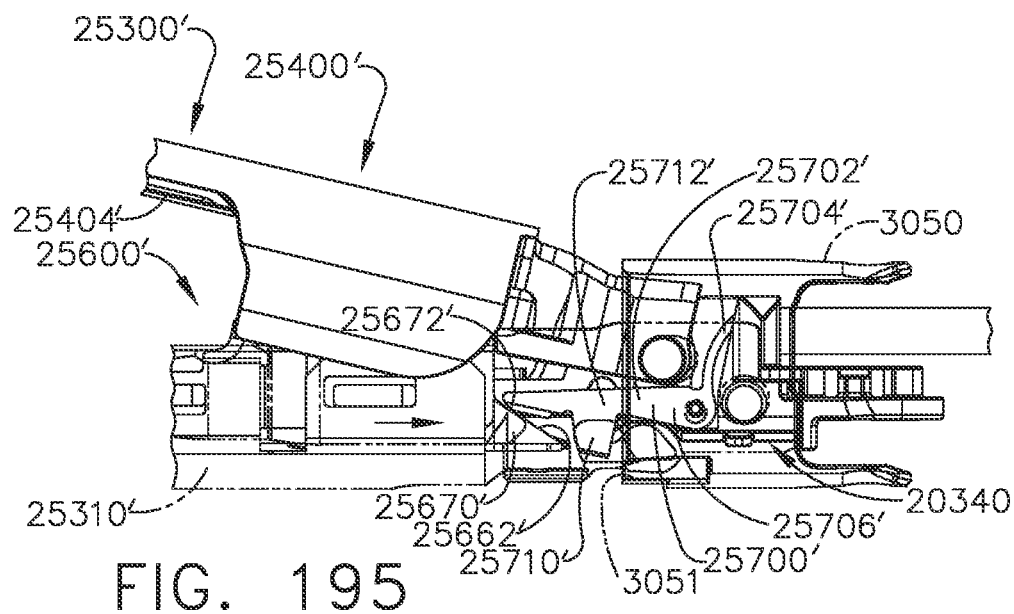
Figure 196:
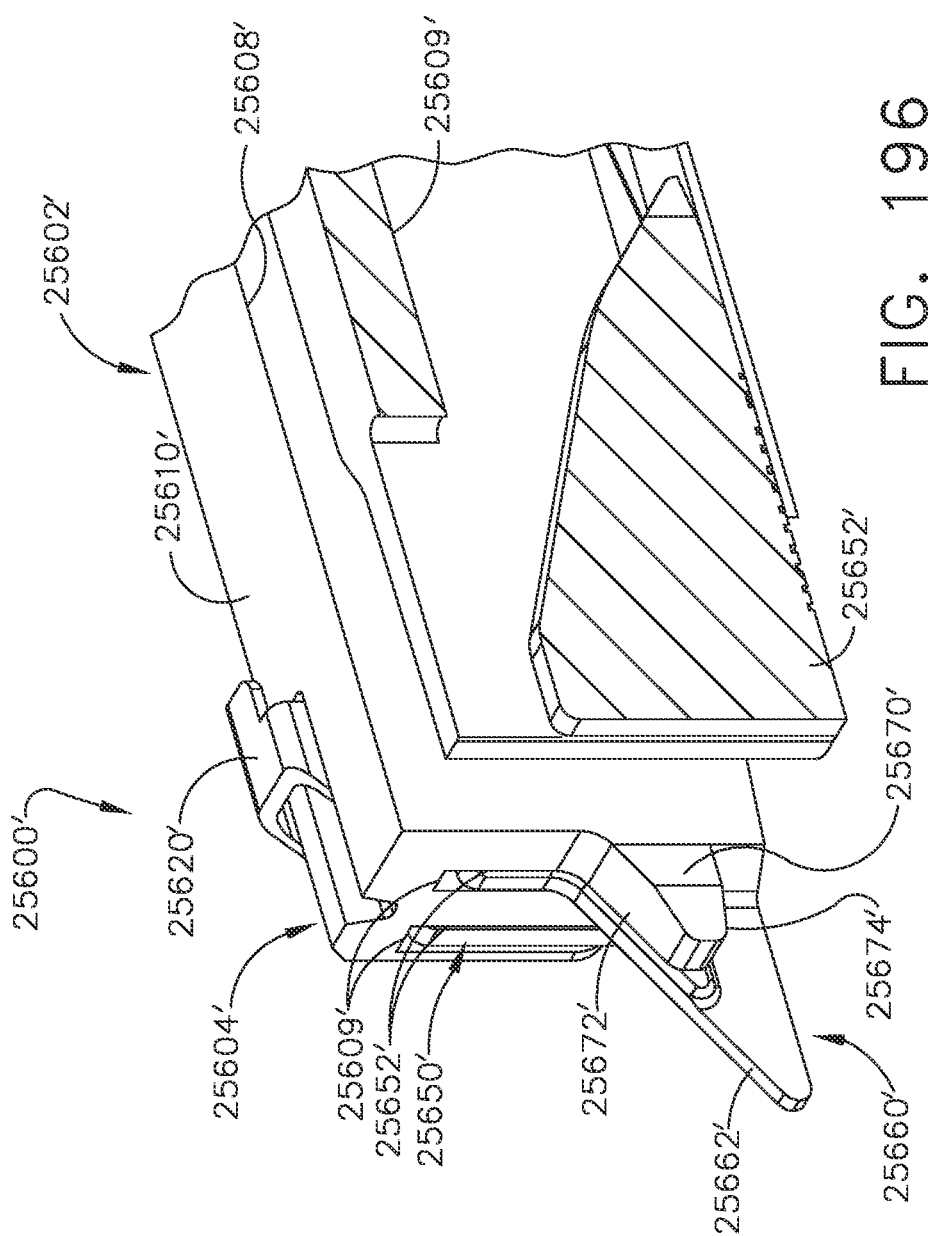
Figure 197:
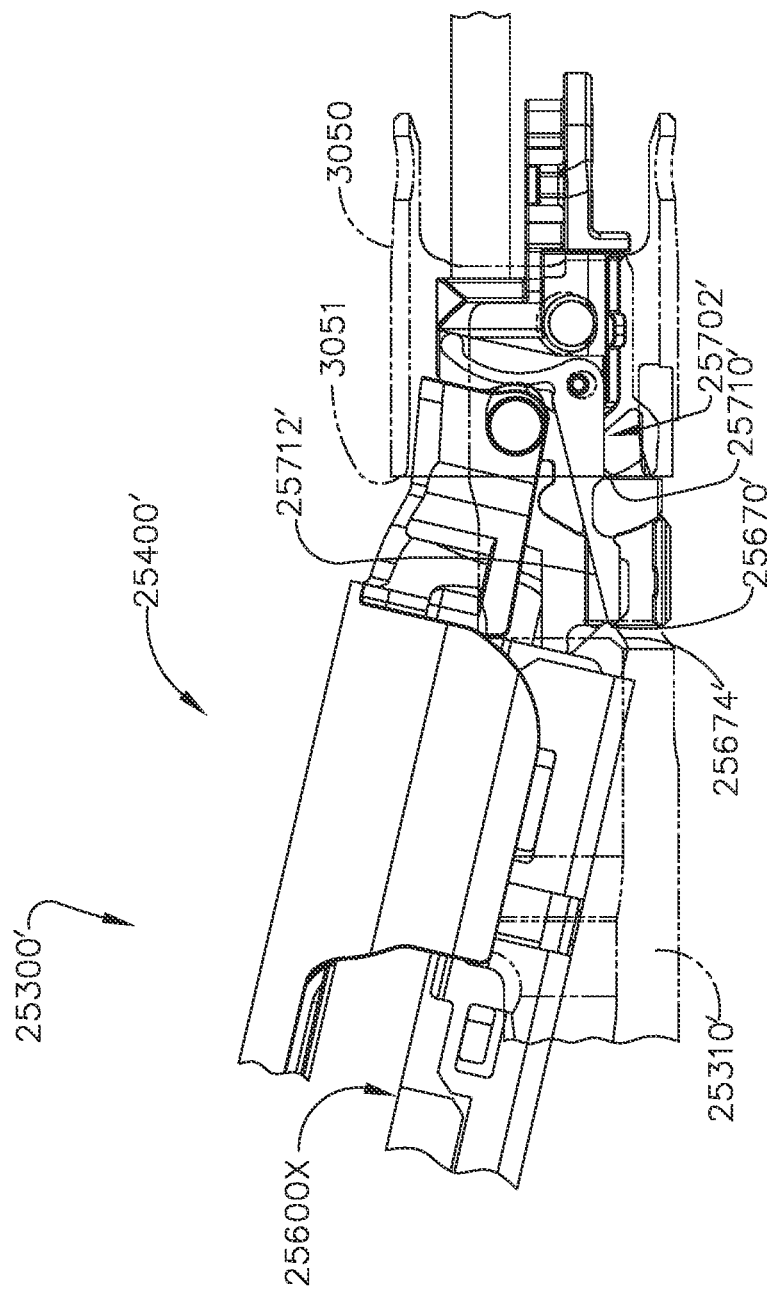
Figure 198:
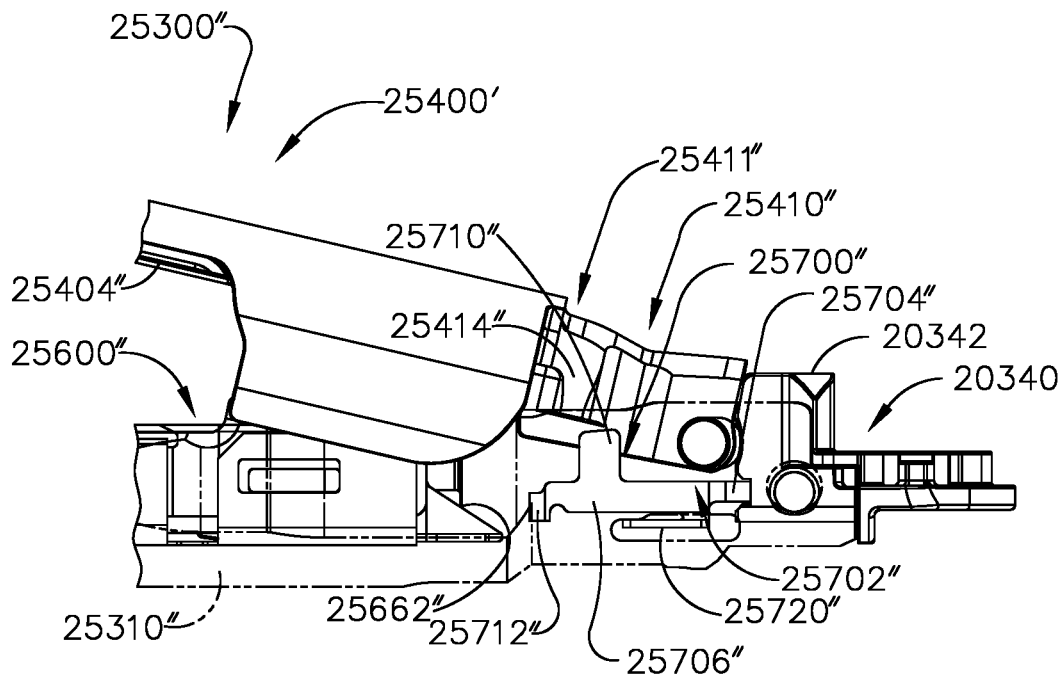
Figure 199:
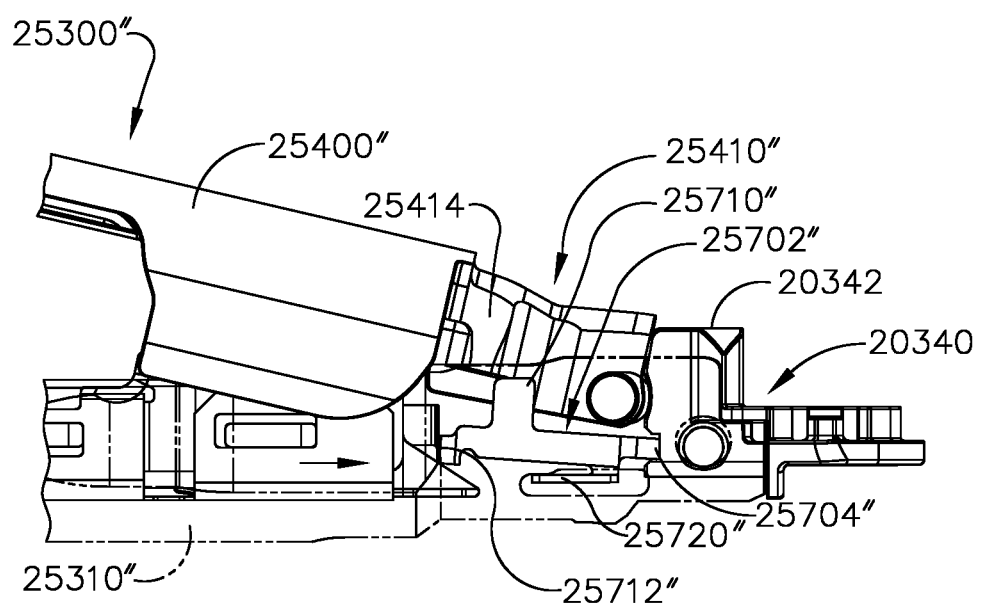
Figure 200:
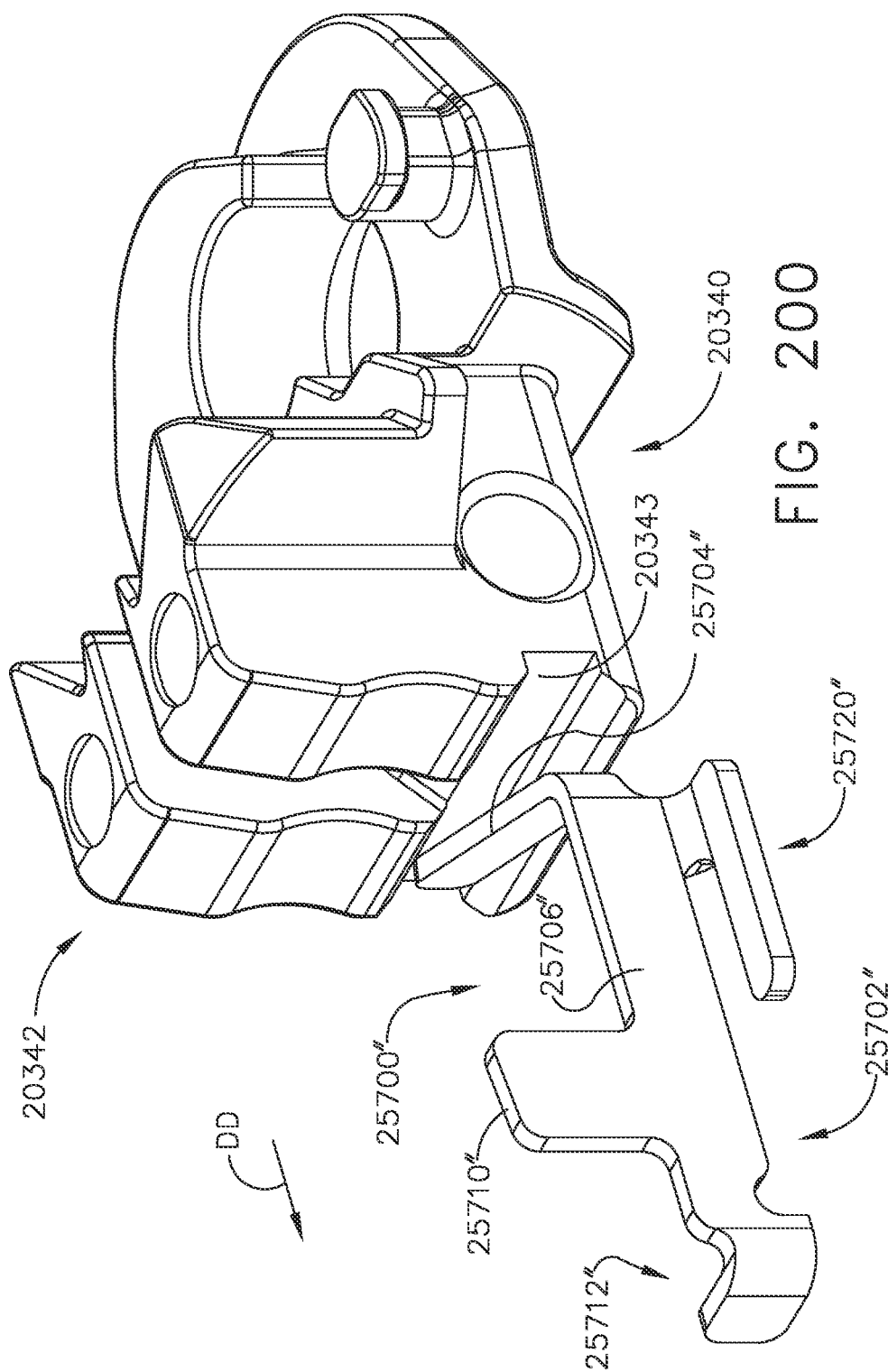
Figure 201:
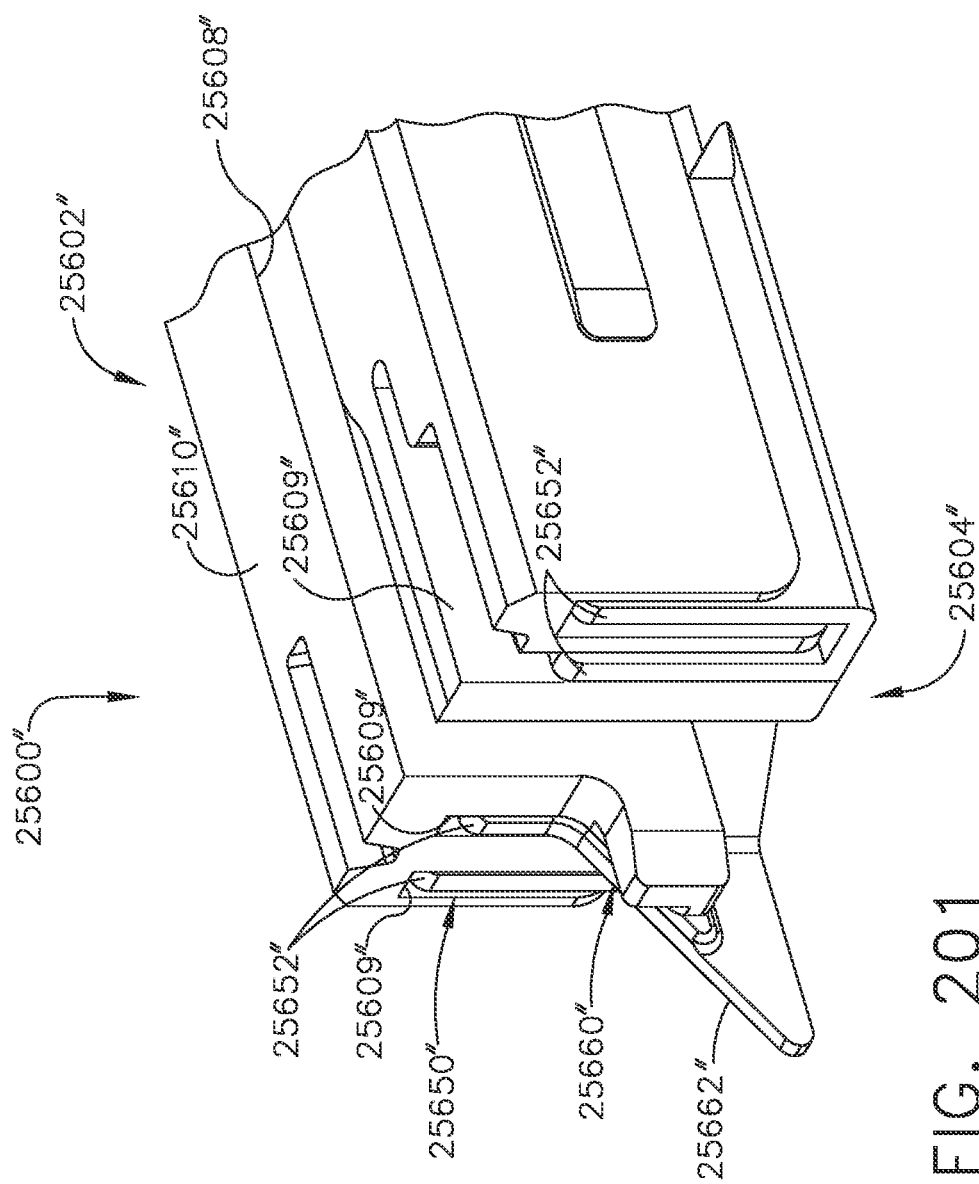
Figure 202:
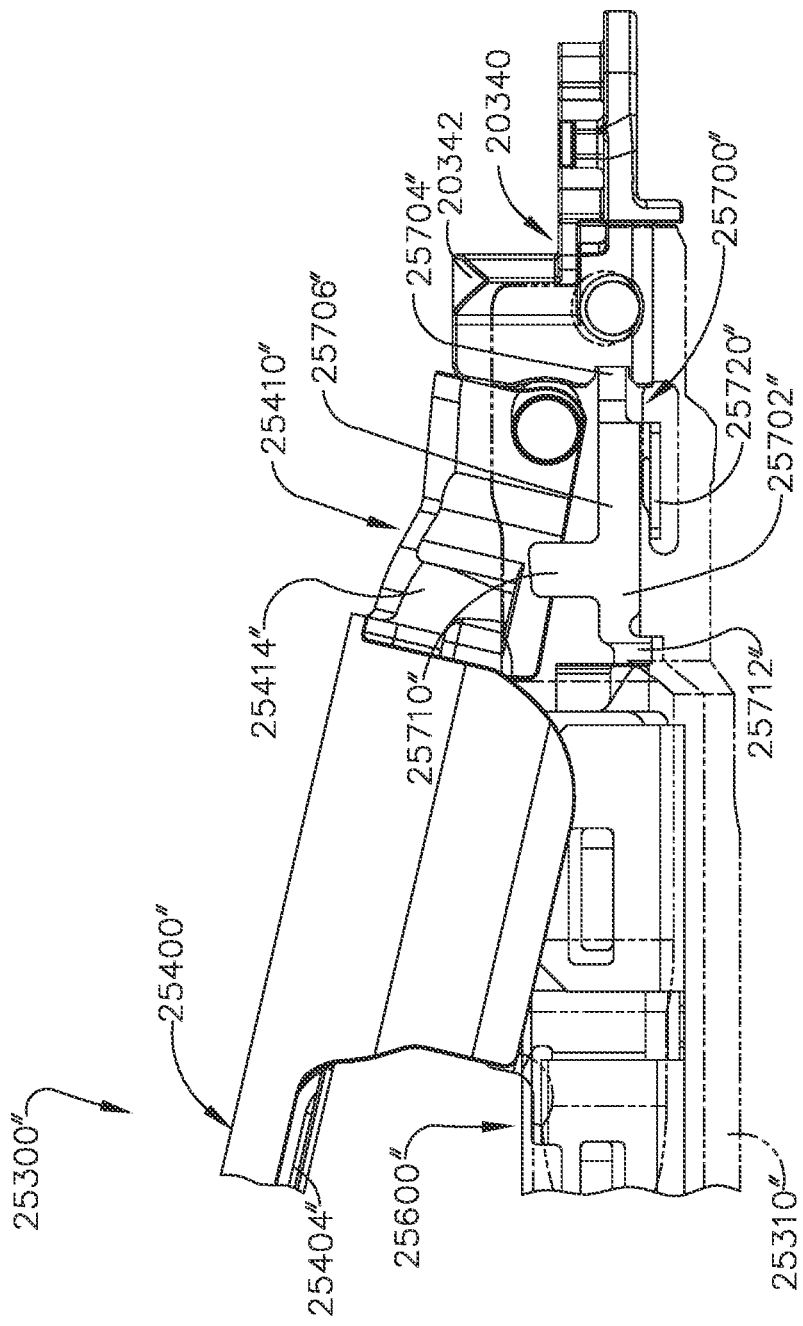
Figure 203:
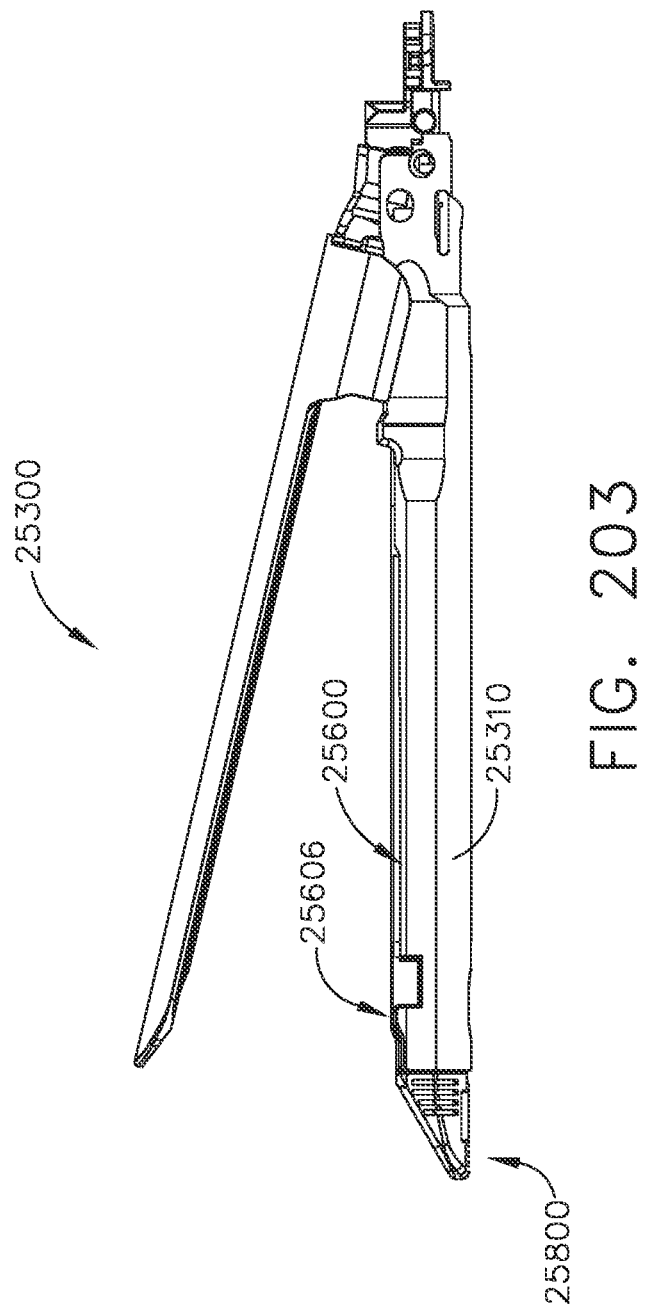
Figure 204:
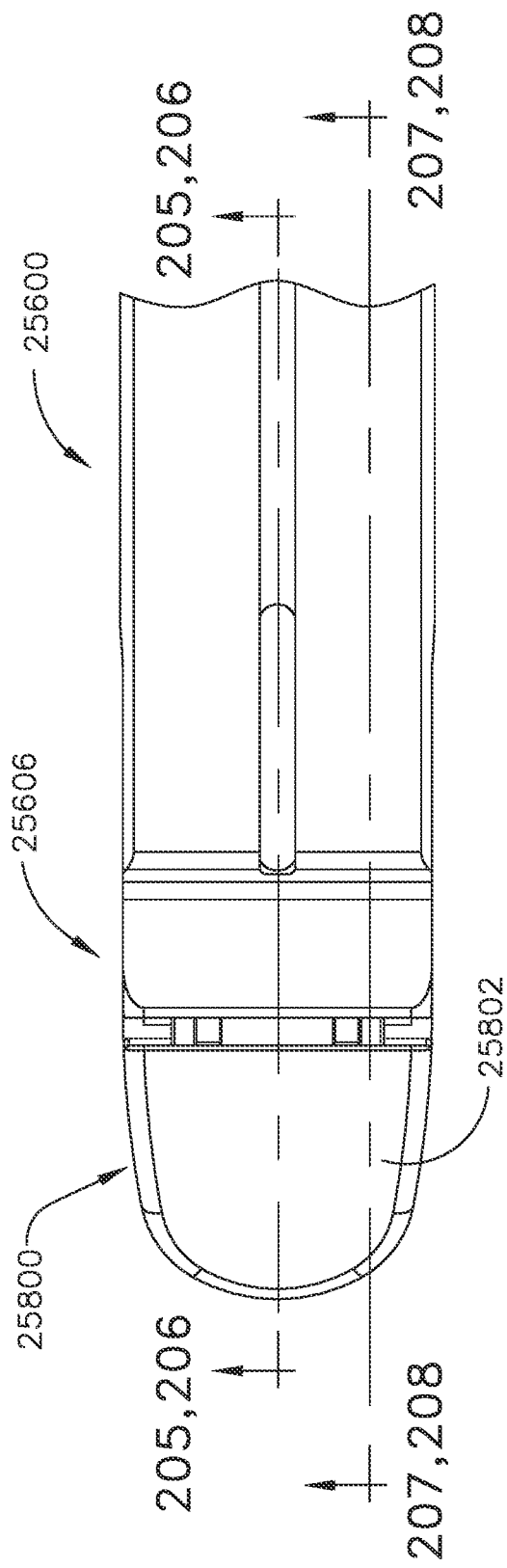
Figure 205:
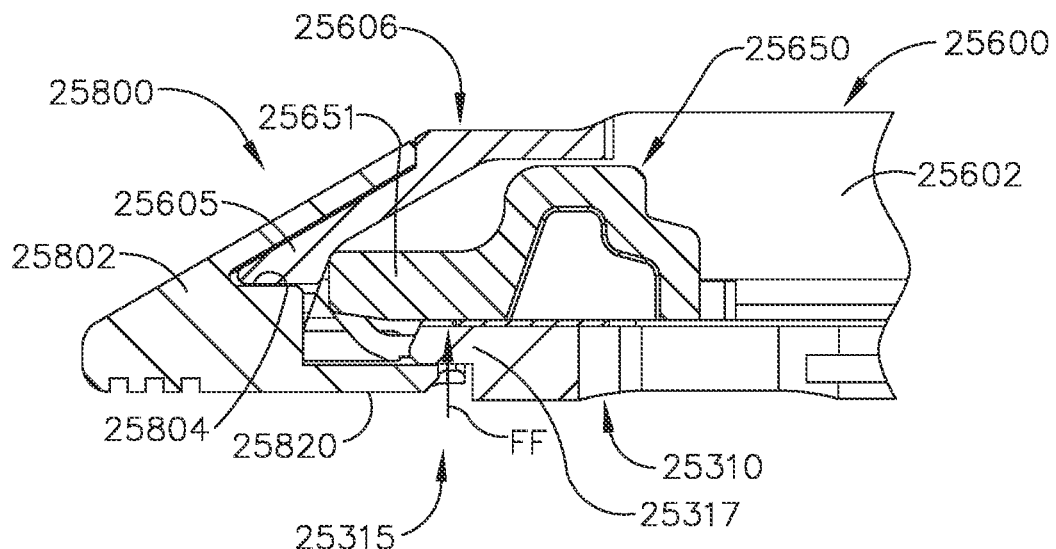
Figure 206:
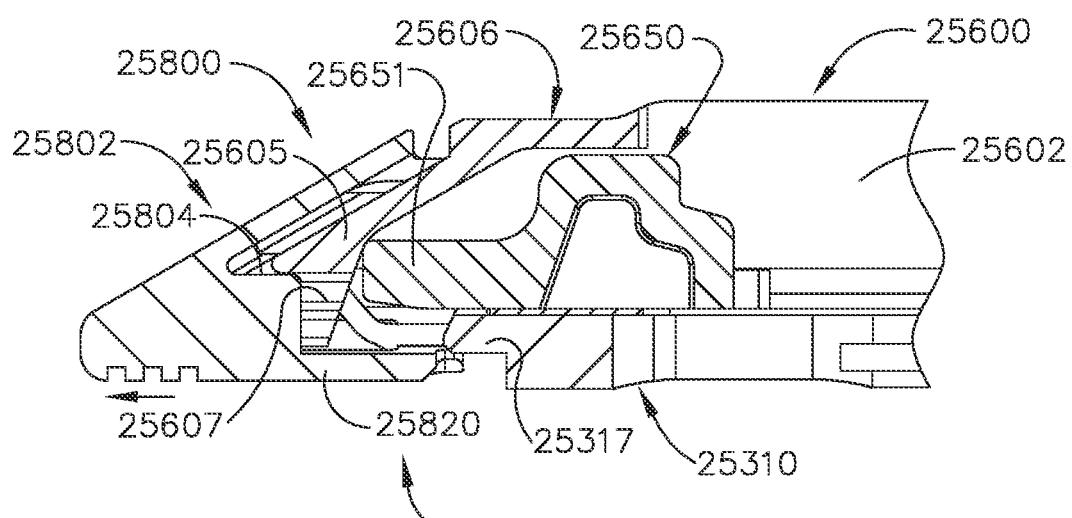
Figure 207:
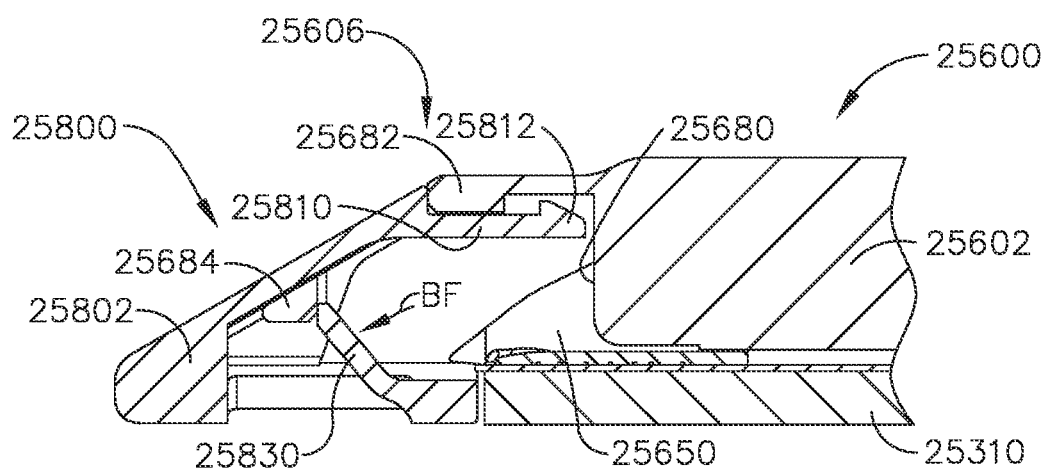
Figure 208:
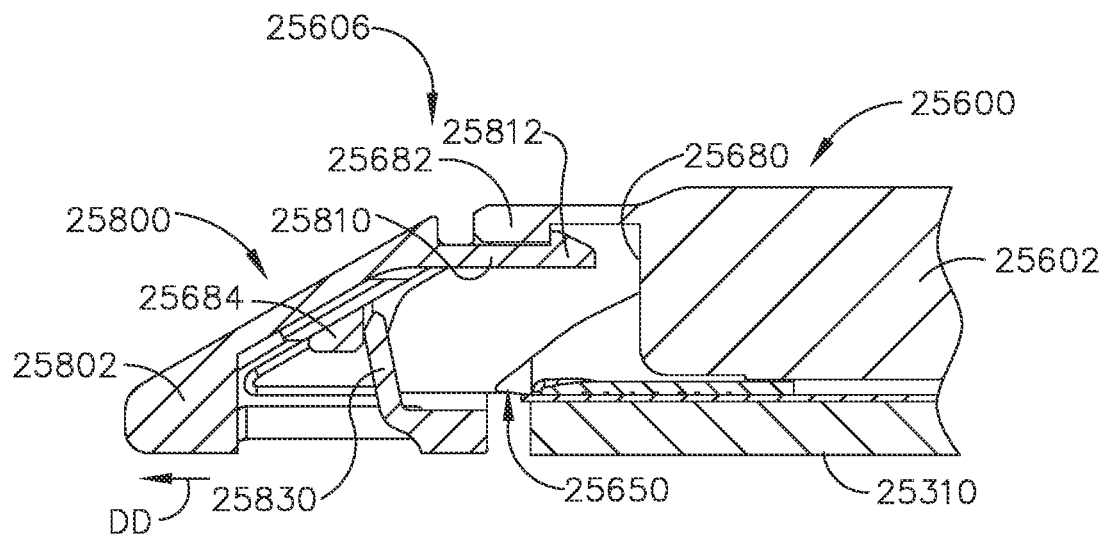
Figure 209:
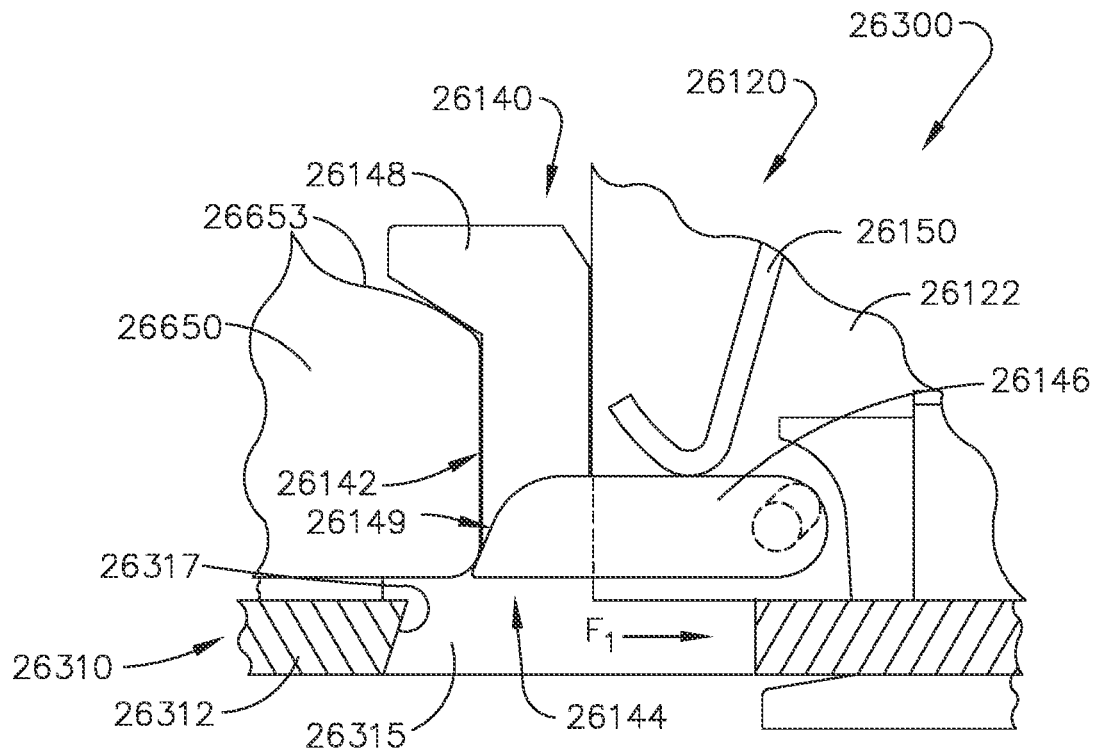
Figure 210:
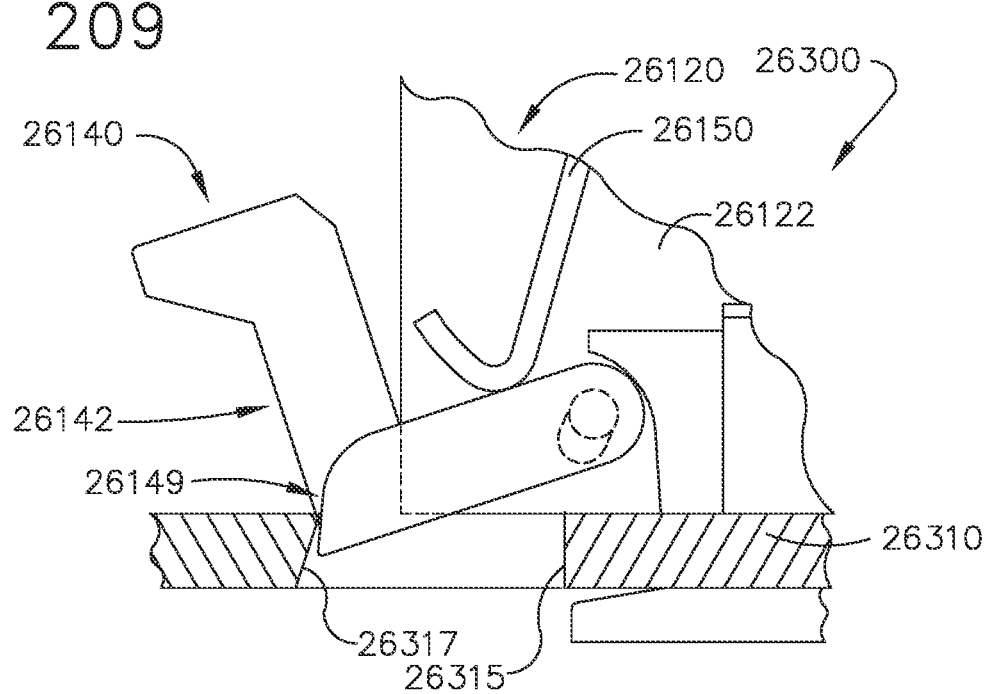
Figure 211:
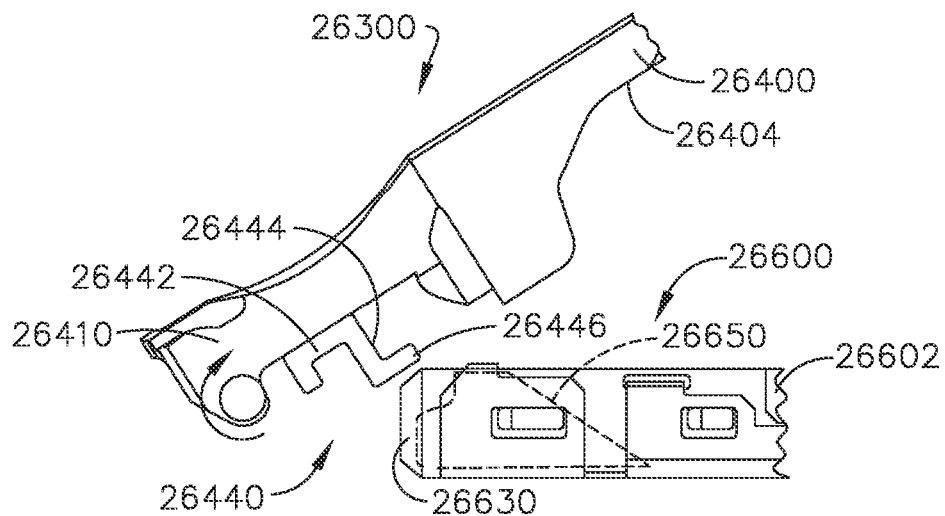
Figure 212:
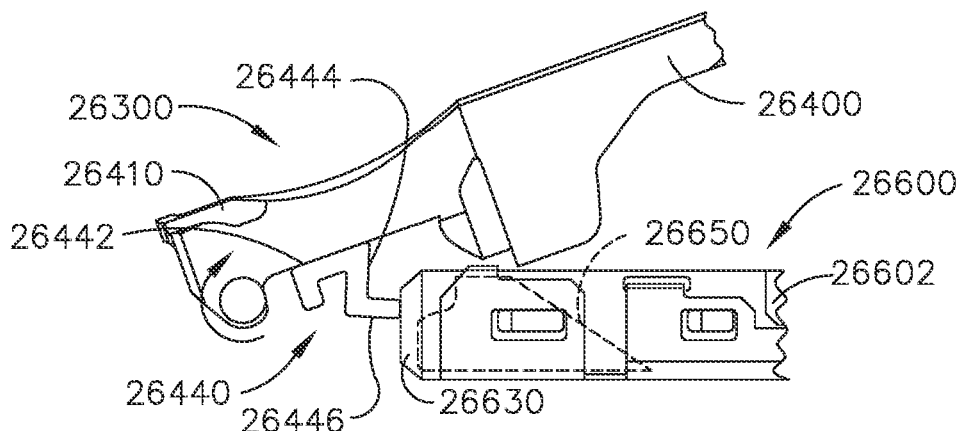
Figure 213:
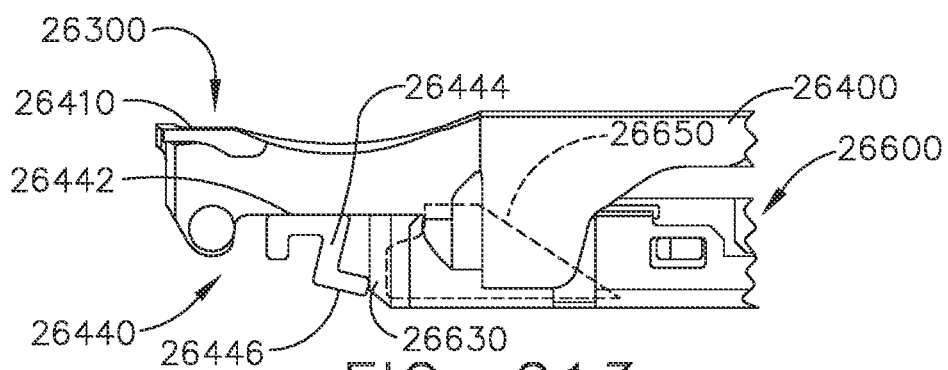
Figure 214:
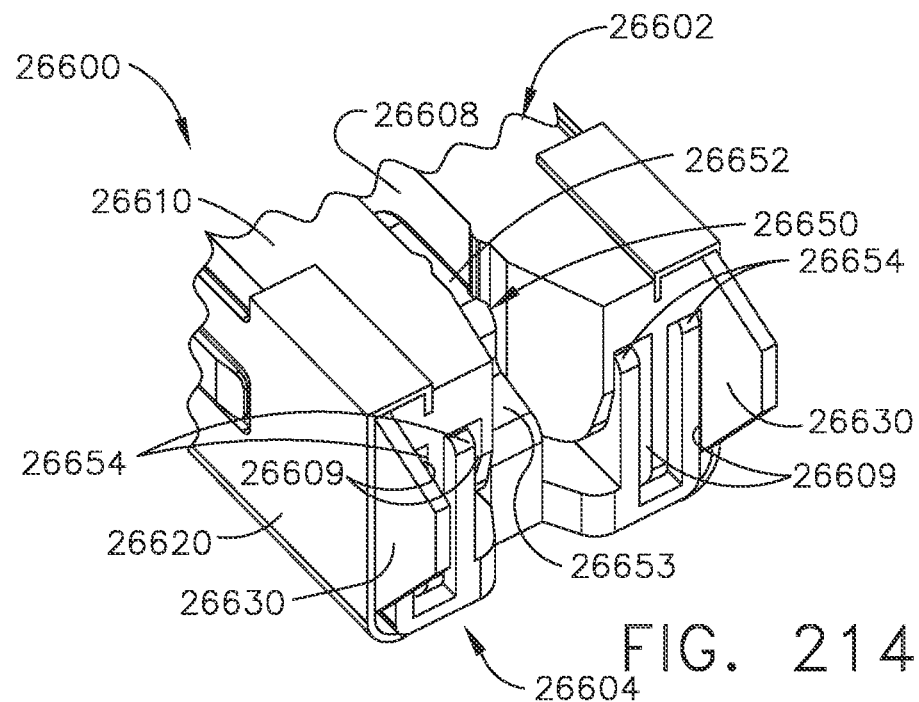
Figure 216:
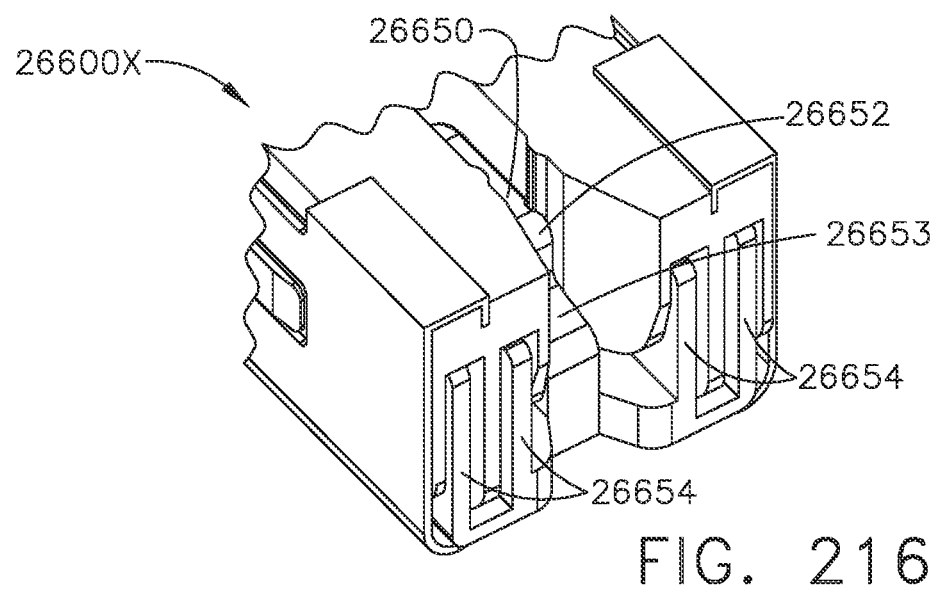
Figure 215:
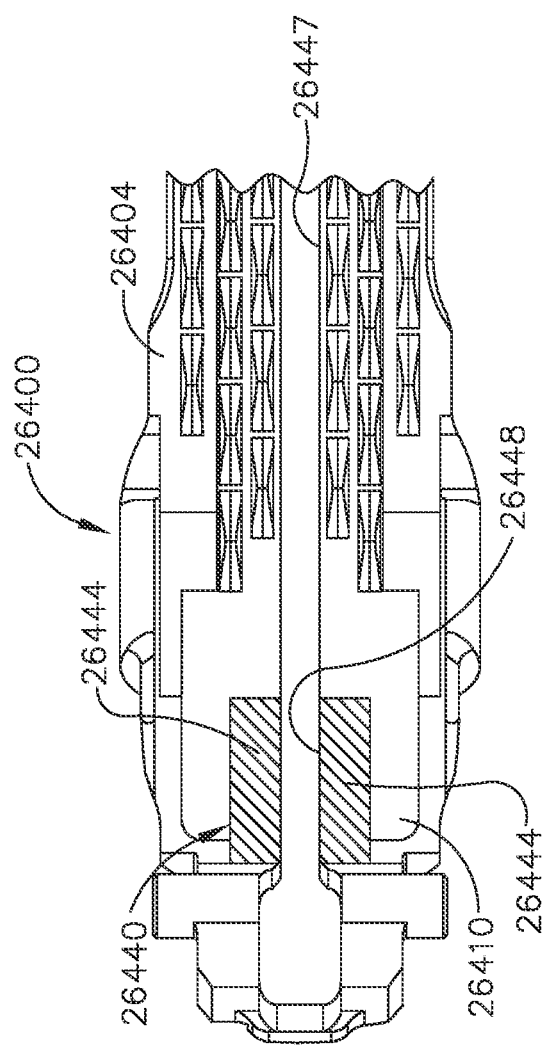
Figure 217:
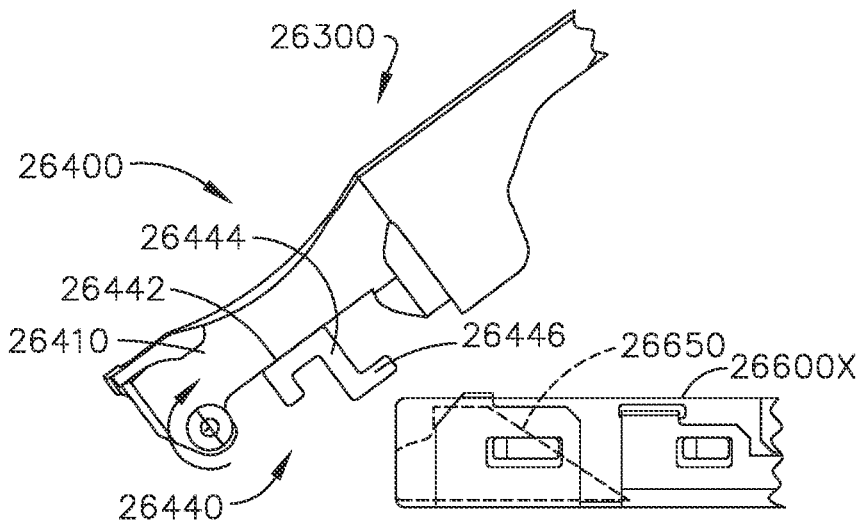
Figure 218:
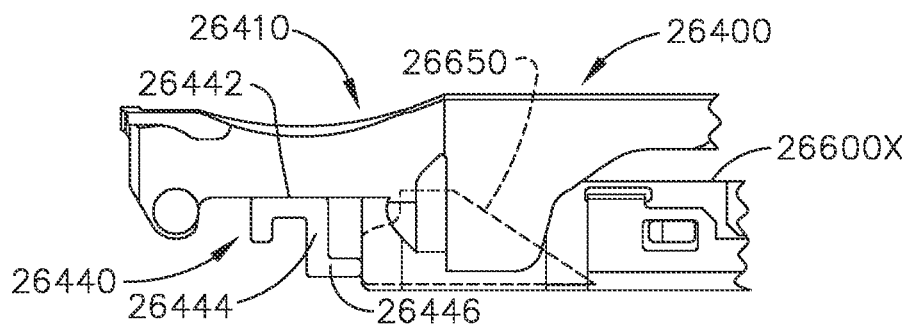
Figure 219:
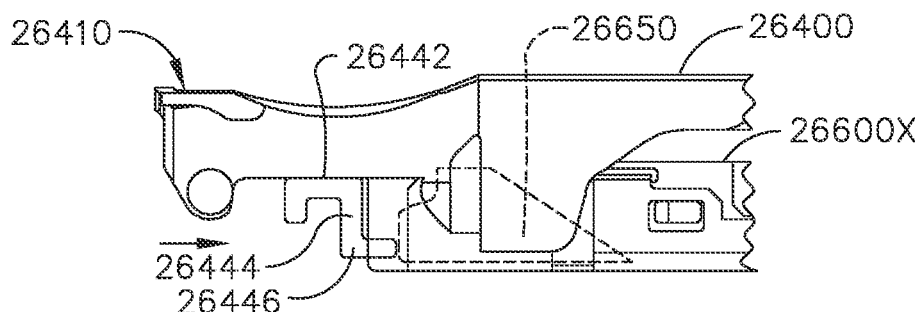
Figure 220:
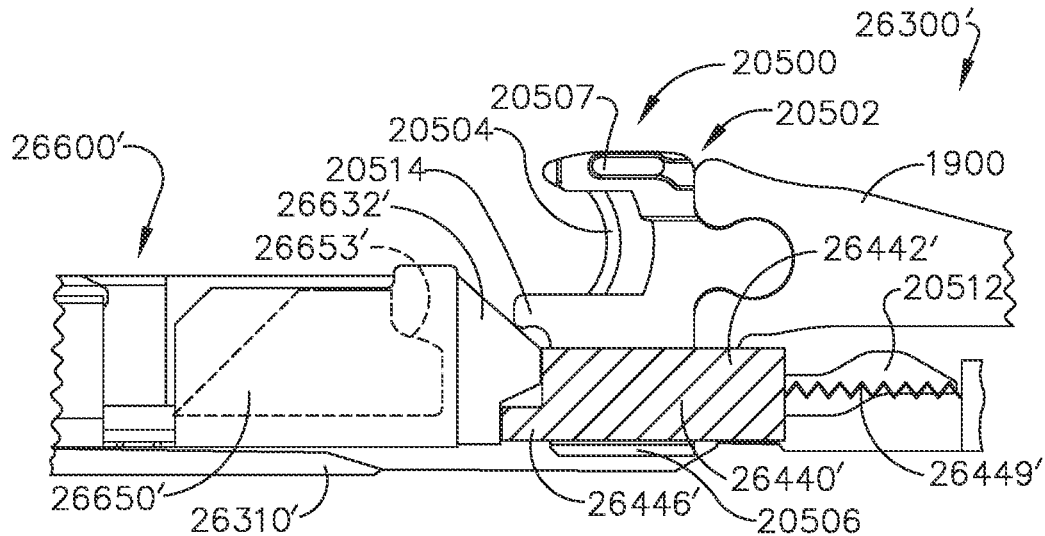
Figure 221:
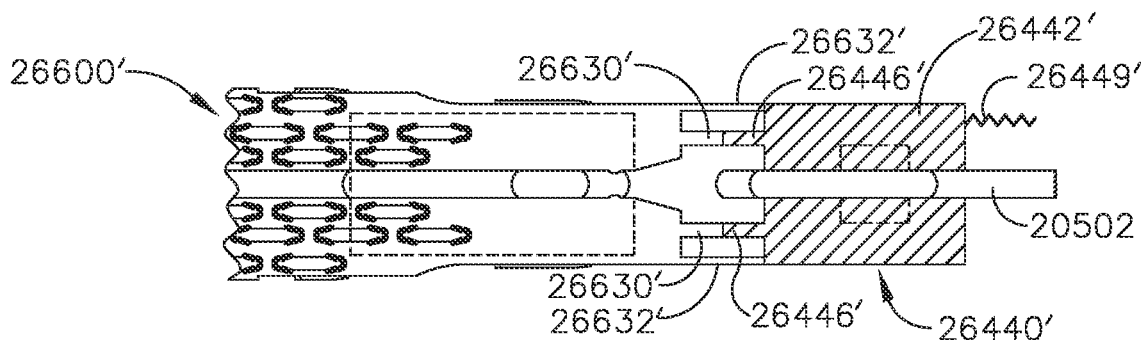
Figure 226:
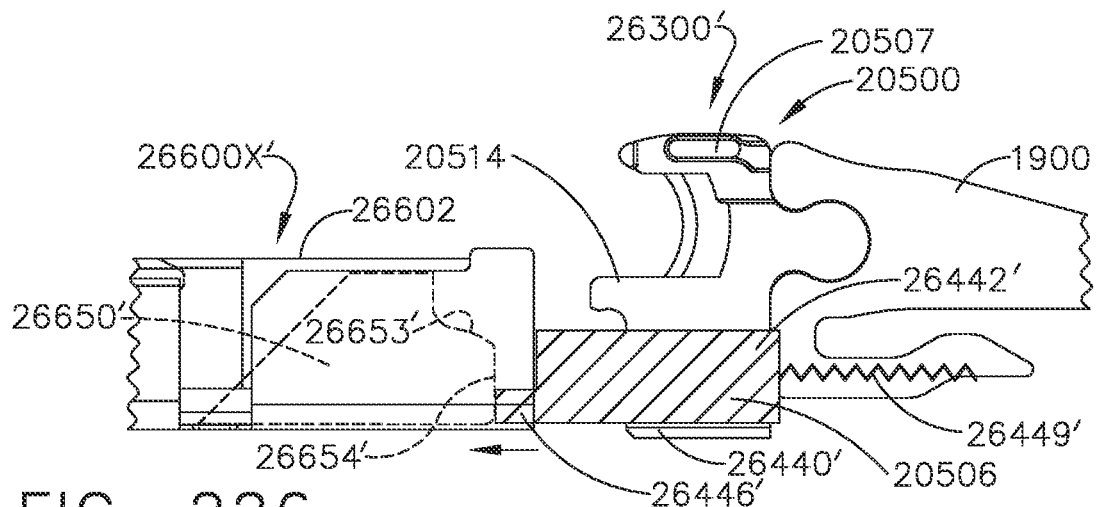
Figure 222:
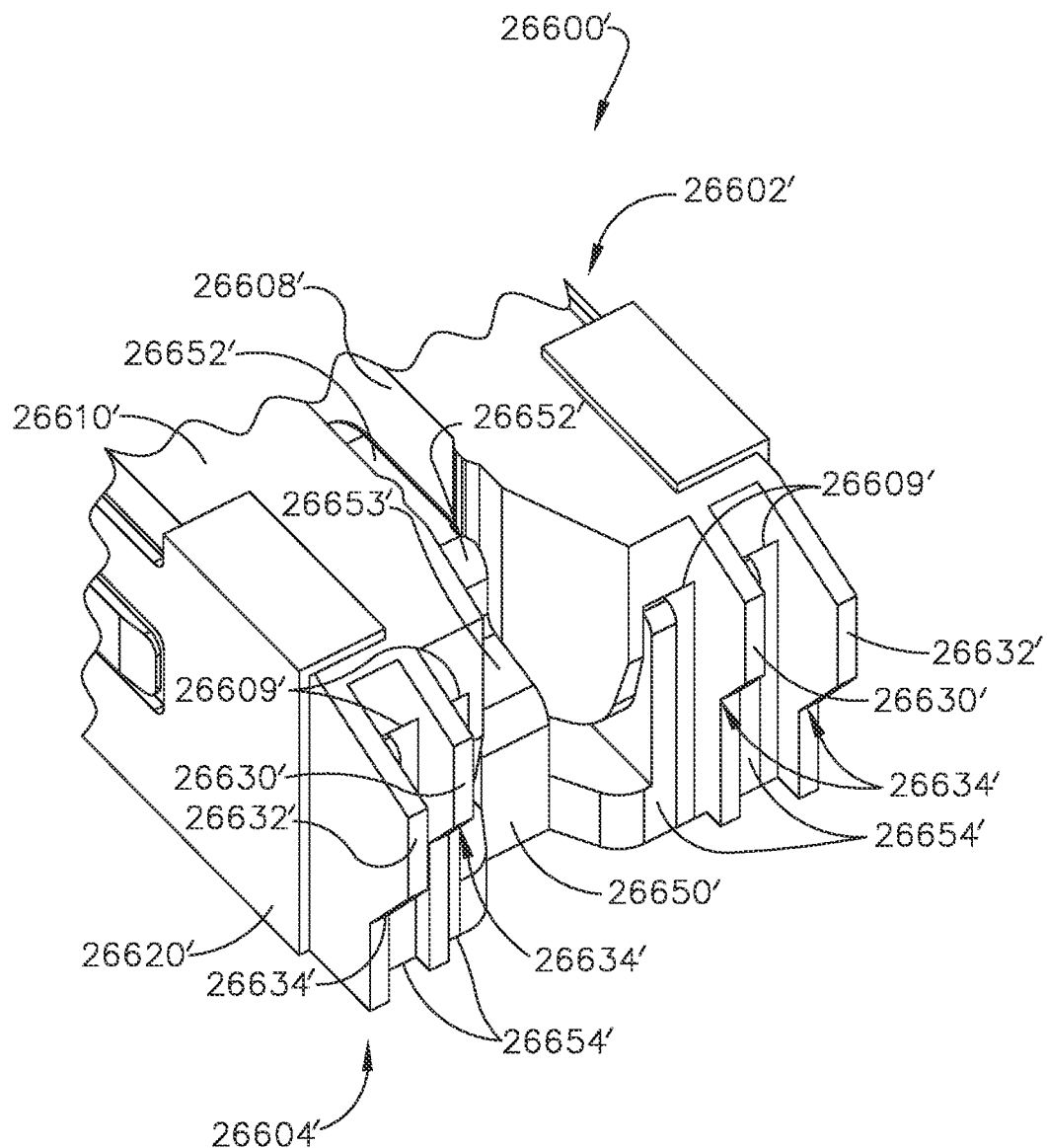
Figure 223:
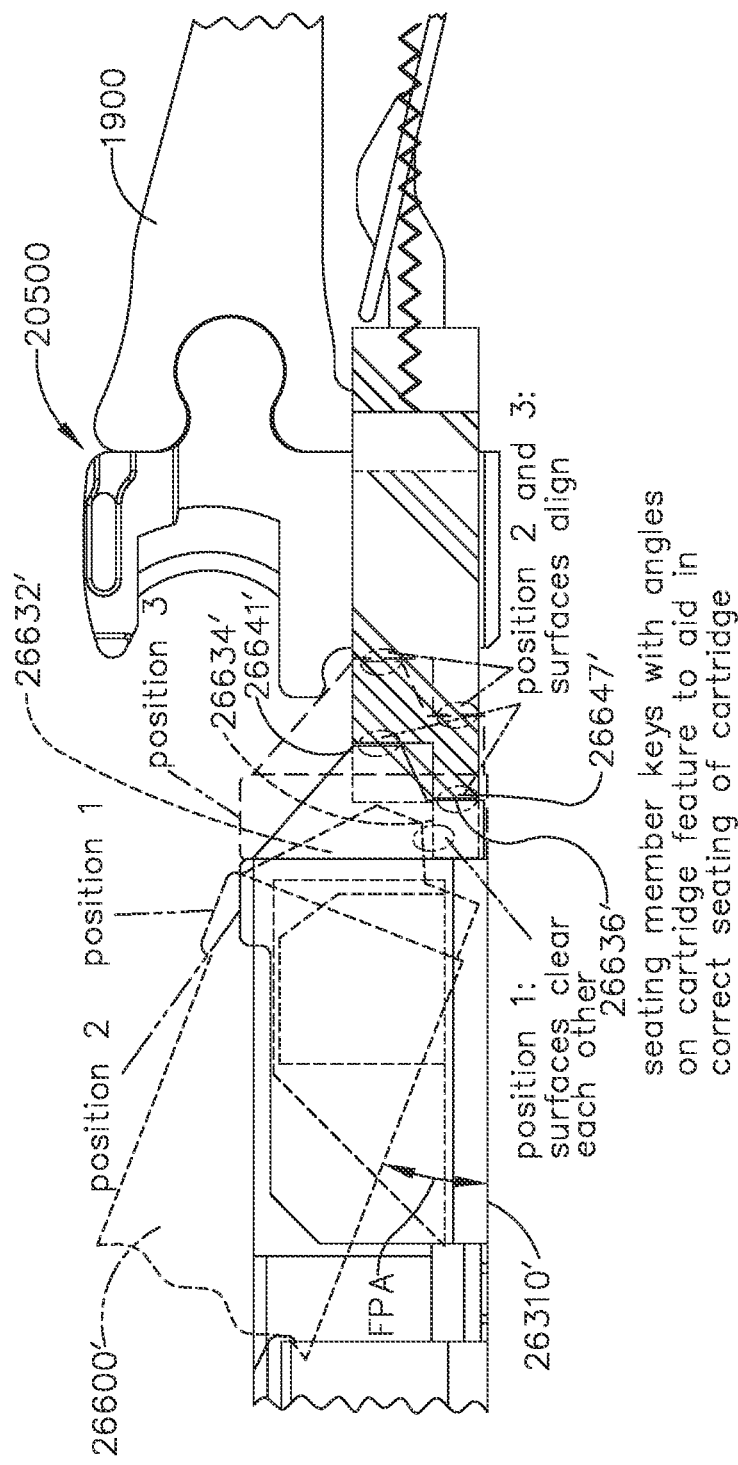
Figure 224:
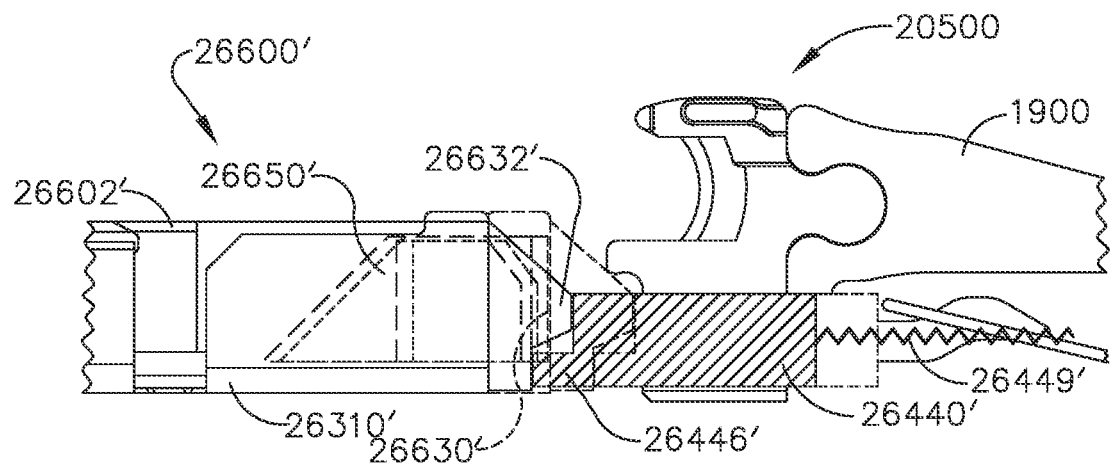
Figure 225:
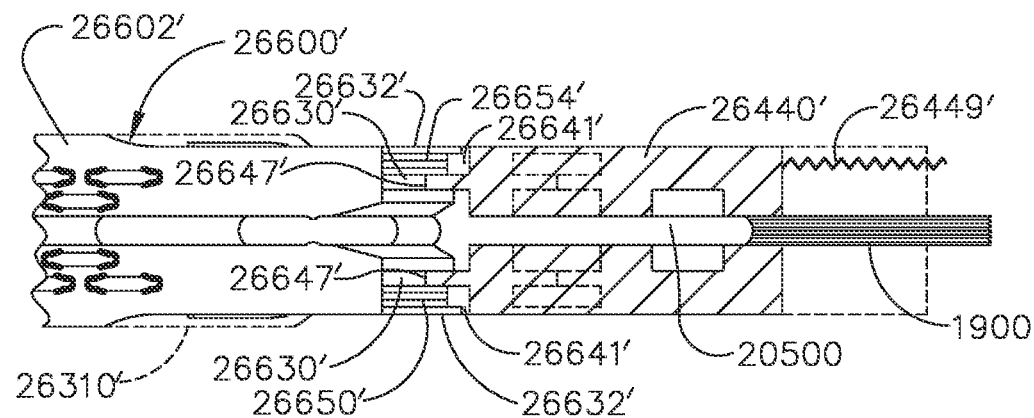
Figure 227:
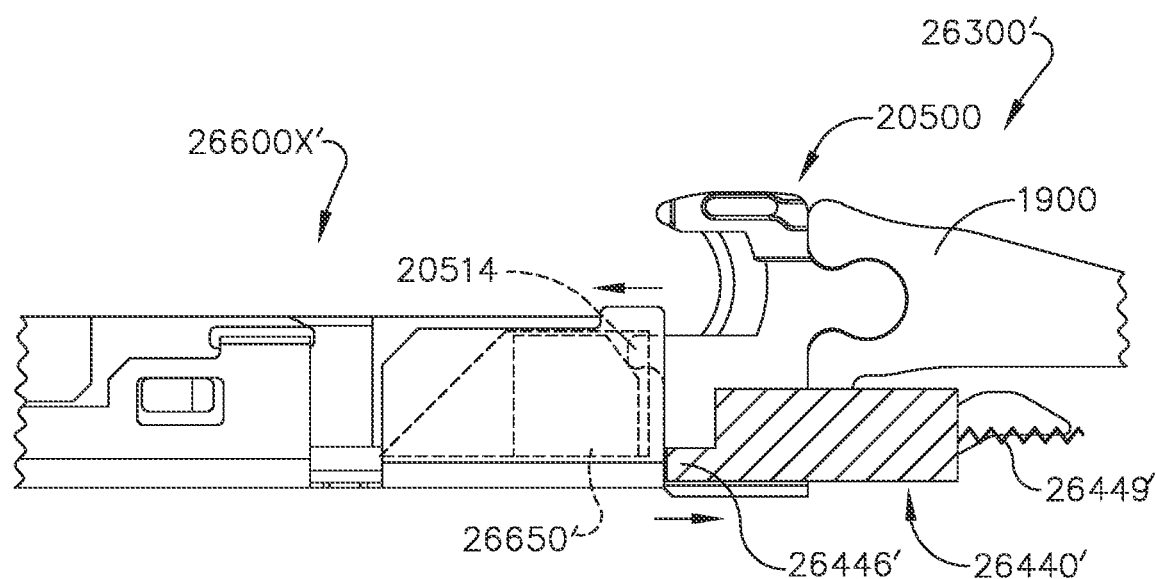
Figure 228:
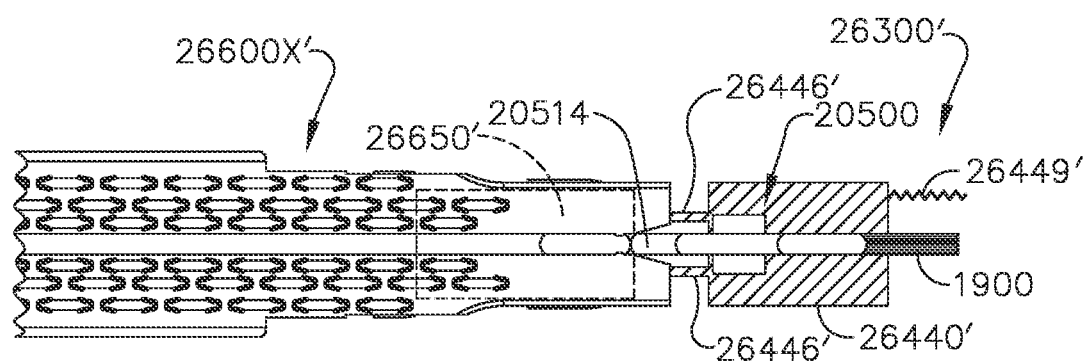
Figure 229:
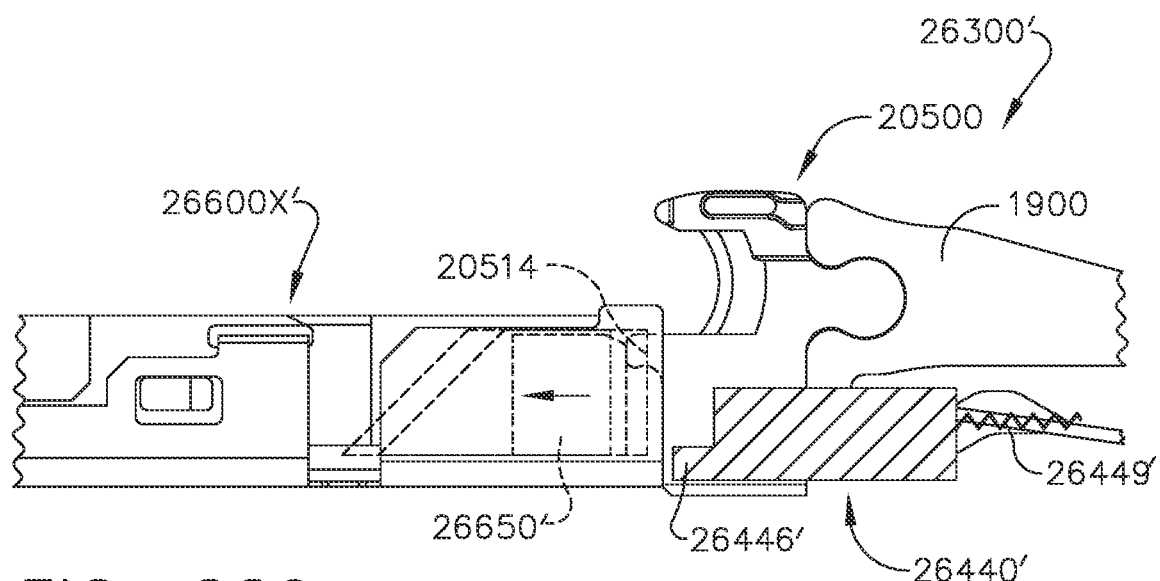
Figure 230:
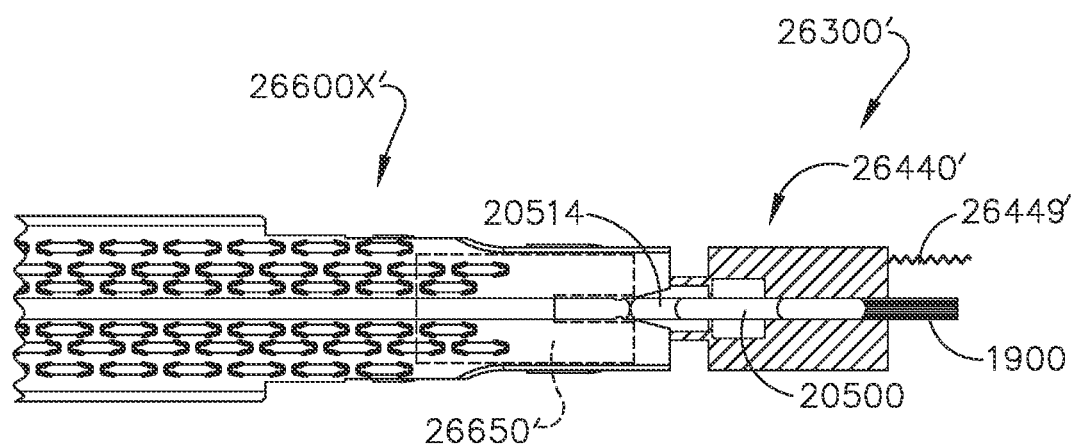
Figure 231:
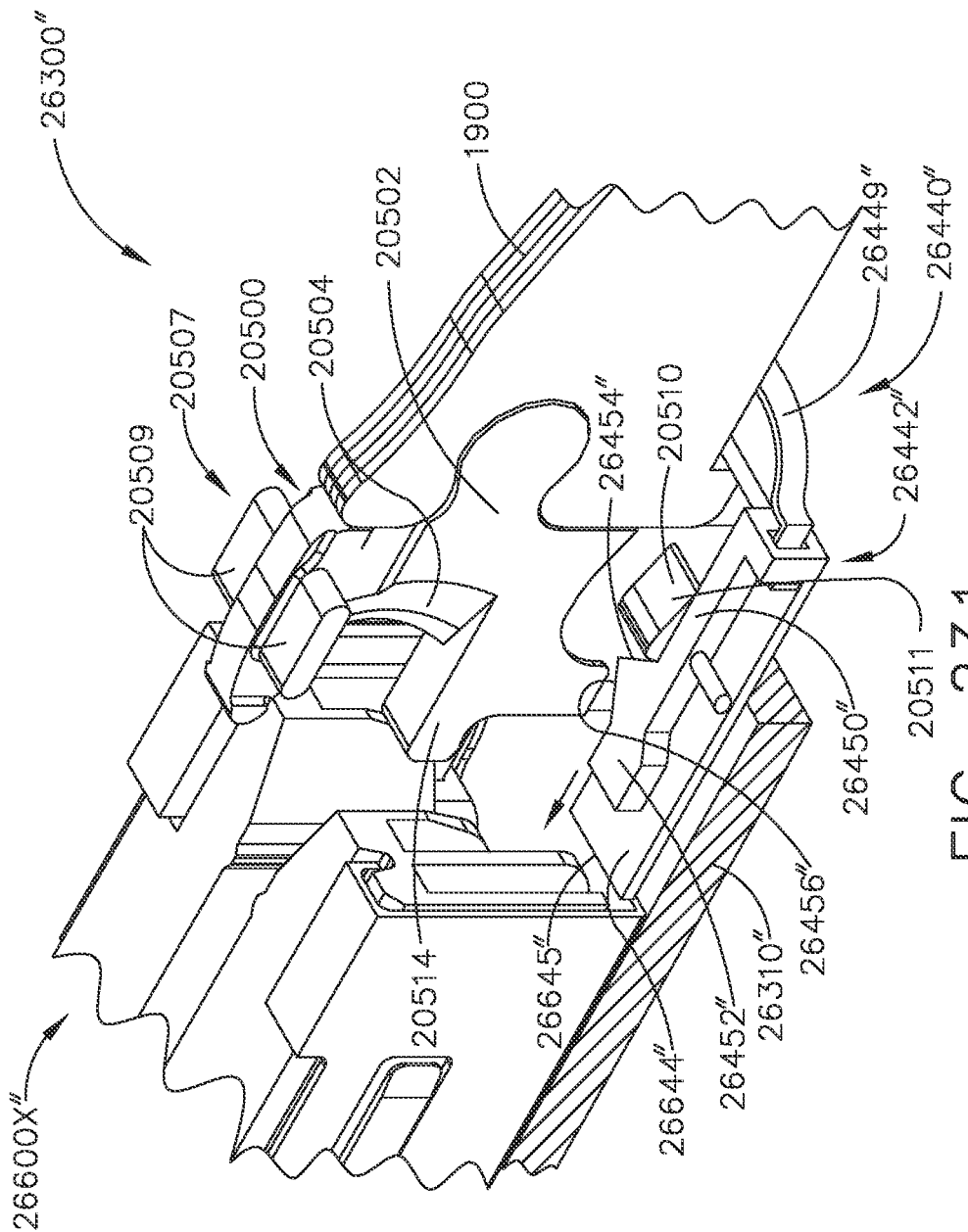
Figure 232:
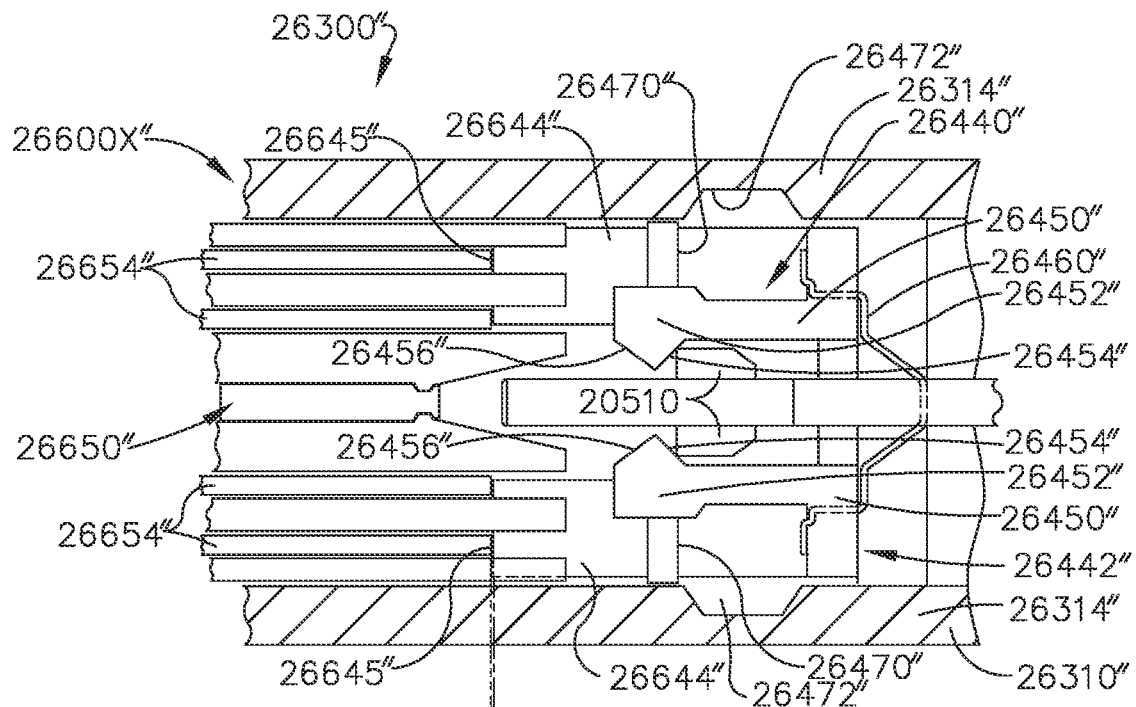
Figure 233:
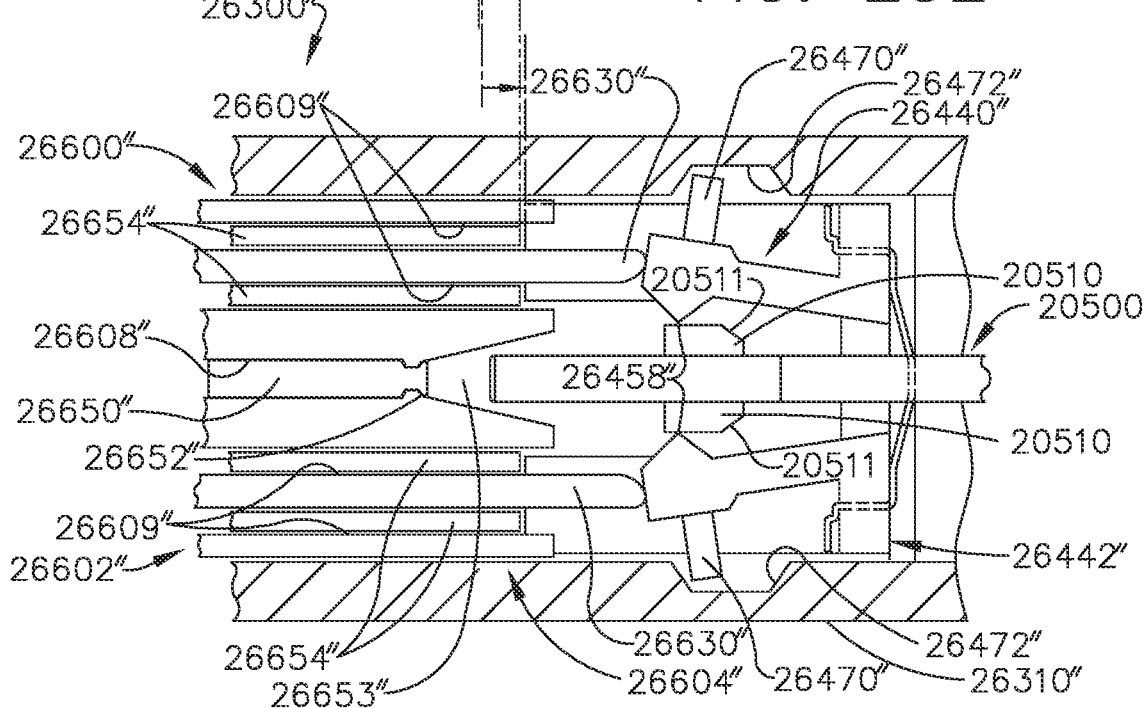
Figure 234:
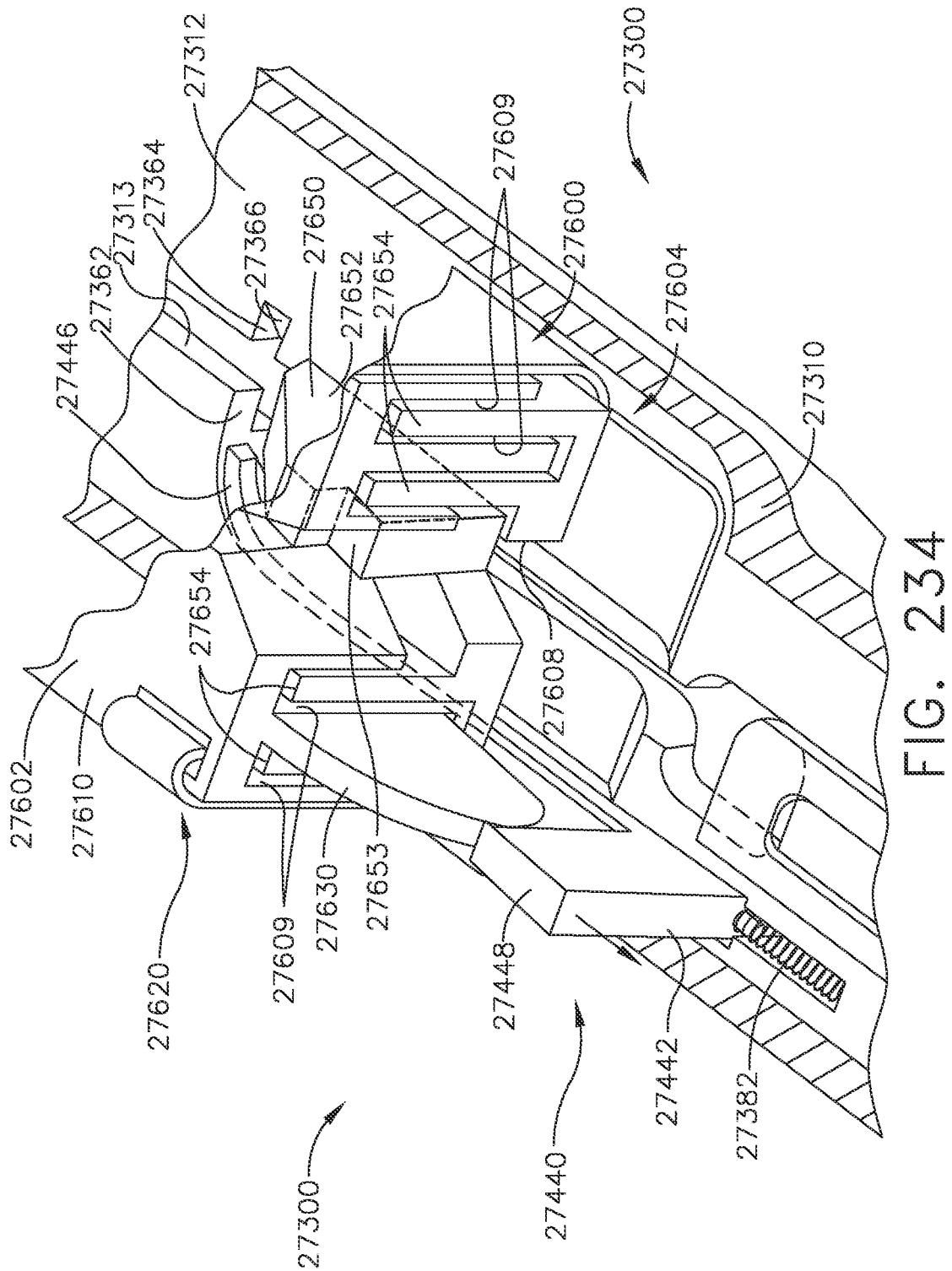
Figure 235:
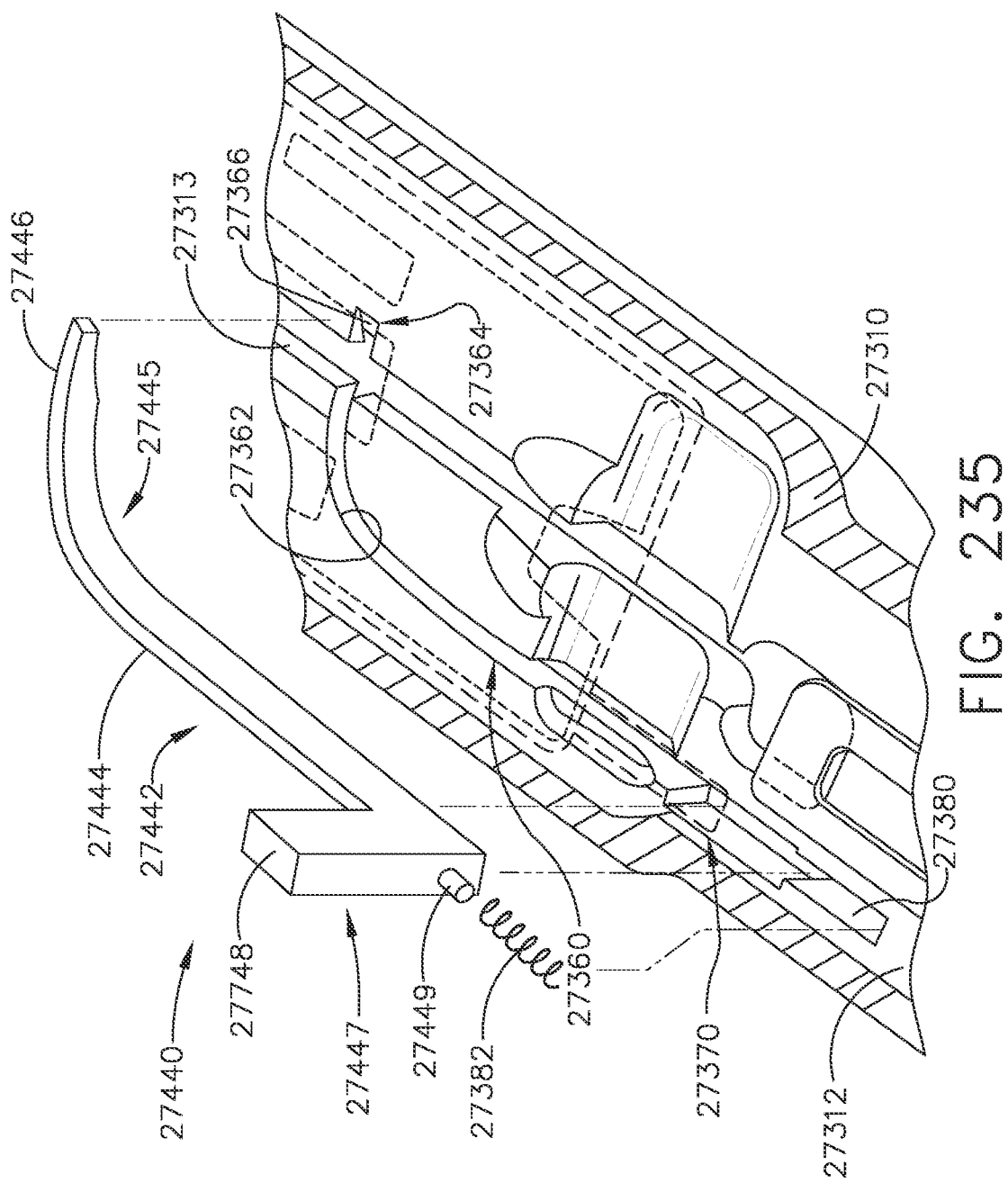
Figure 238:
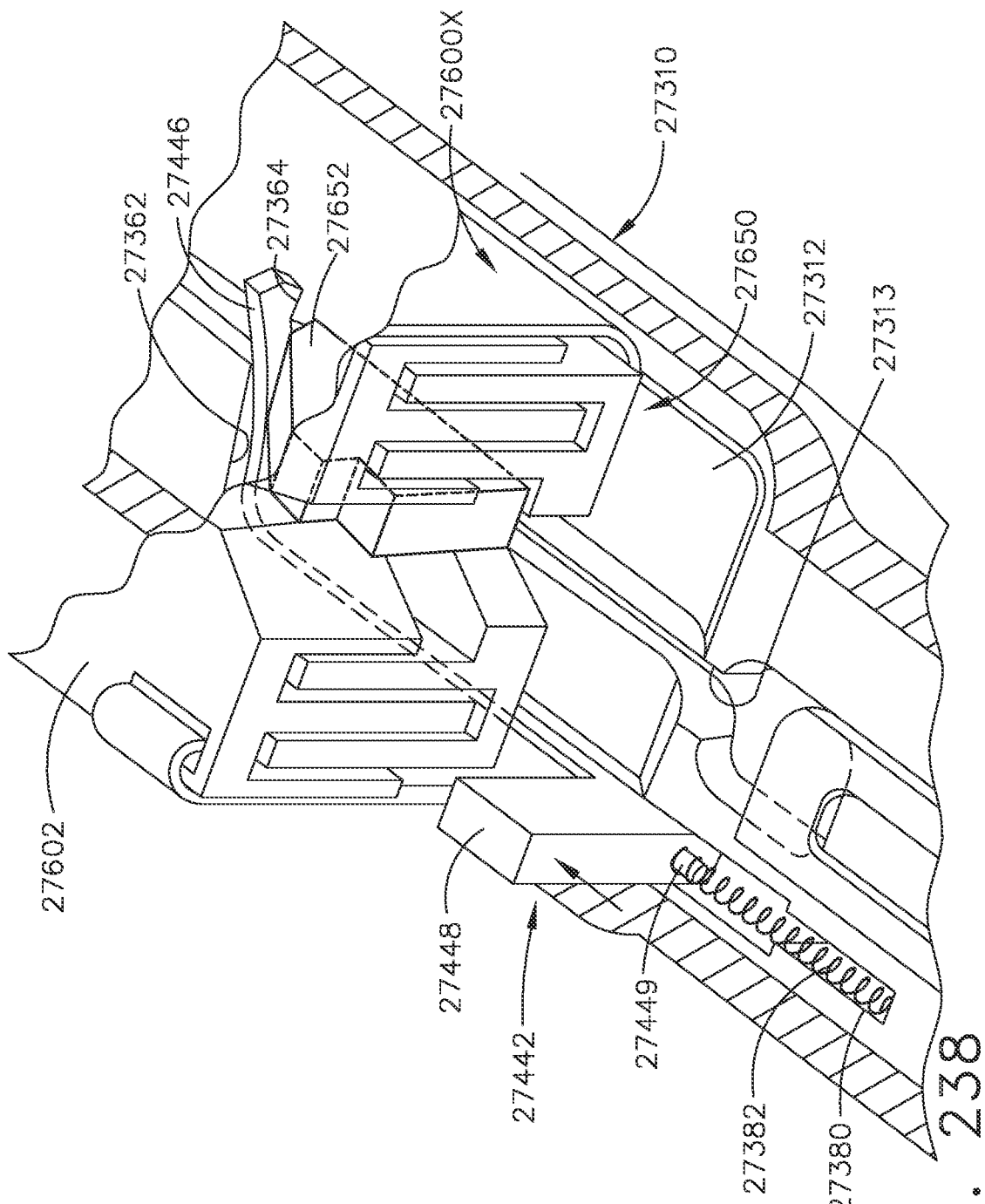
Figure 239:
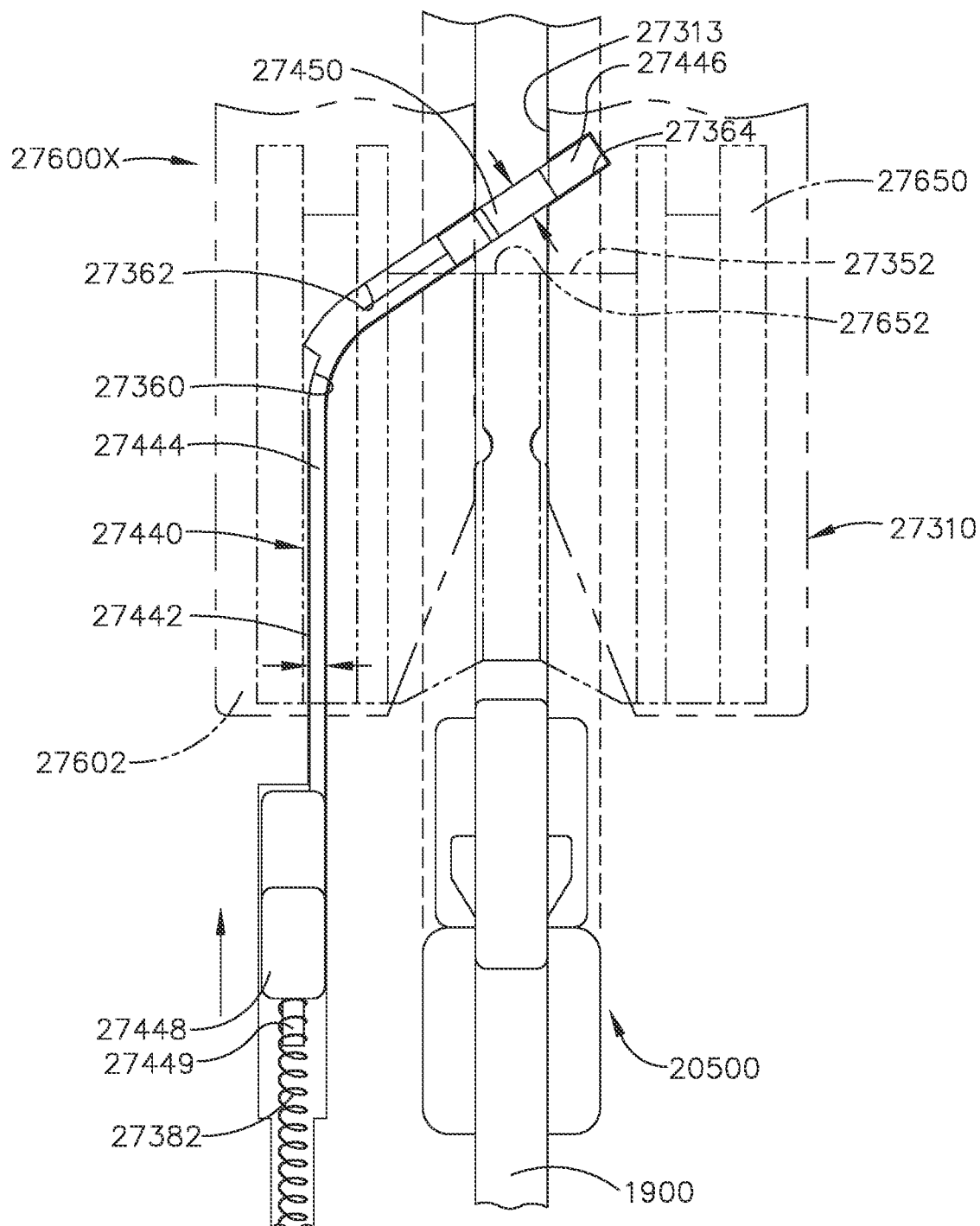
Figure 240:
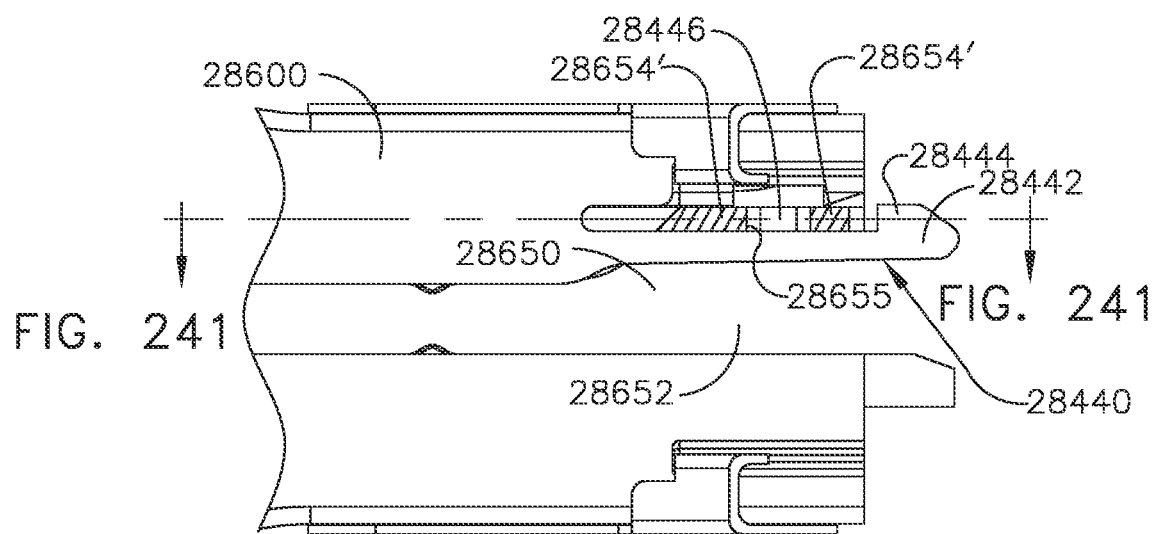
Figure 242:
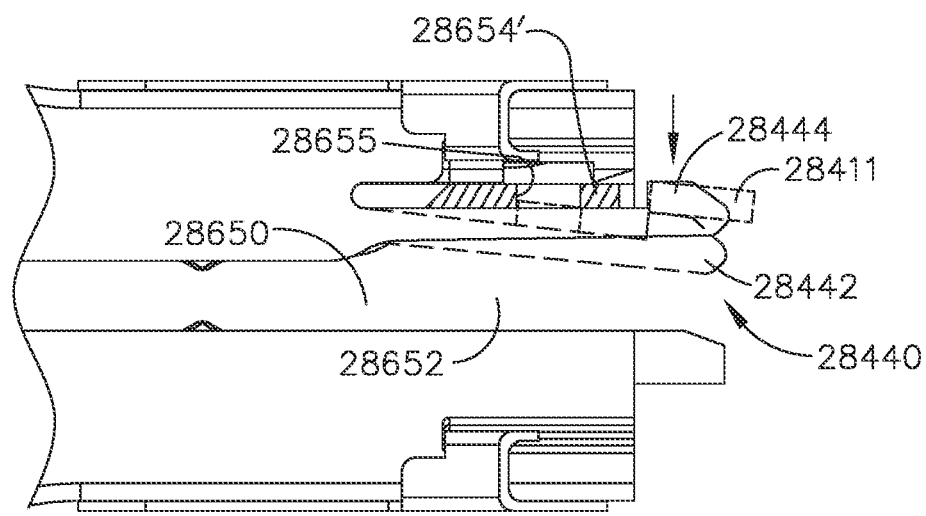
Figure 241:
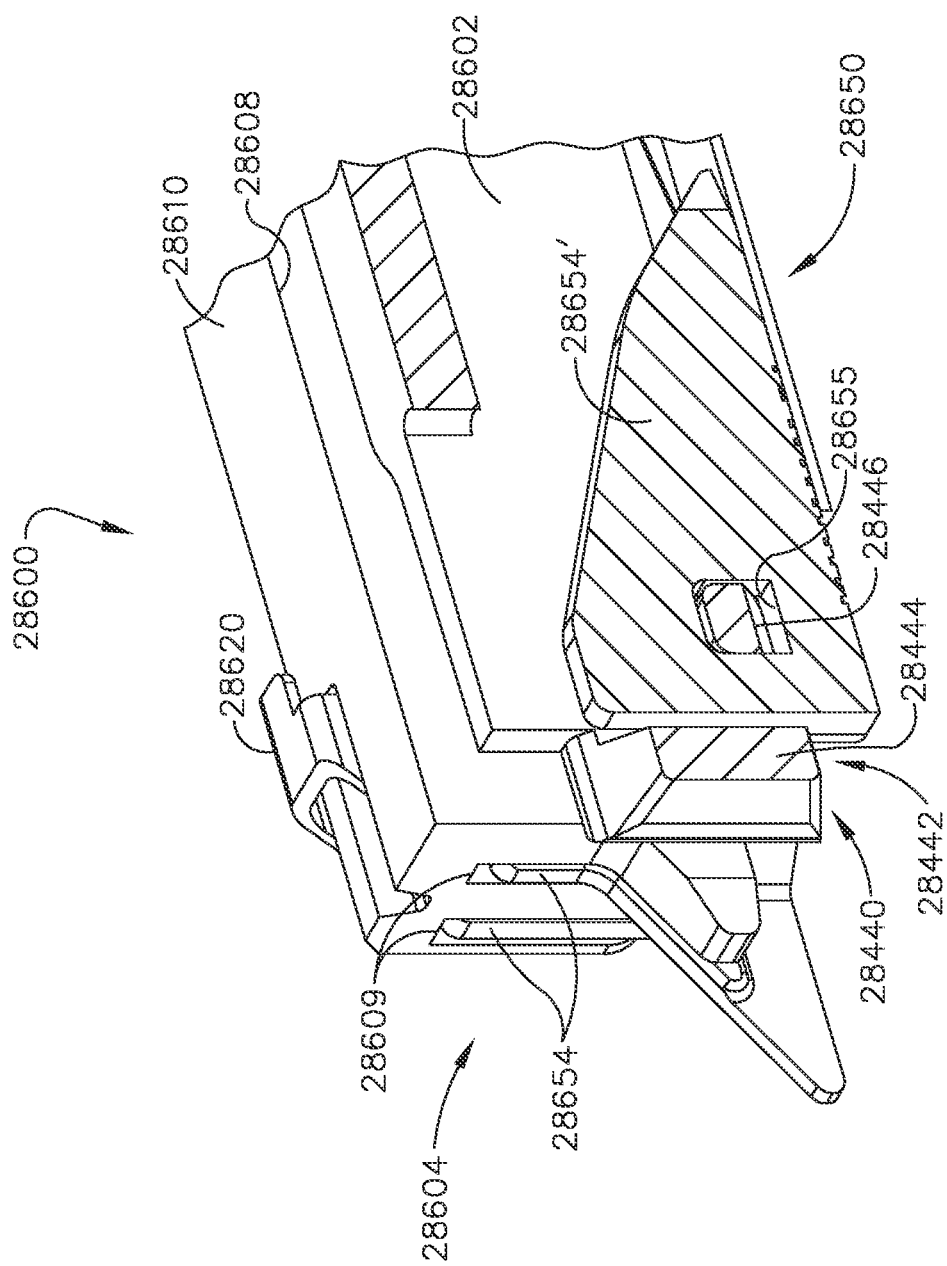
Figure 243:
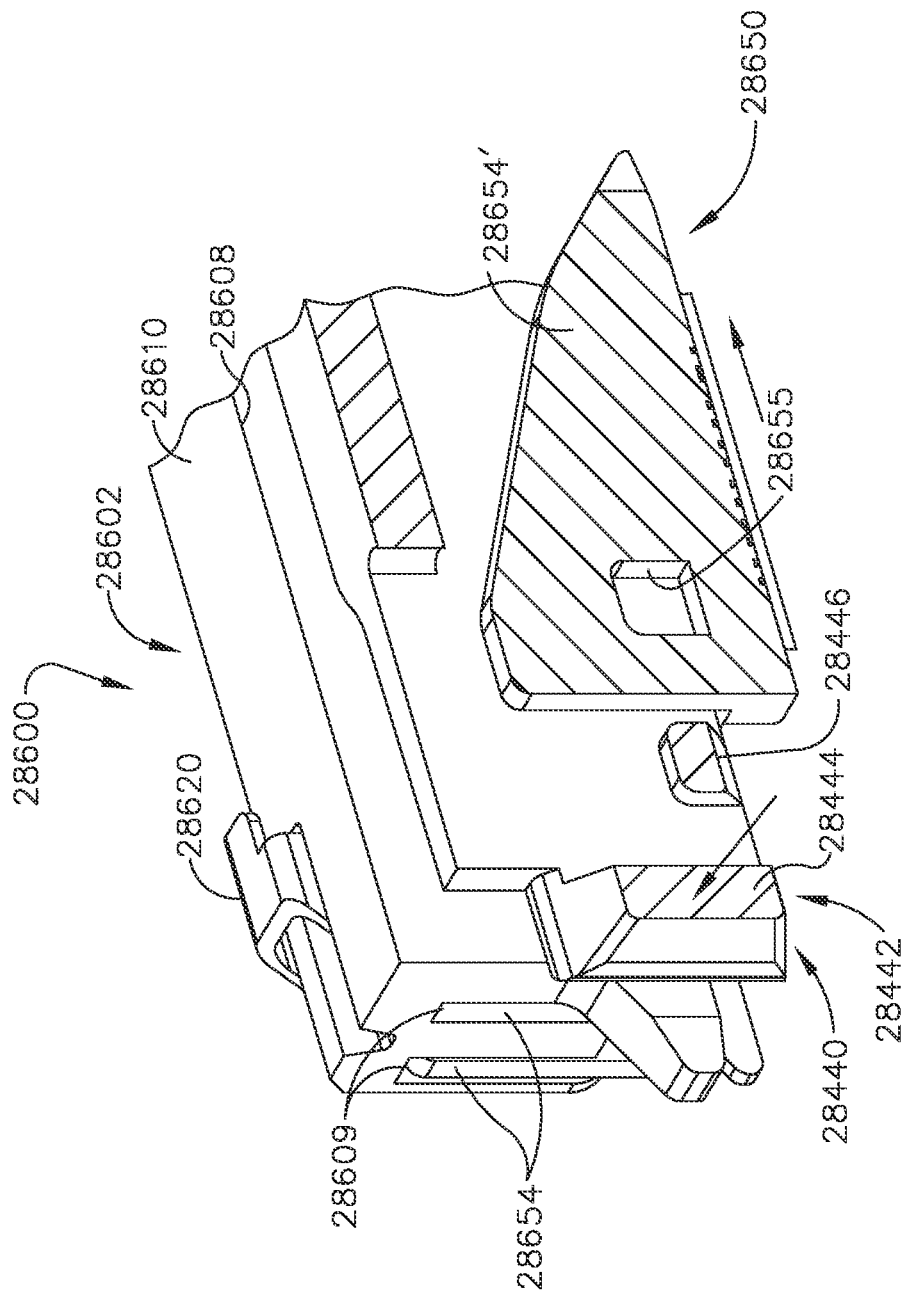
Figure 244:
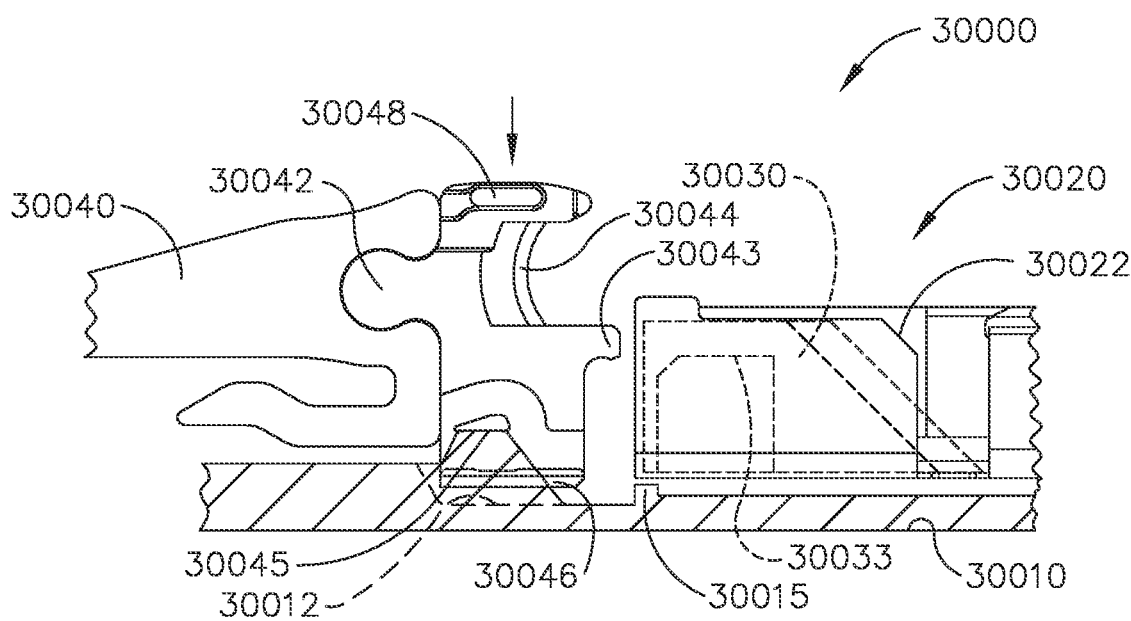
Figure 245:
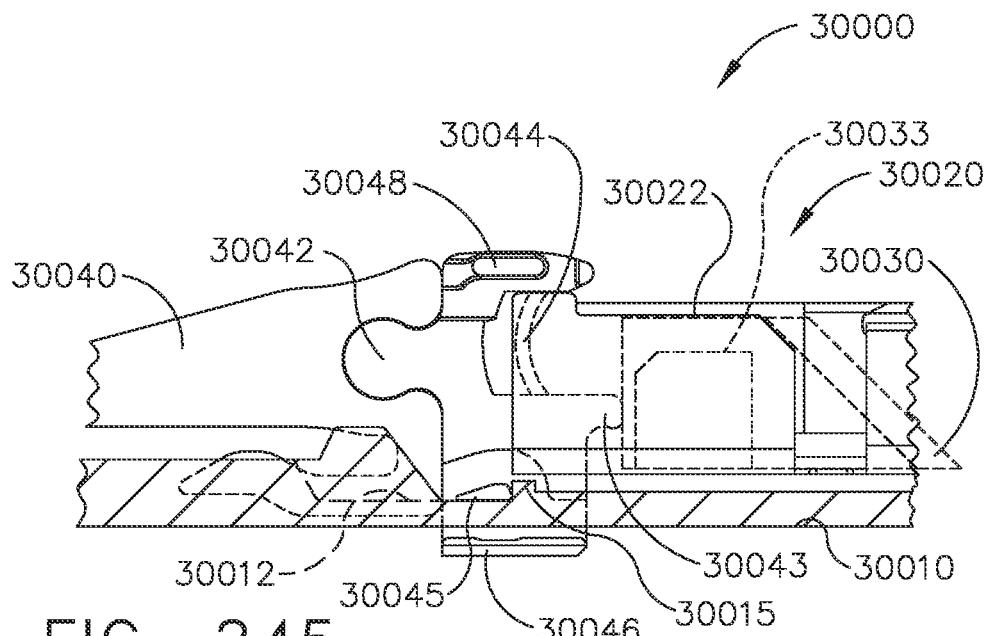
Figure 246:
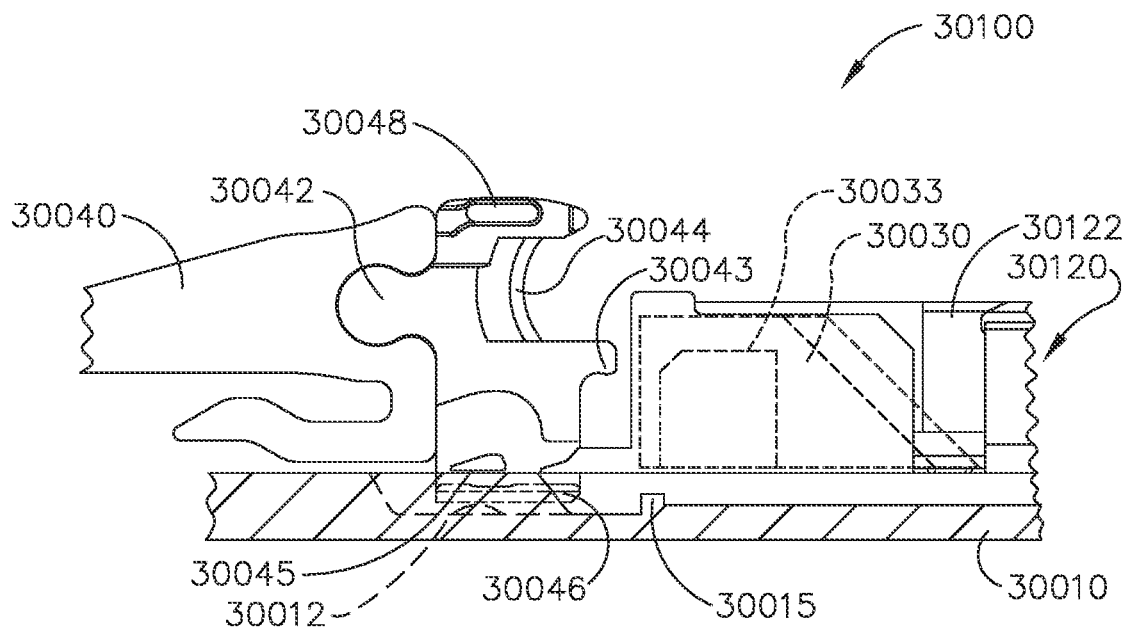
Figure 247:
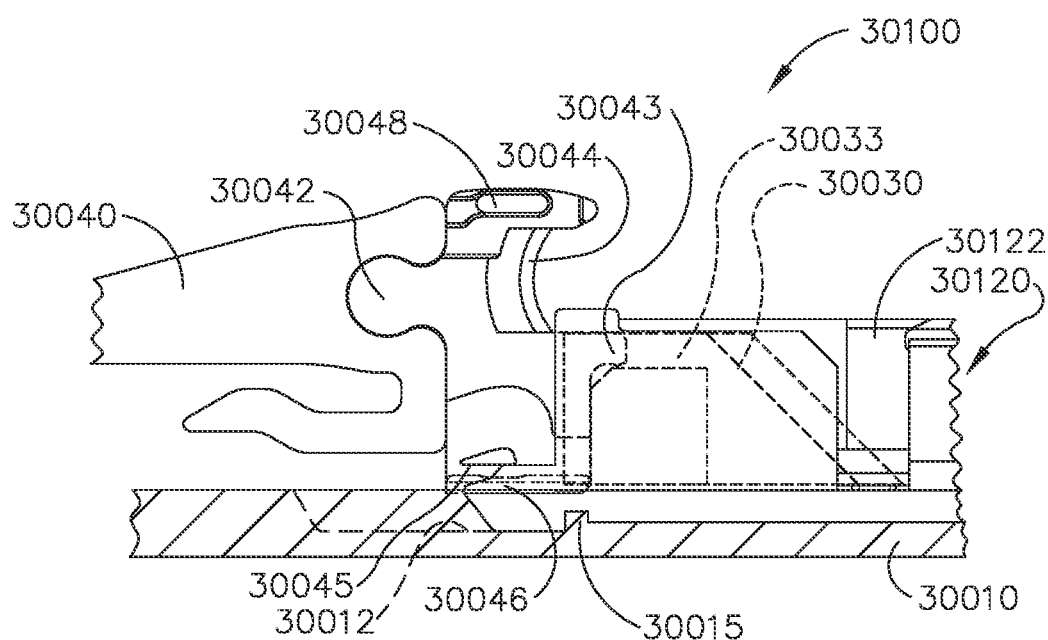
Figure 248:
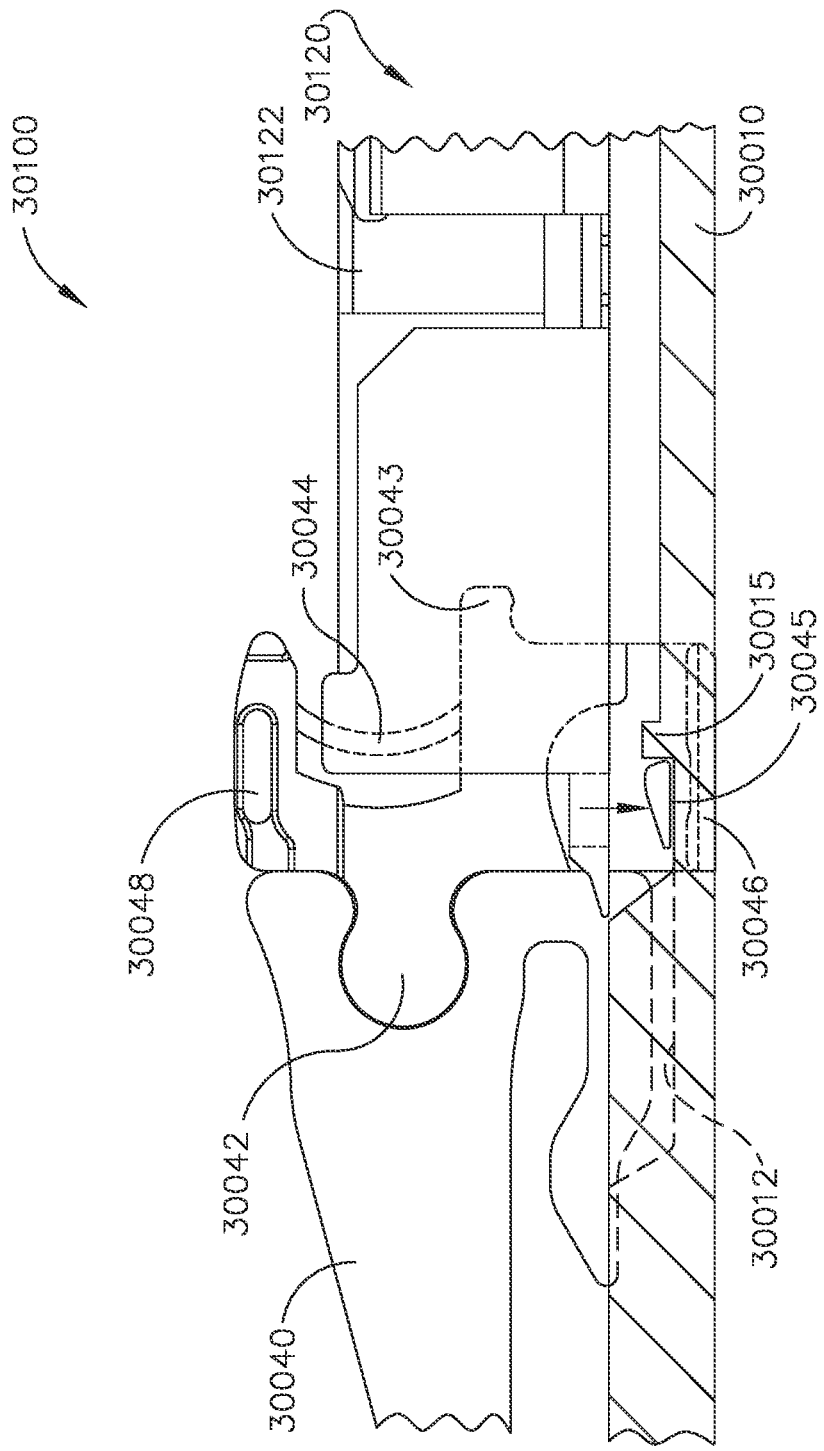
Figure 249:
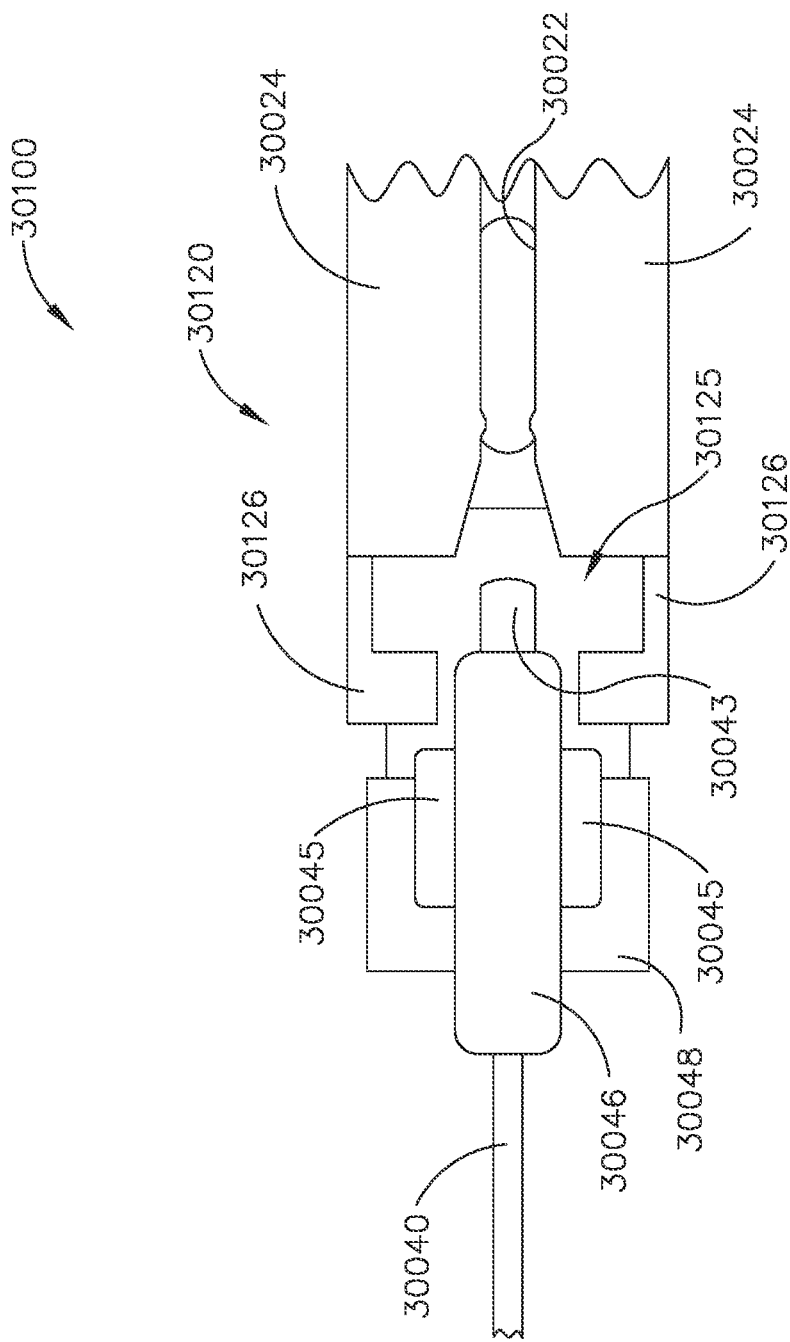
Figure 252:
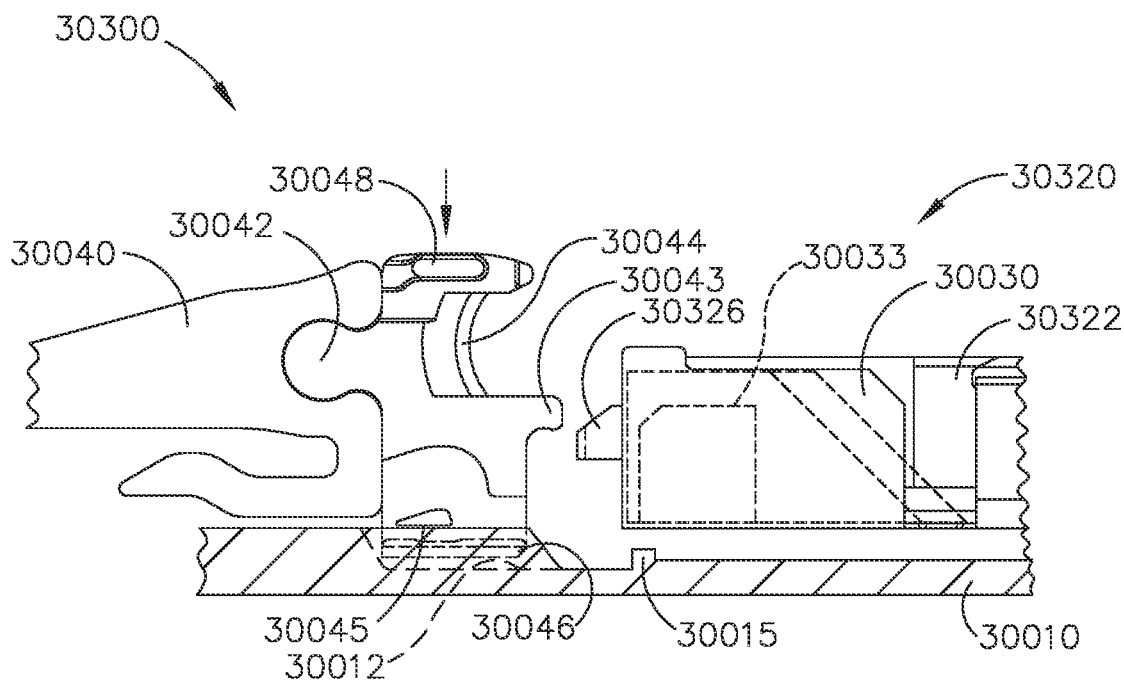
Figure 253:
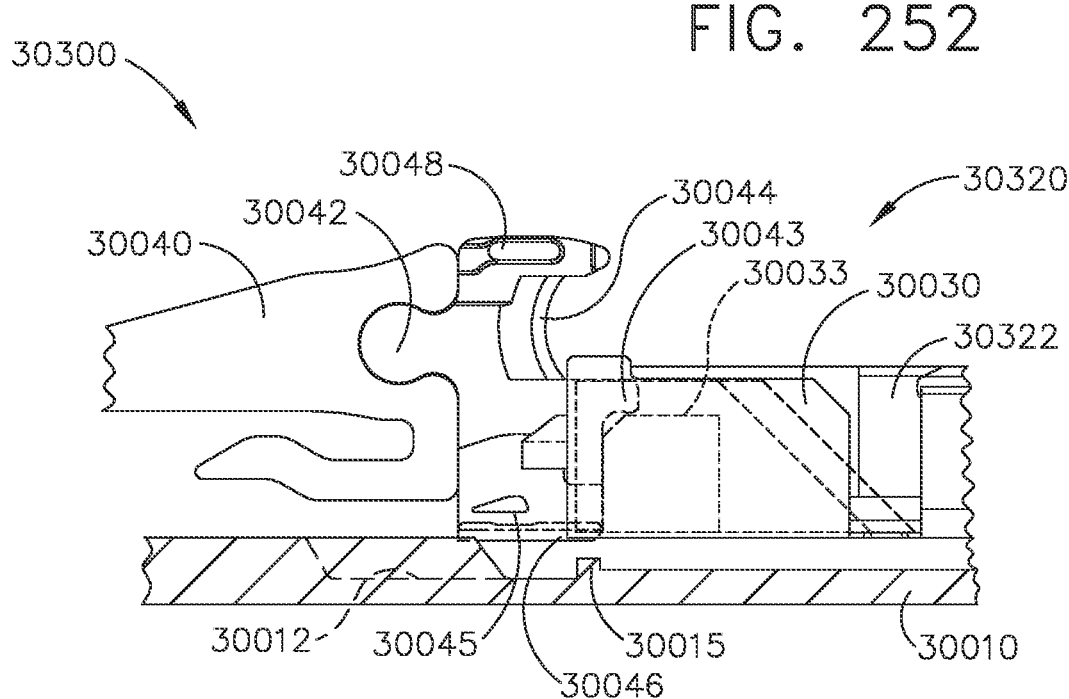
Figure 254:
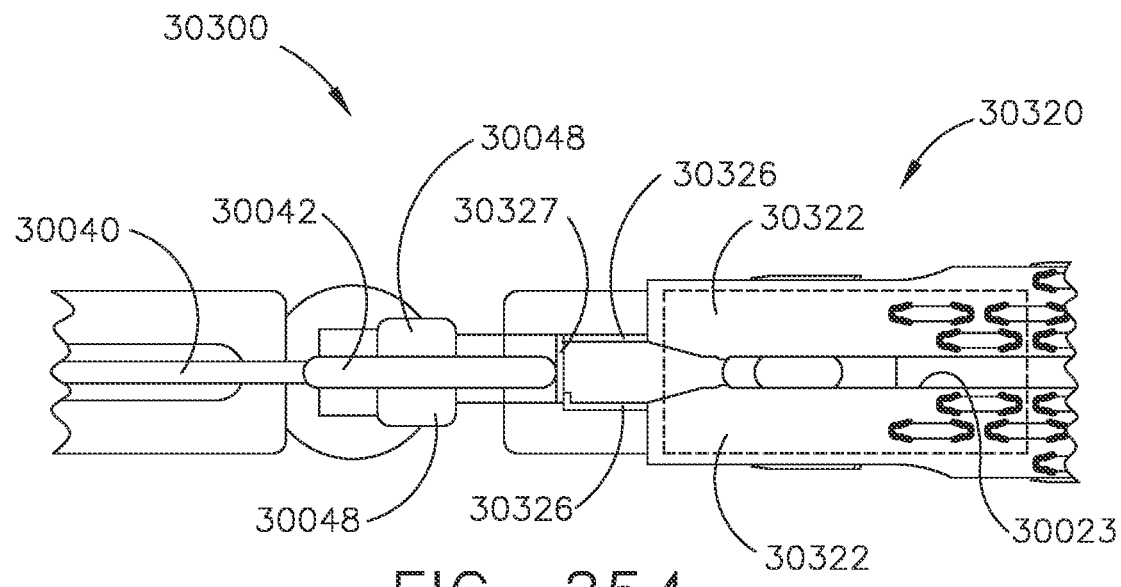
Figure 255:
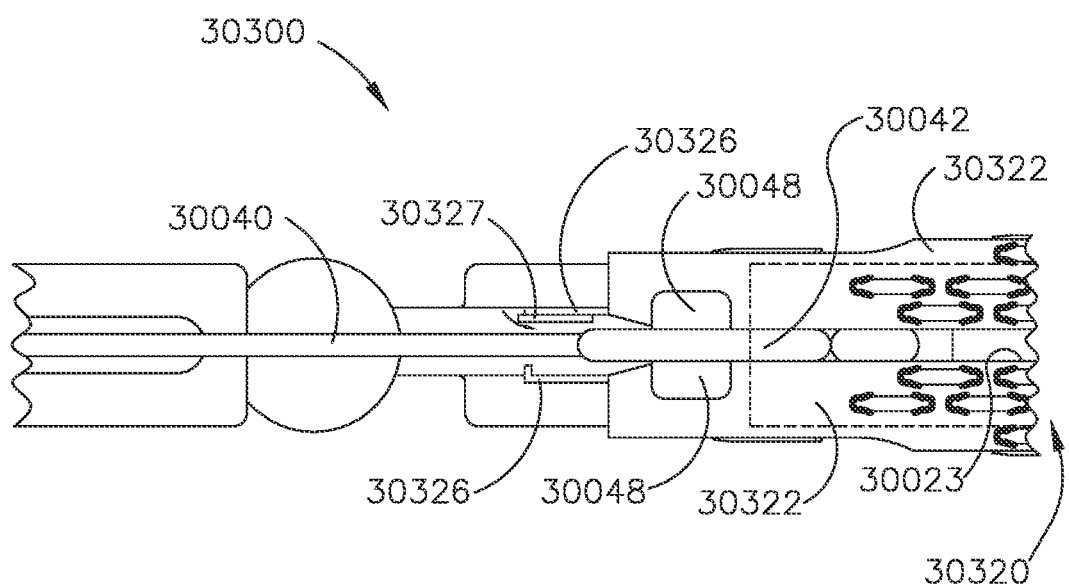
Figure 258:
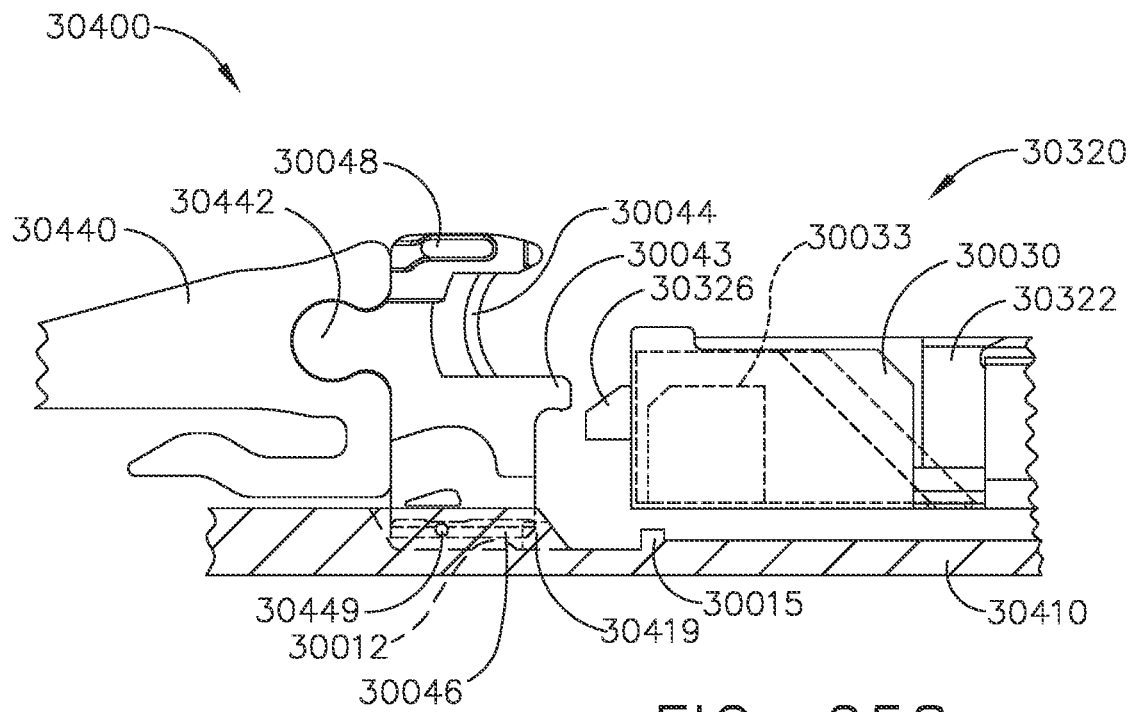
Figure 259:
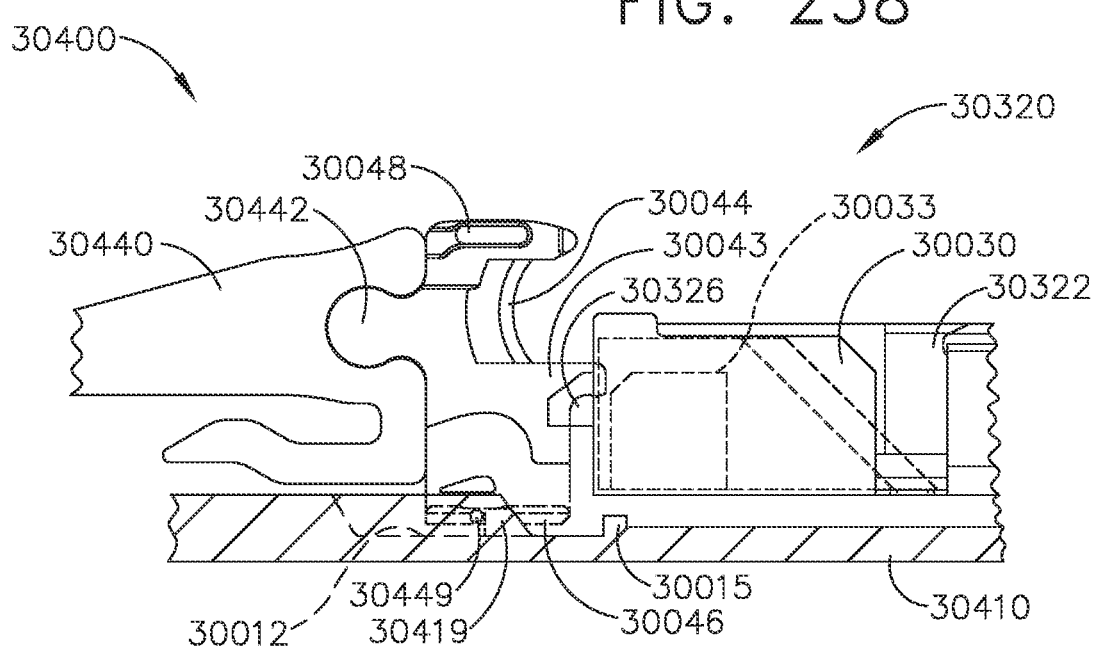
Figure 260:
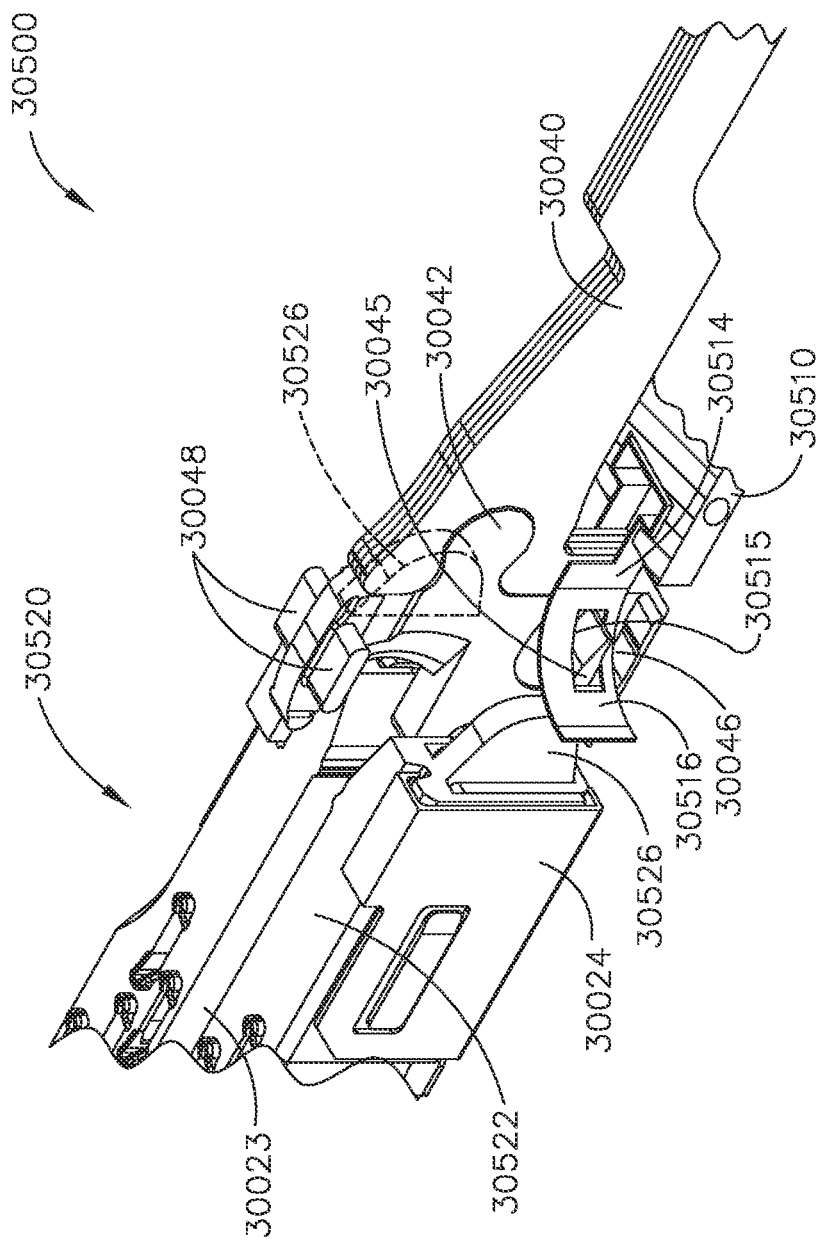
Figure 261:
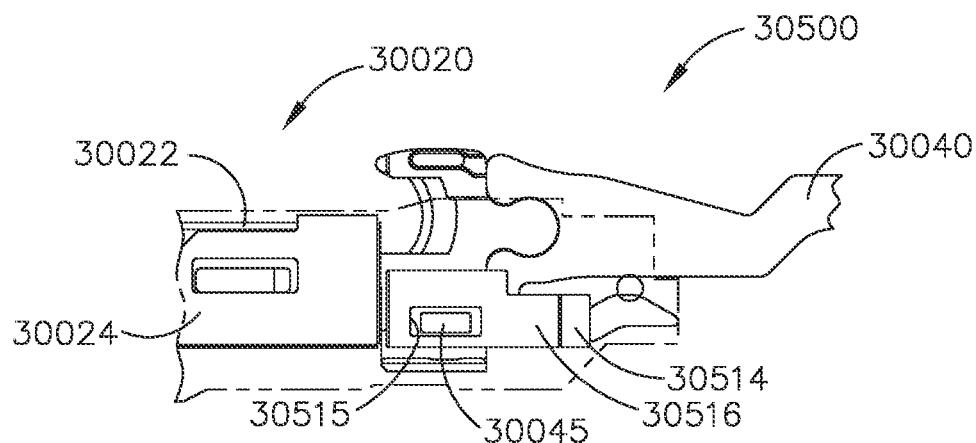
Figure 262:
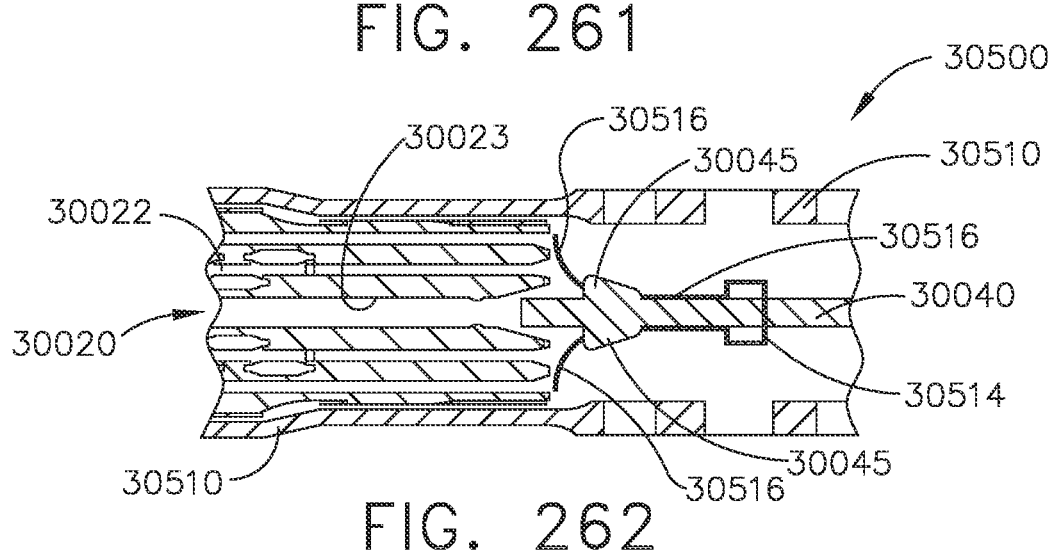
Figure 263:
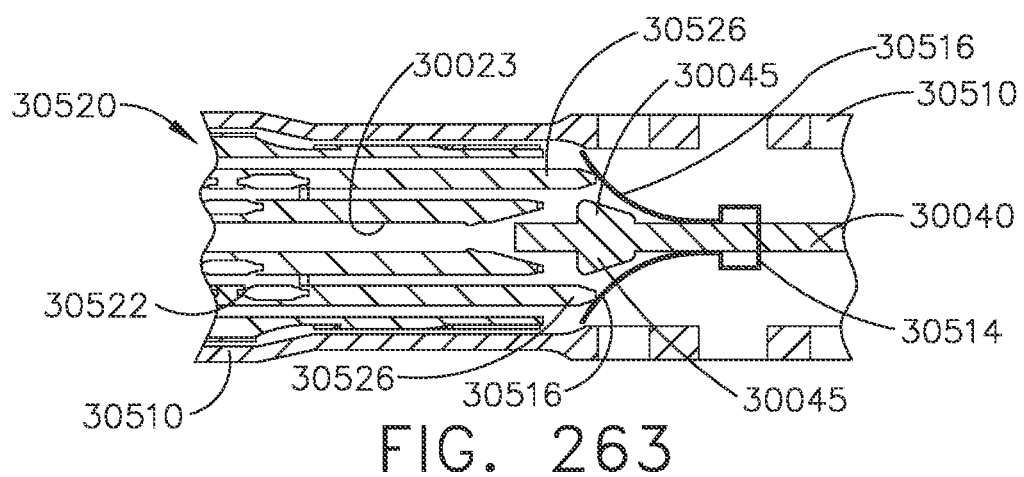
Figure 264:
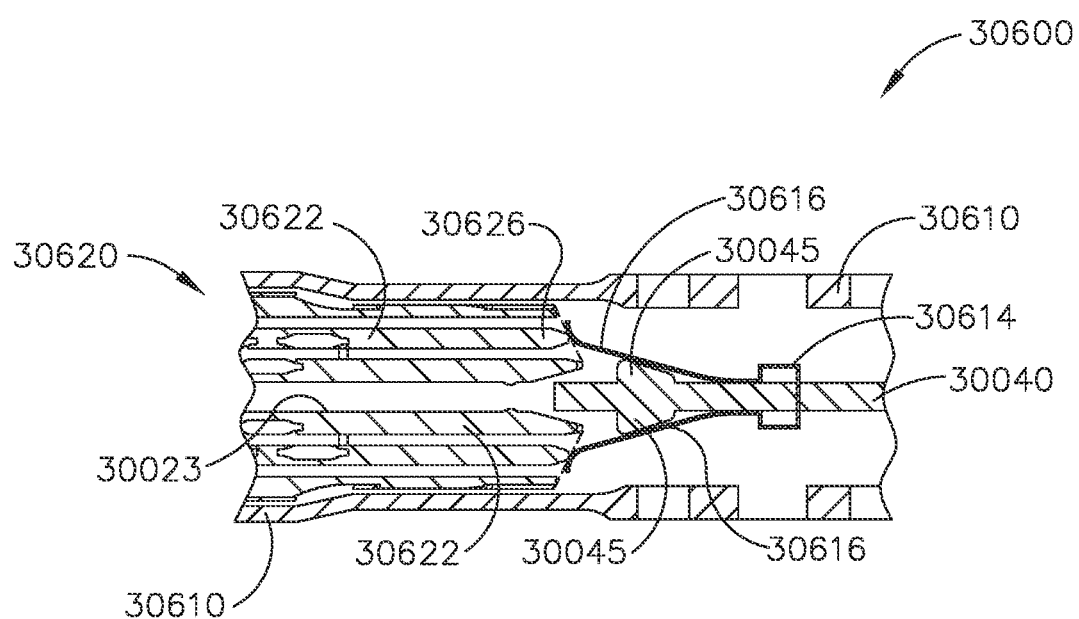
Figure 265:
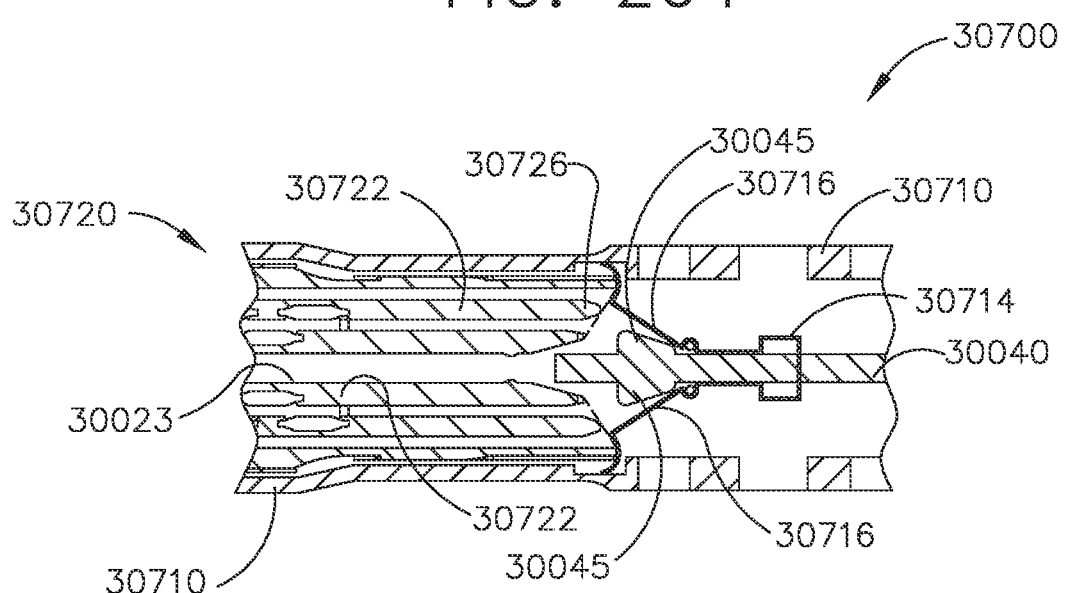
Figure 267:
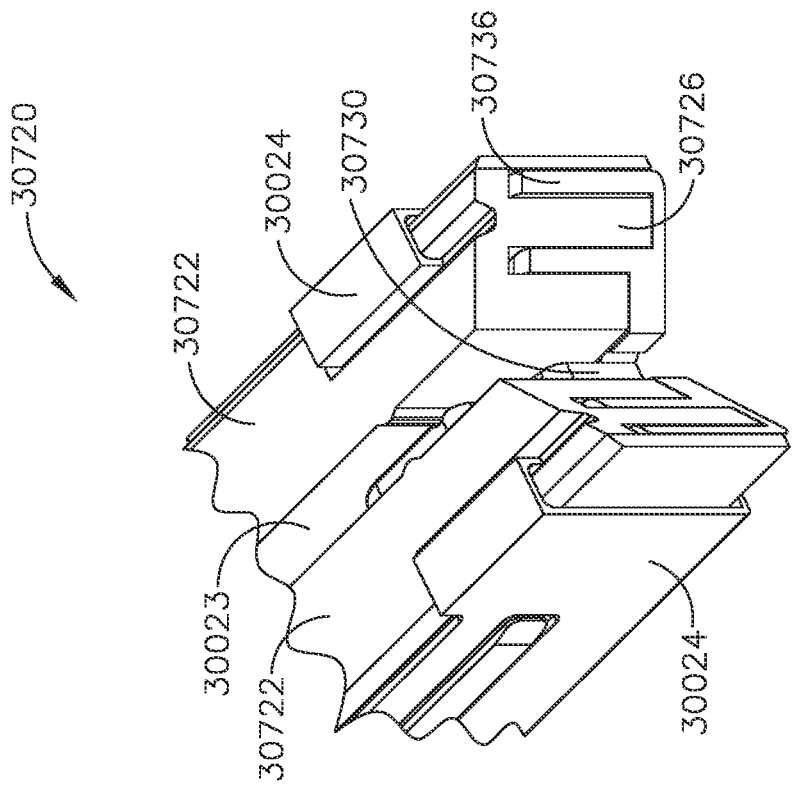
Figure 266:
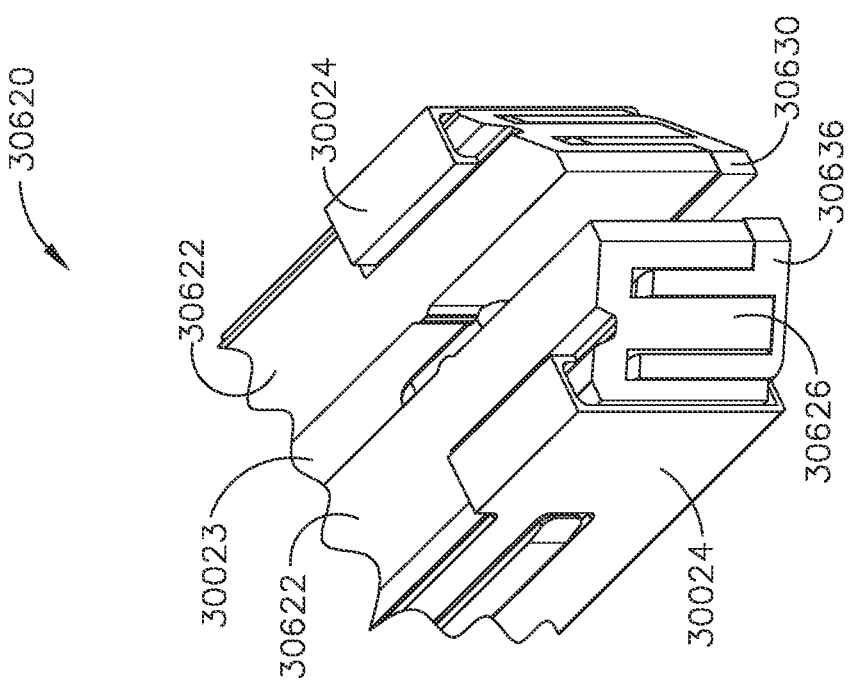
Figure 268:
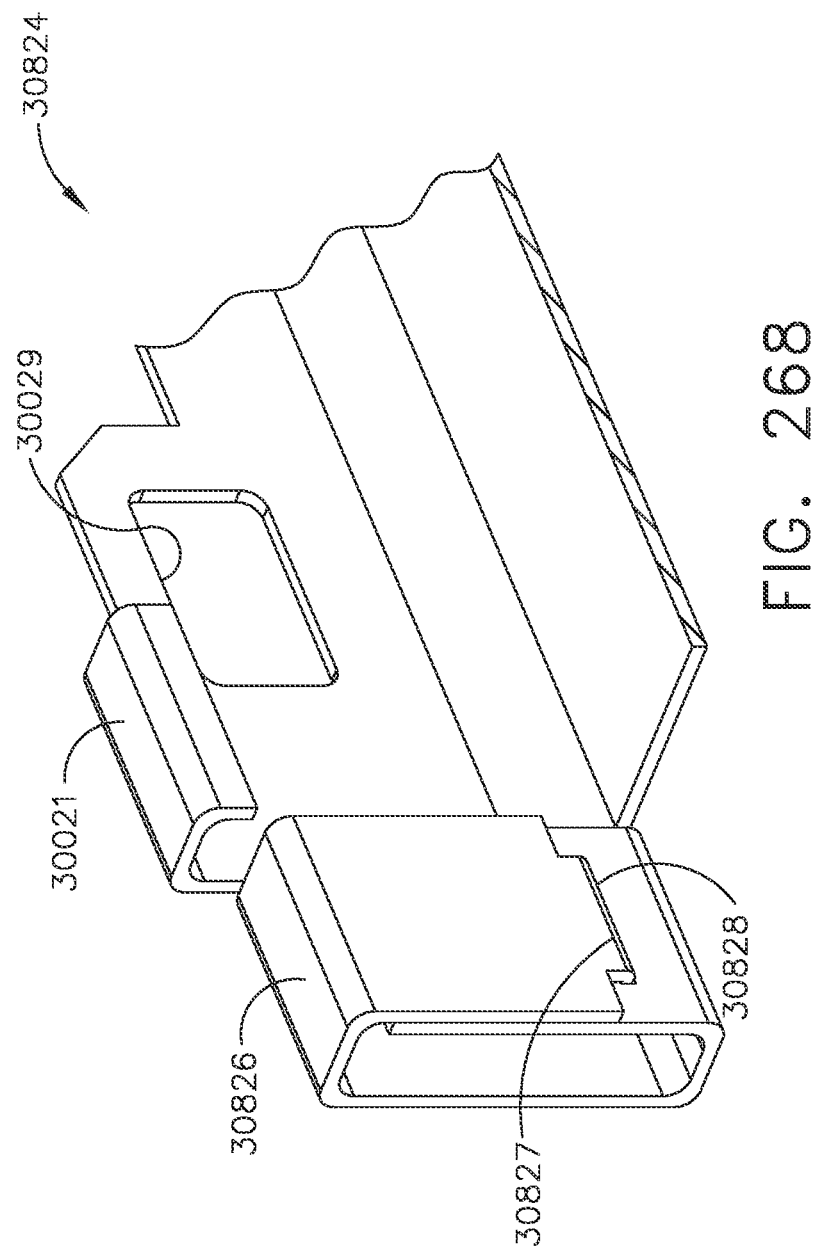
Figure 269:
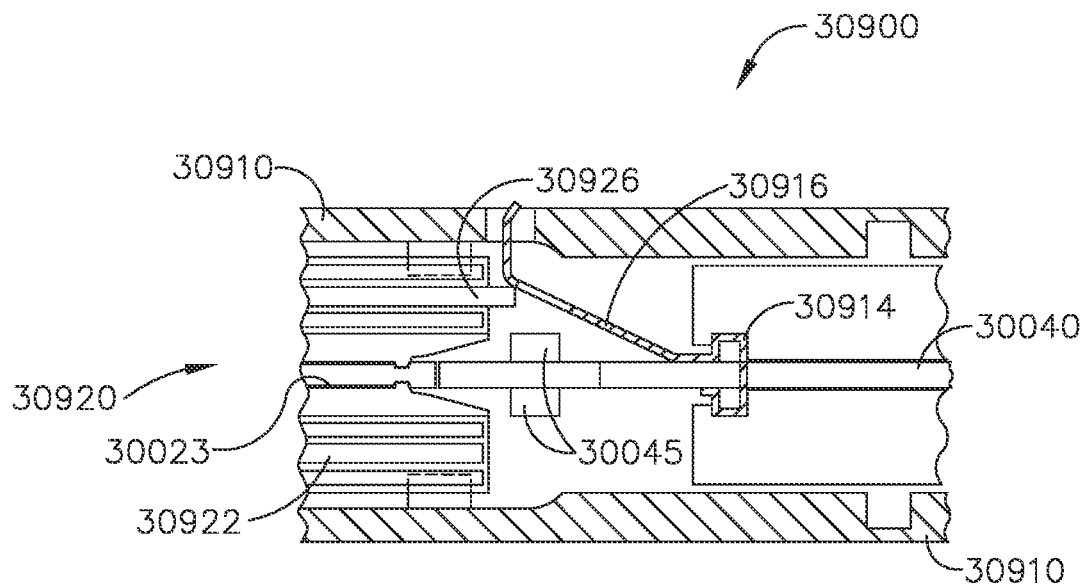
Figure 270:
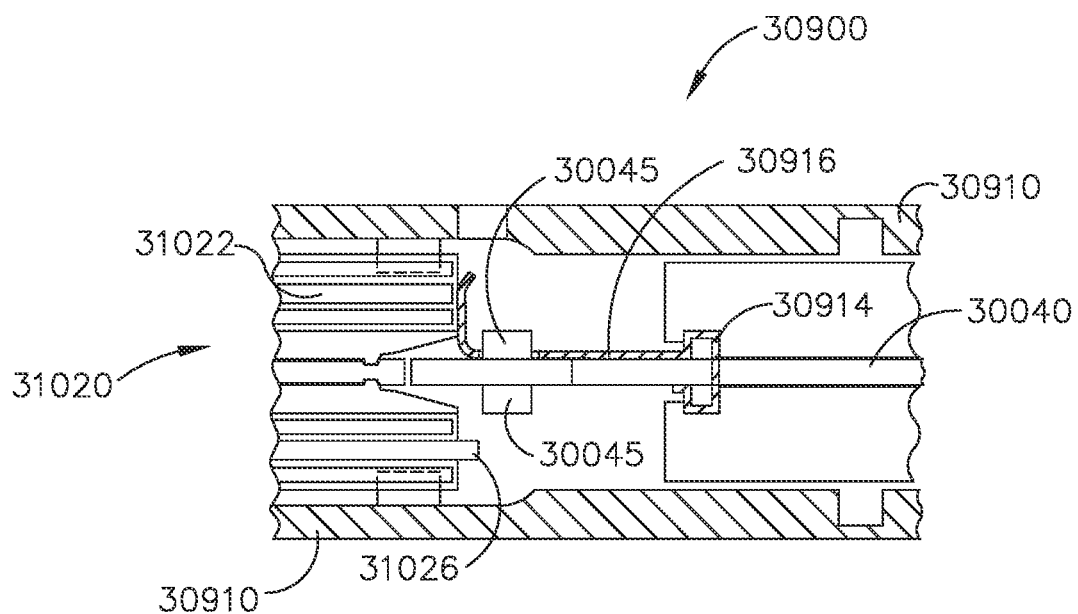
Figure 273:
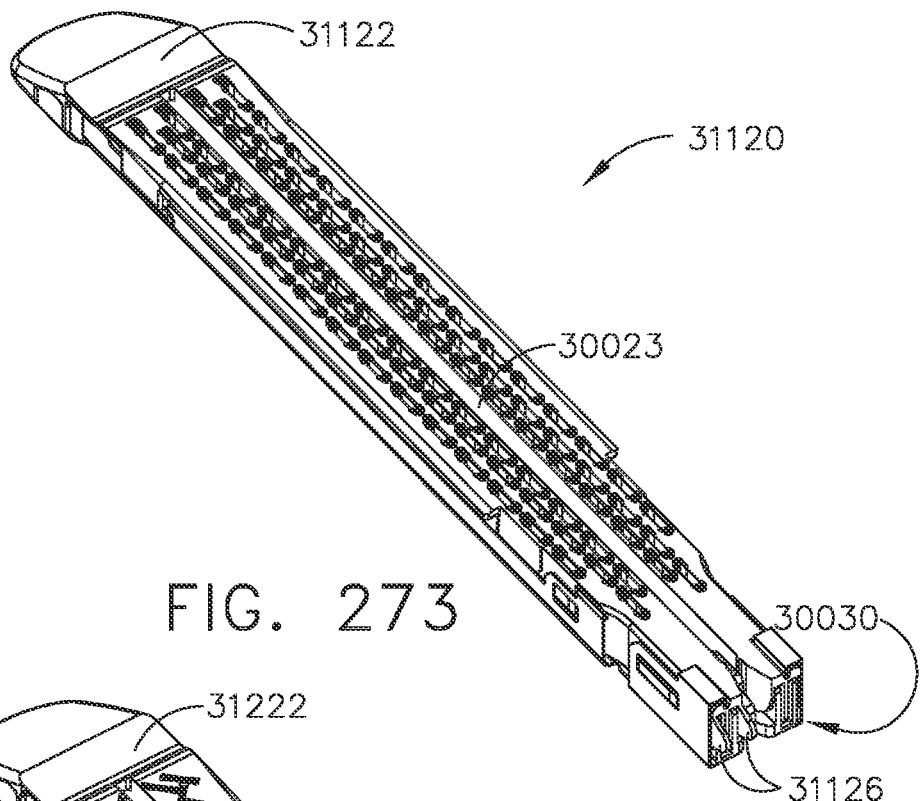
Figure 274:
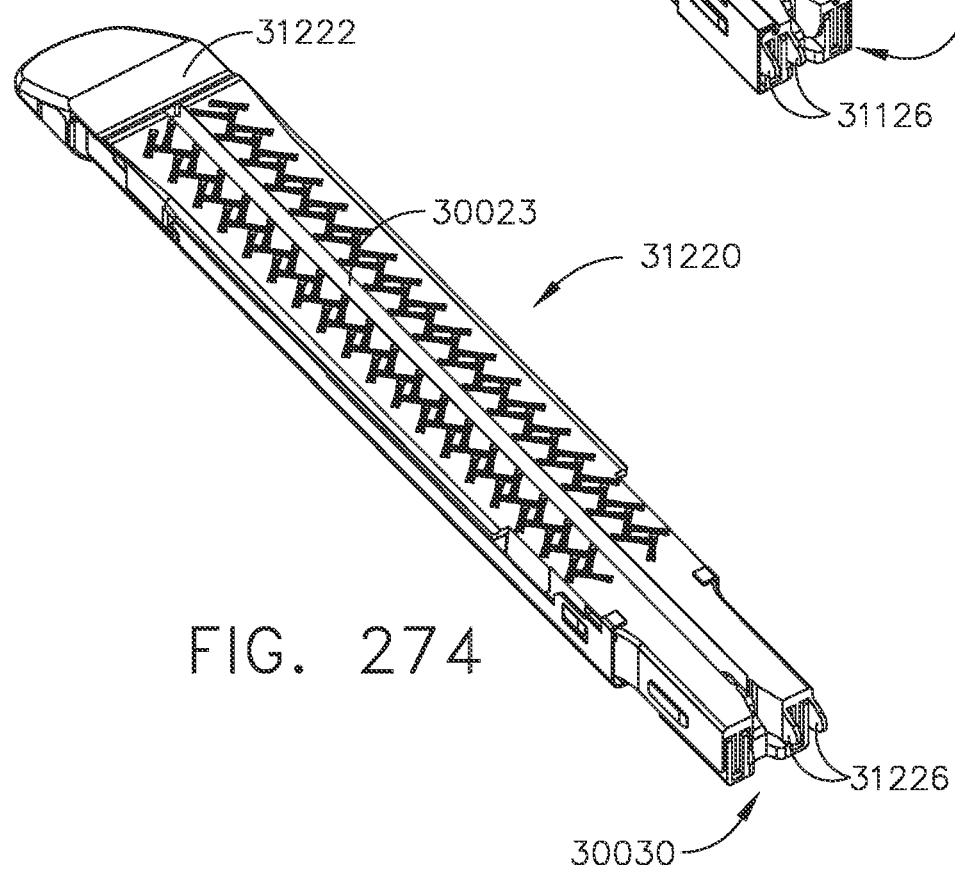
Figure 275:
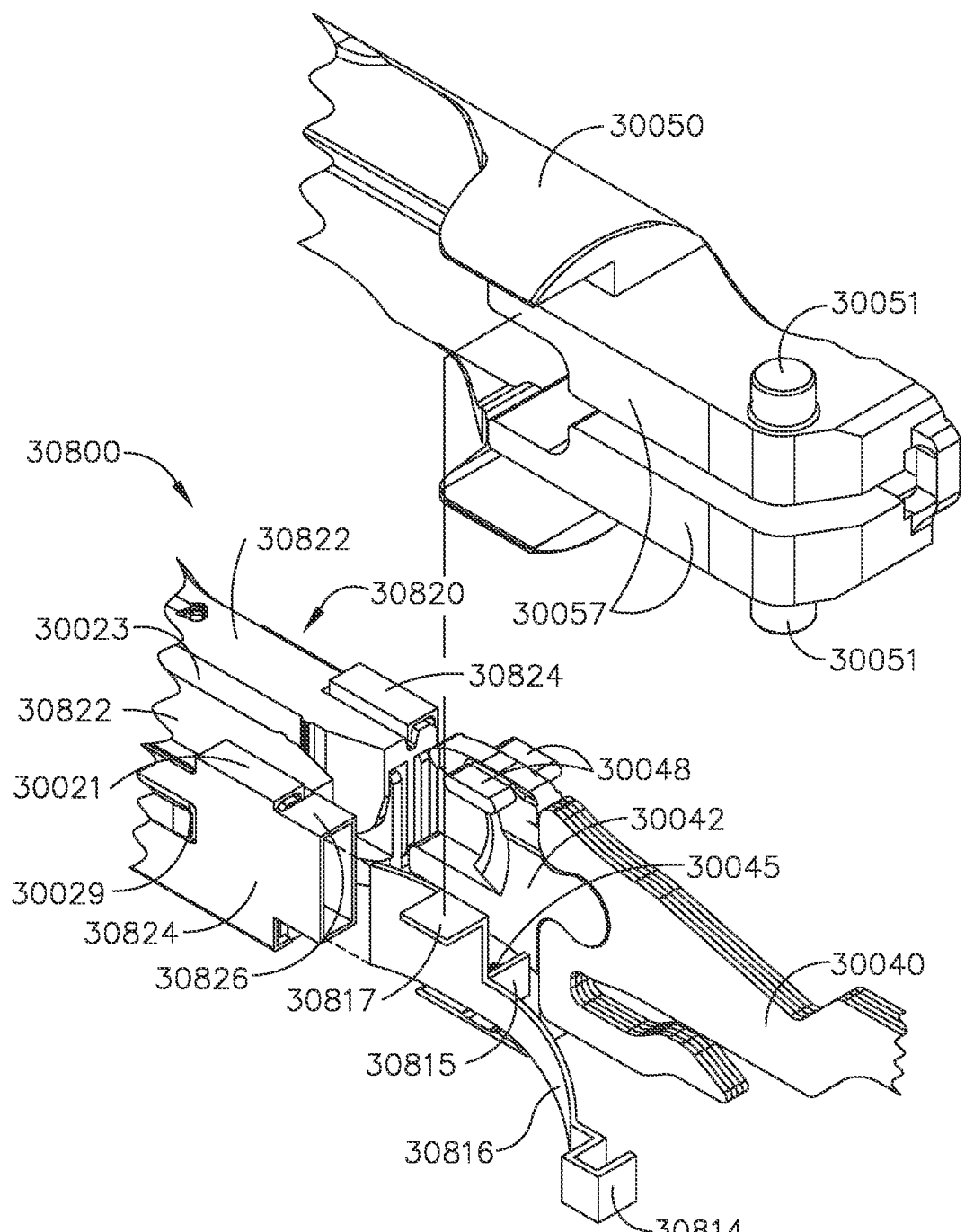
Figure 276:
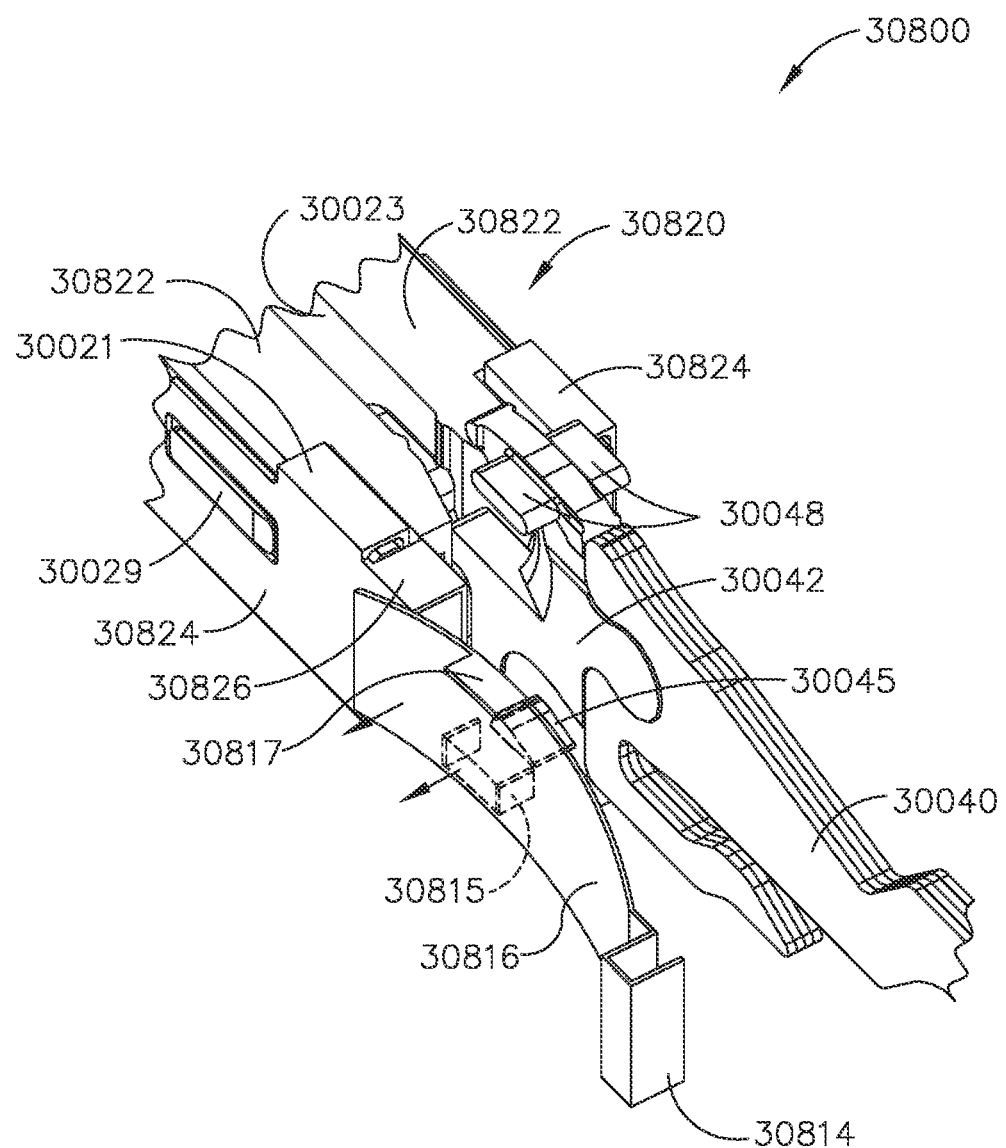
Figure 277:
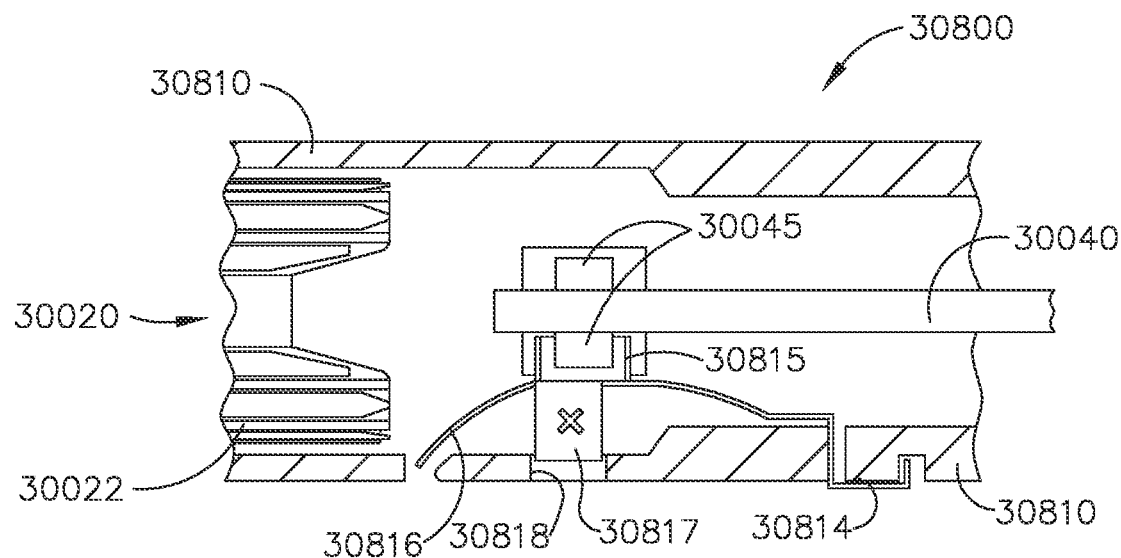
Figure 278:
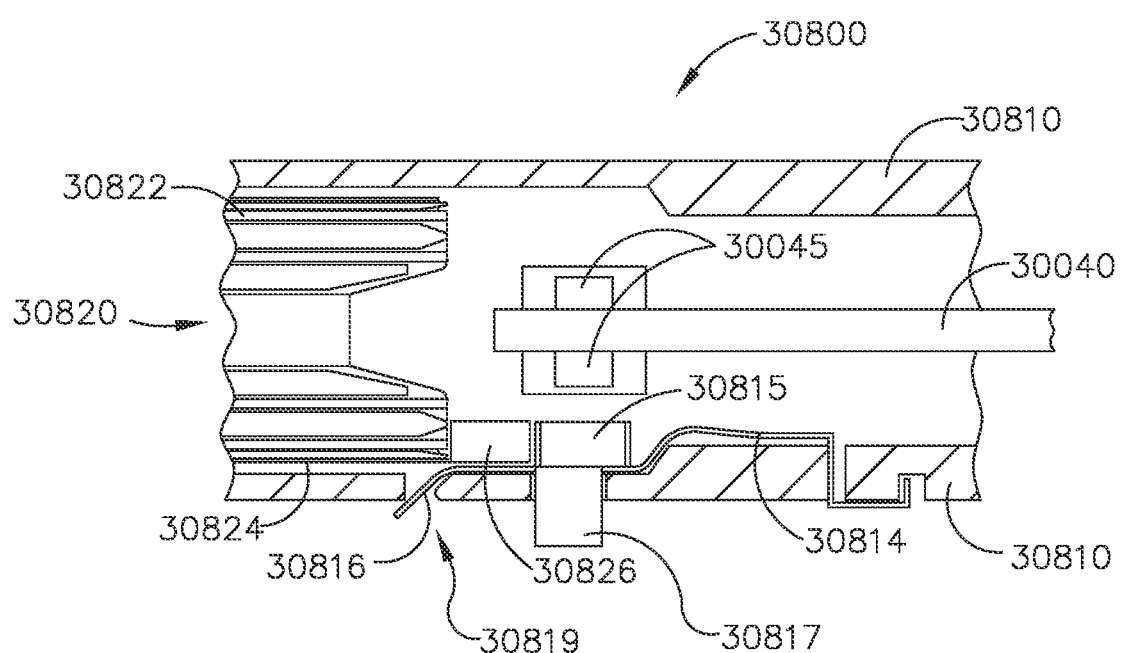
Figure 279:
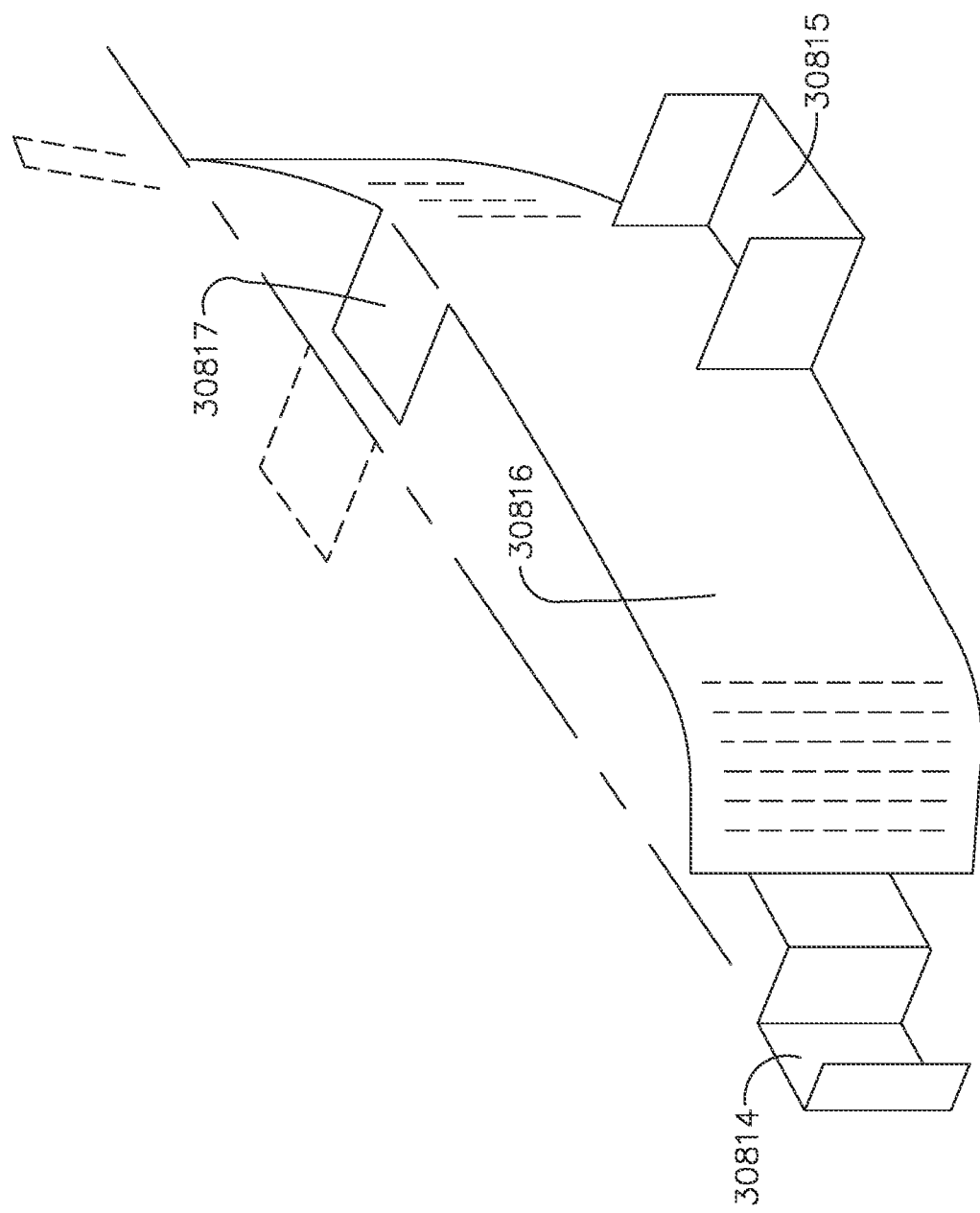
Figure 279B:
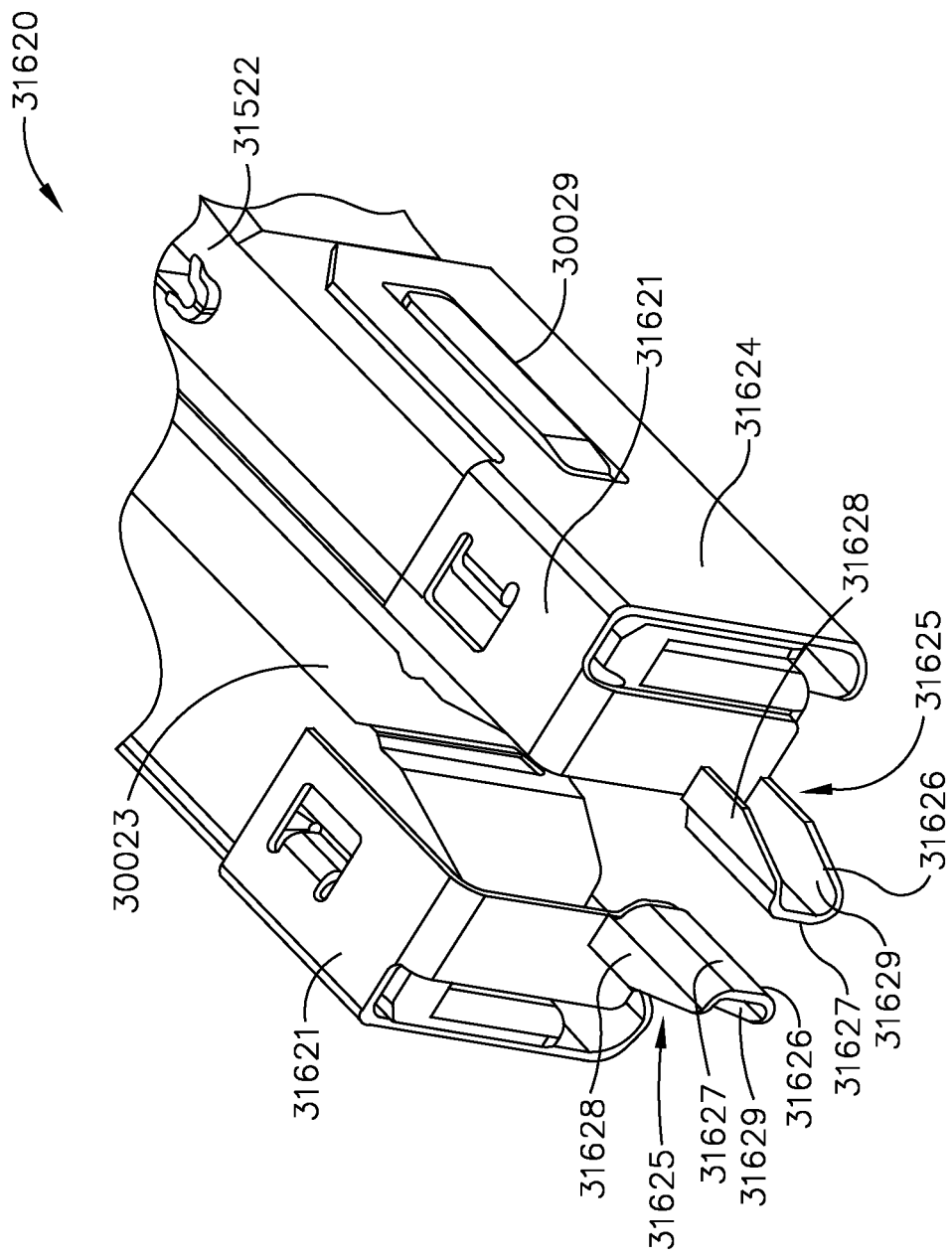
Figure 279C:
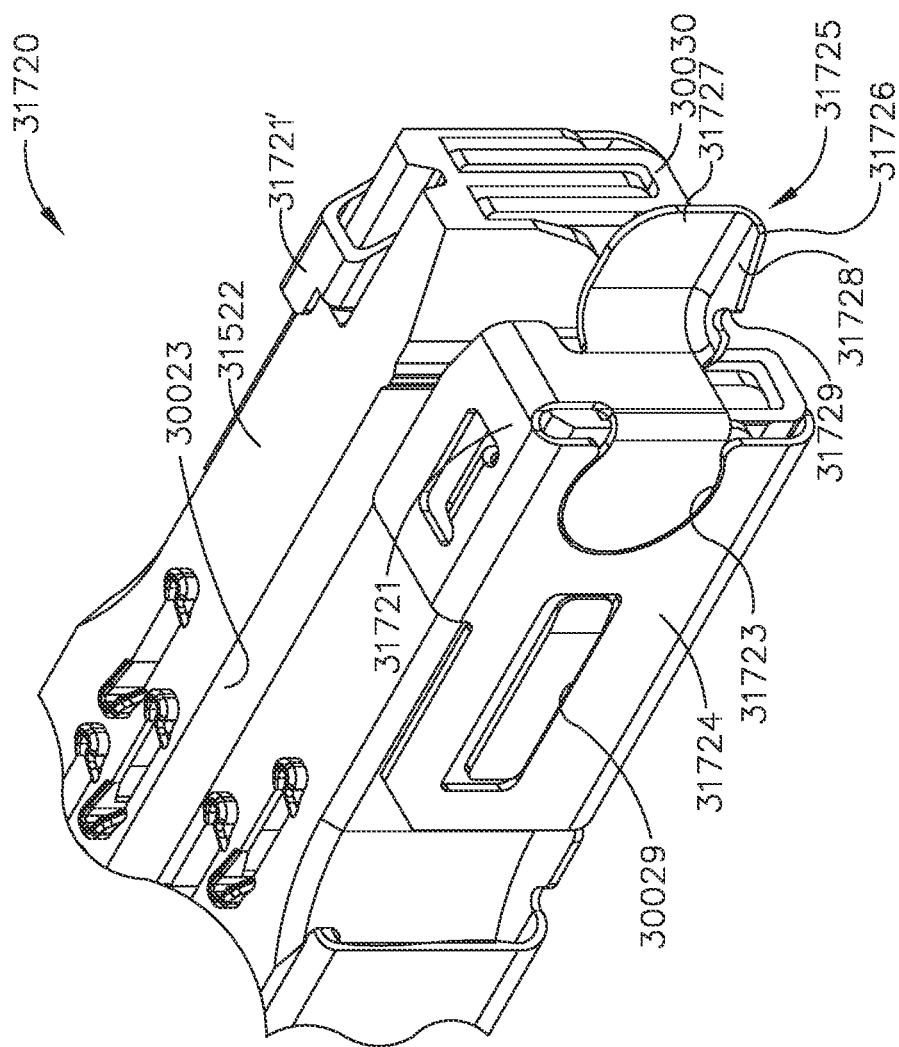
Figure 279D:
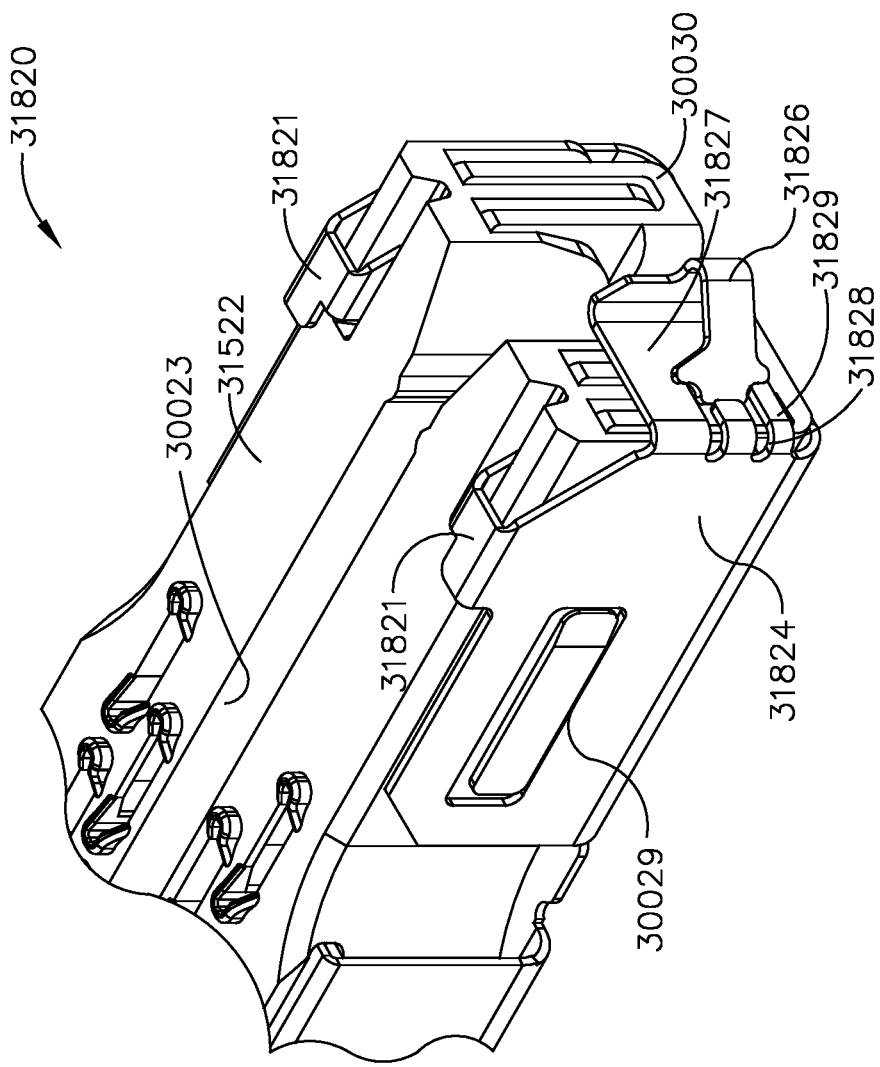
Figure 279E:
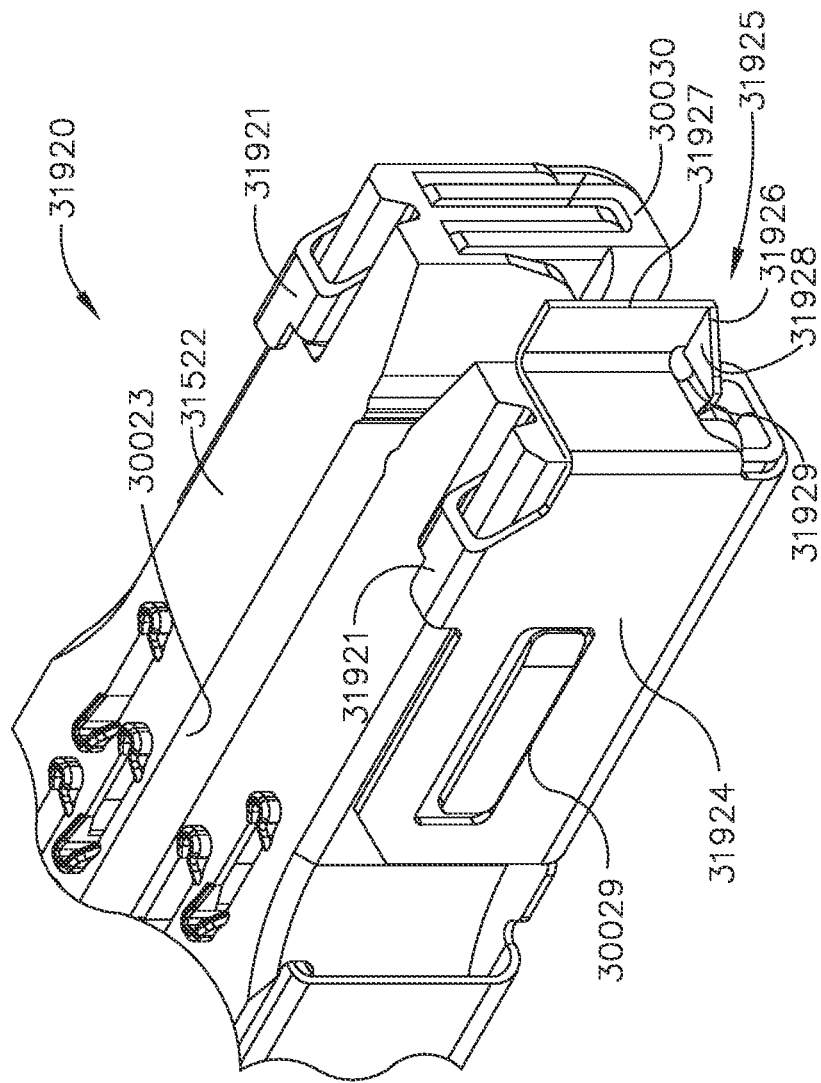
Figure 280:
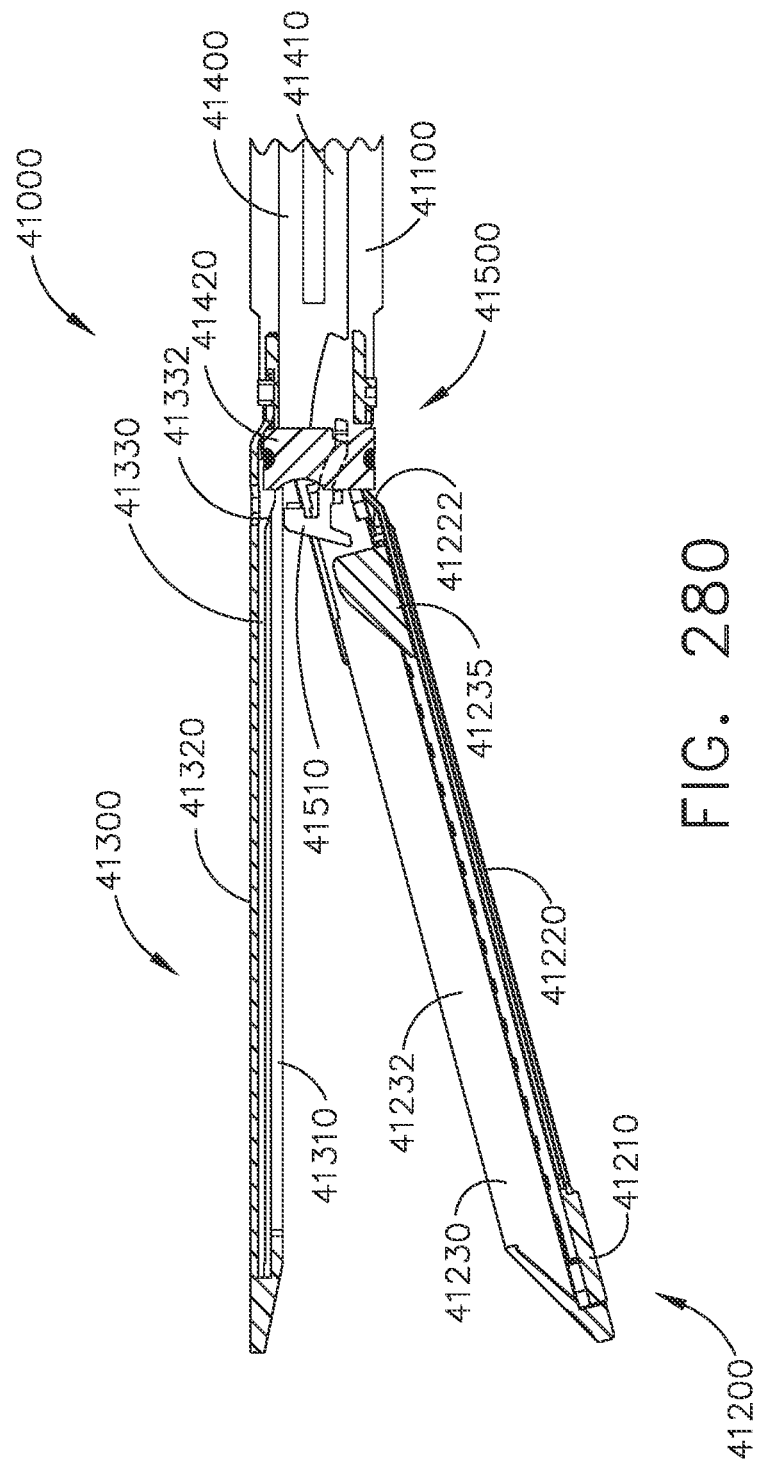
Figure 281:
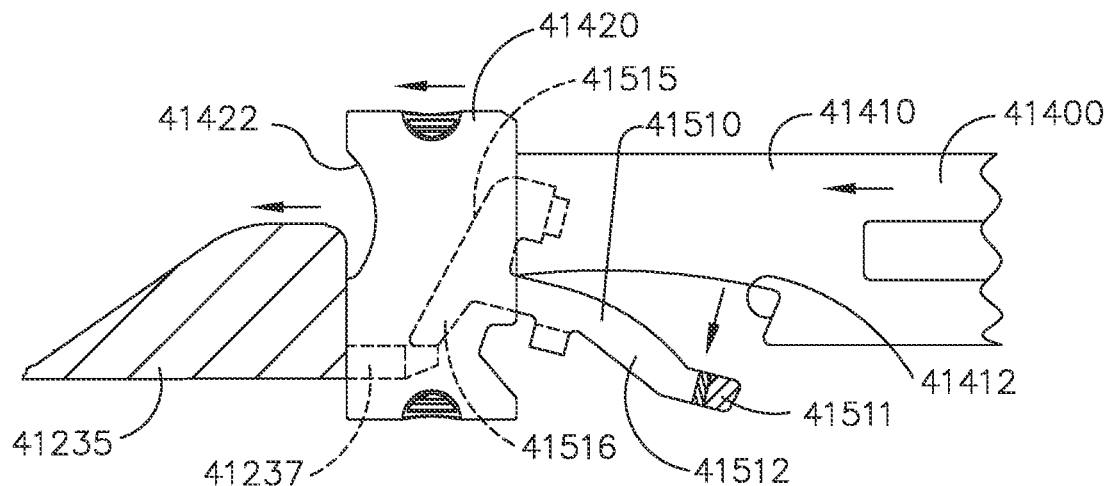
Figure 282:
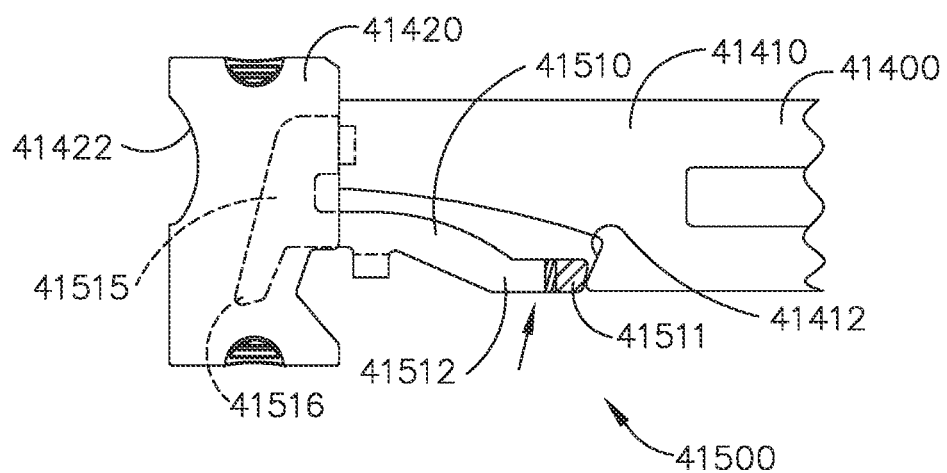
Figure 283:
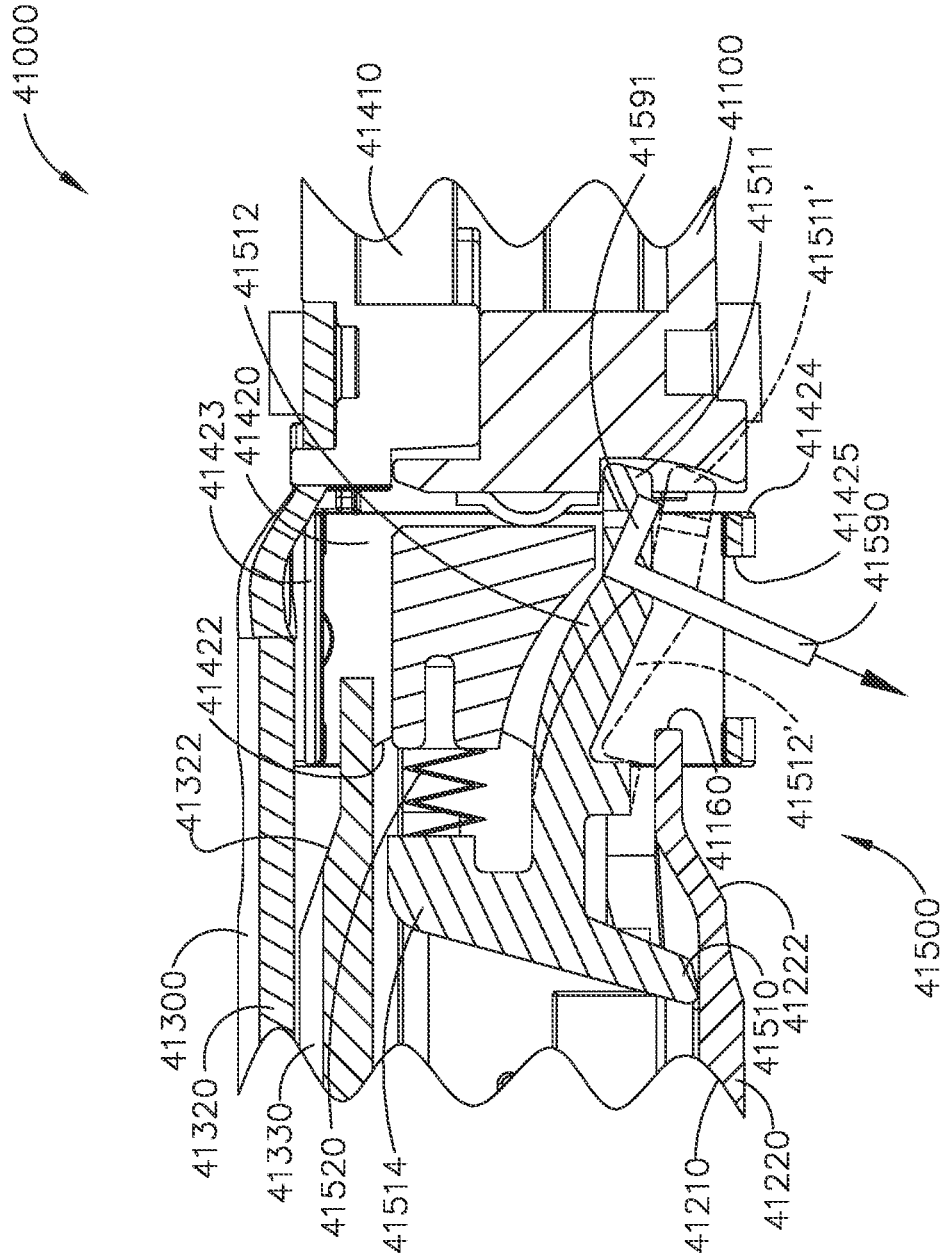
Figure 284:
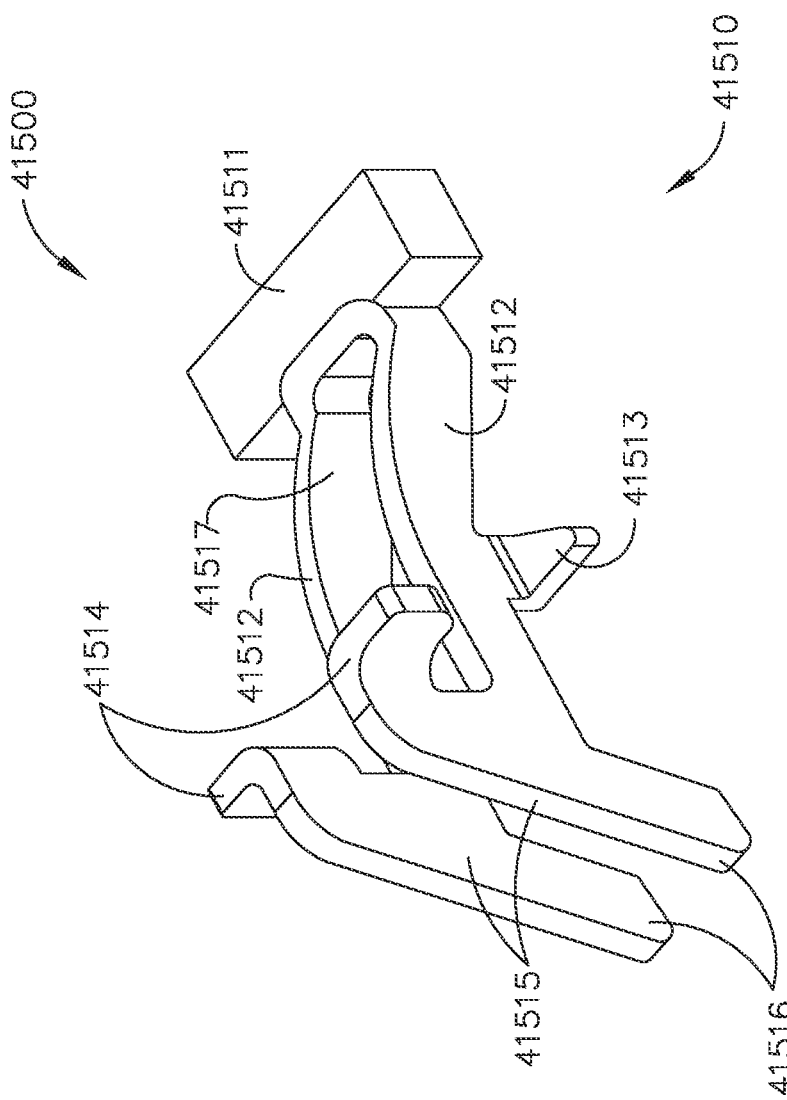
Figure 285:
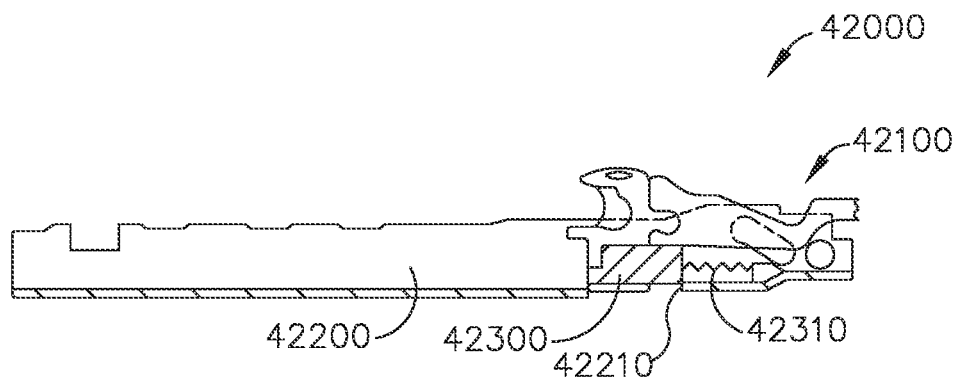
Figure 286:
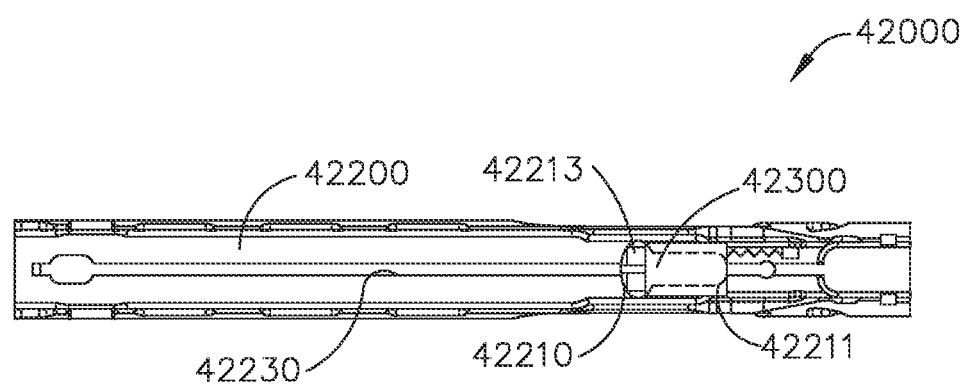
Figure 287:
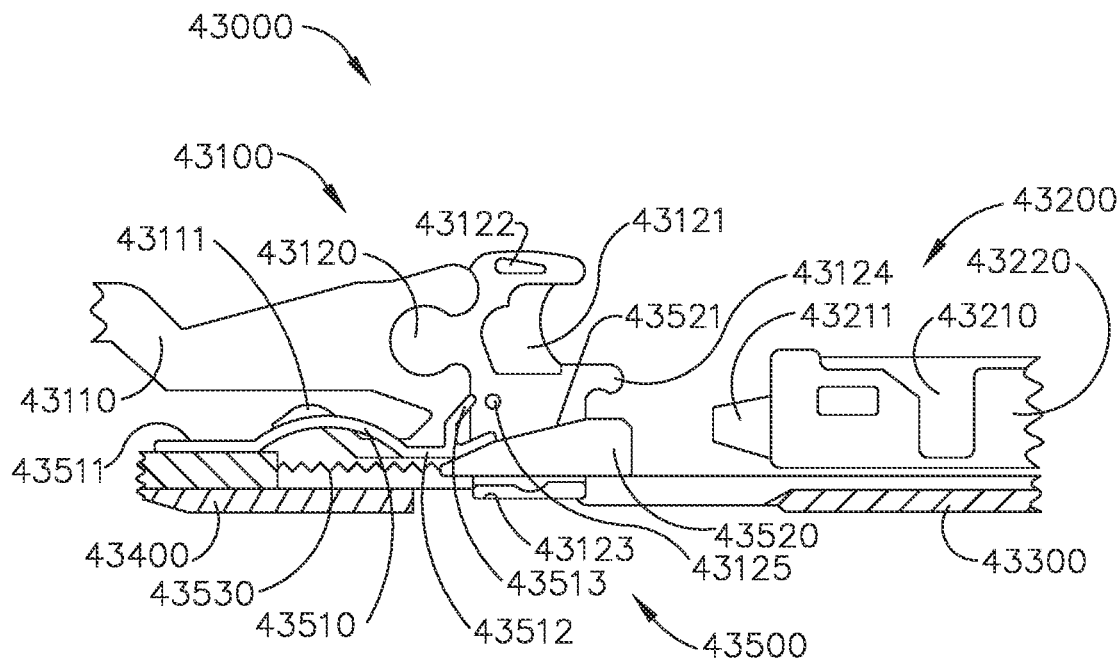
Figure 288:
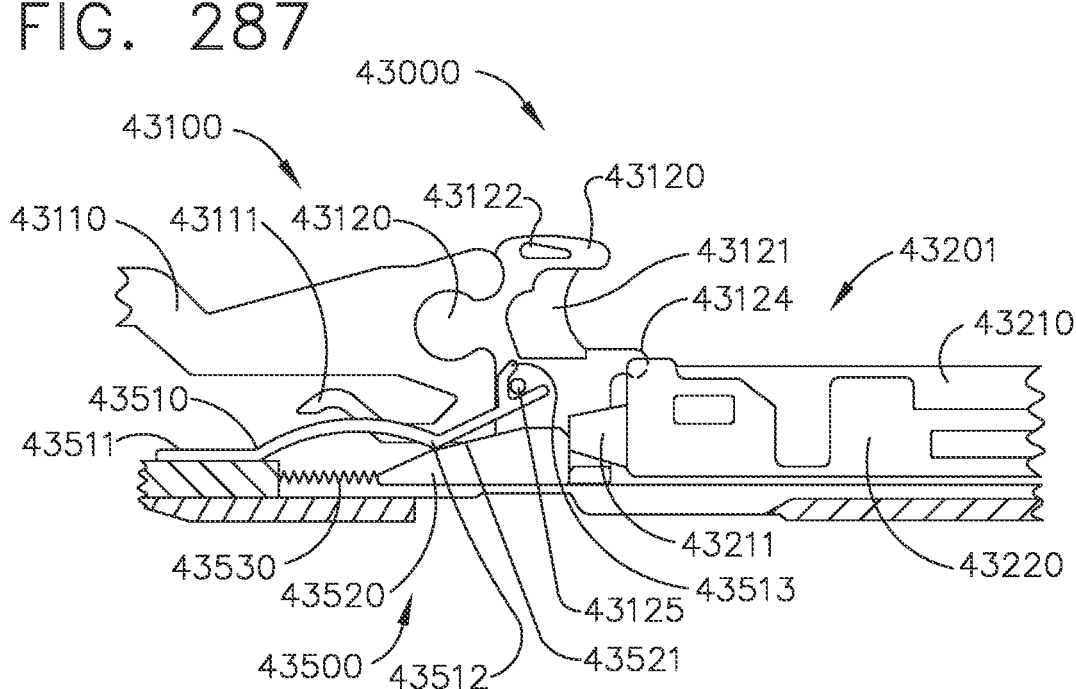
Figure 292:
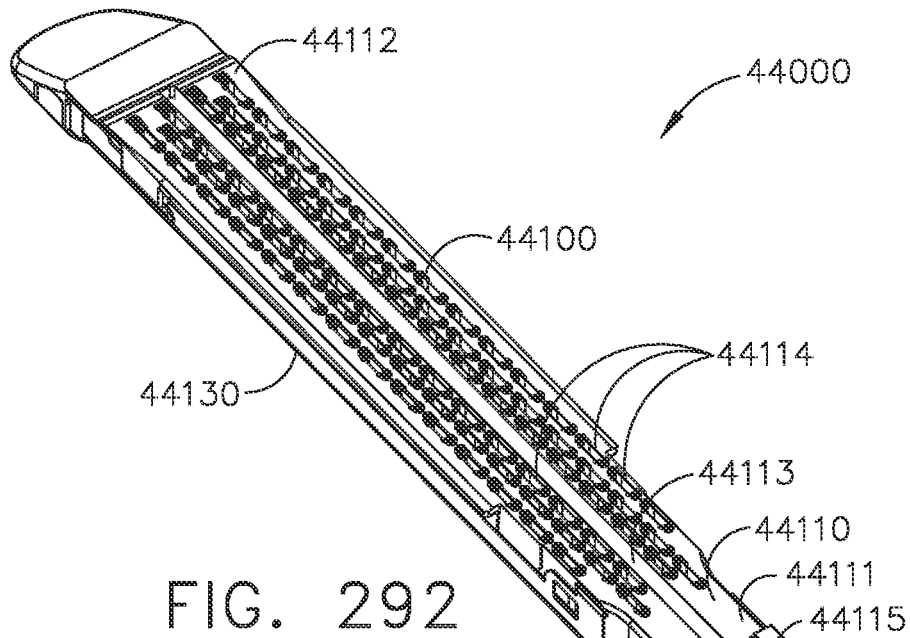
Figure 293:
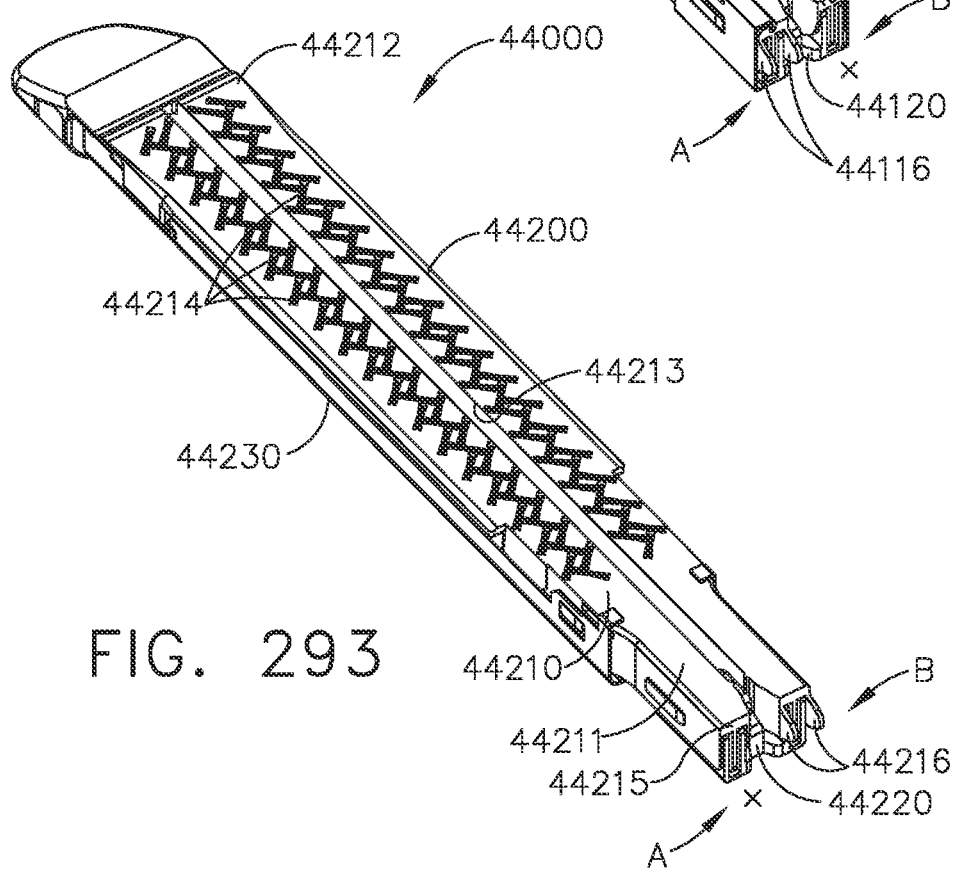
Figure 294:
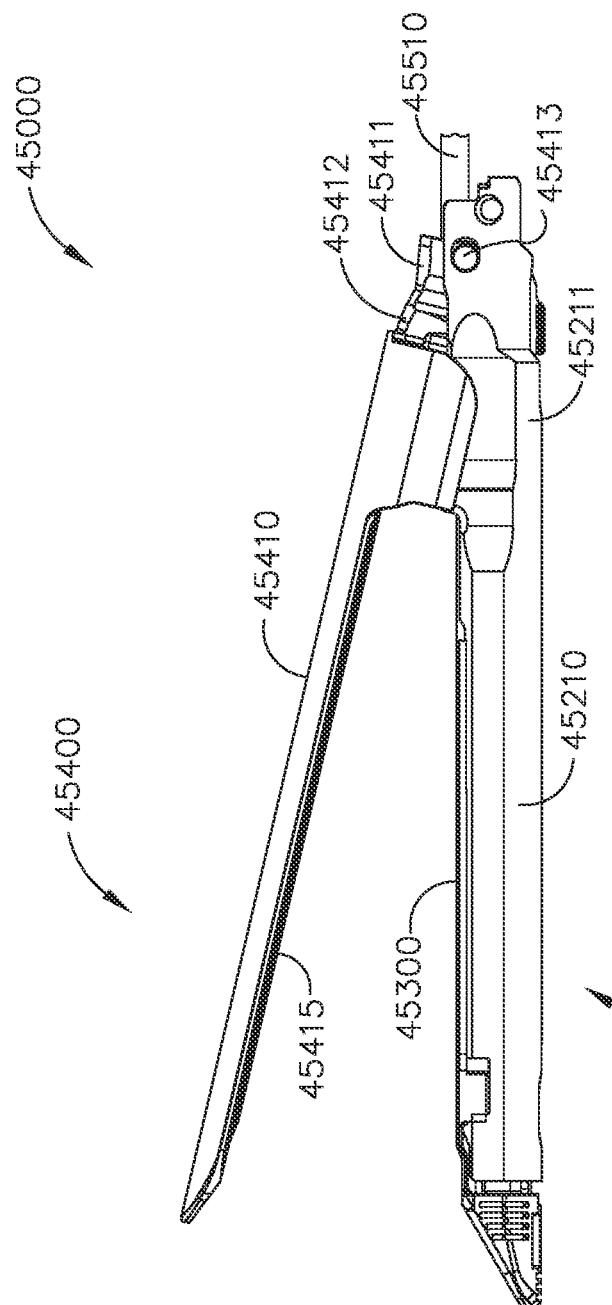
Figure 295:
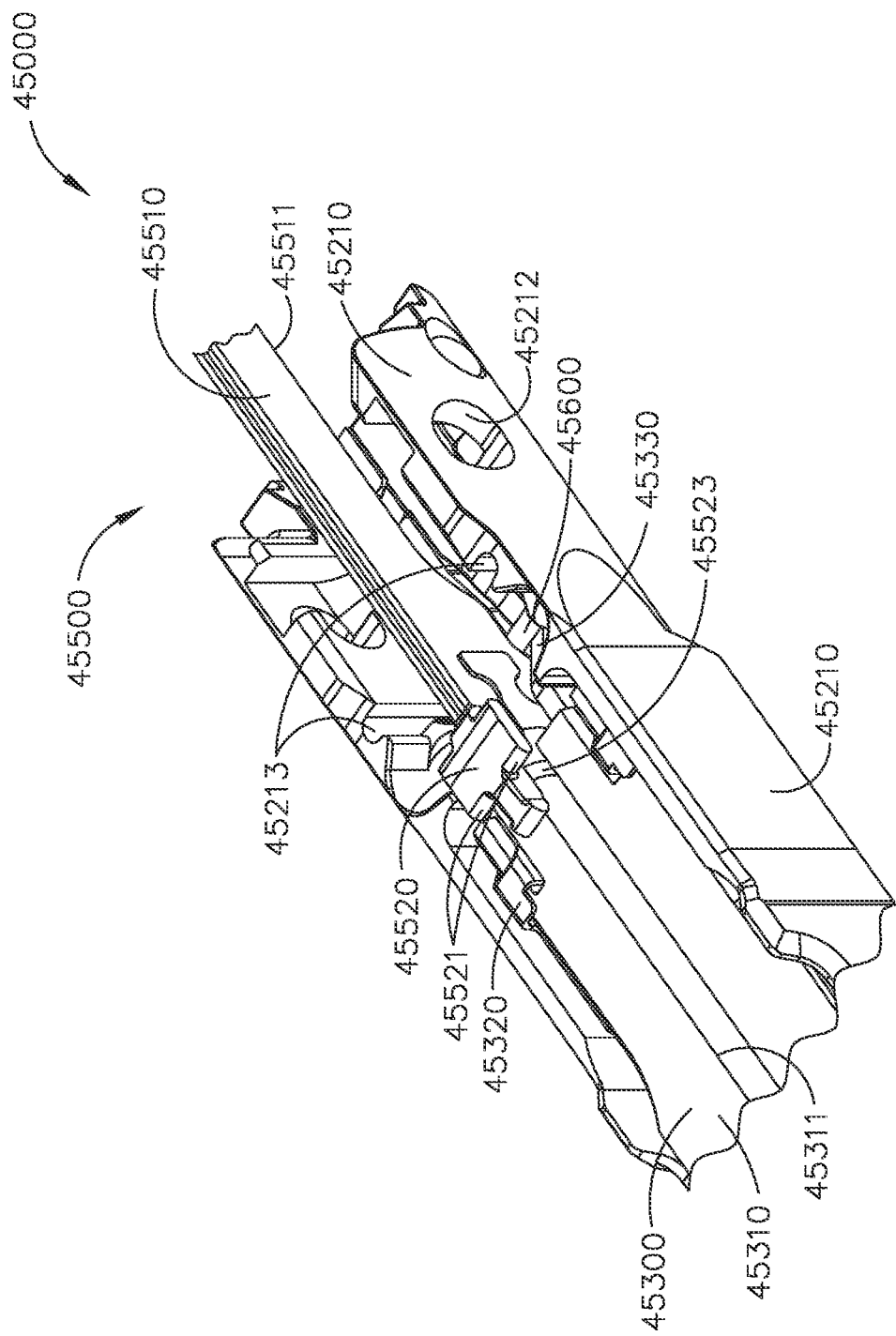
Figure 296:
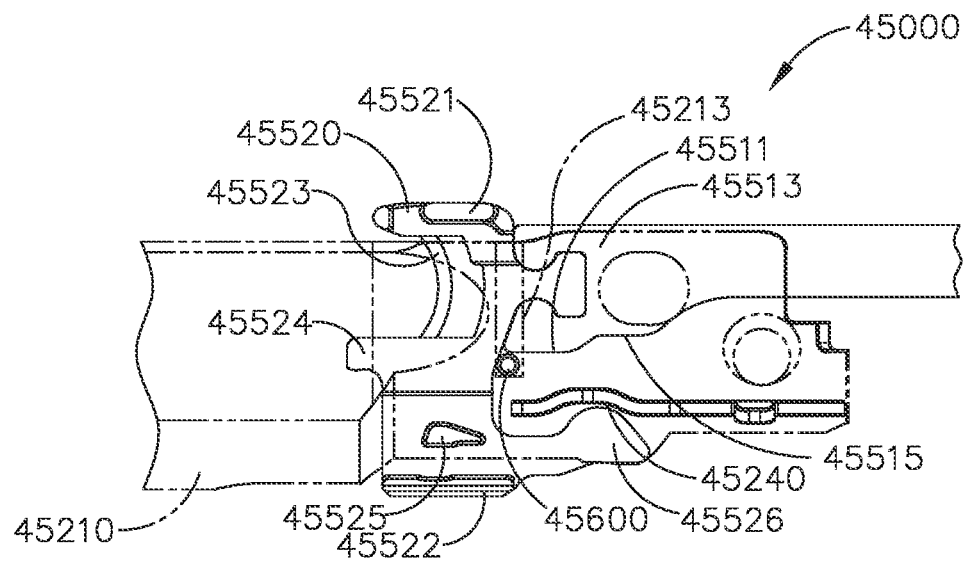
Figure 297:
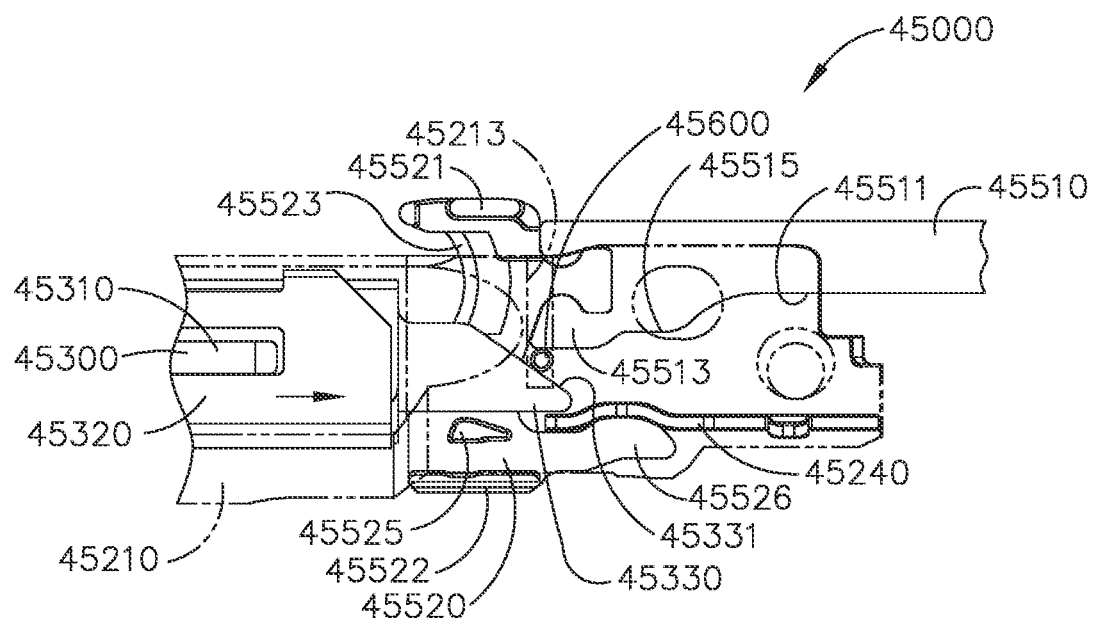
Figure 298:
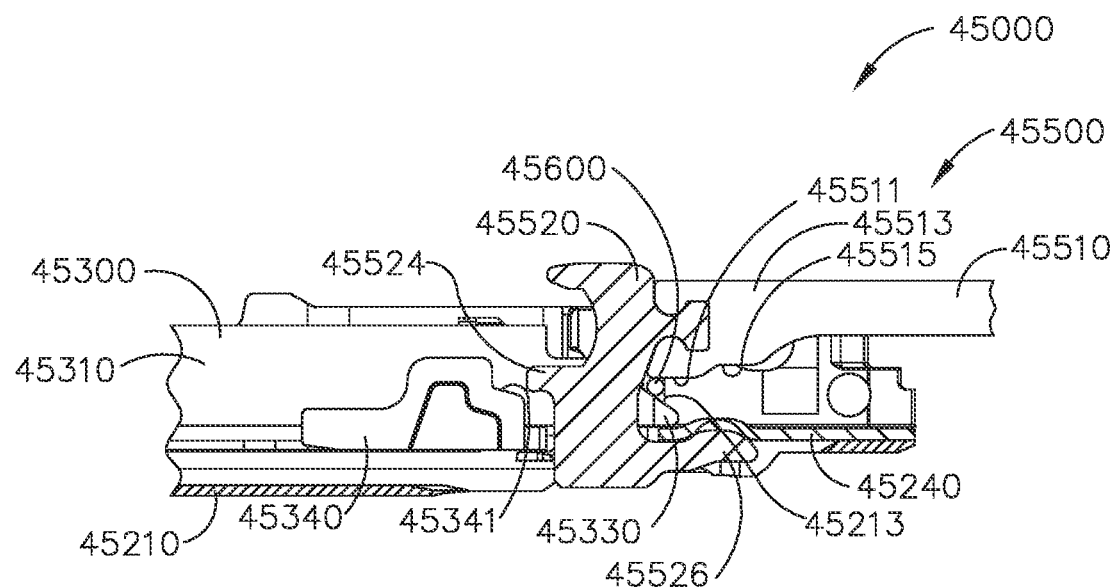
Figure 299:
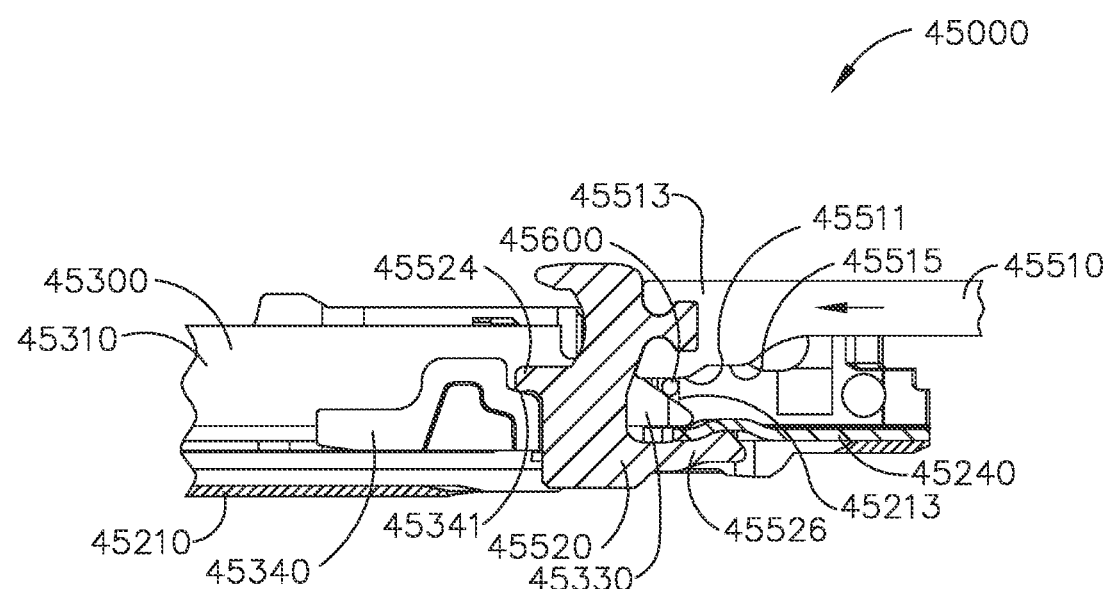
Figure 300:
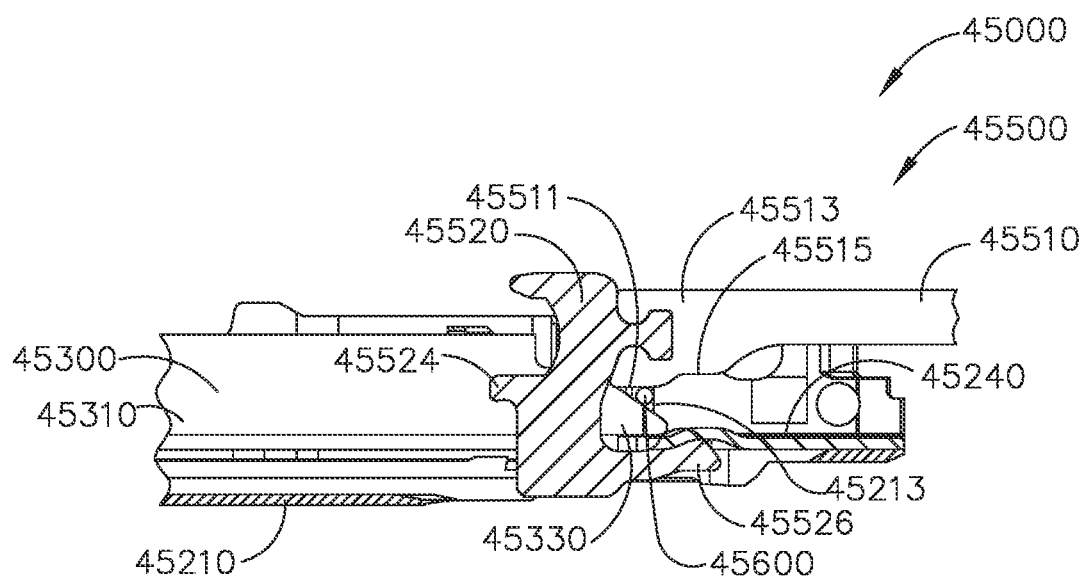
Figure 301:
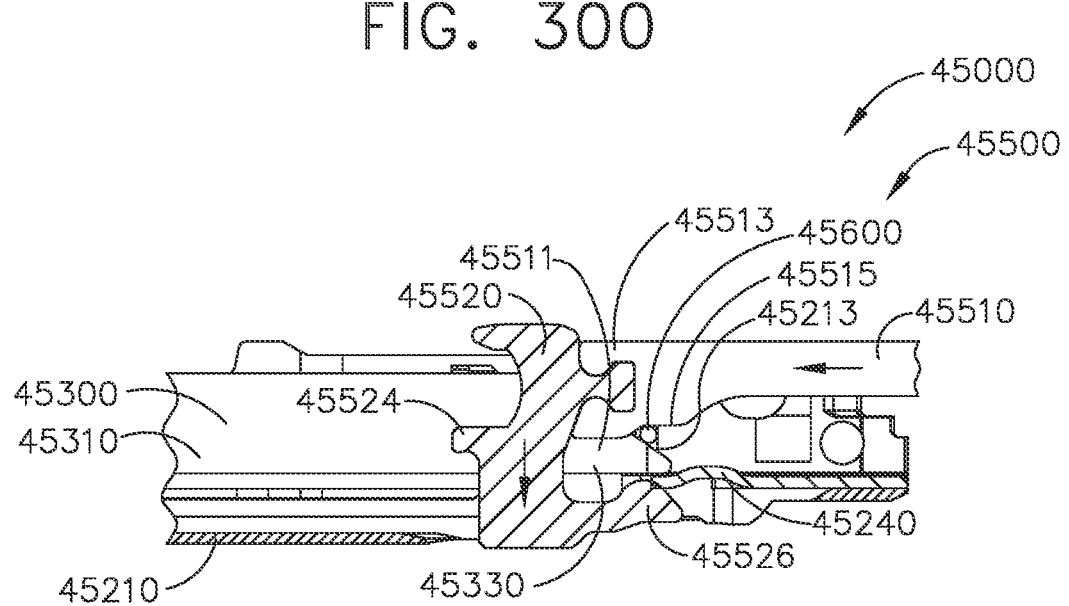
Figure 302:
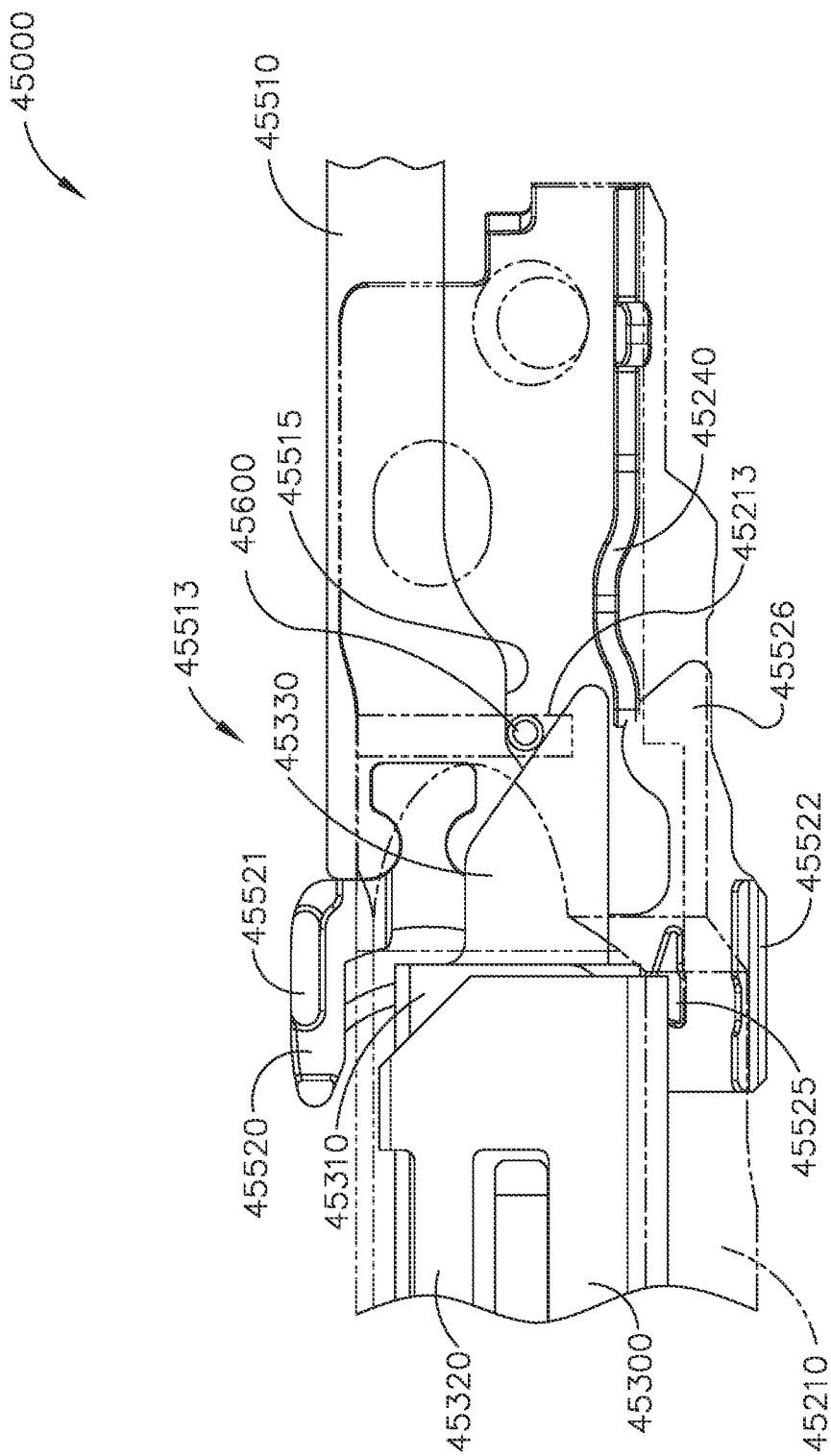
Figure 303:
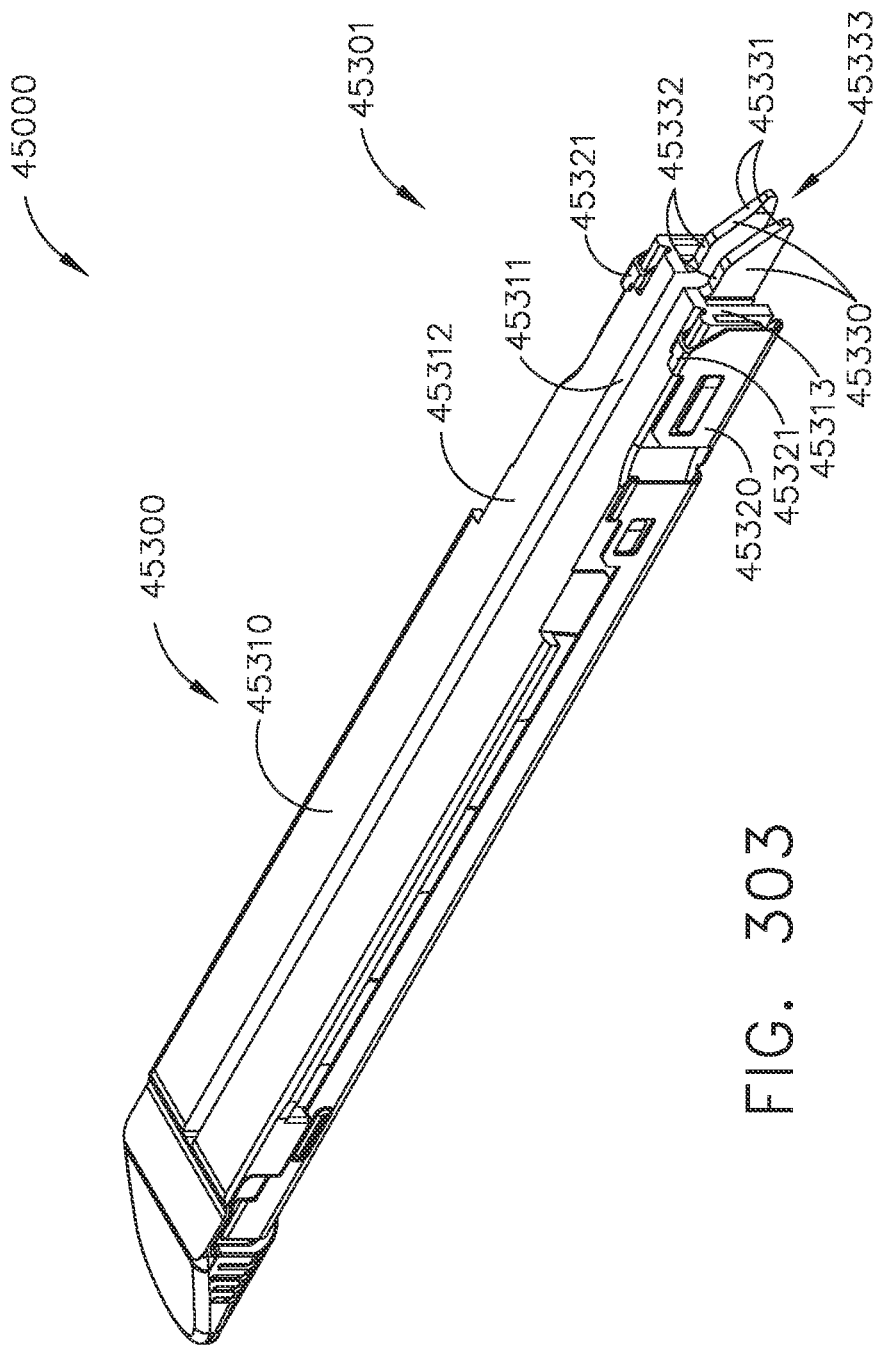

FIG. 131 is a perspective view of another removable blade structure;

FIG. 132 is a perspective view of another surgical staple cartridge and firing member of another powered surgical instrument;

FIG. 133 is a side elevational view of another surgical end effector that may be employed with a rotary powered surgical stapling system;

FIG. 134 is an exploded assembly view of the surgical end effector of FIG. 133;

FIG. 135 is an exploded assembly view of a rotary powered firing member that may be employed with the surgical end effector of FIGS. 133 and 134;

FIG. 136 is a partial cross-sectional view of the surgical end effector of FIG. 133 illustrating initial insertion of a fresh, unfired surgical staple cartridge therein;

FIG. 137 is another partial cross-sectional view of the surgical end effector of FIG. 136, after the surgical staple cartridge has been operably installed therein;

FIG. 138 is an enlarged partial cross-sectional view illustrating a firing member and a camming assembly of the end effector of FIG. 137;

FIG. 139 is another partial cross-sectional view of the surgical end effector of FIG. 133, prior to insertion of a fresh surgical staple cartridge therein and with a firing member lockout assembly thereof in a locked position;

FIG. 140 is an enlarged partial cross-sectional view illustrating a firing member and lockout lugs of the end effector of FIG. 139, with a camming assembly and end effector channel omitted for clarity;

FIG. 141 is a side elevational view of another surgical end effector with an anvil thereof in an open position;

FIG. 142 is a partial bottom perspective view of the surgical end effector of FIG. 141;

FIG. 143 is a perspective view of a channel mount feature and anvil lockout spring of the surgical end effector of FIG. 141;

FIG. 144 is a partial bottom perspective view of the surgical end effector of FIG. 141 without a surgical staple cartridge installed therein and the anvil thereof in a locked position;

FIG. 145 is another partial bottom perspective view of the surgical end effector of FIG. 144 after a compatible surgical staple cartridge has been installed therein and the anvil lockout spring moved to an unlocked position;

FIG. 146 is a perspective view of a proximal end portion of the surgical staple cartridge depicted in FIG. 145;

FIG. 147 is a partial exploded assembly view of a surgical staple cartridge and a corresponding anvil and anvil lockout system of a surgical end effector;

FIG. 148 is a partial exploded assembly view of a surgical staple cartridge and a corresponding anvil and anvil lockout system of another surgical end effector;

FIG. 149 is a partial bottom view of a channel of another end effector with a compatible surgical staple cartridge loaded therein with portions of the compatible surgical staple cartridge omitted for clarity;

FIG. 150 is a side elevational view of a portion of the surgical end effector of FIG. 149, with portions of a channel, anvil and cartridge omitted for clarity;

FIG. 151 is a partial cross-sectional end view of the surgical end effector of FIGS. 149 and 150 with the anvil shown in a closed position on a compatible surgical staple cartridge;

FIG. 152 is another partial cross-sectional end view of the surgical end effector of FIGS. 149 and 150 with the anvil thereof shown in a locked open position;

FIG. 153 is a side elevational of an anvil lock of the surgical end effector of FIGS. 149 and 150 shown in a locked configuration and an unlocked configuration (in phantom lines);

FIG. 154 is a side elevational view of a portion of another surgical end effector, with portions of a channel, anvil and cartridge omitted for clarity;

FIG. 155 is a front elevational view of an anvil lock of the surgical end effector of FIG. 154;

FIG. 156 is a top view of the anvil lock of FIG. 155;

FIG. 157 is a cross-sectional side view of another surgical end effector with an anvil thereof in an open position and with a compatible surgical staple cartridge installed therein;

FIG. 158 is a partial perspective view of a proximal end of a compatible surgical staple cartridge of FIG. 157 in relation to a portion of an anvil lock feature of the surgical end effector of FIG. 157;

FIG. 159 is a top view of a portion of a channel of the surgical end effector of FIG. 157 and an outline of a compatible surgical staple cartridge of FIG. 157 being inserted therein;

FIG. 160 is another cross-sectional side view of the surgical end effector of FIG. 157, with the anvil thereof in an open position during initial installation of an incompatible surgical staple cartridge therein;

FIG. 161 is a cross-sectional side view of another surgical end effector with an anvil thereof in an open position during installation of a compatible surgical staple cartridge therein;

FIG. 162 is a cross-sectional side view of portions of another surgical end effector with an anvil thereof in an open position during installation of a compatible surgical staple cartridge therein;

FIG. 163 is a cross-sectional side view of portions of another surgical end effector with an anvil thereof in an open position during installation of a compatible surgical staple cartridge therein;

FIG. 164 is a cross-sectional side view of the end effector of FIG. 163 during installation of an incompatible cartridge therein;

FIG. 165 is a partial perspective view of a proximal end portion of an anvil;

FIG. 166 is a partial perspective view of a proximal end portion of another anvil;

FIG. 167 is a partial cross-sectional end view of portions of another surgical end effector;

FIG. 168 is a partial perspective view of a proximal end portion of the anvil of the surgical end effector of FIG. 167;

FIG. 169 is a partial cross-sectional perspective view of a portion of a channel and anvil lock of the surgical end effector of FIG. 167, with the anvil lock in a locked position;

FIG. 170 is a partial side elevational view of the surgical end effector of FIG. 167 with the anvil in an open position and the anvil lock thereof shown in a locked position in phantom lines;

FIG. 171 is another partial cross-sectional perspective view of a portion of the channel and anvil lock of the surgical end effector of FIG. 167, with the anvil lock in an unlocked position;

FIG. 172 is another partial side elevational view of the surgical end effector of FIG. 167 with the anvil in a closed position and the anvil lock thereof shown in the unlocked position in phantom lines;

FIG. 173 is a partial cross-sectional end view of portions of another surgical end effector;

FIG. 174 is a partial perspective view of a proximal end portion of the anvil of the surgical end effector of FIG. 173;

FIG. 175 is a partial cross-sectional side view of a portion of a channel and anvil lock of the surgical end effector of FIG. 173, with the anvil lock in a locked position;

FIG. 176 is a partial side elevational view of another surgical end effector with an anvil thereof in an open position and an anvil lock thereof shown in a locked position in phantom lines;

FIG. 177 is a side elevational view of a portion of the anvil of the surgical end effector of FIG. 176;

FIG. 178 is a partial perspective view of a portion of the anvil of FIG. 177;

FIG. 179 is a partial cross-sectional perspective view of a portion of a channel and anvil lock of the surgical end effector of FIG. 176 with the anvil lock in a locked position;

FIG. 180 is another partial cross-sectional perspective view of a portion of the channel and anvil lock of the surgical end effector of FIG. 176, with the anvil lock in an unlocked position;

FIG. 181 is a partial side elevational view of the surgical end effector of FIG. 176 with the anvil in a closed position and the anvil lock thereof shown in the unlocked position in phantom lines;

FIG. 182 is a partial perspective view of another anvil;

FIG. 183 is a partial cross-sectional perspective view of a portion of another channel that may be used in connection with the anvil of FIG. 182;

FIG. 184 is a side elevational view of a portion of another anvil;

FIG. 185 is a perspective view of a portion of the anvil of FIG. 184;

FIG. 186 is a perspective view of a portion of another anvil;

FIG. 187 is a side elevational view of another surgical end effector with an anvil thereof in an open position prior to installation of a surgical staple cartridge therein;

FIG. 188 is another side elevational view of the surgical end effector of FIG. 187 after a compatible surgical staple cartridge has been installed therein;

FIG. 189 is an end elevational view of an surgical end effector closure tube of the surgical end effector of FIG. 187 and with a closure lock thereof in a locked position;

FIG. 190 is another end elevational view of the surgical end effector closure tube and closure lock of FIG. 189, with the closure lock shown in an unlocked position;

FIG. 191 is a partial perspective view of a portion of a compatible surgical staple cartridge and the closure lock of the surgical end effector of FIG. 187;

FIG. 192 is a partial side elevational view of the surgical end effector of FIG. 187 with the anvil thereof in an open position and prior to installation of a surgical staple cartridge therein;

FIG. 193 is another partial side elevational view of the surgical end effector of FIG. 192 with the anvil thereof in an open position and during installation of a compatible surgical staple cartridge therein;

FIG. 194 is a partial side elevational view of the surgical end effector of FIG. 192 with the anvil thereof in an open position and during initial installation of a compatible surgical staple cartridge therein;

FIG. 195 is another partial side elevational view of the surgical end effector of FIG. 194 with the anvil thereof in an open position and after the compatible surgical staple cartridge has been operably seated therein;

FIG. 196 is a partial cross-sectional perspective view of a portion of the compatible surgical staple cartridge shown in FIGS. 194 and 195;

FIG. 197 is another partial side elevational view of the surgical end effector of FIG. 194 with the anvil thereof in an open position and during installation thereof of a surgical staple cartridge lacking a compatible camming assembly in a starting position;

FIG. 198 is a partial side elevational view of another surgical end effector with an anvil thereof in an open position and during initial installation of a compatible surgical staple cartridge therein;

FIG. 199 is another partial side elevational view of the surgical end effector of FIG. 198 with the anvil thereof in an open position and after the compatible surgical staple cartridge has been operably seated therein;

FIG. 200 is a perspective view of an anvil lock and channel mounting feature of the surgical end effector of FIGS. 198 and 199;

FIG. 201 is a perspective view of a portion of a surgical staple cartridge that is compatible with the surgical end effector of FIGS. 198 and 199;

FIG. 202 is another partial side elevational view of the surgical end effector of FIG. 198 with the anvil thereof in an open position and after an incompatible surgical staple cartridge has been seated therein;

FIG. 203 is a side elevational view of another surgical end effector with a compatible surgical staple cartridge loaded therein and an anvil thereof in an open position;

FIG. 204 is a top view of a portion of a surgical staple cartridge that is compatible with the surgical end effector of FIG. 203 with portions thereof omitted for clarity;

FIG. 205 is a partial cross-sectional side view of a portion of the surgical staple cartridge of FIG. 204 installed in the surgical end effector of FIG. 203 taken along line 205-205 in FIG. 204 showing the cartridge nose assembly in a locked position;

FIG. 206 is another partial cross-sectional side view of a portion of the surgical staple cartridge of FIG. 204 installed in the surgical end effector of FIG. 203 taken along line 206-206 in FIG. 204 showing the cartridge nose assembly in an unlocked position;

FIG. 207 is another partial cross-sectional side view of a portion of the surgical staple cartridge of FIG. 204 installed in the surgical end effector of FIG. 203 taken along line 207-207 in FIG. 204 showing the cartridge nose assembly in a locked position;

FIG. 208 is another partial cross-sectional side view of a portion of the surgical staple cartridge of FIG. 204 installed in the surgical end effector of FIG. 203 taken along line 208-208 in FIG. 204 showing the cartridge nose assembly in an unlocked position;

FIG. 209 is a partial cross-sectional view of a portion of a firing member and camming assembly of a surgical staple cartridge wherein the camming assembly is in a starting position and in unlocking engagement with a firing member lock on a firing member;

FIG. 210 is another partial cross-sectional view of a portion of a firing member of FIG. 209, with the firing member lock in a locked position;

FIG. 211 is a side elevational view of a portion of an anvil of another surgical end effector with the anvil in an open position in relation to compatible surgical staple cartridge installed within a corresponding channel that has been omitted for clarity;

FIG. 212 is another side elevational view of the anvil and surgical staple cartridge of FIG. 211 during initial closure of the anvil;

FIG. 213 is another side elevational view of the anvil and surgical staple cartridge of FIG. 211 after the anvil has been moved to a closed position;

FIG. 214 is a perspective view of a portion of the compatible surgical staple cartridge depicted in FIGS. 211-213;

FIG. 215 is a partial bottom view of the anvil of FIGS. 211-213;

FIG. 216 is a perspective view of a portion of surgical staple cartridge that is incompatible with the anvil of FIGS. 211-213;

FIG. 217 is a side elevational view of the anvil of FIGS. 211-213 in an open position in relation to an incompatible surgical staple cartridge of FIG. 216 installed within a corresponding channel that has been omitted for clarity;

FIG. 218 is another side elevational view of the anvil and surgical staple cartridge of FIG. 217 during initial closure of the anvil;

FIG. 219 is another side elevational view of the anvil and surgical staple cartridge of FIG. 217 after the anvil has been moved to a closed position;

FIG. 220 is a partial cross-sectional side view of a portion of another surgical end effector with a compatible surgical staple cartridge loaded therein and an anvil thereof omitted for clarity;

FIG. 221 is a top view of a portion of the surgical staple cartridge and surgical end effector of FIG. 220;

FIG. 222 is a perspective view of a portion of proximal end of a compatible surgical staple cartridge depicted in FIG. 221;

FIG. 223 is another partial cross-sectional side view of a portion of the surgical end effector of FIG. 220 illustrating the installation of a compatible surgical staple cartridge therein;

FIG. 224 is another partial cross-sectional side view of a portion of the surgical end effector of FIG. 220 illustrating the installation of a compatible surgical staple cartridge therein;

FIG. 225 is a top view of the surgical end effector and compatible surgical staple cartridge of FIG. 222;

FIG. 226 is another partial cross-sectional side view of a portion of the surgical end effector of FIG. 220 illustrating the installation of an incompatible surgical staple cartridge therein;

FIG. 227 is another partial cross-sectional side view of a portion of the surgical end effector of FIG. 220 illustrating the installation of an incompatible surgical staple cartridge therein;

FIG. 228 is a top view of the surgical end effector and incompatible surgical staple cartridge of FIG. 227;

FIG. 229 is another partial cross-sectional side view of a portion of the surgical end effector of FIG. 220 illustrating the installation of an incompatible surgical staple cartridge therein;

FIG. 230 is a top view of the surgical end effector and incompatible surgical staple cartridge of FIG. 229;

FIG. 231 is a partial cross-sectional perspective view of portions of another surgical end effector with an incompatible surgical staple cartridge installed therein;

FIG. 232 is a partial top view of portions of the surgical end effector an incompatible surgical staple cartridge of FIG. 231;

FIG. 233 is another partial top view of the surgical end effector of FIG. 229, with a compatible surgical staple cartridge installed therein;

FIG. 234 is a partial cross-sectional perspective view of portions of another surgical end effector with a compatible surgical staple cartridge installed therein;

FIG. 235 is a partial exploded assembly view of portions of the surgical end effector of FIG. 234;

FIG. 236 is a partial cross-sectional end view of the surgical end effector and compatible surgical staple cartridge of FIG. 234;

FIG. 237 is another partial cross-sectional surgical end view of the end effector of FIG. 234 with an incompatible surgical staple cartridge installed therein;

FIG. 238 is another partial cross-sectional perspective view of portions of the surgical end effector of FIG. 234 with an incompatible surgical staple cartridge installed therein;

FIG. 239 is a top view of the surgical end effector and surgical staple cartridge of FIG. 238;

FIG. 240 is a top view of a portion of another surgical staple cartridge;

FIG. 241 is a partial cross-sectional perspective view of a portion of the surgical staple cartridge of FIG. 240 with a camming assembly thereof in a locked position;

FIG. 242 is another top view of the surgical staple cartridge of FIG. 240 interacting with a compatible actuator portion of a surgical end effector;

FIG. 243 is another partial cross-sectional perspective view of a portion of the surgical staple cartridge of FIG. 240 with the camming assembly thereof in an unlocked position;

FIG. 244 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 245 is a partial elevational view of the stapling instrument of FIG. 244 illustrating the firing member in a locked-out position;

FIG. 246 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 247 is a partial elevational view of the stapling instrument of FIG. 246 illustrating the firing member in an unlocked position;

FIG. 248 is a partial elevational view of the stapling instrument of FIG. 246 illustrating the firing member in a locked-out position;

FIG. 249 is a partial bottom view of the stapling instrument of FIG. 246 illustrating the firing member in an unfired position;

FIG. 250 is a partial perspective view of the staple cartridge of FIG. 246;

FIG. 251 is a partial perspective view of a staple cartridge in accordance with at least one embodiment;

FIG. 252 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 253 is a partial elevational view of the stapling instrument of FIG. 252 illustrating the firing member in an unlocked position;

FIG. 254 is a partial top view of the stapling instrument of FIG. 252 illustrated in the unfired position of FIG. 252;

FIG. 255 is a partial top view of the stapling instrument of FIG. 252 illustrated in the unlocked position of FIG. 253;

FIG. 256 is a partial perspective view of the staple cartridge of FIG. 252 in an unspent configuration;

FIG. 257 is a partial perspective view of the staple cartridge of FIG. 252 in a spent configuration;

FIG. 258 is a partial elevational view of a stapling instrument including a cartridge channel, a staple cartridge positioned in the cartridge channel, and a firing member in accordance with at least one embodiment illustrated with some components removed, wherein the firing member is in an unfired position;

FIG. 259 is a partial elevational view of the stapling instrument of FIG. 258 illustrating the firing member in a locked-out position;

FIG. 260 is a partial perspective view of a stapling instrument including a cartridge channel, a staple cartridge positioned in the cartridge channel, a firing member, and a firing member lock in accordance with at least one embodiment illustrated with some components removed, wherein the firing member has been unlocked by the staple cartridge;

FIG. 261 is a partial elevational view of the stapling instrument of FIG. 260 illustrated with an improper staple cartridge seated in the cartridge channel;

FIG. 262 is a partial cross-sectional plan view of the stapling instrument of FIG. 260 illustrated with an improper staple cartridge seated in the cartridge channel;

FIG. 263 is a partial cross-sectional plan view of the stapling instrument of FIG. 260 illustrating the firing member lock unlocked by the staple cartridge;

FIG. 264 is a partial cross-sectional view of a stapling instrument in accordance with at least one embodiment that has been unlocked by a staple cartridge;

FIG. 265 is a partial cross-sectional view of a stapling instrument in accordance with at least one embodiment that has been unlocked by a staple cartridge;

FIG. 266 is a partial perspective view of the staple cartridge of FIG. 264;

FIG. 267 is a partial perspective view of the staple cartridge of FIG. 265;

FIG. 268 is a partial cross-sectional perspective view of a staple cartridge pan in accordance with at least one embodiment;

FIG. 269 is a partial perspective view of a stapling instrument including a cartridge channel, a staple cartridge positioned in the cartridge channel, a firing member, and a firing member lock in accordance with at least one embodiment illustrated with some components removed, wherein the firing member is unlocked by the staple cartridge;

FIG. 270 is a partial perspective view of the stapling instrument of FIG. 269 illustrating a different staple cartridge positioned in the cartridge channel which does not unlock the firing member;

FIG. 271 is a partial perspective view of the stapling instrument of FIG. 269 illustrating the firing member in a locked configuration;

FIG. 272 is a partial perspective view of a stapling instrument configured to be unlocked by the different staple cartridge of FIG. 270;

FIG. 273 is a perspective view of a staple cartridge which is similar to the staple cartridge of FIG. 270 and configured to unlock the stapling instrument of FIG. 272;

FIG. 274 is a perspective view of a staple cartridge which is similar to the staple cartridge of FIG. 269 and configured to unlock the stapling instrument of FIG. 269;

FIG. 275 is a partial exploded view of a stapling instrument comprising a cartridge channel, a staple cartridge positioned in the cartridge channel, a firing member, an anvil, and a dual-purpose firing member/anvil lock in accordance with at least one embodiment illustrated with some components removed, wherein the stapling instrument is illustrated in a locked state;

FIG. 276 is a partial perspective view of the stapling instrument of FIG. 275 being unlocked by the insertion of the staple cartridge into the cartridge channel;

FIG. 277 is a partial cross-sectional view of the stapling instrument of FIG. 275 illustrating the stapling instrument in the locked state of FIG. 275;

FIG. 278 is a partial cross-sectional view of the stapling instrument of FIG. 275 illustrating the stapling instrument in the unlocked state of FIG. 276;

FIG. 279 is a perspective view of the firing member/anvil lock of FIG. 275;

FIG. 279A is a partial perspective view of a staple cartridge in accordance with at least one embodiment;

FIG. 279B is a partial perspective view of a staple cartridge in accordance with at least one embodiment;

FIG. 279C is a partial perspective view of a staple cartridge in accordance with at least one embodiment;

FIG. 279D is a partial perspective view of a staple cartridge in accordance with at least one embodiment;

FIG. 279E is a partial perspective view of a staple cartridge in accordance with at least one embodiment;

FIG. 280 is a partial cross-sectional view of a surgical stapling assembly comprising an anvil, a staple cartridge, a firing member, and a firing lockout;

FIG. 281 is a partial cross-sectional view of the firing member and the firing lockout of FIG. 280 illustrated in an unlocked configuration;

FIG. 282 is a partial cross-sectional view of the firing member and the firing lockout of FIG. 280 illustrated in a locked configuration;

FIG. 283 is a partial cross-sectional view of the surgical stapling assembly of FIG. 280, wherein the surgical stapling assembly further comprises an exterior access aperture configured to permit a user to artificially move the firing lockout into the unlocked configuration with a separate lockout key;

FIG. 284 is a perspective view of a lockout member of the firing lockout of FIG. 280;

FIG. 285 is a partial cross-sectional view of a surgical stapling assembly comprising a lockout and an exterior access orifice configured to permit a user to artificially move the firing lockout into an unlocked configuration with a separate lockout key;

FIG. 286 is a bottom plan view of the surgical stapling assembly of FIG. 285;

FIG. 287 is a partial cross-sectional view of a surgical stapling assembly comprising a firing member, a cartridge channel, a staple cartridge configured be installed into the cartridge channel, and a lockout, wherein the lockout is illustrated in an unengaged configuration;

FIG. 288 is a partial cross-sectional view of the surgical stapling assembly of FIG. 287, wherein the lockout is illustrated in an engaged configuration;

FIG. 289 comprises elevational views of two staple cartridges each comprising a different lockout key;

FIG. 290 is a graph depicting knife lift timing provided by each lockout key of the staple cartridges of FIG. 289;

FIG. 291 is a graph depicting knife lift displacement provided by each lockout key of the staple cartridges of FIG. 289;

FIG. 292 is a perspective view of a first staple cartridge for use with a surgical stapling system, wherein the first staple cartridge comprises a cartridge body, a pan, a sled, and a first lockout key;

FIG. 293 is a perspective view of a second staple cartridge for use with the surgical stapling system with which the first staple cartridge of FIG. 292 is to be used, wherein the second staple cartridge comprises a cartridge body, a pan, a sled, and a second lockout key;

FIG. 294 is an elevational view of a surgical stapling assembly comprising a firing member, a first jaw comprising a staple cartridge, a second jaw comprising an anvil movable relative to the first jaw, and a lockout;

FIG. 295 is partial perspective view of the surgical stapling assembly of FIG. 294;

FIG. 296 is a partial elevational view of the surgical stapling assembly of FIG. 294 where the staple cartridge is not installed within the first jaw;

FIG. 297 is a partial elevational view of the surgical stapling assembly of FIG. 294 where the staple cartridge is installed within the first jaw;

FIG. 298 is a partial cross-sectional view of the surgical stapling assembly of FIG. 294 where the staple cartridge is installed within the first jaw and the firing member is in an unfired position;

FIG. 299 is a partial cross-sectional view of the surgical stapling assembly of FIG. 294 where the staple cartridge is installed within the first jaw and the firing member is in a partially fired position;

FIG. 300 is a partial cross-sectional view of the surgical stapling assembly of FIG. 294 where the staple cartridge is not installed within the first jaw and the firing member is in the unfired position;

FIG. 301 is a partial cross-sectional view of the surgical stapling assembly of FIG. 294 where the staple cartridge is not installed within the first jaw and the firing member is in a locked position;

FIG. 302 is a partial elevational view of the surgical stapling assembly of FIG. 294 where the staple cartridge is installed within the first jaw and the firing member is in the partially fired position, wherein some components are illustrated with hidden lines;

FIG. 303 is a perspective view of the staple cartridge of the surgical stapling assembly of FIG. 294 comprising a lockout key extending from a proximal end thereof;

FIG. 304 is a partial plan view of the staple cartridge of FIG. 303; and

FIG. 305 is a partial plan view of a second staple cartridge configured for use with a system including the staple cartridge of FIG. 303, wherein the second staple cartridge comprises a lockout key comprising a different configuration than the lockout key of the staple cartridge of FIG. 303.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. Patent Applications that were filed on Feb. 21, 2019 and which are each herein incorporated by reference in their respective entireties:

U.S. patent application Ser. No. 16/281,670, entitled STAPLE CARTRIDGE COMPRISING A LOCKOUT KEY CONFIGURED TO LIFT A FIRING MEMBER, now U.S. Patent Application Publication No. 2019/0298340;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN, now U.S. Pat. No. 11,129,611;

U.S. patent application Ser. No. 16/281,685, entitled SURGICAL INSTRUMENT COMPRISING CO-OPERATING LOCKOUT FEATURES, now U.S. Pat. No. 11,213,294;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT, now U.S. Pat. No. 11,197,668;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN, now U.S. Pat. No. 11,259,806;

U.S. patent application Ser. No. 16/281,707, entitled STAPLING INSTRUMENT COMPRISING A DEACTIVATABLE LOCKOUT, now U.S. Pat. No. 11,166,716;

U.S. patent application Ser. No. 16/281,741, entitled SURGICAL INSTRUMENT COMPRISING A JAW CLOSURE LOCKOUT, now U.S. Pat. No. 11,278,280;

U.S. patent application Ser. No. 16/281,762, entitled SURGICAL STAPLING DEVICES WITH CARTRIDGE COMPATIBLE CLOSURE AND FIRING LOCKOUT ARRANGEMENTS, now U.S. Pat. No. 11,219,453;

U.S. patent application Ser. No. 16/281,660 entitled SURGICAL STAPLE CARTRIDGE WITH FIRING MEMBER DRIVEN CAMMING ASSEMBLY THAT HAS AN ONBOARD TISSUE CUTTING FEATURE, now U.S. Pat. No. 10,973,520;

U.S. patent application Ser. No. 16/281,666, entitled SURGICAL STAPLING DEVICES WITH IMPROVED ROTARY DRIVEN CLOSURE SYSTEMS, now U.S. Patent Application Publication No. 2019/0298352;

U.S. patent application Ser. No. 16/281,672, entitled SURGICAL STAPLING DEVICES WITH ASYMMETRIC CLOSURE FEATURES, now U.S. Patent Application Publication No. 2019/0298353;

U.S. patent application Ser. No. 16/281,678, entitled ROTARY DRIVEN FIRING MEMBERS WITH DIFFERENT ANVIL AND CHANNEL ENGAGEMENT FEATURES, now U.S. Pat. No. 11,096,688; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING, now U.S. Pat. No. 11,207,067.

Applicant of the present application owns the following U.S. Provisional Patent Applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. Patent Applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design patent application Ser. No. 29/660,252, entitled SURGICAL STAPLER ANVILS.

Applicant of the present application owns the following U.S. Patent Applications and U.S. Patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Patent Application Publication No. 2018/0168642;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Patent Application Publication No. 2018/0168646;

U.S. patent application Ser. No. 15/386,209, entitled SURGICAL END EFFECTORS AND FIRING MEMBERS THEREOF, now U.S. Patent Application Publication No. 2018/0168645;

U.S. patent application Ser. No. 15/386,198, entitled LOCKOUT ARRANGEMENTS FOR SURGICAL END EFFECTORS AND REPLACEABLE TOOL ASSEMBLIES, now U.S. Patent Application Publication No. 2018/0168644;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Patent Application Publication No. 2018/0168629;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630;

U.S. patent application Ser. No. 15/385,943, entitled SURGICAL STAPLING INSTRUMENTS AND STAPLE-FORMING ANVILS, now U.S. Patent Application Publication No. 2018/0168631;

U.S. patent application Ser. No. 15/385,950, entitled SURGICAL TOOL ASSEMBLIES WITH CLOSURE STROKE REDUCTION FEATURES, now U.S. Patent Application Publication No. 2018/0168635;

U.S. patent application Ser. No. 15/385,945, entitled STAPLE CARTRIDGES AND ARRANGEMENTS OF STAPLES AND STAPLE CAVITIES THEREIN, now U.S. Patent Application Publication No. 2018/0168632;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Patent Application Publication No. 2018/0168636;

U.S. patent application Ser. No. 15/385,953, entitled METHODS OF STAPLING TISSUE, now U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, now U.S. Patent Application Publication No. 2018/0168638;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Patent Application Publication No. 2018/0168640;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, now U.S. Patent Application Publication No. 2018/0168634;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Patent Application Publication No. 2018/0168599;

U.S. patent application Ser. No. 15/385,899, entitled SURGICAL INSTRUMENT COMPRISING IMPROVED JAW CONTROL, now U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602;

U.S. patent application Ser. No. 15/385,902, entitled SURGICAL INSTRUMENT COMPRISING A CUTTING MEMBER, now U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605;

U.S. patent application Ser. No. 15/385,905, entitled FIRING ASSEMBLY COMPRISING A LOCKOUT, now U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Patent Application Publication No. 2018/0168620;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626;

U.S. patent application Ser. No. 15/385,911, entitled SURGICAL STAPLERS WITH INDEPENDENTLY ACTUATABLE CLOSING AND FIRING SYSTEMS, now U.S. Patent Application Publication No. 2018/0168612;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Patent Application Publication No. 2018/0168616;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Patent Application Publication No. 2018/0168622;

U.S. patent application Ser. No. 15/385,924, entitled SURGICAL INSTRUMENT WITH PRIMARY AND SAFETY PROCESSORS, now U.S. Patent Application Publication No. 2018/0168624;

U.S. patent application Ser. No. 15/385,910, entitled ANVIL HAVING A KNIFE SLOT WIDTH, now U.S. Patent Application Publication No. 2018/0168611;

U.S. patent application Ser. No. 15/385,903, entitled CLOSURE MEMBER ARRANGEMENTS FOR SURGICAL INSTRUMENTS, now U.S. Patent Application Publication No. 2018/0168604;

U.S. patent application Ser. No. 15/385,906, entitled FIRING MEMBER PIN CONFIGURATIONS, now U.S. Patent Application Publication No. 2018/0168607;

U.S. patent application Ser. No. 15/386,188, entitled STEPPED STAPLE CARTRIDGE WITH ASYMMETRICAL STAPLES, now U.S. Patent Application Publication No. 2018/0168585;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593;

U.S. patent application Ser. No. 15/385,894, entitled SHAFT ASSEMBLY COMPRISING A LOCKOUT, now U.S. Patent Application Publication No. 2018/0168595;

U.S. patent application Ser. No. 15/385,895, entitled SHAFT ASSEMBLY COMPRISING FIRST AND SECOND ARTICULATION LOCKOUTS, now U.S. Patent Application Publication No. 2018/0168596;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Patent Application Publication No. 2018/0168621;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Patent Application Publication No. 2018/0168576;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Patent Application Publication No. 2018/0168580;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Patent Application Publication No. 2018/0168581;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Patent Application Publication No. 2018/0168582;

U.S. patent application Ser. No. 15/385,936, entitled ARTICULATABLE SURGICAL INSTRUMENTS WITH ARTICULATION STROKE AMPLIFICATION FEATURES, now U.S. Patent Application Publication No. 2018/0168583;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Patent Application Publication No. 2015/0297232;

U.S. patent application Ser. No. 14/318,997, entitled FASTENER CARTRIDGE COMPRISING DEPLOYABLE TISSUE ENGAGING MEMBERS, now U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Patent Application Publication No. 2015/0297235.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Patent Application Publication No. 2017/0367696;

U.S. patent application Ser. No. 15/191,834, entitled STAMPED STAPLES AND STAPLE CARTRIDGES USING THE SAME, now U.S. Patent Application Publication No. 2017/0367699;

U.S. patent application Ser. No. 15/191,788, entitled STAPLE CARTRIDGE COMPRISING OVER-DRIVEN STAPLES, now U.S. Patent Application Publication No. 2017/0367698; and U.S. patent application Ser. No. 15/191,818, entitled STAPLE CARTRIDGE COMPRISING OFFSET LONGITUDINAL STAPLE ROWS, now U.S. Patent Application Publication No. 2017/0367697.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER, now U.S. Design Pat. No. D826,405;

U.S. Design patent application Ser. No. 29/569,227, entitled SURGICAL FASTENER, now U.S. Design Pat. No. D822,206;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Patent Application Publication No. 2017/0281163;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No. 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,262, entitled ROTARY POWERED SURGICAL INSTRUMENT WITH MANUALLY ACTUATABLE BAILOUT SYSTEM, now U.S. Patent Application Publication No. 2017/0281161;

U.S. patent application Ser. No. 15/089,277, entitled SURGICAL CUTTING AND STAPLING END EFFECTOR WITH ANVIL CONCENTRIC DRIVE MEMBER, now U.S. Patent Application Publication No. 2017/0281166;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;

U.S. patent application Ser. No. 15/089,300, entitled SURGICAL STAPLING SYSTEM COMPRISING AN UNCLAMPING LOCKOUT, now U.S. Patent Application Publication No. 2017/0281179;

U.S. patent application Ser. No. 15/089,196, entitled SURGICAL STAPLING SYSTEM COMPRISING A JAW CLOSURE LOCKOUT, now U.S. Patent Application Publication No. 2017/0281183;

U.S. patent application Ser. No. 15/089,203, entitled SURGICAL STAPLING SYSTEM COMPRISING A JAW ATTACHMENT LOCKOUT, now U.S. Patent Application Publication No. 2017/0281184;

U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;

U.S. patent application Ser. No. 15/089,324, entitled SURGICAL INSTRUMENT COMPRISING A SHIFTING MECHANISM, now U.S. Patent Application Publication No. 2017/0281170;

U.S. patent application Ser. No. 15/089,335, entitled SURGICAL STAPLING INSTRUMENT COMPRISING MULTIPLE LOCKOUTS, now U.S. Patent Application Publication No. 2017/0281155;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;

U.S. patent application Ser. No. 15/089,304, entitled SURGICAL STAPLING SYSTEM COMPRISING A GROOVED FORMING POCKET, now U.S. Patent Application Publication No. 2017/0281188;

U.S. patent application Ser. No. 15/089,331, entitled ANVIL MODIFICATION MEMBERS FOR SURGICAL STAPLERS, now U.S. Patent Application Publication No. 2017/0281180;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Patent Application Publication No. 2017/0281169; and U.S. patent application Ser. No. 15/089,349, entitled CIRCULAR STAPLING SYSTEM COMPRISING LOAD CONTROL, now U.S. Patent Application Publication No. 2017/0281174.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Patent Application Publication No. 2017/0189018;

U.S. patent application Ser. No. 14/984,525, entitled MECHANISMS FOR COMPENSATING FOR DRIVETRAIN FAILURE IN POWERED SURGICAL INSTRUMENTS, now U.S. Patent Application Publication No. 2017/0189019; and U.S. patent application Ser. No. 14/984,552, entitled SURGICAL INSTRUMENTS WITH SEPARABLE MOTORS AND MOTOR CONTROL CIRCUITS, now U.S. Patent Application Publication No. 2017/0189020.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Patent Application Publication No. 2017/0224333;

U.S. patent application Ser. No. 15/019,228, entitled SURGICAL INSTRUMENTS WITH MULTIPLE LINK ARTICULATION ARRANGEMENTS, now U.S. Patent Application Publication No. 2017/0224342;

U.S. patent application Ser. No. 15/019,196, entitled SURGICAL INSTRUMENT ARTICULATION MECHANISM WITH SLOTTED SECONDARY CONSTRAINT, now U.S. Patent Application Publication No. 2017/0224330;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Patent Application Publication No. 2017/0224331;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Patent Application Publication No. 2017/0224336;

U.S. patent application Ser. No. 15/019,230, entitled ARTICULATABLE SURGICAL INSTRUMENTS WITH OFF-AXIS FIRING BEAM ARRANGEMENTS, now U.S. Patent Application Publication No. 2017/0224335; and U.S. patent application Ser. No. 15/019,245, entitled SURGICAL INSTRUMENTS WITH CLOSURE STROKE REDUCTION ARRANGEMENTS, now U.S. Patent Application Publication No. 2017/0224343.

Applicant of the present application also owns the U.S. Patent Applications identified below which were filed on Feb. 12, 2016 which are each herein incorporated by reference in their respective entirety:

- U.S. patent application Ser. No. 15/043,254, entitled MECHANISMS FOR COMPENSATING FOR DRIVETRAIN FAILURE IN POWERED SURGICAL INSTRUMENTS, now U.S. Patent Application Publication No. 2017/0231623;
- U.S. patent application Ser. No. 15/043,259, entitled MECHANISMS FOR COMPENSATING FOR DRIVETRAIN FAILURE IN POWERED SURGICAL INSTRUMENTS, now U.S. Patent Application Publication No. 2017/0231626;
- U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and
- U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

- U.S. patent application Ser. No. 14/742,925, entitled SURGICAL END EFFECTORS WITH POSITIVE JAW OPENING ARRANGEMENTS, now U.S. Patent Application Publication No. 2016/0367256;
- U.S. patent application Ser. No. 14/742,941, entitled SURGICAL END EFFECTORS WITH DUAL CAM ACTUATED JAW CLOSING FEATURES, now U.S. Pat. No. 10,052,102;
- U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;
- U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;
- U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and
- U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

- U.S. patent application Ser. No. 14/640,746, entitled POWERED SURGICAL INSTRUMENT, now U.S. Pat. No. 9,808,246;
- U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/0256185;
- U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;
- U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;
- U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;
- U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;
- U.S. patent application Ser. No. 14/640,817, entitled INTERACTIVE FEEDBACK SYSTEM FOR POWERED SURGICAL INSTRUMENTS, now U.S. Pat. No. 9,924,961;
- U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;
- U.S. patent application Ser. No. 14/640,837, entitled SMART SENSORS WITH LOCAL SIGNAL PROCESSING, now U.S. Pat. No. 9,993,248;
- U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;
- U.S. patent application Ser. No. 14/640,799, entitled SIGNAL AND POWER COMMUNICATION SYSTEM POSITIONED ON A ROTATABLE SHAFT, now U.S. Pat. No. 9,901,342; and
- U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

- U.S. patent application Ser. No. 14/633,576, entitled SURGICAL INSTRUMENT SYSTEM COMPRISING AN INSPECTION STATION, now U.S. Pat. No. 10,045,779;
- U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;
- U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Pat. No. 9,993,258; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWREEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Patent Application Publication No. 2014/0246478;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 1:
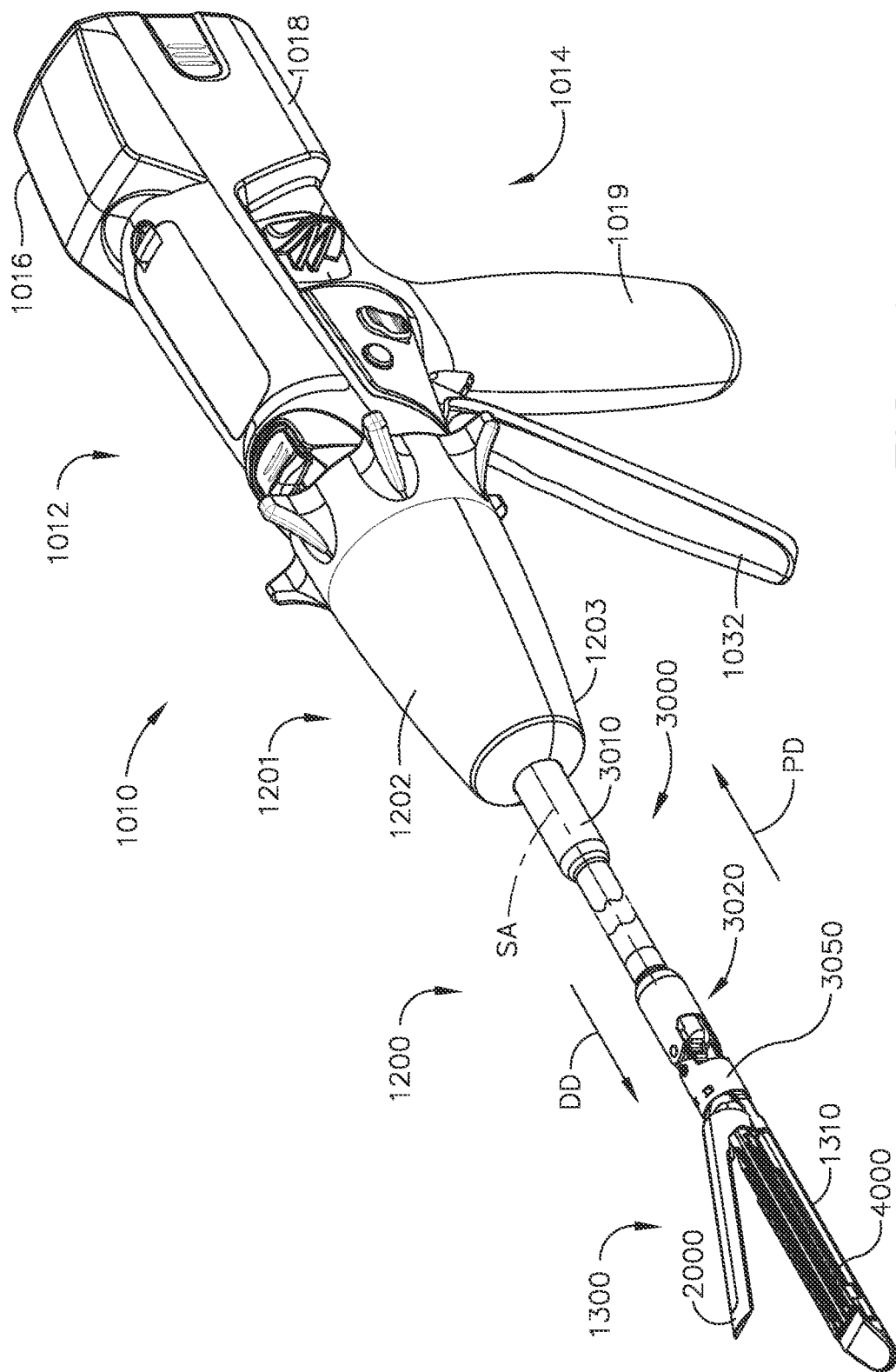
FIG. 1 is a perspective view of a powered surgical stapling system.
Figure 2:
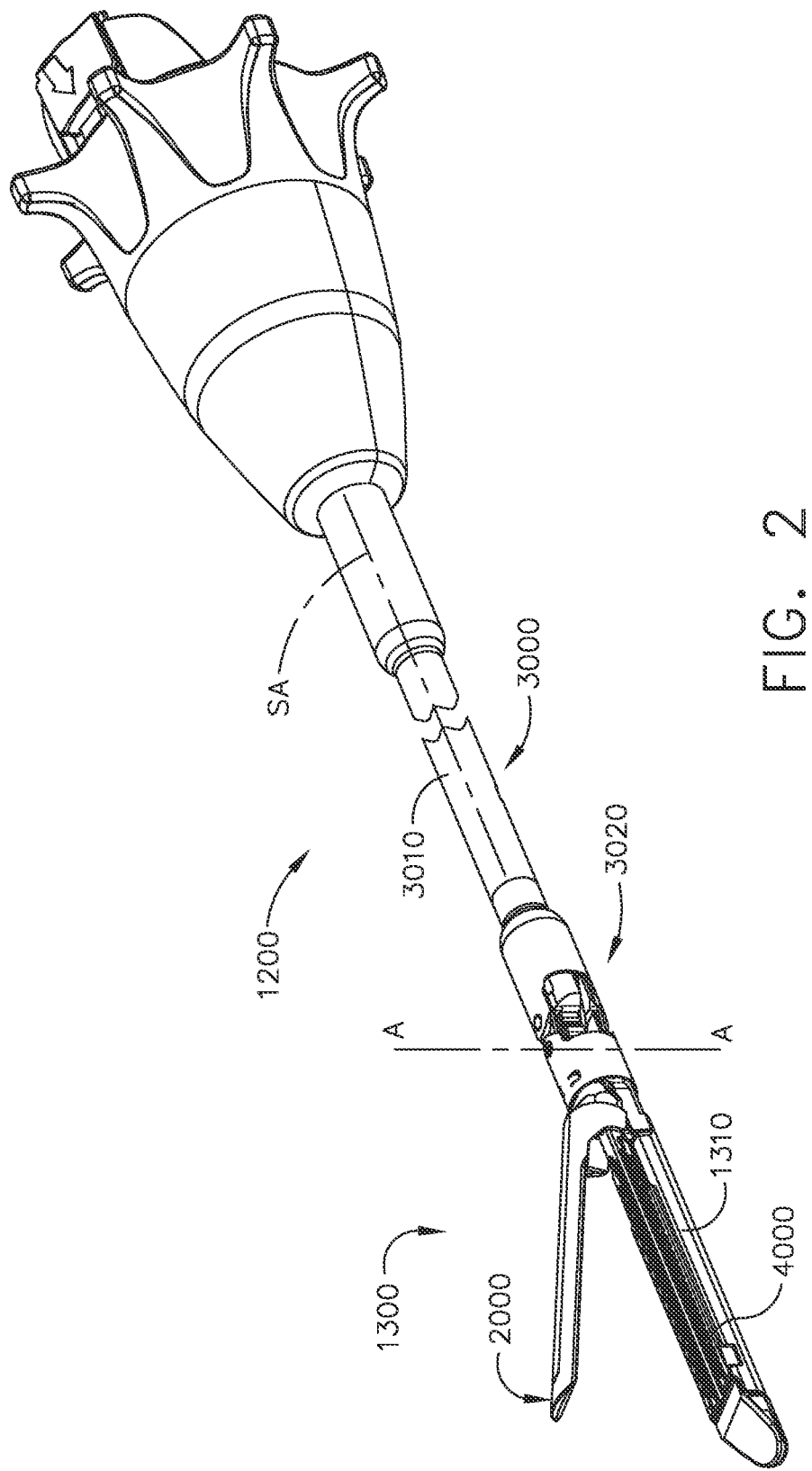
FIG. 2 is a perspective view of an interchangeable surgical shaft assembly of the powered surgical stapling system of FIG. 1.
Figure 3:
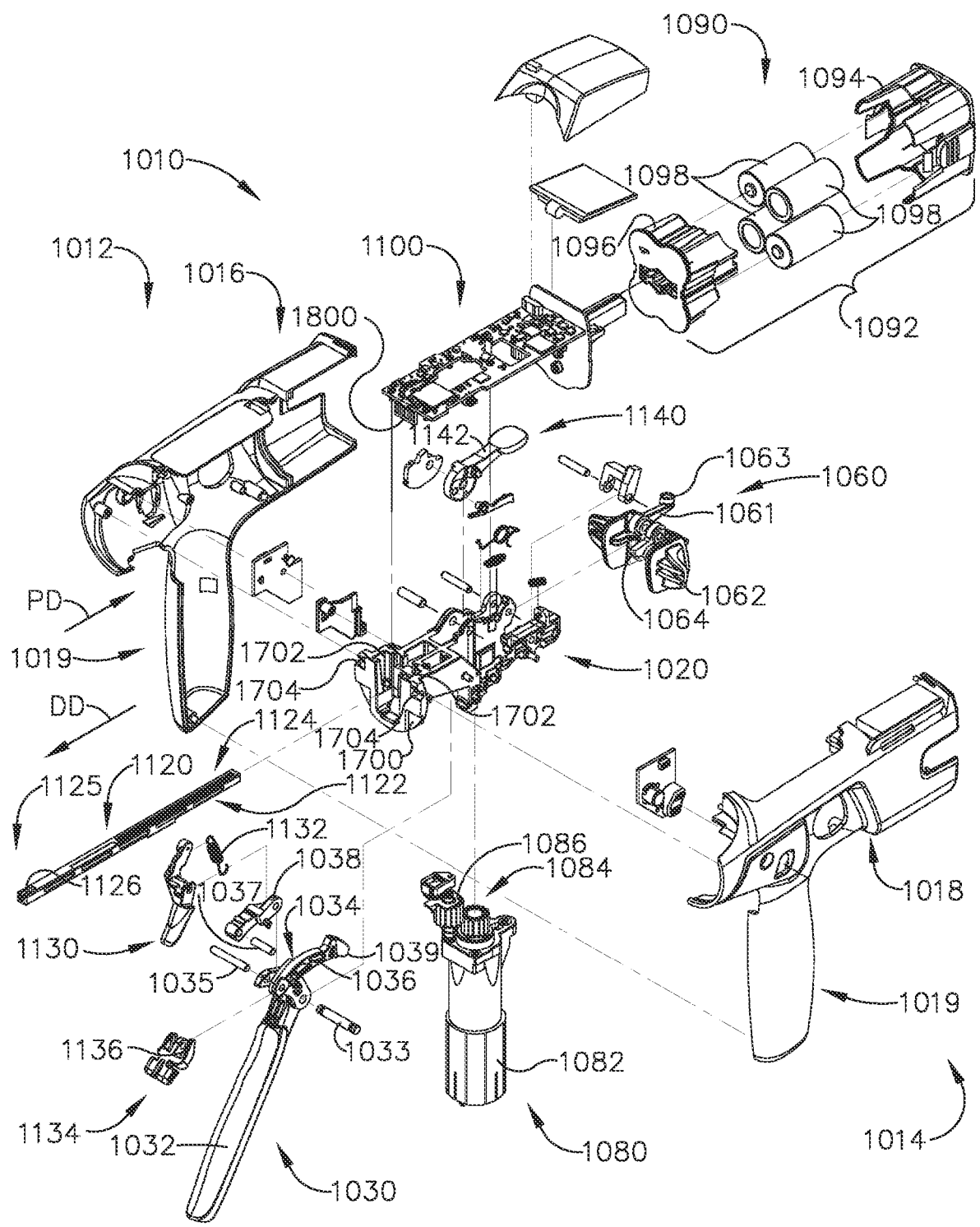
FIG. 3 is an exploded assembly view of portions of a handle assembly of the powered surgical stapling system of FIG. 1.

FIG. 1 illustrates the surgical instrument 1010 that includes an interchangeable shaft assembly 1200 operably coupled to a housing 1012. FIG. 2 illustrates the interchangeable shaft assembly 1200 detached from the housing 1012 or handle 1014. As can be seen in FIG. 3, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019. FIGS. 1 and 3 depict a motor-driven surgical cutting and fastening instrument 1010 that may or may not be reused. In the illustrated embodiment, the instrument 1010 includes a previous housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. In addition, various components may be "housed" or contained in the housing or various components may be "associated with" a housing. In such instances, the components may not be contained within the housing or supported directly by the housing. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, that is incorporated by reference herein in its entirety.

The previous housing 1012 depicted in FIG. 1 is shown in connection with an interchangeable shaft assembly 1200 (FIGS. 2, 4 and 5) that includes an end effector 1300 that comprises a surgical cutting and fastening device that is configured to operably support a surgical staple cartridge 4000 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 3, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 3, the closure trigger 1032 is pivotally coupled to the handle 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 3, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 3, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button 1062. A magnetic element 1063, such as a permanent magnet, for example, may be mounted to the arm 1061. When the closure release button 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system 1080 may also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 3, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally-movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counter-clockwise direction. When the electric motor 1082 is rotated in one direction, the drive member 1120 will be axially driven in the distal direction "DD". When the motor 82 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 1032 as was discussed above. In at least one form, a firing trigger safety button 1134 may be pivotally mounted to the closure trigger 1032 by the pin 1035. The safety button 1134 may be positioned between the firing trigger 1130 and the closure trigger 1032 and have a pivot arm 1136 protruding therefrom. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Pat. No. 8,608,045, entitled POWERED SURGICAL CUTTING AND STAPLING APPARATUS WITH MANUALLY RETRACTABLE FIRING SYSTEM, discloses bailout arrangements and other components, arrangements and systems that may also be employed with the various instruments disclosed herein. U.S. Pat. No. 8,608,045, is hereby incorporated by reference herein in its entirety.

Figure 4:
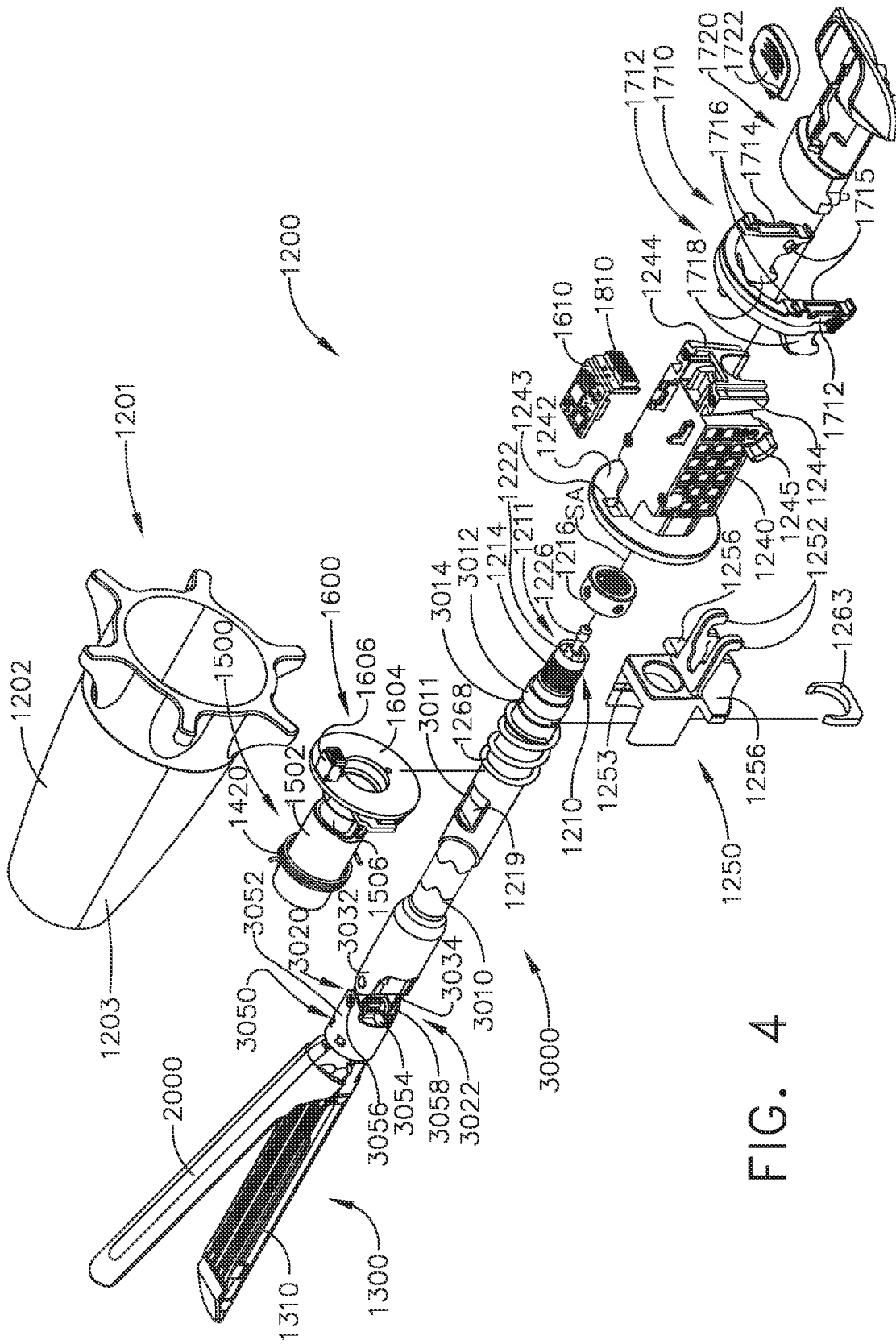
FIG. 4 is an exploded assembly view of the interchangeable surgical shaft assembly of FIG. 2.
Figure 5:
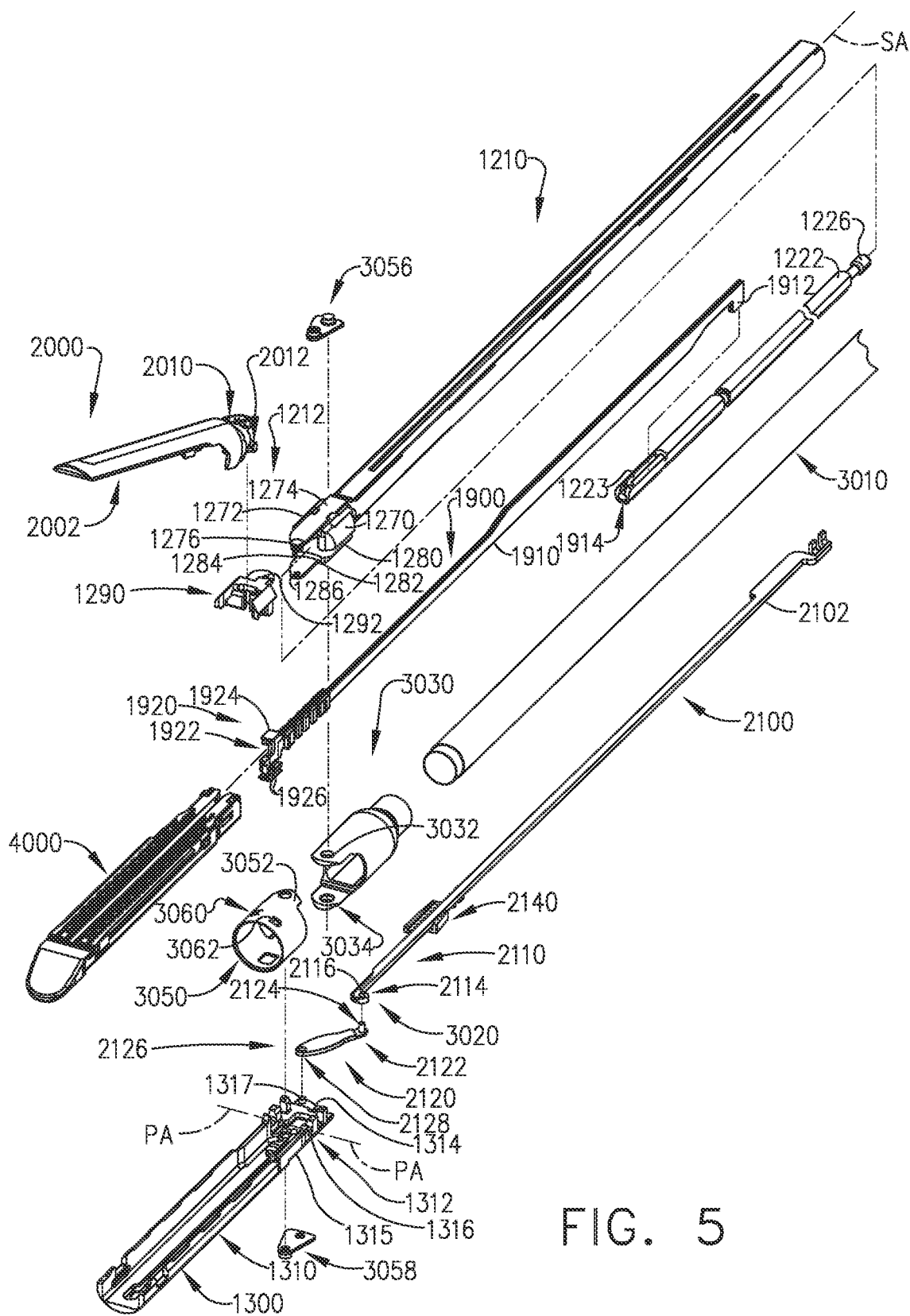
FIG. 5 is another partial exploded assembly view of a portion of the interchangeable surgical shaft assembly of FIG. 4.

Turning now to FIGS. 2 and 5, the interchangeable shaft assembly 1200 includes a surgical end effector 1300 that comprises an elongate channel 1310 that is configured to operably support a staple cartridge 4000 therein. The end effector 1300 may further include an anvil 2000 that is pivotally supported relative to the elongate channel 1310. The interchangeable shaft assembly 1200 may further include an articulation joint 3020 and an articulation lock 2140 which can be configured to releasably hold the end effector 1300 in a desired position relative to a shaft axis SA. Examples of various features of at least one form of the end effector 1300, the articulation joint 3020 and articulation locks may be found in U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541. The entire disclosure of U.S. patent application Ser. No. 13/803,086, filed Mar. 14, 2013, entitled ARTICULATABLE SURGICAL INSTRUMENT COMPRISING AN ARTICULATION LOCK, now U.S. Patent Application Publication No. 2014/0263541, is hereby incorporated by reference herein. As can be seen in FIG. 4, the interchangeable shaft assembly 1200 can further include a proximal housing or nozzle 1201 comprised of nozzle portions 1202 and 1203.

The interchangeable shaft assembly 1200 can further include a closure system or closure member assembly 3000 which can be utilized to close and/or open the anvil 2000 of the end effector 1300. The shaft assembly 1200 can include a spine 1210 that is configured to, one, slidably support a firing member therein and, two, slidably support the closure member assembly 3000 which extends around the spine 1210. As can be seen in FIG. 5, a distal end 1212 of spine 1210 terminates in an upper lug mount feature 1270 and in a lower lug mount feature 1280. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to a proximal end portion 1312 of the elongate channel 1310. The lower mounting link 1284 includes lower pivot pin 1286 that adapted to be received within a pivot hole 1314 formed in the proximal end portion 1312 of the elongate channel 1310. See FIG. 5. The lower pivot pin 1286 is vertically aligned with the pivot socket 1276 to define an articulation axis AA about which the surgical end effector 1300 may articulate relative to the shaft axis SA. See FIG. 2.

In the illustrated example, the surgical end effector 1300 is selectively articulatable about the articulation axis AA by an articulation system 2100. In one form, the articulation system 2100 includes proximal articulation driver 2102 that is pivotally coupled to an articulation link 2120. As can be most particularly seen in FIG. 5, an offset attachment lug 2114 is formed on a distal end 2110 of the proximal articulation driver 2102. A pivot hole 2116 is formed in the offset attachment lug 2114 and is configured to pivotally receive therein a proximal link pin 2124 formed on the proximal end 2122 of the articulation link 2120. A distal end 2126 of the articulation link 2120 includes a pivot hole 2128 that is configured to pivotally receive therein a channel pin 1317 formed on the proximal end portion 1312 of the elongate channel 1310. Thus, axial movement of proximal articulation driver 2102 will thereby apply articulation motions to the elongate channel 1310 to thereby cause the surgical end effector 1300 to articulate about the articulation axis AA relative to the spine 1210. Further details concerning the construction and operation of the articulation system 2100 may be found in various references incorporated by reference herein including U.S. patent application Ser. No. 15/635,631, filed Jun. 28, 2017, entitled SURGICAL INSTRUMENT WITH AXIALLY MOVABLE CLOSURE MEMBER, now U.S. Patent Application Publication No. 2019/0000464, the entire disclosure of which is hereby incorporated by reference herein. In various circumstances, the proximal articulation driver 2102 can be held in position by an articulation lock 2140 when the proximal articulation driver 2102 is not being moved in the proximal or distal directions. Additional details regarding an example of an articulation lock 2140 may be found in U.S. patent application Ser. No. 15/635,631, now U.S. Patent Application Publication No. 2019/0000464, as well as in other references incorporated by reference herein.

In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 4. Such an arrangement facilitates rotatable attachment of the spine 1210 to the chassis 1240 such that the spine 1210 may be selectively rotated about a shaft axis SA relative to the chassis 1240.

Referring primarily to FIG. 4, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIG. 3) that is attached to the second closure link 1038 as will be discussed in further detail below. In at least one example, the closure member assembly 3000 comprises a proximal closure member segment 3010 that has a proximal end 3012 that is coupled to the closure shuttle 1250 for relative rotation thereto. For example, a U shaped connector 1263 is inserted into an annular slot 3014 in the proximal end 3012 of the proximal closure member segment 3010 and is retained within vertical slots 1253 in the closure shuttle 1250. Such an arrangement serves to attach the proximal closure member segment 3010 to the closure shuttle 1250 for axial travel therewith while enabling the proximal closure member segment 3010 to rotate relative to the closure shuttle 1250 about the shaft axis SA. A closure spring 1268 is journaled on the proximal closure member segment 3010 and serves to bias the proximal closure member segment 3010 in the proximal direction "PD" which can serve to pivot the closure trigger 1032 into the unactuated position when the shaft assembly is operably coupled to the handle 1014.

In at least one form, the interchangeable shaft assembly 1200 may further include an articulation joint 3020. Other interchangeable shaft assemblies, however, may not be capable of articulation. As can be seen in FIG. 5, for example, a distal closure member or distal closure tube segment 3030 is coupled to the distal end of the proximal closure member segment 3010. The articulation joint 3020 includes a double pivot closure sleeve assembly 3022. According to various forms, the double pivot closure sleeve assembly 3022 includes an end effector closure tube 3050 having upper and lower distally projecting tangs 3052, 3054. An upper double pivot link 3056 includes upwardly projecting distal and proximal pivot pins that engage respectively an upper distal pin hole in the upper proximally projecting tang 3052 and an upper proximal pin hole in an upper distally projecting tang 3032 on the distal closure tube segment 3030. A lower double pivot link 3058 includes upwardly projecting distal and proximal pivot pins that engage respectively a lower distal pin hole in the lower proximally projecting tang 3054 and a lower proximal pin hole in the lower distally projecting tang 3034. See FIGS. 4 and 5. As will be discussed in further detail below, the closure member assembly 3000 is translated distally (direction "DD") to close the anvil 2000, for example, in response to the actuation of the closure trigger 1032. The anvil 2000 is opened by proximally translating the closure member assembly 3000 which causes the end effector closure sleeve to interact with the anvil 2000 and pivot it to an open position.

As was also indicated above, the interchangeable shaft assembly 1200 further includes a firing member 1900 that is supported for axial travel within the spine 1210. The firing member 1900 includes an intermediate firing shaft portion 1222 that is configured for attachment to a distal cutting portion or knife bar 1910. The intermediate firing shaft portion 1222 may include a longitudinal slot 1223 in the distal end thereof which can be configured to receive a tab 1912 on the proximal end of the distal knife bar 1910. The longitudinal slot 1223 and the proximal end tab 1912 can be sized and configured to permit relative movement therebetween and can comprise a slip joint 1914. The slip joint 1914 can permit the intermediate firing shaft portion 1222 of the firing member 1900 to be moved to articulate the end effector 1300 without moving, or at least substantially moving, the knife bar 1910. Once the end effector 1300 has been suitably oriented, the intermediate firing shaft portion 1222 can be advanced distally until a proximal sidewall of the longitudinal slot 1223 comes into contact with the tab 1912 in order to advance the knife bar 1910 and fire the staple cartridge 4000 positioned within the channel 1310. The knife bar 1910 includes a knife portion 1920 that includes a blade or tissue cutting edge 1922 and includes an upper anvil engagement tab 1924 and lower channel engagement tabs 1926. Various firing member configurations and operations are disclosed in various other references incorporated herein by reference.

As can be seen in FIG. 4, the shaft assembly 1200 further includes a switch drum 1500 that is rotatably received on proximal closure member segment 3010. The switch drum 1500 comprises a hollow shaft segment 1502 that has a shaft boss formed thereon for receive an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle portions 1202, 1203 and permit relative rotation, but not translation, between the switch drum 1500 and the nozzle 1201. The mounts also extend through openings 3011 in the proximal closure member segment 3010 to be seated in recesses 1219 in the spine 1210. Rotation of the switch drum 1500 about the shaft axis SA will ultimately result in the rotation of the actuation pin and the lock sleeve between its engaged and disengaged positions. In one arrangement, the rotation of the switch drum 1500 may be linked to the axial advancement of the closure tube or closure member. Thus, in essence, actuation of the closure system may operably engage and disengage the articulation drive system with the firing drive system in the various manners described in further detail in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. Pat. No. 9,913,642, entitled SURGICAL INSTRUMENT COMPRISING A SENSOR SYSTEM, the entire disclosures of each being hereby incorporated by reference herein. For example, when the closure tube is in its proximal-most position corresponding to a "jaws open" position, the closure member segment 3010 will have positioned the switch drum 1500 so as to link the articulation system with the firing drive system. When, the closure tube has been moved to its distal position corresponding to a "jaws closed" position, the closure tube has rotated the switch drum 1500 to a position wherein the articulation system is delinked from the firing drive system.

As also illustrated in FIG. 4, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis flange 1242. See FIG. 4. Further details regarding slip ring assembly 1600 may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552, and U.S. Pat. No. 9,345,481, entitled STAPLE CARTRIDGE TISSUE THICKNESS SENSOR SYSTEM, for example. U.S. patent application Ser. No. 13/803,086, now U.S. Patent Application Publication No. 2014/0263541, U.S. patent application Ser. No. 13/800,067, now U.S. Patent Application Publication No. 2014/0263552, and U.S. Pat. No. 9,345,481 are each hereby incorporated by reference herein in their respective entireties.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to distal connector flange. In various instances, the shaft assembly 1200 can comprise at least one sensor configured to detect the position of the switch drum 1500.

Referring again to FIG. 4, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 3. Each dovetail slot 1702 may be tapered or, stated another way, be somewhat V-shaped to seatingly receive the attachment portions 1244 therein. As can be further seen in FIG. 4, a shaft attachment lug 1226 is formed on the proximal end of the intermediate firing shaft portion 1222. As will be discussed in further detail below, when the interchangeable shaft assembly 1200 is coupled to the handle 1014, the shaft attachment lug 1226 is received in a firing shaft attachment cradle 1126 formed in a distal end 1125 of the longitudinal drive member 1120. See FIG. 3.

Various shaft assembly embodiments employ a latch system 1710 for removably coupling the shaft assembly 1200 to the housing 1012 and more specifically to the frame 1020. As can be seen in FIG. 4, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange portion 1700 of the frame 1020. See FIG. 3. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button in the distal direction which also causes the lock yoke 1712 to pivot out of retaining engagement with the distal attachment flange portion 1700 of the frame 1020. When the lock yoke 1712 is in "retaining engagement" with the distal attachment flange portion 1700 of the frame 1020, the lock lugs 1716 are retainingly seated within the corresponding lock detents or grooves 1704 in the distal attachment flange portion 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 1032 to grasp and manipulate the target tissue into a desired position. Once the target tissue is positioned within the end effector 1300 in a desired orientation, the clinician may then fully actuate the closure trigger 1032 to close the anvil 2000 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 4, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 2000 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 2000 is in the closed position), the lock yoke 1712 is prevented from being pivoted to an unlocked position. Stated another way, if the clinician were to attempt to pivot the lock yoke 1712 to an unlocked position or, for example, the lock yoke 1712 was inadvertently bumped or contacted in a manner that might otherwise cause it to pivot distally, the lock hooks 1718 on the lock yoke 1712 will contact the lock lug portions 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail receiving slots 1702. In doing so, the shaft attachment lug 1226 on the intermediate firing shaft portion 1222 will also be seated in the cradle 1126 in the longitudinally movable drive member 1120 and the portions of the pin 1037 on the second closure link 1038 will be seated in the corresponding hooks 1252 in the closure shuttle 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame or spine of the shaft assembly 1200 with the frame 1020 of the handle 1014. Another system can comprise a closure drive system 1030 which can operably connect the closure trigger 1032 of the handle 1014 and the closure tube 1260 and the anvil 2000 of the shaft assembly 1200. As outlined above, the closure shuttle 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft portion 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the handle control board 1100. Further details regaining the circuitry and control systems may be found in U.S. patent application Ser. No. 13/803,086, now U.S. Patent Application Publication No. 2014/0263541, and U.S. patent application Ser. No. 14/226,142, now U.S. Pat. No. 9,913,642, the entire disclosures of each which were previously incorporated by reference herein. The fifth system may consist of the latching system for releasably locking the shaft assembly 1200 to the handle 1014.

The anvil 2000 in the illustrated example includes an anvil body 2002 that terminates in an anvil mounting portion 2010. The anvil mounting portion 2010 is movably or pivotably supported on the elongate channel 1310 for selective pivotal travel relative thereto about a fixed anvil pivot axis PA that is transverse to the shaft axis SA. In the illustrated arrangement, a pivot member or anvil trunnion 2012 extends laterally out of each lateral side of the anvil mounting portion 2010 to be received in a corresponding trunnion cradle 1316 formed in the upstanding walls 1315 of the proximal end portion 1312 of the elongate channel 1310. The anvil trunnions 2012 are pivotally retained in their corresponding trunnion cradle 1316 by the channel cap or anvil retainer 1290. The channel cap or anvil retainer 1290 includes a pair of attachment lugs that are configured to be retainingly received within corresponding lug grooves or notches formed in the upstanding walls 1315 of the proximal end portion 1312 of the elongate channel 1310. See FIG. 5.

Still referring to FIG. 5, in at least one arrangement, the distal closure member or end effector closure tube 3050 employs two axially offset, proximal and distal positive jaw opening features 3060 and 3062. The positive jaw opening features 3060, 3062 are configured to interact with corresponding relieved areas and stepped portions formed on the anvil mounting portion 2010 as described in further detail in U.S. patent application Ser. No. 15/635,631, entitled SURGICAL INSTRUMENT WITH AXIALLY MOVABLE CLOSURE MEMBER, now U.S. Patent Application Publication No. 2019/0000464, the entire disclosure which has been herein incorporated by reference. Other jaw opening arrangements may be employed.

Figure 6:
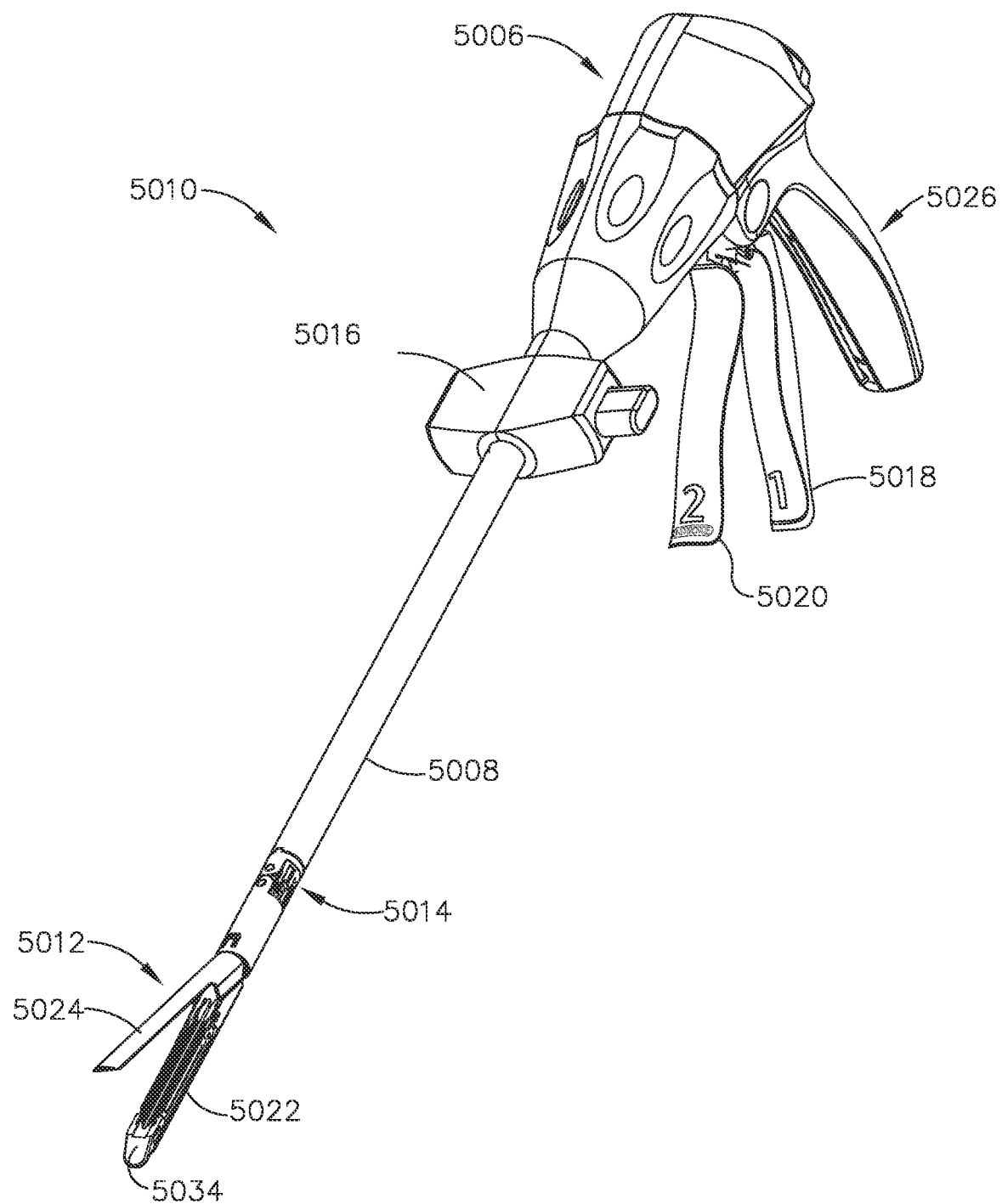
FIG. 6 is a perspective view of another powered surgical stapling system.
Figure 7:
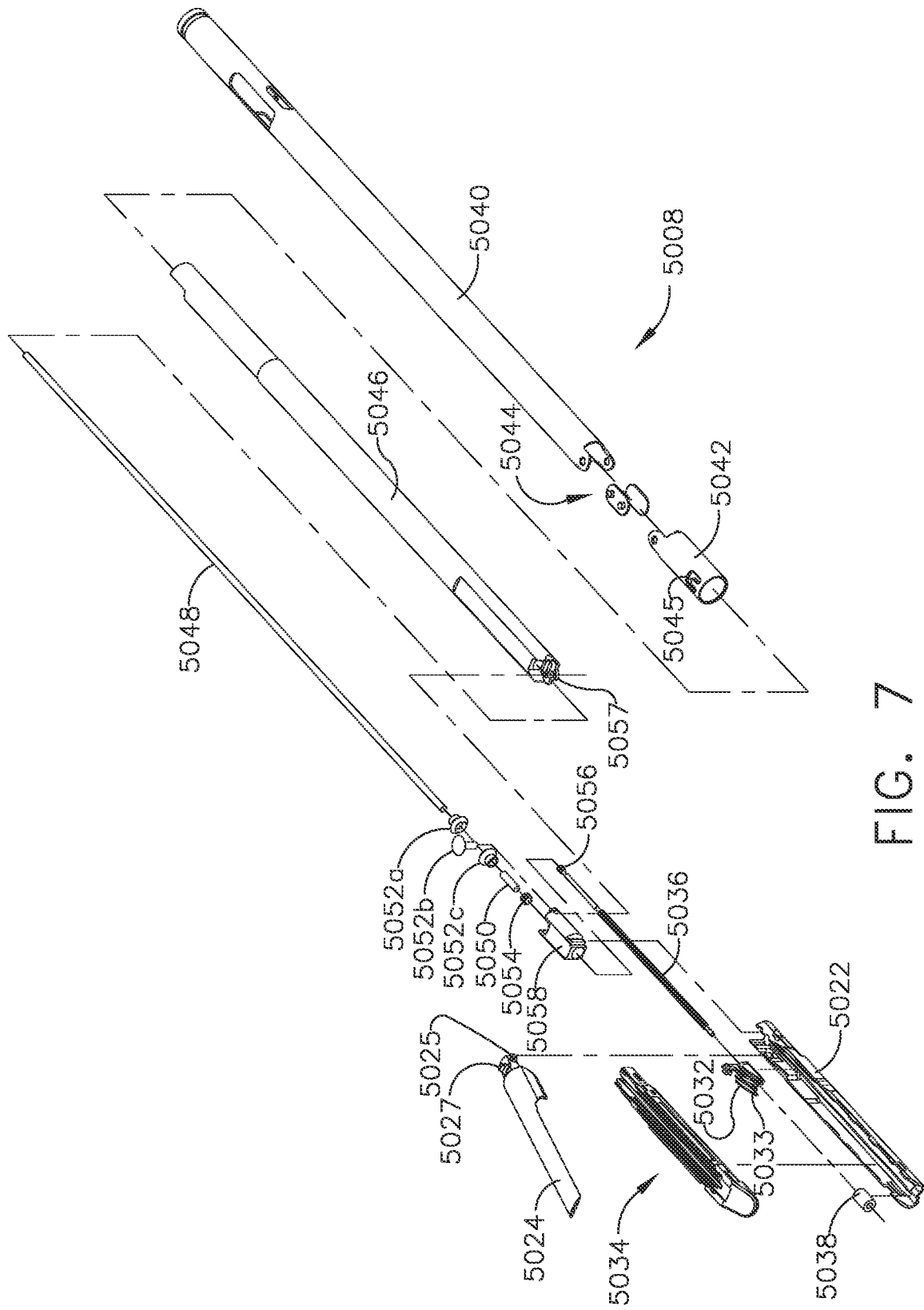
FIG. 7 is an exploded assembly view of portion of a shaft assembly of the power surgical stapling system of FIG. 6.
Figure 8:
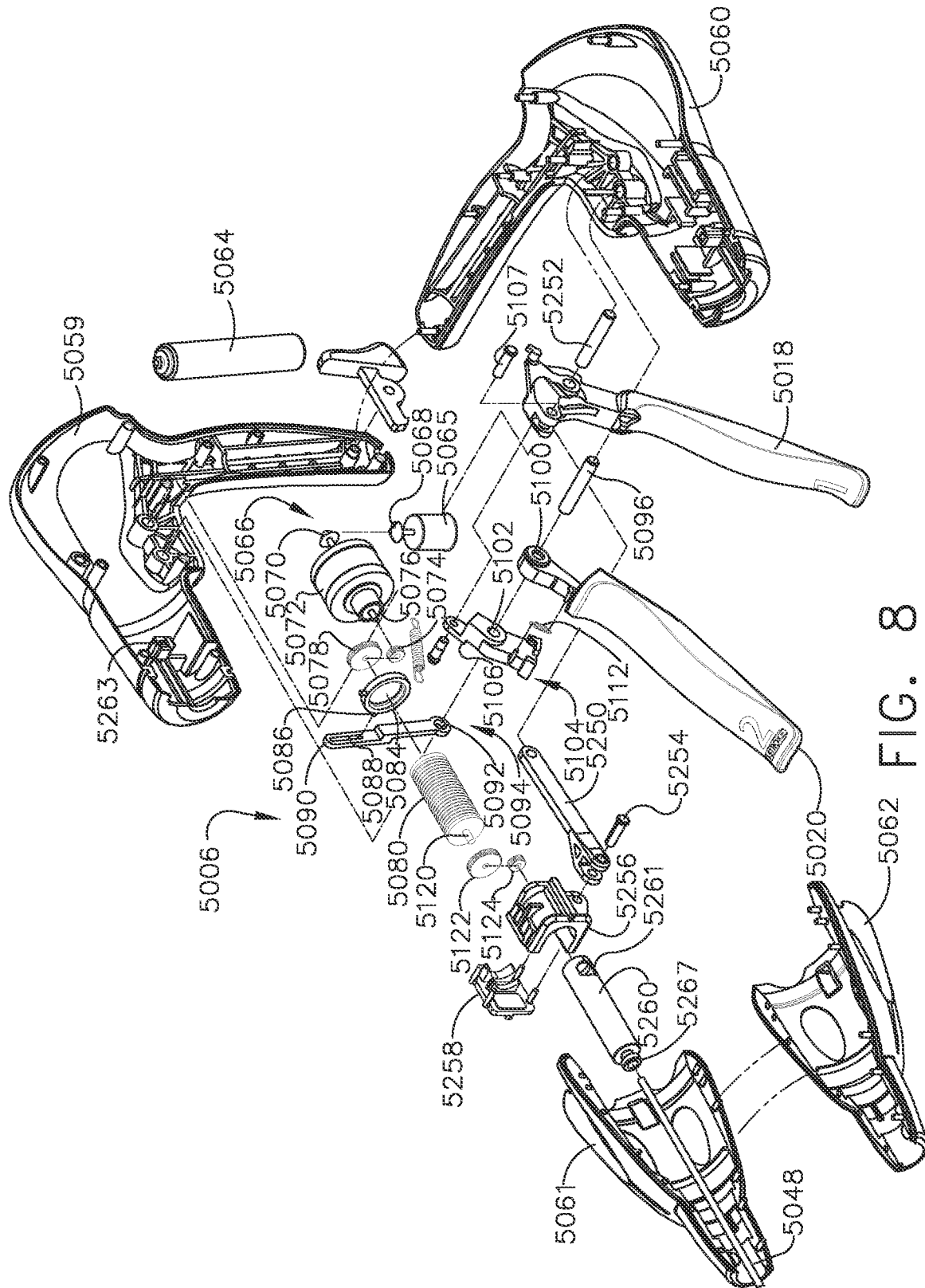
FIG. 8 is an exploded assembly view of portions of a handle assembly of the powered surgical stapling system of FIG. 6.

FIGS. 6-8 depict a previous surgical cutting and fastening instrument 5010 that is configured to generate rotary drive motions for operating a surgical end effector 5012. The endoscopic surgical instrument 5010 comprises a handle 5006, a shaft 5008, and an articulating surgical end effector 5012 pivotally connected to the shaft 5008 at an articulation pivot 5014. An articulation control 5016 may be provided adjacent to the handle 5006 to effect rotation of the end effector 5012 about the articulation pivot 5014. It will be appreciated that various embodiments may include a non-pivoting end effector, and therefore may not have an articulation pivot 5014 or articulation control 5016.

The handle 5006 of the instrument 5010 may include a closure trigger 5018 and a firing trigger 5020 for actuating the end effector 5012. It will be appreciated that instruments having end effectors directed to different surgical tasks may have different numbers or types of triggers or other suitable controls for operating the end effector 5012. In one embodiment, a clinician or operator of the instrument 5010 may articulate the end effector 5012 relative to the shaft 5008 by utilizing the articulation control 5016, as described in more detail in U.S. Pat. No. 7,670,334, entitled SURGICAL INSTRUMENT HAVING AN ARTICULATING END EFFECTOR, the entire disclosure of which is incorporated herein by reference. The end effector 5012 includes in this example, among other things, a staple channel 5022 and a pivotally translatable clamping member, such as an anvil 5024, which are maintained at a spacing that assures effective stapling and severing of tissue clamped in the end effector 5012. The handle 5006 includes a pistol grip 5026 toward which the closure trigger 5018 is pivotally drawn by the clinician to cause clamping or closing of the anvil 5024 towards the staple channel 5022 of the end effector 5012 to thereby clamp tissue positioned between the anvil 5024 and channel 5022.

In the arrangement depicted in FIG. 7, the end effector 5012 includes, in addition to the previously-mentioned channel 5022 and anvil 5024, a cutting instrument 5032, a sled 5033, a staple cartridge 5034 that is removably seated in the channel 5022, and a helical screw shaft 5036. The cutting instrument 5032 may be, for example, a knife. The anvil 5024 includes pivot pins 5025 that are movably supported in corresponding slots in the channel 5022. In one arrangement, the anvil 5024 includes a tab 5027 at its proximate end that is inserted into a component of the mechanical closure system (described further below) to open and close the anvil 5024.

Still referring to FIG. 7, the shaft 5008 includes a proximal closure tube 5040 and a distal closure tube 5042 pivotably linked by a pivot link 5044. The distal closure tube 5042 includes an opening 5045 into which the tab 5027 on the anvil 5024 is inserted in order to open and close the anvil 5024, as further described below. Disposed inside the closure tubes 5040, 5042 may be a proximate spine tube 5046. Disposed inside the proximate spine tube 5046 may be a main rotational (or proximate) drive shaft 5048 that communicates with a secondary (or distal) drive shaft 5050 via a bevel gear assembly 5052a-c. The secondary drive shaft 5050 is connected to a drive gear 5054 that engages a proximate drive gear 5056 of the helical screw shaft 5036. The vertical bevel gear 5052b may sit and pivot in an opening 5057 in the distal end of the proximate spine tube 5046. A distal spine tube 5058 may be used to enclose the secondary drive shaft 5050 and the drive gears 5054, 5056. Collectively, the main drive shaft 5048, the secondary drive shaft 5050, and the articulation assembly (e.g., the bevel gear assembly 5052a-c) are sometimes referred to herein as the "main drive shaft assembly."

A bearing 5038, positioned at a distal end of the staple channel 5022, receives the helical screw shaft 5036, allowing the helical screw shaft 5036 to freely rotate with respect to the channel 5022. The helical screw shaft 5036 may interface a threaded opening (not shown) of the knife 5032 such that rotation of the helical screw shaft 5036 causes the knife 5032 to translate distally or proximately (depending on the direction of the rotation) through the staple channel 5022.

Turning next to FIG. 8, the handle 5006 includes exterior lower side pieces 5059, 5060 and nozzle pieces 5061, 5062 that fit together to form, in general, the exterior of the handle 5006. A battery 5064, such as a Li ion battery, may be provided in the pistol grip portion 5026 of the handle 5006. The battery 5064 powers a motor 5065 disposed in an upper portion of the pistol grip portion 5026 of the handle 5006. The motor 5065 may drive a 90° bevel gear assembly 5066 comprising a first bevel gear 5068 and a second bevel gear 5070. The bevel gear assembly 5066 may drive a planetary gear assembly 5072. The planetary gear assembly 5072 may include a pinion gear 5074 connected to a drive shaft 5076. The pinion gear 5074 may drive a mating ring gear 5078 that drives a helical gear drum 5080 via a drive shaft. A ring 5084 may be threaded on the helical gear drum 5080. Thus, when the motor 5065 rotates, the ring 5084 is caused to travel along the helical gear drum 5080 by means of the interposed bevel gear assembly 5066, planetary gear assembly 5072 and ring gear 5078.

The handle 5006 may include a middle handle piece 5104 adjacent to the upper portion of the firing trigger 5020. The handle 5006 also may comprise a bias spring 5112 connected between posts on the middle handle piece 5104 and the firing trigger 5020. The bias spring 5112 may bias the firing trigger 5020 to its fully open position. In that way, when the operator releases the firing trigger 5020, the bias spring 5112 will pull the firing trigger 5020 to its open position. The distal end of the helical gear drum 5080 includes a distal drive shaft 5120 that drives a ring gear 5122, which mates with a pinion gear 5124. The pinion gear 5124 is connected to the main drive shaft 5048 of the main drive shaft assembly. In that way, rotation of the motor 5065 causes the main drive shaft assembly to rotate, which causes actuation of the end effector 5012. The ring 5084 threaded on the helical gear drum 5080 may include a post 5086 that is disposed within a slot 5088 of a slotted arm 5090. The slotted arm 5090 has an opening 5092 in its opposite end 5094 that receives a pivot pin 5096 that is connected between the handle exterior side pieces 5059, 5060. The pivot pin 5096 is also disposed through an opening 5100 in the firing trigger 5020 and an opening 5102 in the middle handle piece 5104.

The middle handle piece 5104 includes a backside shoulder 5106 that engages the slotted arm 5090. The middle handle piece 5104 also has a forward motion 5107 stop that engages the firing trigger 5020. The movement of the slotted arm 5090 is controlled by rotation of the motor 5065. When the slotted arm 5090 rotates counter clockwise as the ring 5084 travels from the proximate end of the helical gear drum 5080 to the distal end, the middle handle piece 5104 will be free to rotate counter clockwise. Thus, as the user draws in the firing trigger 5020, the firing trigger 5020 will engage the forward motion stop 5107 of the middle handle piece 5104, causing the middle handle piece 5104 to rotate counter clockwise. Due to the backside shoulder 5106 engaging the slotted arm 5090, however, the middle handle piece 5104 will only be able to rotate counter clockwise as far as the slotted arm 5090 permits. In that way, if the motor 5065 should stop rotating for some reason, the slotted arm 5090 will stop rotating, and the user will not be able to further draw in the firing trigger 5020 because the middle handle piece 5104 will not be free to rotate counter clockwise due to the slotted arm 5090.

Components of an exemplary closure system for closing (or clamping) the anvil 5024 of the end effector 5012 by retracting the closure trigger 5018 are also shown in FIG. 8. In the illustrated embodiment, the closure system includes a yoke 5250 connected to the closure trigger 5018. A pivot pin 5252 is inserted through aligned openings in both the closure trigger 5018 and the yoke 5250 such that they both rotate about the same point. The distal end of the yoke 5250 is connected, via a pin 5254, to a first closure bracket 5256. The first closure bracket 5256 connects to a second closure bracket 5258. Collectively, the closure brackets 5256, 5258 define an opening in which the proximate end of the proximal closure tube 5040 (see FIG. 7) is seated and held such that longitudinal movement of the closure brackets 5256, 5258 causes longitudinal motion by the proximal closure tube 5040. The instrument 5010 also includes a closure drive shaft 5260 disposed inside the proximal closure tube 5040. The closure drive shaft 5260 may include a window 5261 into which a post 5263 on one of the handle exterior pieces, such as exterior lower side piece 5059 in the illustrated embodiment, is disposed to fixedly connect the closure drive shaft 5260 to the handle 5006. In that way, the proximal closure tube 5040 is capable of moving longitudinally relative to the closure drive shaft 5260. The closure drive shaft 5260 may also include a distal collar 5267 that fits into a cavity in proximate spine tube 5046 and is retained therein by a cap.

In operation, when the yoke 5250 rotates due to retraction of the closure trigger 5018, the closure brackets 5256, 5258 cause the proximal closure tube 5040 to move distally (i.e., away from the handle end of the instrument 5010), which causes the distal closure tube 5042 to move distally, which causes the anvil 5024 to rotate about the pivot pins 5025 into the clamped or closed position. When the closure trigger 5018 is unlocked from the locked position, the proximal closure tube 5040 is caused to slide proximately, which causes the distal closure tube 5042 to slide proximately, which, by virtue of the tab 5027 being inserted in the opening 5045 of the distal closure tube 5042, causes the anvil 5024 to pivot about the pivot pins 5025 into the open or unclamped position. In that way, by retracting and locking the closure trigger 5018, an operator may clamp tissue between the anvil 5024 and channel 5022, and may unclamp the tissue following the cutting/stapling operation by unlocking the closure trigger 5018 from the locked position. Further details concerning the construction and operation of the existing surgical instrument 5010 may be found in U.S. Pat. No. 7,845,537, entitled SURGICAL INSTRUMENT HAVING RECORDING CAPABILITIES, the entire disclosure of which is hereby incorporated by reference herein. Other rotary drive arrangements configured for use with various forms of robotic systems are disclosed in U.S. Patent Application Publication No. 2016/0287251, entitled STAPLING END EFFECTOR CONFIGURED TO COMPENSATE FOR AN UNEVEN GAP BETWEEN A FIRST JAW AND A SECOND JAW, the entire disclosure of which is hereby incorporated by reference herein.

Figure 9:
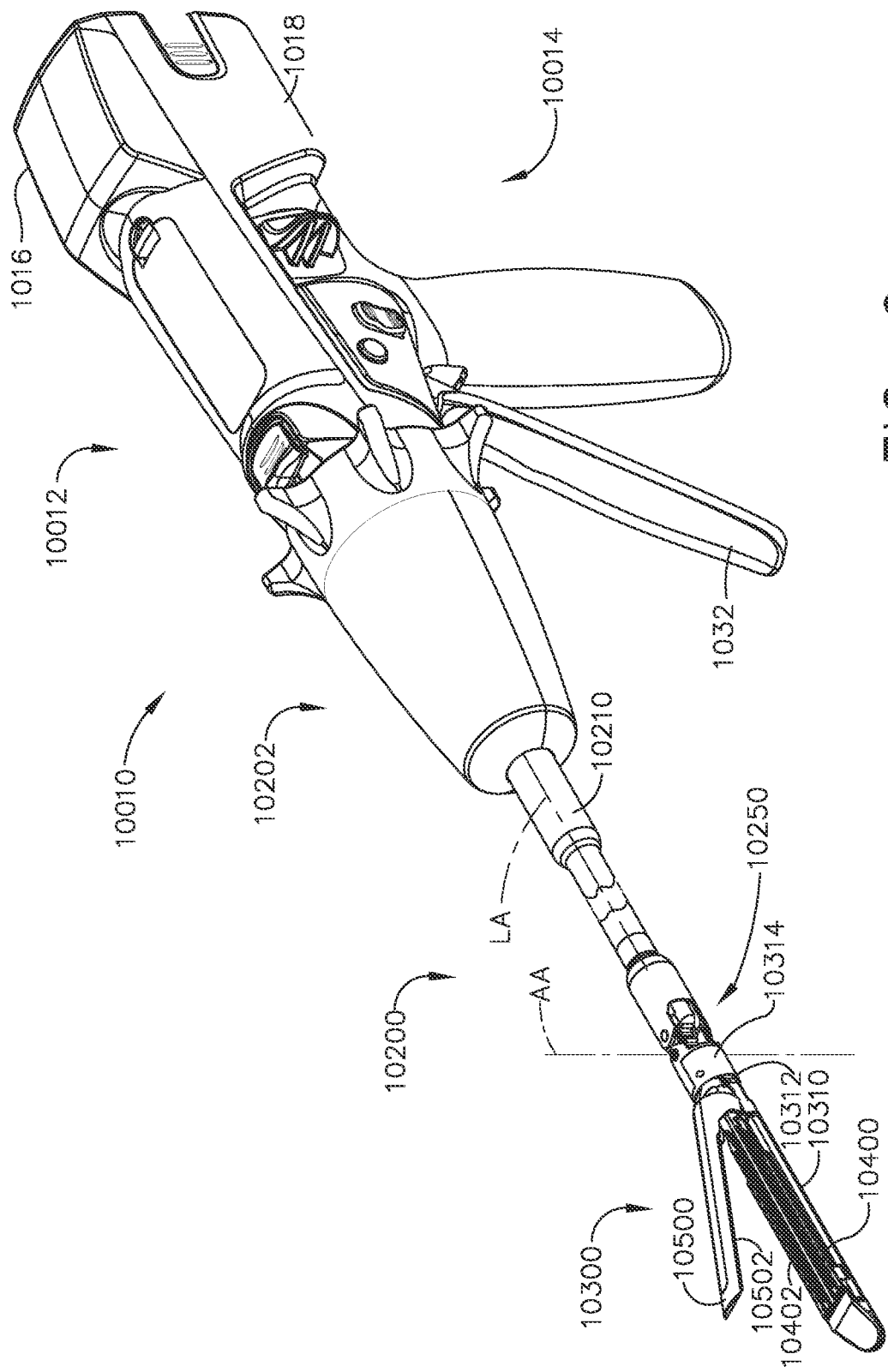
FIG. 9 is a perspective view of another powered surgical stapling system.
Figure 10:
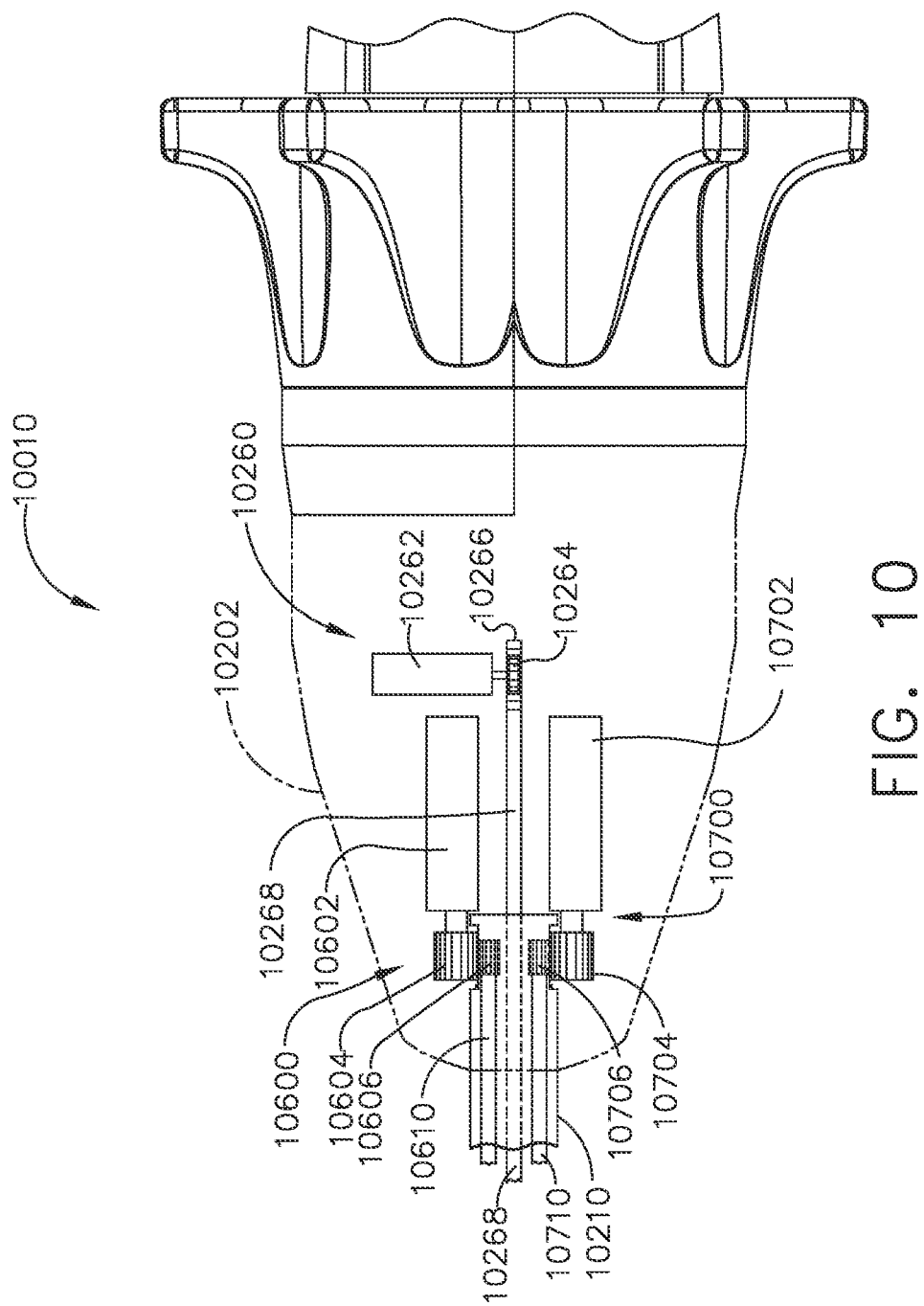
FIG. 10 is a top view of a portion of the powered surgical stapling system of FIG. 9.

Turning next to FIGS. 9 and 10, another motor-driven surgical cutting and fastening instrument 10010 that may or may not be reused is depicted. In the illustrated embodiment, the instrument 10010 includes a housing 10012 that comprises a handle 10014 that is configured to be grasped, manipulated and actuated by the clinician. As can be seen in FIG. 9 for example, the instrument 10010 includes a shaft assembly 10200 that has a surgical end effector 10300 operably coupled thereto that is configured to perform one or more surgical tasks or procedures. In one arrangement, the shaft assembly 10200 comprises an interchangeable shaft assembly that is intended to be removably couplable to the handle assembly 10014 in the various manners disclosed herein. However, the shaft assembly 10200 may also comprise a dedicated shaft assembly that is not intended to be removed from the handle 10014. Only those specific components necessary to understand the functions and operation of the shaft assembly 10200 will be discussed in further detail below.

As can be seen in FIG. 9, for example, the surgical end effector 10300 comprises an elongate channel 10310 that is configured to operably support a staple cartridge 10400 therein. The end effector 10300 also includes an anvil 10500 that is pivotally supported relative to the elongate channel 10310. In one arrangement, for example, the anvil 10500 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein. The shaft assembly 10200 may further include an articulation joint 10250 that facilitates articulation of the surgical end effector 10300 about an articulation axis AA that is transverse to a longitudinal shaft axis LA. Other shaft assemblies, however, may not be capable of articulation. In the illustrated example, the shaft assembly 10200 comprises a proximal outer shaft tube or member 10210 that extends distally from a nozzle assembly 10202. A proximal end 10312 of the elongate channel comprises a tubular portion 10314 that is similar in size to the proximal outer shaft tube 10120 and is coupled to the distal end of the proximal outer shaft tube 10210 to form the articulation joint 10250. The articulation joint 10250 includes a double pivot shaft assembly 10252. See FIGS. 11 and 12. According to various forms, the tubular portion 10314 of the elongate channel 10310 includes upper and lower proximally projecting tangs 10316, 10318. See FIG. 11. An upper double pivot link 10320 includes upwardly projecting distal and proximal pivot pins that engage respectively an upper pin hole in the upper proximally projecting tang 10316 and an upper distal pin hole in an upper distally projecting tang 10212 on the proximal outer shaft tube 10210. A lower double pivot link 10322 includes downwardly projecting distal and proximal pivot pins that engage respectively a lower distal pin hole in the lower proximally projecting tang 10318 and a lower proximal pin hole in a lower distally projecting tang 10214 in the proximal outer shaft tube 10210. See FIG. 11. The shaft assembly 10200 also includes an internal spine member 10230 that is pivotally coupled to an insert assembly 10330 that is received within the tubular portion 10314 of the elongate channel 10310 and is attached thereto by, for example, welding, adhesive, fasteners, etc. A proximal end of the internal spine member 10230 may be rotatably coupled to a chassis (not shown) within the nozzle assembly 10202 in the various manners disclosed herein, for example. The distal end of the internal spine member 10230 may be pinned to the insert assembly 10330 to facilitate pivotal travel of the elongate channel 10310 relative to the internal spine member 10230.

Figure 12:
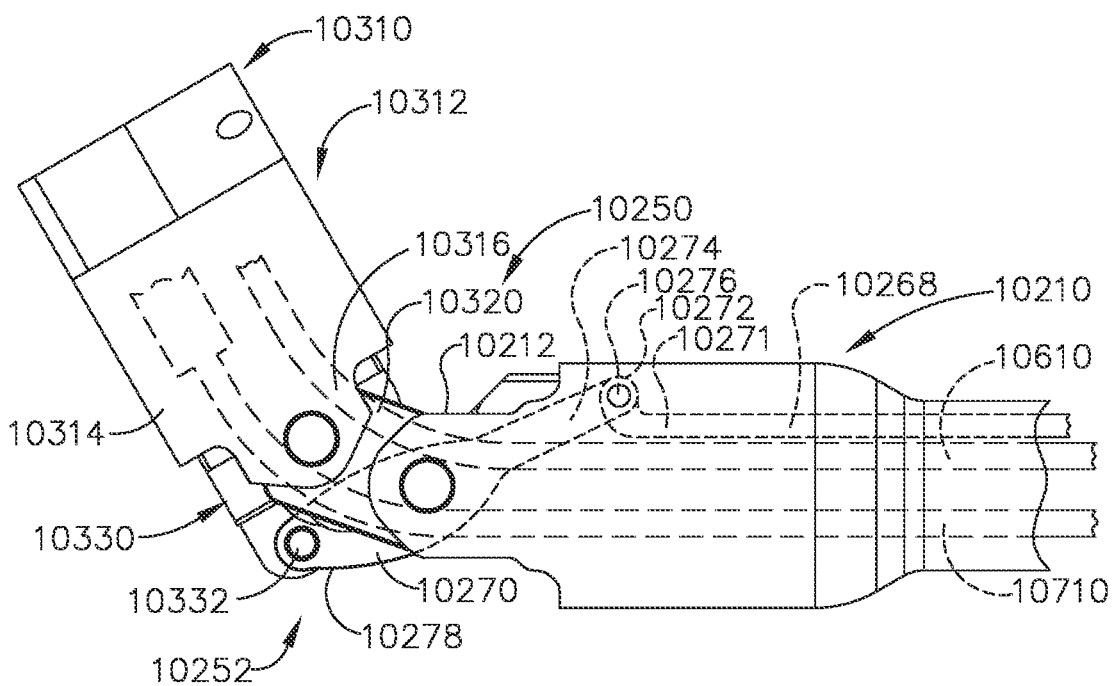
FIG. 12 is a top view of the articulation joint of FIG. 11.

In the illustrated example, the surgical end effector 10300 is selectively articulatable about the articulation axis AA by an articulation system 10260. In one form, the articulation system 10260 includes an articulation motor 10262 that is operably supported in the nozzle assembly 10202, for example. See FIG. 10. In other examples, the articulation motor 10262 may be operably supported in the housing 10012 or handle 10014 or other portion of a robotic system. Referring to FIG. 10, the articulation motor 10262 is coupled to an articulation drive gear 10264 that is in meshing engagement with a drive gear rack 10266 that is attached to or otherwise formed in a proximal articulation driver 10268. A distal end of the proximal articulation driver 10268 is pivotally coupled to a distal articulation link 10270. As can be seen in FIG. 12, an offset attachment lug 10272 is formed on a distal end 10271 of the proximal articulation driver 10268. A pivot hole is formed in the offset attachment lug 10272 and is configured to pivotally receive therein a proximal link pin 10276 formed on the proximal end 10274 of the distal articulation link 10270. A distal end 10278 of the distal articulation link 10270 includes a pivot hole that is configured to pivotally receive therein a channel pin 10332 formed on the insert assembly 10330. Operation of the articulation motor 10262 will cause axial movement of the proximal articulation driver 10268. Axial movement of proximal articulation driver 10268 will apply articulation motions to the elongate channel 10310 to thereby cause the surgical end effector 10300 to articulate about the articulation axis AA relative to the internal spine member 10230. Other articulation systems and arrangements may be employed in the various manners disclosed herein. In other embodiments, the surgical end effector may not be articulatable.

In at least one arrangement, the surgical end effector 10300 includes a firing member that is axially movable within the surgical end effector 10300 between a starting position and an ending position. As will be discussed in further detail below, the firing member may be configured to sever tissue that is clamped between the anvil 10500 and a surgical staple cartridge 10400 that is operably supported in the elongate channel 10310. In one arrangement, the staple cartridge 10400 includes lines of surgical staples or fasteners that are operably supported on corresponding drivers that are movably supported in the cartridge. As the firing member is driven distally, the firing member cooperates with a sled or camming assembly that is supported in the staple cartridge that serves to advance the drivers in a direction toward the closed anvil which causes the staples or fasteners supported thereon to pierce through the clamped tissue into forming contact with the underside of the closed anvil. Once the firing member has been distally advanced from its proximal starting position to its ending position within the end effector, it may be retracted back to its starting position to permit the anvil to be opened to facilitate removal of the cut/stapled tissue from the end effector. In other arrangements, the firing member may be left at the ending position wherein it is permitted to disengage from the anvil to facilitate opening of the anvil.

Figure 11:
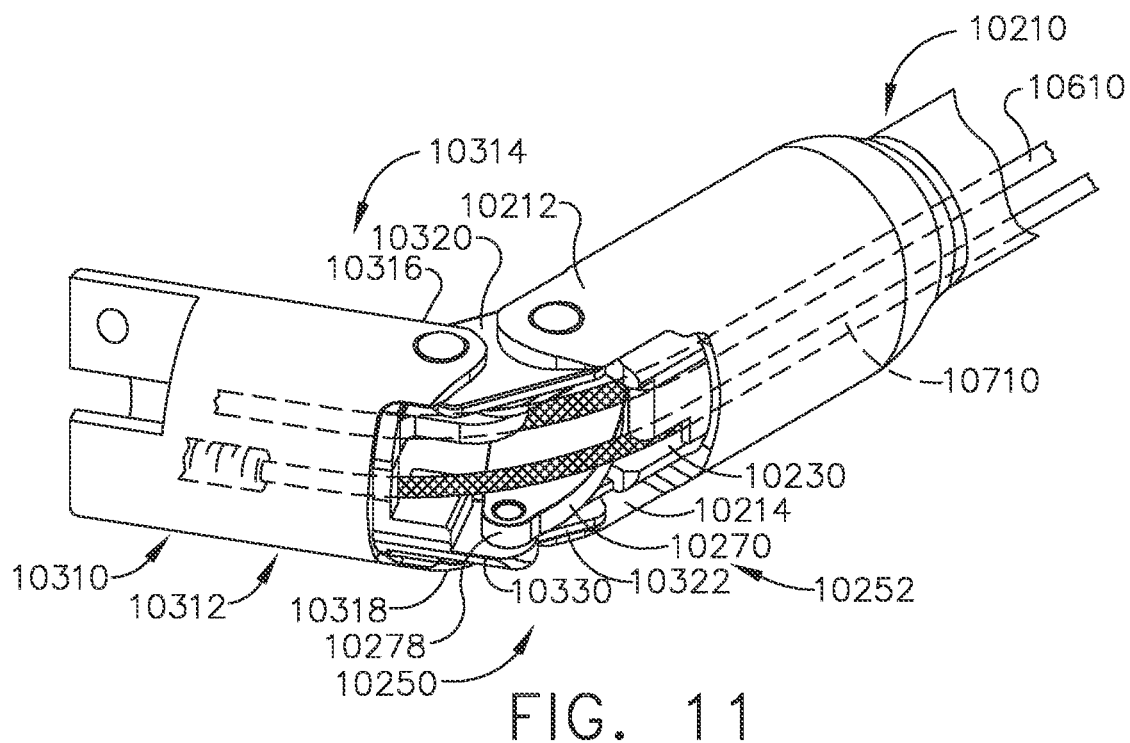
FIG. 11 is a partial perspective view of an articulation joint of the shaft assembly of the surgical stapling system of FIG. 9.

In at least one arrangement, the surgical instrument 10010 also employs a firing system 10600 that is configured to apply rotary drive motions to the firing member to drive the firing member between the starting and end positions. In the example depicted in FIG. 10, the firing system 10600 includes a firing motor 10602 that is operably supported in the nozzle assembly 10202, for example. In other examples, the firing motor 10602 may be operably supported in the housing or handle or other portion of a robotic system. The firing motor 10602 is coupled to a firing drive gear 10604 that is in meshing engagement with a driven gear 10606 that is attached to or otherwise formed in rotary firing drive shaft 10610. As can be seen in FIGS. 11 and 12, the firing drive shaft 10610 may be flexible to permit articulation of the surgical end effector 10300 in the manner described above.

Figure 13:
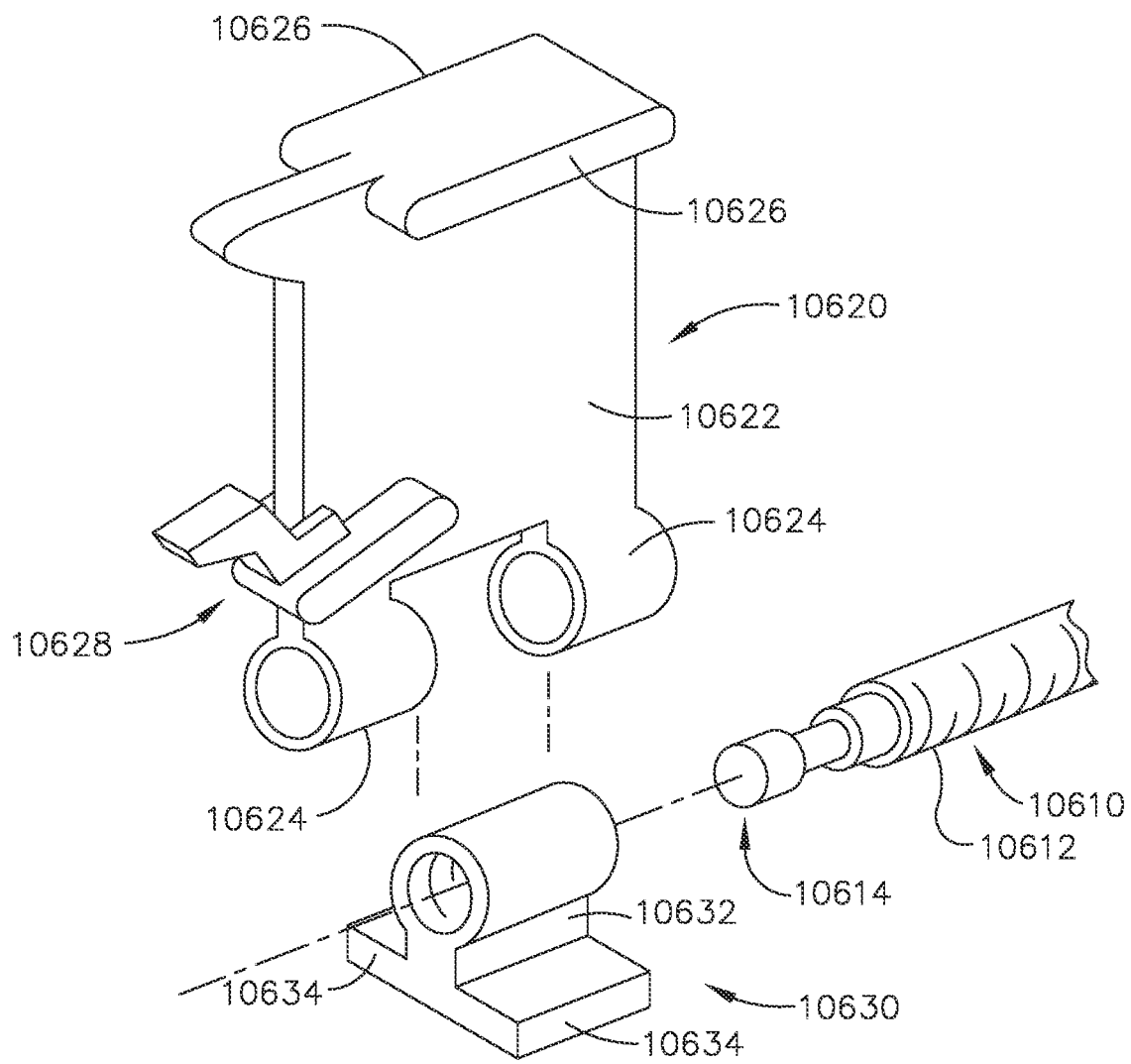
FIG. 13 is a perspective assembly view of a firing member and a firing drive shaft.

FIG. 13 depicts one example of a rotary driven firing member 10620 that may be employed in the surgical end effector 10300. As can be seen in FIG. 13, the firing member 10620 comprises a body portion 10622 that includes two downwardly extending hollow mounting portions 10624 that are unthreaded and spaced from each other to receive a threaded drive nut 10630 therebetween. The threaded drive nut 10630 is threaded onto a threaded portion 10612 of the rotary firing drive shaft 10610. A distal end 10614 of the rotary firing drive shaft 10610 may be configured to be rotatably supported in a bearing (not shown) that is housed within the elongate channel and is configured to rotatably support the rotary firing drive shaft 10610 therein. The drive nut 10630 includes a vertical tab portion 10632 that is sized to extend through an axial slot in the bottom of the elongate channel. Two laterally extending channel engagement flanges 10634 are formed on the threaded drive nut 10630 and are configured to engage the bottom of the elongate channel. In addition, two laterally extending anvil engagement tabs 10626 are formed on the top of the firing member body 10622 and are configured to engage corresponding ledges formed in the anvil 10500 as the firing member 10620 is axially moved within the end effector 10300. In this arrangement, the firing member 10620 includes a camming sled engagement feature 10628 that is configured to operably engage a camming assembly that is movably stored in the staple cartridge. The camming sled or camming assembly (not shown) may include a tissue cutting member or a tissue cutting feature attached to the firing member 10620. The firing member 10620 may be stored within an unfired staple cartridge and is configured to be seated on the threaded drive nut 10630 when the cartridge is operably installed within the elongate channel. However, a variety of other rotary driven firing member arrangements may also be employed. For example, firing and tissue cutting members that are permanently threaded onto the rotary firing drive shaft may also be employed. In various aspects, as the firing member 10620 is distally driven through the surgical staple cartridge 10400, the firing member 10620, through the engagement of the anvil engagement tabs 10626 with the anvil 10500 and the engagement of the channel engagement flanges 10634 with the channel 10310, may serve to maintain a desired amount of tissue gap between a deck surface 10402 on the staple cartridge 10400 and a staple forming undersurface 10502 on the anvil 10500. See FIG. 9.

In the example depicted in FIGS. 10-21, in addition to a rotary driven firing system, the surgical instrument 10010 also includes a rotary driven closure system 10700 that is configured to apply rotary closure motions to the anvil 10500. As can be seen in FIG. 10, for example, in one arrangement, the rotary driven closure system 10700 comprises a closure motor 10702 that is operably supported in the nozzle assembly 10202, for example. In other examples, the closure motor 10702 may be operably supported in the housing or handle or other portion of a robotic system. The closure motor 10702 is coupled to a closure drive gear 10704 that is in meshing engagement with a driven gear 10706 that is attached to or otherwise formed in rotary closure drive shaft 10710. As can be seen in FIGS. 11 and 12, the closure drive shaft 10710 may be flexible to permit articulation of the surgical end effector 10300 in the manner described above.

In the illustrated example, the surgical end effector 10300 includes the anvil 10500 that includes a proximally-extending mounting tab 10510 that is configured to be pivotally attached to a distal insert portion 10334 of the insert assembly 10330. In alternative arrangements, the distal insert portion 10334 may be separate from the insert assembly 10330 and otherwise be attached to the proximal end portion 10312 of the elongate channel 10310 by welding, adhesive, fasteners, etc. In still other arrangements, the distal insert portion 10334 may actually comprise a portion of the elongate channel 10310 and be integrally formed therewith. In the illustrated arrangement, the anvil mounting tab 10510 includes a distal portion 10512 through which a transverse slot 10514 extends therethrough and is aligned with a transverse slot 10336 in the distal insert portion 10334 as well as a slot 10315 in the tubular portion 10314 of the elongate channel 10310. See FIG. 18. The anvil mounting tab 10510 is pivotally attached to the elongate channel 10310 by a rivet 10340. The anvil mounting tab 10510, as well as the distal insert portion 10334, are sufficiently robust to provide a sufficient amount of strength where the rivet 10340 operates which provides the ability to locate the pivoting attachment point above the centerline or midpoint of the end effector and thereby afford sufficient room therein for the firing member components and rotary drive components. Orbit forming of the rivet 10340 pivotally cinches the anvil mounting tab 10510 to the elongate channel 10310 and can remove excessive play or movement (tolerance slop) which serves to place the rivet 10340 in complete or significantly complete shear for resistance against closure loads. In addition, the relatively broad contact between such components may also serve to prevent or minimize twisting between the anvil mounting tab 10510 and the elongate channel 10310.

Figure 14:
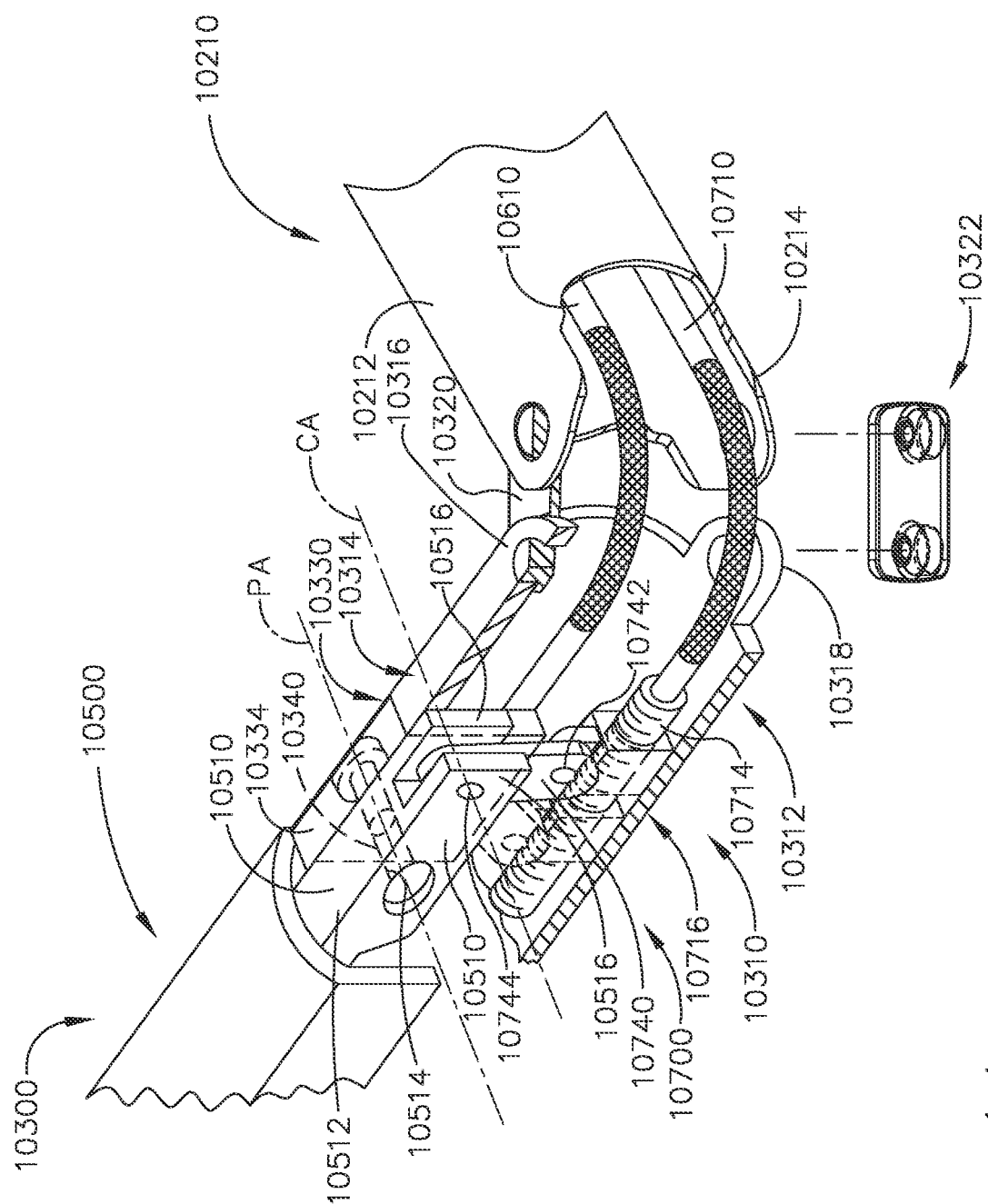
FIG. 14 is a perspective view of portions of an end effector and articulation joint of the powered surgical stapling system of FIG. 9.
Figure 15:
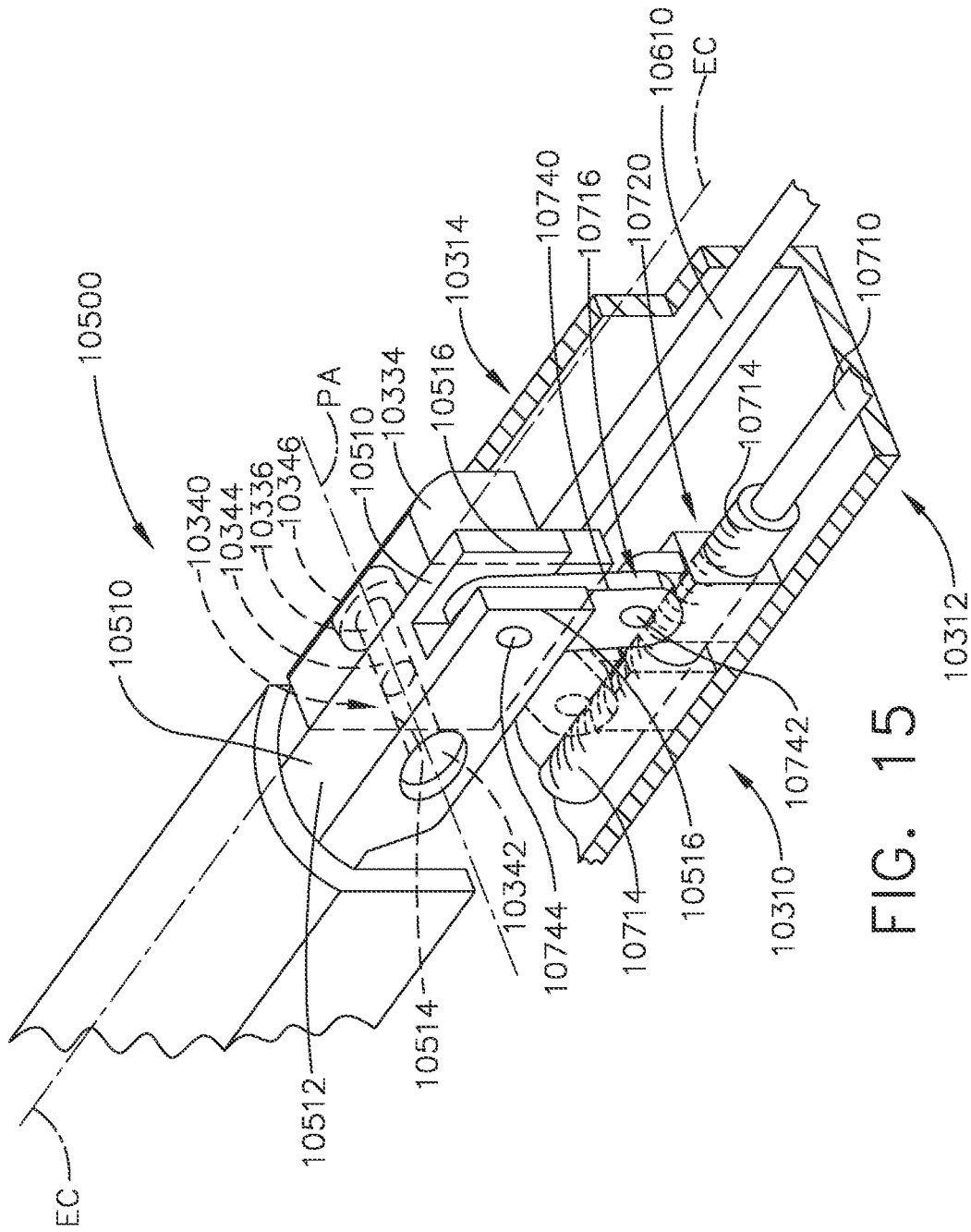
FIG. 15 is another perspective view of the end effector and articulation joint of FIG. 14.

As can be seen in FIGS. 14, 15 and 17, the anvil 10500 is asymmetrically coupled to the elongate channel 10310. Stated another way, the location in which the anvil 10500 is attached to the elongate channel 10310 is laterally offset from the end effector centerline EC. In at least one arrangement, the rivet 10340 comprises solid core rivet with a diameter of 0.05"-0.1" and an orbit formed head 10342 on one end of the rivet shank 10344 and a machined head 10346 on the other end of the rivet shank 10344. In one arrangement, the riveting is done in such a way that the rivet 10340 would hold a final formed height that would ensure intimate contact between the anvil mounting tab 10510 and the corresponding attachment portions of the elongate channel 10310. The "orbit formed" head 10342 would swell the rivet shank 10344 on that side of the anvil mounting tab 10510 and elongate channel portions which may prevent the rivet from rotating relative to that part while the other "premachined" side 10346 would not have a swelled shank portion which may permit the adjacent components to rotate. In one example, the rivet 10340 is fixed relative to the channel portion to avoid a condition wherein the anvil pivots freely relative to the insert and elongate channel.

Figure 20:
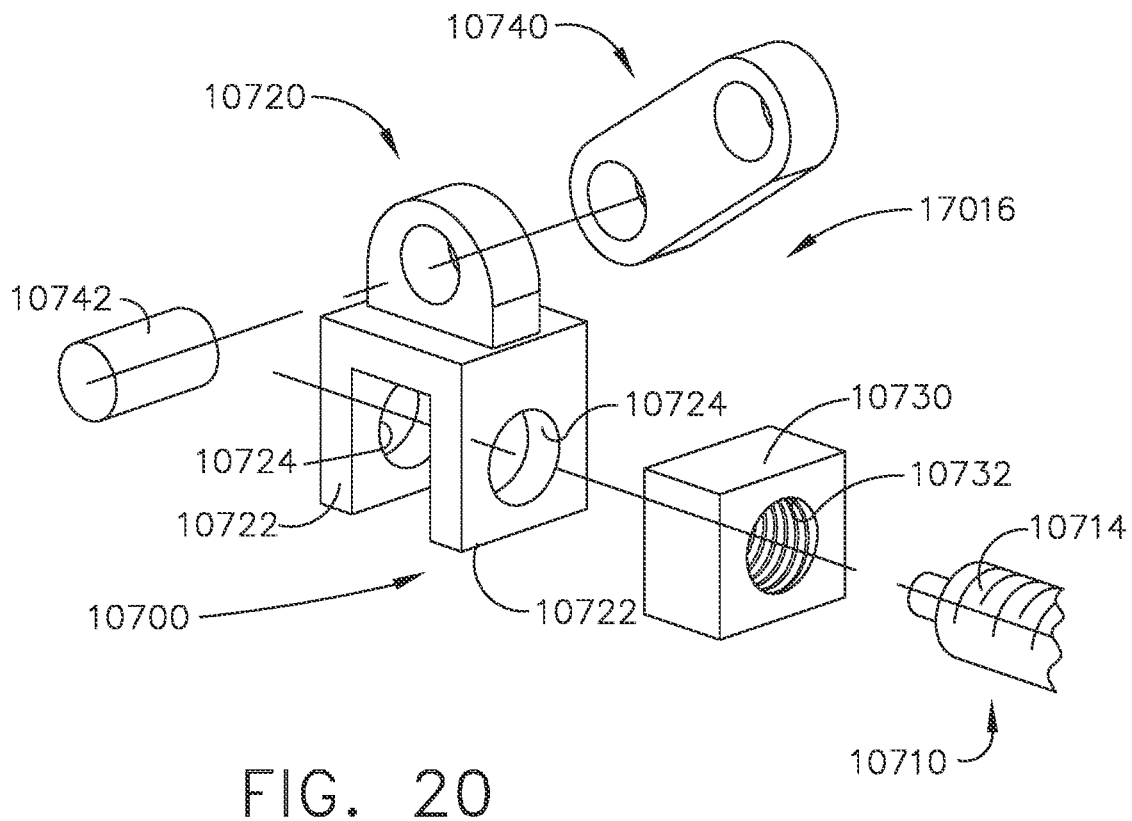
FIG. 20 is an exploded assembly view of a closure linkage assembly of the end effector of FIG. 14 and a closure drive shaft.
Figure 21:
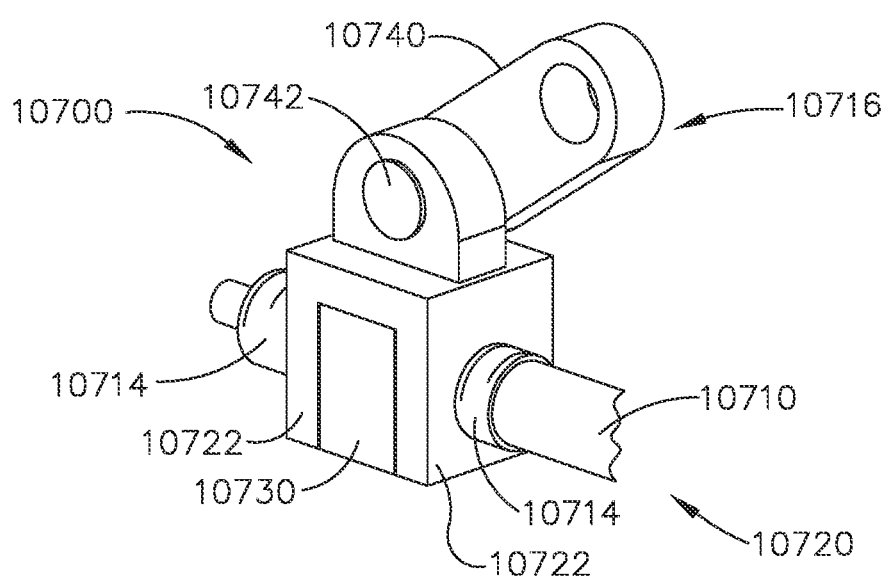
FIG. 21 is a perspective view of the closure linkage assembly and closure drive shaft of FIG. 20.

The example illustrated in FIGS. 10-19 employs a rotary actuated closure system 10700 that is configured to apply opening and closure motions to the anvil 10500. In one arrangement, closure system 10700 comprises a closure linkage assembly 10716 that is pivotally coupled to the anvil mounting tab 10510 for pivotal travel relative thereto about a common closure axis CA. As can be seen in FIGS. 19 and 20, the closure drive shaft 10710 comprises a threaded drive segment 10714 that is configured to threadably engage a drive nut 10730 that is supported by a drive yoke 10720. The drive yoke 10720 includes two yoke arms 10722 that have unthreaded holes 10724 therethrough to permit the closure drive shaft 10710 to pass therethrough. The drive nut 10730 has a threaded hole 10732 therethrough that is threaded onto the threaded drive segment 10714 of the closure drive shaft 10710 and is received between the yoke arms 10722. A closure link 10740 is pivotally coupled to the drive yoke 10720 by a pin 10742. The closure link 10740 is also pivotally attached (pinned) to the anvil mounting tab 10510 by a pin 10744. See FIG. 19. As can be seen in FIG. 19, a spacer member 10746 is provided to fill the space between the closure link 10740 and spaced arms 10516 of the anvil mounting tab 10510. Alternatively, the closure link may be sized and shaped to fill in that space. As can be further seen in FIG. 19, a retainer tab 10311 is formed in the elongate channel 10310 to define an axial trough 10313 for slidably receiving the drive yoke 10720 therein. Rotation of the rotary closure drive shaft 10710 in a first rotary direction will cause the drive yoke 10720 to move distally and cause the closure link 10740 to pull the anvil mounting tab 10510 in an opening direction which causes the anvil 10500 to pivot to an open position about the pivot axis PA. Likewise, rotation of the rotary closure drive shaft 10710 in a second rotary direction will cause the drive yoke 10720 to move proximally and cause the closure link 10740 to push the anvil mounting tab 10510 in a closing direction which causes the anvil 10500 to pivot to a closed position about the pivot axis PA. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

Figure 22:
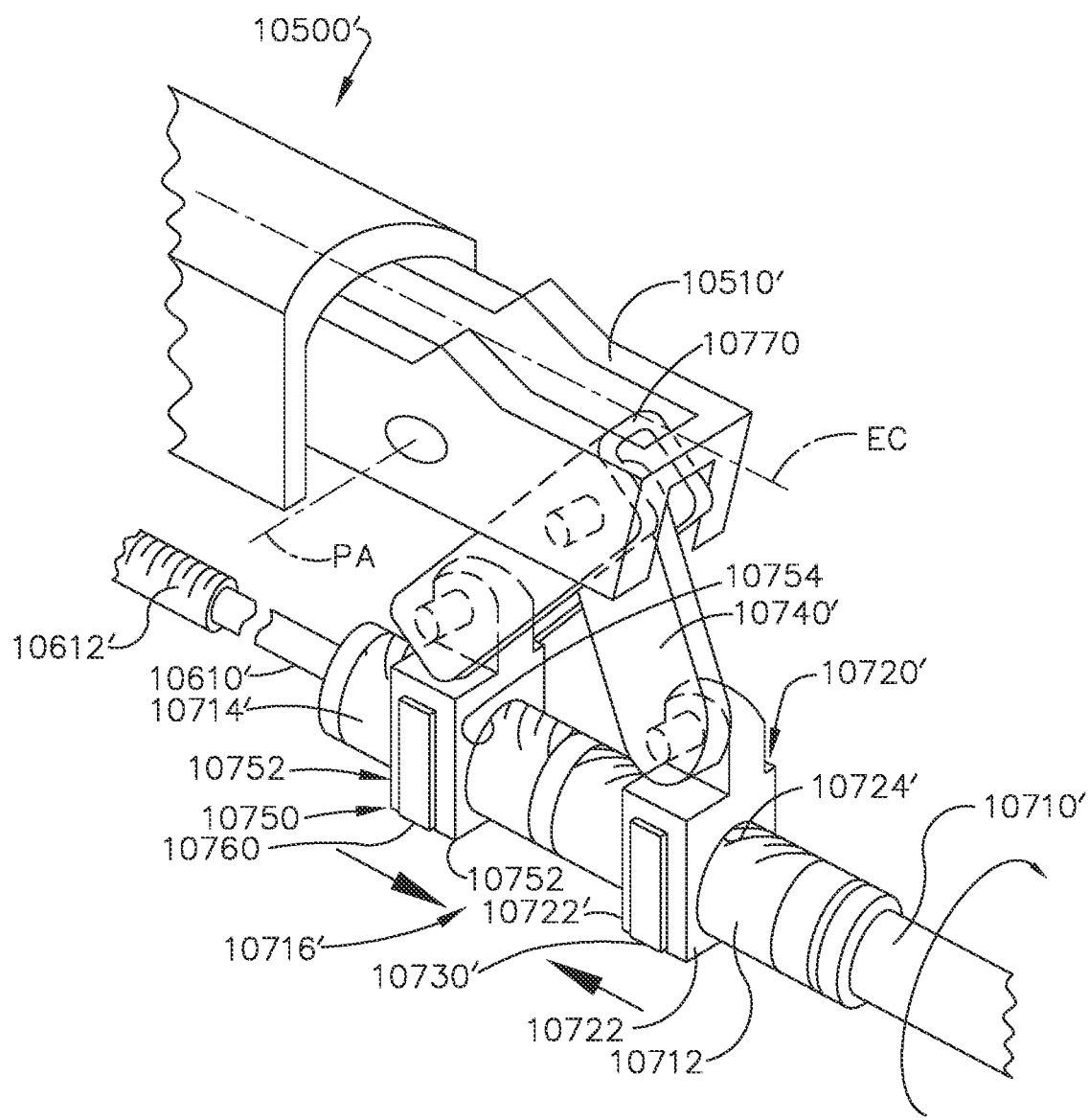
FIG. 22 is a partial perspective view of an anvil, closure linkage assembly, and closure drive shaft of another rotary powered surgical end effector.
Figure 23:
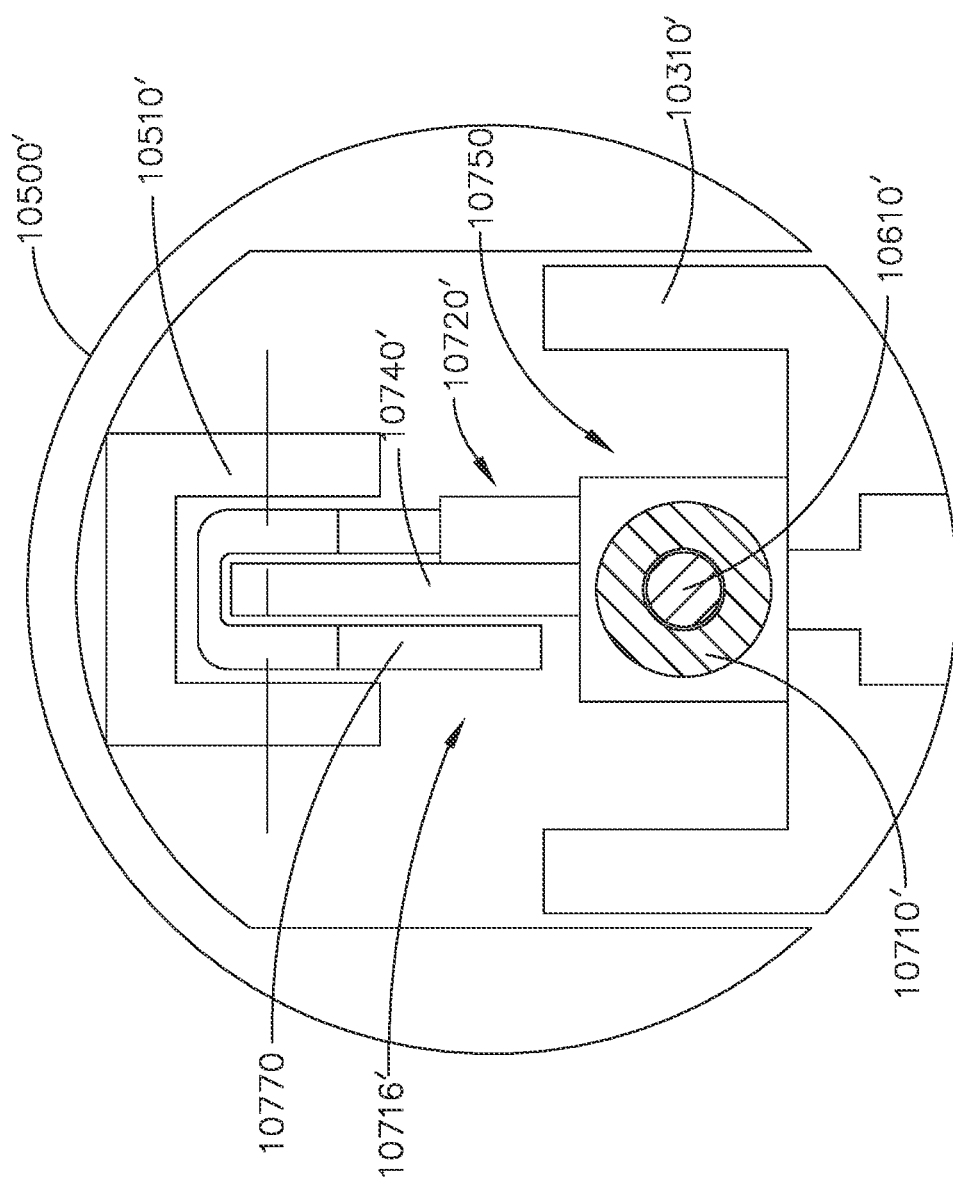
FIG. 23 is a partial end elevational view of the anvil, closure linkage assembly, and closure drive shaft of FIG. 22, with the drive shaft shown in cross-section.

FIGS. 22 and 23 illustrate an alternate closure drive arrangement wherein the anvil mounting tab 10510' of the anvil 10500' is generally centrally supported within the end effector. The anvil mounting portion 10510' may be pivotally coupled to the elongate channel 10310' in the manner described above. In this arrangement, the rotary closure drive shaft 10710' is hollow and concentrically supports the rotary firing shaft 10610' therein. The rotary closure drive shaft 10710' and the rotary firing drive shaft 10610' are centrally disposed within the elongate channel 10310' as can be seen in FIG. 23. The rotary firing drive shaft 10610' rotatably extends through the rotary closure drive shaft 10710' and includes a distal threaded portion 10612' that is configured to threadably drive the firing member 10620 in the manner described above, for example.

The example illustrated in FIGS. 22 and 23 employs a rotary actuated closure linkage assembly 10716' that is configured to apply opening and closure motions to the anvil 10500'. In one arrangement, the closure linkage assembly 10716' comprises a proximal drive yoke assembly 10720' and a distal drive yoke assembly 10750. The proximal drive yoke assembly 10720' includes two spaced yoke arms 10722' that have unthreaded holes 10724' therethrough to permit the closure drive shaft 10710' to pass therethrough. A proximal drive nut 10730' is received between the spaced yoke arms 10722' and includes a threaded hole for threadably engaging a proximal thread segment 10712' on the rotary closure drive shaft 10710'. The proximal drive yoke assembly 10720' is pivotally coupled to a proximal closure link 10740' that is pivotally pinned to the anvil mounting portion 10510'. The distal drive yoke assembly 10750 includes two spaced yoke arms 10752 that have unthreaded holes 10754 therethrough to permit the closure drive shaft 10710' to pass therethrough. A distal drive nut 10760 is received between the spaced yoke arms 10752 and includes a threaded hole for threadably engaging a distal thread segment 10714' on the rotary closure drive shaft 10710'. The proximal threaded segment 10712' and the distal threaded segment 10714' are thread in opposite directions. The distal drive yoke assembly 10750 is pivotally coupled to a U-shaped distal closure link 10770 that is pivotally pinned to the anvil mounting portion 10510'. The U-shaped distal closure link 10770 affords the closure linkage assembly 10716' with a symmetric load bearing arrangement. Rotation of the rotary closure drive shaft 10710' in a first rotary direction will cause the proximal drive yoke 10720' and the distal drive yoke assembly 10750 to axially move away from each other to pull the anvil mounting tab 10510' in an opening direction causing the anvil 10500' to pivot to an open position about the pivot axis PA. Likewise, rotation of the rotary closure drive shaft 10710' in a second rotary direction will cause the proximal drive yoke 10720' and distal drive yoke assembly 10750 to move towards each other and push the anvil mounting tab 10510' in a closing direction causing the anvil 10500' to pivot to a closed position about the pivot axis PA. Such arrangement may serve to apply generally higher closure forces to the anvil 10500'. It will be appreciated that the rotary firing drive shaft 10610' is independently rotatable relative to the rotary closure drive shaft 10710'. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

Figure 24:
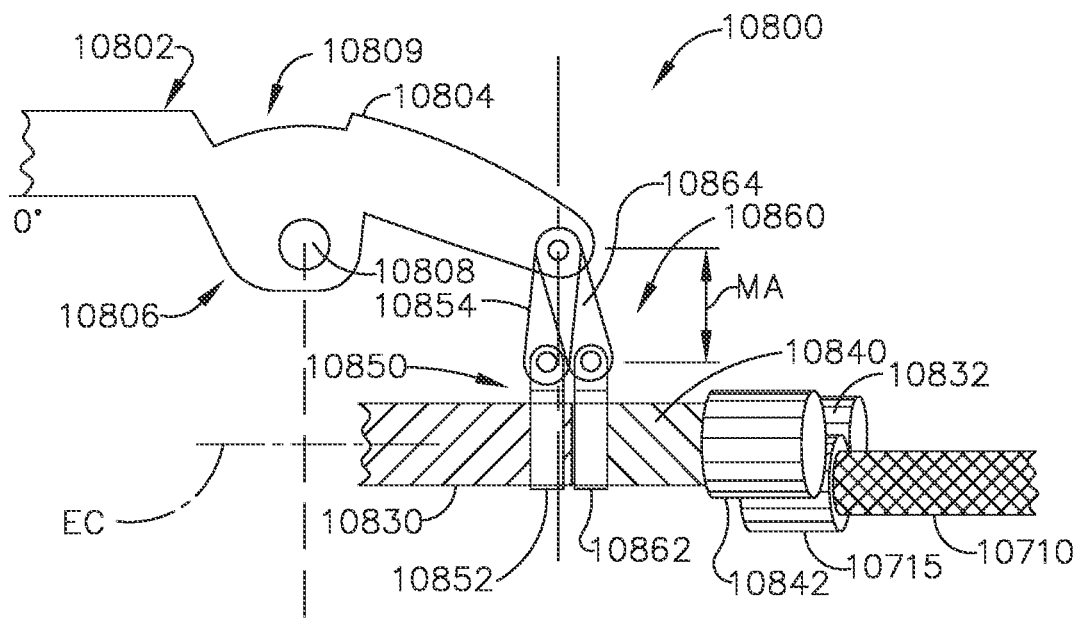
FIG. 24 is a side elevational view of an anvil, closure linkage assembly, rotary firing drive shaft, and closure drive shaft of another rotary powered surgical end effector with an anvil thereof in a closed position.
Figure 25:
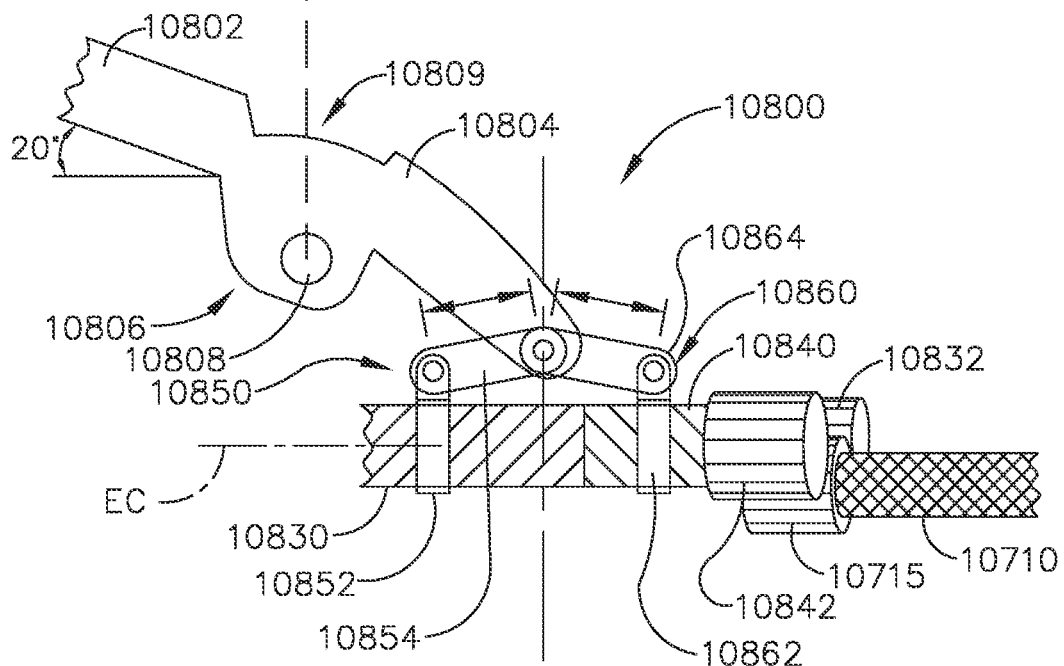
FIG. 25 is another side elevational view of the anvil, closure linkage assembly, rotary firing drive shaft, and closure drive shaft of FIG. 24 with the anvil in an open position.
Figure 28:
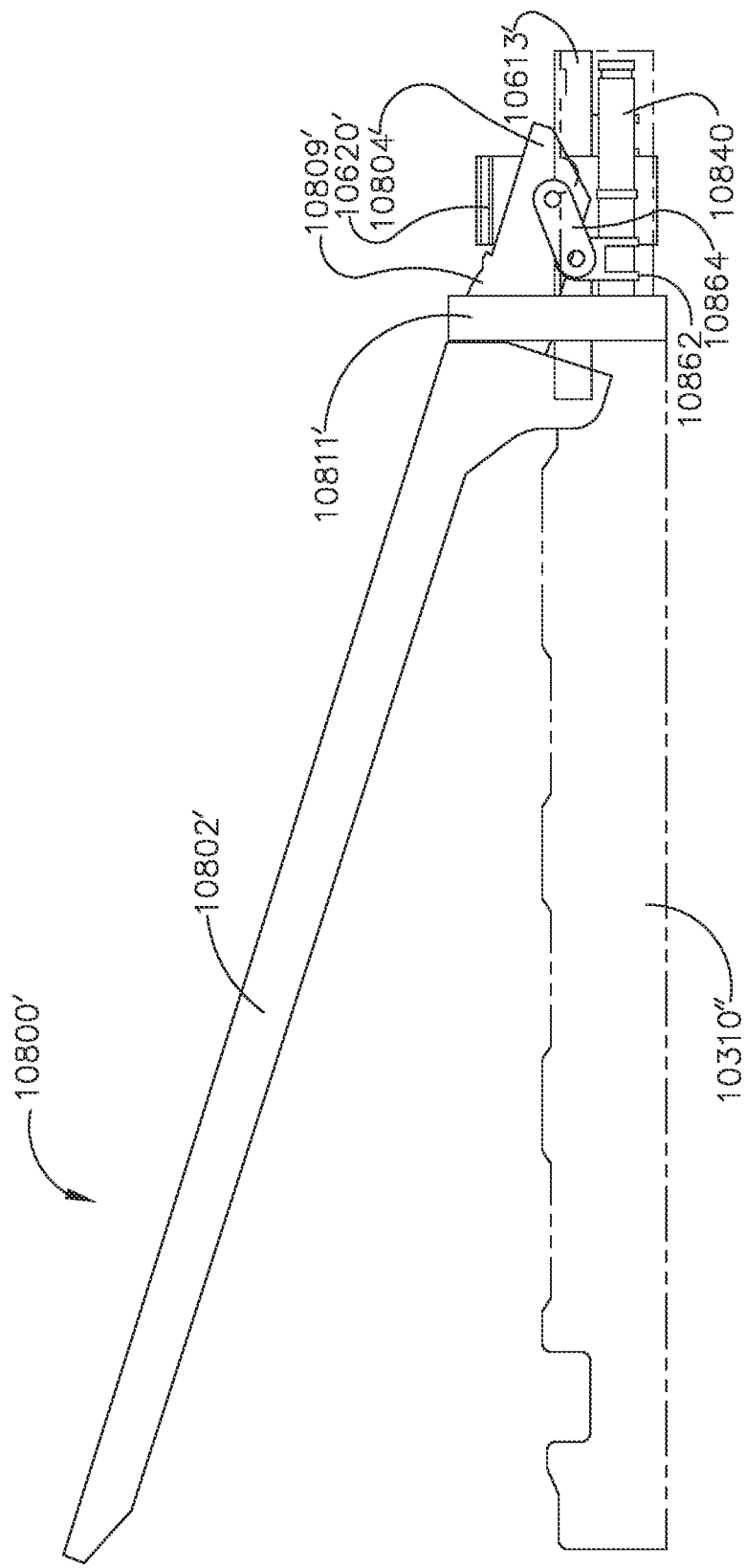
FIG. 28 is a side elevational view of a portion of another rotary powered surgical end effector with an anvil thereof in an open position.
Figure 29:
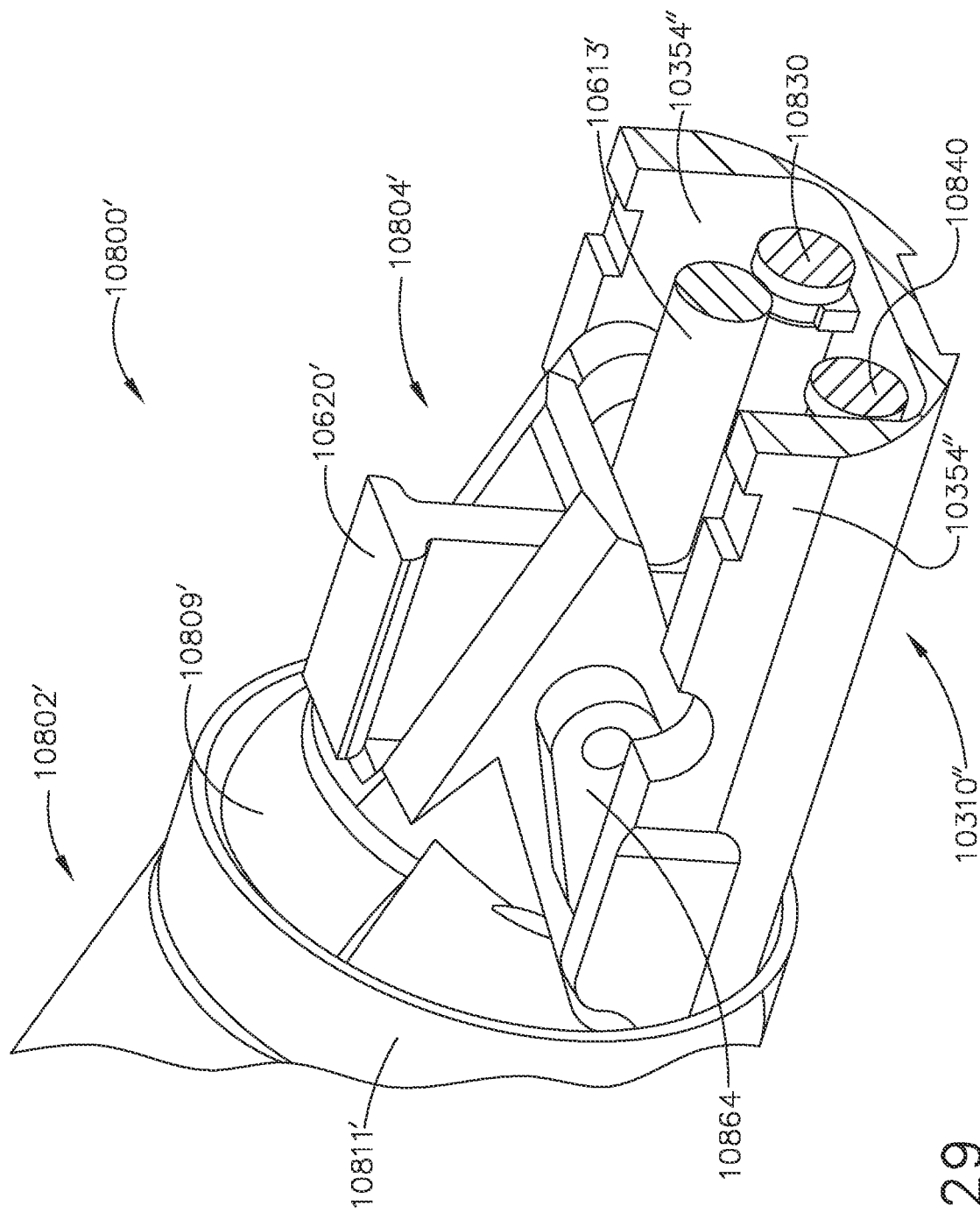
FIG. 29 is an enlarged partial perspective view of a portion of the rotary powered surgical end effector of FIG. 28.

FIGS. 24-27 illustrate an another surgical end effector 10800 that employs a closure drive arrangement wherein an anvil mounting tab 10804 of an anvil 10802 is centrally supported within the end effector 10800 and two rotary closure shafts 10830 and 10840 are employed to apply closure motions to the anvil 10802. In this arrangement, a distal portion 10806 of the anvil mounting tab 10804 includes a pair of laterally extending pivot members 10808 that are adapted to be pivotally cradled in pivot cradles 10356 in upstanding walls 10354 of a distal mounting portion of the elongate channel 10310". See FIG. 27. Thus, the pivot members 10808 are vertically movable or "floatable" within their corresponding pivot cradles 10356. In this arrangement, the rotary firing drive shaft 10610 (FIG. 26) is vertically supported above the rotary closure drive shaft 10710 (FIGS. 24 and 25). In the illustrated example, the rotary firing drive shaft 10610 includes a firing drive gear 10611 that is configured to drivingly engage a driven gear (not shown) on a distal firing drive shaft 10613 that is rotatably supported in the elongate channel 10310" in the various manners described herein. See FIG. 27. A firing member drive nut 10630 is threaded on the distal firing drive shaft 10613 and serves to drive a firing member 10620 within the end effector 10800 as the rotary firing drive shaft 10610 is rotated in the manner described herein.

As can be seen in FIGS. 24 and 25, the rotary closure drive shaft 10710 includes a closure drive gear 10715 that is centrally disposed between a right distal closure shaft 10830 and a left distal closure shaft 10840. The right distal closure shaft 10830 includes a right driven gear 10832 that is in meshing engagement with the closure drive gear 10715 and the left distal closure shaft 10840 includes a left driven gear 10842 that is also in meshing engagement with the closure drive gear 10715. Rotation of the rotary closure drive shaft 10710 will result in the rotation of the right distal closure shaft 10830 in a first rotary direction and the rotation of the left distal closure shaft 10840 in a second rotary direction.

The example illustrated in FIGS. 24-26 employs a rotary actuated right closure linkage assembly 10850 and a rotary actuated left closure linkage assembly 10860 that are configured to apply opening and closure motions to the anvil 10802. In one arrangement, the right closure linkage assembly 10850 comprises a proximal drive nut assembly 10852 that is threaded onto the right distal closure shaft 10830 and is coupled to a right closure link 10854 that is attached to the anvil mounting tab 10804. Likewise, the left closure linkage assembly 10860 comprises a left drive nut assembly 10862 that is threaded onto the left distal closure shaft 10840 and is coupled to a left closure link 10864 that is attached to the anvil mounting tab 10804. In one arrangement, the diameter D of the right distal closure shaft 10830 and the left distal closure shaft 10840 may be approximately 0.078". See FIG. 26. The space "E" between the right drive nut assembly 10852 and the left drive nut assembly 10862 may be approximately 0.093" and the width "W" of the channel 10310" may be approximately 0.256". However, other sizes and shapes of end effector components may be employed. Rotation of the rotary closure drive shaft 10710 in a first rotary direction will cause the right drive nut assembly 10852 and the left drive nut assembly 10862 to move in a synchronized fashion to open the anvil 10802 in a balanced uniform manner. Rotation of the rotary closure drive shaft 10710 in a second rotary direction will cause the right drive nut assembly 10852 and the left drive nut assembly 10862 to move in a synchronized fashion to close the anvil 10802 in a balanced uniform manner and reduce any twisting moment on the anvil 10802 as the anvil 10802 is pivoted closed.

As can also be seen in FIGS. 24 and 25, the anvil mounting tab 10804 includes a domed or spherical distal surface portion 10809. A closure ring 10811 (FIG. 27) is movably journaled on the spherical distal surface portion 10809. As the anvil 10802 is pivoted to the closed position by the right closure linkage assembly 10850 and the left closure linkage assembly 10860, the closure ring 10811 serves to constrain the anvil 10802 to the elongate channel 10310". FIG. 24 illustrates the anvil 10802 in a closed position. As can be seen in FIG. 24, the links 10854 and 10864 are nearly vertical (perpendicular) to the end effector axis EC. Such arrangement establishes a maximum moment arm MA for retaining the anvil 10802 in the closed position. FIG. 25 illustrates the anvil 10802 in an open position. For example, the anvil 10802 is pivoted upward at an angle that is approximately 20° from the horizontal as shown. When in that position, the links 10854 and 10864 are nearly horizontal (relative to each other) which results in the application of a reduced amount of closure force than was established when the anvil was moved to the closed position. In one arrangement, the links 10854 and 10864 may have a length L of approximately 0.150", for example. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

FIGS. 28-31 illustrate another surgical end effector 10800' that employs a closure drive arrangement wherein an anvil mounting tab 10804' of an anvil 10802' is also centrally supported within the end effector 10800' and two rotary closure shafts 10830 and 10840 are employed to apply closure motions to the anvil 10802'. See FIG. 29. In one arrangement, for example, the anvil 10802' may be fabricated using various fabricating techniques described in U.S. Patent Application Ser. No. 16/105,101, entitled METHOD FOR FABRICATING SURGICAL STAPLER ANVILS, the entire disclosure of which is hereby incorporated by reference herein. In this arrangement, a distal portion 10806' of the anvil mounting tab 10804' includes a pair of laterally extending pivot members 10808' that are adapted to be pivotally cradled in pivot cradles 10356" in upstanding walls 10354" of a distal mounting portion 10352" of the elongate channel 10310". See FIGS. 30 and 31. Thus, the pivot members 10808' are vertically movable or "floatable" within their corresponding pivot cradles 10356". In this arrangement, the rotary firing drive shaft 10610 (similar to that shown in FIG. 26) is vertically supported above the rotary closure drive shaft 10710 (FIGS. 24 and 25) in the elongate shaft. As was discussed above, in the illustrated example, the rotary firing drive shaft (not shown) includes a firing drive gear (not shown) that is configured to drivingly engage a driven gear (not shown) on a distal firing drive shaft 10613' that is rotatably supported in the elongate channel 10310" in the various manners described herein. See FIGS. 28 and 29. The distal firing drive shaft 10613' is configured to threadably drive a firing member 10620' within the end effector 10800' as the rotary firing drive shaft and distal firing drive shaft 10613' are rotated in the manners described herein.

As was described above, the rotary closure drive shaft 10710 includes a closure drive gear 10715 that is centrally disposed between a right distal closure shaft 10830 and a left distal closure shaft 10840. See FIGS. 29-31. The right distal closure shaft 10830 includes a right driven gear that is in meshing engagement with the closure drive gear 10715 and the left distal closure shaft 10840 includes a left driven gear 10842 that is also in meshing engagement with the closure drive gear 10715. Rotation of the rotary closure drive shaft 10710 will result in the rotation of the right distal closure shaft 10830 in a first rotary direction and the rotation of the left distal closure shaft 10840 in a second rotary direction. The example illustrated in FIGS. 30 and 31 employs a rotary actuated right closure linkage assembly 10850 and a rotary actuated left closure linkage assembly 10860 that are configured to apply opening and closure motions to the anvil 10802'. In one arrangement, the right closure linkage assembly 10850 comprises a proximal drive nut assembly 10852 that is threaded onto the right distal closure shaft 10830 and is coupled to a right closure link 10854 that is attached to the anvil mounting tab 10804'. Likewise, the left closure linkage assembly 10860 comprises a left drive nut assembly 10862 that is threaded onto the left distal closure shaft 10840 and is coupled to a left closure link 10864 that is attached to the anvil mounting tab 10804'. Rotation of the rotary closure drive shaft 10710 in a first rotary direction will cause the right drive nut assembly 10852 and the left drive nut assembly 10862 to move in a synchronized fashion to open the anvil 10802' in a balanced uniform manner. Rotation of the rotary closure drive shaft 10710 in a second rotary direction will cause the right drive nut assembly 10852 and the left drive nut assembly 10862 to move in a synchronized fashion to close the anvil 10802' in a balanced uniform manner and reduce any twisting moment on the anvil 10802' as the anvil 10802' is pivoted closed.

Figure 30:
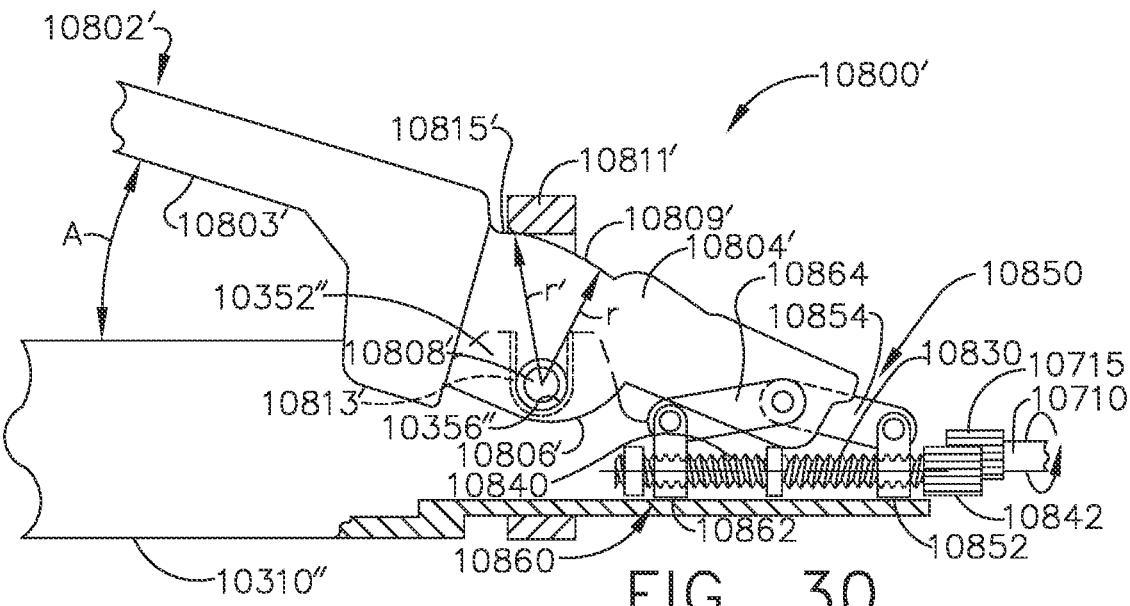
FIG. 30 is a partial side elevational view of portions of the rotary powered surgical end effector of FIGS. 28 and 29, with the anvil thereof in an open position.
Figure 31:
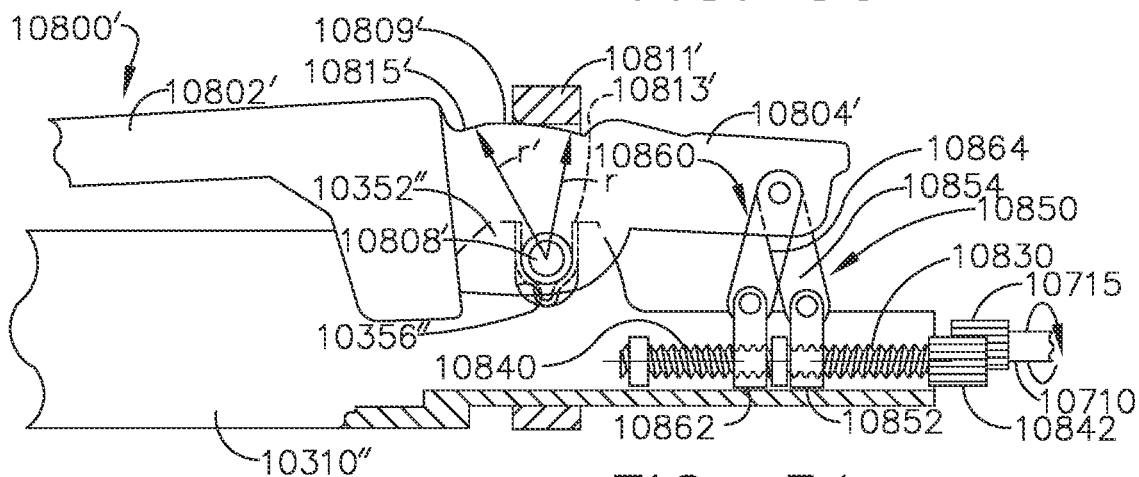
FIG. 31 is another partial side elevational view of portions of the rotary powered surgical end effector of FIG. 30, with the anvil thereof in a closed position.
Figure 32:
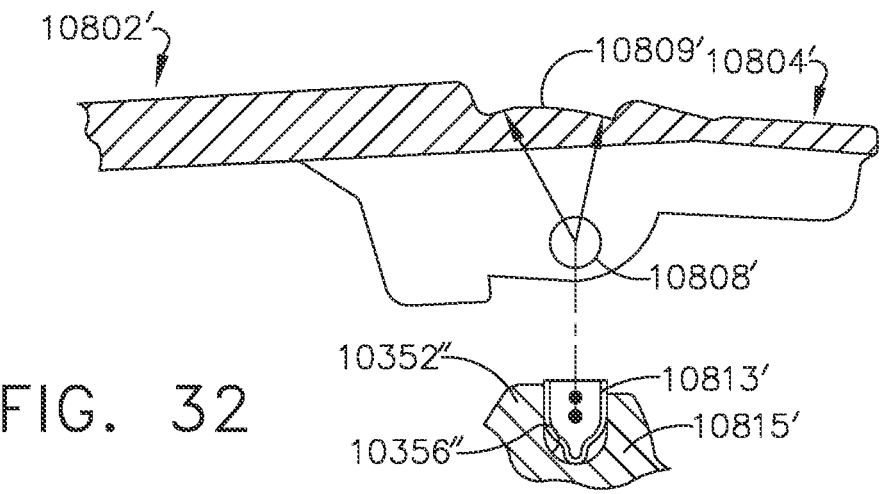
FIG. 32 is a cross-sectional side view of a portion of the anvil and elongate channel of the rotary powered surgical end effector of FIG. 31.

As can be seen in FIGS. 30-32, the anvil mounting tab 10804' includes a domed or spherical distal surface portion 10809'. A closure ring 10811' is movably journaled on the spherical distal surface portion 10809'. As the anvil 10802' is pivoted to the closed position by the right closure linkage assembly 10850 and the left closure linkage assembly 10860, the closure ring 10811' serves to constrain the anvil 10802 to the elongate channel 10310". In the illustrated example, a pivot spring 10813' is seated in each of the cradles 10356" which serves to bias the pivot members 10808' upward in their respective cradles 10356". In at least one arrangement, a distal portion of the spherical surface portion 10809' comprises a shallow notch area 10815' that provides additional clearance for the closure ring 10811' to enable the anvil 10802' to pivot further open, for example, wherein the undersurface 10803' of the anvil 10802' is at least 20° (angle A) from the deck surface of the surgical staple cartridge seated within the channel 10310". See FIG. 30. For example, the radial distance between the center of the pivot members 10808' to the spherical surface 10809' is designated as "r" in FIGS. 30 and 31. The radial distance from the centerline of the pivot members 10808' to the notched area 10815' is designated as "r'", wherein r'>r.

FIG. 30 illustrates the anvil 10802' in a fully open position. As can be seen in FIG. 30, the closure ring 10811' is approximately axially aligned with the pivot members 10808' which serves to drive the pivot members 10808' into the bottom of their respective cradle 10356" and compress the pivot spring 10813' therein. FIG. 31 illustrates the anvil 10802' in the closed position wherein the closure ring 10811' is slightly proximally axially offset from the pivot members 10808' which permits the pivot springs 10813' to bias the pivot members 10808' upward within their respective cradles 10356".

The closure rings in these embodiments essentially encircle the corresponding anvil and elongate channel portions. To facilitate opening of the anvil to a desired opening aperture or angle, the closure ring is permitted to move proximally to distally a small amount (e.g., 0.0"-0.1") while being spring biased to the distal position. The ring does not induce closure but merely constrains the anvil and channel from moving apart vertically allowing a pivoting motion to occur between the two components. Such arrangement facilitates use of a thicker anvil particularly in the anvil mounting area which may improve anvil strength and reliability. This configuration may further enable the jaws (anvil and channel) to pivot in a fashion that improves the moment arm condition of the anvil proximal to the pivot location and facilitate opening of the end effector to greater opening angles. In various aspects, the rotary driven closure system 10700 may be actuated during the actuation of the rotary driven firing system 10600 such that the closure system 10700 continues to apply additional closure motions to the anvil as the firing member is axially driven through the staple cartridge.

Figure 33:
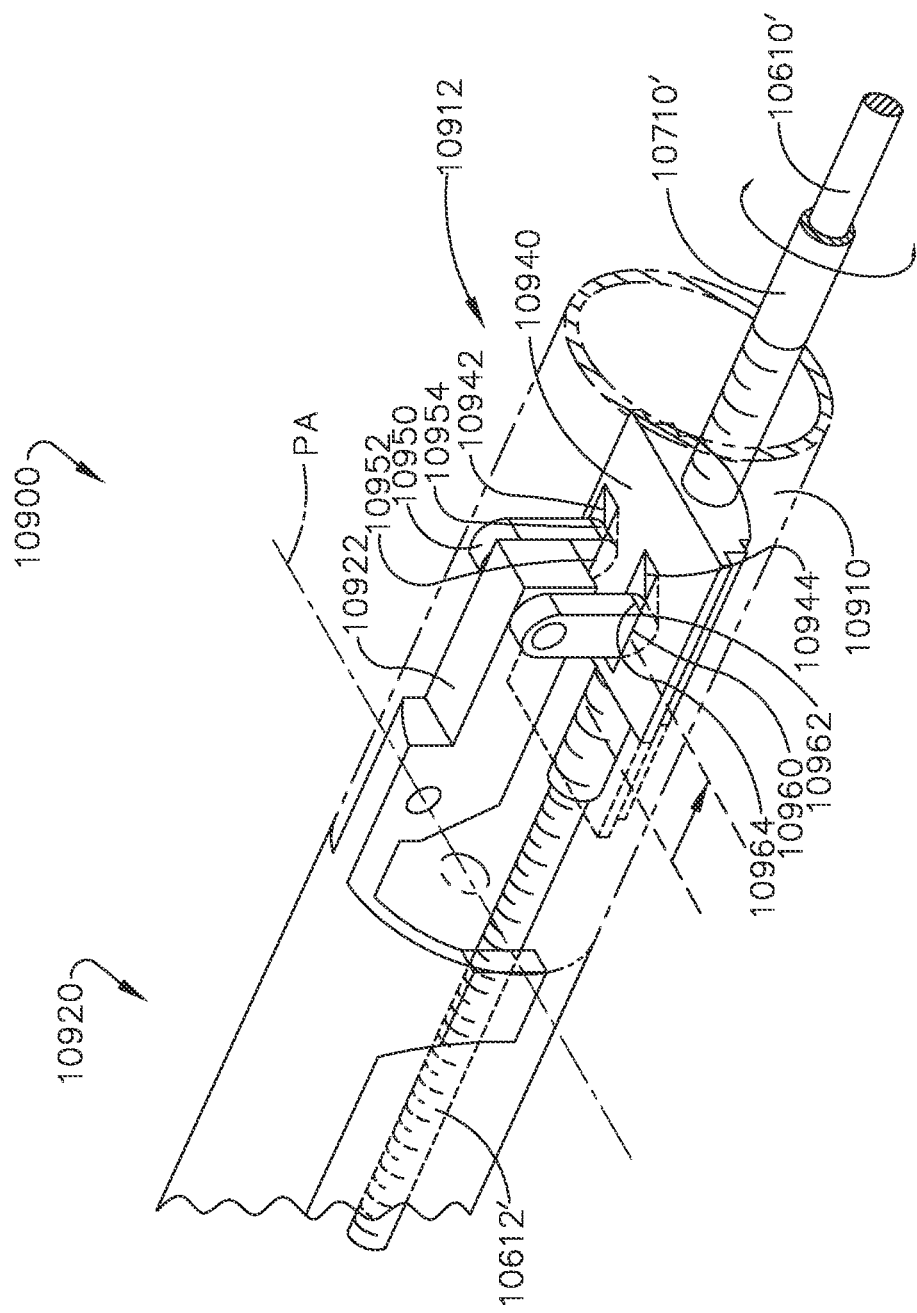
FIG. 33 is a partial perspective view of another rotary powered surgical end effector with an anvil thereof in a closed position.
Figure 34:
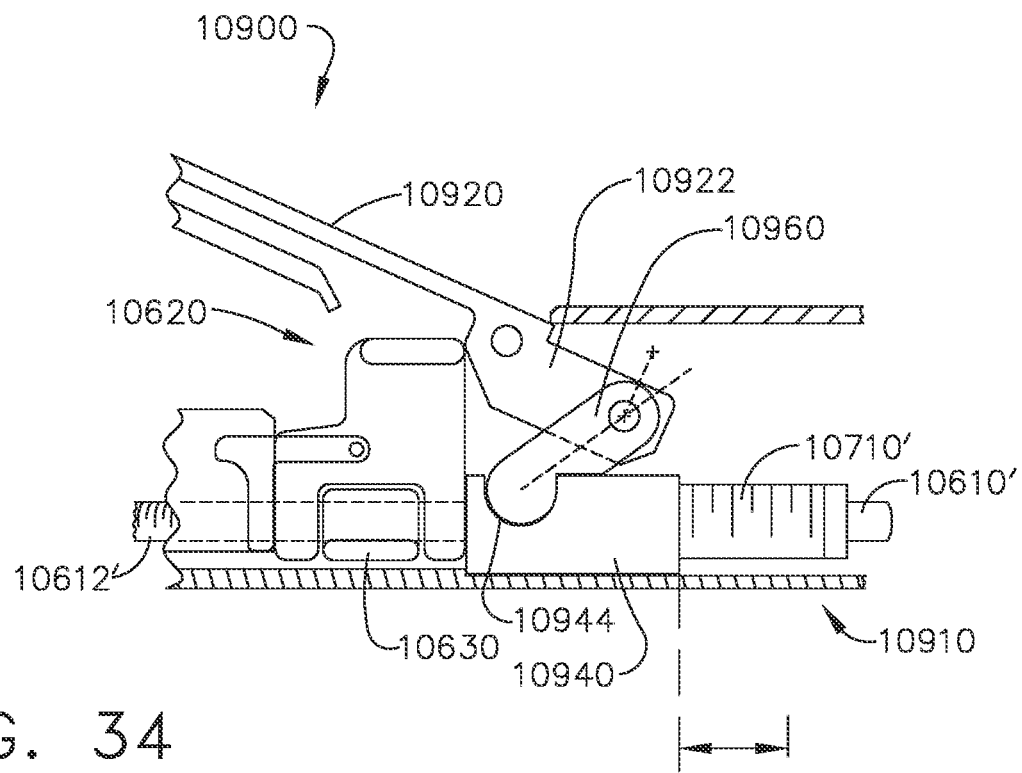
FIG. 34 is a side elevational view of a portion of the rotary powered surgical end effector of FIG. 33 with the anvil in an open position.
Figure 35:
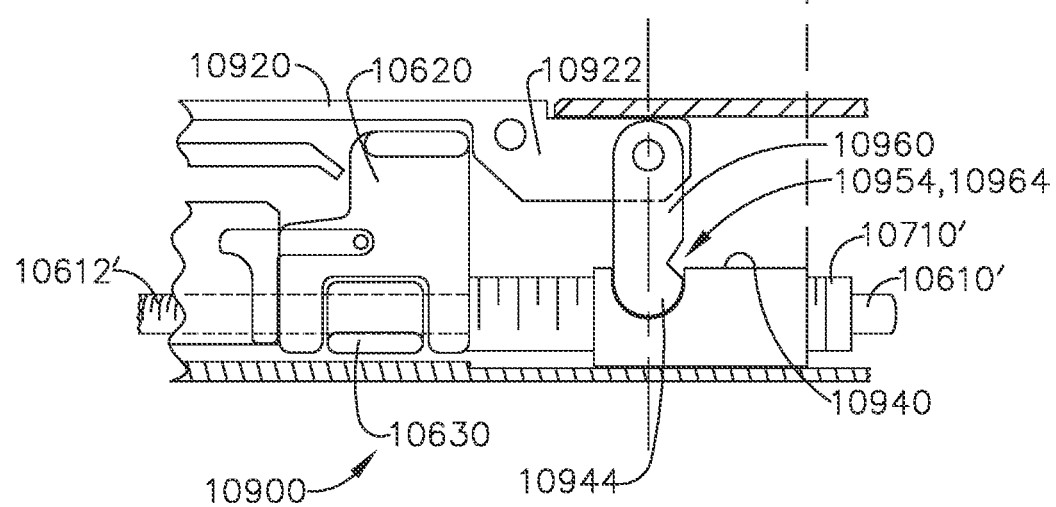
FIG. 35 is another side elevational view of a portion of the rotary powered surgical end effector of FIG. 34 with the anvil in a closed position.

FIGS. 33-35 illustrate another end effector 10900 that employs an alternate closure drive arrangement for opening and closing an anvil 10920 relative to an elongate channel 10910 thereof. The anvil 10920 includes an anvil mounting tab 10922 that protrudes proximally along a centerline of the anvil 10920 and is pivotally coupled to a proximal end 10912 of the elongate channel 10910 in the various manners disclosed herein. In one arrangement, for example, the anvil 10920 may be fabricated using various fabricating techniques described in U.S. Patent Application Ser. No. 16/105, 101, entitled METHOD FOR FABRICATING SURGICAL STAPLER ANVILS, the entire disclosure of which is hereby incorporated by reference herein. In this arrangement, a rotary closure drive shaft 10710' is hollow and concentrically supports a rotary firing drive shaft 10610' therein. The rotary closure drive shaft 10710' and the rotary firing drive shaft 10610' are centrally disposed within the elongate channel 10910 as can be seen in FIG. 33. The rotary firing drive shaft 10610' rotatably extends through the rotary closure drive shaft 10710' and includes a distal threaded portion 10612' that is configured to threadably drive a firing member 10620 in the manner described above, for example.

Referring to FIG. 33, a closure shuttle 10940 is supported for axial travel within the elongate channel 10910. The closure shuttle 10940 is threadably journaled on the threaded closure drive shaft 10710' such that rotation of the threaded closure drive shaft 10710' in a first direction causes the closure shuttle 10940 to move distally and rotation of the threaded closure drive shaft 10710' in a second rotary direction causes the closure shuttle 10940 to move proximally within the elongate channel 10910. As can be seen in FIG. 33, a right closure link 10950 and a left closure link 10960 are pivotally coupled to the anvil mounting tab 10922. The right closure link 10950 also includes an actuation end 10952 that is received within a corresponding right actuation notch 10942 in the closure shuttle 10940 and the left closure link 10960 includes an actuation end 10962 that is received within a corresponding left actuation notch 10944 in the closure shuttle 10940. Also in the illustrated arrangement, a right drive notch 10954 is provided in the actuation end 10952 of the right closure link 10950 and a left drive notch 10964 is provided in the actuation end 10962 of the left closure link 10960. The drive notches 10954, 10964 are configured to drivingly engage the actuation notches 10942, 10944, respectively.

Figure 36:
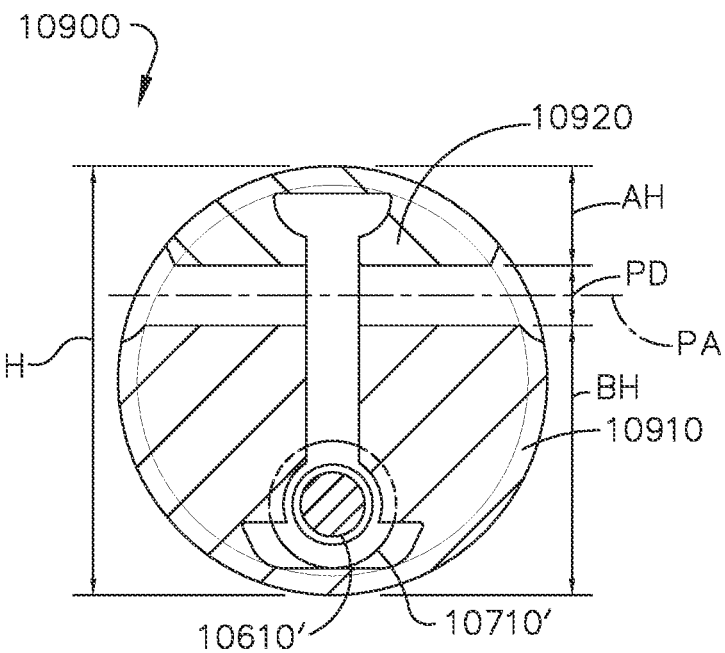
FIG. 36 is a cross-sectional end view of a portion of the rotary powered surgical end effector of FIG. 33.
Figure 37:
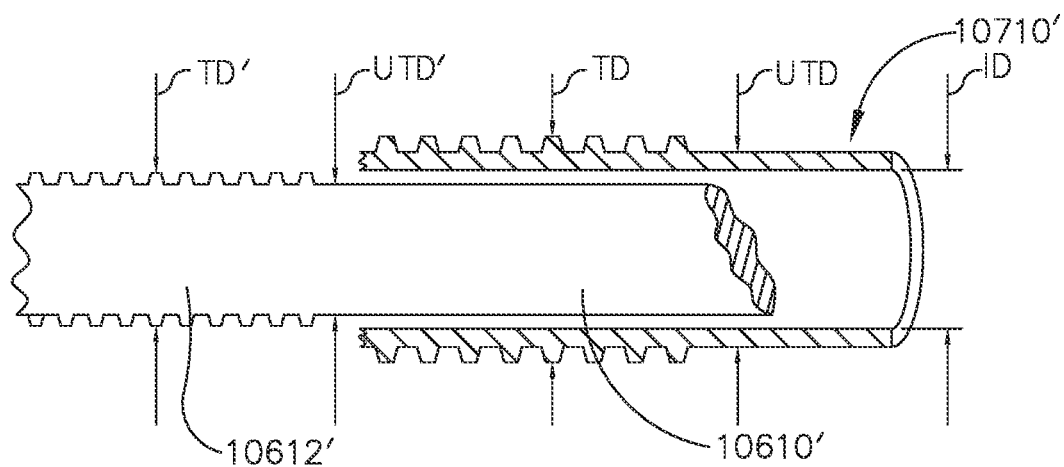
FIG. 37 is a partial cross-sectional side view of a rotary firing drive shaft and a rotary closure drive shaft of the rotary powered surgical end effector of FIG. 33.

FIGS. 33 and 35 illustrate the closure shuttle 10940 in a proximal-most, retracted position. When in that position, the right and left closure links 10950, 10960 push up on the anvil mounting tab 10922 and cause the anvil 10920 to pivot about the pivot axis PA to a closed position. When the closure shuttle 10940 has been moved to its distal-most, extended position, the right and left closure links 10950, 10960 pull the anvil tab 10922 downward and pivot the anvil 10920 to the open position as shown in FIG. 34. FIG. 36 illustrates some exemplary dimensions of various components of the surgical end effector 10900. In one arrangement for example, the overall height "H" may be approximately 0.500". The anvil height "AH" may be approximately 0.120". The rivet passage may have a diameter "PD" of approximately 0.070" and the base height "BH" may be approximately 0.310", for example. Referring to FIG. 37, the hollow closure drive shaft 10710' may have an internal diameter "ID" of approximately 0.100" and an unthreaded outer diameter "UTD" of approximately 0.129" and a threaded outer diameter "TD" of approximately 0.164": The firing drive shaft 10610' may have an unthreaded diameter "UTD'" of approximately 0.0668" and a threaded outer diameter "TD'" of approximately 0.0854", for example. Other diameters, component sizes and dimensions may also be employed.

Figure 39:
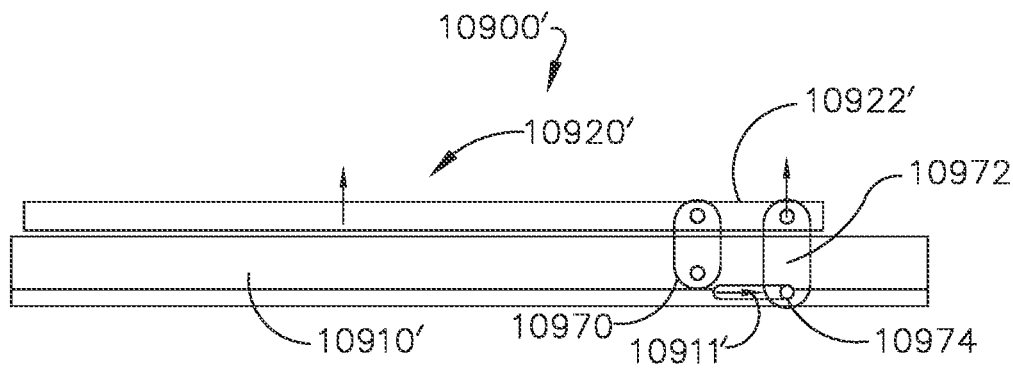
FIG. 39 is another diagrammatical depiction of the end effector of FIG. 38, with the jaws in a closed position.
Figure 38:
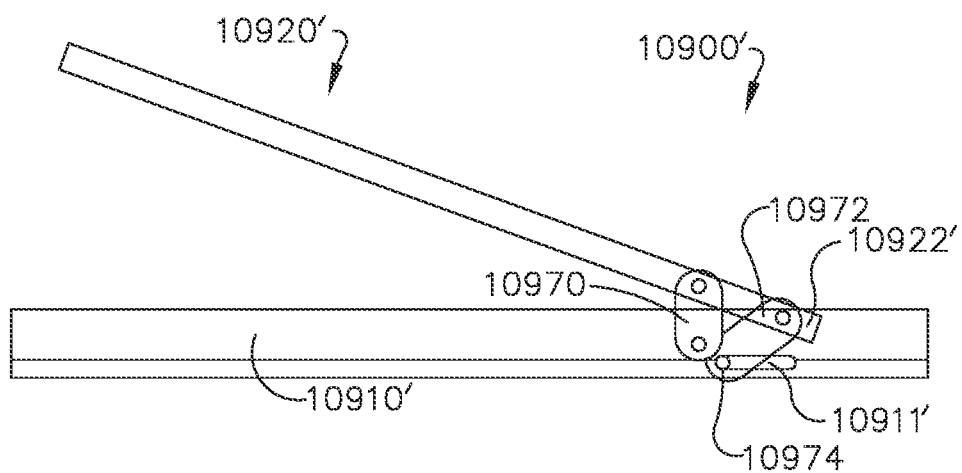
FIG. 38 is a diagrammatical depiction of an end effector that employs a closure link arrangement for opening and closing jaws of the end effector, with the jaws shown in an open position.

FIGS. 38 and 39 are diagrammatical depictions of an end effector 10900' that employs alternative closure link arrangements. As can be seen in those Figures, a distal closure link (or links) 10970 are pivotally pinned or otherwise pivotally coupled to an anvil 10920' and an elongate channel 10910'. In addition, proximal closure links 10972 are attached to an anvil mounting tab portion 10922' and are slidably coupled via a corresponding pin 10974 that is received in a corresponding axial slot 10911' in the elongate channel 10910' or in a closure shuttle or other member (not shown) that is configured to move the proximal closure links 10972 between a first position (FIG. 38) corresponding to an open position of the anvil 10920' and a second position (FIG. 39) corresponding to the closed position of the anvil 10920'.

Figure 41:
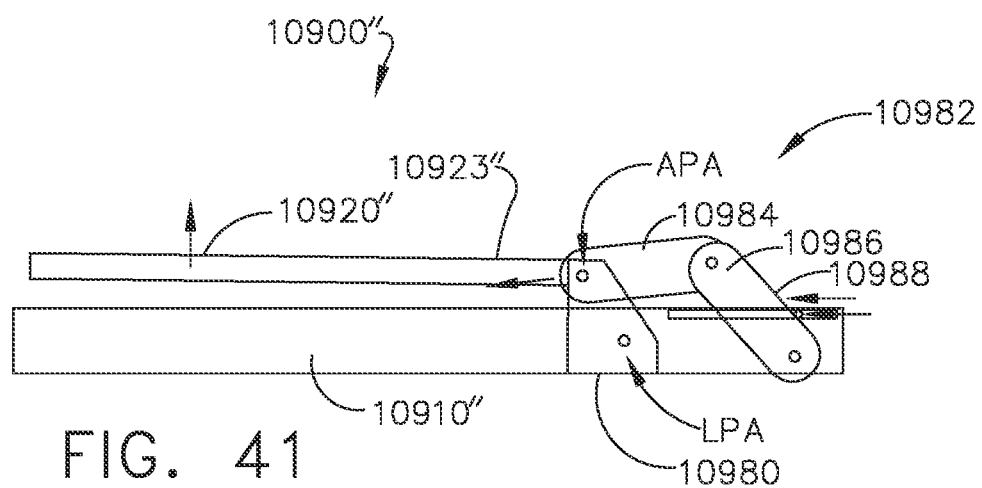
FIG. 41 is another diagrammatical depiction of the end effector of FIG. 40, with the jaws in a closed position.
Figure 40:
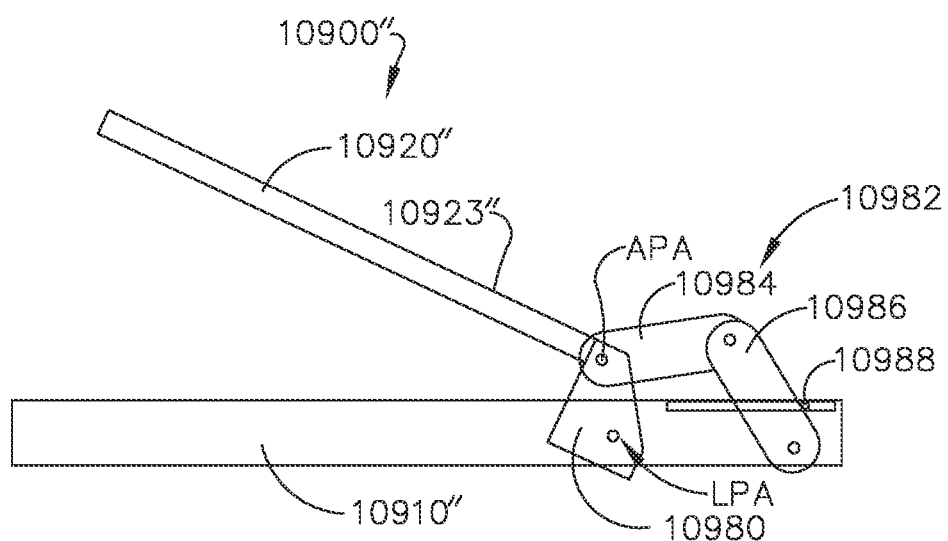
FIG. 40 is a diagrammatical depiction of another end effector that employs a closure link arrangement for opening and closing jaws of the end effector, with the jaws shown in an open position.

FIGS. 40 and 41 are diagrammatical depictions of an end effector 10900" that employs alternative closure link arrangements. As can be seen in those Figures, a proximal end portion 10923" of an anvil 10920" is pivotally coupled to an elongate channel 10910" by proximal mounting links 10980. The proximal mounting links 10980 (only one is shown in the Figures) are pivotally attached to the elongate channel 10910" for pivotal travel relative thereto about a lower pivot axis LPA. The proximal mounting links 10980 are also pivotally coupled to the proximal end portion 10923" for pivotal travel relative thereto about an anvil pivot axis APA. The end effector 10900" further includes a closure linkage assembly 10982 that comprises at least one distal link 10984 and one proximal link 10986. In other arrangements, the closure linkage assembly 10982 comprises a pair of distal links 10984 (one on each side of the elongate channel) and a pair of proximal links 10986 (one on each side of the elongate channel). The distal link(s) 10984 is attached to the anvil 10920" for pivotal travel about the anvil pivot axis APA as well as to the corresponding proximal link(s) 10986. The other end of the proximal link(s) is pivotally attached to the elongate channel 10910". The closure linkage assembly 10982 is actuated by a slider pin or pins 10988 that are constrained to move axially either in the elongate channel or in a closure shuttle or other member (not shown) that is configured to move the pin(s) 10988 between a first position (FIG. 40) corresponding to an open position of the anvil 10920" and a second position (FIG. 41) corresponding to the closed position of the anvil 10920". As indicated, the closure linkage assembly 10982 could comprise a compound set of links. Such arrangement may have interactive surfaces that limit the rotation of one linkage with respect to the second linkage. In this manner, the closure of the anvil 10920" for a given rate of angular rotation could induce first and second closure rate as well establish different mechanical advantages for closing the anvil. For example, a rapid rate of closure may be initially employed for an initial portion of the closure stroke of the closure actuator and then a slower rate of closure may be employed during the remaining portion of the closure stroke which may result in the application of increased closure forces to the anvil.

Figure 43:
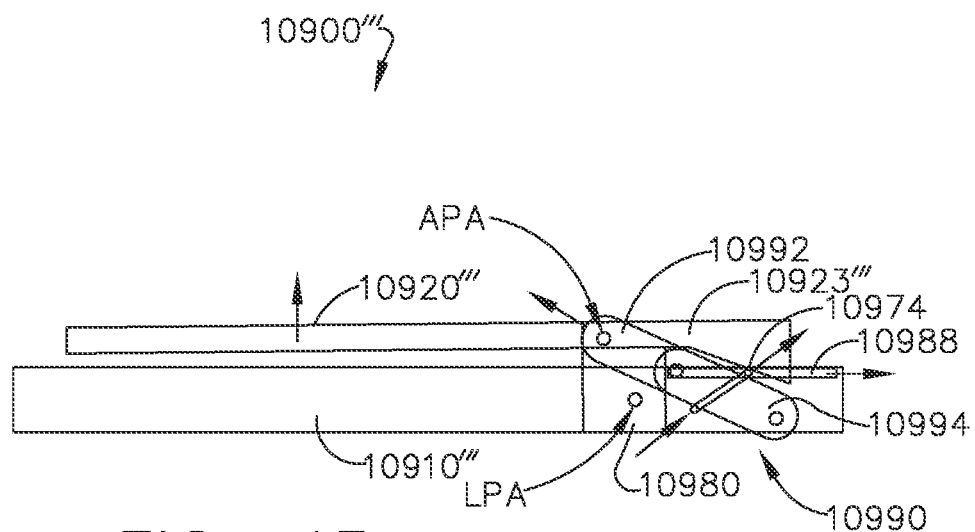
FIG. 43 is another diagrammatical depiction of the end effector of FIG. 42, with the jaws in a closed position.
Figure 42:
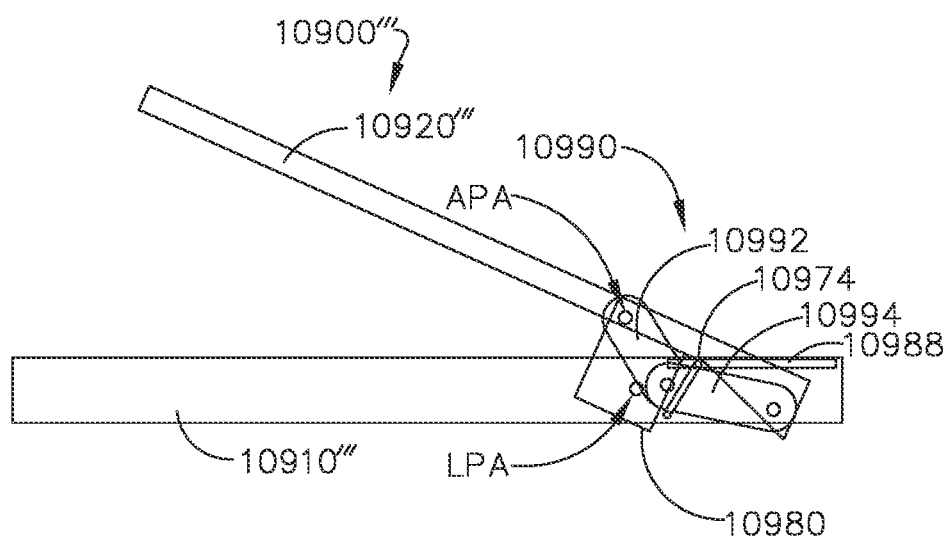
FIG. 42 is a diagrammatical depiction of another end effector that employs a closure link arrangement for opening and closing jaws of the end effector, with the jaws shown in an open position.
Figure 44:
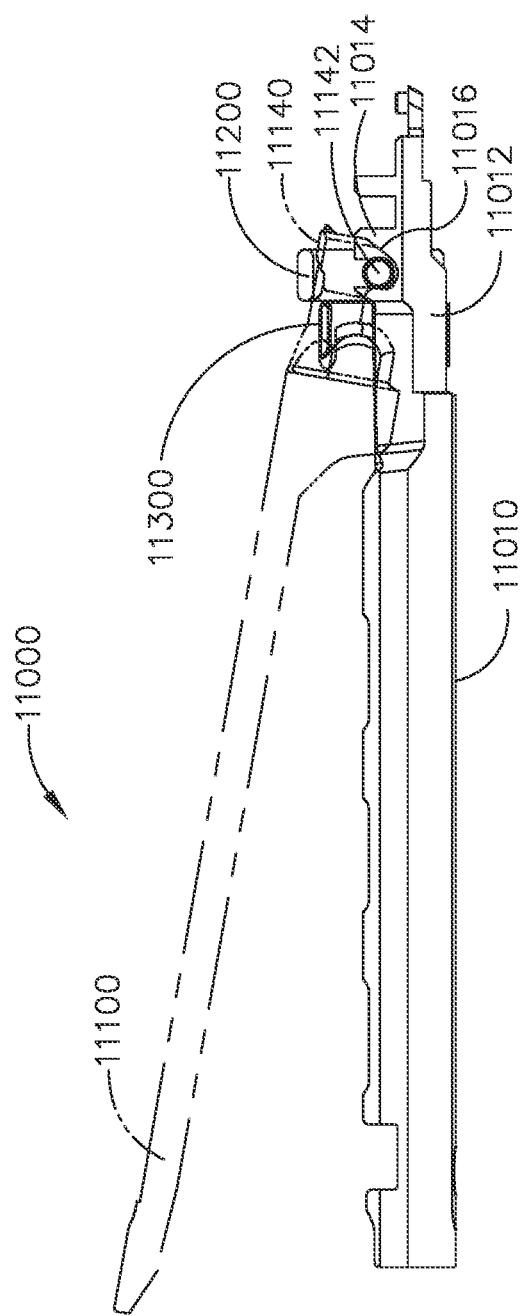
FIG. 44 is a side elevational view of portions of another surgical end effector with an anvil thereof shown in phantom lines in an open position.
Figure 45:
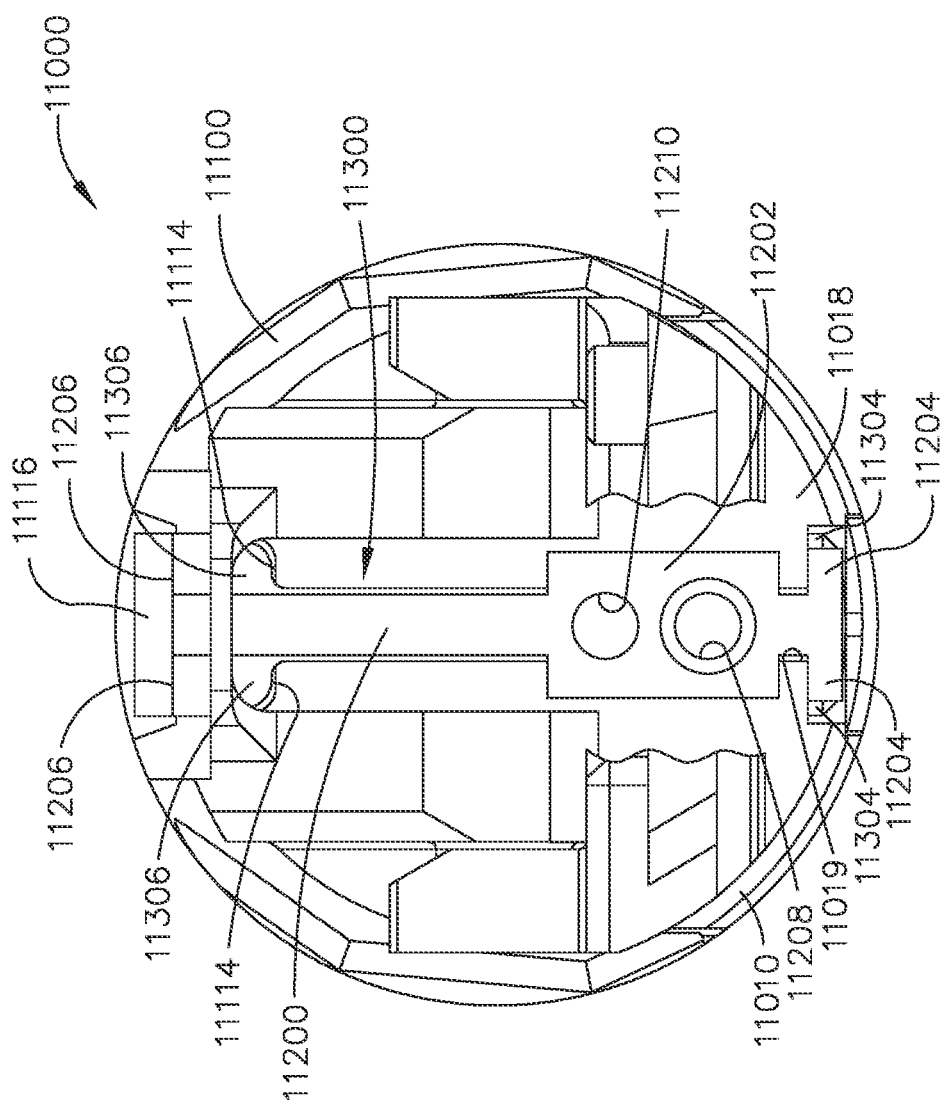
FIG. 45 is an end view of the surgical end effector of FIG. 44.

FIGS. 42 and 43 are diagrammatical depictions of an end effector 10900' that employs alternative closure link arrangements. As can be seen in those Figures, a proximal end portion 10923' end portion of an anvil 10920' is pivotally coupled to the elongate channel 10910' by proximal mounting links 10980. The proximal mounting links 10980 (only one is shown in the Figures) are pivotally attached to the elongate channel 10910' for pivotal travel relative thereto about a lower pivot axis LPA. The proximal mounting links 10980 are also pivotally coupled to the proximal end portion 10923' for pivotal travel relative thereto about an anvil pivot axis APA. The end effector 10900' further includes a closure linkage assembly 10990 that comprises at least one distal link 10992 and one proximal link 10994. In other arrangements, the closure linkage assembly 10990 comprises a pair of distal links 10992 (one on each side of the elongate channel) and a pair of proximal links 10994 (one on each side of the elongate channel). The distal link(s) 10992 is attached to the anvil 10920' for pivotal travel about the anvil pivot axis APA as well as to the corresponding proximal link(s) 10994. The other end of the proximal link(s) is pivotally attached to the elongate channel 10910'. The closure linkage assembly 10990 is actuated by a slider pin or pins 10988 that are constrained to move axially either in a corresponding slot in the elongate channel or in a closure shuttle or other member (not shown) configured to move the pin(s) 10988 between a first position (FIG. 42) corresponding to an open position of the anvil and a second position (FIG. 43) corresponding to the closed position of the anvil. The slider pin(s) 10988 is coupled to the proximal link(s) 10994. In the open state, the slider pin(s) 10988 is in the distal-most position (FIG. 42). To close the anvil 10920', the slider pin(s) 10988 is moved in a proximal direction which pulls the proximal closure link(s) 10994 to the position shown in FIG. 43 wherein the distal closure link(s) 10992 pop over center to retain the anvil 10920' in the closed state. The force vector during closure is provided by the proximal and distal closure links being in compression to thereby resist load generated by the tissue clamped in the end effector during closure.

Turning next to FIGS. 44-52, there is shown another surgical end effector 11000 that includes an anvil 11100 that is pivotally supported on an elongate channel 11010 that is configured to operably support a surgical staple cartridge (not shown) therein. This arrangement also employs two rotary actuation shafts—one for closure (i.e., moving the anvil and elongate channel between open and closed positions) and one for firing (i.e., axially moving a firing member) within the anvil and elongate channel. In the illustrated example, the anvil 11100 includes an elongate anvil body 11110 and an anvil mounting portion 11140. In one arrangement, for example, the anvil 11100 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein. A pair of anvil trunnions 11142 protrudes laterally from the anvil mounting portion 11140. Each anvil trunnion is pivotally supported in a corresponding trunnion cradle 11016 that is formed in a corresponding upstanding wall 11014 of a proximal end portion 11012 of the elongate channel 11010. See FIG. 44. The proximal end portion 11012 of the elongate channel 11010 may be pivotally coupled to an elongate shaft assembly 10200 of a surgical instrument 10010 of the type described herein, for example to facilitate articulation of the end effector 11000. In other arrangements, the elongate channel 11010 may not be capable of articulation. The anvil trunnions 11142 may be retained within their respective trunnion cradles 11016 by an anvil retainer (not shown) that may be similar in construction and operation to channel cap or anvil retainer 1290 that was described above.

Figure 47:
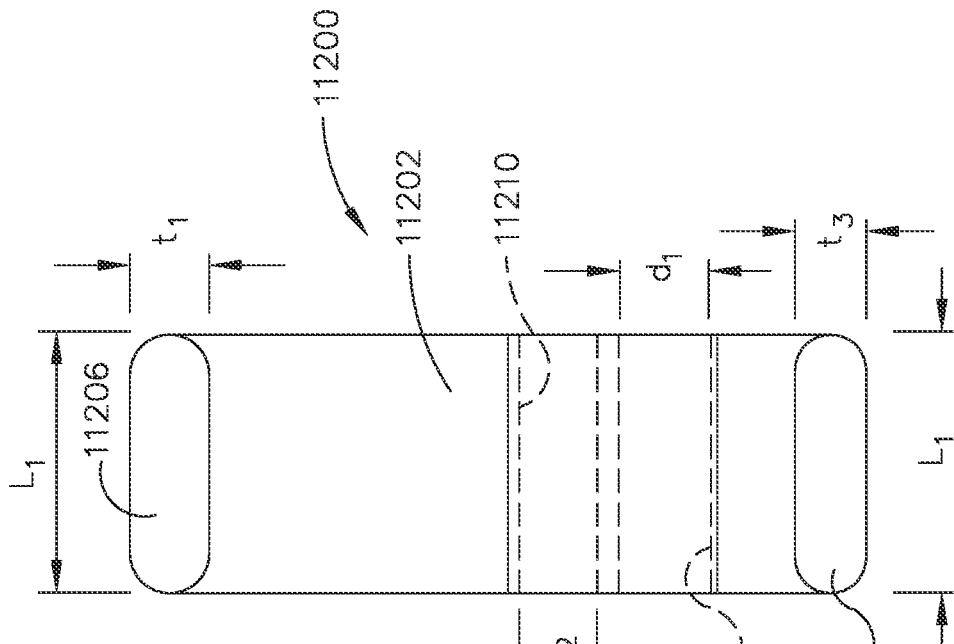
FIG. 47 is a side elevational view of an anvil closure member of the surgical end effector of FIG. 44.

In the illustrated example, the surgical end effector 11000 includes an anvil closure member 11200 and a firing member 11300 that are each independently controlled and axially movable. FIG. 47 illustrates one form of a closure member 11200 that may be employed. As can be seen in FIG. 47, the closure member 11200 includes a vertically extending closure body 11202 that has two bottom channel tabs 10204 laterally protruding therefrom. A portion of the closure body 11202 is configured to extend through a slot 11019 in a bottom surface 11018 of the elongate channel 11010 and channel tabs 11204 extend laterally outward to slidably engage the bottom of the channel 11010. Similarly, a pair of anvil engaging tabs 11206 protrude laterally from the top of the closure body 11202 to slidably engage the anvil 11100. The closure body 11202 includes a threaded through hole 11208 for threadably engaging a threaded portion 10712 of a rotatable closure drive shaft 10710 for axially driving the closure member 11200 in the various manners described herein.

Figure 48:
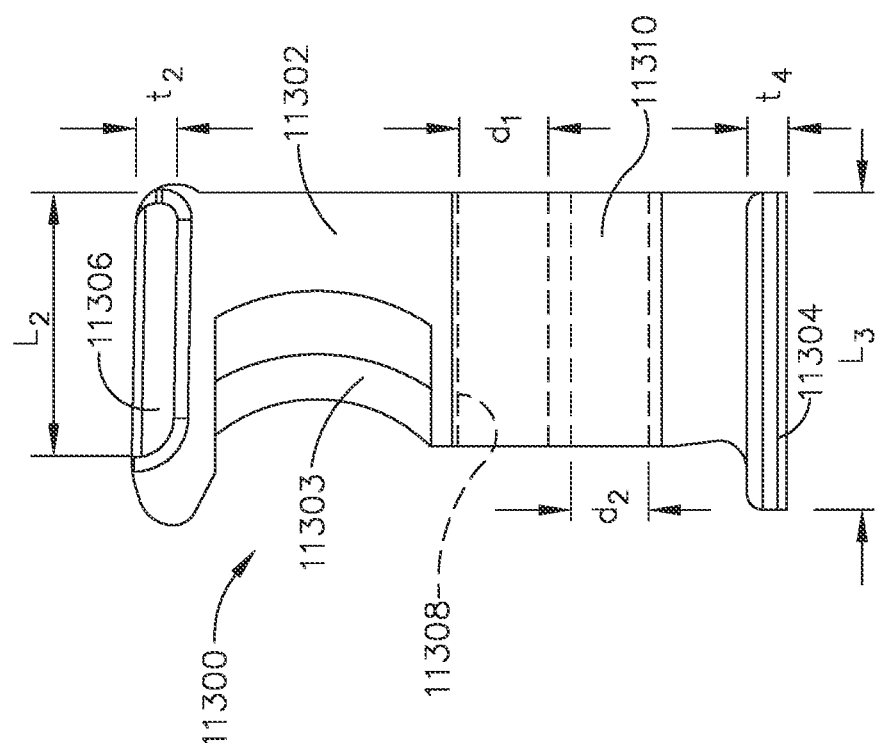
FIG. 48 is a side elevational view of a firing member of the surgical end effector of FIG. 44.

As indicated above, the surgical end effector 11000 further includes an axially movable firing member 11300. FIG. 48 illustrates one form of a firing member 11300 that may be employed. As can be seen in FIG. 48, the firing member 11300 includes a vertically extending firing member body 11302 that has a tissue cutting surface 11303 as well as two bottom channel tabs 11304 laterally protruding therefrom. A portion of the firing member body 11302 is configured to extend through the slot 11019 in the bottom surface 11018 of the elongate channel 11010 and the channel tabs 11304 extend laterally outward to slidably engage the bottom of the channel 11010. See FIG. 45. Similarly, a pair of anvil engaging tabs 11306 protrudes laterally from the top of the firing member body 11302 to slidably engage the anvil 11100. The firing member body 11302 includes a threaded through hole 11308 for threadably engaging a threaded portion of a rotatable firing drive shaft such as a firing drive shaft 10610 described above. The distal firing shaft 10610 passes through an unthreaded clearance hole 11210 in the closure body 11202. See FIG. 47. The firing drive shaft 10610 extends axially down the elongate channel 11010 and is rotatably supported in a distal end portion thereof by a bearing (not shown) or other arrangement. Similarly, the closure drive shaft 10710 may extend axially down the elongate channel 11010 and to be rotatably supported in a distal end portion thereof by a bearing (not shown) or other arrangement. Thus, the firing member body 11302 similarly has an unthreaded clearance hole 11310 therethrough to accommodate the closure drive shaft 10710. It will be appreciated that in such arrangements, the closure drive shaft 10710 and the firing drive shaft 10610 may be supported in a vertical stacked arrangement so that they may be independently rotatable.

Figure 46:
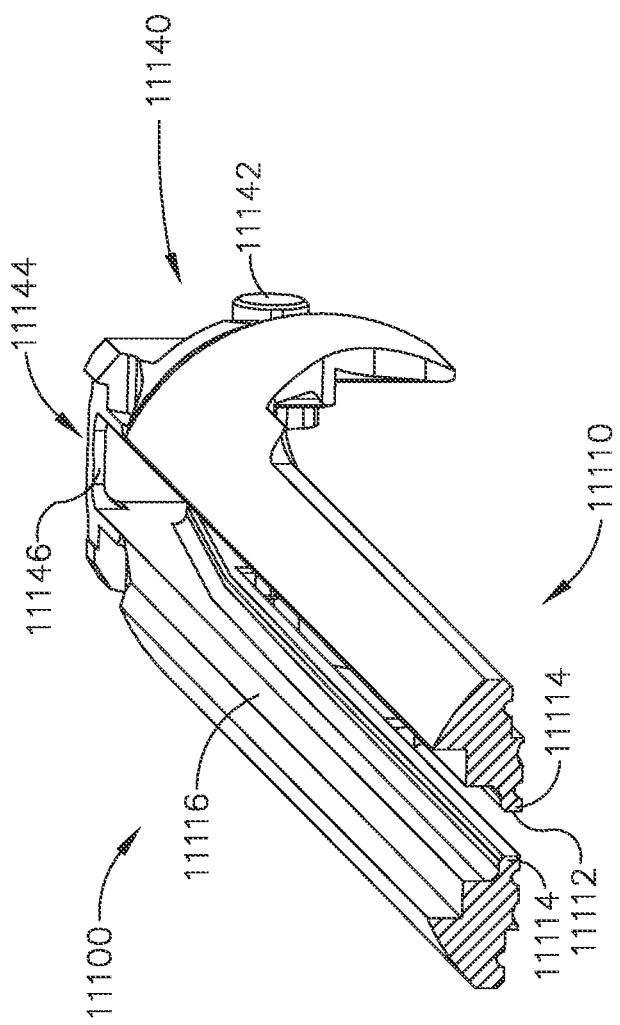
FIG. 46 is a partial cross-sectional perspective view of the anvil of the end effector of FIG. 45.
Figure 49:
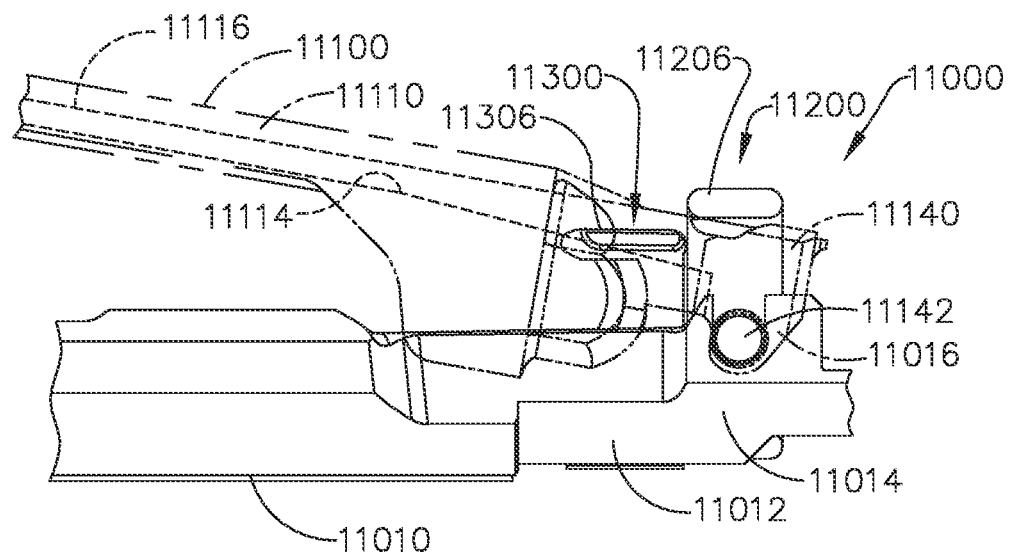
FIG. 49 is a partial side elevational view of the surgical end effector of FIG. 44 with an anvil thereof shown in phantom lines in an open position.
Figure 50:
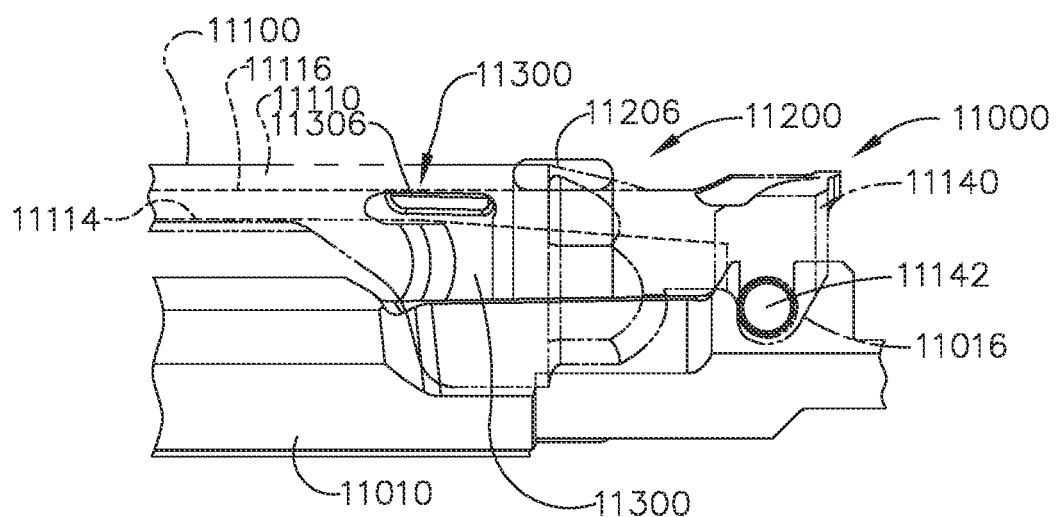
FIG. 50 is another partial side elevational view of the surgical end effector of FIG. 49, with an anvil thereof in a closed position.
Figure 51:
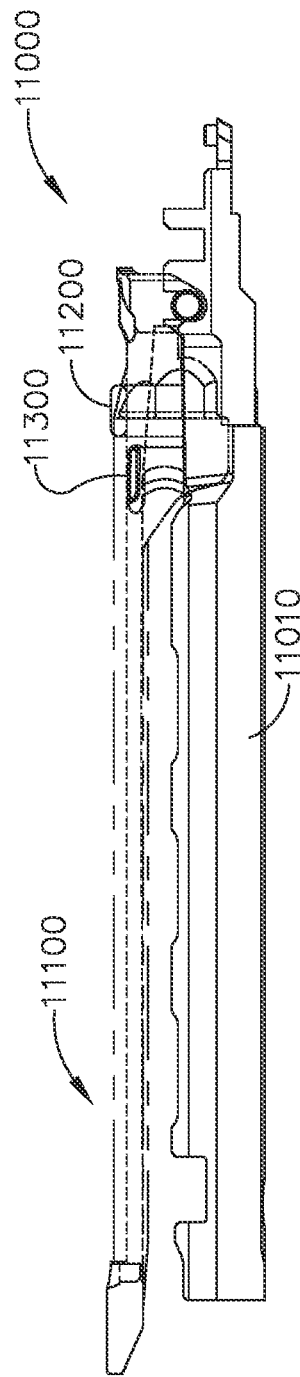
FIG. 51 is another side elevational view of the surgical end effector of FIG. 50 with a firing member thereof beginning a firing process.
Figure 52:
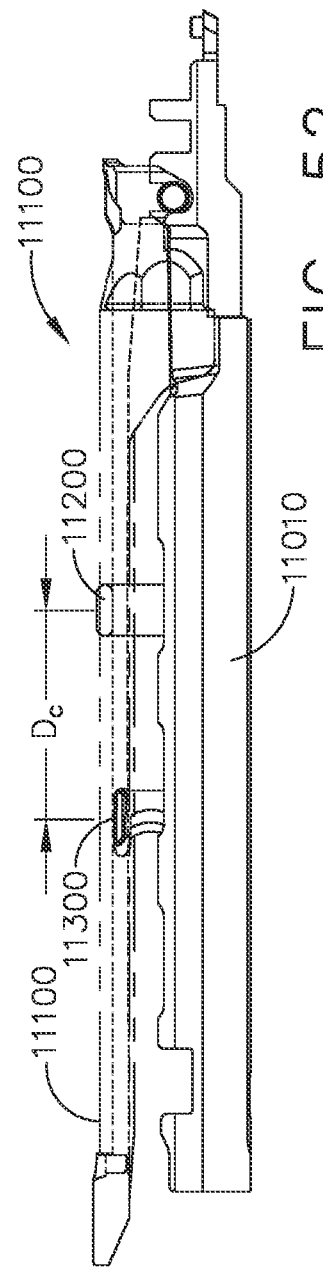
FIG. 52 is another side elevational view of the surgical end effector of FIG. 50 with the anvil closure member and the firing member being partially distally deployed in the end effector.

FIG. 46 illustrates one form of anvil 11100 with portions thereof shown in cross-section. The anvil mounting portion 11140 includes a central cross brace 11144 that serves to define an opening 11146 for accommodating the closure member 11200 therein when the closure member 11200 is in its proximal-most position which corresponds to an open position of the anvil 11100. As can be seen in FIG. 46, the anvil body 11110 defines an elongate slot 11112 for accommodating the firing member body 11302 and closure body 11202 therethrough. The firing member 11300 is located distal to the closure member 11200. The anvil engagement tabs 11306 on the firing member 11302 are configured to slidably engage corresponding first or lower ledges 11114 that are formed on each side of the slot 11112. As can be seen in FIGS. 49 and 50, the lower ledges 11114 taper slightly downward at their proximal ends to accommodate the anvil engagement tabs 11306 on the firing member 11300 when the anvil is pivoted to its open position. The anvil engagement tabs 11206 on the closure member 11200 are configured to slidably engage corresponding second or higher ledges 11116 that are formed on each side of the slot 11112. See FIG. 46. To open the anvil 11100, the closure drive shaft is rotated to threadably drive the closure member 11200 proximally into its proximal-most position (FIG. 49). When the closure member 11200 is in its proximal-most position, the anvil engagement tabs 11206 thereon apply a pivotal opening motion to the anvil 11100 to pivot the anvil open. The firing member 11300 is in its starting position so that the anvil engagement tabs 11306 of the firing member 11300 do not apply a closure motion to the anvil 11100.

To close the anvil 11100, the closure drive shaft 10710 is rotated in an opposite direction to distally advance the closure member 11200 into a closed position. The firing drive shaft 10610 may also be simultaneously rotated to distally advance the firing member 11300 into a starting position. When the closure member 11200 and the firing member 11300 are in those positions, the anvil 11100 is closed and the firing member 11300 is ready to be fired. Thus, assuming that an unspent surgical staple cartridge has been first operably supported in the elongate channel 11010 and the end effector 11000 was manipulated to capture the target tissue between the staple cartridge and the anvil, the user may close the anvil 11100 onto the tissue in the above described manner to ready the end effector to be fired. During this closing process, the firing drive shaft 10610 is rotated to drive the firing member 11300 distally into the clamped tissue to cut the tissue and cause the staples stored in the staple cartridge to be formed into the cut tissue on both sides of the cut. During this process, the closure member 11200 may also be driven distally to apply additional closure motions to the anvil 11100 and elongate channel 11010. Depending upon the amount of resistance experienced by the firing member 11300, for example, the closure member 11200 can be advanced with the firing member 11300, stop and then go again. The closure member 11200 may be advanced distally at a different rate from the firing member's rate of distal advancement. The distance Dc between the closure member 11200 and the firing member 11300 may be controlled to balance the loads experienced during the firing process. See FIG. 52. For example, if the user wanted to decrease an amount of vertical load being experienced by the firing member 11300, the closure member 11200 could be moved closer to the firing member 11300 during advancement. The vertical loads experienced by the firing member 11300 may be increased by increasing the distance between the firing member 11300 and the closure member 11200.

Returning to FIGS. 47 and 48, the thickness $t_1$ of the anvil engagement tabs 11206 on the closure member 11200 is greater than the thickness $t_2$ of the anvil engagement tabs 11306 on the firing member 11300. In one arrangement, the length $L_1$ of the anvil engagement tabs 11206 on the closure member 11200 is slightly less than the length $L_2$ of the anvil engagement tabs 11306 on the firing member 11300. Likewise, the thickness $t_3$ of the channel tabs 11204 on the closure member 11200 is greater than the thickness $t_4$ of the channel tabs 11304 on the firing member 11300. In one arrangement, the length $L_1$ of the channel tabs 11204 on the closure member 11200 are shorter than the length $L_3$ of the channel tabs 11304 on the firing member 11300. In both cases, the diameters $d_1$ of the threaded holes 11208, 11308 may be greater than the diameters $d_2$ of the unthreaded through holes 11210, 11310. In addition, the relative attack angles between the anvil engagement tabs 11206, 11306 and their corresponding anvil ledges and the channel tabs 11204, 11304 and their corresponding channel ledges may be varied, the same or different. In one arrangement, the anvil engagement tabs 11306 on the firing member 11300 are arranged at a slightly higher attack angle relative to their corresponding anvil ledges than the attack angle of the anvil engagement tabs 11206 on the closure member 11200. In one arrangement, the channel tabs 11204 and 11304 ride on the same ledges that are formed in the bottom of the elongate channel 11010. See FIG. 45. The closure member 11200 and the firing member 11300 have separate acting paths which can permit the closure member to be designed to accommodate larger moment arms from the anvil pivot for better firing efficiency.

One advantage that may be experienced when using the foregoing configuration is that the closure member 11200 can be moved away from the firing member 11300 to gain a significant amount of mechanical advantage during closure. The closure member 11200 does not need to travel the complete length of the firing stroke. For example, if the closure member 11200 were to be advanced about half way down the end effector, the relative stiffness of the anvil 11100 would reduce the amount of load being encountered by the firing member 11300. A control system employing sensors (e.g., strain gauges, etc.) for detecting amounts of loads being experienced by the firing system components and closure system components, as well as algorithms, can be used to balance the loads being encountered by both systems. For example, a maximum threshold of vertical load experienced by the firing member 11300 can be set in the controller based on the geometry and composition of that firing member component. When the load approaches that threshold, the algorithm can automatically advance the closure member 11200 so that it absorbs more of the load and reduces the amount of load being experienced by the firing member 11300. In various aspects, as the firing member 11300 is distally driven through the surgical staple cartridge, the firing member 11300, through the engagement of the anvil engagement tabs 11306 with the anvil 11100 and the engagement of the channel engagement tabs 11304 with the channel 11010, may serve to maintain a desired amount of tissue gap between a deck surface on the staple cartridge and a staple forming undersurface on the anvil 11100. Other closure control methods may also be employed in connection with opening and closing the surgical end effector 11000 such as those disclosed in U.S. Patent Application Ser. No. 16/105,081, entitled METHOD FOR OPERATING A POWERED ARTICULATABLE SURGICAL INSTRUMENT, the entire disclosure of which is hereby incorporated by reference herein.

Figure 53:
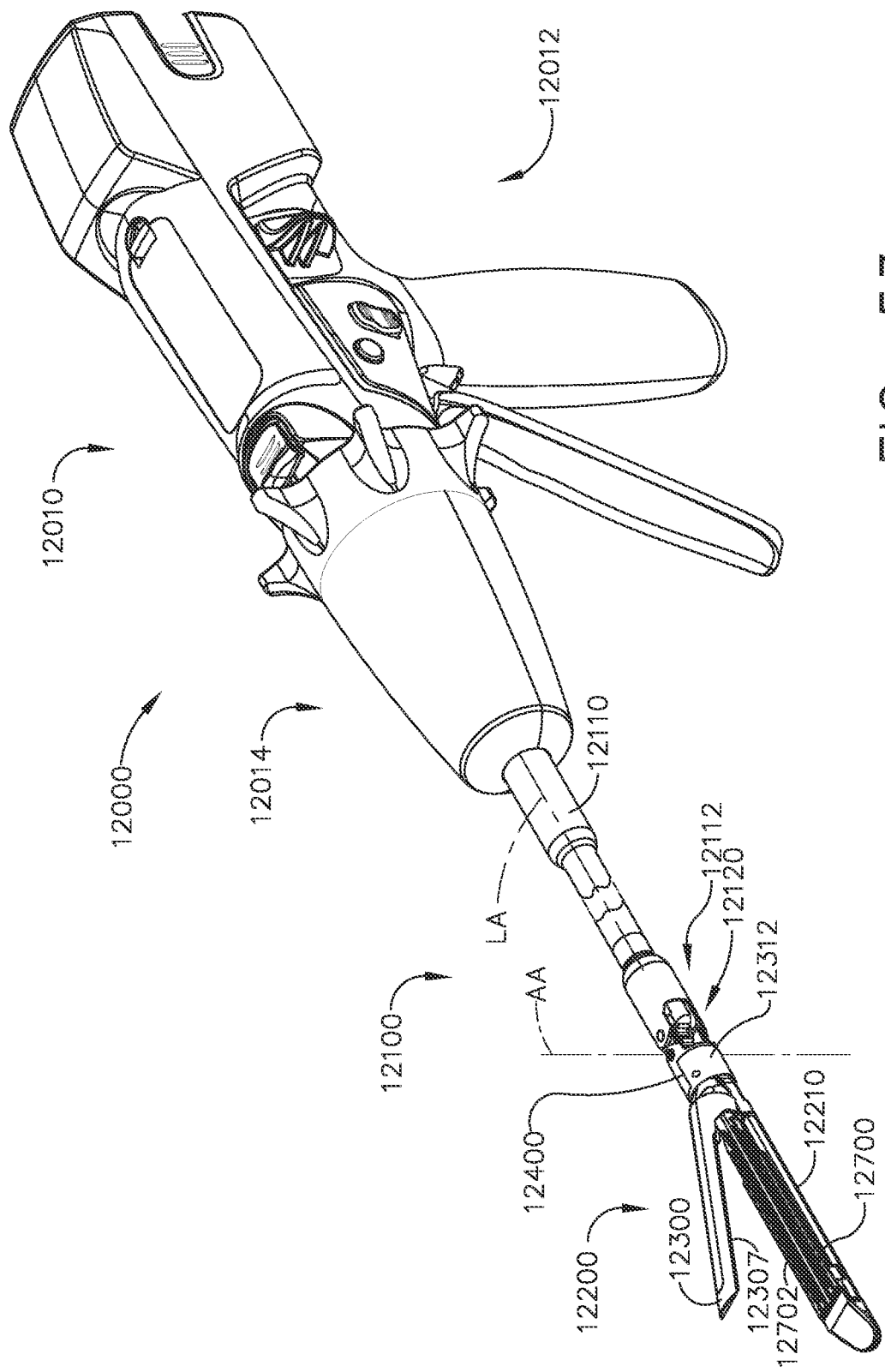
FIG. 53 is a perspective view of another powered surgical instrument.

FIG. 53 depicts a surgical instrument 12000 that may be used to cut and staple tissue. The instrument comprises a housing 12010 that comprises a handle 12012 that is configured to be grasped, manipulated and actuated by the clinician. As can be seen in FIG. 53, for example, the instrument 12000 includes a shaft assembly 12100 that has a surgical end effector 12200 operably coupled thereto that is configured to perform one or more surgical tasks or procedures. The shaft assembly 12100 comprises an interchangeable shaft assembly that is intended to be removably couplable to the handle assembly 12012 in the various manners disclosed herein. However, in other arrangements, the shaft assembly 12100 may comprise a dedicated shaft assembly that is not intended to be removed from the handle 12012. In still other arrangements, the shaft assembly 12100 may be operably coupled to or operably interface with a robotic system that is capable of generating the rotary operating motions necessary to operate the surgical end effector in the various manners disclosed herein. Only those specific components necessary to understand the functions and operation of the shaft assembly 12100 will be discussed in further detail below.

In the illustrated example, the elongate shaft assembly 12100 includes an articulation joint 12120 that facilitates articulation of the surgical end effector 12200 about an articulation axis AA that is transverse to a longitudinal shaft axis LA. Other shaft assemblies, however, may not be capable of articulation. In the illustrated example, the shaft assembly 12100 comprises a proximal outer shaft tube or member 12110 that extends distally from a nozzle assembly 12014 as will be discussed in further detail below, the surgical end effector 12200 is operably attached to an end cap attachment feature 12400. In one arrangement, the end cap attachment feature 12400 comprises a tubular shape body 12402 that is similar in size to the proximal outer shaft tube 12110 and is coupled to the distal end 12112 of the proximal outer shaft tube 12110 to form an articulation joint 12120. The shaft assembly 12100 may also include an internal spine member (not shown) that is pivotally coupled to the end cap 12400. A proximal end of the internal spine member may be rotatably coupled to a chassis (not shown) within the nozzle assembly 12014 in the various manners disclosed herein, for example.

Figure 54:
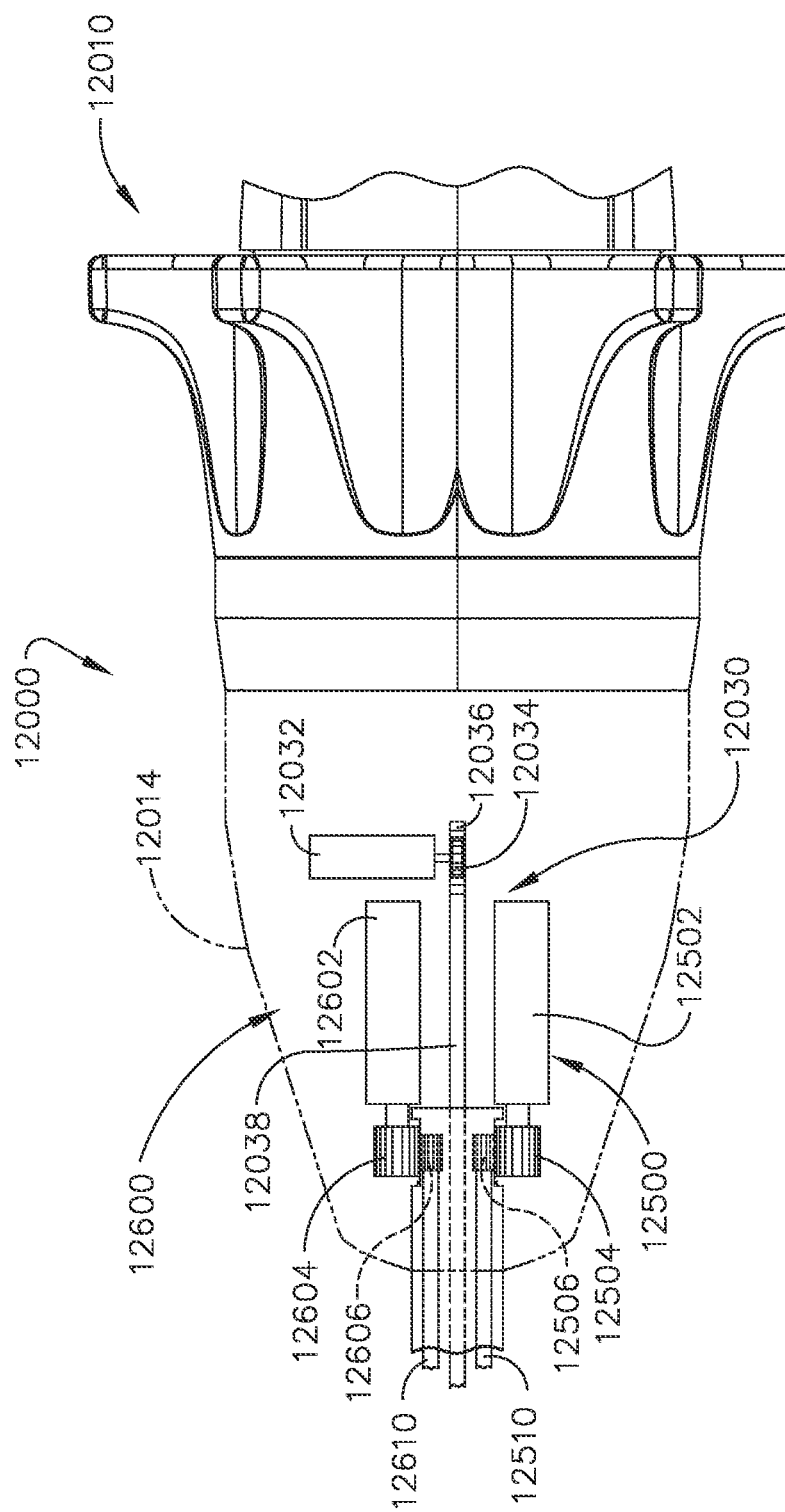
FIG. 54 is a top view of a portion of the powered surgical instrument of FIG. 53.

In the illustrated example, the surgical end effector 12200 is selectively articulatable about the articulation axis AA by an articulation system 12030. In one form, the articulation system 12030 includes an articulation motor 12032 that is operably supported in the nozzle assembly 12014, for example. See FIG. 54. In other examples, the articulation motor may be operably supported in the housing or handle or other portion of a robotic system. Referring to FIG. 54, the articulation motor 12032 is coupled to an articulation drive gear 12034 that is in meshing engagement with a drive gear rack 12036 that is attached to or otherwise formed in a proximal articulation driver 12038. A distal end of the proximal articulation driver 12038 is pivotally coupled to a distal articulation link (not shown) that spans the articulation joint and is coupled to the end cap 12400. Operation of the articulation motor 12032 will cause axial movement of the proximal articulation driver 12038. Axial movement of proximal articulation driver 12038 will apply articulation motions to the end cap 12400 and an elongate channel 12210 attached thereto to thereby cause the surgical end effector 12200 to articulate about the articulation axis AA relative to the shaft assembly 12100. Other articulation systems and arrangements may be employed in the various manners disclosed herein or in other embodiments, the surgical end effector may not be articulatable.

The surgical end effector 12200 further includes an anvil 12300 that is selectively pivotable relative to the elongate channel 12210 between open and closed configurations by a closure system 12500. In one arrangement, for example, the anvil 12300 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein. In at least one arrangement, the surgical end effector 12200 also includes a firing member 12620 that is axially movable within the surgical end effector 12200 between a starting position and an ending position. See FIG. 55. As will be discussed in further detail below, the firing member 12620 may be configured to sever tissue that is clamped between the anvil 12300 and a surgical staple cartridge 12700 that is operably supported in the elongate channel 12210. In one arrangement, the staple cartridge 12700 includes lines of surgical staples or fasteners (not shown) that are operably supported on corresponding drivers (not shown) that are movably supported in the cartridge. As the firing member 12620 is driven distally, the firing member 12620 cooperates with a sled or camming assembly (not shown) that is supported in the staple cartridge 12700 that serves to cam the drivers in a direction toward the closed anvil 12300 which causes the staples or fasteners supported thereon to pierce through the clamped tissue into forming contact with the underside of the closed anvil. Once the firing member 12620 has been distally advanced from its proximal starting position to its ending position within the end effector 12200, it may be retracted back to its starting position to permit the anvil 12300 to be opened to facilitate removal of the cut/stapled tissue from the end effector 12200. In other arrangements, the firing member 12620 may be left at the ending position wherein it is permitted to disengage from the anvil to facilitate opening of the anvil.

Figure 55:
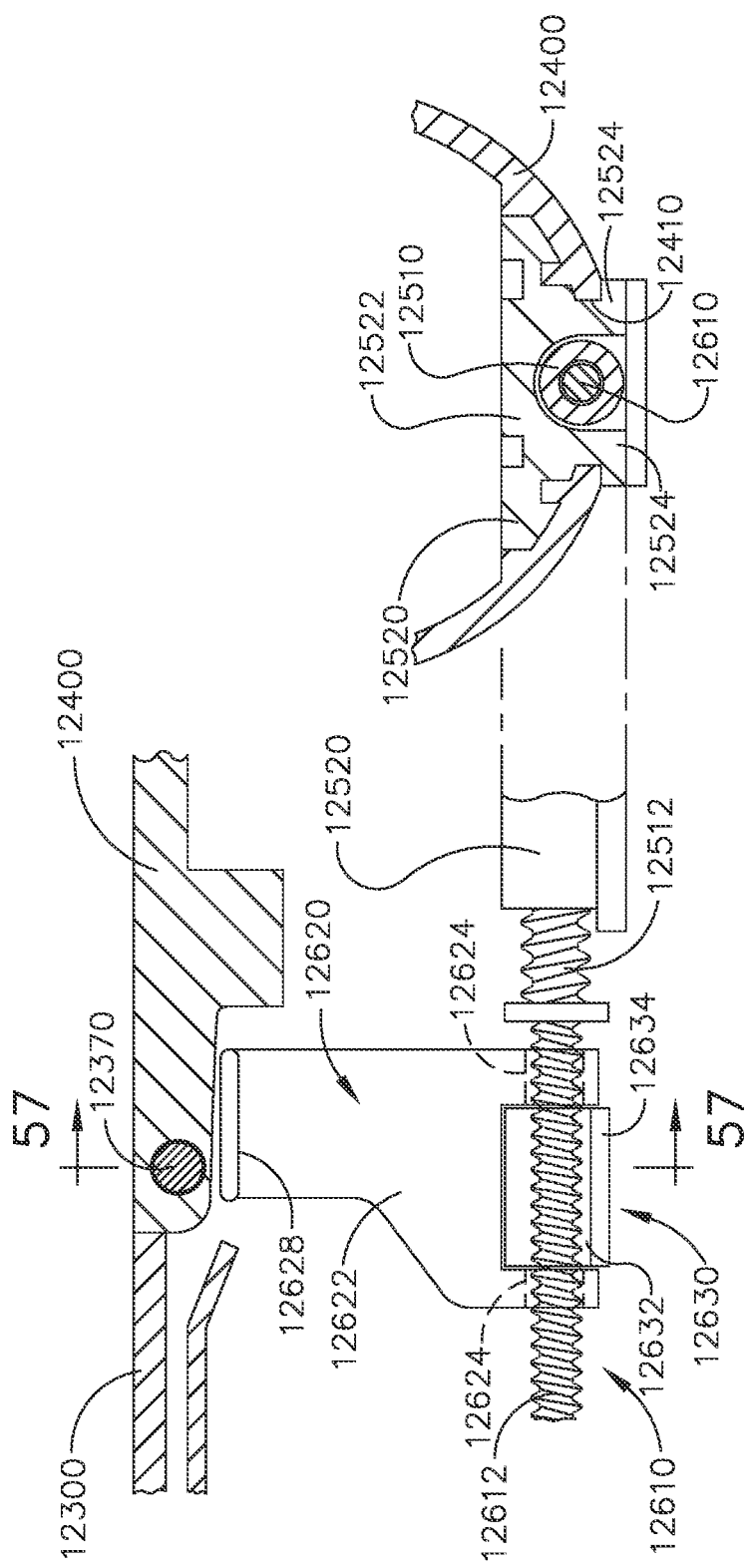
FIG. 55 is a partial cross-sectional view of portions of the surgical end effector of the surgical instrument of FIG. 53.
Figure 62:
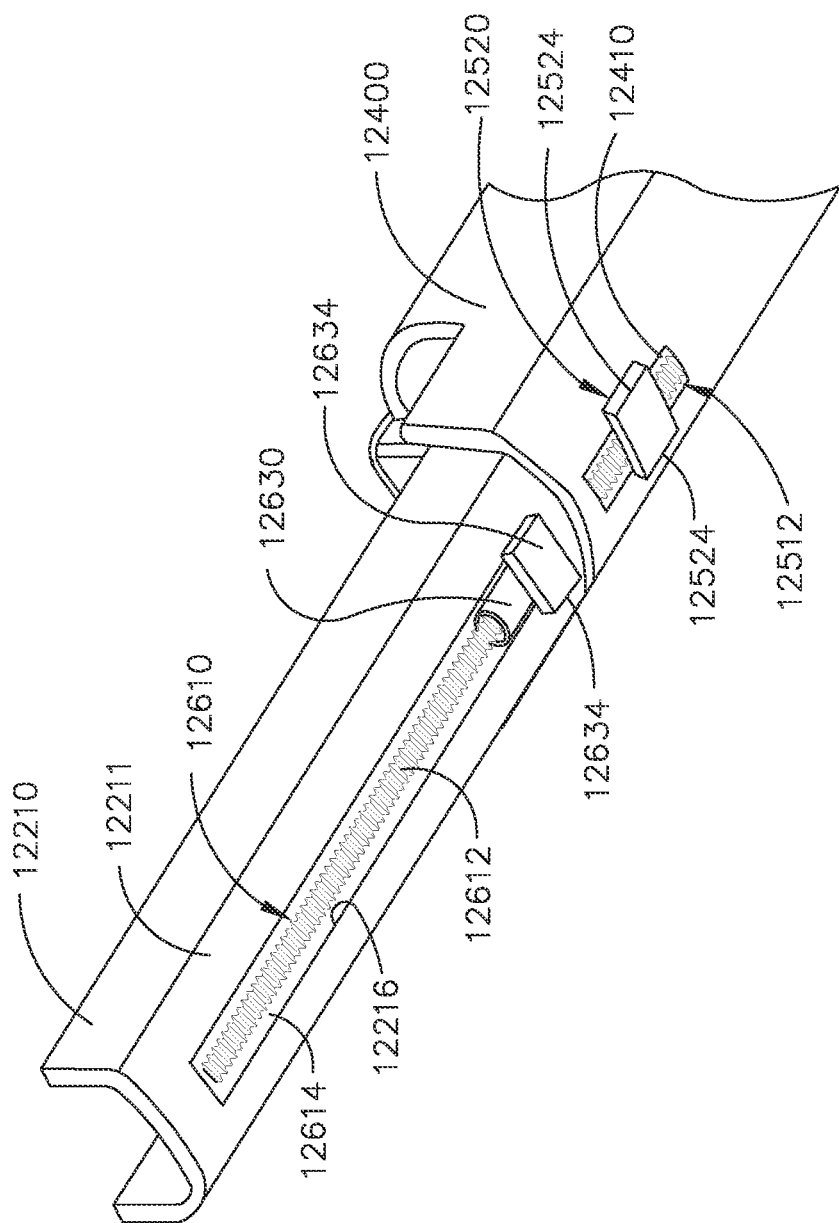
FIG. 62 is a partial bottom perspective view of the elongate channel and firing member of the surgical end effector of FIG. 59.

In at least one arrangement, the surgical instrument 12000 also employs a firing system 12600 that is configured to apply rotary drive motions to the firing member 12620 to drive the firing member between the starting and ending positions. In the example depicted in FIG. 54, the firing system 12600 includes a firing motor 12602 that is operably supported in the nozzle assembly 12014, for example. In other examples, the firing motor 12602 may be operably supported in the housing or handle or other portion of a robotic system. The firing motor 12602 is coupled to a firing drive gear 12604 that is in meshing engagement with a driven gear 12606 that is attached to or otherwise formed in rotary firing drive shaft 12610. The firing drive shaft 12610 may be flexible to permit articulation of the surgical end effector 12200 in the manner described above. As can be seen in FIG. 55, the firing member 12620 comprises a body portion 12622 that includes two downwardly extending hollow mounting portions 12624 that are unthreaded and spaced from each other to receive a threaded drive nut 12630 therebetween. The threaded drive nut 12630 is threaded onto a threaded portion 12612 of the rotary firing drive shaft 12610. A distal end 12614 of the rotary firing drive shaft 12610 may be configured to be rotatably supported in a bearing (not shown) housed within the elongate channel to rotatably support the rotary firing drive shaft 12610 therein. The drive nut 12630 includes a vertical tab portion 12632 that is sized to extend through an axial slot 12216 in the bottom surface 12211 of the elongate channel 12210. See FIG. 62. Two laterally extending retention flanges 12634 are formed on the vertical tab portion 12632 to slidably engage the bottom surface 12211 of the elongate channel 12210. In addition, two laterally extending anvil engagement tabs 12628 are formed on the top of the body portion 12622 of the firing member 12620 and are configured to engage the anvil 12300 as the firing member 12620 is axially moved within the end effector. The threaded drive nut 12630 is threaded onto a threaded portion 12612 of the rotary firing drive shaft 12610. A distal end of the rotary firing drive shaft 12610 may be configured to be rotatably supported in a bearing (not shown) housed within the elongate channel 12210 to rotatably support the rotary firing drive shaft 12610 therein. In various aspects, as the firing member 12620 is distally driven through the surgical staple cartridge 12700, the firing member 12620, through the engagement of the anvil engagement tabs 12628 with the anvil 12300 and the engagement of the laterally extending retention flanges 12634 with the channel 12210, may serve to maintain a desired amount of tissue gap between a deck surface 12702 on the staple cartridge 12700 and a staple forming undersurface 12307 on the anvil 12300. See FIG. 53.

In the illustrated example, in addition, to a rotary driven firing system 12600, the surgical instrument 12000 also includes a rotary driven closure system 12500 that is configured to apply rotary closure motions to the anvil 12300. As can be seen in FIG. 54, for example, in one arrangement, the rotary driven closure system 12500 comprises a closure motor 12502 that is operably supported in the nozzle assembly 12014, for example. In other examples, the closure motor 12502 may be operably supported in the housing or handle or other portion of a robotic system. The closure motor 12502 is coupled to a closure drive gear 12504 that is in meshing engagement with a driven gear 12506 that is attached to or otherwise formed in rotary closure drive shaft 12510. The closure drive shaft 12510 may be flexible to permit articulation of the surgical end effector 12200 in the manner described above.

Figure 56:
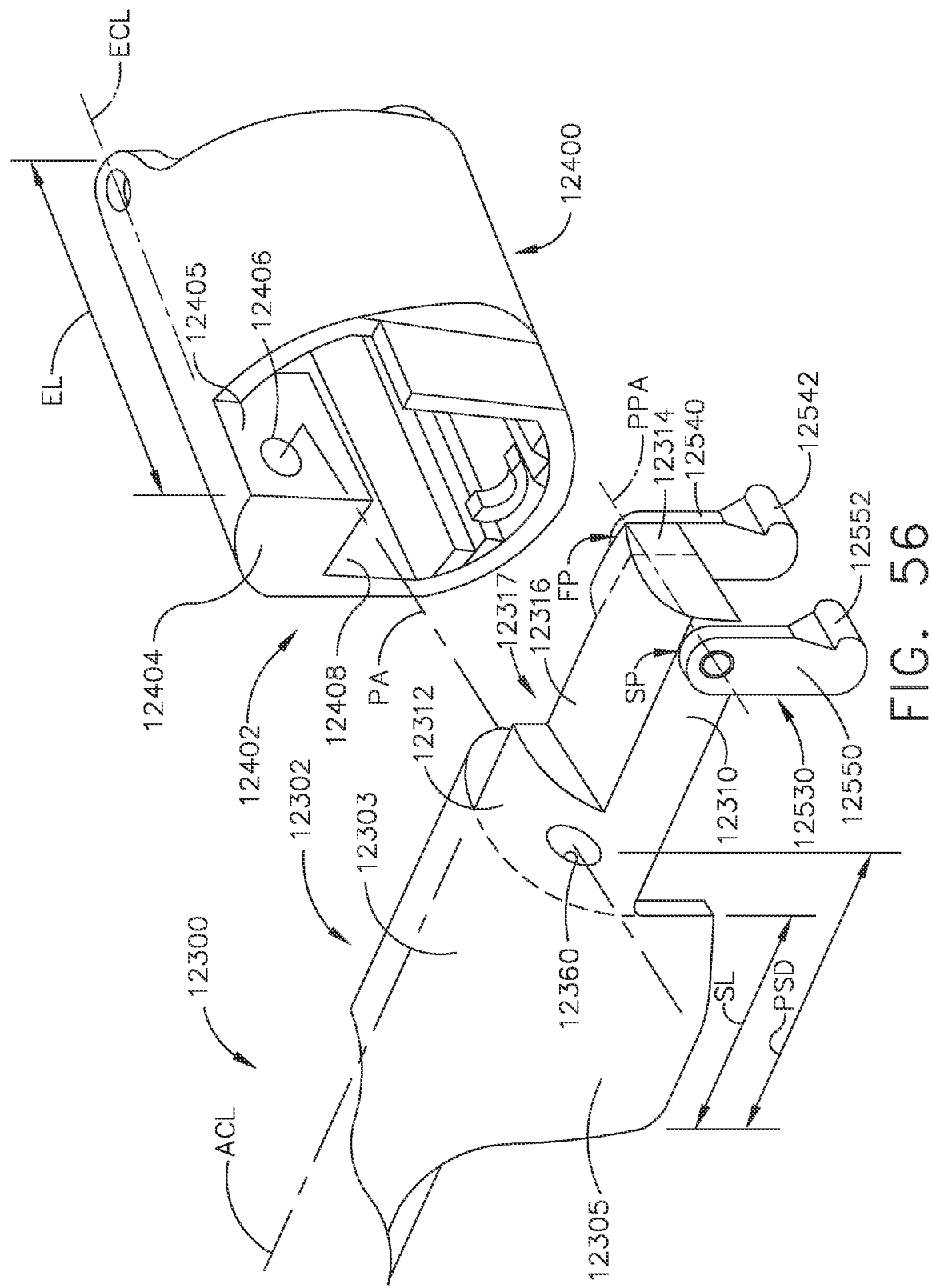
FIG. 56 is a partial exploded assembly view of an anvil and end cap portion of the surgical end effector of the surgical instrument of FIG. 53.

As can be seen in FIG. 56, the anvil 12300 includes a proximally protruding anvil mounting tab 12310 that is configured to be pivotally coupled to a corresponding pivot lug portion 12404 of the end cap 12400. For example, the pivot lug portion 12404 is formed on a first or right side of the endcap centerline ECL and a corresponding anvil mounting portion 12312 of the anvil mounting tab 12310 is formed on a second or left side of the anvil centerline ACL that corresponds to (aligned with) the endcap centerline ECL when the two components are coupled together. When the anvil 12300 is movably coupled to the end cap 12400, the anvil centerline ACL and the endcap centerline ECL are aligned along an end effector axis or end effector center plane ECP that extends axially through a center of the end effector 12200. Stated another way, the end effector center plane ECP bisects the end effector 12200. See FIGS. 60 and 61. In one aspect, the pivot lug portion 12404 comprises a vertically extending pivot lug attachment face 12405 that is adapted to slidably confront a vertically extending anvil attachment face 12317 formed on a central portion 12316 of the anvil mounting tab 12310. Still referring to FIG. 56, the proximal end 12314 of the anvil mounting tab 12310 is laterally wider than the central portion 12316. When the anvil 12300 is attached to the end cap 12400, the proximal end portion 12314 of the anvil mounting tab 12310 is proximal to the pivot lug portion 12404 and the pivot lug attachment face 12405 and the vertically extending anvil attachment face 12317 movably confront each other along the centrally disposed end effector central plane ECP. See FIG. 60. In the illustrated arrangement, an upper surface 12303 of an anvil body portion 12302 of the anvil 12300 and the anvil mounting portion 12312 of the anvil mounting tab 12310 are rounded to match or at least approximately match the radius of the end cap 12400 to facilitate easy insertion of the surgical end effector and elongate shaft through a trocar, for example.

Figure 57:
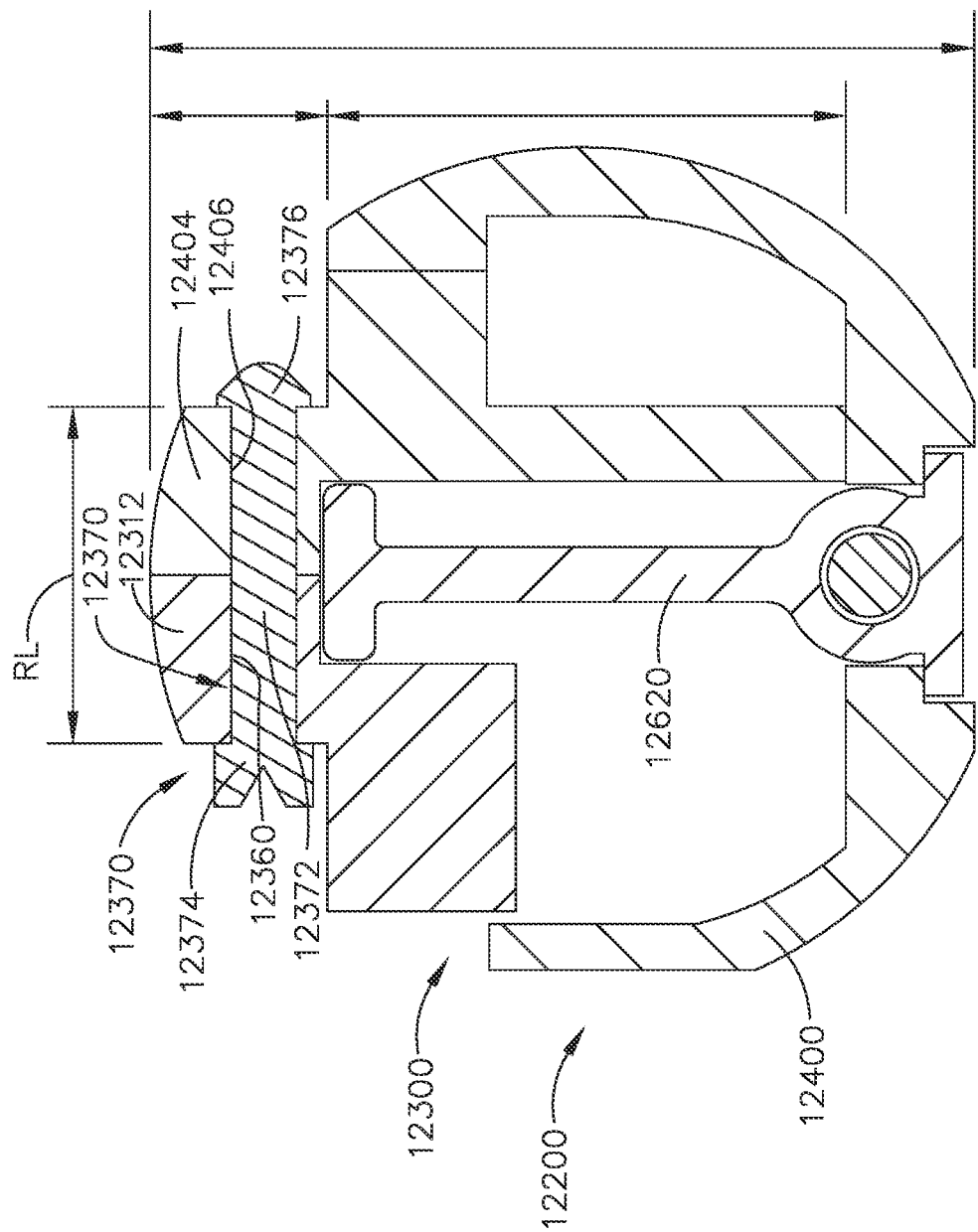
FIG. 57 is a partial cross-sectional end view of the surgical end effector of the surgical instrument of FIG. 53.

In one aspect, the anvil 12300 is pivotally coupled to the end cap 12400 by a rivet 12370 that extends through a passage 12360 in the anvil mounting portion 12312 of the anvil mounting tab 12310 and a corresponding passage 12406 in the pivot lug portion 12404 of the end cap 12400. In at least one arrangement, the rivet 12370 comprises a solid core rivet with a shank 12372 having diameter of, for example, 0.05"-0.1" with an orbit formed head 12374 on one end and a machined end 12376 formed on the other end. See FIG. 57. The rivet 12370 may be installed such that it may maintain a final formed height that would ensure intimate contact between the anvil mounting portion 12312 and the pivot lug portion 12404. The orbit formed rivet head 12374 would swell the rivet shank 12372 on that side of the anvil 12300 or end cap 12400 preventing the rivet 12370 from rotating with respect to that component while the machined end 12376 would not have a swelled shank allowing the adjacent part to rotate with respect to the rivet 12370 and the other part (anvil mounting portion 12312 or pivot lug portion 12404). In the example illustrated in FIG. 57, the end of the rivet 12370 that is adjacent to the anvil mounting portion 12312 is orbit formed so that part of the rivet 12370 does not rotate relative to the anvil mounting portion 12312 and the part of the rivet 12370 extending through the end cap 12400 is free to rotate allowing the anvil 12300 to freely pivot relative to the pivot lug portion 12404. As can be seen in FIG. 57, the rivet shank 12372 has a predefined final form length RL that is sized to facilitate such rotational travel. Also, as can be seen in FIG. 56, in one arrangement for example, the end cap 12400 may have a length EL of approximately 0.675". The anvil body 12302 may also be formed with downwardly extending tissue stop members 12305 that are configured to prevent the clamped tissue from extending proximally beyond the proximal-most staples or fasteners in a staple cartridge 12700 that is seated in the elongate channel 12210. In the illustrated example, the tissue stops 12305 may have a stop length SL of approximately 0.400" and the distance PSD from a distal end of each tissue stop 12305 to the centerline of the passage 12360 is approximately 0.500". This distance may correspond to the distance from the proximal-most staples or fasteners to the pivot axis PA about which the anvil 12300 pivots relative to the endcap 12400.

Figure 58:
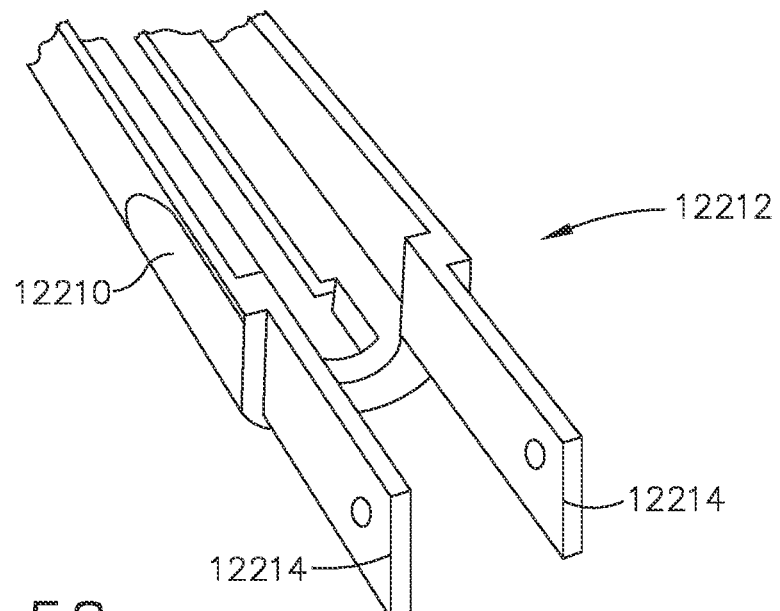
FIG. 58 is a perspective proximal end view of a portion of an elongate channel of the surgical end effector of FIG. 57.

As can be seen in FIG. 58, a pair of channel attachment tabs 12214 protrude from a proximal end 12212 of the elongate channel 12210. The channel attachment tabs 12214 are configured to be seated in corresponding grooves 12408 in the endcap 12400. See FIG. 60. The tabs 12214 may be welded, glued, pinned etc. to the end cap 12400.

Turning now to FIGS. 55 and 59-61, the rotary driven closure system 12500 also comprises an axially movable closure shuttle 12520 that is in threaded engagement with a threaded portion 12512 of the closure drive shaft 12510. In the illustrated arrangement, the closure shuttle 12520 comprises a shuttle base portion 12522 that extends through a proximal cap slot 12410 formed in the bottom of the end cap 12400. A lateral flange 12524 extends laterally from each side of the shuttle base portion 12522 to slidably engage the bottom of the end cap 12400. See FIG. 55. As can be further seen in FIG. 55, the closure drive shaft 12510 is hollow to permit the firing drive shaft 12610 to concentrically extend therethrough. Thus, rotation of the closure drive shaft 12510 in a first rotary direction will cause the closure shuttle 12520 to move distally and rotation of the closure drive shaft 12510 in an opposite rotary direction will cause the closure shuttle 12520 to move in a proximal direction.

Figure 59:
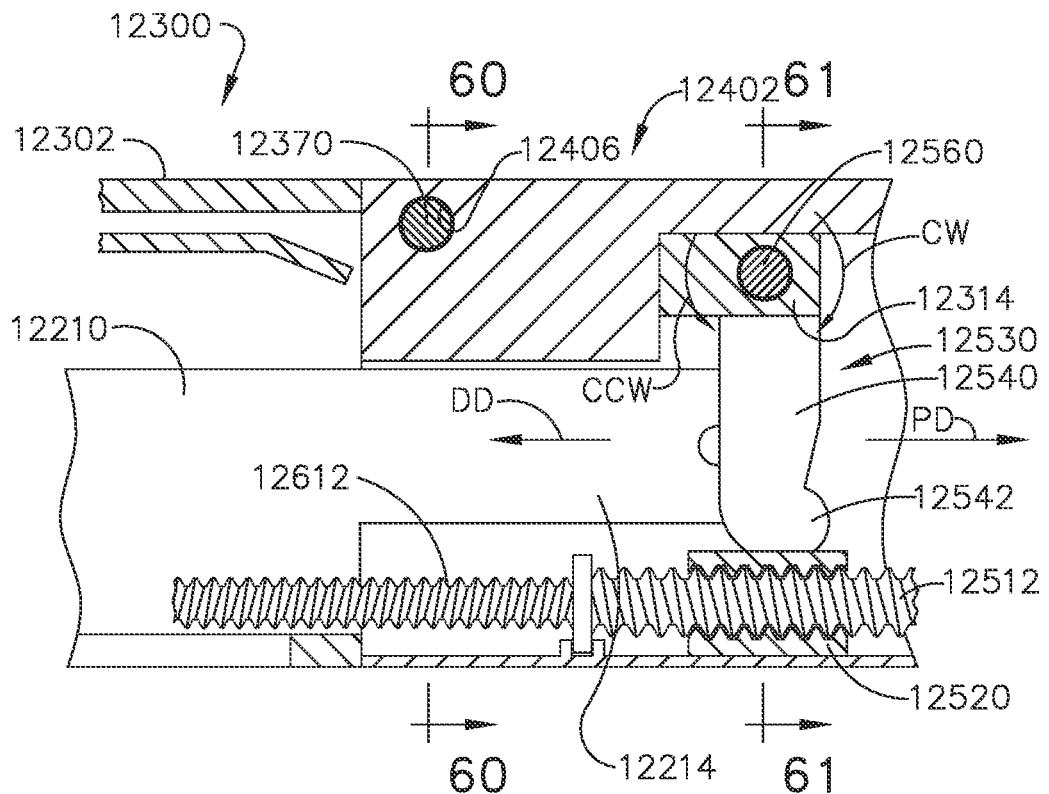
FIG. 59 is a partial side elevational view of a portion of the surgical end effector of FIG. 57, with some components shown in cross-section and with the anvil thereof in a closed position.

In the illustrated example, the axial movement of the closure shuttle 12520 is transferred to the anvil 12300 by a pivoting closure linkage assembly 12530. In one arrangement, the closure linkage assembly 12530 includes a first pivot arm 12540 and a second pivot arm 12550 that are each pivotally attached to the proximal end portion 12314 of the anvil mounting tab 12310 and suspended therefrom. As can be seen in FIG. 61, for example, the first pivot arm 12540 and the second pivot arm 12550 may be pivotally coupled to the proximal end portion 12314 of the anvil mounting tab 12310 by a pivot pin 12560 that defines a common proximal pivot axis PPA about which the pivot arms 12540 and 12550 can pivot. The first pivot arm 12540 comprises a first free end 12542 that is wider than the remaining portion of the first pivot arm 12540 and is configured to be movably and drivably engaged in a first drive groove 12526 in the closure shuttle base portion 12522. See FIG. 61. The first pivot arm 12540 is coupled to the anvil mounting tab 12310 at a first point FP that is located a first pivot arm distance FPD from the end effector center plane ECP. Likewise, the second pivot arm 12550 comprises a second free end 12552 that is wider than the remaining portion of the second pivot arm 12550 and is configured to be movably and drivably engaged in a second drive groove 12528 in the closure shuttle base portion 12522. The second pivot arm 12550 is coupled to the anvil mounting tab 12310 at a second point SP that is located a second pivot arm distance SPD from the end effector center plane ECP. In the illustrated arrangement the closure system is asymmetrically coupled to the anvil 12300. For example, as can be seen in FIG. 61, SPD>FPD. When the closure shuttle 12520 is driven in the distal direction DD, the pivot arms 12540 and 12550 by virtue of their engagement with the closure shuttle 12520 are caused to pivot in a first direction (clockwise CW in FIG. 59) which causes a pivotal opening motion to be applied to the anvil mounting tab 12310 to pivot the anvil 12300 about the pivot axis PA relative to the end cap 12400 to an open position. When the closure shuttle 12520 is axially moved in a proximal direction PD, the pivot arms 12540, 12550 pivot in a second direction (counterclockwise CCW in FIG. 59) which causes a closure motion to be applied to the anvil mounting tab 12310 to pivot the anvil 12300 about the pivot axis PA relative to the end cap 12400 to a closed position (FIG. 59). The larger free end portions 12542, 12552 of the pivot arms 12540, 12550, respectively are more robust than the remaining portions of the pivot arms to better distribute the closure forces through the pivot arms.

Figure 63:
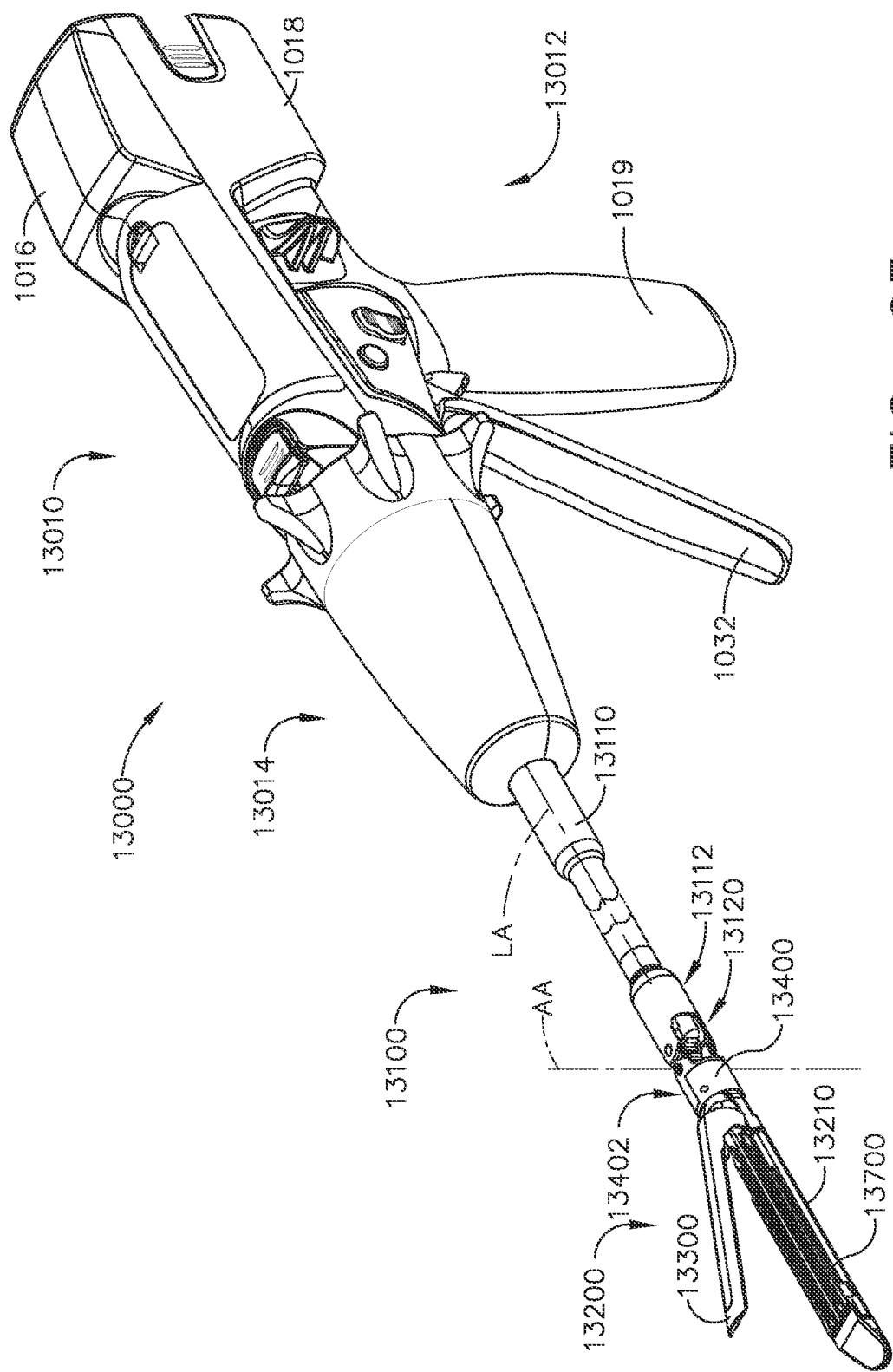
FIG. 63 is a perspective view of another powered surgical instrument.

FIG. 63 depicts a surgical instrument 13000 that may be used to cut and staple tissue. The instrument includes a housing 13010 that comprises a handle 13012 that is configured to be grasped, manipulated and actuated by the clinician. As can be seen in FIG. 63, for example, the instrument 13000 includes a shaft assembly 13100 that has a surgical end effector 13200 operably coupled thereto that is configured to cut and staple tissue. As will be discussed in further detail below, for example, the surgical end effector 13200 comprises an elongated channel 13210 that is configured to operably support a replaceable surgical staple cartridge 13700 therein and an anvil 13300 that is movably supported relative thereto for movement between open and closed positions. The shaft assembly 13100 comprises an interchangeable shaft assembly that is intended to be removably couplable to the handle assembly 13012 in the various manners disclosed herein. However, in other arrangements, the shaft assembly 13100 may comprise a dedicated shaft assembly that is not intended to be removed from the handle 13012. In still other arrangements, the shaft assembly 13100 may be operably coupled to or operably interface with a robotic system that is capable of generating the rotary operating motions necessary to operate the surgical end effector in the various manners disclosed herein. Only those specific components necessary to understand the functions and operation of the shaft assembly 13100 will be discussed in further detail below.

In the illustrated example, the shaft assembly 13100 includes an articulation joint 13120 that facilitates articulation of the surgical end effector 13200 about an articulation axis AA that is transverse to a longitudinal shaft axis LA. Other shaft assemblies, however, may not be capable of articulation. In accordance with one aspect, the shaft assembly 13100 comprises a proximal outer shaft tube or member 13110 that extends distally from a nozzle assembly 13014 as will be discussed in further detail below, the surgical end effector 13200 is operably attached to an end cap attachment feature 13400. In one arrangement, the end cap attachment feature 13400 comprises a tubular shape body 13402 that is similar in size to the proximal outer shaft tube 13110 and is coupled to a distal end 13112 of the proximal outer shaft tube 13110 to form the articulation joint 13120. The end cap 13400 may also comprise a proximal portion of the elongate channel 13210. The shaft assembly 13100 may also include an internal spine member (not shown) that is pivotally coupled to the end cap 13400. A proximal end of the internal spine member may be rotatably coupled to a chassis (not shown) within the nozzle assembly 13014 in the various manners disclosed herein, for example.

Figure 64:
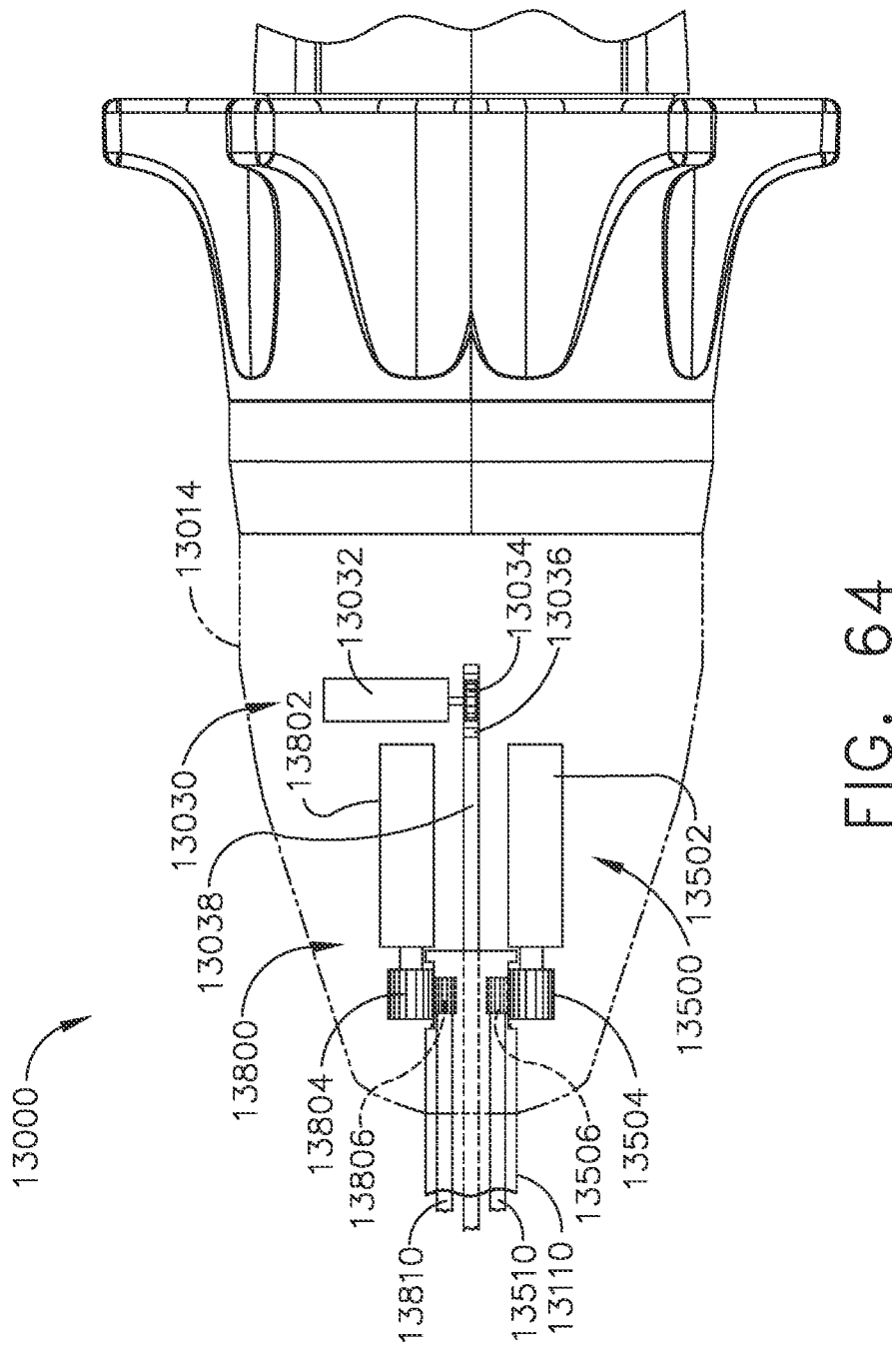
FIG. 64 is a top view of the powered surgical instrument of FIG. 63.

In the illustrated example, the surgical end effector 13200 is selectively articulatable about the articulation axis AA by an articulation system 13030. In one form, the articulation system 13030 includes an articulation motor 13032 that is operably supported in the nozzle assembly 13014, for example. See FIG. 64. In other examples, the articulation motor may be operably supported in the housing or handle or other portion of a robotic system. Referring to FIG. 64, the articulation motor 13032 is coupled to an articulation drive gear 13034 that is in meshing engagement with a drive gear rack 13036 that is attached to or otherwise formed in a proximal articulation driver 13038. A distal end of the proximal articulation driver 13038 is pivotally coupled to a distal articulation link (not shown) that spans the articulation joint and is coupled to the end cap 13400. Operation of the articulation motor 13032 will cause axial movement of the proximal articulation driver 13038. Axial movement of proximal articulation driver 13038 will apply articulation motions to the end cap 13400 and the elongate channel 13210 attached thereto to thereby cause the surgical end effector 13200 to articulate about the articulation axis AA relative to the shaft assembly 13100. Other articulation systems and arrangements may be employed in the various manners disclosed herein. In other embodiments, the surgical end effector may not be articulatable.

As indicated above, the surgical end effector 13200 includes an anvil 13300 that is selectively movable relative to the elongate channel 13210 between open and closed configurations by a rotary driven closure system 13500. As can be seen in FIG. 64, in one arrangement, the rotary driven closure system 13500 comprises a closure motor 13502 that is operably supported in the nozzle assembly 13014, for example. In other examples, the closure motor 13502 may be operably supported in the housing or handle or other portion of a robotic system. The closure motor 13502 is coupled to a closure drive gear 13504 that is in meshing engagement with a driven gear 13506 that is attached to or otherwise formed in rotary closure drive shaft 13510. The closure drive shaft 13510 may be flexible to permit articulation of the surgical end effector 13200 in the manner described above.

Figure 65:
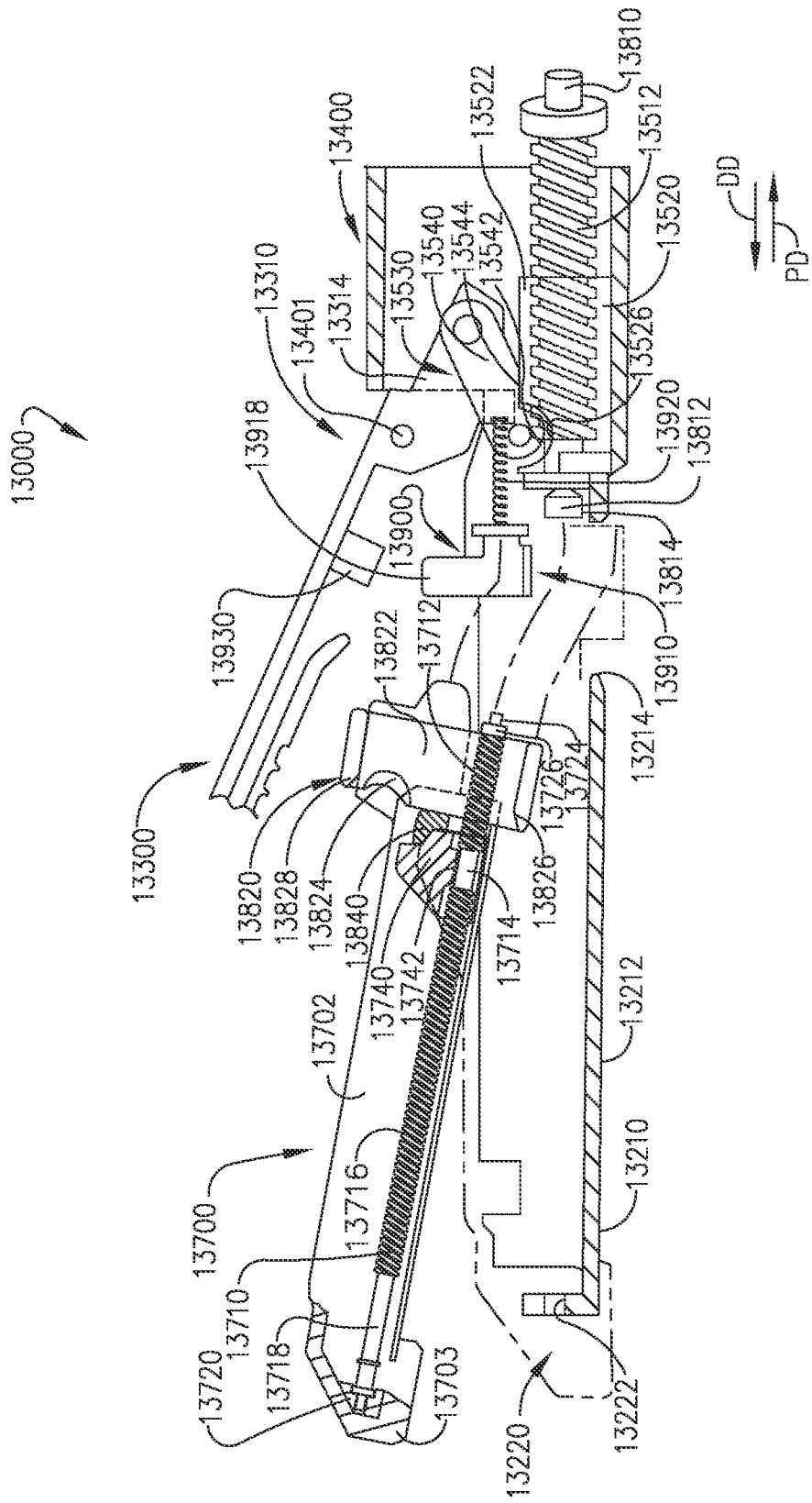
FIG. 65 is a partial cross-sectional side view of a surgical end effector of the powered surgical instrument of FIG. 63, with a surgical staple cartridge being operably installed therein.

As can be seen in FIG. 65, the anvil 13300 includes a proximally protruding anvil mounting tab 13310 that is configured to be pivotally coupled to a corresponding portion of the end cap 13400 by, for example, a rivet 13401 or other pivot arrangements disclosed herein. In the illustrated arrangement, the rotary driven closure system 13500 also comprises an axially movable closure shuttle 13520 that is in threaded engagement with a threaded distal closure shaft segment 13512 that is configured to be drivingly coupled the closure drive shaft 13510. In the illustrated arrangement, the closure shuttle 13520 comprises a shuttle base portion 13522 that extends through a proximal cap slot (not shown) that is formed in the bottom of the endcap 13400. A lateral flange (not shown) extends laterally from each side of the shuttle base portion 13522 to slidably engage the bottom of the endcap 13400 in the various manners disclosed herein. In one arrangement, for example, the anvil 13300 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein.

In the illustrated example, the axial movement of the closure shuttle 13520 is transferred to the anvil 13300 by a pivoting closure link assembly 13530. In one arrangement, the closure link assembly 13530 includes a pair of pivot arms 13540 (only one can be seen in FIG. 65) that are each pivotally attached to a proximal end portion 13314 of the anvil mounting tab 13310 and suspended therefrom. Each pivot arm 13540 comprises a free end 13542 that includes a notch 13544 that is configured to drivingly engage a corresponding drive groove 13526 in the closure shuttle base portion 13522. When the closure shuttle 13520 is driven in the distal direction DD, the pivot arms 13540, by virtue of their engagement with the closure shuttle 13520, pivot in a first direction to apply pivotal opening motion to the anvil mounting tab 13310. This opening motion causes the anvil 13300 to pivot to an open position. When the closure shuttle 13520 is axially moved in a proximal direction PD, the pivot arms 13540 pivot in a second direction which causes a pivot closure motion to be applied to the anvil mounting tab 13310 and pivot the anvil 13300 to a closed position.

As also indicated above, the surgical end effector 13200 is configured to operably support a replaceable surgical staple cartridge 13700 therein. The staple cartridge 13700 includes an onboard firing member 13820 that is configured to be rotatably driven between a starting and ending position within the staple cartridge 13700. The firing member 13820 comprises a vertically extending firing member body 13822 that has a tissue cutting surface 13824 formed thereon or attached thereto. A pair of channel engagement tabs 13826 extend laterally from the bottom of the firing member body 13822 and a pair of anvil engagement tabs 13828 extend from the top portion of the firing member body 13822 such that the firing member 13820 resembles an I-beam configuration when viewed from an end thereof. As can be seen in FIG. 66, in the illustrated example, the surgical staple cartridge 13700 comprises an elongate cartridge body 13702 that includes a deck surface 13707. The cartridge body 13702 further comprises a centrally disposed elongate cartridge slot 13704 that is configured to accommodate the axial travel of the firing member 13820 therein. Also in the illustrated example, three lines of surgical staple pockets 13706 are formed on each side of the elongate slot 13704 and open through the deck surface 13707. Each staple pocket 13706 may have a staple driver (not shown) associated therewith that supports a surgical staple or fastener (not shown) thereon.

As can be seen in FIG. 65, the cartridge body 13702 operably supports an onboard rotary firing drive shaft 13710. The firing drive shaft 13710 includes a proximal thread segment 13712, an unthreaded segment 13714 and a distal thread segment 13716 that extends from the unthreaded segment 13714 to an unthreaded distal end 13718. The unthreaded distal end 13718 of the firing drive shaft 13710 is rotatably supported in a distal bearing 13720 that is supported in a distal end 13703 of the cartridge body 13702. In the illustrated example, the firing member body 13822 is threaded onto the proximal thread segment 13712 when in a proximal-most, "loading position". As can be seen in FIG. 66, a safety garage 13732 is formed on a proximal end 13730 of the cartridge body 13702 such that the tissue cutting surface 13824 is protected thereby (unexposed) when the firing member 13820 is in the loading position. When the firing member 13820 is in the loading position, the bottom of the firing member body 13822 is configured to extend through a loading opening 13214 in the bottom 13212 of the elongate channel 13210 during installation of the cartridge 13700 into the elongate channel 13210. As can be seen in FIG. 67, a channel slot 13216 is provided in the bottom 13212 of the elongate channel 13210 and extends distally from the loading opening 13214. When the staple cartridge 13700 is operably seated in the elongate channel 13210, the bottom portion of the firing member 13820 protrudes through the loading opening 13214 such that when the firing member 13820 is advanced distally, the firing member body 13822 is aligned with the channel slot 13216 and the channel engagement tabs 13826 are positioned to slidably engage the bottom 13212 of the elongate channel 13210 on each side of the channel slot 13216.

In one example, at least one C-shaped clip 13890 may be journaled within the cartridge body 13702 such that a center portion 13892 of the clip 13890 extends through the elongate cartridge slot 13704 in the cartridge body 13702 such that an upper leg 13894 of the clip 13890 rides on an inside surface or ledge 13708 in the cartridge body 13702 adjacent the cartridge slot 13704. A lower leg 13896 of the clip 13890 rides on a bottom surface 13213 of the channel bottom 13212 as shown in FIG. 68. When the cartridge 13700 is initially installed, the C-shaped clip(s) 13890 may be positioned proximally of the elongate channel slot 13216 such that the cartridge 13700 may be properly seated therein. When the firing member 13820 is distally advanced, the C-shaped clip(s) 13890 is advanced distally down the aligned cartridge slot 13704 and channel slot 13216 to provide additional stabilization of the cartridge 13700 during the firing operation.

As can also be seen in FIG. 67, in at least one arrangement, at least one cartridge locator member 13722 is formed on or otherwise attached to the cartridge body 13702 and is located and sized to be seated in a corresponding notch 13218 or other mating feature formed in the elongate channel 13210 to ensure that the cartridge 13700 is properly seated in the elongate channel 13210 during installation. In one example, locator members 13722 are formed on each lateral side of the cartridge body 13702. Also in the illustrated example, a drive shaft support cradle 13222 is formed on a distal end 13220 of the channel 13210 and is configured to rotatably cradle the unthreaded distal end 13718 of the firing drive shaft 13710 (proximal to the support bearing 13720). See FIG. 65.

Returning to FIG. 64, the surgical instrument 13000 also employs a rotary driven firing system 13800 that is configured to apply rotary drive motions to the firing member 13820 to drive the firing member 13820 between the starting and ending positions within the staple cartridge 13700. In the example depicted in FIG. 64, the rotary driven firing system 13800 includes a firing motor 13802 that is operably supported in the nozzle assembly 13014. In other examples, the firing motor 13802 may be operably supported in the housing or handle or other portion of a robotic system. The firing motor 13802 is coupled to a firing drive gear 13804 that is in meshing engagement with a driven gear 13806 that is attached to or otherwise formed in rotary firing drive shaft 13810. The firing drive shaft 13810 may be flexible to permit articulation of the surgical end effector 13200 in the manner described above. As can be seen in FIGS. 65 and 67, the firing drive shaft 13810 extends through the hollow distal closure shaft segment 13512 that is configured to be drivingly coupled to the closure drive shaft 13510 and has a drive coupler 13812 attached thereto. In one arrangement, the drive coupler 13812 comprises a female drive socket 13814 that is configured to drivably receive a corresponding male coupler 13724 on the firing drive shaft 13710. When the male coupler 13724 is brought into driving engagement with the female drive socket 13814, rotation of the firing drive shaft 13810 will result in rotation of the firing drive shaft 13710 in the surgical staple cartridge 13700.

FIG. 65 illustrates the firing member 13820 in the loading position. When in that position, the firing member 13820 may abut a collar portion 13726 of the male coupler 13724. As can also be seen in FIG. 65, the staple cartridge 13700 also includes a sled or camming assembly 13740 that is movably supported in the staple cartridge 13700. The camming assembly 13740 is threadably journaled on the firing drive shaft 13710 by a series of internal threads 13742. As can be seen in FIG. 65, when the firing member 13820 is in the loading position, the internal threads 13742 in the camming assembly 13740 are located on the unthreaded segment 13714 of the firing drive shaft 13710.

Figure 70:
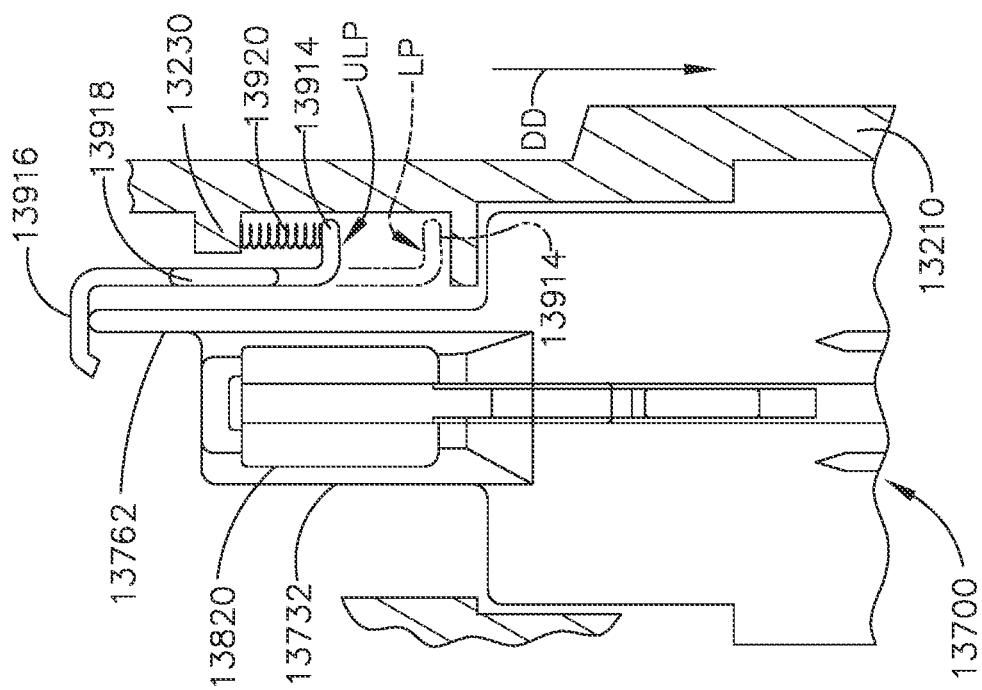
FIG. 70 is a top cross-sectional view of the firing lockout assembly of FIG. 69 in engagement with a portion of the surgical staple cartridge of FIG. 66.
Figure 69:
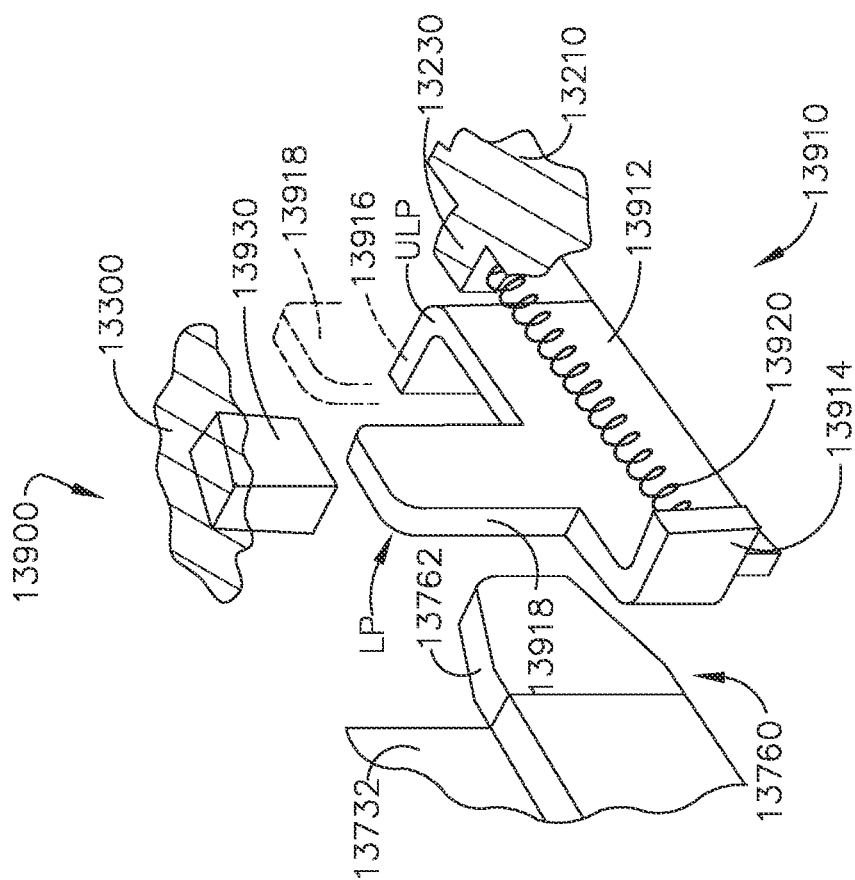
FIG. 69 is a partial exploded assembly view of a firing lockout assembly of the surgical end effector of FIG. 65.

The illustrated example also employs an anvil lockout assembly 13900 that is configured to prevent the closure of the anvil 13300 until the cartridge 13700 has been properly seated in the elongate channel 13210. In one arrangement, the anvil lockout assembly 13900 comprises an anvil lockout member 13910 that is movably supported in the elongate channel 13210. Turning to FIGS. 69 and 70, in one arrangement, the anvil lockout member 13910 comprises a clip body 13912 that has a distal spring tab 13914 protruding laterally from a distal end thereof and a proximal key tab 13916 protruding laterally from an opposite lateral side of the clip body 13912. The clip body 13912 further includes a vertically extending lock tab 13918 that protrudes upward from the clip body 13912. As can be seen in FIGS. 69 and 70, the lockout member 13910 is axially movable between a distal locking position LP and a proximal unlocked position ULP. A lock spring 13920 is provided between a channel lug 13230 and the distal spring tab 13914 to bias the lockout member 13910 distally into the locked position LP. FIGS. 65 and 69 illustrate the anvil lockout assembly 13900 in the locked position LP. As can be seen in FIGS. 65 and 69, the vertically extending lock tab 13918 is vertically aligned with an anvil lockout protrusion 13930 formed on the anvil 13300. Thus, when the anvil lockout assembly 13900 is in the locked position, the user cannot move the anvil 13300 to the closed position.

In the illustrated arrangement, the cartridge body 13702 includes a key member 13760 that is configured to move the lockout member 13910 from the locked position LP to the unlocked position ULP when the cartridge 13700 has been properly seated within the elongate channel 13210. In one example, the key member 13760 comprises a proximally extending fin 13762 that is configured to contact the proximal key tab 13916 on the clip body 13912. When the cartridge 13700 has been operably seated in the elongate channel 13210, the fin 13762 moves the lockout member 13910 proximally from the locked position LP to the unlocked position ULP.

Figure 71:
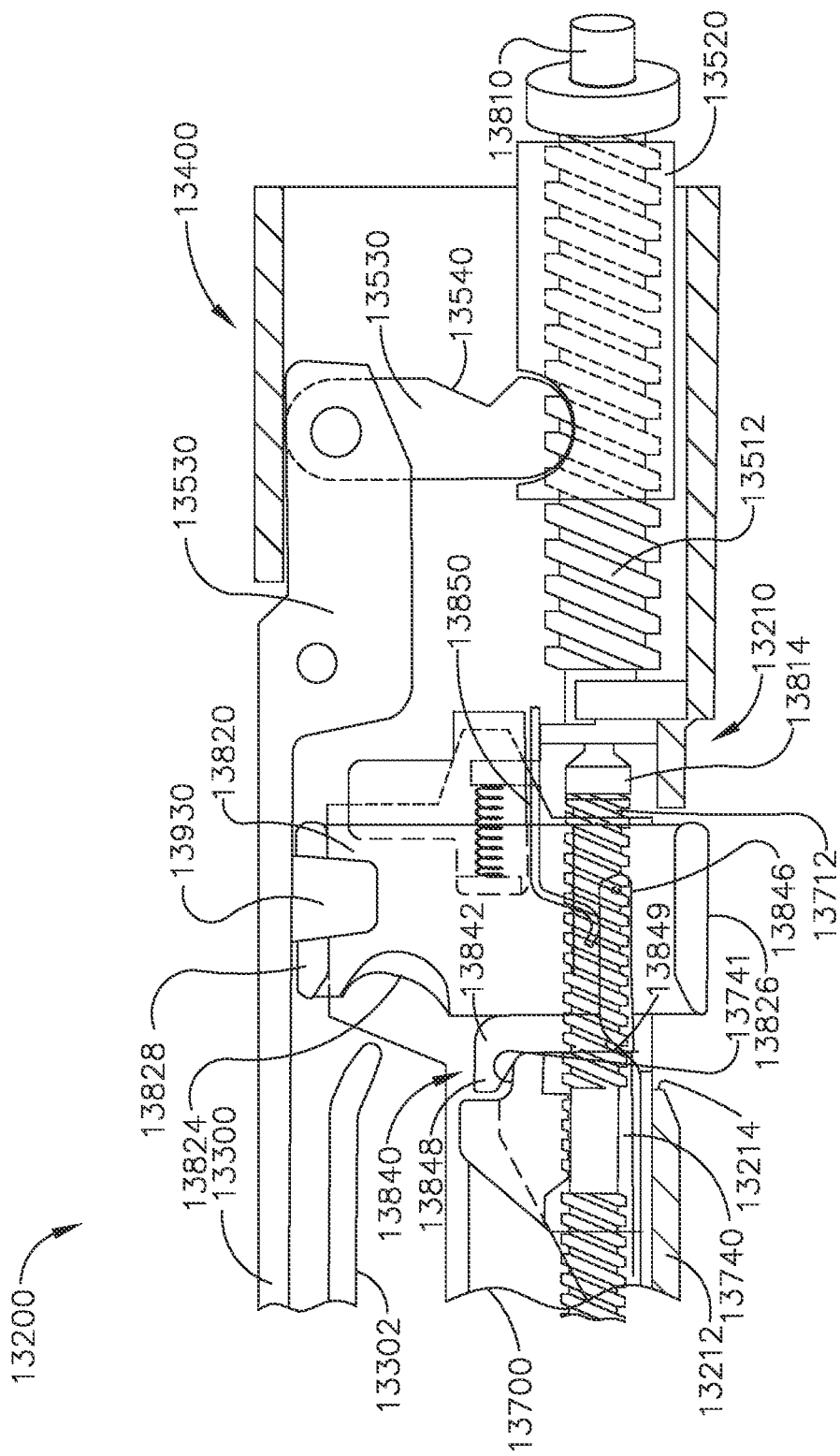
FIG. 71 is a side cross-sectional view of the surgical end effector of FIG. 65 with a surgical staple cartridge operably installed therein and the firing lockout assembly in an unlocked position.

As can be seen in FIG. 71, the firing member 13820 may also be equipped with an onboard firing member lockout assembly 13840 that comprises a lockout member 13842 that is pivotally coupled to the firing member body 13822 by pivot pins 13846. The lockout member 13842 includes a sled latch 13848 that is configured to be engaged by the camming assembly 13740 when the camming assembly 13740 is in an unfired position. As can be seen in FIG. 71, the camming assembly 13740 includes a firing member ledge 13741 that is configured to engage the sled latch 13848 on the lockout member 13482. A lockout spring 13850 is mounted in the elongate channel 13210 and is configured to bias the lockout member 13842 downward such that if the camming assembly 13740 is not in its unfired position, a distal edge 13849 of the lockout member 13842 engages a distal edge of the loading opening 13214. When in that position, should the user inadvertently attempt to distally advance the firing member 13820, the lockout member 13842 contacts the distal edge of the loading opening 13214 to prevent the distal advancement of the firing member 13820.

Figure 72:
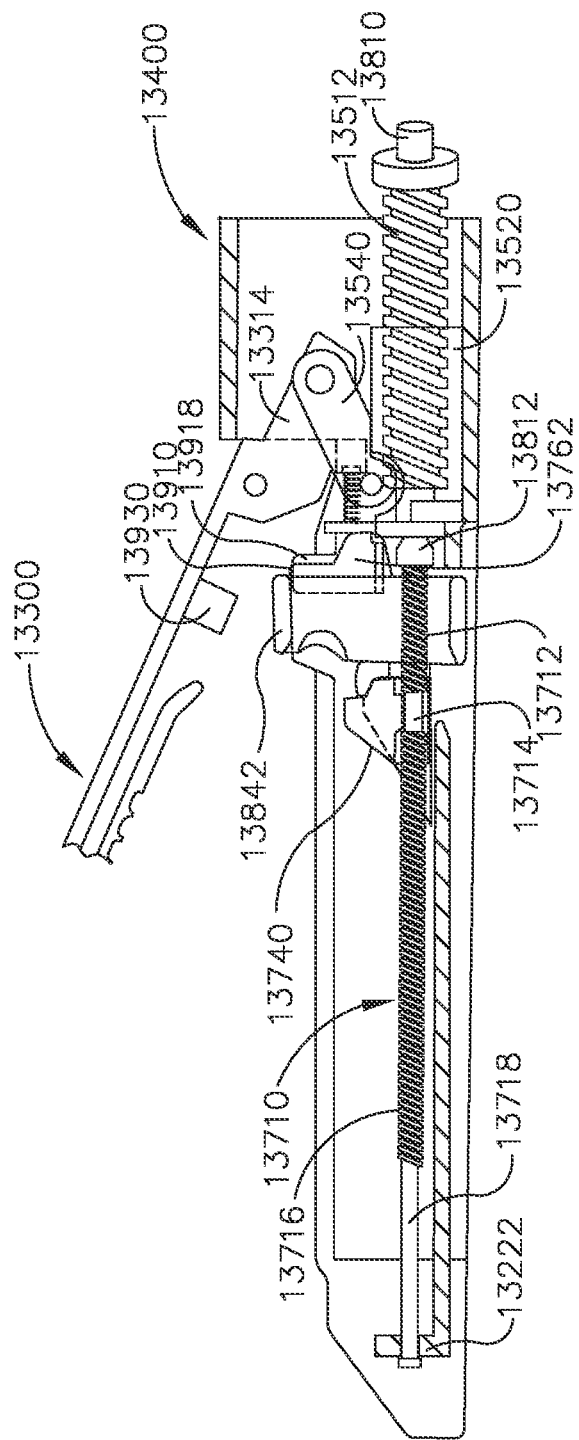
FIG. 72 is another side cross-sectional view of the surgical end effector of FIG. 65 with a surgical staple cartridge operably installed therein and the anvil thereof in an open position.

FIGS. 65 and 67 illustrate insertion of a fresh, unfired staple cartridge 13700 into the end effector 13200. As the user inserts the cartridge 13700 into the channel 13210, the male coupler 13724 is inserted into the female coupler 13812 and the cartridge body 13702 is seated in the channel 13210 as shown in FIG. 72. When in that position, the fin 13762 biases the lockout member 13910 into an unlocked position. The user may then move the anvil 13300 to a closed position by activating the closure drive system 13500 (FIG. 64) to rotate the closure drive shaft 13510 in a first rotary direction to drive the closure shuttle 13520 in a proximal direction PD. Once the closure shuttle 13520 has moved the anvil 13300 to the closed position, the user may then activate the firing system 13800. As can also be seen in FIG. 72, the camming assembly 13740 has pivoted the firing member lockout member 13842 into an unlocked position. As the firing drive shaft 13810 is rotated in a first rotary direction, the proximal threaded segment 13712 of the cartridge firing drive shaft 13710 drives the firing member 13820 distally (distal direction DD). As the firing member 13820 moves distally, the camming assembly 13740 is urged into threaded engagement with the distal thread segment 13716 of the cartridge firing drive shaft 13710. Continued rotation of the cartridge firing drive shaft 13710 causes the firing member 13820 and the camming assembly 13740 to move distally to their respective ending positions. As the camming assembly 13740 is driven distally, the camming portions thereon drive the drivers that are supported in the staple cartridge 13700 toward the closed anvil 13300 such that the staples or fasteners supported thereon are forced through the tissue that is clamped between the anvil 13300 and the cartridge 13700 and into forming contact with the underside of the anvil 13300. The firing member 13820 is proximal to the camming assembly 13740 so that the tissue cutting surface thereon 13824 cuts the clamped tissue after it has been stapled. In various aspects, as the firing member 13820 is distally driven through the surgical staple cartridge 13700, the firing member 13820, through the engagement of the anvil engagement tabs 13828 with the anvil 13300 and the engagement of the channel engagement tabs 13826 with the channel 13210, may serve to maintain a desired amount of tissue gap between the deck surface 13707 on the staple cartridge 13700 and a staple forming undersurface 13302 on the anvil 13300. Once the camming assembly 13740 and firing member 13820 have reached their ending positions, the firing drive shaft 13810 may be rotated in a reverse rotary direction to drive the firing member 13820 and camming assembly 13740 back to their respective starting positions. Once the firing member 13820 has returned to the starting position, the closure drive shaft 13510 may be rotated in a second rotary direction to drive the closure shuttle 13520 in a distal direction DD to pivot the anvil 13300 to the open position (FIG. 72) to enable to the stapled tissue to be unclamped from the end effector 13200. In the example that includes the C-shaped clip(s) 13890, the clips are also driven distally by the camming assembly 13740 and/or firing member 13820 until the clip(s) 13890 reach an ending position wherein the lower leg(s) 13896 thereof are located in an opening (not shown) in the channel bottom 13212 to enable the spent cartridge 13700 to be removed from the elongate channel 13210.

FIGS. 73-80 depict another surgical end effector 14200 that is employed with a surgical instrument 14000 that is very similar to instrument 13000 described above. The surgical end effector 14200 is somewhat similar to end effector 13200 described above, except for the differences discussed below. At least some of the components of surgical instrument 14000 that are identical to the components of surgical instrument 13000 are set forth herein with like element numbers. The surgical end effector 14200 comprises an elongate channel 14210 that is configured to operably support a replaceable surgical staple cartridge 14700 therein. The surgical end effector 14200 further includes an anvil 14300 that is selectively pivotable relative to the elongate channel 14210 between open and closed configurations by the rotary driven closure system 13500 (FIG. 64). As can be seen in FIGS. 73 and 74, the anvil 14300 includes a proximally protruding anvil mounting tab 14310 that is configured to be pivotally coupled to a corresponding portion of an end cap 14400 that is either attached to or comprises a portion of the elongate channel 14210. The anvil mounting tab 14310 is attached to the end cap 14400 by, for example, a rivet 14401 or other pivot arrangements disclosed herein. The end effector 14200 also employs the rotary driven closure system 13500 described above. In one arrangement, for example, the anvil 14300 may be fabricated using various fabricating techniques described in U.S. patent application Ser. No. 16/105,101, entitled METHOD FOR FABRICATING SURGICAL STAPLER ANVILS, the entire disclosure of which is hereby incorporated by reference herein.

As was discussed above, the rotary driven closure system 13500 comprises an axially movable closure shuttle 13520 that is threaded onto a threaded distal closure shaft segment 13512 that is configured to be drivingly coupled the closure drive shaft 13510 (FIG. 64). In the illustrated arrangement, the closure shuttle 13520 comprises a shuttle base portion 13522 that extends through a proximal cap slot (not shown) that is formed in the bottom of the end cap 14400. A lateral flange (not shown) extends laterally from each side of the shuttle base portion 13522 to slidably engage the bottom of the end cap 14400 in the various manners disclosed herein.

In the illustrated example, the axial movement of the closure shuttle 13520 is transferred to the anvil 14300 by a pivoting closure link assembly 13530. In one arrangement, the closure link assembly 13530 includes a pair of pivot arms 13540 (only one can be seen in FIGS. 73 and 74) that are each pivotally attached to a proximal end portion 14314 of the anvil mounting tab 14310 and suspended therefrom. Each pivot arm 13540 comprises a free end 13542 that includes a notch 13544 that is configured to drivingly engage a corresponding drive groove 13526 in the closure shuttle base portion 13522. When the closure shuttle 13520 is driven in the distal direction DD, the pivot arms 13540, by virtue of their engagement with the closure shuttle 13520, apply a pivotal opening motion to the anvil mounting tab 14310 to pivot the anvil 14300 to an open position (FIG. 73). When the closure shuttle 13520 is axially moved in a proximal direction PD, the pivot arms 13540 pivot in a second direction which causes a pivot closure motion to be applied to the anvil mounting tab 13310 to pivot the anvil 13300 to a closed position (FIG. 80).

Unlike the surgical end effector 13200 wherein the firing member 13820 is contained within the replaceable surgical staple cartridge 13700, the surgical end effector 14200 employs a dedicated firing member 14820 that is permanently journaled on the rotary firing drive shaft 13810. In the illustrated example, the rotary firing drive shaft 13810 and the threaded distal closure shaft segment 13512 are rotatably supported in the elongate channel 14210. As will be discussed in further detail below, a portion of the rotary firing drive shaft 13810 that is distal to the threaded distal closure shaft segment 13512 includes a proximal threaded segment 13811, an unthreaded segment 13815, and a distal threaded segment 13817.

Figure 75:
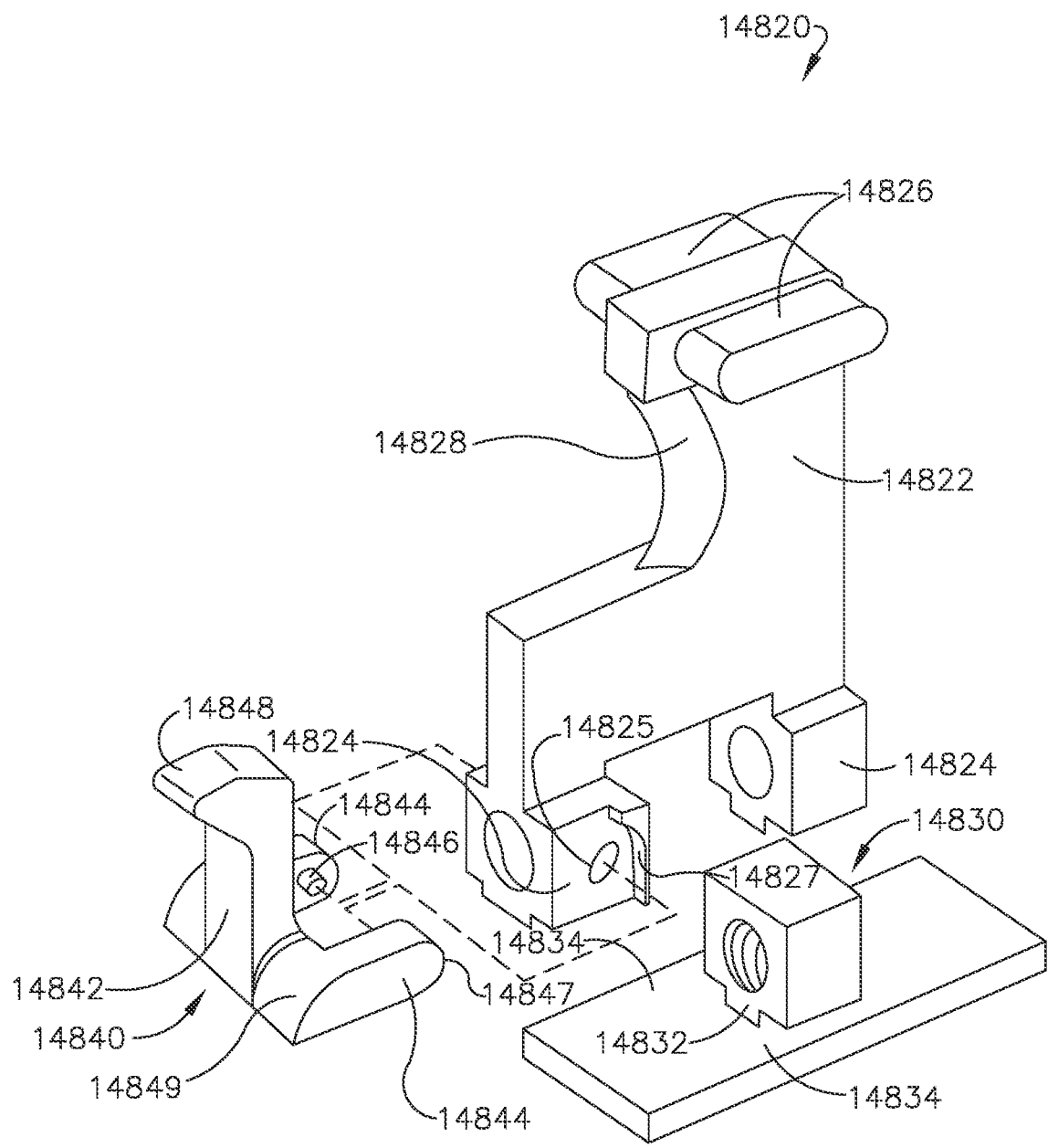
FIG. 75 is an exploded assembly view of a firing member and firing member lockout feature of the surgical end effector of FIG. 73.

FIG. 75 illustrates one form of a firing member 14820 that may be employed with the end effector 14200. As can be seen in FIG. 75, the firing member 14820 comprises a body portion 14822 that includes two downwardly extending hollow mounting portions 14824 that are unthreaded and spaced from each other to receive a threaded drive nut 14830 therebetween. The threaded drive nut 14830 is configured to threadably engage the threaded segments 13811, 13817 of the rotary firing drive shaft 13810. The drive nut 14830 includes a vertical tab portion 14832 that is sized to extend through an axial slot 14216 in the bottom of the elongate channel 14210. Two laterally extending retention flanges 14834 are formed on the threaded drive nut 14830 and are configured to engage the bottom of the elongate channel 14210. In addition, two laterally extending anvil engagement tabs 14826 are formed on the top of the firing member body 14822 and are configured to engage the anvil 14300 as the firing member 14820 is axially moved within the end effector 14200. A tissue cutting surface 14828 is formed or attached to the firing member body 14822.

In this arrangement, the firing member 14820 includes a firing member lockout feature 14840 that is configured to prevent the distal advancement of the firing member 14820 from its starting position unless a fresh unfired staple cartridge has been properly seated in the elongate channel 14210. As can be seen in FIG. 75, in one example, the firing member lockout feature 14840 comprises a lockout body 14842 that has two spaced attachment legs 14844 protruding therefrom that extend around the mounting portions 14824 of the firing member body 14822. Each attachment leg 14844 includes an inwardly extending pivot pin 14846 that is adapted to be pivotally received in a corresponding slotted opening 14825 provided in the mounting portions 14824. The lockout feature 14840 further includes a sled latch 14848 that is configured for contact with a camming sled or assembly 14740 (FIG. 77) operably supported in a staple cartridge 14700.

Figure 77:
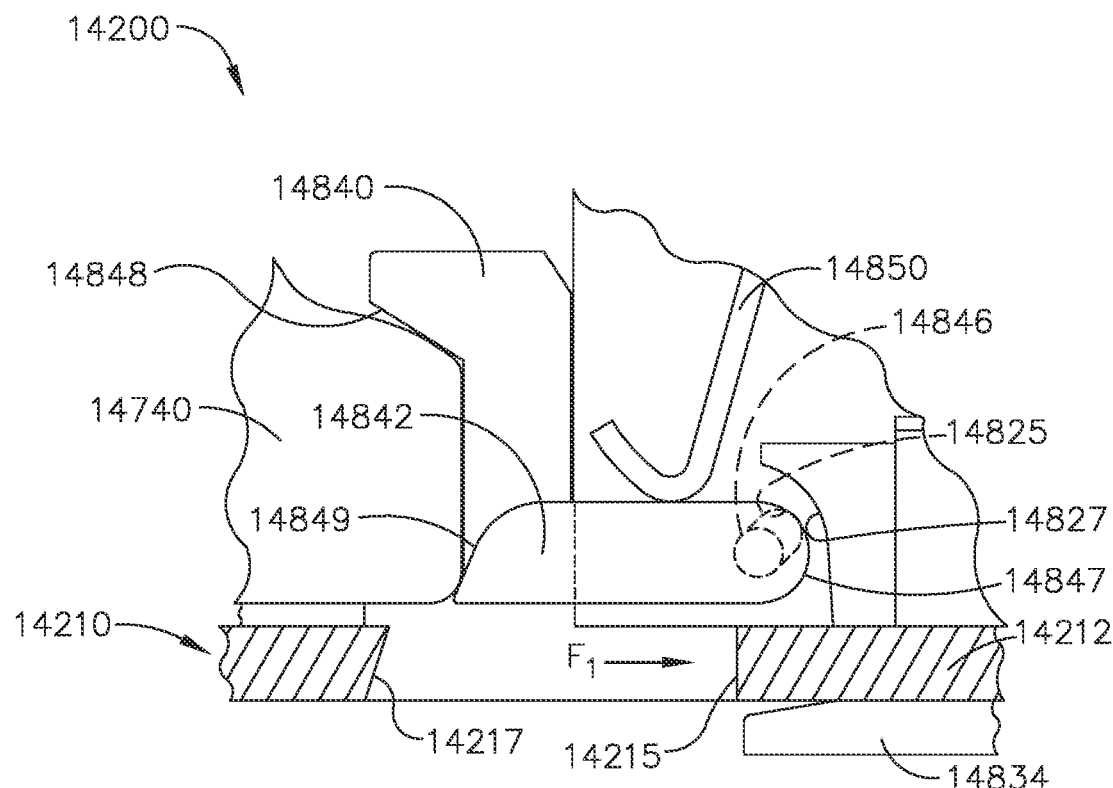
FIG. 77 is another enlarged view of a portion of the firing member lockout feature of FIG. 76 in a locked position prior to installation of a surgical staple cartridge into the elongate channel of the surgical end effector of FIG. 73.
Figure 76:
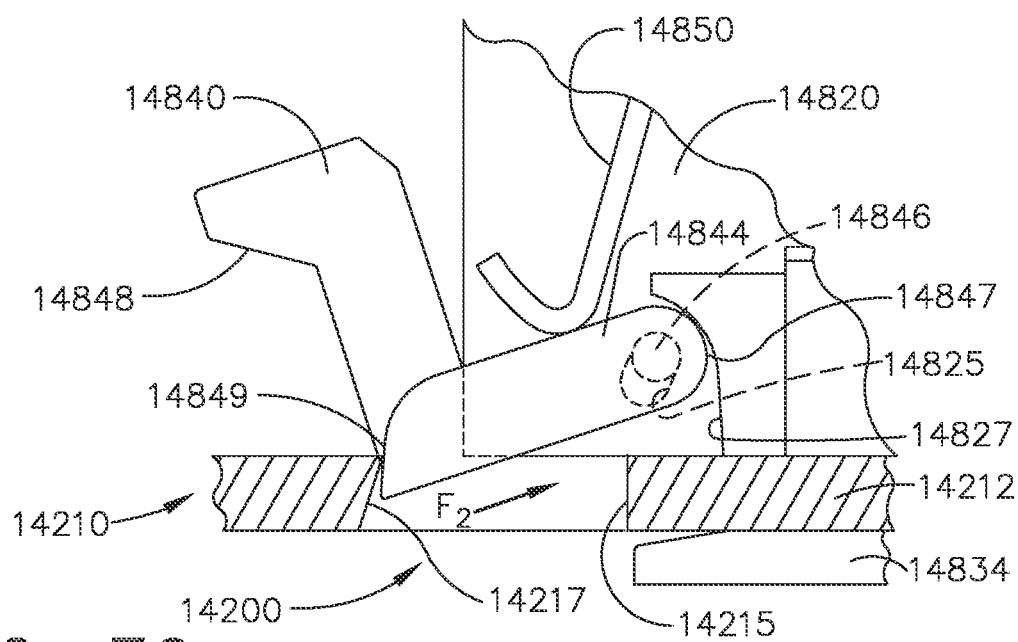
FIG. 76 is an enlarged view of a portion of the firing member lockout feature of FIG. 75 in engagement with a portion of a surgical staple cartridge installed in an elongate channel of the surgical end effector of FIG. 73.

FIGS. 76 and 77 illustrate the firing member 14820 in a proximal-most starting position. As can be seen in FIGS. 76 and 77, a firing lockout hole 14215 is provided through the bottom of the elongate channel 14210. A lockout spring 14850 is mounted in the elongate channel 14210 and is configured to bias the lockout feature 14840 downward such that, if a fresh unfired staple cartridge has not been properly loaded into the elongate channel 14210, a distal edge 14849 of the lockout body 14842 engages the angled distal edge 14217 of the firing lockout hole 14215. When in that position, should the user inadvertently attempt to distally advance the firing member 14820, the lockout feature 14840 prevents the distal advancement of the firing member 14820. As noted in FIG. 76, under high force "$F_2$" the pins 14846 slide up their respective slot 14825. As the pins 14846 slide up their respective slots 14825, the proximal ends 14847 of the attachment legs 14844 engage a corresponding backstop wall 14827 that is formed on the mounting portions 14824 of the firing member body 14822 to reduce stress placed on the pivot pins 14846. See FIG. 76.

Figure 78:
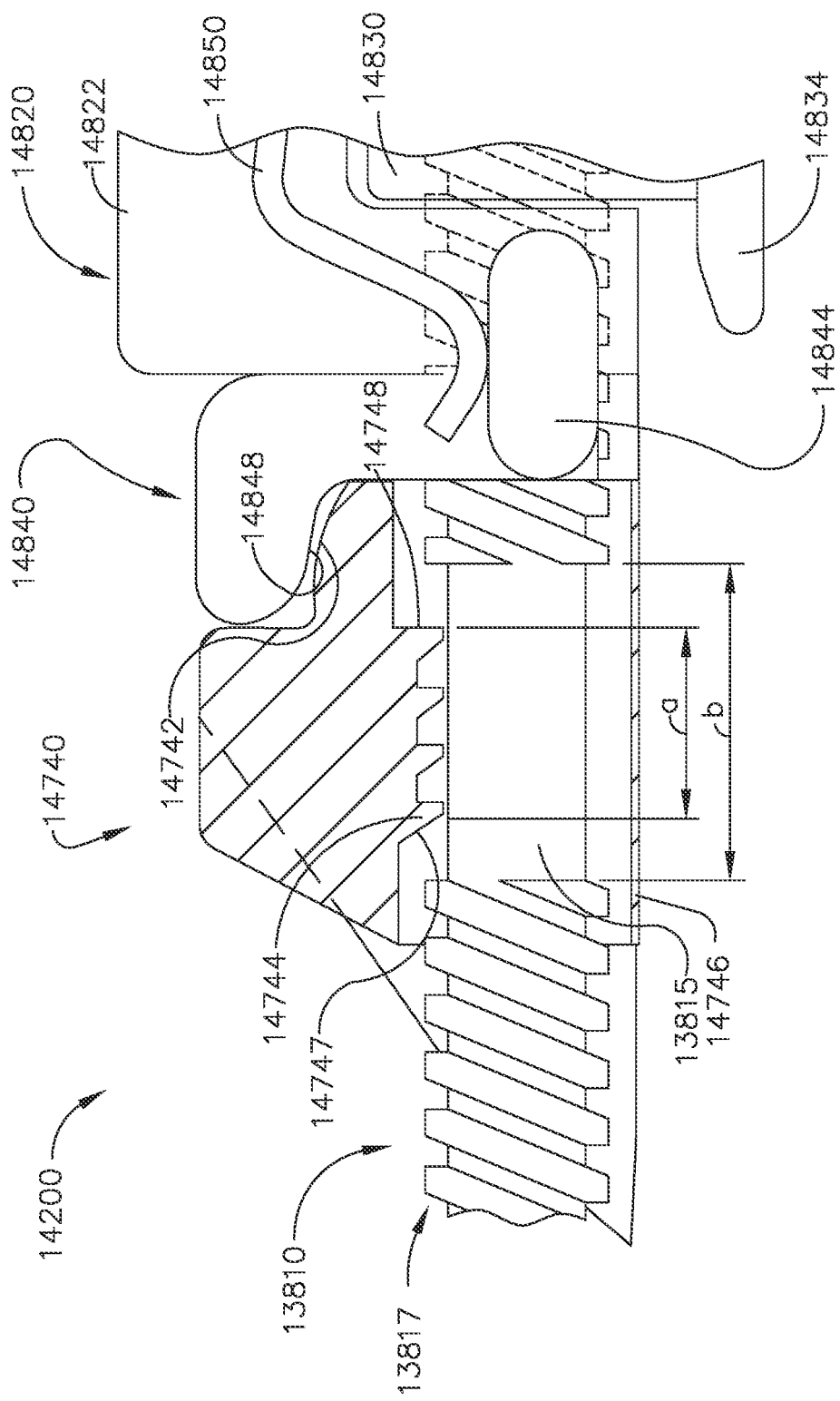
FIG. 78 is a cross-sectional view of a portion of the surgical end effector of FIG. 73 and a camming assembly of a surgical staple cartridge installed in the end effector.

A fresh, unfired surgical staple cartridge 14700 contains a camming assembly 14740 that is located in a starting position that is proximal to the lines of staple drivers that are supported in the cartridge body. As used herein, the terms "fresh, unfired" means that the staple cartridge has all of its intended staples or fasteners in their respective unfired positions and the camming assembly is in a proximal unfired starting position. When a fresh, unfired surgical staple cartridge 14700 has been properly seated within the elongate channel 14210, a proximally extending unlocking portion 14742 on the camming assembly 14740 engages the sled latch 14848 on the lockout feature 14840 to pivot the lockout feature 14840 into an unlocked position wherein the lockout feature 14840 does not extend into the firing lockout hole 14215 in the elongate channel. FIG. 78 illustrates a camming assembly 14740 in the starting position. The remaining portions of the surgical staple cartridge 14700 have been omitted for clarity. As can be seen in FIG. 78, the camming assembly 14740 includes a segment of internal threads 14744 that has a length "a" that is less than the axial length "b" of the unthreaded portion 13815 on the rotary firing drive shaft 13810. The bottom 14746 of the camming assembly 14740 is open to enable the camming assembly 14740 to snap over the rotary firing drive shaft 13810 when the cartridge 14700 is seated in the elongate channel 14210.

In one example, the internal threads 14744 in the camming assembly 14740 are configured to only drive the camming assembly 14740 in the distal direction. For example, the internal threads 14744 may have a leading portion 14747 that is configured to facilitate threaded engagement with the threaded segment 13817 on the firing drive shaft 13810. However, the internal threads 14744 may have a trailing portion 14748 that is configured to prevent threaded engagement with the threads 13817 when the camming assembly 14740 has been driven to its ending position and the firing drive shaft 13810 is rotated in an opposite direction to drive the firing member 14820 back to the starting position. In FIGS. 79 and 80, the ending position of the camming assembly 14740 is illustrated in phantom lines. As can be seen in FIGS. 79 and 80, a distal portion 13819 of the firing drive shaft 13810 is devoid of threads.

When the camming assembly 14740 has been distally driven into its ending position, the internal threads 14744 disengage the threaded segment 13817 of the firing drive shaft 13810. When the firing drive shaft 13810 is rotated in the opposite direction, the internal threads 14744 are designed to slip and not re-engage the threaded segment 13817 such that the camming assembly 14740 remains in the ending position within the staple cartridge 14700 as the firing member 14820 is retracted back to the starting position. Thus, once a staple cartridge 14700 has been spent (e.g., completely fired) the camming assembly 14740 is not returned to its starting position. Thus, if the spent cartridge were to be inadvertently re-installed in the end effector 14200, the camming assembly 14740 is not in position to unlock the lockout feature 14840. This condition may be assisted by interference with fallen staple drivers located within the cartridge body after the cartridge was fired. In addition, the internal threads 14744 may have a pitch diameter that is larger than a pitch diameter of the threads 13817 on the firing drive shaft 13810 to facilitate some "play" therebetween which may permit the firing member 14820 to make contact with the camming assembly 14740 as they are driven distally. Such arrangement may facilitate some movement of the camming assembly 14740 when the cartridge body 14702 is installed in the elongate channel 14210 while still establishing threaded driving contact with the threaded segment 13817 of the firing drive shaft 13810.

The end effector 14200 as depicted also includes an anvil lockout assembly 13900 that is configured to prevent the closure of the anvil 14300 unless a staple cartridge 14700 has been properly seated therein. Operation of the anvil lockout member 13910 was described above and will not be repeated for the sake of brevity.

FIG. 73 illustrates the surgical end effector 14200 without a surgical staple cartridge installed therein and with the anvil 14300 in a fully open position. As can be seen in FIG. 73, the closure shuttle 13520 is in its distal-most position. As can be further seen in FIG. 73, the vertically extending lock tab 13918 of the anvil lockout member 13910 is aligned with the anvil lockout protrusion 14930 that is formed on the anvil 14300. FIG. 74 illustrates that the anvil 14300 cannot be closed during the inadvertent actuation of the closure drive system. In FIG. 73, the closure shuttle 13520 has moved proximally from its starting position, but the anvil 14300 is prevented from closing due to the contact between the lock tab 13918 and the lockout protrusion 14930. As can also be seen in FIGS. 73 and 74, the firing member lockout feature 14840 is biased into the locked position wherein the lockout feature 14840 is aligned to contact the elongate channel bottom 14212. In the event that the user inadvertently actuates the firing drive system, the lockout feature 14840 will contact the bottom 14212 of the elongate channel 14210 to prevent the distal advancement of the firing member 14820.

FIG. 79 illustrates the end effector 14200 after a fresh, unfired surgical staple cartridge 14700 has been installed therein. As can be seen in that Figure, the camming assembly 14740 within the cartridge body 14702 is in a proximal-most, starting position wherein the unlocking portion 14742 on the camming assembly 14740 is in engagement with the sled latch 14848 on the lockout feature 14840. This contact between the unlocking portion 14742 and the sled latch 14848 moves the lockout feature 14840 into the unlocked position. As can also be seen in FIG. 79, a proximally extending fin 14762 on the cartridge body 14702 has biased the lockout member 13910 proximally from the locked position to the unlocked position to thereby permit the anvil 14300 to be closed. As was discussed above, the length a of the internal thread segment 14744 in the camming assembly 14740 is less than the length b of the unthreaded segment 13815 on the firing drive shaft 13810. In addition, a length "c" of the threads within the threaded firing nut 14830 is greater than the length b of the unthreaded segment 13815 on the firing drive shaft 13810. Thus: $a<b<c$.

FIG. 80 illustrates the surgical end effector 14200 of FIG. 79 with the anvil 14300 in the fully closed position. As can be seen in FIG. 80, the distal closure shaft segment 13512 has been rotated in the first rotary direction to cause the closure shuttle 13520 to move axially to its proximal-most position to thereby cause the closure link assembly 13530 to pivot the anvil 14300 to its fully closed position. As can be seen in FIG. 80, when the anvil 14300 is in the fully closed position, the pivot arms 13540 are nearly vertical relative to the drive shaft axis DSA. Such configuration results in the application of a maximum closure moment to the anvil (e.g., moment arm angle MA is approximately 90°). As can be further seen in FIG. 80, the anvil engagement features 14826 are aligned with corresponding elongate passages 14301 that are formed on each lateral side of the anvil slot to permit axial travel therein as the firing member 14820 is distally advanced from its starting position to ending position. To distally advance the firing member 14820, the user activates the firing drive system 13800 (FIG. 64) to rotate the firing drive shaft 13810 in a first rotary direction. As the firing member 14820 is driven distally, the firing member 14820 advances the camming assembly 14740 on the unthreaded segment 13815 until the segment of internal threads 14744 threadably engage the threaded segment 13817. Once threads 14744 are in threaded engagement with the threaded segment 13817, rotation of the drive shaft 13810 causes the camming assembly 14740 to continue to move distally. As the camming assembly 14740 moves distally, the camming surfaces thereon drive the staple drivers that are stored in the cartridge 14700 upward. The upward movement of the staple drivers causes the staples or fasteners supported thereon to pierce through the tissue that is clamped between the anvil 14300 and the cartridge 14700 and into forming contact with the staple forming underside 14303 of the anvil 14300. As the firing member 14820 is driven distally, the tissue cutting surface 14828 cuts through the clamped tissue after the fasteners have been formed in the tissue. The firing drive shaft 13810 continues to be rotated until the firing member 14820 has reached its ending position at which time, a sensor or sensors may stop the firing motor 13802 from rotating in the first direction. An instrument controller may then cause the firing motor 13802 to rotate in an opposite direction to retract the firing member 14820 back to its starting position or the controller may require the user to initiate a retraction rotation. In either event, the camming assembly 14740 remains in the distal end of the cartridge 14700. The user may then remove the spent cartridge from the end effector and discard it. Because the camming assembly 14740 remains in the distal end of the spent cartridge, should the spent cartridge be inadvertently mistaken for a fresh unfired cartridge and reloaded into the end effector, the lockout feature 14840 will remain in the locked position to prevent inadvertent firing of the firing member. As can be seen in FIG. 80, the axial length "e" of laterally extending retention flanges 14834 of the firing member 14820 is longer than the axial length "d" of the firing lockout hole 14215 in the bottom 14212 of the channel 14210. In addition, an installation hole 14213 is provided through a distal portion of the cartridge bottom 4212 to facilitate installation of the firing member 14820 therethrough. Thus, the axial length "f" of the installation hole 14213 is greater than the axial length "e" of laterally extending retention flanges 14834 of the firing member 14820. Thus: d<e<f.

Figure 81:
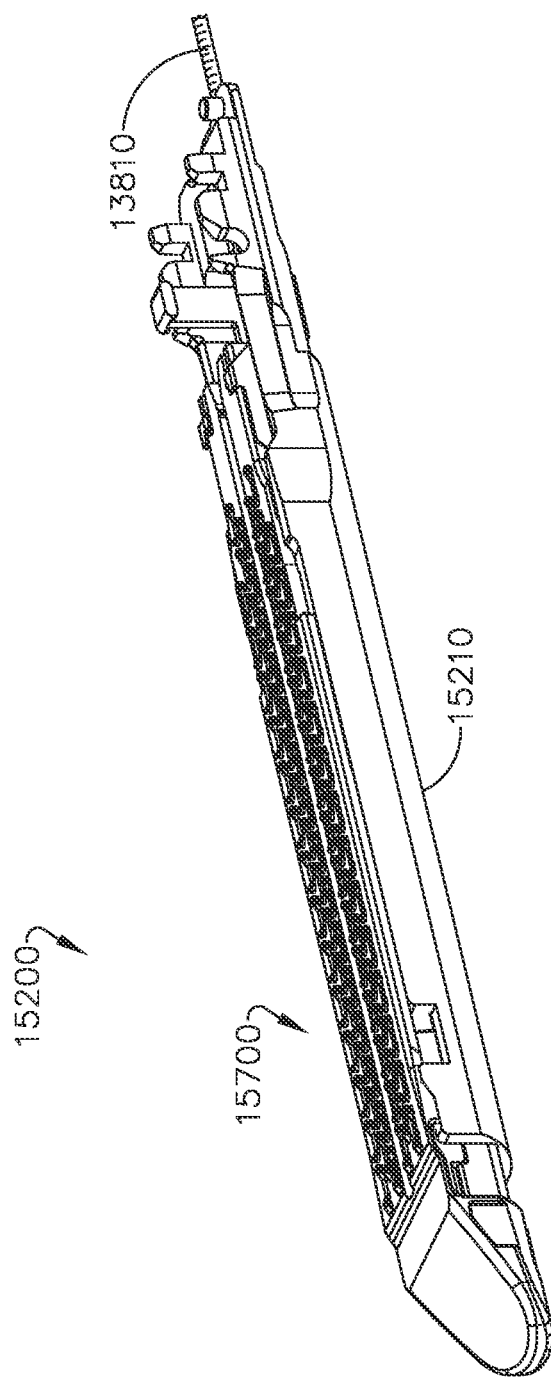
FIG. 81 is a perspective view of a portion of another surgical end effector with a surgical staple cartridge installed therein.

FIG. 81 illustrates a portion of another surgical end effector 15200 with the anvil thereof omitted for clarity. The surgical end effector 15200 includes a two piece firing member 15820 that is axially driven between a starting position and an ending position within the end effector 15200. The end effector 15200 may employ a rotary closure shuttle 13520 that is axially driven by a closure drive shaft 13510 for applying opening and closing motions to the anvil. As was described above, the closure shuttle 13520 is supported for axial travel within the end cap 14400 as shown in FIGS. 82 and 83. See e.g., FIGS. 64 and 65 for further details concerning the opening and closing of the anvil. In addition, the two piece firing member 15820 is axially driven by a rotary firing drive shaft 13810 that extends through a distal closure drive shaft segment in the various manners disclosed herein.

As can be seen in FIG. 82, the firing member 15820 comprises a body portion 15822 that includes two downwardly extending hollow mounting portions 15824 that are unthreaded and spaced from each other to receive a threaded drive nut 15830 therebetween. The threaded drive nut 15830 is configured to threadably engage the threaded rotary firing drive shaft 13810. The drive nut 15830 includes a vertical tab portion (not shown) that is sized to extend through an axial slot (not shown) in the bottom of an elongate channel 15210 of the surgical end effector 15200. Two laterally extending retention flanges 15834 are formed on the threaded drive nut 15830 and are configured to engage the bottom of the elongate channel 15210. In addition, two laterally extending anvil engagement tabs 15826 are formed on the top of the firing member body 15822 and are configured to engage the anvil as the firing member 15820 is axially moved within the end effector 15200. In the illustrated example, the firing member 15820 is configured to operably interface with a camming assembly 15740 that has an onboard tissue cutting knife 15743 thereon. See FIGS. 87 and 89. In alternative arrangements, a tissue cutting surface is formed or attached to the body member 15822.

Figure 87:
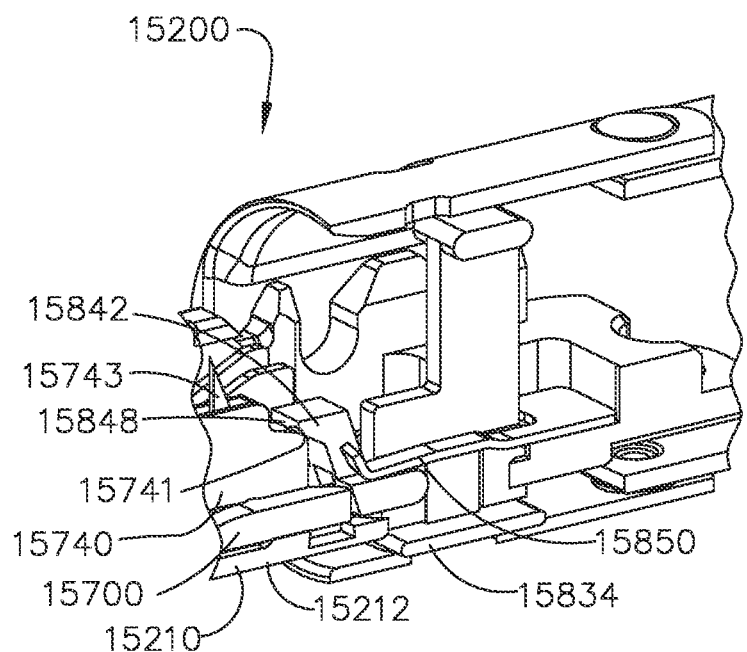
FIG. 87 is another partial perspective view of the surgical end effector of FIG. 86 with a portion of the cartridge removed to enable the firing lockout member to be viewed in engagement with the camming assembly of the cartridge.
Figure 89:
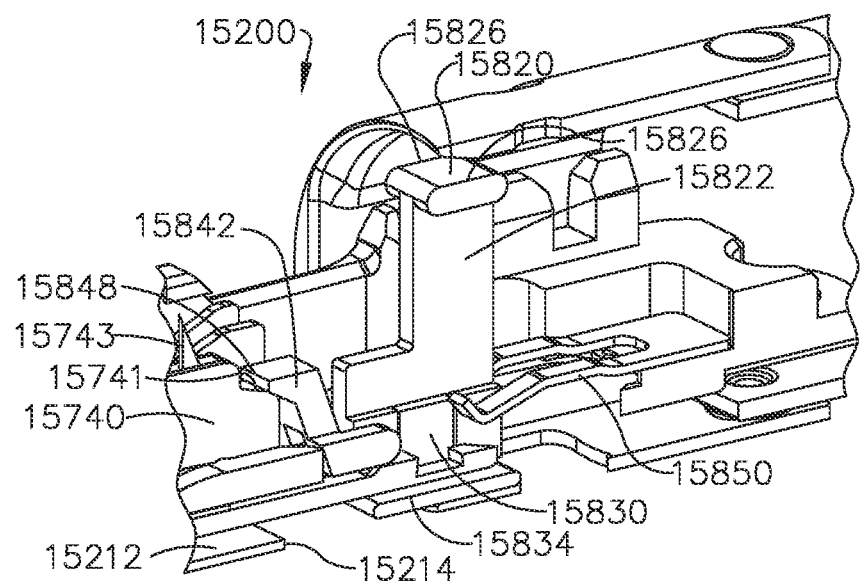
FIG. 89 is another partial perspective view of the surgical end effector of FIG. 86 with a portion of the cartridge omitted to enable the firing lockout member to be viewed in engagement with the camming assembly of the cartridge.

As can also be seen in FIG. 82, the firing member 15820 may also be equipped with an onboard firing member lockout assembly 15840 that comprises a lockout member 15842 that is pivotally coupled to the firing member body 15822. The lockout member 15842 includes a sled latch 15848 that is configured to be engaged by the camming assembly 15740 when the camming assembly 15740 is in an unfired position. As can be seen in FIGS. 87 and 89, the camming assembly 15740 includes a firing member ledge 15741 configured to engage the sled latch 15848 on the lockout member 15482. A lockout spring 15850 is mounted in the elongate channel 15210 and is configured to bias the lockout member 15842 downward such that if the camming assembly 15740 is not in its unfired position, a distal edge 15849 engages a distal edge of a lockout cavity 15214 in a bottom 15212 of the channel 15210. When in that position, should the user inadvertently attempt to distally advance the firing member 15820, the lockout member 15842 contacts the distal edge of the lockout cavity 15214 to prevent the distal advancement of the firing member 15820.

Figure 84:
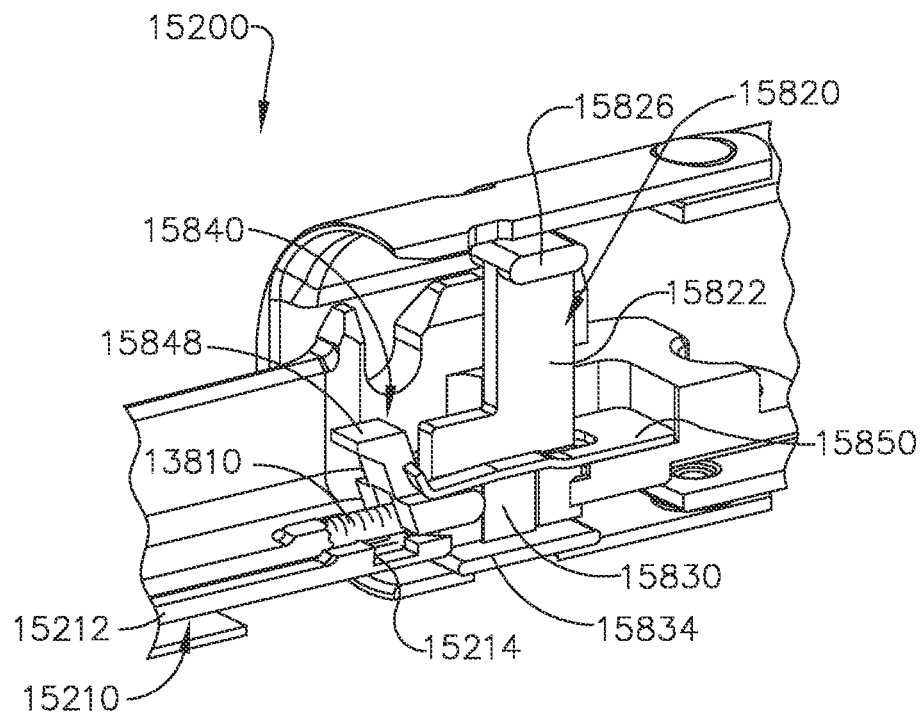
FIG. 84 is a partial perspective view of the surgical end effector of FIG. 81 prior to installing a staple cartridge therein.
Figure 85:
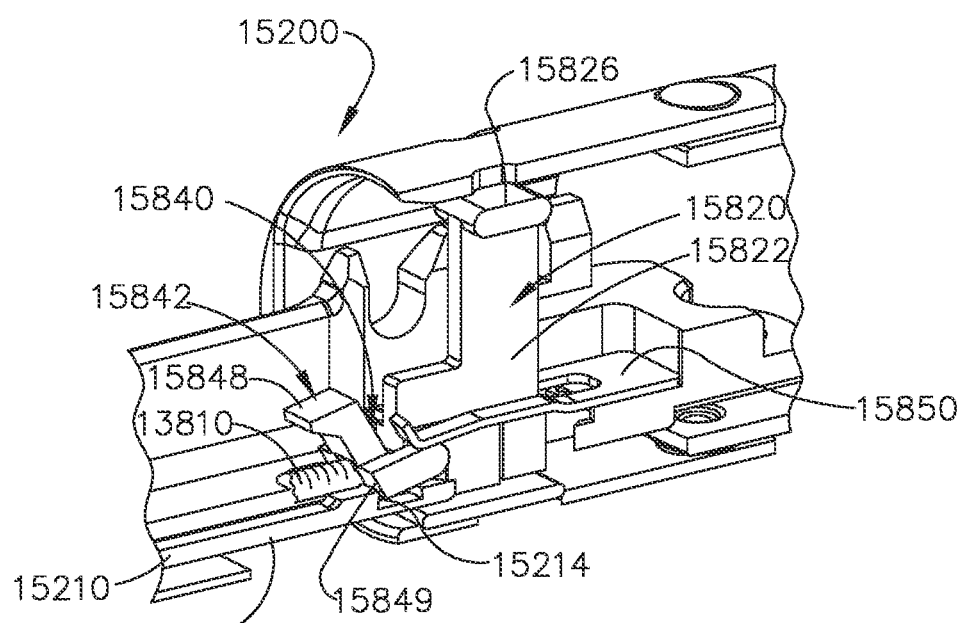
FIG. 85 is another partial perspective view of the surgical end effector of FIG. 84 with a firing lockout member thereof in a locked position because no cartridge has been installed in the end effector.
Figure 86:
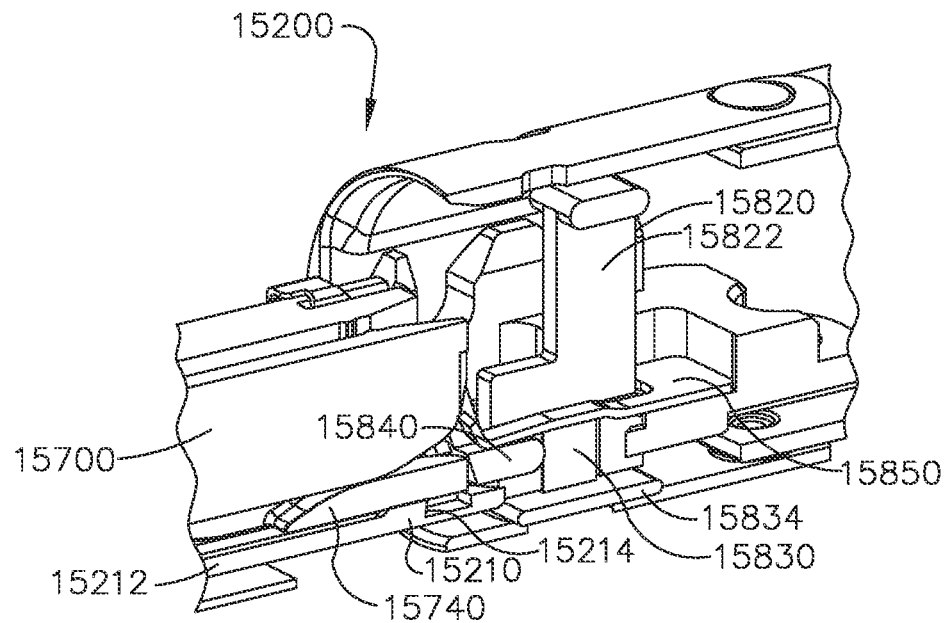
FIG. 86 is another partial perspective view of the surgical end effector of FIG. 84 with a cartridge installed therein.
Figure 88:
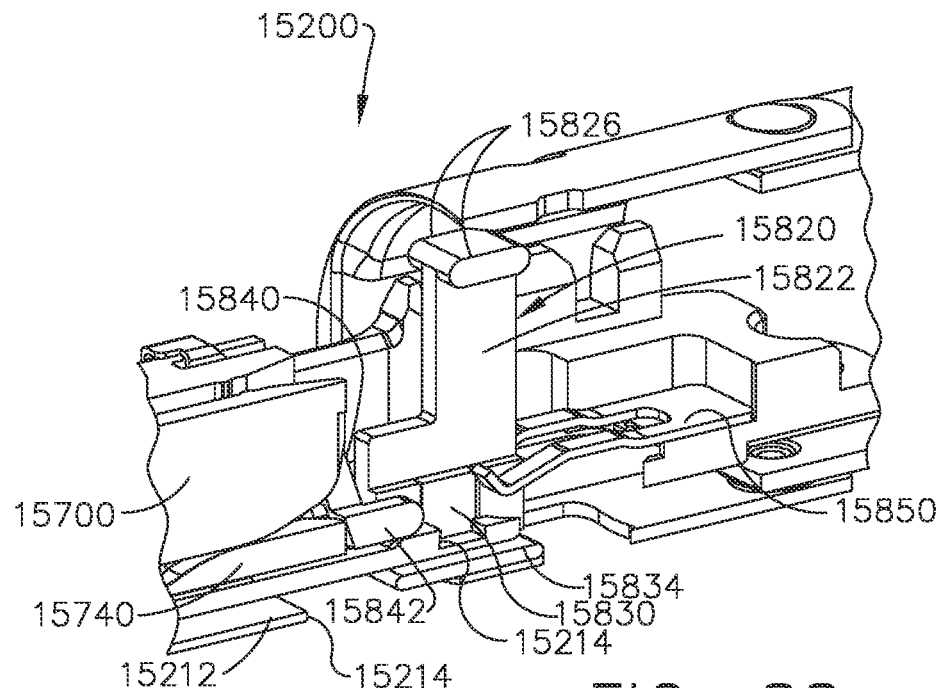
FIG. 88 is another partial perspective view of the surgical end effector of FIG. 86 with a cartridge installed therein and a firing member of the surgical end effector moved distally forward.

FIG. 84 illustrates the end effector 15200 prior to installation of a surgical staple cartridge 15700 (FIG. 81) therein. As can be seen in FIG. 84, the firing member 15820 is in its proximal-most starting position. FIG. 85 illustrates what happens if the firing member 15820 is inadvertently distally advanced when no cartridge is present. As can be seen in FIG. 85, the lockout member 15842 has been biased downward by spring 15850 such that the distal end surface 15849 of the lockout member 15842 has contacted the distal edge of the lockout cavity 15214 in the channel 15210 to prevent further distal advancement of the firing member 15820. FIGS. 86 and 87 illustrate the end effector 15200 with an unfired surgical staple cartridge 15700 operably loaded in the elongate channel 15210. As can be seen in FIG. 89, the firing member ledge 15741 on the camming assembly 15740 is in unlocking engagement with the sled latch 15848 on the lockout member 15482 which lifts the firing member 15820 out of locking engagement with the lockout cavity 15214. FIGS. 88 and 89 illustrate the position of the firing member 15820 after the firing process has been commenced and the firing member 15820 has started to move in the distal direction.

Figure 90:
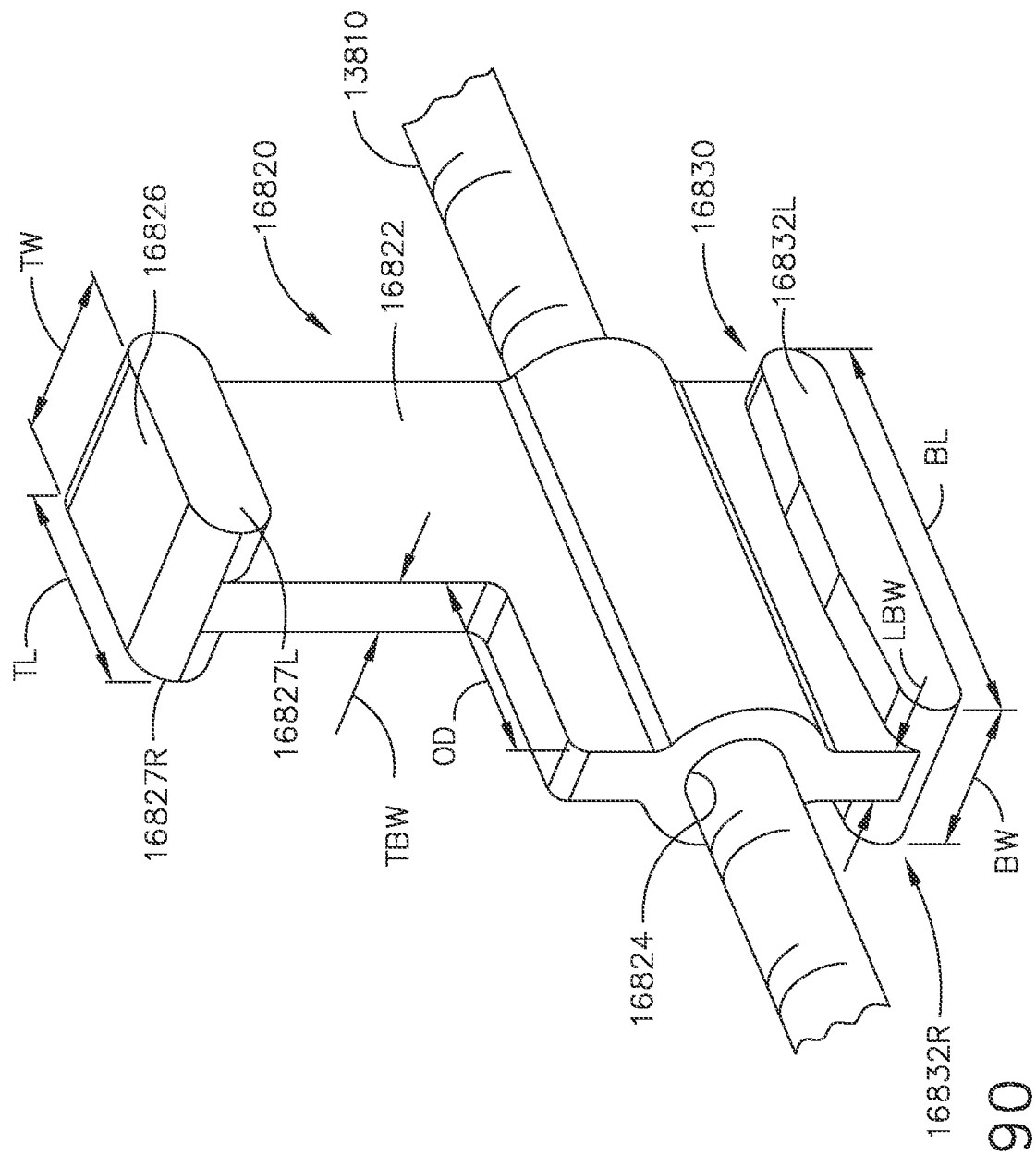
FIG. 90 is a perspective view of another firing member threadably engaged with a rotary firing drive shaft of a surgical end effector.

FIG. 90 illustrates an alternative firing member 16820 that may be used in connection with the end effector 15200 described above, as well as with various other end effector arrangements disclosed herein. As can be seen in FIG. 90, the firing member 16820 comprises a body portion 16822 that includes an axially extending threaded passage 16824 that is adapted to be threadably engaged by the firing drive shaft 13810 in the various manners disclosed herein for example. During the firing process, the firing member body 16822 is configured to extend through an axial slot in a surgical staple cartridge that has been installed in the elongate channel of the end effector. The axial slot in the staple cartridge is vertically aligned with an axial slot in the bottom of the elongate channel 15210 to enable a bottom portion of the firing member body 16822 to extend therethrough during the firing process. A bottom channel engagement member or base 16830 is attached to or formed on the firing member body 18622 as shown in FIG. 90. The base 16830 is configured to slidably engage the bottom of the channel during firing. In addition, a top anvil engagement member 16826 is formed on or attached to the top portion of the firing member body 16822.

Still referring to FIG. 90, in one aspect, the base 16830 comprises a left flange assembly 16832L that protrudes laterally from a left side of the firing member body 16822 and a right flange assembly 16832R that protrudes laterally from a right side of the firing member body 16822. The base 16830 has a base width BW that is greater than the width LBW of the lower portion of the firing member body 16822. In one aspect, the lower body width LBW is less that the widths of the axial slots in the surgical staple cartridge and elongate channel and the base width BW is greater than the widths of the axial slots in the surgical staple cartridge and the elongate channel. The top anvil engagement member 16826 comprises a left top flange assembly 16827L that protrudes laterally from a left side of the firing member body 16822 and a right top flange assembly 16827R that protrudes laterally from a right side of the firing member body 16822. The top anvil engagement member 16826 has a width TW that is greater than the width TBW of the upper portion of the firing member body 16822. In one aspect, the top body width TBW is less that the width of an axial slot in the anvil to enable the top portion of the firing member body 16822 to slidably pass therethrough, while the width TW of the top anvil engagement member 16826 is greater than the width of the anvil slot.

Figure 91:
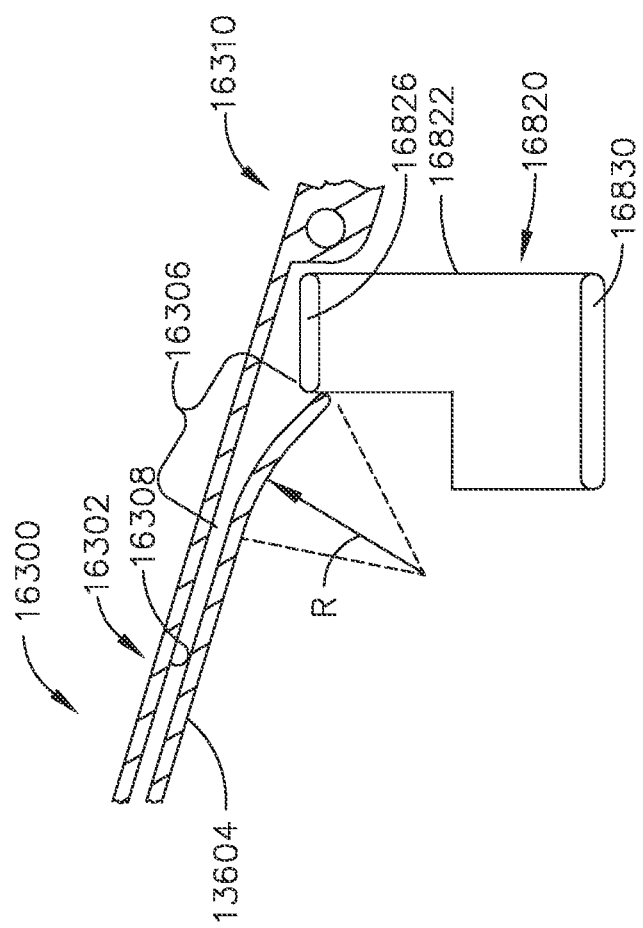
FIG. 91 is a side elevational view of the firing member of FIG. 90 in relation to an anvil of a surgical end effector with the anvil in an open position and shown in cross-section.

FIG. 91 illustrates the firing member 16820 and an anvil 16300 which may be identical to many of the anvil configurations disclosed herein except for the differences noted below. As can be seen in FIG. 91, the anvil 16300 comprises an elongate anvil body 16302 and an anvil mounting portion 16310. The elongate anvil body portion 16302 comprises an elongate anvil slot (not shown) that is configured to accommodate the axial passage of the top anvil engagement member 16826 of the firing member body 16822 therethrough. The anvil body 16302 further includes an axially extending ledge 16304 that defines an axial flange passage 16308 on each side of the anvil slot for accommodating the corresponding right top flange 16827R and left top flange 16827L therein. In the example illustrated in FIG. 91, a proximal portion 16306 of the ledge 16304 is formed with a radial or gradual slope as shown. FIG. 91 also illustrates the firing member 16820 in a position wherein the top anvil engagement member 16826 is ready to ride on the proximal portion 16306 of the ledge 16304 and commence the application of a closing motion to the anvil 16300. In this example, the proximal portion 16306 of the ledge 16304 is arcuate or gradually sloped to facilitate easy transition of the top anvil engagement member 16826 onto the ledge 16304. In one example, the slope may be from approximately 0°-8°. This may reduce the amount of friction and binding forces that may occur between the firing member 16820 and the anvil 16300 during initial closure of the anvil 16300. As the firing member 16820 enters the flange passage 16308 in the anvil body 16302, the firing member body 16820 may tip slightly (tip angle TA—See FIG. 92) relative to a reference axis RA that is perpendicular to the channel bottom 15212. The distal ends of the bottom flanges 16832R, 16832L are radiused to assist in such transition. In addition, by having the top anvil engagement member 16826 proximally axially offset by an offset distance OD and/or by making the axial length TL of the top anvil engagement member 16826 less than the axial base length BL, the amount of binding between the top anvil engagement member 16826 and the proximal portion 16306 of the ledge 16304 may be reduced. Of course, all of the friction and binding forces that are created during this process generally add to the amount of the closure forces that must be applied to the firing member 16820 to close the anvil 16300.

Figure 93:
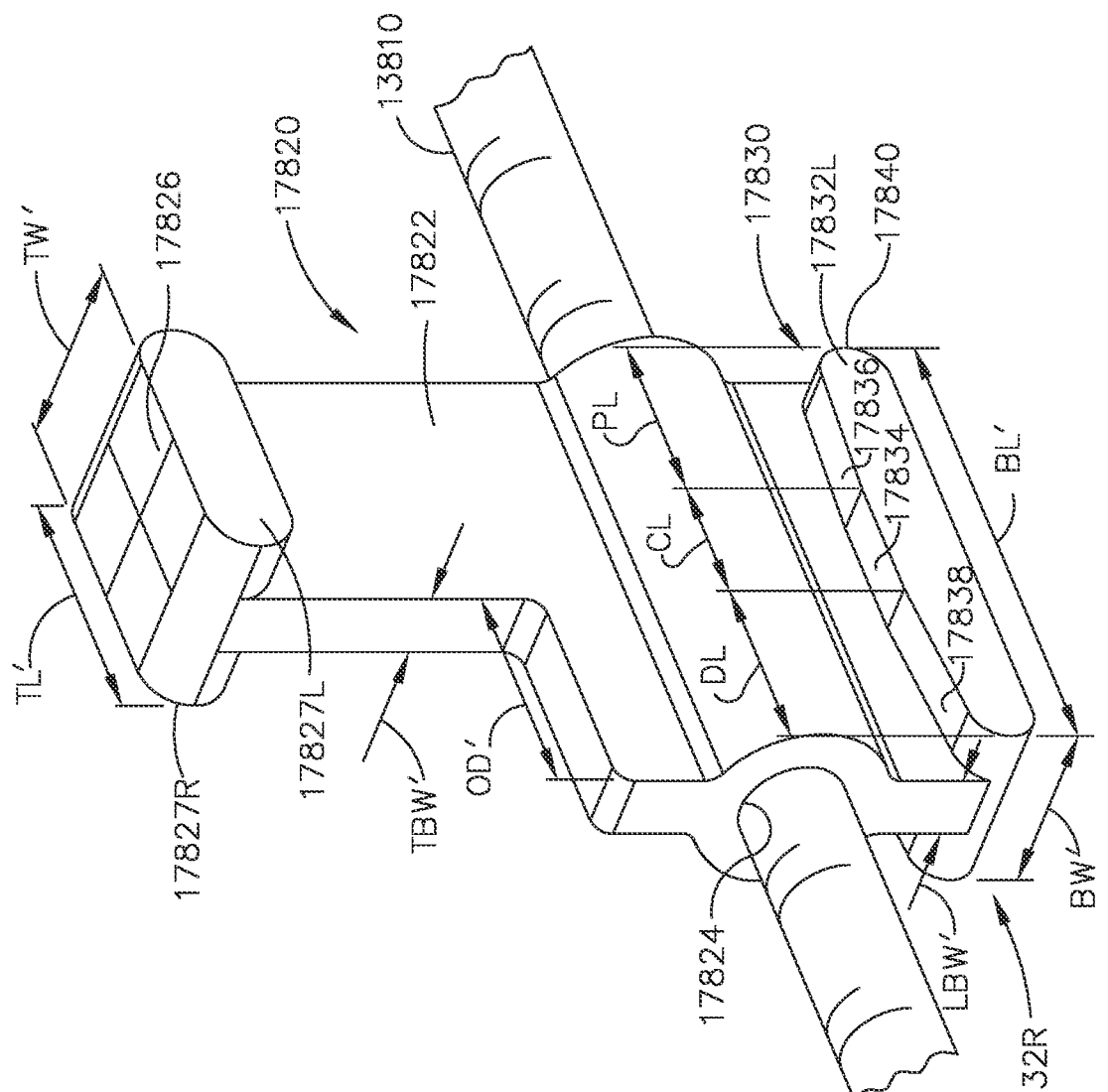
FIG. 93 is a perspective view of another firing member in threaded engagement with a rotary firing drive shaft of a surgical end effector.

FIG. 93 illustrates an alternative firing member 17820 that may be used in connection with the end effector 15200 described above, as well as with various other end effector arrangements disclosed herein. As can be seen in FIG. 93, the firing member 17820 comprises a body portion 17822 that includes an axially extending threaded passage 17824 that is adapted to be threadably engaged by the firing drive shaft 13810 in the various manners disclosed herein for example. As was discussed above, during the firing process, the firing member body 17822 is configured to extend through an axial slot in a surgical staple cartridge that has been installed in the elongate channel of the end effector. The axial slot in the staple cartridge is vertically aligned with an axial slot in the bottom of the elongate channel to enable a bottom portion of the firing member body 17822 to extend therethrough during the firing process. A bottom channel engagement member or base 17830 is attached to or formed on the firing member body 17822 as shown in FIG. 93. The base 17830 is configured to slidably engage the bottom of the channel during firing. In addition, a top anvil engagement member 17826 is formed on or attached to the top portion of the firing member body 17822.

Still referring to FIG. 93, in one aspect, the base 17830 comprises a left flange assembly 17832L that protrudes laterally from a left side of the firing member body 17822 and a right flange assembly 17832R that protrudes laterally from a right side of the firing member body 17822. The base 17830 has a base width BW' that is greater than the width LBW' of the lower portion of the firing member body 17822. In one aspect, the lower body width LBW' is less that the widths of the axial slots in the surgical staple cartridge and elongate channel. The base with BW' is greater than the widths of the axial slots in the surgical staple cartridge and the elongate channel. The top anvil engagement member 17826 comprises a left top flange assembly 17827L that protrudes laterally from a left side of the firing member body 17822 and a right top flange assembly 17827R that protrudes laterally from a right side of the firing member body 17822. The top anvil engagement member 17826 has a width TW' that is greater than the width TBW' of the upper portion of the firing member body 17822. In one aspect, the top body width TBW' is less that the width of an axial slot in the anvil to enable the top portion of the body 17822 to slidably pass therethrough, while the width TW' of the top anvil engagement member 17826 is greater than the width of the anvil slot.

In on aspect, each of the left and right flange assemblies 17832L, 17832R comprises a central segment 17834 having an axial length CL, a proximal segment 17836 having an axial proximal length PL and a distal segment 17838 having an axial distal length DL. See FIG. 93. The base 16830 has an overall axial length BL'. Thus: BL'=PL+CL+DL. In one example, PL and DL are each >CL. In one arrangement PL=DL>CL. For each flange assembly 17832L and 17832R, a proximal end 17840 of the proximal segment 17836 is radiused to reduce frictional engagement with the elongate channel during retraction of the firing member 17820 back to a starting position. In addition, the proximal segment 17836 may have a proximal tapered upper surface 17842 that tapers proximally from the central segment 17834 to the radiused proximal end 17840. For example, the thickness HC of the central segment 17834 is greater than the thickness HD of the proximal end 17840 as shown. In one arrangement, for example, the proximal tapered upper surface 17842 may angle downward from a horizontal upper surface 17837 of the central segment 17834 at a proximal flange angle PFA of approximately less than 8 degrees and preferably below four degrees and greater than zero degrees. Thus, in at least one example, $8°>PFA<4°$. Likewise, a distal end 17844 of the distal segment 17838 is radiused to reduce frictional engagement with the elongate channel during the firing process. In addition, the distal segment 17838 may have a distal tapered upper surface 17846 that tapers proximally from the central segment 17834 to the radiused distal end 17844. See FIG. 95. For example, the thickness HC of the central segment 17834 is greater than the thickness HD of the distal end 17844 as shown. In one arrangement, for example, the distal tapered upper surface 17846 may angle downward from the horizontal upper surface 17837 of the central segment 17834 at a distal flange angle DFA of approximately less than 8 degrees and preferably below four degrees and greater than zero degrees. Thus, in at least one example, $8°>DFA<4°$.

FIG. 96 illustrates the firing member 17820 and an anvil 17300 which may be identical to many of the anvil configurations disclosed herein except for the differences noted below. As can be seen in FIG. 96, the anvil 17300 comprises an elongate anvil body 17302 and an anvil mounting portion 17310. The elongate anvil body portion 17302 comprises an elongate anvil slot (not shown) configured to accommodate the axial passage of the upper portion of the firing member body 17822 therethrough. The anvil body 17302 further includes an axially extending ledge 17304 that defines an axial flange passage 17308 on each side of the anvil slot for accommodating the corresponding right top flange 17827R and left top flange 17827L therein. In the example illustrated in FIG. 96, the ledge 17304 includes a distal portion 17305, a transition portion 17306 and a proximal portion 17307. The distal portion 17305 is formed with no axial slope, i.e., horizontal. The transition portion 17306 is formed at a transition angle TLA relative to the distal portion 17305. The proximal portion 17307 is formed at a proximal angle PLA relative to the distal portion 17305 that is greater than the transition angle TLA. This arrangement serves to reduce the amount of friction and binding forces established between the firing member 17820 and the anvil 17300 during the closure process. In addition, by having the top anvil engagement member 17826 proximally axially offset by an offset distance OD' and/or by making the axial length TL' of the top anvil engagement member 17826 less than the axial base length BL', the amount of binding between the top anvil engagement member 17826 and the proximal portion 17307 of the ledge 17304 may be reduced. Of course, all of the friction and binding forces that are created during this process generally add to the amount of the closure forces that must be applied to the firing member 17820 to close the anvil 17300. Such configuration may also serve to improve the guidance of the firing member 17820 as well as to reduce twist or bending loads applied to the rotary firing drive shaft 13810 during the firing process.

Figure 97:
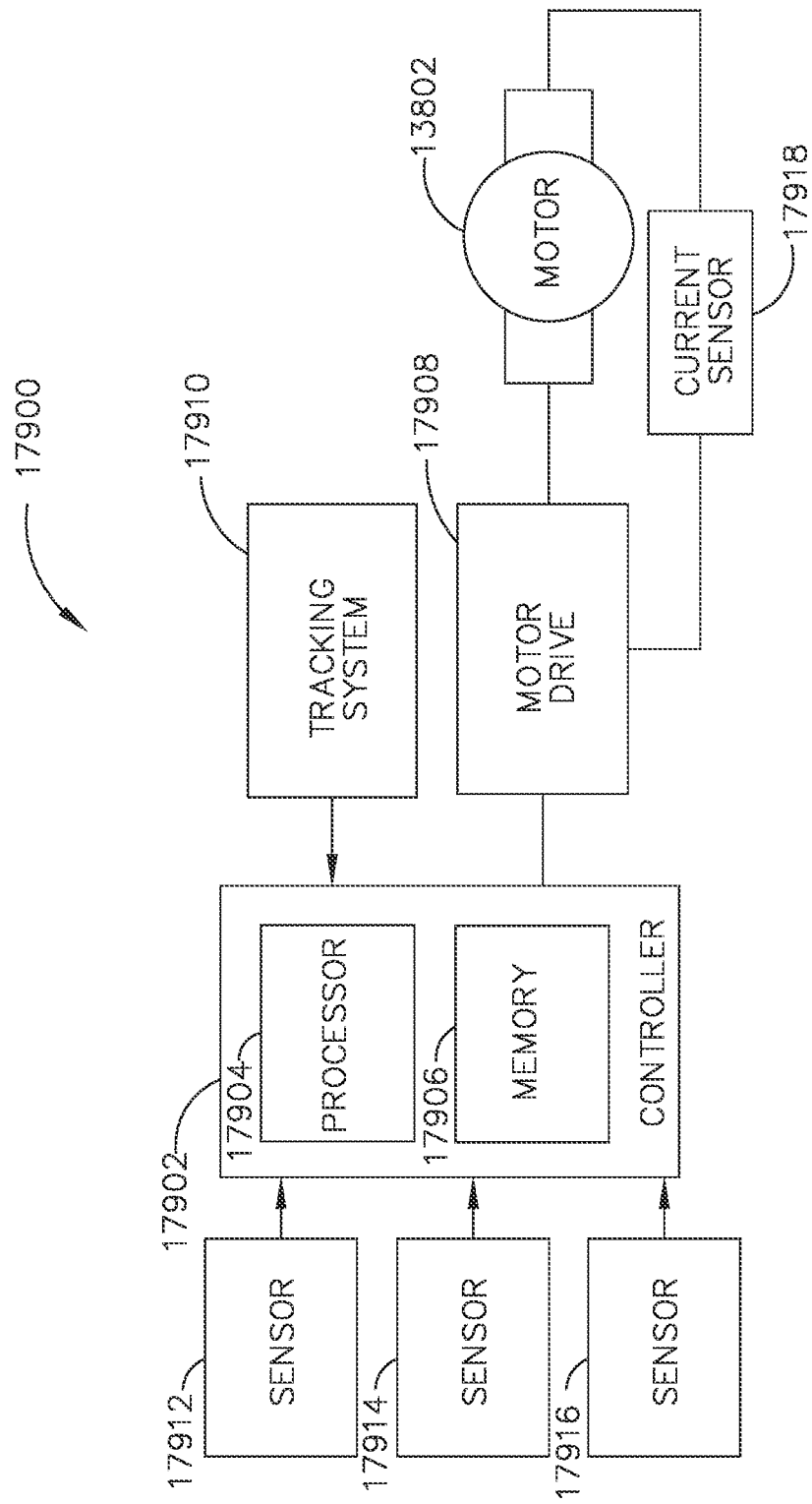
FIG. 97 is a logic diagram of a feedback system example of a powered surgical instrument.

FIG. 97 illustrates an example of a logic diagram of a feedback system 17900 that may be employed by many of the motor driven surgical instruments disclosed herein in connection with the firing systems thereof. For example, the feedback system 17900 may be employed by the firing system 13800 of the surgical instrument 13000. The feedback system 17900 comprises a circuit. The circuit includes a controller 17902 comprising a processor 17904 and a memory 17906. The firing motor 13802 is driven by a motor driver 17908 to rotate the firing drive shaft 13810 to axially drive the firing member 13820. A tracking system 17910 is configured to determine the position of the firing member 13820. The position information is provided to the processor 17904, which can be programmed or configured to determine the position of the firing member 13820 as well as the position of the camming assembly 13740, and the firing drive shaft 13810, etc.

In the aspect illustrated in FIG. 97, a sensor 17912, such as, for example, a strain gauge or a micro-strain gauge, is configured to measure one or more parameters of the end effector 13200, such as, for example, the amplitude of the strain exerted on the anvil 13300 during a clamping operation, which can be indicative of the closure forces applied to the anvil 13300. The measured strain is converted to a digital signal and provided to the processor 17904. Alternatively, or in addition to the sensor 17912, a sensor 17914, such as, for example, a load sensor, can measure the closure force applied by the closure drive system 13500 to the anvil 13300. The sensor 17916, such as, for example, a load sensor, can measure the firing force applied to an I-beam in a firing stroke of the surgical instrument 13000. Alternatively, a current sensor 17918 can be employed to measure the current drawn by the firing motor 13802. The force required to advance the firing member 13820 can correspond to the current drawn by the firing motor 13802, for example. The measured force is converted to a digital signal and provided to the processor 17904.

Figure 98:
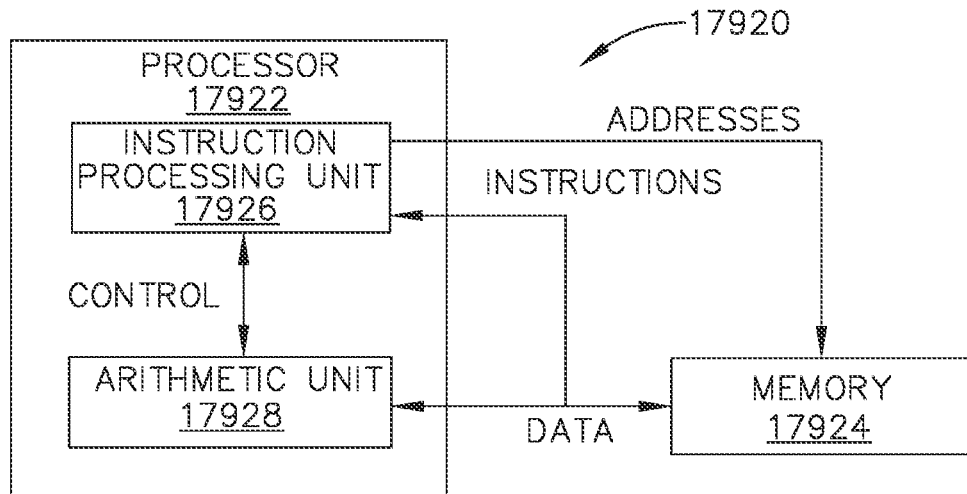
FIG. 98 is a diagram of a control circuit example for a powered surgical instrument.

FIG. 98 illustrates a control circuit configured to control aspects of the surgical instrument 13000 or other surgical instruments/systems disclosed herein. FIG. 98 illustrates a control circuit 17920 that is configured to control aspects of the surgical instrument 13000 according to one aspect of this disclosure. The control circuit 17920 can be configured to implement various processes described herein. The control circuit 17920 may comprise a controller comprising one or more processors 17922 (e.g., microprocessor, microcontroller) coupled to at least one memory circuit 17924. The memory circuit 17924 stores machine executable instructions that when executed by the processor 17922, cause the processor 17922 to execute machine instructions to implement various processes described herein. The processor 17922 may be any one of a number of single or multi-core processors known in the art. The memory circuit 17924 may comprise volatile and non-volatile storage media. The processor 17922 may include an instruction processing unit 17926 and an arithmetic unit 17928. The instruction processing unit may be configured to receive instructions from the memory circuit 17924 of this disclosure.

Figure 99:
FIG. 99 is a diagram of combinational logic circuit example for a powered surgical instrument.

FIG. 99 illustrates a combinational logic circuit 17930 that is configured to control aspects of the surgical instrument 13000 or other surgical instruments/systems disclosed herein. The combinational logic circuit 17930 can be configured to implement various processes described herein. The circuit 17930 may comprise a finite state machine comprising a combinational logic circuit 17932 that is configured to receive data associated with the surgical instrument 13000 at an input 17934, process the data by the combinational logic 17932, and provide an output 17936.

Figure 100:
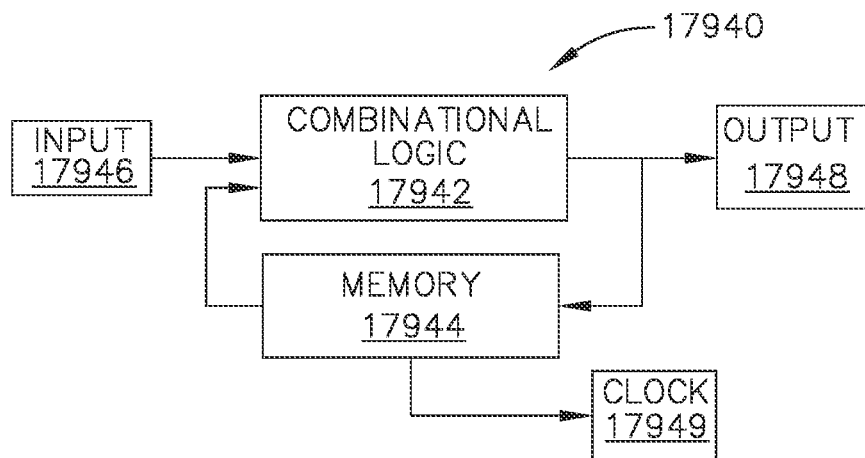
FIG. 100 is a diagram of a sequential logic circuit example for a powered surgical instrument.

FIG. 100 illustrates a sequential logic circuit 17940 configured to control aspects of the surgical instrument 13000 or other surgical instruments/systems disclosed herein. The sequential logic circuit 17940 can be configured to implement various processes described herein. The circuit 17940 may comprise a finite state machine comprising a combinational logic circuit 17942. The sequential logic circuit 17940 may comprise the combinational logic circuit 17942, at least one memory circuit 17944, and a clock 17949, for example. The at least one memory circuit 17944 can store a current state of the finite state machine. In certain instances, the sequential logic circuit 17940 may be synchronous or asynchronous. The combinational logic circuit 17942 is configured to receive data associated with the surgical instrument 13000 or other surgical instruments/systems disclosed herein at an input 17946, process the data by the combinational logic circuit 17942, and provide an output 17948. In other aspects, the circuit may comprise a combination of the processor 17922 and the finite state machine to implement various processes herein. In other aspects, the finite state machine may comprise a combination of the combinational logic circuit 17930 and the sequential logic circuit 17940.

Aspects may be implemented as an article of manufacture. The article of manufacture may include a computer readable storage medium arranged to store logic, instructions, and/or data for performing various operations of one or more aspects. For example, the article of manufacture may comprise a magnetic disk, optical disk, flash memory, or firmware containing computer program instructions suitable for execution by a general purpose processor or application specific processor. Each of the motors disclosed herein may comprise a torque sensor to measure the output torque on the shaft of the motor. The force on an end effector may be sensed in any conventional manner such as by force sensors on the outer sides of the jaws or by a torque sensor for the motor actuating the jaws.

When clamping on thick tissue, as can happen when using longer end effectors such as, for example, 60 mm end effectors, the anvil can be considerably stressed. For example, the anvil may actually bend which can cause the staple-forming undersurface thereof to bend upward away from the deck of the surgical staple cartridge. Such condition is generally undesirable not only from a component reliability stand point, but the condition can also lead to malformed staples. In extreme conditions, in its initial closing position, the anvil position may be at an angle relative to the surgical staple cartridge.

Figure 101:
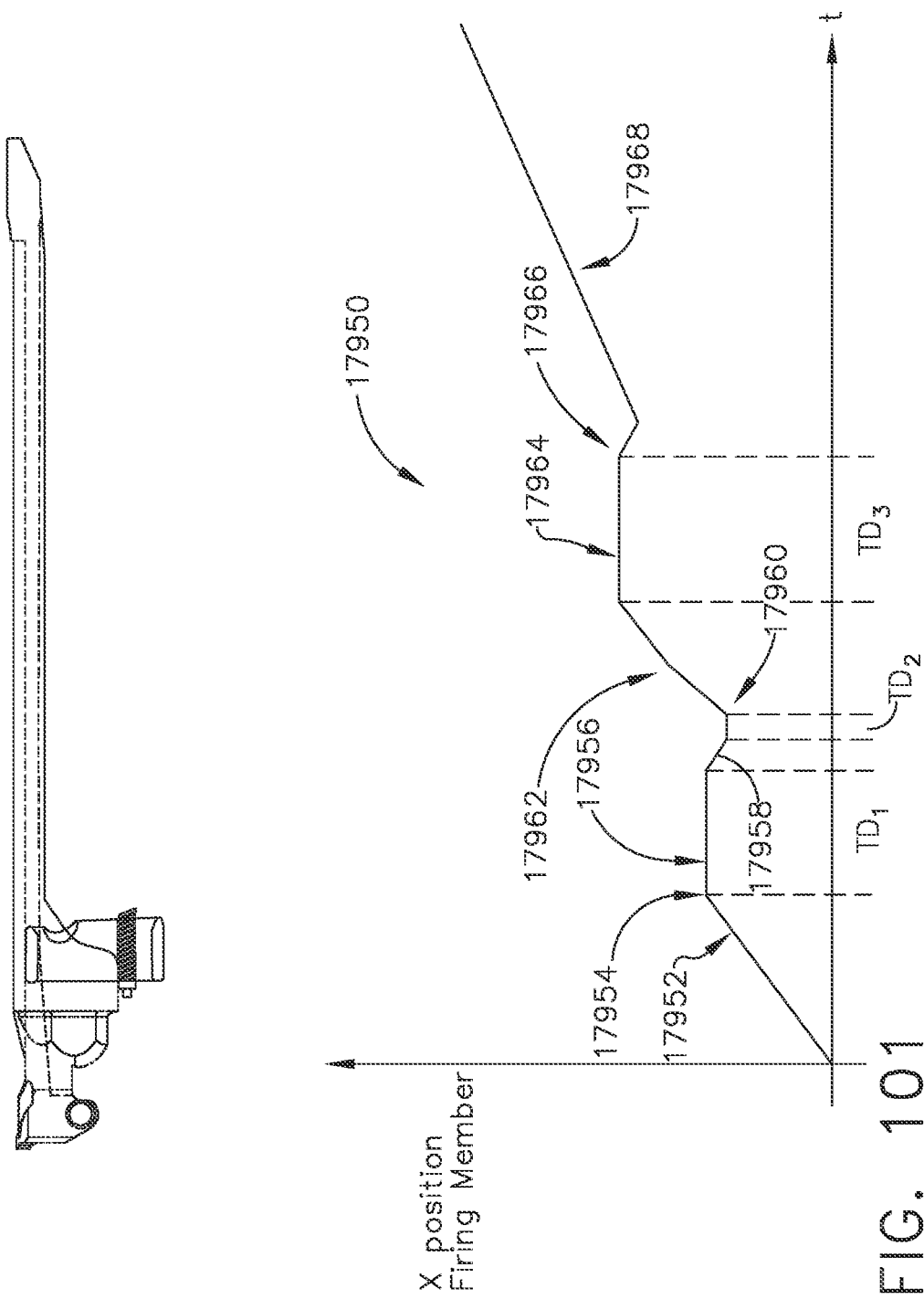
FIG. 101 is a graphical depiction of a firing process control system example for a powered surgical instrument.
Figure 102:
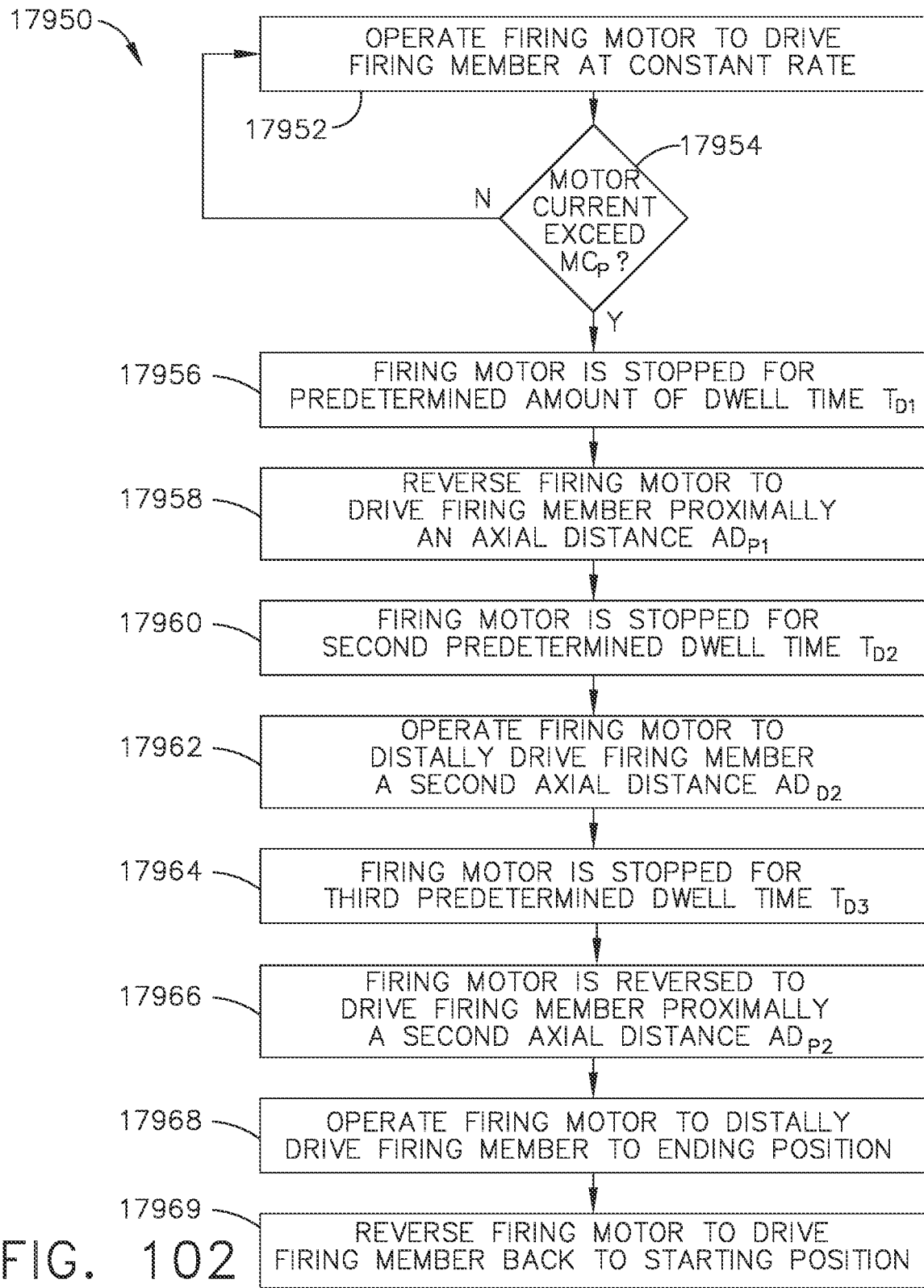
FIG. 102 is a sequential logic circuit example for operating a firing control system of a powered surgical instrument.

FIGS. 101 and 102 illustrate a process 17950 that may be used to operate various firing control systems disclosed herein. FIG. 101 illustrates one form of process 17950 in graphical form relating the x position of the firing member 14820 (or firing member 13820, for example) to an amount of time that has elapsed during the firing process. The firing process is commenced 17952 by operating the firing motor 13802 to drive the firing member 14820 at a constant rate. As the firing motor 13802 is operated to drive the firing member 14820 at a constant rate forward (17952), the control circuit monitors the firing motor 13802 current at 17954 until the motor current exceeds a predefined motor current threshold $MC_P$ associated with the final closed position of the anvil. The predetermined motor current threshold $MC_P$ may be selected based on an axial distance that the firing member 14820 must travel until the anvil 13300 reaches a final closed position. In one arrangement, for example, the firing member 14820 may initially travel about (0.250") distally from its starting position. At this stage, the firing motor 13802 is stopped 17956 for a predetermined first amount of dwell time $T_{D1}$ which allows fluid in the clamped tissue to begin to flow or migrate out of the clamped tissue (tissue creep). Further, after the waiting period, the firing member 14820 may encounter a lower amount of vertical load or resistance improving the likelihood of traversing through that location. In one arrangement, $T_{D1}$ may be 1-5 seconds, for example. After the expiration of the first amount of dwell time $T_{D1}$, the firing motor 13802 may be driven in a reversed rotary direction 17958 to retract (axially move in a proximal direction) the firing member 14820 a predetermined axial distance $AD_{P1}$. In one example, $AD_{P1}$ may be approximately 0.1"-0.15", for example. Such action allows the tissue to continue to creep (fluid to exit the clamped tissue). Once the firing member 14820 has been retracted the predetermined axial distance $AD_{P1}$, the firing motor 13802 is stopped 17960 for a second predetermined amount of dwell time $TD_2$. In one example, $TD_2$ may be approximately 0.5-1.0 seconds, for example. After the expiration of $TD_2$, the firing motor 13802 is operated 17962 to distally drive the firing member 14820 a second axial distance $AD_{D2}$. In one example, the second axial distance $AD_{D2}$ may be approximately 0.0125"-0.250", for example. At this stage 17964, the firing motor 13802 is stopped for a third predetermined amount of dwell time $TD_3$ to facilitate additional tissue creep. In one arrangement, $TD_3$ may be 1-5 seconds, for example. After the expiration of the third amount of dwell time $TD_3$, the firing motor 13802 is driven in a reversed rotary direction 17966 to retract (axially move in a proximal direction) the firing member 14820 a second predetermined axial distance $AD_{P2}$. In one example, $AD_{P2}$ may be approximately 0.1"-0.15", for example. At this point, the firing motor 13802 may be operated 17968 to drive the firing member 14820 distally until it reaches its ending position. In the alternative, after the firing member 14820 has been proximally driven the axial distance $AD_{P2}$, the firing motor 13802 may be stopped for another dwell time $TD_4$ before being operated to drive the firing member distally. In one example, $TD_4$ may be approximately 0.5-1.0 seconds, for example. In a preferred arrangement, the firing member 14820 has entered the portion of the anvil track that is parallel to the elongate channel at 17968. Once the firing member 14820 has reached its ending position (as may be detected by a sensor), the firing motor 13802 may be reversed 17969 to retract the firing member 14820 back to the starting position. Such process may serve to reduce an amount of bending and other stresses encountered by the anvil during clamping and stapling of robust tissue.

Figure 103:
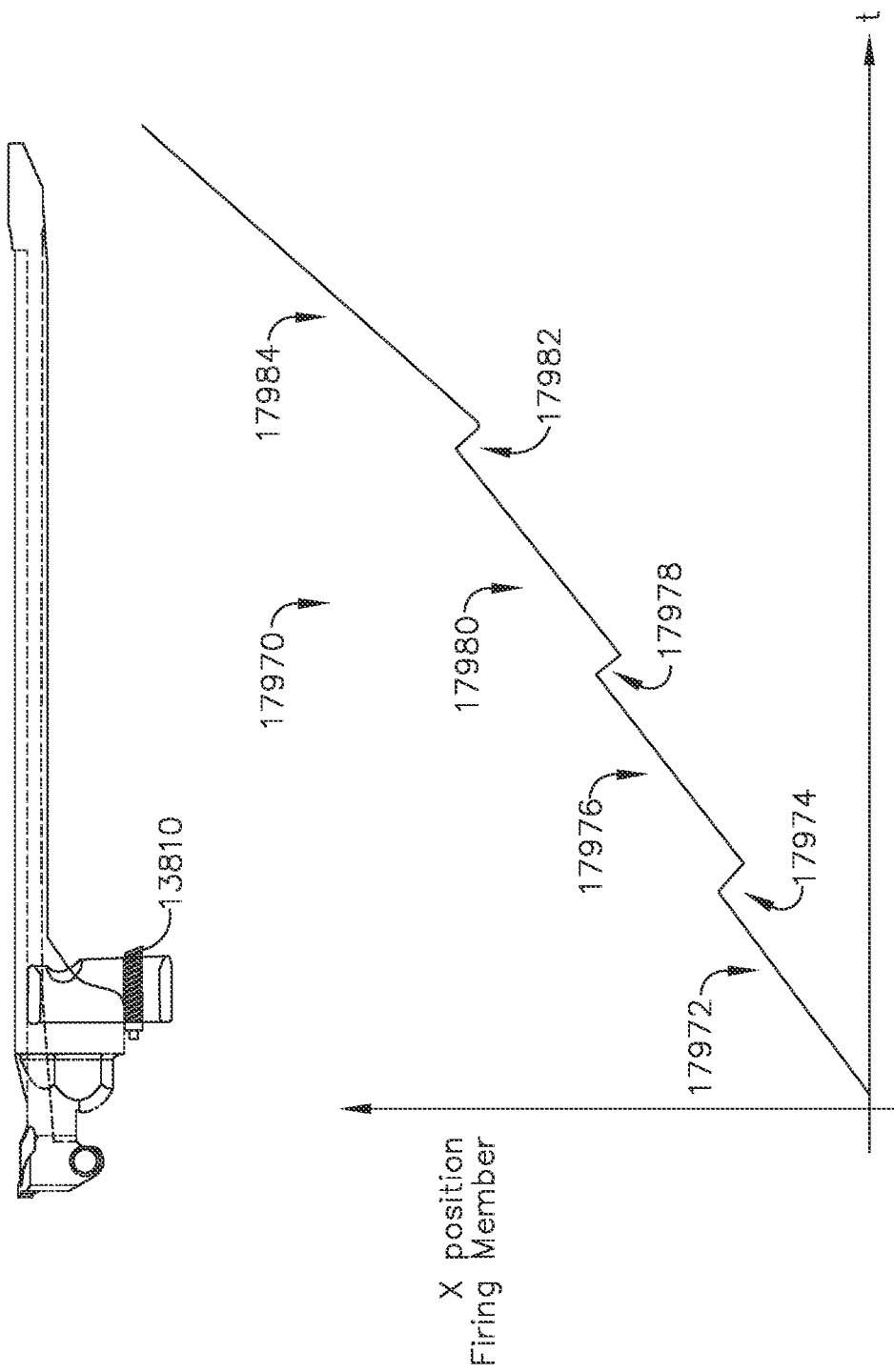
FIG. 103 is a graphical depiction of another firing process control system example for a powered surgical instrument.
Figure 104:
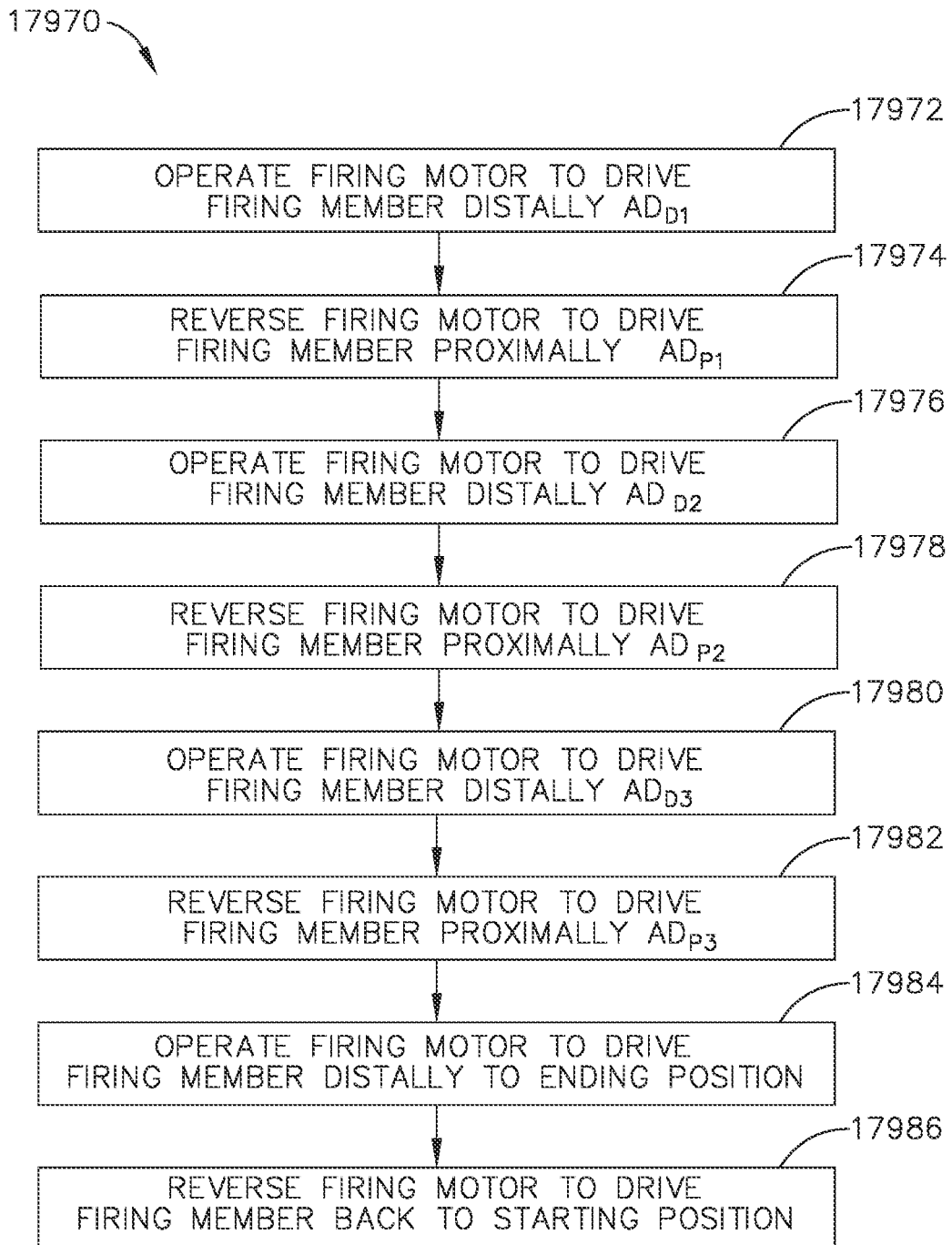
FIG. 104 is a sequential logic circuit example for operating a firing control system of another powered surgical instrument.
Figure 105:
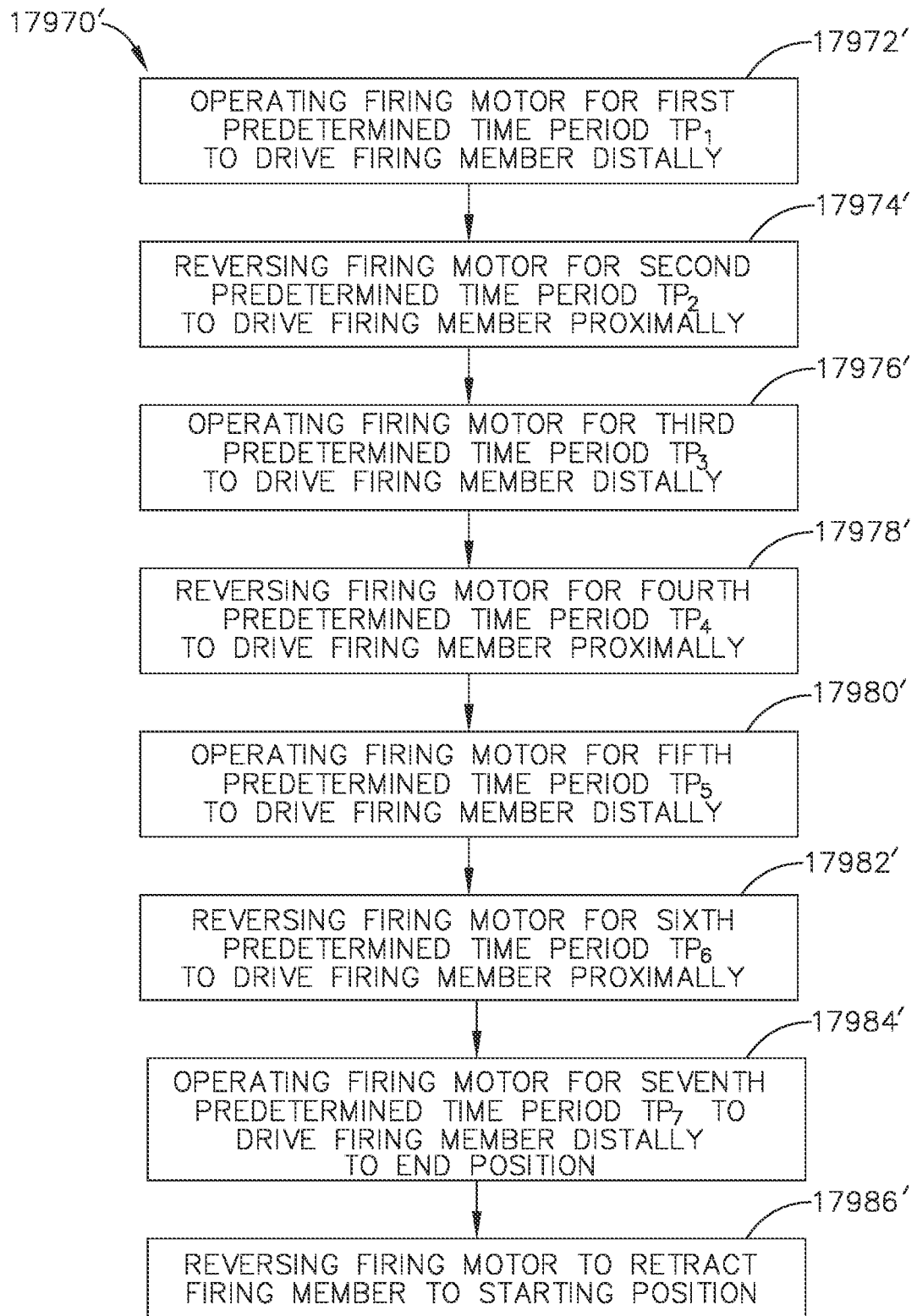
FIG. 105 is a sequential logic circuit example for operating a firing control system of another powered surgical instrument.

FIGS. 103 and 104 illustrate another process 17970 of operating the various firing control systems disclosed herein. FIG. 103 illustrates one process 17970 in graphical form relating the x position of the firing member 14820 (or 13820, for example) to the amount of time elapsed during the firing process. The firing process is commenced 17972 by operating the firing motor 13802 to drive the firing member 14820 a first axial distal distance $AD_{D1}$. The position of the firing member 14820 may be detected by sensors (Hall effect, etc.) positioned in the anvil 14300 and conveyed to the control circuit 17920. In an alternative process 17970', the firing motor 13802 may be operated for a first predetermined time period $TP_1$ (17972') to drive the firing member 14820 the first axial distal distance $AD_{D1}$. See FIG. 105. Thereafter, the firing motor 13802 is driven in a reversed rotary direction 17974 to retract (axially move in a proximal direction) the firing member 14820 a predetermined axial proximal distance $AD_{P1}$. In one example, $AD_{P1}$ may be approximately 0.1"-0.15", for example. Such action allows the tissue to continue to creep (fluid to migrate out of or exit the clamped tissue). In process 17970', the firing motor 13802 may be operated for a second predetermined time period $TP_2$ (17974') to drive the firing member 13820 the first axial proximal distance $AD_{P1}$. Once the firing member 14820 has been retracted the predetermined axial proximal distance $AD_{P1}$, the firing motor 13802 is driven at 17976 to distally drive the firing member 14820 a second axial distal distance $AD_{D2}$. In the alternative process 17970', the firing motor 13802 may be operated for a third predetermined time period $TP_3$ (17976') to drive the firing member 14820 the second axial distal distance $AD_{D2}$. Thereafter, the firing motor 13802 is driven in a reversed rotary direction 17978 to retract the firing member 14820 a second predetermined axial proximal distance $AD_{P2}$. In one example, $AD_{P2}$ may be approximately 0.1"-0.15", for example. In the alternative process 17970', the firing motor 13802 may be operated for a fourth predetermined time period $TP_4$ (17978') to drive the firing member 14820 the second axial proximal distance $AD_{P2}$. Thereafter, the firing motor 13802 is driven at 17980 to distally drive the firing member 14820 a third axial distal distance $AD_{D3}$. In the alternative process 17970', the firing motor 13802 may be operated for a fifth predetermined time period $TP_5$ (17980') to drive the firing member 14820 the third axial distal distance $AD_{D3}$. Thereafter, the firing motor 13802 is driven in a reversed rotary direction 17982 to retract the firing member 14820 a third predetermined axial proximal distance $AD_{P3}$. In one example, $AD_{P3}$ may be approximately 0.1"-0.15", for example. In the alternative process 17970', the firing motor 13802 may be operated for a sixth predetermined time period $TP_6$ (17982') to drive the firing member 14820 the third axial proximal distance $AD_{P3}$. Thereafter, the firing motor 13802 is driven at 17984 to distally drive the firing member 14820 to its ending position. In the alternative process 17970', the firing motor 13802 may be operated for a seventh predetermined time period $TP_7$ (17984') to drive the firing member 14820 to the ending position. Once the firing member 14820 has reached its ending position (as detected by a sensor, for example), the firing motor 13802 may be reversed 17986, 17986' to retract the firing member 14820 back to the starting position.

In a preferred arrangement, the firing member 14820 has entered the portion of the anvil track that is parallel to the elongate channel at 17984. Such process may serve to reduce the bending and stressing of the anvil during clamping and stapling of robust tissue. The various axial distal distances and the time periods may be altered in other arrangements. In one arrangement, the axial distal distanced $AD_{D1}$, $AD_{D2}$, ADDS may be equal or they may be different. Likewise the time periods $TP_1$, $TP_3$, $TP_5$ may be equal or they may be different.

The processes 17950, 17970, 17970' may be particularly useful when clamping and firing through relatively thick tissue. Some rotary driven end effector arrangements may be constructed with a relatively short anvil mounting joint which may necessarily include relatively steep anvil starting ramps adjacent the anvil mounting portion of the anvil. Such steep starting ramps can be particularly difficult to traverse when using conventional closure and firing system processes. Various processes and procedures disclosed herein allow/facilitate the complete closure of the anvil while reducing/minimizing the amount of binding stresses normally encountered by the firing member when otherwise using convention firing and closing processes.

Figure 106:
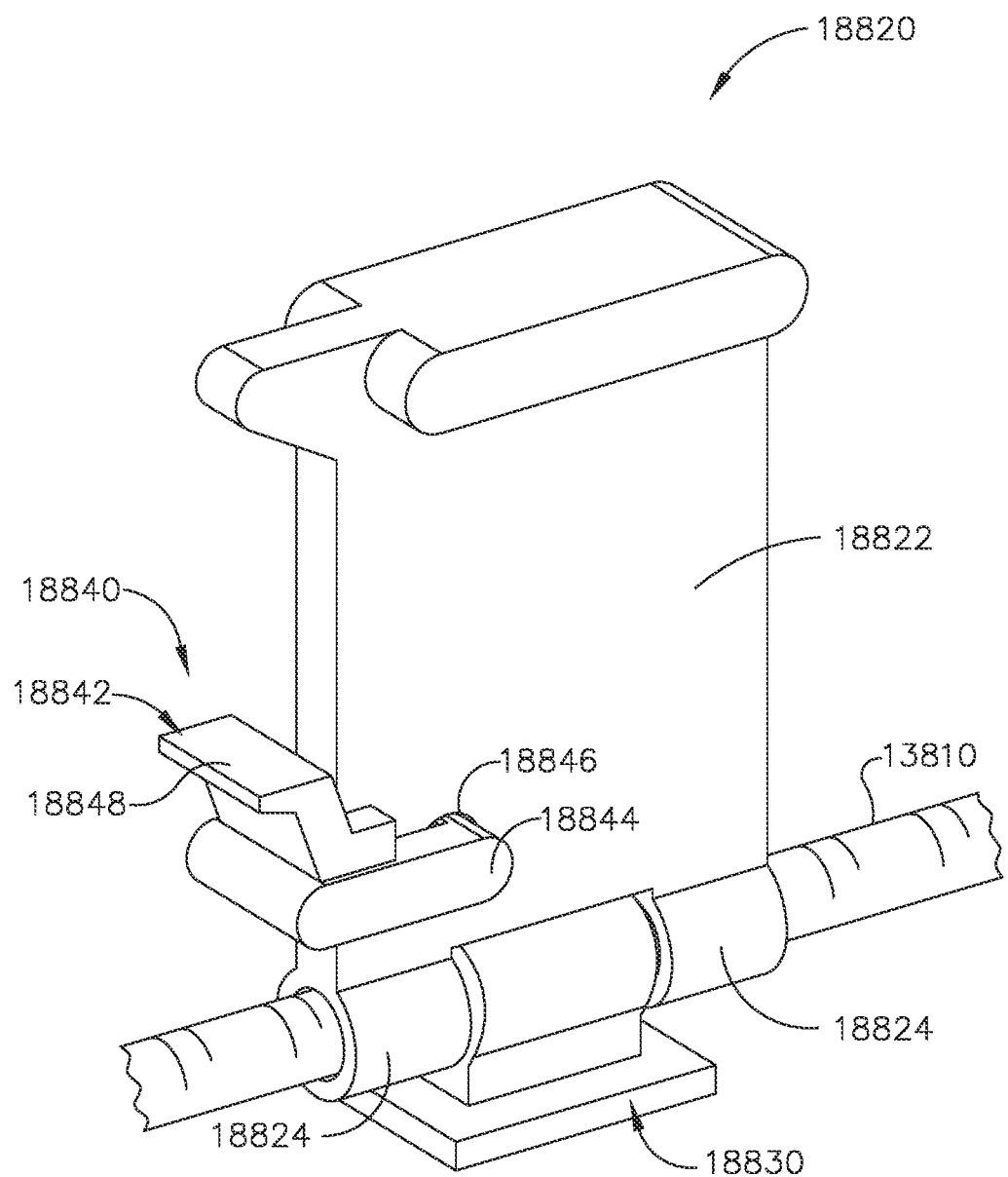
FIG. 106 is a perspective view of another firing member of a surgical end effector in installed on a rotary firing drive shaft thereof.
Figure 107:
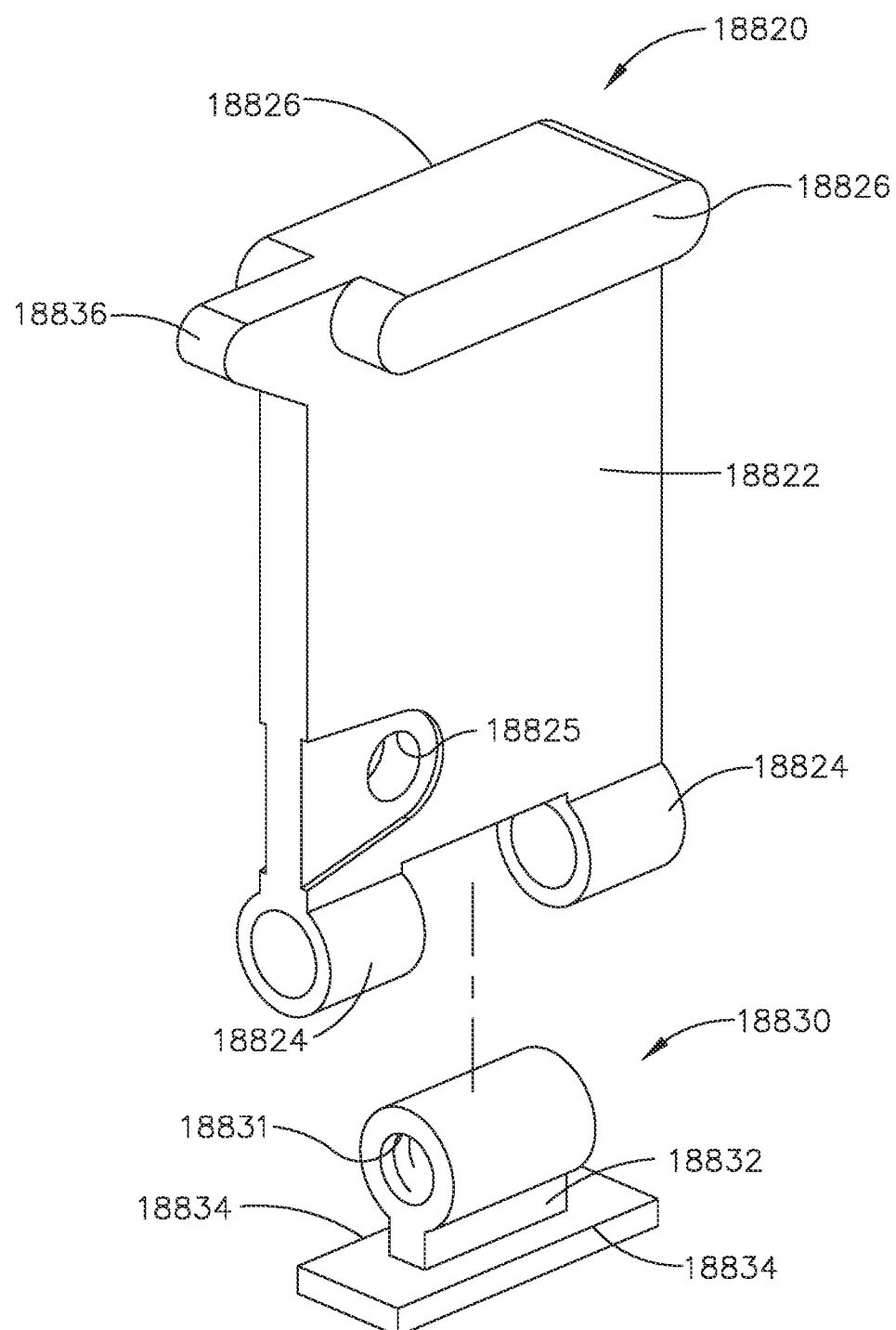
FIG. 107 is an exploded assembly view of portions of the firing member of FIG. 106.
Figure 108:
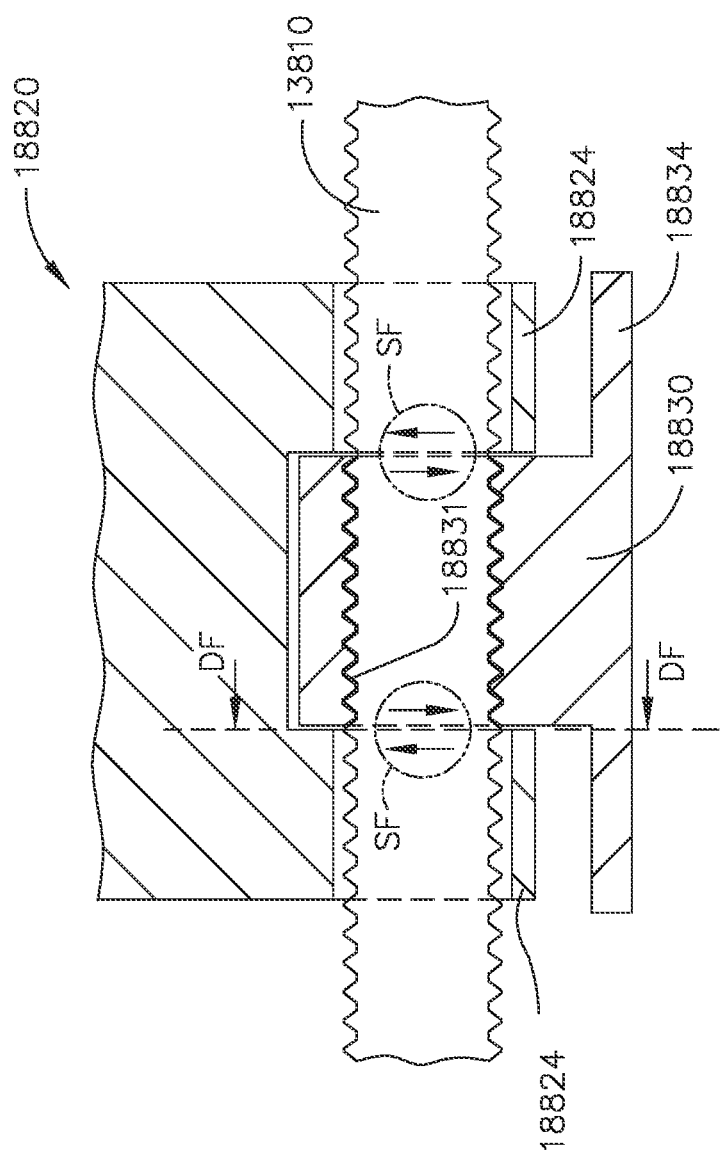
FIG. 108 is a partial cross-sectional view of the firing member and a drive nut arrangement installed on the rotary firing drive shaft of FIG. 106.

FIGS. 106 and 107 illustrates another form of firing member 18820 that may be similar in many aspects to firing member 14820. As can be seen in FIGS. 106 and 107, the firing member 18820 comprises a body portion 18822 that includes two downwardly extending hollow mounting portions 18824 that are unthreaded and spaced from each other to receive a threaded drive nut 18830 therebetween. As can be seen in FIGS. 107 and 108, the drive nut 18830 includes a threaded passage 18831 that is configured to threadably engage the firing drive shaft 13810. The drive nut 18830 includes a vertical tab portion 18832 that is sized to extend through an axial slot in the bottom of the elongate channel as was described above. Two laterally extending channel engagement flanges 18834 are formed on the threaded drive nut 18830 and are configured to engage the bottom of the elongate channel. Rotation of the firing drive shaft 13810 causes the drive nut 18830 to move axially. As the drive nut 18830 moves axially, the drive nut 18830 applies axial drive forces DF to the firing member body 18822 as shown in FIG. 108 to drive the firing member 18820 axially. Such configuration causes shear forces SF to be applied to the firing drive shaft 13810 as shown. This loading arrangement puts the firing drive shaft 13810 into a shear failure mode, which may be preferred to bending. See FIG. 108. The system is assembled by passing the firing drive shaft 13810 through one of the hollow mounting portions 18824 and threading it into the threaded passage 18831 in the drive nut 18830 until the firing drive shaft 13810 passes through the second hollow mounting portion 18824 and the assembled firing member 18820 is in the desired position on the firing drive shaft 13810. In addition, two laterally extending anvil engagement tabs 18826 are formed on the top of the firing member body 18822 and are configured to engage an anvil as the firing member 18820 is axially moved within an end effector. The top portion of the firing member body 18822 further comprises a distally extending anvil nose portion 18836.

In this arrangement, the firing member 18820 includes a firing member lockout feature 18840 that is configured to prevent the distal advancement of the firing member 18820 from its starting position unless a fresh unfired staple cartridge has been properly seated in the elongate channel. In one example, the firing member lockout feature 18840 comprises a lockout body 18842 that has two spaced attachment legs 18844 protruding therefrom that extend around the firing member body 18822. Each attachment leg 18844 includes an inwardly extending pivot pin 18846 that is adapted to be pivotally received in an opening 18825 in the mounting portions 18824. The lockout feature 18840 further includes a sled latch 18848 that is configured for contact with a camming assembly 18740 in a staple cartridge.

Figure 109:
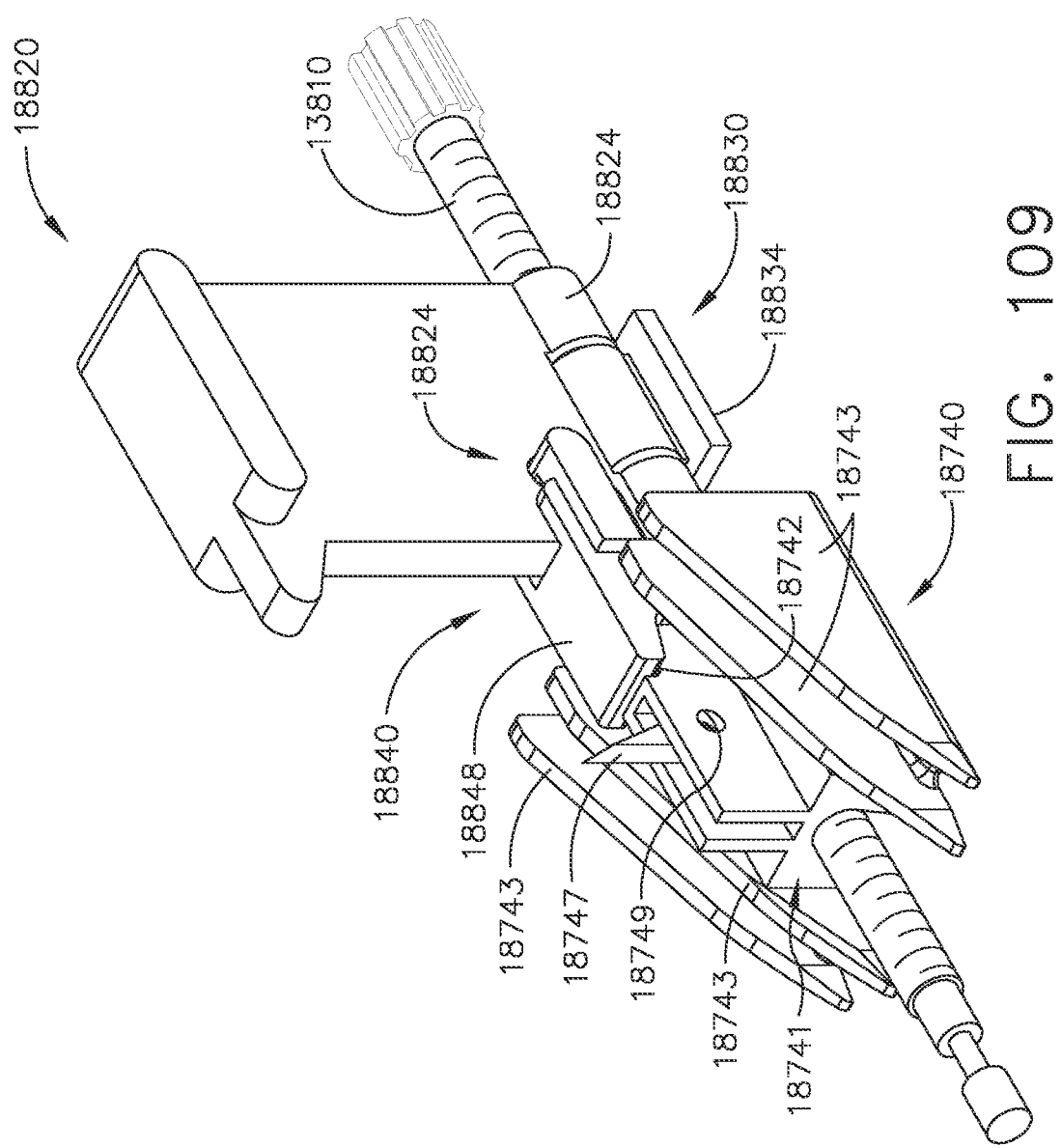
FIG. 109 is a partial perspective view of another firing member of a surgical end effector installed on a rotary firing drive shaft thereof an in unlocking engagement with a camming assembly of a surgical staple cartridge with a tissue cutting member thereof in a deployed position.
Figure 110:
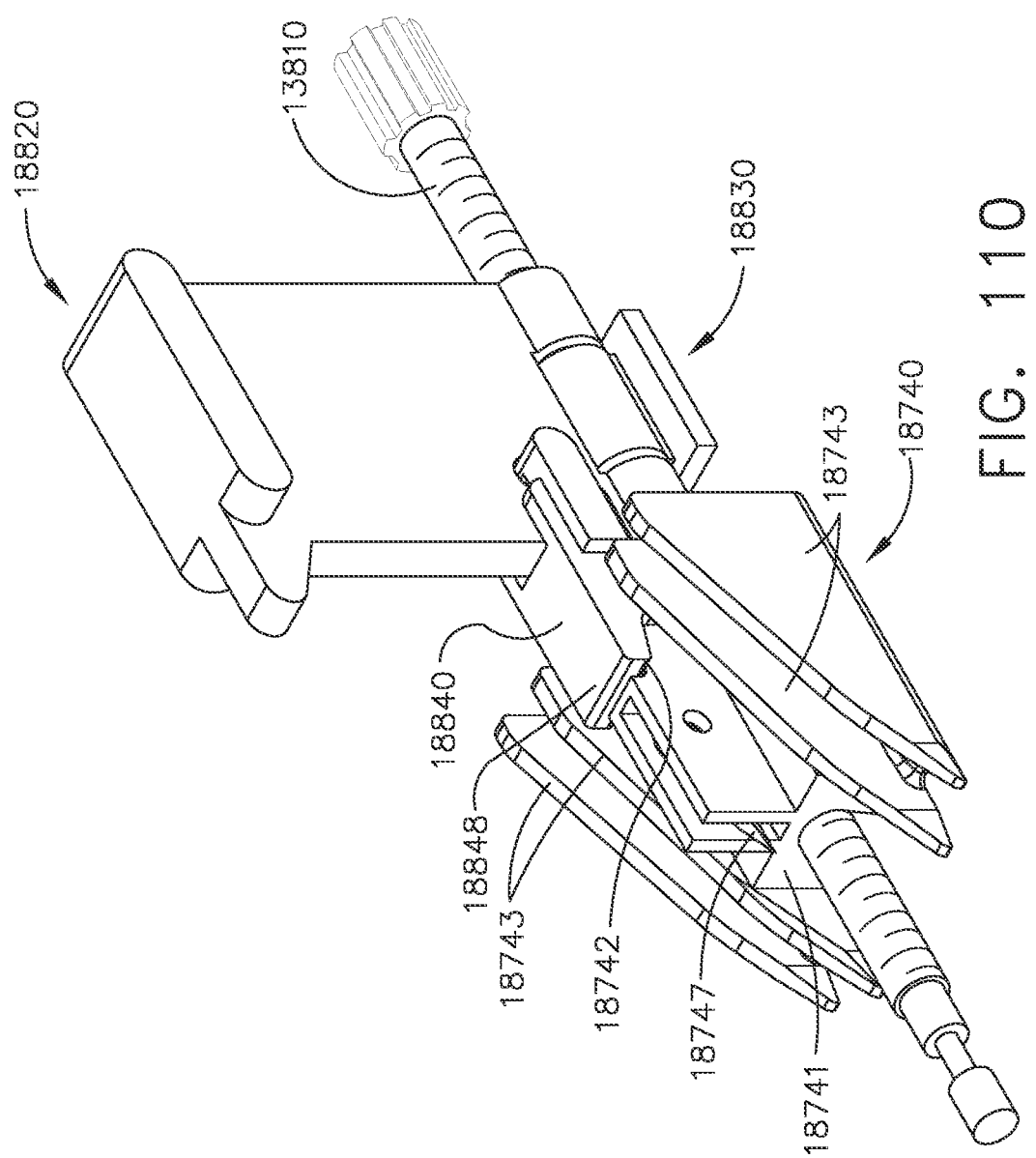
FIG. 110 is another partial perspective view of the firing member and camming assembly of FIG. 109 with the tissue cutting member in a stored position.

Turning to FIGS. 109 and 110, the firing member 18820 is configured to operably interface with camming assembly 18740 that is similar in many aspects to camming assembly 14740 described above. For example, in one aspect, the camming assembly 18740 is operably supported in the staple cartridge and is configured to be snapped over or otherwise operably interface with the firing drive shaft 13810 in any of the various manners described herein. For example, the camming assembly 18740 comprises a camming assembly body 18741 that may have a series of internal thread segments (not shown) that are configured to threadably engage threads or thread segments on the firing drive shaft 13810 in the manners described above. In other arrangements, the camming assembly 18740 may not have threads. In such configurations the firing member body 18822 is configured to extend around the firing drive shaft 13810 (without threaded engagement), for example. In such configuration, the camming assembly 18740 is driven distally through the staple cartridge by the firing member 18820. Once the firing member 18820 and the camming assembly 18740 have been driven into their distal-most ending positions, the firing member 18820 may be retracted back to its starting position by rotating the firing drive shaft 13810 in a reverse rotary direction while the camming assembly 18740 remains in its ending position.

As can further be seen in FIGS. 109 and 110, the camming assembly body 18741 comprises a proximally extending unlocking portion 18742 that is configured to engage the sled latch 18848 on the lockout feature 18840. Thus, as was described above, when a fresh, unfired surgical staple cartridge that contains a camming assembly 18740 has been properly seated within the elongate channel of the end effector, the unlocking portion 18742 on the camming assembly 18740 engages the sled latch 18848 on the lockout feature 18840 to pivot the lockout feature 18840 into an unlocked position wherein the lockout feature 18840 does not extend into a lockout hole in the elongate channel. As can also be seen in FIGS. 109 and 110, the camming assembly body 18741 includes a series of cam members 18743 that are aligned with corresponding staple drivers supported in lines within the staple cartridge.

Once a fresh staple cartridge containing the camming assembly 18740 therein in its unfired starting position has been properly loaded into the elongate channel of the end effector and the anvil thereof has been moved to a closed position through activation of the closure system, the firing system can then be activated to drive the firing member 18820 distally. Continued distal movement of the firing member 18820 causes the internal threads (if present) in the camming assembly 18740 to engage the corresponding threads on the firing drive shaft 13810. Continued rotation of the firing drive shaft 13810 causes the camming assembly 18740 and firing member 18820 to move distally through the staple cartridge in the manners described herein. As the cam members 18743 contact the corresponding staple drivers in the cartridge body, the cam members 18743 drive the drivers upward in their respective pockets. As the drivers are driven upwardly, the staples or fasteners supported thereon are forced through the tissue that is clamped between the cartridge and the anvil and into forming contact with the staple-forming undersurface of the anvil.

Unlike camming assembly 14740, the camming assembly 18740 contains a tissue cutting member or blade 18747. In one aspect, the tissue cutting member 18747 is movably supported on the camming assembly body 18741 such that it is movable from a deployed position (FIG. 109) to a recessed or stored position (FIG. 110). In one aspect, the cam members 18743 extend distally beyond the tissue cutting member 18747 such that the staples or fasteners are deployed through the tissue before the tissue cutting member 18747 cuts through the tissue. Thus, the clamped tissue is stapled and thereafter cut as the firing member 18820 and camming assembly 18740 are driven distally. In one aspect, the tissue cutting member 18747 is pivotally supported on a pivot pin 18749 such that it is pivotable between the deployed position and the stored position. The tissue cutting member 18747 is mounted in a blade mounting portion 18746 defined in the camming assembly body 18741. In one example, the tissue cutting member 18747 may be releasably retained in the deployed position by a detent (not shown) in the tissue cutting member 18747 that is configured to releasably engage a corresponding recess in the camming assembly body 18741. Other releasable tissue cutting retainer arrangements are contemplated. In at least one arrangement, once the camming assembly 18740 has been driven to a distal-most ending position within the staple cartridge, the tissue cutting member 18747 is configured to be pivoted to the stored position through contact with a corresponding actuation feature provided in a distal end of the cartridge body. At the completion of the firing stroke, the firing drive shaft 13810 is rotated in an opposite direction to cause the firing member 18820 to be proximally driven back to the starting position within the end effector. The camming assembly 18740 disengages from the firing drive shaft 13810 and remains in the ending position. After the firing member 18820 has returned to the starting position, the closure system may be activated to move the anvil to the open position to thereby release the stapled tissue from the end effector. Thereafter, the "spent" staple cartridge may be removed from the elongate channel of the end effector. Should the user attempt to reuse the spent cartridge, because the camming assembly 18740 is not in the starting position, the lockout feature 18840 will prevent the inadvertent actuation of the firing member 18820.

Figure 111:
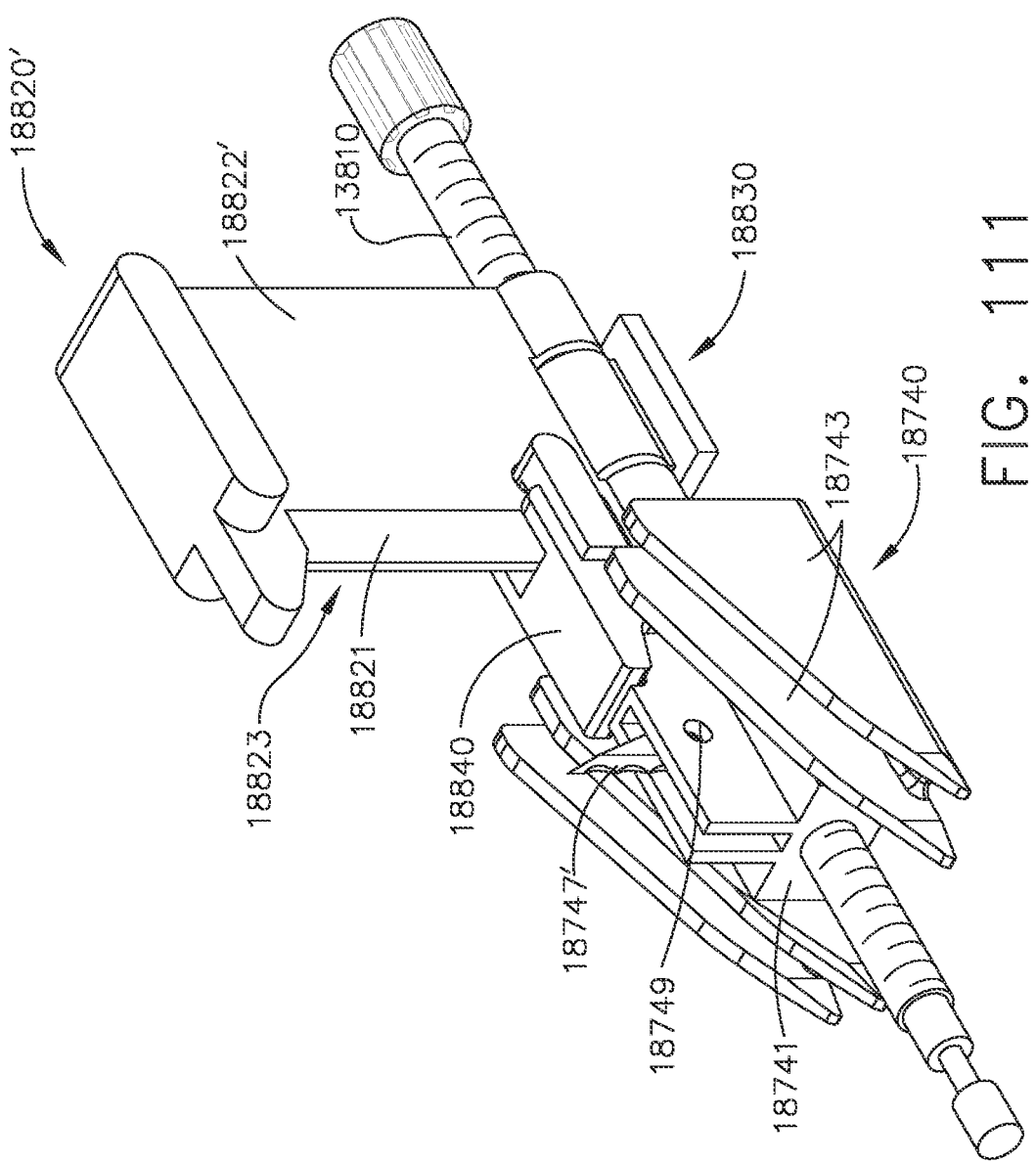
FIG. 111 is a partial perspective view of another firing member of a surgical end effector installed on a rotary firing drive shaft thereof and in unlocking engagement with a camming assembly of a surgical staple cartridge with a tissue cutting member thereof in a deployed position.

FIG. 111 illustrates an alternative firing member arrangement 18820' that is identical to firing member 18820 described above, except that a tissue separating feature 18821 is formed on a distal edge 18823 of the firing member body 18822'. Stated another way, the distal edge 18823 of the firing member body 18822' tapers to a thinner cross-section without forming a tissue cutting edge thereon. This tissue separating feature may be formed using various metal injection molding techniques, for example. Such feature helps to spread the tissue (without additionally cutting) after it has been cut by the tissue cutting member 17847' on the camming assembly 18740.

Such camming assembly arrangements provide a fresh cutting surface with each new cartridge. In addition, tissue cutting members across different cartridges may have different profiles, thicknesses and aggressiveness depending upon the particular application. For example, a cartridge that is configured for use with a buttress material may have a more robust tissue cutting member (e.g., the tissue cutting member may be sharper, thicker have a lesser hone angle, be serrated, etc.). FIG. 111 illustrates a serrated tissue cutting member 18747', for example. Thus, the particular configuration of the tissue cutting member may be tailored to the particular type and thickness of tissue to be cut and stapled.

Figure 112:
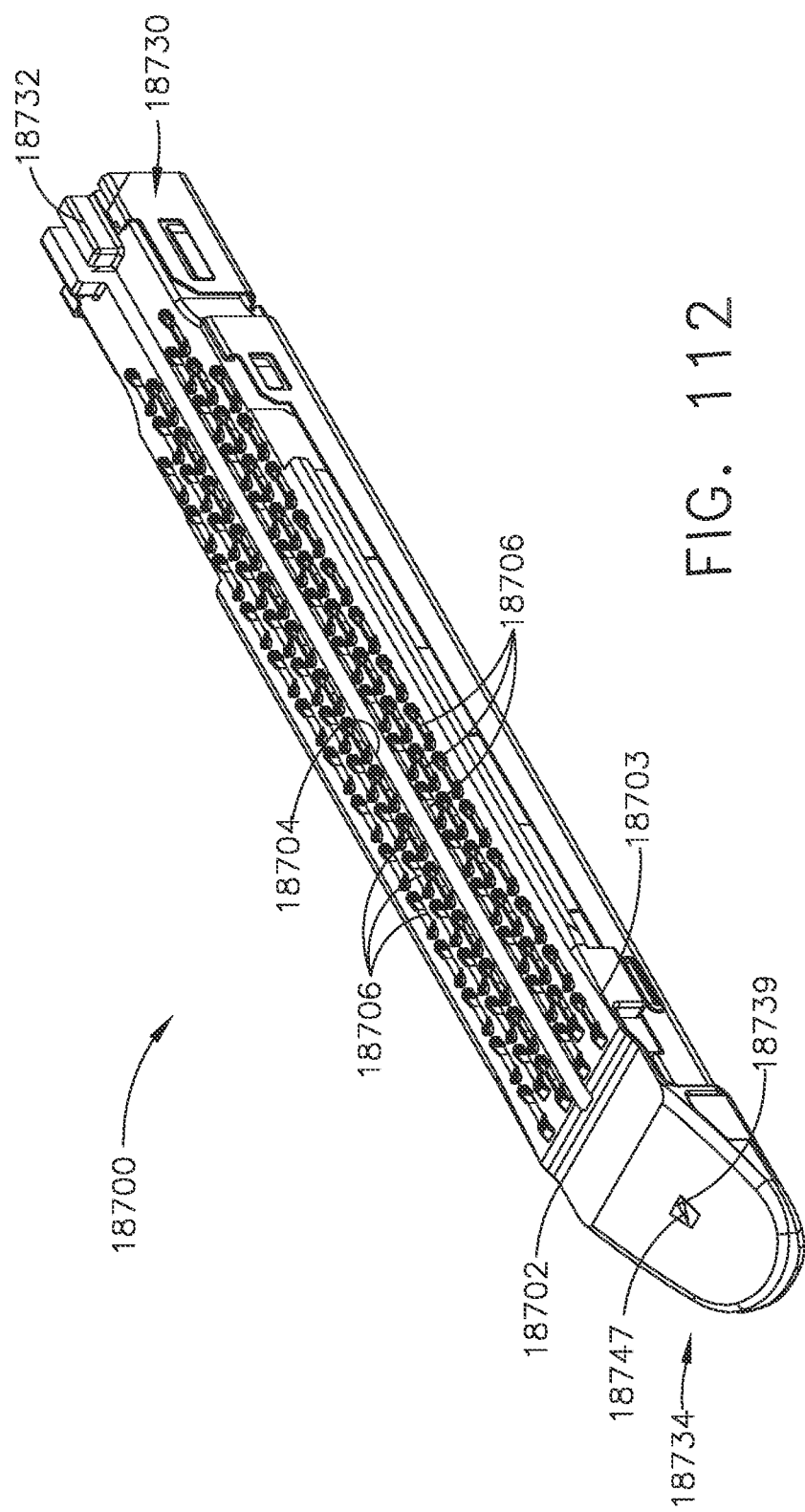
FIG. 112 is a perspective view of another surgical staple cartridge.
Figure 113:
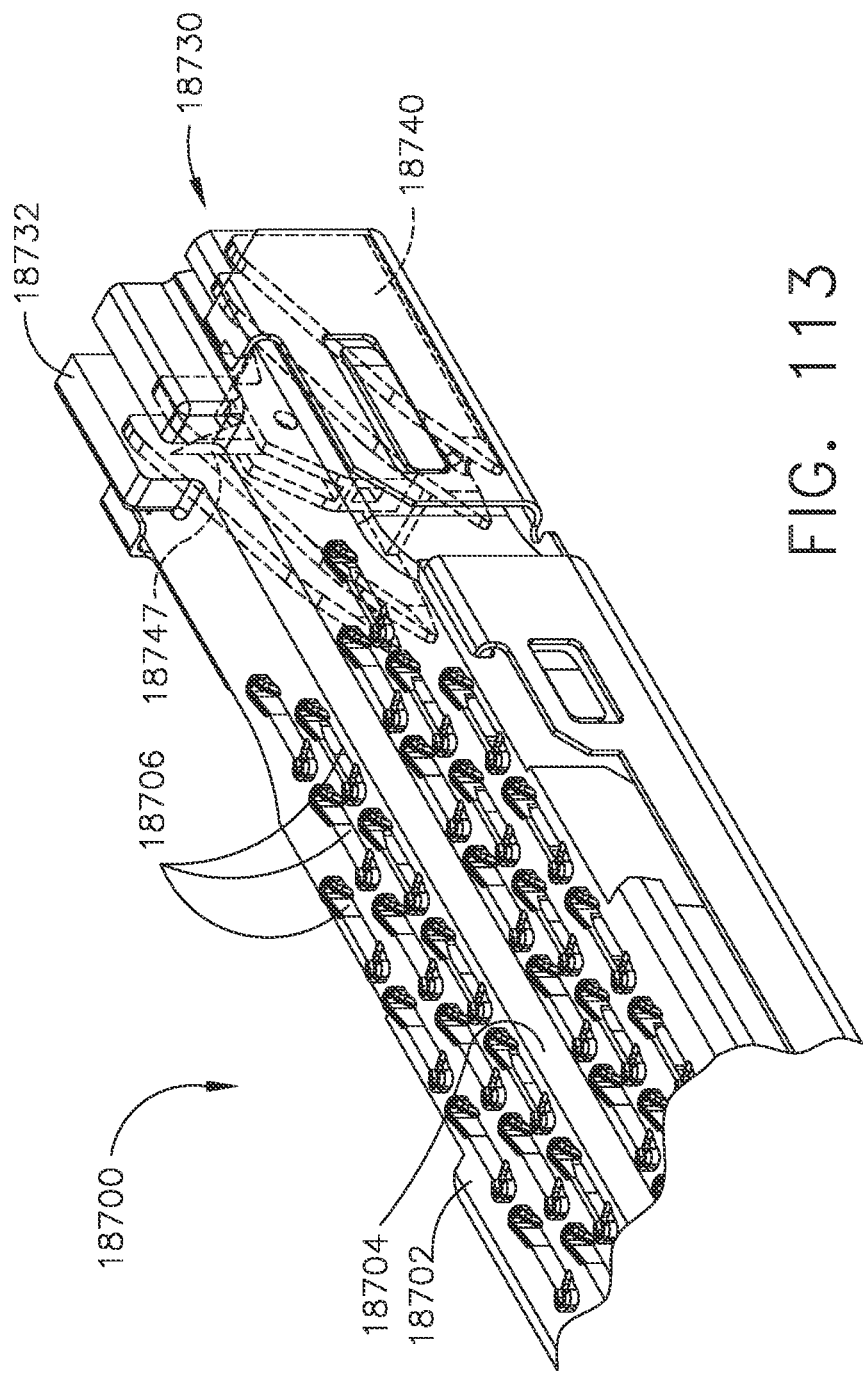
FIG. 113 is an enlarged perspective view of a proximal end of the surgical staple cartridge of FIG. 112 with a camming assembly thereof shown in broken lines.

FIGS. 112 and 113 depict a surgical staple cartridge 18700 that includes a camming assembly 18740' that may be identical to the camming assembly 18740 except for the differences noted below, for example. The cartridge 18700 comprises an elongate cartridge body 18702 that has a centrally disposed elongate cartridge slot 18704 that is configured to accommodate the axial travel of the firing member 18820 therein. Also in the illustrated example, three lines of surgical staple pockets 18706 are formed on each side of the elongate slot 18704. Each staple pocket 18706 defines an opening in a cartridge deck surface 18703 of the cartridge body 18702. Each staple pocket 18706 may have a staple driver (not shown) associated therewith that supports one or more surgical staples or fasteners (not shown) thereon. As can seen in FIG. 113, a safety garage 18732 is formed on a proximal end 18730 of the cartridge body 13702 such that the tissue cutting member 18747 (in its deployed position) is protected thereby (unexposed) when the camming assembly 18740 is in its starting position.

Figure 114:
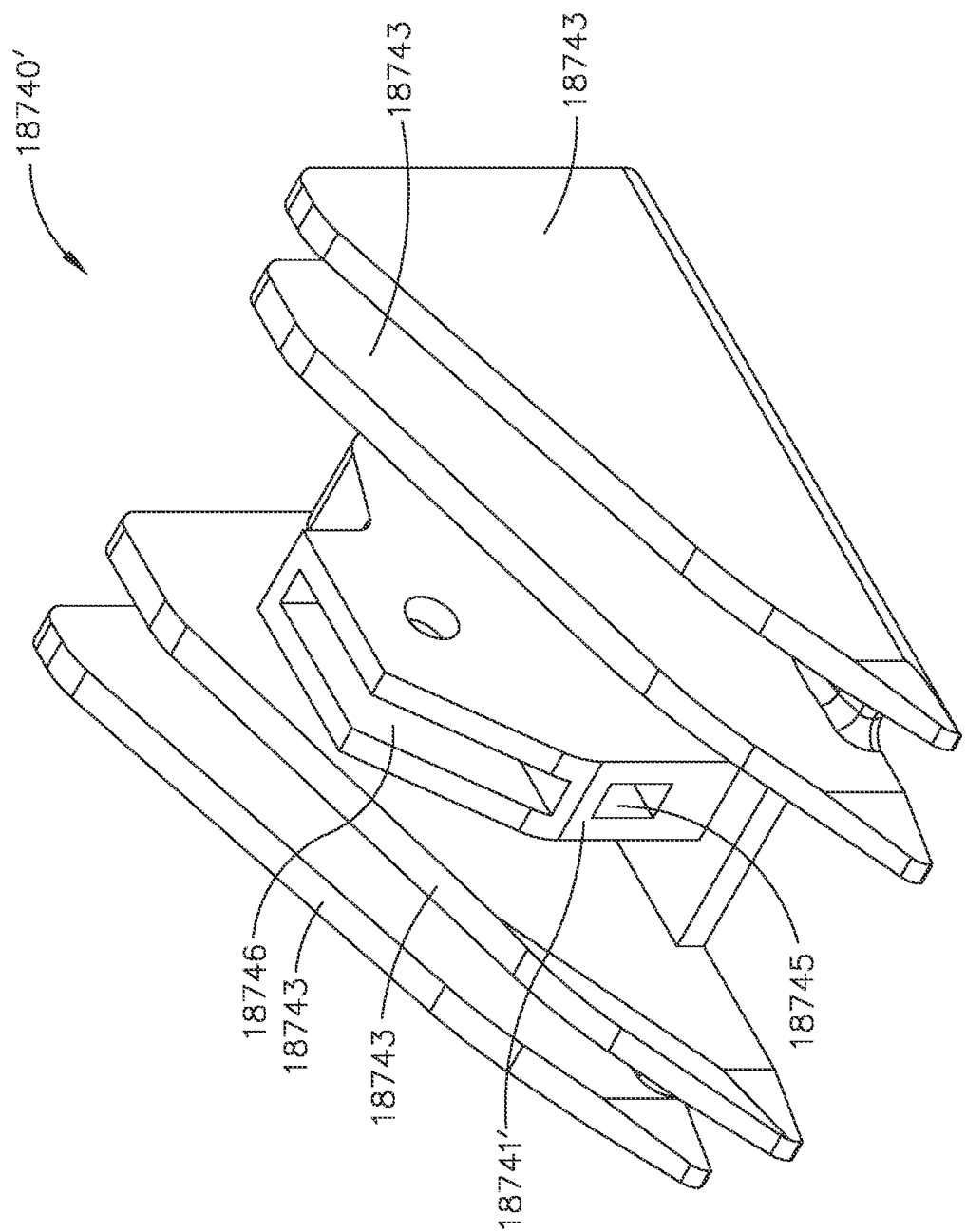
FIG. 114 is a perspective view of the camming assembly of the surgical staple cartridge of FIG. 112 with a tissue cutting member thereof omitted.
Figure 115:
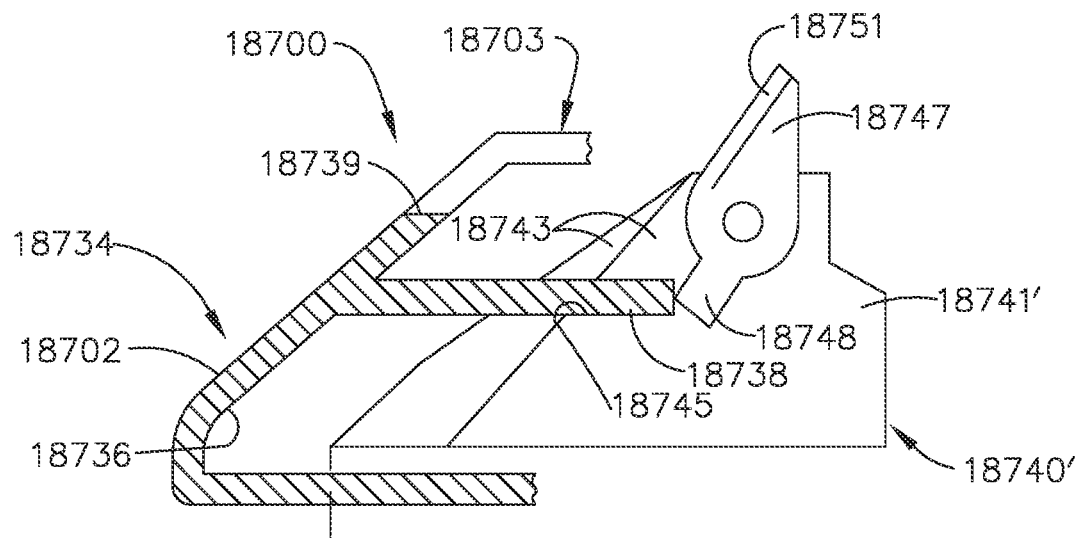
FIG. 115 is a cross-sectional view of a distal end of the surgical staple cartridge of FIG. 112, with the camming assembly thereof approaching a distalmost, ending position therein.
Figure 116:
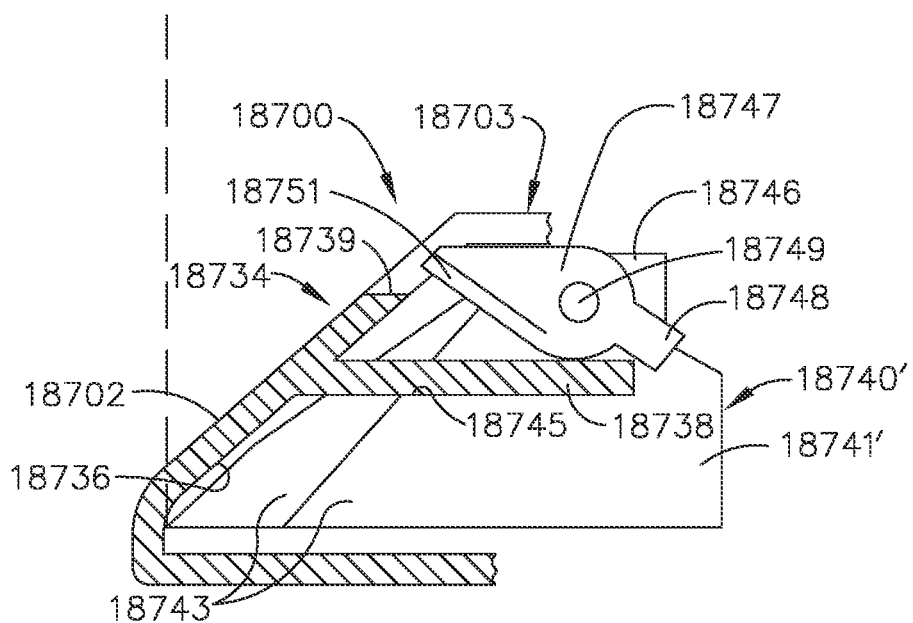
FIG. 116 is another cross-sectional view of the distal end of the surgical staple cartridge of FIG. 112, after the camming assembly has reached the ending position and the tissue cutting member thereof has been moved to a stored position.

FIG. 114 illustrates one form of the camming assembly 18740' with the tissue cutting member omitted for clarity. The camming assembly 18740' is substantially identical to the camming assembly 18740, except that the camming assembly body 18741' additional includes a retraction passage 18745 that extends into the blade mounting portion 18746. Turning to FIGS. 115 and 116, in one aspect, the tissue cutting member 18747 includes an actuation tail 18748 that, when contacted by retraction member 18738 that is formed on a distal end 18734 of the cartridge body 18702, can pivot the tissue cutting member 18747 from its deployed position (FIG. 115) to its recessed or stored position (FIG. 116). As can be seen in FIG. 115, as the camming assembly 18740' approaches the ending position, the retraction member 18738 extends through the retraction passage 18745 in the camming assembly body 18741' to contact the actuation tail 18748 on the tissue cutting member 18747. The retraction member 18738 pivots the tissue cutting member 18747 to the recessed or stored position (FIG. 116) when the camming assembly 18740' reaches the final distal-most position in distal end 18734 of the cartridge body 18702. As can be seen in FIG. 116, in one example, the cam members 18743 contact an end wall 18736 in the distal end 18734 of the cartridge body 18702. A clearance opening 18739 is provided in the distal end of the cartridge body 18702 to provide sufficient clearance for the tissue cutting member 18747 to pivot to the recessed or stored position. As can be further seen in FIG. 116, when the tissue cutting member 18747 is in the recessed or stored position, the cutting surface 18751 thereon is stored below the cartridge deck surface 18703 of the cartridge body 18702 to prevent access thereto.

Figure 117:
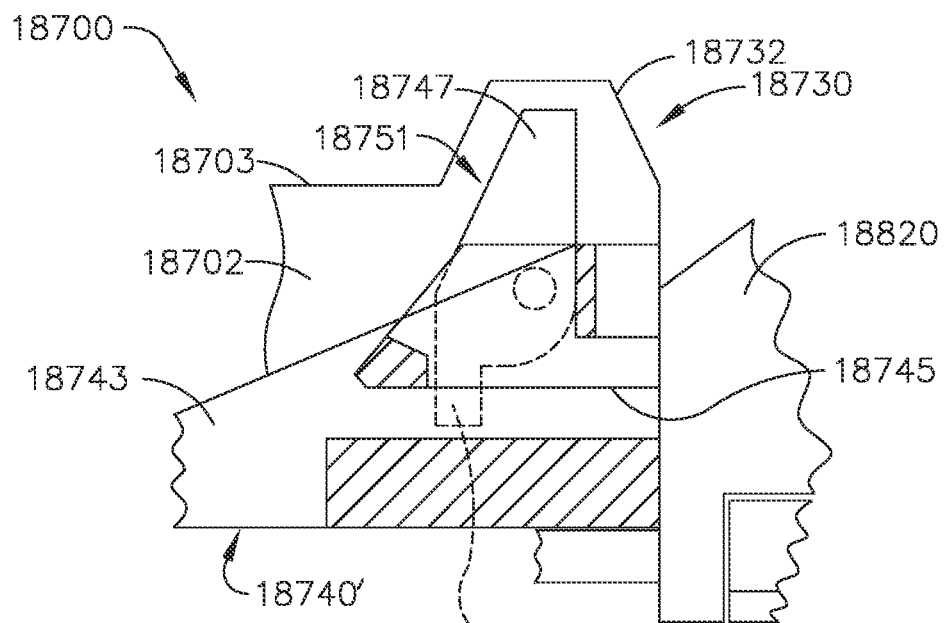
FIG. 117 is a partial cross-sectional side view of a proximal end of the surgical staple cartridge of FIG. 112 with the tissue cutting member thereof in a deployed position.
Figure 118:
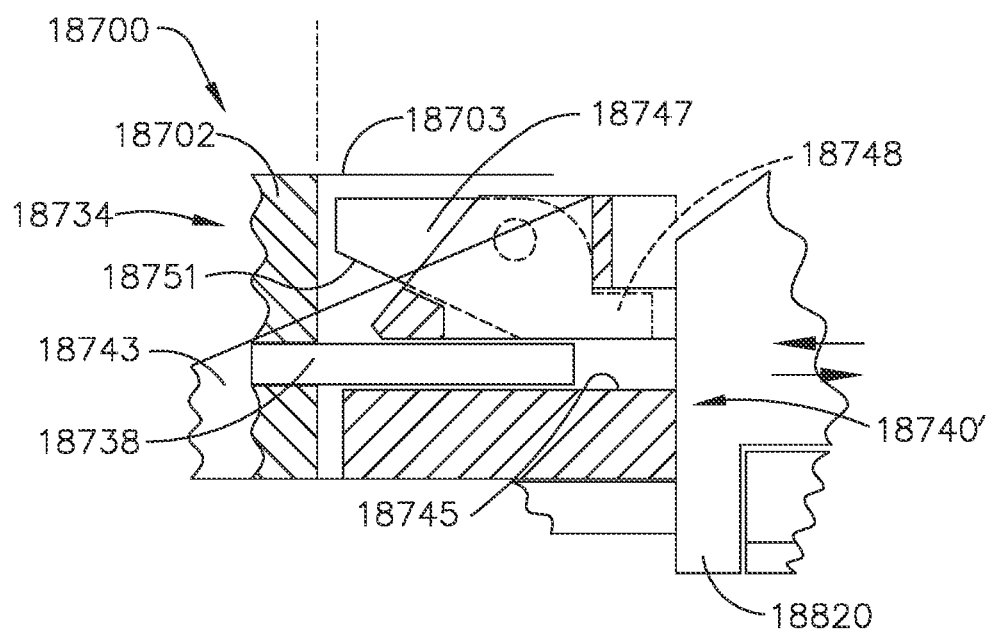
FIG. 118 is another partial cross-sectional side view of a distal end of the surgical staple cartridge of FIG. 112 with the tissue cutting member thereof in a stored position.
Figure 119:
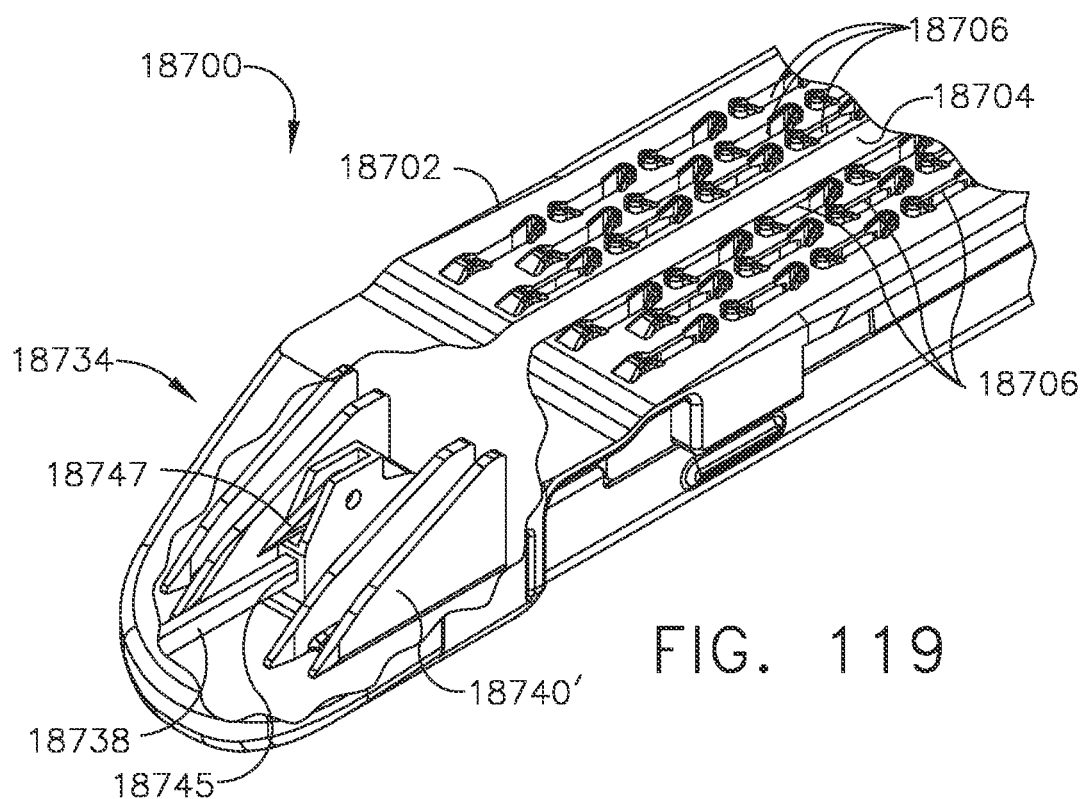
Figure 120:
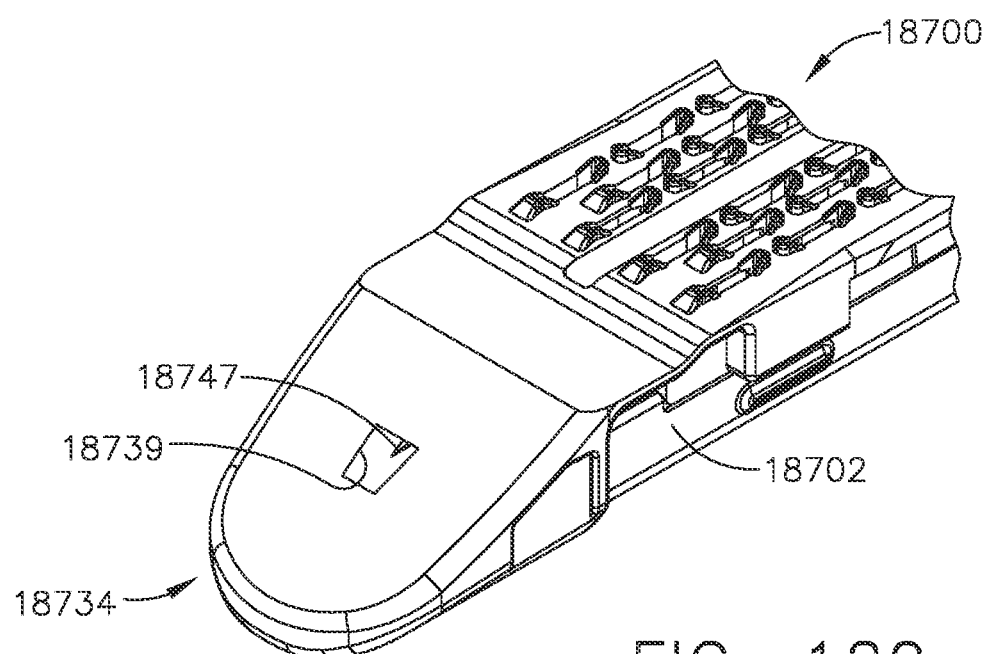

FIG. 117 illustrates the camming assembly 18740' in the starting position with the tissue cutting member 18747 in the deployed state. As can be seen in FIG. 117, the tissue cutting member 18747 is positioned within the garage portion 18732 on the proximal end 18730 of the cartridge body 18702 such that the tissue cutting surface 18751 thereon is completely received therein and not exposed to prevent the user from being injured while handling the cartridge 18700. FIG. 118 illustrates the tissue cutting member 18747 after being moved into to the recessed or stored position at the distal end of the cartridge. As can be seen in FIG. 118, the tissue cutting surface 18751 is safely located below the cartridge deck surface 18703 to prevent inadvertent injury during removal and disposal of the spent cartridge after firing. See also FIGS. 119 and 120.

Figure 121:
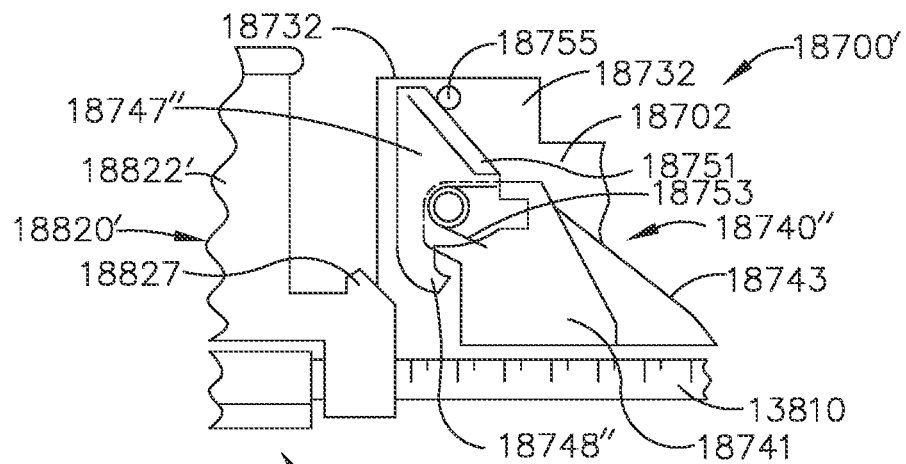
Figure 122:
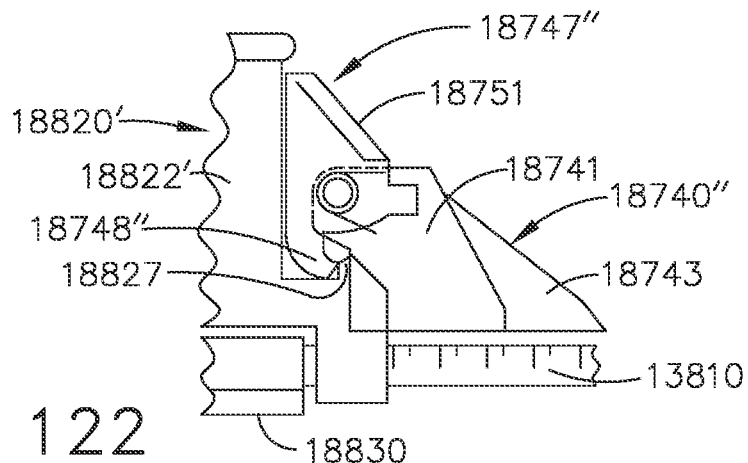
Figure 123:
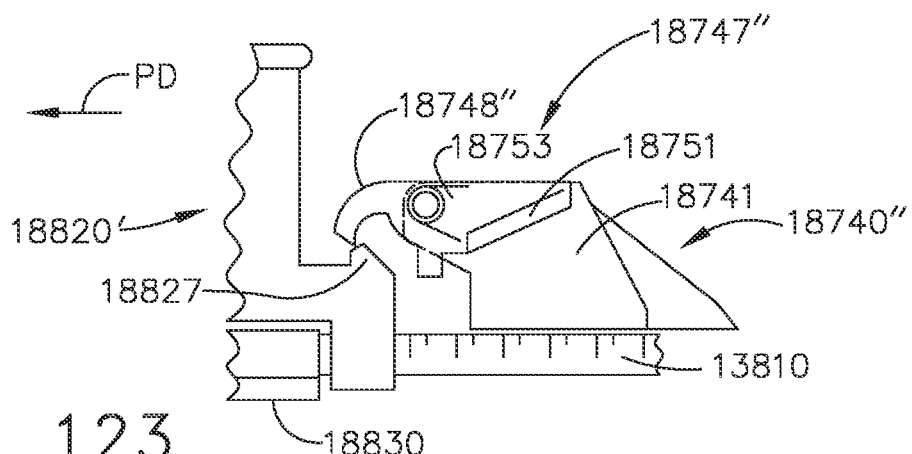

FIGS. 121-123 illustrate an alternative tissue cutting member 18747" that is configured to interact with a cutting member retainer that is provided on the firing member. FIG. 121 illustrates a firing member 18820' which is otherwise identical to firing member 18820 described above. However, firing member 18820' also includes a cutting member retainer 18827. As can be seen in FIG. 121, the camming assembly 18740" is in its starting position within the staple cartridge 18700'. The tissue cutting member 18747" is in its deployed position and is received within the garage portion 18732 of the cartridge body 18702. A torsion spring 18753 is mounted on the camming assembly body 18741 and is configured to apply a biasing motion to the tissue cutting member 18747" that would cause the tissue cutting member 18747" to pivot to the storage position. To retain the tissue cutting member 18747" in the deployed position against the biasing motion applied by the spring 18753 prior to firing, a frangible blade retainer 18755 is supported in the garage 18732 to retain the tissue cutting member 18747" in the deployed position. The blade retainer 18755 may be fabricated from a soft material such as rubber, etc., that may be severed by the tissue cutting surface 18751 on the tissue cutting member 18747" when the camming assembly 18740" is distally advanced through the cartridge 18700" during the firing process.

FIG. 121 illustrates the position of the staple cartridge 18700' and the firing member 18820' after the cartridge 18700' has been properly loaded into the end effector and prior to firing. As can be seen in FIG. 121, the firing member 18820' is in the starting position and has not been distally advanced into engagement with the camming assembly 18740". In FIG. 122, the firing member 18820' has been initially distally advanced to contact the camming assembly 18740" to a point wherein the cutting member retainer 18827 on the firing member 18820' has engaged an actuation tail 18748" on the tissue cutting member 18747" to retain the tissue cutting member 18747" in the deployed position during the firing process. Distal advancement of the firing member 18820' and the camming assembly 18740" will cause the tissue cutting member 18747" to cut through the frangible blade retainer 18755 in the cartridge body garage 18732 as the firing process proceeds. FIG. 123 illustrates the camming assembly 18740" in its ending position and after the firing member 18820' has initially began the retraction movement in a proximal direction PD. As can be seen in FIG. 122, the cutting member retainer 18827 has disengaged from the actuation tail 18748" on the tissue cutting member 18747" to permit the torsion spring 18753 to bias the tissue cutting member 18747" into the storage position. The firing member 18820' is retracted back into the starting position to enable the spent cartridge to be removed form the end effector. If, at any time during the firing process (i.e., during the distal advancement of the firing member 18820' and the camming assembly 18740") the firing process is stopped and it becomes necessary to retract the firing member 18820', proximal movement of the firing member 18820" will result in the disengagement of the actuation tail 18748" from the cutting member retainer 18827 at which point the torsion spring 18753 will bias the tissue cutting member 18747" into the storage position. Thus, the camming assembly 18470" does not have to be in the ending position to have the tissue cutting member 18747" be biased into the storage position.

Figure 124:
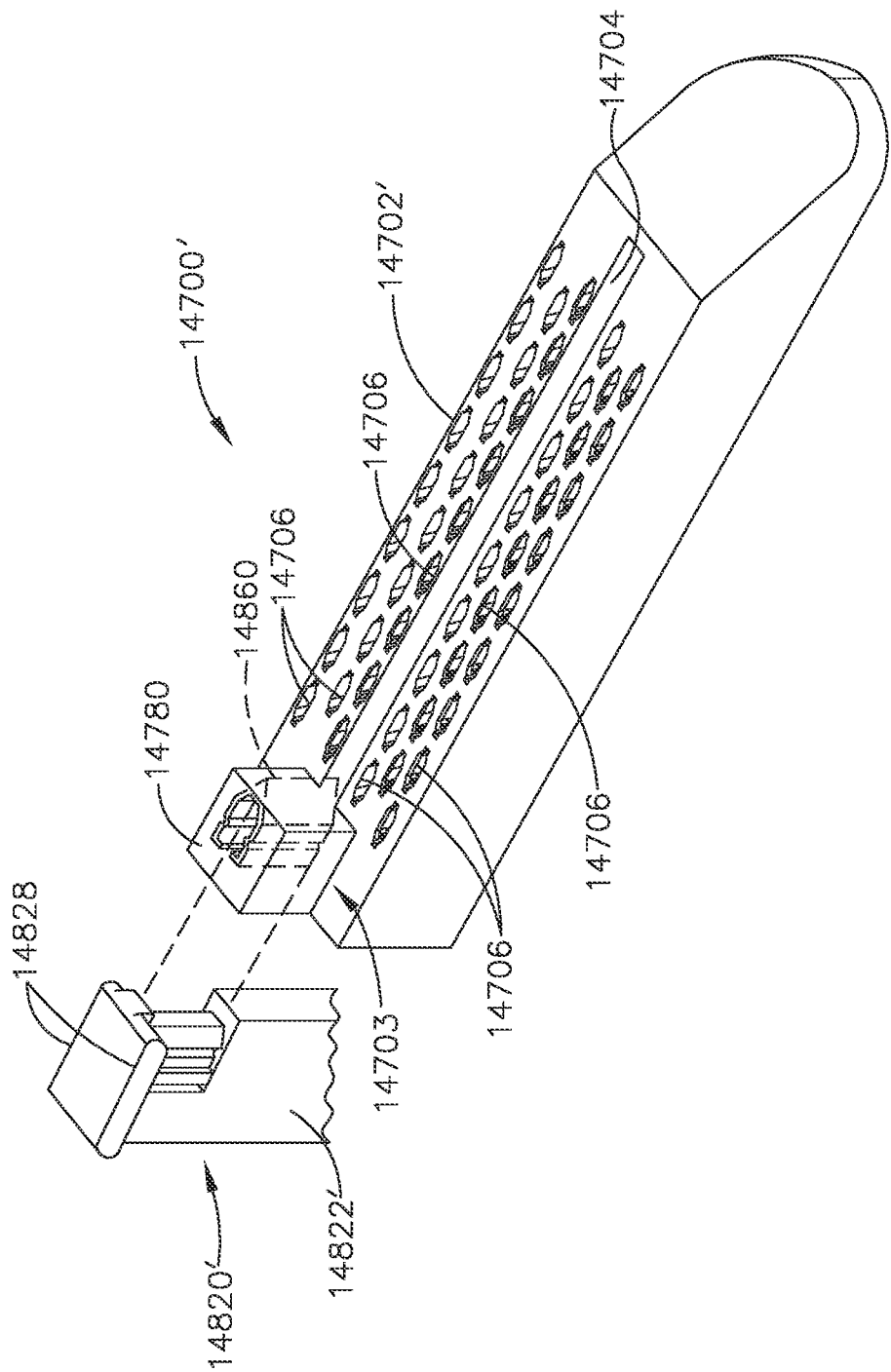

FIG. 124 illustrates one form of a replaceable staple cartridge 14700' that is substantially identical to the staple cartridge 14700 described in detail above except for the differences discussed below. The staple cartridge 14700' may be used in connection with the surgical instrument 14000 described above, for example. In one aspect, the surgical instrument 14000 includes a firing member 14820' that is very similar to firing member 14820 described above, except for the differences discussed below. The firing member 14820' comprises a body portion 14822' that includes two downwardly extending hollow mounting portions that are unthreaded and spaced from each other to receive a threaded drive nut therebetween. The threaded drive nut is configured to threadably engage the threaded segments of the rotary firing drive shaft in the manner described above. The firing member 14820' has a pair of channel engagement tabs that extend laterally from the bottom of the firing member body 14822' and a pair of anvil engaging tabs 14828 extend from the top portion of the firing member body 14822' such that the firing member 14820' resembles an I-beam configuration when viewed from an end thereof.

Still referring to FIG. 124, the surgical staple cartridge 14700' comprises an elongate cartridge body 14702' that has a centrally disposed elongate cartridge slot 14704 that is configured to accommodate the axial travel of the firing member 14820' therein. Also in the illustrated example, three lines of surgical staple pockets 14706 are formed on each side of the elongate slot 14704. Each staple pocket 14706 may have a staple driver (not shown) associated therewith that supports a surgical fastener (not shown) thereon. In one aspect, the replaceable staple cartridge 14700' includes a replaceable blade structure 14860 that may be specifically tailored to the type and composition of tissue that the cartridge 14700' is intended to cut and staple. More specifically, the cartridge body 14702' includes a blade storage garage 14780 that is formed on a proximal end 14703 of the cartridge body 14702'.

Figure 125:
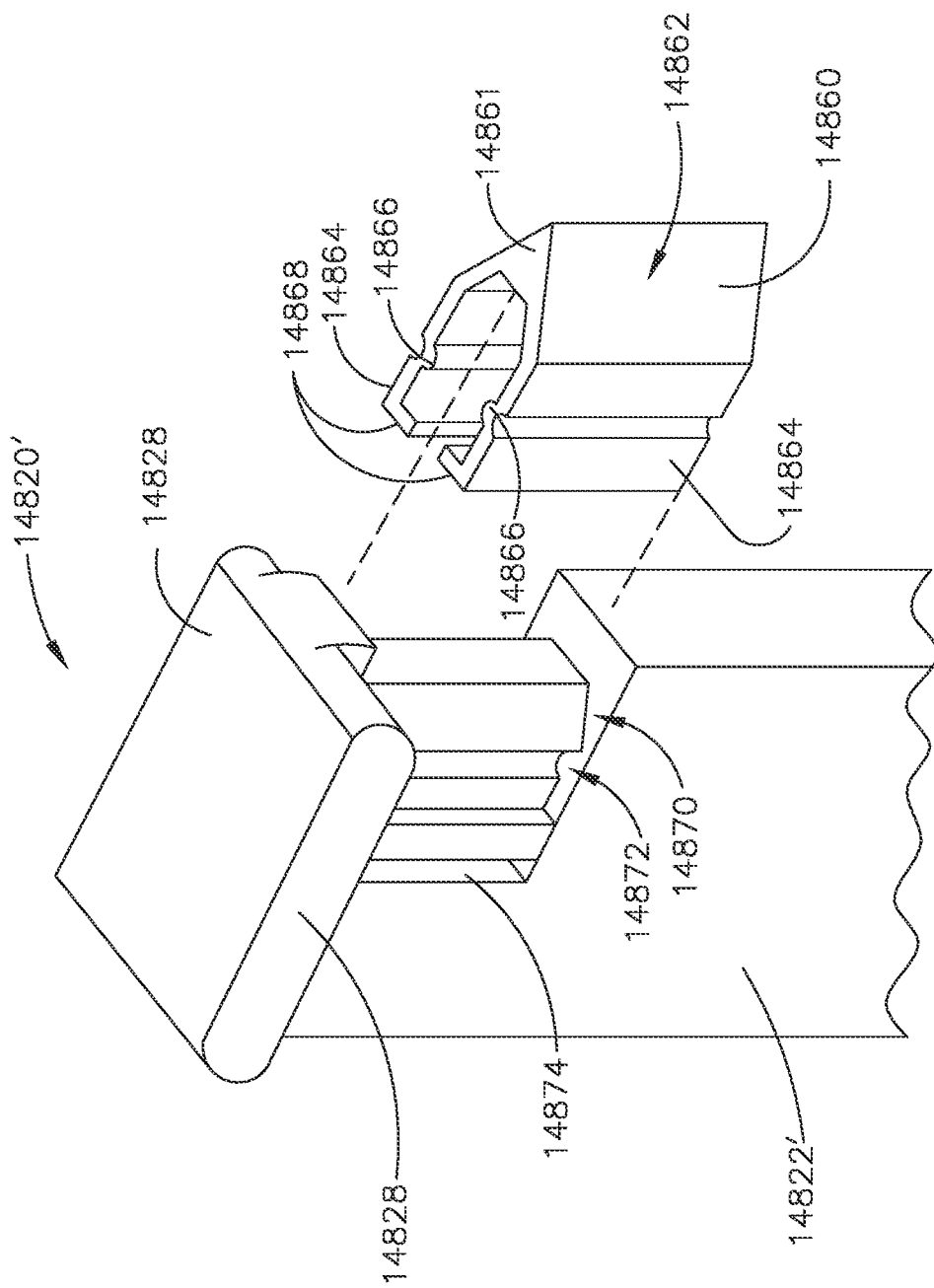
Figure 126:
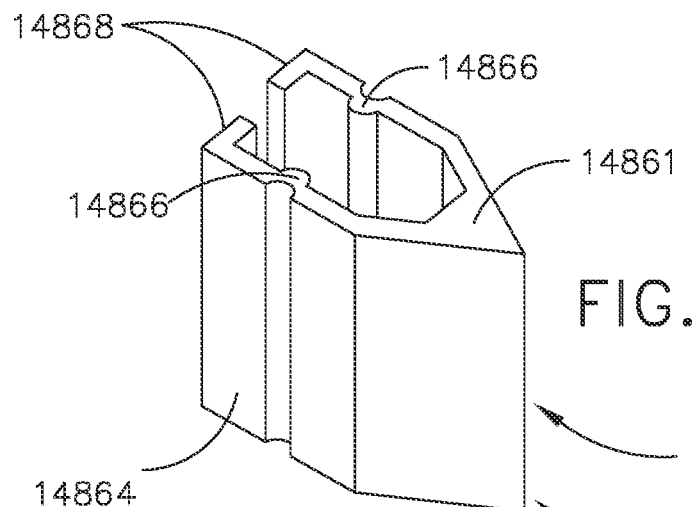

In the illustrated example, the firing member 14820' is configured to removably support a removable blade structure 14860 that is stored in the blade storage garage 14780 in the cartridge 14700'. In one aspect, the removable blade structure 14860 comprises a blade body 14861 that terminates in a tissue cutting edge 14862. See FIGS. 125 and 126. The blade body 14861 additionally comprises two flexible attachment legs 14864 that each has a locating detent 14866 and a retainer tab 14868 thereon. As can be seen in FIG. 125, the upper portion of the firing member body 14822' is formed with a blade mounting feature 14870 that is configured to snappingly receive the blade structure 14860 thereon. The blade mounting feature 14870 includes locating grooves 14872 corresponding to the locating detents 14866 on the blade body 14861 and two latch cavities 14874 that correspond to the retainer tabs 14868 on the blade body 14861.

Turning to FIG. 127, the blade structure 14860 is stored in a cavity 14782 in the blade storage garage 14780. The firing member body 14822' is sized to pass through an opening 14784 that is defined between two inwardly extending ejection tabs 14786 that are formed in a proximal end 14781 of the blade storage garage 14780. When the surgical staple cartridge 14700' is initially installed in the elongate channel of the surgical end effector, the firing member 14820' is in a starting position which is proximal to the proximal end 14781 of the blade storage garage 14780. Initial actuation of the firing member 14820' in the distal direction DD will cause the blade mounting feature 14870 to enter through the opening 14784 in the blade storage garage 14780 into engagement with the blade structure 14860 therein. See FIG. 127. Continued distal advancement of the firing member 14820' will cause the blade structure 14860 to snap into engagement with the blade mounting feature 14870 such that the blade structure 14860 travels with the firing member 14820' axially down the slot 14704 to cut tissue that is clamped between the anvil and the surgical staple cartridge 14700'. See FIG. 128. As can be seen in FIG. 128, the retainer tabs 14868 are seated in the corresponding latch cavities 14874 in the blade mounting feature 14870. The blade structure 14860 is sized relative to the axial slot 14704 in the cartridge body 14702' such that the retainer tabs 14868 are tightly retained in their respective latch cavities 14874 during firing and retraction back into the blade storage garage 14780. FIG. 129 depicts the retraction of the firing member 14820' in the proximal direction PD. As can be seen in FIG. 128, when the retainer tabs 14868 contact the rejection tabs 14786, the retainer tabs 14868 are prevented from moving proximally to enable the blade mounting feature 14870 to disengage the blade structure 14860. In one aspect, the cavity 14782 in the blade storage garage 14780 is wider than the slot 14704 in the cartridge body 14702' to thereby enable the flexible attachment legs 14864 of the blade structure 14860 to splay laterally outward and disengage the blade mounting feature 14870. Thus, the blade structure 14860 remains in the blade storage garage 14780 to be discarded with the spent staple cartridge 14700'.

Figure 130:
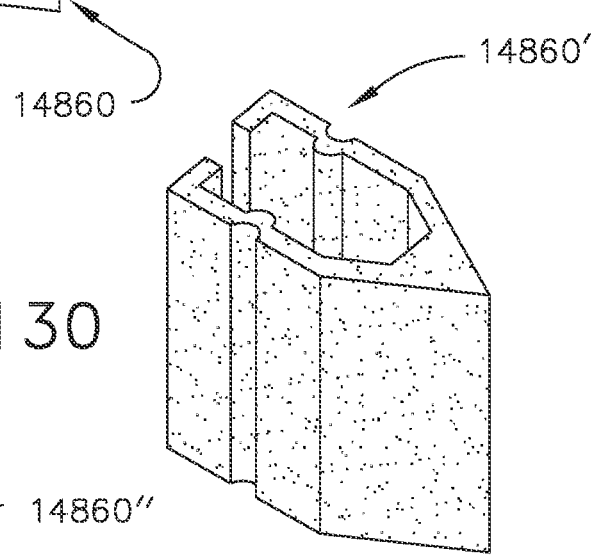

The replaceable staple cartridges 14700' may contain a particular blade structure that is specifically tailored to the type and composition of the tissue to be cut. For example, a blade structure 14860' that is fabricated from hardened metal may be used in applications wherein the blade structure may have to transect staple lines. See FIG. 130. In applications wherein the blade may have to cut through a buttress material, a blade structure 14860" that has a serrated cutting edge 14862" may be advantageously employed. See FIG. 131. Such arrangement provides the user with a fresh blade with each new staple cartridge.

FIG. 132 illustrates another form of a replaceable staple cartridge 13700' that is substantially identical to the staple cartridge 13700 described above except for the differences discussed below. The staple cartridge 13700' may be used in connection with the surgical instrument 13000 described above, for example. In one aspect, the staple cartridge 13700' includes an onboard firing member 13820' that is identical to firing member 13820 described above, except for the differences discussed below. In the manner discussed above, for example, the firing member 13820' comprises a vertically extending firing member body 13822' that is configured to be axially driven within the surgical staple cartridge 13700' by an onboard rotary firing drive shaft 13710 as described herein. The firing member 13820' has a pair of channel engagement tabs that extend laterally from the bottom of the firing member body 13822' and a pair of anvil engagement tabs 13828 extend from the top portion of the firing member body 13822 such that the firing member 13820' resembles an I-beam configuration when viewed from an end thereof.

Still referring to FIG. 132, the surgical staple cartridge 13700' comprises an elongate cartridge body 13702' that has a centrally disposed elongate cartridge slot 13704 that is configured to accommodate the axial travel of the firing member 13820' therein. Also in the illustrated example, three lines of surgical staple pockets 13706 are formed on each side of the elongate slot 13704. Each staple pocket 13706 may have a staple driver (not shown) associated therewith that supports a surgical fastener (not shown) thereon. In one aspect, the firing member 13820' is configured to removably support a removable blade structure 14860 in the manner described above. The blade structure 14860 is stored in a blade storage garage 13780 that is formed in the proximal end 13701 of the cartridge body 13702' as was discussed in detail above. In this case however, the blade structure 14860 remains on the onboard firing member 13820' and may be discarded with the cartridge and onboard firing member 13820'.

FIGS. 133-140 depict a surgical end effector 20012 that may be used for example in connection with the powered surgical instrument 5010 described above. The surgical end effector 20012 may also be effective employed with various other rotary powered or robotically powered surgical systems which are disclosed in the various references incorporated herein by reference. Those components shown in FIGS. 133-140 that are identical to the components of the powered surgical instrument 5010 have been labeled with like component numbers. In the illustrated example, the surgical end effector 20012 comprises an elongate channel 20020 that is configured to operably support a surgical staple cartridge 20040 therein. The elongate channel 20020 is similar to channel 5022 described above, except for the noted differences. Turning to FIG. 134, the elongate channel 20020 comprises a pair of spaced upstanding walls 20022 and a bottom 20024. A helical screw shaft 5036 is supported in the channel 20020 by a bearing 5038 which enables the helical screw shaft 5036 to freely rotate with respect to the channel 20020. The surgical end effector 20012 further comprises an anvil 5024 that has pivot pins or trunnions 5025 that are received in corresponding slots 20026 provided in the upstanding channel walls 20022.

In the illustrated arrangement, the staple cartridge 20040 includes an elongate cartridge body 20042 that is sized to be removably seated in the elongate channel 20020. The cartridge body 20042 includes a cartridge slot 20050 that extends from a proximal end portion 20046 to a distal end portion 20044 of the cartridge body 20042. The cartridge body 20042 further comprises a cartridge deck surface 20043 that confronts a staple-forming undersurface 5029 of the anvil 5024 when the cartridge 20040 is seated in the channel 20020 and the anvil 5024 is pivoted to a closed position. Also in the illustrated example, three lines of surgical staple pockets 20052 are formed on each side of the cartridge slot 20050 and open through the cartridge deck surface 20043. Each staple pocket 20052 may have a staple driver (not shown) associated therewith that supports a surgical staple or fastener (not shown) thereon.

Still referring to FIG. 134, the staple cartridge 20040 further includes a camming assembly 20060 that comprises a camming assembly body 20062 that has a passage 20064 therethrough that is configured to straddle the helical screw shaft 5036 without affecting the rotation thereof. In other embodiments, the camming assembly 20060 may have a series of internal threads (not shown) that are configured to threadably engage the helical screw shaft 5036 to be driven thereby. In such arrangements, for example, the helical screw shaft 5036 may be provided with an unthreaded portion that corresponds to a starting position of the camming assembly 20060. Such camming assembly arrangements are further described in various references that have been herein incorporated by reference. In the illustrated example, the camming assembly 20060 is driven distally through the cartridge body 20042 by a firing member 20120.

As can further be seen in FIG. 134, the camming assembly body 20062 includes a series of cam members 20066 that are aligned with corresponding staple drivers supported in lines within the staple cartridge body 20042. In the illustrated example, the camming assembly 20060 includes an onboard tissue cutting member or blade 20068. The tissue cutting member 20068 extends above the deck surface 20043 so that as the camming assembly 20060 is driven distally, the tissue cutting member 20068 cuts the tissue that is clamped between the anvil 5024 and the staple cartridge 20040. When the staple cartridge is "fresh" or new (i.e., the cartridge has never been fired and contains staples or fasteners therein ready to be fired), the camming assembly 20060 is in a starting position within the cartridge 20040. When the camming assembly 20060 is in the starting position, the tissue cutting member 20068 is located within a garage portion 20048 formed on the proximal end portion 20046 of the cartridge body 20042 to prevent injury when handling the fresh cartridge 20040. In one aspect, the cam members 20066 extend distally beyond the tissue cutting member 20068 such that the staples or fasteners are deployed through the tissue before the tissue cutting member 20068 cuts through the tissue. Thus, the clamped tissue is stapled and thereafter cut as the firing member 20120 and camming assembly 20060 are driven distally. Once the firing member 20120 and the camming assembly 20060 have been driven into their distal-most ending positions, the firing member 20120 may be retracted back to its starting position by rotating the helical screw shaft 5036 in a reverse rotary direction while the camming assembly 20060 remains in its ending position. In at least one arrangement, the tissue cutting member 20068 is movable from a deployed cutting position to a storage position wherein the tissue cutting member 20068 is stored below the cartridge deck surface 20043 to prevent injury when handling the fired or spent cartridge 20040. For example, a retraction member (not shown) may be strategically located in the distal end 20044 of the cartridge body 20042 to contact and move the tissue cutting member 20068 from the deployed position to the storage position when a portion of the tissue cutting member 20068 is brought into contact with the retraction member.

FIG. 135 depicts one form of a firing member 20120. As can be seen in FIG. 135, the firing member 20120 comprises a body portion 20122 that includes two downwardly extending hollow mounting portions 20124 that are unthreaded and spaced from each other to receive a threaded drive nut 20130 therebetween. The threaded drive nut 20130 is configured to threadably engage the helical screw shaft 5036. The drive nut 20130 includes a vertical tab portion 20131 that is sized to extend through an axial slot 20025 (FIG. 134) in the bottom 20024 of the elongate channel 20020. Two laterally extending retention flanges 20134 are formed on the threaded drive nut 20130 and are configured to engage the bottom 20024 of the elongate channel 20020. In addition, two laterally extending anvil engagement tabs 20126 are formed on the top of the firing member body 20122 and are configured to engage corresponding ledges 20102 formed in the anvil 5024 as the firing member 20120 is axially moved within the surgical end effector 20012.

As can also be seen in FIG. 135, the firing member 20120 may also be equipped with an onboard firing member lockout assembly 20140 that comprises a lockout member 20142 that is pivotally coupled to the firing member body 20122. The lockout member 20142 includes a sled latch 20148 that is configured to be engaged by the camming assembly 20060 when the camming assembly 20060 is in an unfired position. As can be seen in FIGS. 136 and 137, the camming assembly 20060 includes a firing member ledge 20061 configured to engage the sled latch 20148 on the lockout member 20142. A lockout spring 20150 is mounted in the elongate channel 20020 and is configured to bias the lockout member 20142 downward such that if the camming assembly 20060 is not in its unfired starting position, the lockout member 20142 contacts lockout lugs 20028 that are formed on portions of the inside surface of each upstanding sidewall 20022 of the elongate channel 20020. See FIG. 139. When in that position, should the user inadvertently attempt to distally advance the firing member 20120, the lockout member 20142 contacts the lockout lugs 20028 on the channel 20020 to prevent the distal advancement of the firing member 20120.

FIG. 136 illustrates the initial insertion of a fresh unfired surgical staple cartridge 20040 into the channel 20020. As can be seen in FIG. 136, the camming assembly 20060 is in a starting position and the proximal end portion 20046 of the surgical staple cartridge 20040 is inserted at an angle relative to the channel 20020 and then pushed in the proximal direction PD until the firing member ledge 20061 on the camming assembly 20060 unlockingly engages the sled latch portion 20148 of the lockout member 20142. FIGS. 137 and 138 illustrate the surgical staple cartridge 20040 in a properly installed position. As can be seen in FIG. 137, the firing member lockout assembly 20140 is in an unlocked position. Rotary actuation of the helical screw shaft 5036 in a first rotary direction will cause the firing member 20120 to move distally in the distal direction DD. As the firing member 20120 moves distally, the camming assembly 20060 is also driven distally thereby. The cam members 20066 cam the drivers stored in the cartridge 20040 upward in the cartridge body 20042. As the drivers are cammed upwardly, the staples or fasteners supported thereon are driven through the tissue that has been clamped between the anvil 5024 and the cartridge 20040 and into forming contact with the staple-forming undersurface 5029 on the anvil 5024. The stapled tissue is then cut by the tissue cutting member 20068. Once the firing member 20120 has been driven to its distalmost position in the cartridge 20040, the helical screw shaft 5036 may be rotated in a second opposite rotary direction to retract the firing member 20120 back to its beginning position. The camming assembly 20060 remains in the distal end portion 20044 of the cartridge body 20042. The spent cartridge 20040 may then be removed from the channel 20020.

FIG. 138 illustrates the end effector 20012 after the spent cartridge has been removed from the channel 20020. As can be seen in FIG. 138, the spring 20150 biases the lockout member 20142 of the firing member lockout assembly 20140 into locking engagement with the lockout lugs 20028 in the channel 20020. Should the user attempt to fire the surgical end effector 20012 (distally advance the firing member 20120), the lockout member 20142 will prevent the firing member 20120 from moving distally. Likewise, should the user attempt to reuse the spent cartridge, because the camming assembly 20060 is not in the starting position, the firing member lockout assembly 20140 will prevent the distal advancement of the firing member 20120.

In the illustrated arrangement, the lockout member 20142 is pivotally coupled to the firing member body 20122 by pivot pins 20143 that are received in a hole 20123 extending through the firing member body 20122. See FIGS. 138 and 140. In at least one arrangement, the pivot pins 20143 are sized relative to the holes 20123 in the firing member body 20122 to facilitate free pivotal travel of the lockout member 20142 and to account for tolerance differences of the components. As can be seen in FIG. 138, the firing member 20120 includes a proximally-facing, firing surface 20145 that is configured to abut a distal-facing bearing surface 20125 on the firing member body 20122 when the firing member lockout assembly 20140 is in the unlocked position. Thus, when the firing member 20120 is advanced distally, the resistive forces encountered by the camming assembly 20060 during its distal movement are directly applied to the distal-facing bearing surface 20125 on the firing member body 20122. Such arrangement may prevent the transfer of these resistive forces back to the pivot pins 20143, which might cause the pivot pins 20143 to fail under such load. Similarly, as can be seen in FIG. 140, the proximally-facing angled bearing surface 20145 of the firing member 20120 is configured to abut the distal-facing bearing surface 20125 on the firing member body 20122 when the firing member lockout assembly 20140 is in the locked position. Such arrangement may prevent the transfer of the resistive locking forces resulting from the locking engagement of the lockout member 20142 with the lock lugs 20028 back to the pivot pins 20143, which might cause the pivot pins 20143 to fail under such load. The loose fit between the pins 20143 and the hole 20123 in the firing member body 20122 facilitate some translation of the lockout member 20142 when under load to facilitate transfer of the loads into the firing member body 20122 and not to the pins 20143 themselves.

In another arrangement, or in addition to the foregoing described lockout member 20142 arrangement, the amount of current being drawn by the motor used to apply the rotary motions to the helical screw shaft 5036 is monitored. Once the current increases beyond a predetermined threshold, a control circuit for the surgical instrument or robotic system, etc., may stop the motor to prevent any further rotation of the helical screw shaft 5036 and movement of the firing member 20120 to prevent damage to the above-described components.

Some previous firing member lockout arrangements that are configured to prevent advancement of a firing member of the end effector unless a fresh unfired staple cartridge has been properly installed in the surgical end effector, require the user to actively retract the firing member back to is proximal-most beginning position before the anvil is permitted to open. If the user attempts to open the anvil before the firing member is moved back to its proximal-most position, the may not understand why the anvil cannot come open. The above-described arrangement may prevent such confusion.

FIGS. 141-145 depict a surgical end effector 20300 that may be used for example in connection with the powered surgical instrument 1010 described above. The surgical end effector 20300 may also be effective employed with various other robotically powered surgical systems which are disclosed in the various references incorporated herein by reference. Those components shown in FIGS. 141-145 that are identical to the components of surgical instrument 1010 have been labeled with like component numbers. Those construction and function of those components of surgical instrument 1010 that are not necessary to understand the operation of the surgical end effector 20300 will not be repeated herein for the sake of brevity.

Referring to FIGS. 141-145, the surgical end effector 20300 comprises an elongate channel 20310 that is configured to operably support a surgical staple cartridge 20600 therein. In the illustrated example, the elongate channel 20310 comprises a channel bottom 20312 and a pair of upstanding sidewalls 20314. The channel 20310 is coupled to the elongate shaft assembly 1200 (FIG. 5) by a channel mount feature 20340 which may facilitate articulation thereof about articulation joint 3020 (FIG. 5). As can be seen in FIG. 143, in one arrangement for example, the channel mount feature 20340 comprises a body portion 20342 that consists of an upstanding support 20344 that has a slot 20346 extending therethrough to receive the firing member beam 1900 (FIG. 5) therethrough. The channel mount feature 20340 may be movably or pivotally mounted to a proximal end 20316 of the channel 20310 by a channel mount feature, or channel pin 20320. In particular, the channel mount feature 20320 further includes a transverse pin opening 20348 that is configured to be coaxially aligned with holes 20318 in the sidewalls 20314 of the channel 20310 to receive the channel pin 20320 therethrough.

As described above, the shaft assembly 1200 includes a spine 1210 that terminates in an upper lug mount feature 1270 and in a lower lug mount feature 1280. See FIG. 5. The upper lug mount feature 1270 is formed with a lug slot 1272 therein that is adapted to mountingly support an upper mounting link 1274 therein. Similarly, the lower lug mount feature 1280 is formed with a lug slot 1282 therein that is adapted to mountingly support a lower mounting link 1284 therein. The upper mounting link 1274 includes a pivot socket 1276 therein that is adapted to rotatably receive therein a pivot pin 1292 that is formed on a channel cap or anvil retainer 1290 that is attached to the proximal end portion 20316 of the elongate channel 20310. As can be seen in FIG. 143, the channel mount feature 20340 further includes a shaft mount flange 20350 that extends proximally therefrom. In one arrangement for example, the shaft mount flange 20350 has a centrally disposed pivot hole 20352 therethrough that may pivotally receive the lower pivot pin 1286 on the lower mounting link 1284 of the lower lug mount feature 1280 (FIG. 5). The lower pivot pin 1286 is vertically aligned with the pivot socket 1276 to define an articulation axis AA about which the surgical end effector 20300 may articulate relative to the spine 1210. In one arrangement, the proximal articulation driver 2102 (FIG. 5) may be directly coupled to an articulation lug 20354 formed on the shaft mount flange 20350. In other arrangements, the proximal articulation driver 2102 may be attached to one or more articulation links that are attached to the shaft mount flange 20350. In either case, axial movement of the proximal articulation driver 2102 in the above-described manner will cause the channel mount feature to pivot about the articulation axis relative to the spine 1210 (FIG. 5) to articulate the end effector 20300 about the articulation axis AA.

The surgical end effector 20300 further comprises an anvil 20400 that is very similar to anvil 2000 described above, except for the differences discussed below. The anvil 20400 includes an elongate anvil body portion 20402 that has a staple-forming undersurface 20404 and an anvil mounting portion 20410 that is configured to interact with the end effector closure tube 3050 (FIG. 5) in the manner described above. The anvil 20400 is pivotally mounted on the elongate channel 20310 by a pair of laterally extending anvil pins or trunnions 20412 that are received in corresponding elongate trunnion slots 20322 formed in the upstanding channel walls 20314. Axial movement of the end effector closure tube 3050 in a distal direction will cause the anvil 20400 to pivot to a closed position about a pivot axis defined by the anvil trunnions 20412 and movement of the end effector closure tube 3050 in a proximal direction will cause the anvil to pivot to an open position relative to the elongate channel 20310.

FIG. 146 illustrates one form of a staple cartridge 20600 that may be used in connection with the surgical end effector 20300. In at least one arrangement, the surgical staple cartridge 20600 comprises an elongate cartridge body 20602 that is sized to be removably seated in the elongate channel 20310. The cartridge body 20602 includes a cartridge slot 20608 that extends from a proximal end portion 20604 to a distal end portion 20606 (FIG. 141) of the cartridge body 20602. The cartridge body 20602 further comprises a cartridge deck surface 20610 that confronts the staple-forming undersurface 20404 of the anvil 20400 when the cartridge 20600 is seated in the channel 20310 and the anvil 20400 is pivoted to a closed position. Also in the illustrated example, three lines of surgical staple pockets 20612 are formed on each side of the cartridge slot 20608 and open through the cartridge deck surface 20610. Each staple pocket 20612 may have a staple driver (not shown) associated therewith that supports a surgical staple or fastener (not shown) thereon. In at least one example, the cartridge body 20602 is molded from a polymer material with the staple pockets 20612 molded or machined therein. In one arrangement, the staple pockets 20612 also open through a bottom of the cartridge body 20602 to facilitate installation of the drivers and fasteners into their respective pockets 20612. Once the drivers and fasteners are inserted into their respective staple pockets 20612, a cartridge pan 20620 is attached to the bottom of the cartridge body 20602. In one form, the cartridge pan 20620 is fabricated from a metal material and includes a bottom 20622 that spans across the bottom of the cartridge body 20602 and two upstanding sidewalls 20624 that correspond to each side of the cartridge body 20602. The cartridge pan 20620 may be removably affixed to the cartridge body 20602 by a series of hooks 20626 that are formed on the sidewalls 20624 and configured to hookingly engage corresponding portions of the cartridge body 20602. See FIG. 146. When installed, the cartridge pan 20620 may, among other things, prevent the drivers and fasteners from falling out of the bottom of the cartridge body 20602 during handling and installation of the cartridge 20600 into the elongate channel 20310.

As was discussed above in connection with cartridge 20040, cartridge 20600 operably supports a camming assembly therein. The camming assembly comprises a series of spaced cam members that are configured to move axially within corresponding cam slots 20609 formed on each side of the cartridge slot 20608 in the cartridge body 20602. The cam slots 20609 are aligned with corresponding lines of drivers in the cartridge body 20602 to facilitate camming contact with a corresponding cam member as the camming assembly is driven through the staple cartridge 20600 from a beginning position within the proximal end portion 20604 of the cartridge body 20602 to an ending position within the distal end portion 20606.

The example illustrated in FIGS. 144 and 145 also employs a firing member 20500 that is attached to a distal end of the firing member beam 1900 and is configured to operably interface with the camming assembly in the staple cartridge 20600 to driven the camming assembly from its starting position to its ending position within the cartridge 20600. In at least one arrangement, the firing member 20500 is configured to interact with a camming assembly (not shown) in a staple cartridge 20600 that has been properly installed in the elongate channel 20310. For example, the firing member 20500 includes a firing member body 20502 that has a tissue cutting surface or blade 20504 formed thereon or attached thereto. The firing member body 20502 is sized to axially move within an axial anvil slot (not shown) in the anvil 20400 as well as the cartridge slot 20608 in the cartridge body 20602 and a channel slot (not shown) in the elongate channel 20310. A lower foot assembly 20506 that comprises a pair of laterally extending lower flanges 20508 extends from a bottom end of the firing member body 20502 to slidably engage corresponding channel ledges (not shown) that are formed on each side of the channel slot. An upper foot (not shown) that comprises two laterally extending anvil tabs may be formed on an upper end of the firing member body 20502 and is configured to slidably engage anvil ledges (not shown) that are formed on each side of the anvil slot. In at least one arrangement, the firing member 20500 further includes a pair of central tabs 20510 that extend laterally from each side of the firing member body 20502.

Still referring to FIGS. 144 and 145, in one arrangement, the firing member body 20502 is configured with a proximally extending spring tail 20512 that may be configured to operably interface with a firing member lockout spring 20520 that is mounted in the elongate channel 20310 and is configured to bias the firing member 20500 downward (arrow DN) in the elongate channel 20310 into a locked position. When in the locked position, the firing member foot 20506 and/or the central tabs 20510 are misaligned with corresponding passages in the channel 20310 and as such, should the user attempt to distally advance the firing member 20500 when in that locked out state, the firing member 20500 would not move distally due to such misalignment. That is, the foot 20506 and/or central tabs 20510 contact portions of the elongate channel to thereby prevent the distal advancement of the firing member 20500. In one arrangement, a sled latch 20514 is formed on the firing member body 20502 and is configured to be engaged by a corresponding portion formed on a camming assembly that is operably supported in the surgical staple cartridge 20600. When a fresh unfired staple cartridge 20600 with the camming assembly thereof in its starting position has been operably installed in the elongate channel 20310, a portion of the camming assembly engages the sled latch 20514 on the firing member body 20502 and moves the firing member 20500 upward (arrow UP in FIG. 144) into an unlocked position wherein the lower foot assembly 20506 and/or the central tabs 20510 are aligned with their respective passages in the channel 20310 to permit the firing member 20500 to axially advance therein. As the user distally advances the firing member 20500 into the cartridge 20600, the firing member 20500 also drives the camming assembly therein which cams the drivers upward to drive the staples or fasteners supported thereon into forming contact with the underside of the anvil. The tissue cutting member 20504 on the firing member 20500 then cuts through the stapled tissue. Once the firing member 20500 has been driven to its distal-most position corresponding to the ending position of the camming assembly, the firing member 20500 is retracted back to its proximal-most position, leaving the camming assembly in the distal end 20606 of the cartridge 20600. When the firing member 20500 returns to its proximal-most beginning position, the firing member lockout spring 20520 once again biases the firing member 20500 back into its locked position. Thus, should the user inadvertently try to reuse the spent cartridge 20600, the camming assembly is not in its starting position which is required to unlock the firing member 20500.

The surgical end effector 20300 may also employ a closure lockout system 20700 for preventing the anvil 20400 from being moved from an open position to a closed (clamped) position unless a corresponding compatible surgical staple cartridge 20600 has been operably installed in the elongate channel 20310. In the illustrated example, the closure lockout system 20700 comprises an anvil lock 20702 that is configured to move between an anvil locked position and an anvil unlocked position in response to installation of a staple cartridge 20600 therein. FIG. 143 illustrates one form of an anvil lock 20702. The anvil lock 20702 may be fabricated from spring steel or other suitable metal and include a proximal biasing arm 20704 that may be configured to be seated in a transverse spring mounting slot 20343 provided in the body portion 20342 of the channel mount feature 20340. The anvil lock 20702 further includes a distally extending body portion 20706 that has a downwardly extending mounting tab 20708 and an upwardly extending anvil lockout tab 20710 protruding therefrom. As can be seen in FIGS. 141, 142, and 144 the mounting tab 20708 extends into a clearance window 20319 that is formed in the elongate channel 20310.

FIG. 143 illustrates the surgical end effector 20300 without a surgical staple cartridge installed therein. As can be seen in FIG. 143, the proximal biasing arm 20704 has biased the anvil lock 20702 in the distal "anvil locked" position. When in this position, the anvil lockout tab 20710 is aligned with a portion of an anvil lock lug 20414 that is formed on the anvil mounting portion 20410 of the anvil 20400. Should the user attempt to close the anvil 20400, the anvil lock lug 20414 will contact the anvil lockout tab 20710 to thereby prevent any further travel of the anvil 20400 in the closure direction.

Returning to FIG. 145, in at least one arrangement, the staple cartridge 20600 includes an anvil unlocking feature or tab 20630 that protrudes proximally from the cartridge body 20602 and is aligned to unlockingly engage an actuation tab 20712 that is formed on the distal end of the anvil lock 20702 when the cartridge 20600 has been operably installed in the elongate channel 20310. FIG. 144 depicts the surgical staple cartridge 20600 operably installed in the elongate channel 20310. As can be seen in FIG. 145, the anvil unlocking tab 20630 on the staple cartridge body 20602 has contacted the actuation tab 20712 of the anvil lockout 20702 and biased the anvil lockout 20702 in the proximal direction PD to an unlocked position, wherein the anvil lockout tab 20710 is no longer aligned with the anvil lock lug 20414 on the anvil 20400. When in that position, the user may pivot the anvil 20400 to a closed position. Should the user attempt to install an inappropriate cartridge that lacks the anvil unlocking tab 20630 or similar feature designed to unlockingly engage the anvil lockout 20702, the user will be unable to close the anvil 20400 to complete the surgical stapling procedure.

FIG. 147 illustrates an alternative closure lockout system 20700' for preventing an anvil 20400' of a surgical end effector 20300' from being moved from an open position to a closed (clamped) position unless a corresponding proper surgical staple cartridge 20600' has been operably installed in the corresponding elongate channel (not shown). The surgical end effector 20300' is substantially identical to surgical end effector 20300 described above, except for the differences discussed below. The closure lockout system 20700' comprises an anvil lockout 20702' that is substantially identical to anvil lockout 20702 described above, except for the following differences. For example, the anvil lockout 20702 may be fabricated from spring steel or other suitable metal and include a distally extending body portion 20706' that has a spring portion 20707' formed therein. A proximal end of the anvil lockout 20702' has an anchor tab 20703' formed thereon that serves to couple the anvil lockout 20702' to the channel mount feature 20340 (FIG. 143). Additionally, the body portion 20706' includes a downwardly extending mounting tab 20708' and an upwardly extending anvil lockout tab 20710' that protrudes therefrom. An actuation tab 20712' is formed on the distal end of the body portion 20706'.

The surgical staple cartridge 20600' is similar to the surgical staple cartridge 20600 described above and includes a cartridge body 20602' that is sized to be removably seated in the elongate channel 20310. The cartridge body 20602' includes a cartridge slot 20608' that extends from a proximal end portion 20604' to a distal end portion of the cartridge body 20602'. The cartridge body 20602' further comprises a cartridge deck surface 20610' and three lines of surgical staple pockets 20612' located on each side of the cartridge slot 20608'. As can be seen in FIG. 147, the staple pockets 20612', as well as the staples or fasteners therein (not shown) are aligned on pocket axes PA' that are parallel to the cartridge slot 20608'. Thus, the staples/fasteners are applied in lines that are approximately parallel to the cartridge slot 20608' and the tissue cutline. Like surgical staple cartridge 20600, surgical staple cartridge 20600' includes a cartridge pan 20624' and an anvil unlocking feature or tab 20630' that protrudes proximally from the cartridge body 20602'.

Still referring to FIG. 147, the anvil 20400' is similar to anvil 20400, except for the differences discussed below. The anvil 20400' includes an elongate anvil body portion 20402' and an anvil mounting portion 20410' that is configured to interact with the end effector closure tube 3050 (FIG. 5) in the manner described above. The anvil body portion 20402' includes a staple-forming undersurface 20404' that is bisected by an anvil slot 20405' that is configured to accommodate passage of the firing member 20500 therethrough. As can be seen in FIG. 147, the staple-forming undersurface 20404' comprises three lines of staple-forming pockets 20407' that are arranged on forming pocket axes FPA that are a parallel with the anvil slot 20405'. When the anvil 20400' is moved to a closed position, the anvil slot 20405' is vertically aligned with the cartridge slot 20608' to permit passage of the firing member 20500 therethrough. The lines of staple-forming pockets 20407' are aligned with the staple pockets 20612' such that as the staples are driven from the cartridge 20600', they contact a corresponding pair of staple-forming pockets 20407' to be crimped. Thus, the array of staple-forming pockets in the anvil 20400' must correspond to the array of staple pockets 20612' in the cartridge 20600' to ensure that the staples are properly formed. As can be further seen in FIG. 147, in this arrangement, the anvil 20400' includes a downwardly extending anvil lock lug 20414' that is formed distal to the anvil mounting portion 20410' but is otherwise configured to contact the anvil lockout tab 20710' when the anvil lockout 20702' is in the locked position (e.g., no cartridge has been inserted into the channel 20310 or an improper cartridge has been seated in the channel 20310). When the cartridge 20600' has been properly seated in the elongate channel 20310, the anvil unlocking feature 20630' thereon contacts the actuation tab 20712' on the anvil lockout 20702' to bias the lockout 20702' proximally into the unlocked position wherein the anvil lockout tab 20710' is out of locking alignment with the anvil lock lug 20414' to permit the anvil 20400' to be pivoted to the closed position.

FIG. 148 illustrates an alternative closure lockout system 20700" for preventing an anvil 20400" of another surgical end effector 20300" from being moved from an open position to a closed (clamped) position unless a compatible surgical staple cartridge 20600" has been operably installed in the elongate channel 20310. The surgical end effector 20300" is substantially identical to surgical end effector 20300 described above, except for the differences discussed below. The closure lockout system 20700" comprises an anvil lockout 20702" that is substantially identical to anvil lockout 20702 described above, except for the following differences. For example, the anvil lockout 20702" may be fabricated from spring steel or other suitable metal and include a distally extending body portion 20706″ that has a spring portion 20707″ formed therein. A proximal end of the anvil lockout 20702″ has an anchor tab 20703″ formed thereon that serves to couple the anvil lockout 20702″ to the channel mount feature 20340 (FIG. 143). Additionally, the body portion 20706″ includes a downwardly extending mounting tab 20708″ and an upwardly extending anvil lockout tab 20710″ that protrudes therefrom. An actuation tab 20712″ is formed on the distal end of the body portion 20706″.

The surgical staple cartridge 20600″ is similar to the surgical staple cartridge 20600 described above and includes a cartridge body 20602″ that is sized to be removably seated in the elongate channel 20310. The cartridge body 20602″ includes a cartridge slot 20608″ that extends from a proximal end portion 20604″ to a distal end portion of the cartridge body 20602″. The cartridge body 20602″ further comprises a cartridge deck surface 20610″ and two lines of surgical staple pockets 20612″ located on each side of the cartridge slot 20608″. As can be seen in FIG. 148, the staple pockets 20612″, as well as the staples or fasteners therein (not shown), are aligned on pocket axes PA″ that are transverse to the cartridge slot 20608″. Thus, the staples/fasteners are applied in lines that are approximately transverse to the cartridge slot 20608″ and the tissue cutline. Such arrangements of fasteners create "flexible" or "stretchable" staple lines. Further details regarding cartridges for developing flexible or stretchable lines of staples may be found in U.S. patent application Ser. No. 14/498,121, entitled FASTENER CARTRIDGE FOR CREATING A FLEXIBLE STAPLE LINE, now U.S. Pat. No. 9,801,627, the entire disclosure of which is hereby incorporated by reference herein. Like surgical staple cartridge 20600, surgical staple cartridge 20600″ includes a cartridge pan 20624″ and an anvil unlocking feature or tab 20630″ that protrudes proximally from the cartridge body 20602'.

Still referring to FIG. 148, the anvil 20400″ is similar to anvil 20400, except for the differences discussed below. The anvil 20400″ includes an elongate anvil body portion 20402″ and an anvil mounting portion 20410″ that is configured to interact with the end effector closure tube 3050 (FIG. 5) in the manner described above. The anvil body portion 20402″ includes a staple-forming undersurface 20404″ that is bisected by an anvil slot 20405″ that is configured to accommodate passage of the firing member 20500 therethrough. As can be seen in FIG. 148, the staple-forming undersurface 20404″ comprises lines of staple-forming pockets 20407″ that are arranged on forming pocket axes FPA that are transverse to the anvil slot 20405″. When the anvil 20400″ is moved to a closed position, the anvil slot 20405″ is vertically aligned with the cartridge slot 20608″ to permit passage of the firing member 20500 therethrough. The lines of staple-forming pockets 20407″ are aligned with the staple pockets 20612″ such that as the staples are driven from the surgical staple cartridge 20600″, they contact a corresponding pair of forming pockets 20407″ to be crimped. Thus, the array of staple-forming pockets 20407″ in the anvil 20400″ must correspond to the array of staple pockets 20612″ in the cartridge 20600″ to ensure that the staples are properly formed. As can be further seen in FIG. 148, in this arrangement, the anvil 20400″ includes a downwardly extending anvil lock lug 20414″ that is formed or attached to the anvil mounting portion 20410″ and is configured to contact the anvil lockout tab 20710″ when the anvil lockout 20702″ is in the locked position (e.g., no cartridge has been inserted into the channel 20310 or an improper cartridge is inserted in the channel 20310). When the cartridge 20600″ has been properly seated in the elongate channel 20310, the anvil unlocking feature 20630″ thereon contacts the actuation tab 20712″ on the anvil lockout 20702″ to bias the anvil lockout 20702″ proximally into the unlocked position wherein the anvil lockout tab 20710″ is out of locking alignment with the anvil lock lug 20414″ to permit the anvil 20400″ to be pivoted close.

As was discussed above, various surgical staple cartridges may have different arrays of and/or orientations of staples/fasteners therein. The sizes of the staples or fasteners, as well as the number of fasteners may vary from cartridge type to cartridge type depending upon a particular surgical procedure or application. To ensure that the staples are properly crimped or formed, the surgical staple cartridges must be used in connection with corresponding anvils that have the proper array of staple-forming pockets therein. Should a "non-compatible" cartridge be loaded into an end effector that has an anvil that is mismatched to the cartridge, the staples may not be properly formed during the firing process which could lead to catastrophic results. For example, the surgical staple cartridge 20600' depicted in FIG. 147 is matched to or "compatible with" the anvil 20400' shown in FIG. 147. The surgical staple cartridge 20600″ shown in FIG. 148 is matched to or compatible with the anvil 20400″ shown in FIG. 148. However, the surgical staple cartridge 20600″ of FIG. 148 is incompatible with the anvil 20400' shown in FIG. 147, for example.

The closure lockout systems employed in the examples described above may avoid the activation of a mismatched cartridge that has otherwise been loaded into the end effector. For example, the anvil unlocking feature or tab 20630' on the staple cartridge 20600' is located on the left side of the cartridge slot 20608' and is positioned to contact the actuator tab 20712' on the anvil lockout spring 20707' when the cartridge 20600' is properly loaded in the channel 20310 of end effector 20300'. Conversely, the anvil unlocking feature or tab 20630″ on the cartridge 20600″ is located on the right side of the cartridge slot 20608″ and aligned to contact the actuator tab 20712″ on the anvil lockout 20702″ when the cartridge 20600″ is properly loaded in the channel 20310. Should the user load cartridge 20600″ into the channel 20310 of the end effector 20300', anvil unlocking feature or tab 20630″ on the staple cartridge 20600″ will not contact the he actuator tab 20712' on the anvil lockout 20702' to move it into the unlocked position and the user will be unable to pivot the anvil 20400' closed. Likewise, should the user load cartridge 20600' into the channel of the end effector 20300″, anvil unlocking feature or tab 20630' on the staple cartridge 20600' will not contact the he actuator tab 20712″ on the anvil lockout 20702″ to move it into the unlocked position and the user will be unable to pivot the anvil 20400″ closed. If the user unwittingly loads another cartridge that lacks the proper anvil unlocking feature or tab that corresponds to the anvil lockout in the end effector, the user will be unable to close the anvil. The location, shape, length, etc. of the anvil unlocking feature(s) or tab(s) on a surgical staple cartridge may vary from cartridge type to cartridge type and be interrelated to the actuator member (size, location, shape, number, etc.) on the correspond anvil lockout located in a corresponding surgical end effector. For example, the anvil unlocking feature or tab may be integrally formed on the cartridge body, be machined or molded into the cartridge body, be attached to the cartridge body, be attached to or integrally formed on the camming assembly of the cartridge or comprise a portion of the cartridge pan, for example. All such variations are contemplated herein and are intended to be encompassed by the appended claims.

FIGS. 149-153 illustrate a surgical end effector 21300 that is very similar to the surgical end effectors 20300, 20300', 20300" described above, except for the differences discussed below. In this embodiment, for example, the end effector 21300 comprises an elongate channel 21310 that is configured to operably support a surgical staple cartridge 21600 therein. In the illustrated example, the elongate channel 21310 comprises a channel bottom 21312 and a pair of upstanding sidewalls 21314. Although not shown, the channel 21310 may be coupled to the elongate shaft assembly 1200 (FIG. 5) by a channel mount feature 20340 (described above) which may facilitate articulation thereof about articulation joint 3020 (FIG. 5). The surgical end effector 21300 further comprises an anvil 21400 that may be very similar to anvil 20400 described above, except for the differences discussed below. The anvil 21400 includes an elongate anvil body portion 21402 that has a staple-forming undersurface and an anvil mounting portion 21410 that is configured to interact with an end effector closure tube 3050 (FIG. 5) in the manner described above. The anvil 21400 is pivotally mounted on the elongate channel 21310 by a pair of laterally extending anvil pins or trunnions 21412 that are received in corresponding elongate trunnion slots 21320 that are formed in the upstanding channel walls 21314. Axial movement of the end effector closure tube 3050 in a distal direction will cause the anvil 21400 to translate distally until the trunnions 21412 contact the distal ends of their respective trunnion slots 21320 and pivot to a closed position. Conversely, movement of the end effector closure tube 3050 in a proximal direction will cause the anvil 21400 to pivot to an open position relative to the elongate channel 21310.

The end effector 21300 is configured to operably support a surgical staple cartridge 21600 that may be substantially the same as the surgical staple cartridge 20600, except that the anvil unlocking feature or tab 21630 comprises a portion of the cartridge pan 21620. The anvil unlocking feature 21630 is configured to operably interact with an axially movable anvil lock 21702 that is supported by the channel 21310. Turning to FIG. 151, the anvil lock 21702 is supported for axial movement between a distal locked position and a proximal locked position by a guide block 21720 that is attached to a portion of the channel 21310. In one example, anvil lock 21702 may be formed from metal and the guide block 21720 may be fabricated from 40% carbon filled Nylon 6/6 and be attached to the sidewall of 21314 of the channel 21310 by appropriate adhesive or other fastening means. The guide block 21720 may define a guide channel 21722 that is configured to support a locking tab portion 21710 of the anvil lock 21702. The anvil lock 21702 additionally comprises a vertical body portion 21706 that has an actuation tab 21712 formed on a distal end thereof. The anvil lock 21702 is biased to a distal locked position by an extension spring 21730 that is attached to the anvil lock 21702 and the channel sidewall 21314. When no cartridge is present, the extension spring 21730 biases the anvil lock 21702 into a distal locked position wherein the locking tab portion 21710 contacts a portion of the anvil 21400 to prevent the anvil 21400 from pivoting to a closed position. When a proper or compatible cartridge 21600 is loaded into the elongate channel 21310, the unlocking feature or tab 21630 of the cartridge pan 21620 contacts the actuation tab 21712 on the anvil lock 21702 to move the anvil lock 21702 proximally into an unlocked position wherein the locking tab portion 21710 of the anvil lock 21702 no longer prevents pivotal motion of the anvil 21400. As can be seen in FIG. 149, the anvil unlocking feature 21630 of the surgical staple cartridge 21600 is "asymmetric" in design. That is, the anvil unlocking feature 21630 is only located on one side of a proximal end of the cartridge 21600. FIG. 149 illustrates an old relief area 21315 that is present in previous channel arrangements and new relief areas 21317, 21319 that are provided in the channel 21310 to accommodate cartridge 21600 therein.

FIG. 154 illustrates portions of a surgical end effector 21300' that is identical to end effector 21300, except that the end effector 21300' employs an anvil lock 21702' as depicted in FIGS. 155 and 156. In one example, the anvil lock 21702' may be fabricated from 40% carbon filled Nylon 6/6 and include a vertical body portion 21706' that has a locking portion 21710' formed on the upper end thereof. An actuation tab 21712' is formed on a distal end and a gusset 21714' is also employed to provide additional support to the actuation tab 21712'. As discussed above, when a proper or compatible surgical staple cartridge 21600 is loaded into the elongate channel 21310, the unlocking feature or tab 21630 of the cartridge pan 21620 contacts the actuation tab 21712' on the anvil lock 21702' to move the anvil lock 21702' proximally into an unlocked position wherein the locking portion 21710' of the anvil lock 21702' no longer prevents pivotal motion of the anvil 21400.

FIG. 157 illustrates another surgical end effector 22300 that employs an anvil lockout system 22700. The end effector 22300 is similar to the end effector 20300 described above, except for the noted differences. In this embodiment, the end effector 22300 comprises an elongate channel 22310 that is configured to operably support a surgical staple cartridge 22600 therein. In the illustrated example, the elongate channel 22310 comprises a channel bottom 22312 and a pair of upstanding sidewalls 22314. Although not shown, the channel 22310 may be coupled to the elongate shaft assembly 1200 (FIG. 5) by a channel mount feature 20340 (described above) which may facilitate articulation thereof about articulation joint 3020 (FIG. 5). The surgical end effector 22300 further comprises an anvil 22400 that is very similar to anvil 20400 described above, except for the differences discussed below. The anvil 22400 includes an elongate anvil body portion 22402 and an anvil mounting portion 22410 that is configured to interact with an end effector closure tube 3050 (FIG. 5) in the manner described above. The anvil 22400 is pivotally mounted on the elongate channel 22310 by a pair of laterally extending anvil pins or trunnions 22412 that are received in corresponding elongate trunnion slots 22320 formed in the upstanding channel sidewalls 22314. Axial movement of the end effector closure tube 3050 in a distal direction will cause the anvil trunnions 22412 to translate distally up the trunnion slots 22320 to pivot the anvil 22400 to a closed position. Conversely, movement of the end effector closure tube 3050 in a proximal direction will cause the anvil 22400 to pivot to an open position relative to the elongate channel 22310.

The end effector 22300 is configured to operably support a surgical staple cartridge 22600 that may be substantially the same as the surgical staple cartridge 20600, except that the anvil unlocking feature or tab 22630 is formed on a right side of a proximal end proximal end portion 22604 of the cartridge body 22602 and has a contoured proximal end surface 22632. In the illustrated example, the contoured proximal end surface 22632 has an arcuate shape. The anvil unlocking feature 22630 is configured to operably interact with an axially movable anvil lock 22702 of the anvil lockout system 22700 that is supported by the channel 22310. In the illustrated example, the anvil lock 22702 is supported for axial movement between a distal locked position and a proximal unlocked position within a proximal end portion 22316 of the elongate channel 22310. In the illustrated example, the anvil lock 22702 comprises an elongate body portion 22706 that has an anvil lock tab 22710 formed on a proximal end thereof and configured to lockingly interact with a lock lug 22413 formed on the anvil mounting portion 22410 of the anvil 22400. See FIG. 157. An actuation tab 22712 is formed on a distal end of the body portion 22706. The actuation tab 22712 has a contoured actuation surface 22714 formed therein that is configured to substantially match or mate with the contoured proximal end surface 22632 on the anvil unlocking feature 22630. See FIG. 158.

In at least one arrangement, a spring or biasing member 22730 (leaf spring, coil spring, etc.) may be attached to or mounted within the channel 22310 and configured to bias the anvil lock 22702 in the distal direction DD to the locked position wherein the anvil lock tab 22710 thereon is in blocking alignment with the lock lug 22413 on the anvil mounting portion 22410 to prevent closing of the anvil 22400. When a proper or compatible surgical staple cartridge 22600 is operably loaded into the channel 22310, the anvil unlocking feature or tab 22630 is brought into engagement with the contoured surface 22714 on the actuation tab 22712 of the anvil lock 22702. The surgical staple cartridge 22600 is then moved proximally to seat the cartridge 22600 within the channel 22310. As the surgical staple cartridge 22600 is moved proximally, the anvil unlocking feature 22630 contacts the actuation tab 22712 of the anvil lock 22702 and biases the anvil lock 22702 proximally into the unlocked position wherein the anvil lock tab 22710 thereon is moved out of blocking alignment with the lock lug 22413 on the anvil mounting portion 22410 to permit the anvil 22400 to pivot closed. When the surgical staple cartridge 22600 is removed from the channel 22310, the spring 22730 biases the anvil lock 22702 distally back to the locked position. FIG. 159 illustrates that the contoured proximal end 22632 of the anvil unlocking feature 22630 formed on a right side of the proximal end portion 22604 of the cartridge body 22602 and the matching contoured surface 22714 on the actuation tab 22712 of the anvil lock 22702 enable the cartridge 22600 to facilitate unlocking interaction between the unlocking feature 22630 and actuation tab 22712 even when the cartridge is installed at an installation angle IA relative to the central axis EA of the end effector 22300. See FIG. 159.

FIG. 160 illustrates the attempted use of an incompatible cartridge 22600X that lacks an unlocking feature to move the anvil lock 22702 from the locked position to the unlocked position. As can be seen in FIG. 160, the lockout tab 22710 is in blocking alignment with the lock lug 22413 on the anvil 22400 to thereby prevent the anvil 22400 from being closed even after the cartridge 22600X has been seated in the channel 22310.

FIG. 161 illustrates another surgical end effector 22300' that is substantially identical to surgical end effector 22300 described above, except for the noted differences. The end effector 22300' is configured to operably support a staple cartridge 22600' that is substantially the same as cartridge 20600 and includes an anvil unlocking feature or tab 22630' that has a contoured proximal end surface 22632'. In the illustrated example, the anvil lock 22702' comprises an elongate body portion 22706' that has an anvil lock tab 22710' formed on a proximal end 22711' thereof and configured to lockingly interact with a lock lug 22413' formed on the anvil mounting portion 22410 of the anvil 22400. A distal end 22712' of the anvil lock 22702' includes a contoured actuation surface 22714' formed therein that is configured to substantially match or mate with the contoured proximal end surface 22632' on the anvil unlocking feature 22630' in the manners described above. A spring or biasing member 22730' (leaf spring, coil spring, etc.) may be attached to or mounted within the channel 22310' and configured to bias the anvil lock 22702' in the distal direction DD to the locked position wherein the anvil lock tab 22710' thereon is in blocking alignment with the lock lug 22413' on the anvil mounting portion 22410 to prevent closing of the anvil 22400.

When a proper or compatible surgical staple cartridge 22600' is operably loaded into the channel 22310', the anvil unlocking feature or tab 22630' is brought into engagement with the contoured surface 22714' of the anvil lock 22702'. The cartridge 22600' is then moved proximally in a proximal direction PD to seat the cartridge 22600' within the channel 22310'. As the cartridge 22600' is moved proximally, the anvil unlocking feature 22630' contacts the distal end of the anvil lock 22702' and biases the anvil lock 22702' proximally into the unlocked position wherein the anvil lock tab 22710' thereon is moved out of blocking alignment with the lock lug 22413' on the anvil mounting portion 22410 to permit the anvil 22400 to pivot closed. When the cartridge 22600' is removed from the channel 22310', the spring 22730' biases the anvil lock 22702' distally back to the locked position. As can be seen in FIG. 161, when compared to anvil lock 22702 described above, the anvil lock 22702' has a more robust body portion 22706'. In at least one example, a clearance notch 22709' is provided in the body portion 22706' to provide sufficient clearance for the lock lug 22413' when the anvil 22400 is pivoted to the closed position. In addition, a channel stop 22313' is formed on a bottom 22312' of the channel 22310' and is configured for contact with the proximal end 22711' of the anvil lock 22702' when the anvil lock 22702' is in the unlocked position to prevent the anvil lock 22702' from moving any further proximally to ensure that the lock lug 22413' remains aligned with the clearance notch 22709' in the anvil lock 22702' during closing of the anvil 22400.

FIG. 162 illustrates another surgical end effector 22300" that is substantially identical to surgical end effector 22300 described above, except for the noted differences. The end effector 22300" comprises an elongate channel 22310" that includes an anvil 22400" that is pivotally supported thereon. The channel 22310" is configured to operably support a surgical staple cartridge 22600 that is compatible with the staple-forming undersurface of the anvil 22400" and employs an anvil locking system 22700" that is configured to prevent closure of the anvil 22400" unless a surgical staple cartridge 22600 has been operably installed in the end effector 22300". In the illustrated example, the anvil locking system 22700" includes an anvil lock 22702" that comprises a body portion 22706" that has a distal end portion 22712" that is higher than a proximal portion of the body 22706". When the anvil lock 22702" is in its distal-most locked position, a portion of the anvil 22400" contacts the higher distal end portion 22712" to prevent the anvil 22400" from being closed. The distal end portion 22712" of the anvil lock 22702" includes a contoured actuation surface 22714" that is configured to substantially match or mate with the contoured proximal end surface 22632 on the anvil unlocking feature 22630 formed on the cartridge 22600 in the manners described above. A spring or biasing member 22730" (leaf spring, coil spring, etc.) may be attached to or mounted within the channel 22310" and be configured to bias the anvil lock 22702" in the distal direction DD to the locked position wherein the distal end portion 22712" is in blocking alignment with corresponding portion of the anvil 22400" to prevent closing of the anvil 22400".

When a proper or compatible surgical staple cartridge 22600 is operably loaded into the channel 22310", the anvil unlocking feature 22630 on the cartridge 22600 is brought into engagement with the contoured surface 22714" on the distal end 22712" of the anvil lock 22702". The cartridge 22600 is then moved proximally to seat the cartridge 22600 within the channel 22310". As the cartridge 22600 is moved proximally, the anvil unlocking feature 22630 contacts the distal end 22712" of the anvil lock 22702" and biases the anvil lock 22702" proximally into the unlocked position wherein the distal end portion 22712" is moved out of blocking alignment with the corresponding portion of the anvil 22400" to permit the anvil 22400" to pivot to a closed position. When the cartridge 22600 is removed from the channel 22310", the spring 22730" biases the anvil lock 22702" distally back to the locked position. As can also be seen in FIG. 162, a channel stop 22313" is formed on a bottom 22312" of the channel 22310" and is configured for contact with a proximal end 22711" of the anvil lock 22702" to prevent the cartridge 22600 from being inserted too far proximally into the end effector 22300".

FIGS. 163 and 164 illustrate another surgical end effector 23300 that is similar to the other surgical end effectors described herein with the exception of the various differences noted below. The end effector 23300 comprises an elongate channel 23310 that includes an anvil 23400 that is pivotally supported thereon. The channel 23310 is configured to operably support a surgical staple cartridge 22600 that is compatible to the staple-forming undersurface of the anvil 23400 and employs an anvil locking system 23700 that is configured to prevent closure of the anvil 23400 unless a cartridge 22600 has been operably installed in the end effector 23300. In the illustrated example, anvil locking system 23700 comprises an anvil lock 23702 comprising a body portion 23706 that has a distal end portion 23712. The distal end portion 23712 of the anvil lock 23702 includes a contoured actuation surface 23714 that is configured to substantially match or mate with the contoured proximal end surface 22632 on the anvil unlocking feature 22630 that is formed on the cartridge 22600 in the manners described above. A spring or biasing member 23730 is mounted within the channel 23310 and is configured to bias the anvil lock 23702 in the distal direction DD to a "locked" position.

In the illustrated example, the anvil 23400 includes an elongate anvil body 23402 that an anvil mounting portion 23410 that is configured to interact with the end effector closure tube 3050 (FIG. 5) in the manner described above. The anvil 23400 is pivotally mounted on the elongate channel 22310 by a pair of laterally extending trunnion formations 23412 that are received in corresponding trunnion slots 23320 formed in upstanding sidewalls of the channel 23310. At least one trunnion formation 23412 comprises a laterally protruding actuator lobe 23414 that defines an actuator ledge 23416. A trunnion pin 23418 protrudes outwardly from the actuator lobe 23414 and is sized to translate and pivot within a corresponding trunnion slot 23320.

As can be seen in FIG. 163, at least one trunnion slot 23320 comprises an arcuate actuation portion 23322 and a locking offset portion 23324 that is formed at a proximal end 23321 of the trunnion slot 23320. FIG. 163 illustrates insertion of a cartridge 22600 into the elongate channel 23310. To install a cartridge 22600 into the elongate channel 23310, the anvil 23400 is first moved to an open position. This may be accomplished by actuating the closure system to move the end effector closure tube 3050 (FIG. 5) in a proximal direction PD. As the closure tube 3050 is moved proximally, it interacts with an opening tab 23411 formed on the anvil mounting portion 23410. As the closure tube 3050 interacts with the anvil mounting portion 23410, the anvil 23400 translates proximally and starts to pivot open which results in the trunnion formation 23412 translating down the arcuate actuation portion 23322 of the corresponding trunnion slot 23320 and into the proximal end 23321 of the trunnion slots 23320 when the anvil 23400 reaches its fully open position.

During installation of a proper or compatible surgical staple cartridge 22600 into the channel 23310, the anvil unlocking feature or tab 22630 is brought into engagement with the contoured surface 23714 on the distal end 23712 of the anvil lock 23702. The cartridge 22600 is then moved proximally to seat the cartridge 22600 within the channel 22310. As the cartridge 22600 is moved proximally, the anvil unlocking feature 22630 contacts the distal end 23712 of the anvil lock 23702 and biases the anvil lock 23702 proximally an unlocking distance UD to bring a proximal end 23710 of the anvil lock body 23706 into engagement with actuator lobe 23414 on at least one trunnion formation 23412 to move the trunnion formation 23412 into a position wherein the trunnion formation 23412 can translate up the arcuate actuation portion 23322 of the corresponding trunnion slot 23320 when a closing motion is applied to the anvil mounting portion 23410. Stated another way, the proximal end 23710 of the anvil lock 23702 prevents the trunnion formation 23412 from entering the locking offset portion 23324 formed at the proximal end 23321 of the trunnion slot 23320 to enable the trunnion formation 23412 to progress into the arcuate actuation portion 23322 of the trunnion slot 23320.

FIG. 164 illustrates an attempted insertion of an incompatible cartridge 22600X that lacks the requisite unlocking feature or tab 22630 to move the anvil lock 23702 out of the distal locked position. If the user nonetheless seats the incompatible cartridge 22600X in the channel 23310 and then attempts to close the anvil 23400, the anvil locking system 23700 will prevent closure of the anvil 23400. For example, to close the anvil 23400, the closure system is activated to move the closure tube (or other closure member) distally into operably contact with the anvil mounting portion 23410 of the anvil 23400 to apply closure motions thereto. The initial application of closure motions to the anvil mounting portion 23410 causes the anvil mounting portion 23410 to move downwardly (arrow DL in FIG. 164) which results in the anvil trunnion formations 23412 entering the locking offset portions 23324 formed in the trunnion slots 23320. Thus, the anvil trunnion formations 23412 cannot translate into the arcuate actuation portion 23322 of the corresponding trunnion slot 23320 during the application of the closure motion to the anvil 23400 and the anvil 23400 is then prevented from closing.

FIG. 165 illustrates a portion of an alternative anvil 23400' that comprises an anvil mounting portion 23410' that has trunnion formations 23412' formed thereon. Each trunnion formation 23412' comprises a laterally protruding actuator lobe 23414' that defines an actuator ledge 23416' that is configured to interact with an anvil locking system 23700 in the manner described above. As can be seen in FIG. 165, the actuator ledge 23416' is vertically offset (distance OD) from a bottom surface 23415' of the anvil mounting portion 23410'. A trunnion pin 23418' protrudes outwardly from the actuator lobe 23414' and is sized to translate and pivot within a corresponding trunnion slot 23320. In this example, the trunnion pin 23418' has a trunnion pin diameter TRD that is approximately equal to the width LW of the actuator lobe 23414'.

FIG. 166 illustrates a portion of an alternative anvil 23400" that comprises an anvil mounting portion 23410" that has trunnion formations 23412" formed thereon. Each trunnion formation 23412" comprises a laterally protruding actuator lobe 23414" that defines an actuator ledge 23416" that is configured to interact with an anvil locking system 23700 in the manner described above. As can be seen in FIG. 166, the actuator ledge 23416" is coextensive with (e.g., not offset from) a bottom edge 23415" of the anvil mounting portion 23410". A trunnion pin 23418" protrudes outwardly from the actuator lobe 23414" and is sized to translate and pivot within a corresponding trunnion slot 23320. In this example, the trunnion pin 23418" has a trunnion pin diameter TRD' that is approximately equal to the width LW' of the actuator lobe 23414'.

FIG. 167 is a partial cross-sectional end elevational view of a surgical end effector 24100 that comprises an anvil 24400 that is pivotally supported on an elongate channel 24310. The anvil 24400 comprises an anvil mounting portion 24410 that has trunnion formations 24412 formed thereon. Each trunnion formation 24412 comprises a laterally protruding actuator lobe 24414 that defines a bottom lobe surface 24416 that is configured to interact with an anvil locking system 24700 in the manner described above. As can be seen in FIG. 168, the bottom lobe surface 24416 is vertically offset (distance $OD_1$) from a bottom surface 24415 of the anvil mounting portion 24410. A trunnion pin 24418 protrudes outwardly from the actuator lobe 24414 and is sized to translate and pivot within a corresponding trunnion slot 24320 formed in the elongate channel 24310. In this example, the trunnion pin 24418 has a trunnion pin diameter $TRD_1$ that is approximately equal to the width $LW_1$ of the actuator lobe 24414.

Channel 20310 comprises a channel bottom 24312 and a pair of upstanding sidewalls 24314. The channel 24310 may be coupled to an elongate shaft assembly 1200 (FIG. 5) by a channel mount feature 20340 which may facilitate articulation thereof about articulation joint 3020 (FIG. 5). FIG. 169 illustrates a portion of a proximal end 24316 of the channel 24310. In one example, each channel wall 24314 has a trunnion slot 24320 formed therein. In the illustrated arrangement, a lobe ledge 24340 is formed in each channel wall 24314 such that a top surface 24342 of the lobe ledge 24340 is coextensive with a bottom surface 24321 of the corresponding trunnion slot 24320. Each trunnion 24418 is received within a corresponding trunnion slot 24320 and is free to rotate and translate therein.

Still referring to FIG. 169, a portion of an anvil lock 24702 of the anvil locking system 24700 is shown. The anvil lock 24702 operates in the same manner as the anvil lock 20702 described above and includes a lockout body 24706 that has an actuator tab (not shown) that is formed on a distal end thereof that is configured to be contacted by an unlocking feature that protrudes proximally from a compatible cartridge. The anvil lock 24702 may be fabricated from spring steel or other suitable metal and include a proximal biasing arm 24704 that may be configured to be seated in a transverse spring mounting slot (not shown) that is provided in the body portion of a channel mount feature (not shown). The anvil lock 24702 further includes an upwardly extending anvil lockout tab 24710 that protrudes therefrom that is configured to extend above the corresponding lobe ledge 24340 and contact a corresponding lobe 24414 as will be described below.

FIGS. 169 and 170 illustrate the anvil lock 24702 in the locked position wherein the anvil 24400 is pivoted to an open position. This may occur when no cartridge has been inserted into the channel 24310 or a non-compatible cartridge (e.g. a cartridge that lacks, among other things, the proper anvil unlocking feature that is necessary to bias the anvil lock spring proximally) has been inserted into the channel 24310. Should the user unwittingly attempt to close the anvil 24400 when the anvil lock 24702 is in the distal locked position shown in FIGS. 169 and 170, the corresponding lobe 24414 will contact the anvil lockout tab 24710 and prevent the anvil 24400 from pivoting to the closed position. FIGS. 171 and 172 illustrate the position of the anvil lock 24702 in the proximal unlocked position wherein the anvil lockout tab 24710 is positioned proximal to the lobe 24414 to permit the lobe 24414 to pivot to the closed position.

FIG. 173 is a partial cross-sectional end elevational view of a surgical end effector 24100' that comprises an anvil 24400' that is pivotally supported on an elongate channel 24310'. The anvil 24400' comprises an anvil mounting portion 24410' that has trunnion formations 24412' formed thereon. Each trunnion formation 24412' comprises a laterally protruding actuator lobe 24414' that defines a bottom lobe surface 24416' that is configured to interact with an anvil locking system 24700' in the manner described above. As can be seen in FIG. 174, the bottom lobe surface 24416' is coextensive with a bottom surface 24415' of the anvil mounting portion 24410'. A trunnion pin 24418' protrudes outwardly from the actuator lobe 24414' and is sized to translate and pivot within a corresponding trunnion slot 24320' formed in the elongate channel 24310'. In this example, the trunnion pin 24418' has a trunnion pin diameter $TRD_2$ that is smaller than the width $LW_2$ of the actuator lobe 24414'.

Channel 20310' comprises a channel bottom 24312' and a pair of upstanding sidewalls 24314'. The channel 24310' may be coupled to an elongate shaft assembly 1200 (FIG. 5) by a channel mount feature 20340 which may facilitate articulation thereof about articulation joint 3020 (FIG. 5). FIG. 175 illustrates a portion of a proximal end 24316' of the channel 24310'. In one example, each channel wall 24314' has a trunnion slot 24320' formed therein. In the illustrated arrangement, a lobe ledge 24340' is formed in each channel wall 24314' such that a top surface 24342' of the lobe ledge 24340' is offset vertically from a bottom surface 24321' of the corresponding trunnion slot 24320' an offset distance OSD. Offset distance OSD may be approximately equal to a distance TSD between the trunnion pin 24418' and the bottom lobe surface 24416'. See FIG. 174. Each trunnion pin 24418' is received within a corresponding trunnion slot 24320' and is free to rotate and translate therein.

Still referring to FIG. 175, a portion of an anvil lock 24702' of the anvil locking system 24700' is shown. The anvil lock 24702' operates in the same manner as the anvil lock 20702 described above and includes a lockout body 24706' that has an actuator tab (not shown) formed on a distal end thereof that is configured to be contacted by an unlocking feature that protrudes proximally from a compatible cartridge. The anvil lock 24702' may be fabricated from spring steel or other suitable metal and include a proximal biasing arm 24704' that may be configured to be seated in a transverse spring mounting slot (not shown) provided in the body portion of a channel mount feature (not shown). The anvil lock 24702' further includes an upwardly extending anvil lockout tab 24710' that protrudes therefrom that is configured to extend above the corresponding lobe ledge 24340' and contact a corresponding lobe 24414' as was described above.

FIG. 175 illustrates the anvil lock 24702' in the locked position wherein the anvil 24400 is pivoted to an open position. This may occur when no cartridge has been inserted into the channel or a non-compatible cartridge (e.g. a cartridge that lacks, among other things, the proper anvil unlocking feature that is required to bias the anvil lock spring proximally) has been inserted into the channel 24310'. Should the user unwittingly attempt to close the anvil 24400' when the anvil lock 24702' is in the distal locked position shown in FIG. 169, the corresponding lobe 24414' will contact the anvil lockout tab 24710' and prevent the anvil 24400' from pivoting to the closed position. Once a compatible surgical staple cartridge has been loaded into the end effector 24100', the anvil lock 24702' will be biased to the unlocked position (see e.g., FIG. 171) and the anvil 24400' will be free to pivot to the closed position.

FIG. 176 depicts a portion of a surgical end effector 24100" that comprises an anvil 24400" that is pivotally supported on an elongate channel 24310". The anvil 24400" comprises an anvil mounting portion 24410" that has trunnion formations 24412" formed thereon. As can be seen in FIGS. 177 and 178, each trunnion formation 24412" comprises a laterally protruding actuator lobe 24414" that defines a bottom lobe surface 24416" that is configured to interact with an anvil locking system 24700" in the manner described above. As can be seen in FIG. 177, the actuator lobe 24414", as well as the bottom lobe surface 24416" of the actuator lobe 24414", are located at an angle relative to an end effector axis EA as well as a bottom edge 24419" of the anvil mounting portion 24410" and/or the bottom 24312" of the channel 24310". As further illustrated in FIG. 177, the bottom lobe surface 24416" is parallel to a lobe axis LBA that is located at a lobe angle LA relative to the end effector axis EA. A trunnion pin 24418" protrudes outwardly from the actuator lobe 24414" and is sized to translate and pivot within a corresponding trunnion slot 24320" that is formed in the elongate channel 24310". See FIG. 179. In this example, the trunnion pin 24418" has a trunnion pin diameter $TRD_3$ that is equal to the width $LW_3$ of the actuator lobe 24414".

Referring to FIG. 179, the channel 24310" comprises a channel bottom 24312" and a pair of upstanding sidewalls 24314". The channel 24310" may be coupled to an elongate shaft assembly 1200 (FIG. 5) by a channel mount feature 20340 which may facilitate articulation thereof about articulation joint 3020 (FIG. 5) in the various manners described herein. FIG. 179 illustrates a portion of a proximal end 24316" of the channel 24310". In one example, each channel wall 24314" has a trunnion slot 24320" formed therein. In the illustrated arrangement, a lobe ledge 24340" is formed in each channel wall 24314" such that a proximal surface portion 24344" of a top surface 24342" of the lobe ledge 24340" is coextensive with a bottom surface 24321" of the corresponding trunnion slot 24320". In the illustrated arrangement, the bottom surface 24321" of the trunnion slot 24320" is approximately parallel to the end effector axis EA and/or the bottom 24312" of the channel 24310". As can be seen in FIG. 180, a ramped portion 24346" of the top surface 24342" extends distally from the proximal surface portion 24344" at an angle TSA and terminates in a horizontal distal surface portion 24348". In one arrangement, for example, the distal surface portion 24348" is approximately parallel with the end effector axis EA and/or the bottom 24312" of the channel 24310" and the angle TSA=angle LA. However, angle TSA may be different from angle LA in other embodiments. Each trunnion 24418" is received within a corresponding trunnion slot 24320" and is free to rotate and translate therein.

Referring to FIGS. 179 and 180, a portion of an anvil lock 24702" of the anvil locking system 24700" is shown. The anvil lock 24702" operates in the same manner as the anvil lock 20702 described above and includes a lockout body 24706" that has an actuator tab (not shown) formed on a distal end thereof that is configured to be contacted by an unlocking feature that protrudes proximally from a compatible surgical staple cartridge. The anvil lock 24702" may be fabricated from spring steel or other suitable metal and include a proximal biasing arm 24704" that may be configured to be seated in a transverse spring mounting slot (not shown) that is provided in the body portion of a channel mount feature (not shown). The anvil lock 24702" further includes an upwardly extending anvil lockout tab 24710" that protrudes therefrom and is configured to extend above the distal surface portion 24348" of the corresponding lobe ledge 24340" and be even or level with the proximal surface portion 24344" of the lobe ledge 24340".

FIG. 179 illustrates the anvil lock 24702' in the distal, locked position with the anvil 24400" pivoted to an open position. This may occur when no surgical staple cartridge has been inserted into the channel 24310" or a non-compatible surgical staple cartridge (e.g., a surgical staple cartridge that lacks, among other things, a proper anvil unlocking feature required to bias the anvil lock 24702" proximally) has been inserted into the channel 24310". When the anvil lock 24702" is in that position, the anvil trunnions 24418" are located in the proximal end of their respective trunnion slot 24320" and the bottom lobe surface 24416" of at least one lobe 24414" is resting on the proximal surface portion 24344" of the corresponding lobe ledge 24340" as well as on the anvil lockout tab 24710". Should the user unwittingly attempt to close the anvil 24400" when the anvil lock 24702" is in the distal, locked position shown in FIGS. 176 and 179, the anvil lockout tab 24710" will prevent the lobe 24414" from pivoting downward onto the ramp surface portion 24346" of the lobe ledge 24340" which prevents the anvil 24400" from pivoting to the closed position. See FIG. 176. Once a compatible surgical staple cartridge has been loaded into the end effector 24100", the anvil lockout feature thereon will bias the anvil lock 24702" proximally into to the unlocked position. See FIGS. 180 and 181. When the anvil lock 24702" is in the proximal unlocked position, the anvil lock out tab 24710" is locked proximal to the ramp surface 24346" on the lobe ledge 24340" to thereby permit the lobe 24414" to pivot downwardly thereon which results in the closure of the anvil 24400".

FIG. 182 depicts a proximal portion of another anvil 24400''' that is configured to be pivotally supported in an elongate channel 24310''' that is similar to channel 24310" except for the differences discussed below. The anvil 24400''' comprises an anvil mounting portion 24410''' that has trunnion formations 24412''' formed thereon. Each trunnion formation 24412''' comprises a laterally protruding actuator lobe 24414''' that defines a bottom lobe surface 24416''' that is configured to interact with an anvil locking system 24700" in the manner described above. The actuator lobe 24414''' as well as the bottom lobe surface 24416''' of the actuator lobe 24414''' are located at an angle that is the same as the angle LA described above with respect to actuator lobe 24414". A trunnion pin 24418''' protrudes outwardly from the actuator lobe 24414''' and is sized to translate and pivot within a corresponding trunnion slot

24320''' that is formed in the elongate channel 24310'''. See FIG. 183. In this example, the trunnion pin 24418''' has a trunnion pin diameter $TRD_4$ that is equal to the width $LW_4$ of the actuator lobe 24414'''.

As can be seen in FIG. 183, the channel 24310''' comprises a channel bottom 24312''' and a pair of upstanding sidewalls 24314'''. The channel 24310''' may be coupled to an elongate shaft assembly 1200 (FIG. 5) by a channel mount feature 20340 which may facilitate articulation thereof about articulation joint 3020 (FIG. 5). FIG. 183 illustrates a portion of a proximal end 24316''' of the channel 24310'''. In one example, each channel wall 24314''' has a trunnion slot 24320''' formed therein. In the illustrated arrangement, a lobe ledge 24340''' is formed in each channel wall 24314''' such that a top surface 24342' of the lobe ledge 24340''' is offset vertically from a bottom surface 24321''' of the corresponding trunnion slot 24320''' an offset distance $OSD_1$. Offset distance $OSD_1$ may be approximately equal to a distance between the trunnion 24418''' and the bottom lobe surface 24416'''. In the illustrated arrangement, the top surface 24342' of the lobe ledge 24340''' is identical to the top surface 24342'' of the lobe ledge 24340'' and includes a proximal portion 24344' that is parallel to the bottom surface 24321''' of the trunnion slot 24320''' as well as a ramped surface 24346' and a distal surface 24348'.

The anvil locking system 24700'' works in the same manner to prevent the anvil 24400''' from closing. When no cartridge is present in the channel 24310''' or a non-compatible cartridge (e.g. a cartridge that lacks the proper anvil unlocking feature to bias the anvil lock spring proximally) has been inserted into the channel 24310''' the anvil lock tab 24710'' is in its distal-most locked position preventing the corresponding actuator lobe 24414''' from pivoting down onto the ramp surface 24346' thereby retaining the anvil 24400''' in the open position. Once a compatible surgical staple cartridge has been loaded into the end effector 24100''', the anvil lockout feature thereon will bias the anvil lock 24702'' proximally into to the unlocked position. When the anvil lock 24702'' is in the proximal, unlocked position, the anvil lock out tab 24710'' is locked proximal to the ramp surface 24346' on the lobe ledge 24340''' to thereby permit the lobe 24414''' to pivot downwardly thereon which results in the closure of the anvil 24400'''.

FIGS. 184 and 185 illustrate another anvil 24400$_A$ that is identical in construction and operation to anvil 24400 described above, except that the trunnion formation 24412$_A$ is offset vertically from a bottom edge 24415$_A$ of an anvil mounting portion 24410$_A$ of the anvil 24400$_A$. FIG. 186 illustrates another anvil 24400$_B$ that is identical in construction and operation to anvil 24400' described above, except that the trunnion formation 24412$_B$ is offset vertically from a bottom edge 24415$_B$ of an anvil mounting portion 24410$_B$ of the anvil 24400$_B$.

The examples depicted in FIGS. 165-186 employ trunnion formations that comprise various shapes and configurations of lobe structures that serve to interact with an anvil lock feature such that the interaction between the anvil lock feature and the corresponding lobe structure serves to facilitate positioning of the anvil trunnions within their respective trunnion slots. This positioning of the lob structures permits the anvil to close upon application of closure motions thereto when a compatible surgical staple cartridge has been loaded into the end effector. In instances wherein an incompatible surgical staple cartridge has been loaded into the end effector, the anvil lock feature will retain the corresponding trunnion formation in a position wherein the anvil will be unable to close even upon application of a closure motion thereto. Thus, the initial positions of the trunnion formations prevent closure, but loading of a proper or compatible surgical staple cartridge into the channel changes positions of the trunnion formations to allow closure to occur. The various lobe features described herein are also generally more robust that previous trunnion arrangements which may lead to improved anvil reliability.

FIGS. 187-193 depict a surgical end effector 25300 that may be used for example in connection with the powered surgical instrument 1010 described above. The surgical end effector 25300 comprises an anvil 25400 that is pivotally supported on an elongate channel 25310 that is configured to operably support a surgical staple cartridge 25600. The anvil 25400 is movable between an open position and a closed position through interaction with an axially movable closure member in the various manners disclosed herein. In the illustrated example, the anvil 25400 comprises an anvil body 25402 and an anvil mounting portion 25410. The anvil mounting portion 25410 comprises a pair of laterally extending trunnions 25412 that are operably received within corresponding trunnion slots provided in upstanding sidewalls 25314 of the channel 25310 in the various manners disclosed herein. As was discussed above with respect to end effector 1300, anvil 25400 may be pivoted between an open and a closed position by interaction with an end effector closure tube 3050 in the various manners described herein. For example, the end effector closure tube 3050 may be axially moved by actuation of a closure trigger 1032 of the surgical instrument 1010. In other arrangements, the end effector 25300 and shaft assembly to which it is attached may operably interface with a robotic system as is described in detail in many of the references which have been incorporated herein by reference. In such applications, the end effector closure tube 3050 may be axially advanced and retracted through actuation of a closure control system of the robotic system.

In the illustrated arrangement, distal movement of the end effector closure tube 3050 causes a distal end 3051 of the end effector closure tube 3050 to operably interact with a camming surface 25411 that is formed on the anvil mounting portion 25410 to cam the anvil 25400 to a closed position. When the end effector closure tube 3050 is axially retracted in the proximal direction, the end effector closure tube 3050 may be configured to interact with various formations, ledges or tabs to apply an opening motion to the anvil 25400. Further details may be found in various other references which have been herein incorporated by reference.

The elongate channel 25310 may be coupled to an elongate shaft assembly 1200 (FIG. 5) by a channel mount feature 20340 which may facilitate articulation thereof about articulation joint 3020 (FIG. 5) in the various manners described herein. The illustrated example also includes a firing member 20500 (FIG. 144) that is attached to a distal end of a firing member beam 1900 (FIG. 5) and is configured to operably interface with a camming assembly in a surgical staple cartridge 25600 that has been loaded into the channel 25310. To ensure that a compatible surgical staple cartridge 25600 has been loaded into the end effector 25300 prior to closure of the anvil 25400, the end effector employs a closure lockout system 25700. In the illustrated example, the closure lockout system 25700 is configured to prevent a distal movement of the end effector closure tube 3050 unless a compatible cartridge 25600 has been properly seated within the channel 25310. In one example, the closure lockout system 25700 comprises a closure lock 25702 that is configured to move between a locked position and an unlocked position in response to installation of a compatible surgical staple cartridge 25600 therein. FIGS. 189-193 illustrate one form of a closure lock 25702 that may be fabricated from spring steel or other suitable metal and include a body portion 25706 that is pivotally pinned to the body portion 20342 of the channel mount feature 20340 by a pivot pin 25709 that extends through a pivot hole 25707 in the body portion 25706. The closure lock 25702 further includes a proximal biasing arm 25704 that may be configured to be seated in a slot (not shown) that is provided in the body portion 20342 of the channel mount feature 20340. Such arrangement serves to bias the closure lock 25702 downward within the channel 25310.

As can be most particularly seen in FIGS. 189 and 190 in the illustrated example, the closure lock 25702 further includes a blocking feature 25710 that protrudes from a bottom of the body portion 25706 and extends laterally outward. As illustrated in FIG. 189, when the closure lock 25702 is in the locked position, the blocking feature 25710 is positioned to block the distal advancement of the end effector closure tube 3050. When the closure lock 25702 is in the unlocked position as shown in FIG. 190, the blocking feature 25710 is moved away from the blocking position to permit the distal advancement of the end effector closure tube 3050.

Turning to FIG. 191, the closure lock 25702 further includes an actuator portion 25712 that extends proximally to be engaged by a closure unlocking feature 25630 formed on a proximal end 25604 of a compatible surgical staple cartridge 25600. In at least one arrangement, the surgical staple cartridge 25600 comprises an elongate cartridge body 25602 that is sized to be removably seated in the elongate channel 25310. The cartridge body 25602 includes a cartridge slot 25608 that extends from the proximal end portion 25604 to a distal end portion 25606 (FIG. 188) of the cartridge body 25602. The cartridge body 25602 further comprises a cartridge deck surface 25610 that confronts a staple-forming undersurface 25404 of the anvil 25400 when the cartridge 25600 is seated in the channel 25310 and the anvil 25400 is pivoted to a closed position. Although not shown in FIG. 191, the surgical staple cartridge 25600 may have a plurality of (usually three) lines of surgical staple pockets on each side of the cartridge slot 25608 that open through the cartridge deck surface 25610. Each staple pocket may have a staple driver (not shown) associated therewith that supports a surgical staple or fastener (not shown) thereon. In at least one example, the cartridge body 25602 is molded from a polymer material with the staple pockets molded or machined therein. In one arrangement, the staple pockets also open through a bottom of the cartridge body 25602 to facilitate installation of the drivers and fasteners into their respective pockets. Once the drivers and fasteners are inserted into their respective staple pockets, a cartridge pan 25620 is attached to the bottom of the cartridge body 25602. When installed, the cartridge pan 25620 may, among other things, prevent the drivers and fasteners from falling out of the bottom of the cartridge body 25602 during handling and installation of the cartridge 25600 into the elongate channel 25310. As was discussed above in connection with cartridge 20040, cartridge 25600 operably supports a camming assembly therein. The camming assembly comprises a series of spaced cam members that are configured to move axially within corresponding cam slots 25609 formed on each side of the cartridge slot 25608 in the cartridge body 25602. The cam slots 25609 are aligned with corresponding lines of drivers in the cartridge body 25602 to facilitate camming contact with a corresponding cam member as the camming assembly is driven through the staple cartridge 25600 from a beginning position within the proximal end portion 25604 of the cartridge body 25602 to an ending position within the distal end portion 25606.

FIGS. 187 and 192 illustrate the surgical end effector 25300 without a surgical staple cartridge installed therein. As can be seen in FIG. 192, the proximal biasing arm 25704 has biased the closure lock 25702 downward in the channel 25310 which results in the blocking feature 25710 moving into blocking alignment with the distal end 3051 of the end effector closure tube 3050 (locked position). Should the user activate the closure system to move the end effector closure tube 3050 distally, the blocking feature 25710 will block the distal advancement of the end effector closure tube 3050 thereby preventing an application of closure motions to the anvil 25400. Returning to FIG. 191, in at least one arrangement, the staple cartridge 25600 includes an anvil unlocking feature or tab 25630 that protrudes proximally from the cartridge body 25602 and is aligned to unlockingly engage the actuation tab 25712 that is formed on the distal end of the closure lock 25702 when the cartridge 25600 has been operably installed in the elongate channel 25310. In one example, the unlocking feature 25630 has a somewhat ramped surface 25632 that is configured to operably interact with an angled surface 25713 on the actuation tab 25712 so that the when the ramped surface 25632 and the angled surface 25713 are brought into engagement, the closure lock 25702 is pivoted in an upward direction. When the closure lock 25702 is pivoted upward into the unlocked position, the blocking feature 25710 is no longer in blocking alignment with the end effector closure tube 3050. See FIG. 190.

FIGS. 188 and 193 depict the surgical end effector 25300 with a compatible surgical staple cartridge 25600 operably installed in the elongate channel 25310. As can be seen in FIG. 193, the ramped surface 25632 on the unlocking feature 25630 on the staple cartridge body 25602 has contacted the angled surface 25713 (shown in FIG. 192) on the actuation tab 25712 on the closure lock 25702 to bias the closure lock 25702 into the unlocked position. When in that position, the user may distally advance the end effector closure tube 3050 distally to apply closing motions to the anvil 25400. Should the user attempt to install an inappropriate cartridge that lacks the unlocking feature 25630 in an appropriate position or similar feature designed to unlocking engage the closure lock 25702, the user will be unable to distally advance the end effector closure tube 3050 to close the anvil 25400.

FIGS. 194 and 195 illustrate a surgical end effector 25300' that comprises an anvil 25400' that is pivotally supported on a channel 25310' and is substantially identical to end effector 25300 described above except that the closure locking system 25700' employs a different closure lock 25702' that is configured to interact with an unlocking feature provided on a camming assembly 25650' within a surgical staple cartridge 25600'. As can be seen in FIGS. 194 and 195, the closure lock 25702' comprises an elongate body 25706' that has a tapered actuator tab portion 25712' on its distal end. The body 25706' is pivotally attached to the channel mount feature 20340 and a proximal biasing arm 25704' biases the closure lock 25702' within the channel 25310'.

FIG. 196 illustrates a surgical staple cartridge 25600' that comprises an elongate cartridge body 25602' that is sized to be removably seated in the elongate channel 25310'. The cartridge body 25602' includes a cartridge slot 25608' that extends from a proximal end portion 25604' to a distal end portion of the cartridge body 25602'. The cartridge body 25602' further comprises a cartridge deck surface 25610' that confronts a staple-forming undersurface 25404' of the anvil 25400' when the cartridge 25600' is seated in the channel 25310' and the anvil 25400' is pivoted to a closed position. Although not shown in FIG. 196, the surgical staple cartridge 25600' may have a plurality of (usually three) lines of surgical staple pockets on each side of the cartridge slot 25608' that open through the cartridge deck surface 25610'. Each staple pocket may have a staple driver (not shown) associated therewith that supports a surgical staple or fastener (not shown) thereon. In at least one example, the cartridge body 25602' is molded from a polymer material with the staple pockets molded or machined therein. In one arrangement, the staple pockets also open through a bottom of the cartridge body 25602' to facilitate installation of the drivers and fasteners into their respective pockets. Once the drivers and fasteners are inserted into their respective staple pockets, a cartridge pan 25620' is attached to the bottom of the cartridge body 25602'. When installed, the cartridge pan 25620' may, among other things, prevent the drivers and fasteners from falling out of the bottom of the cartridge body 25602' during handling and installation of the cartridge 25600' into the elongate channel 25310'. A camming assembly 25650' is operably supported in the cartridge body 25602'. In at least one arrangement, the camming assembly 25650' comprises a series of spaced cam members 25652' that are configured to move axially within corresponding cam slots 25609' that are formed on each side of the cartridge slot 25608' in the cartridge body 25602'. The cam slots 25609' are aligned with corresponding lines of drivers in the cartridge body 25602' to facilitate camming contact with a corresponding cam member 25652' as the camming assembly 25650' is driven through the staple cartridge 25600' from a beginning position within the proximal end portion 25604' of the cartridge body 25602' to an ending position within the distal end portion. In at least one example, the camming assembly 25650' includes a closure unlocking feature or tab 25660' that protrudes proximally from the camming assembly 25650' and is aligned to unlockingly engage the actuation tab 25712' that is formed on the distal end of the closure lock 25702' when the cartridge 25600' has been operably installed in the elongate channel 25310' and the camming assembly 25650' is in its unfired beginning position within the cartridge 25600'.

Returning to FIG. 195, in one example, the unlocking feature 25660' has a tapered nose portion 25662' that is configured to operably interact with the actuation tab 25712' so that the when the tapered nose portion 25662' is brought into engagement with the actuation tab 25712', the closure lock 25702' is pivoted upward. When the closure lock 25702' is pivoted upward into the unlocked position, a blocking feature 25710' on the closure lock 25702' is no longer in blocking alignment with the end effector closure tube 3050.

As can be seen in FIG. 196, the cartridge body 25602' may further include a locking safety 25670' that protrudes proximally from a proximal end of the cartridge body 25602' and adjacent to the tapered nose portion 25662'. An upper surface 25672' of the locking safety 25670' is angled to match the tapered nose portion 25662' but when the camming assembly 25650' is in its proximal-most beginning position, the tapered nose portion 25662' protrudes proximally beyond the end of the locking safety 25670'.

FIG. 194 illustrates an initial insertion of an unfired compatible surgical staple cartridge 25600' into the channel 25310'. As can be seen in FIG. 194 the tapered nose portion 25662' has made initial contact with the actuator tab portion 25712' on the closure lock 25702'. The closure lock 25702' remains biased downward to a locked position wherein the blocking feature 25710' of the closure lock 25702' is in blocking alignment with the distal end 3051 of the end effector closure tube 3050. As the cartridge 25600' is further advanced proximally into a seated position within the channel 25310', the tapered nose portion 25662' on the camming assembly 25650' lifts the actuation tab 25712' upward above the angled upper surface 25672' of the locking safety 25670' to enable the closure lock 25702' to pivot into the unlocked position wherein the blocking feature 25710' is no longer in blocking alignment with the distal end 3051 of the end effector closure tube 3050. When in that position, the user may advance the end effector closure tube 3050 distally to apply closing motions to the anvil 25400'. Thus, in this embodiment, the closure locking system 25700' is actuated by the camming assembly 25650', but only when the camming assembly 25650' is in an unfired beginning position.

FIG. 197 illustrates insertion of a staple cartridge 25600X wherein the camming assembly thereof is not in a proximal-most unfired position. This may occur when the user attempts to use the staple cartridge 25600X that has been previously used, for example. Because the camming assembly is not in its unfired beginning position, the tapered nose portion is absent to begin to bias the closure lock 25702' into an upward position above the closure safety 25670'. When the cartridge 25600X is fully seated in the channel 25310', the action tab 25712' of the closure lock 25702' is positioned under a lower lock surface 25674'. The closure lock 25702' remains in the locked position wherein the blocking feature 25710' thereof is in blocking alignment with the distal end 3051 of the end effector closure tube 3050. Should the user unwittingly attempt to distally advance the end effector closure tube 3050 to close the anvil 25400', the distal end 3051 will contact the blocking feature 25710' and the closure safety 25670' will further prevent the closure lock 25702' from pivoting upwardly to an unlocked position under the closure load.

FIGS. 198 and 199 illustrate a surgical end effector 25300" that comprises an anvil 25400" that is pivotally supported on a channel 25310" and is substantially identical to end effector 25300' described above. End effector 25300" employs a closure locking system 25700" that comprises a closure lock 25702". As can be seen in FIG. 200, the closure lock 25702" comprises an elongate body 25706" that has an actuator tab portion 25712" on its distal end. The body 25706" includes a lower spring arm 25720" that is mounted within the channel 25310". The lower spring arm 25720" is mounted so as to apply a downwardly biasing force to the closure lock 25702" which will be discussed below. As will also be discussed in further detail below, the closure lock 25702" further includes a vertically extending anvil locking tab 25710" that is configured to lockingly interact with a lock lug 25414" that is formed on an anvil mounting portion 25410" of the anvil 25400". In addition, the closure lock 25702" comprises a proximal biasing spring 25704" which serves to bias the closure lock 25702" in the distal direction DD (FIG. 200). As can be seen in FIG. 198, the elongate channel 25310" may be coupled to an elongate shaft assembly 1200 (FIG. 5) by a channel mount feature 20340 which may facilitate articulation thereof about articulation joint 3020 (FIG. 5) in the various manners described herein. As can be seen in FIG. 200, the proximal biasing spring 25704" is configured to be seated within the transverse slot 20343 in the body portion 20342 of the channel mount feature 20340.

Similar to the closure of anvil 25400' discussed above, distal movement of an end effector closure tube causes a distal end of the end effector closure tube to operably interact with a camming surface 25411" formed on an anvil mounting portion 25410" of the anvil 25400" to cam the anvil 25400" to a closed position. When the end effector closure tube is axially retracted in the proximal direction, the end effector closure tube may be configured to interact with various formations, ledges or tabs to apply an opening motion to the anvil 25400". Further details may be found in various other references which have been herein incorporated by reference.

FIG. 201 illustrates a surgical staple cartridge 25600" that comprises an elongate cartridge body 25602" that is sized to be removably seated in the elongate channel 25310". The cartridge body 25602" includes a cartridge slot 25608" that extends from a proximal end portion 25604" to a distal end portion of the cartridge body 25602". The cartridge body 25602" further comprises a cartridge deck surface 25610' that confronts a staple-forming undersurface 25404" of the anvil 25400" when the cartridge 25600" is seated in the channel 25310" and the anvil 25400" is pivoted to a closed position. Although not shown in FIG. 201, the surgical staple cartridge 25600" may have a plurality of (usually three) lines of surgical staple pockets on each side of the cartridge slot 25608" that open through the cartridge deck surface 25610". Each staple pocket may have a staple driver (not shown) associated therewith that supports a surgical staple or fastener (not shown) thereon. In at least one example, the cartridge body 25602' is molded from a polymer material with the staple pockets molded or machined therein. In one arrangement, the staple pockets also open through a bottom of the cartridge body 25602" to facilitate installation of the drivers and fasteners into their respective pockets. A camming assembly 25650" is operably supported in the cartridge body 25602". In at least one arrangement, the camming assembly 25650" comprises a series of spaced cam members 25652" that are configured to move axially within corresponding cam slots 25609" that are formed on each side of the cartridge slot 25608" in the cartridge body 25602". The cam slots 25609" are aligned with corresponding lines of drivers in the cartridge body 25602" to facilitate camming contact with a corresponding cam member 25652" as the camming assembly 25650" is driven through the staple cartridge 25600" from a beginning position within the proximal end portion 25604" of the cartridge body 25602" to an ending position within the distal end portion. In at least one example, the camming assembly 25650' includes a closure unlocking feature or tab 25660" that protrudes proximally from the camming assembly 25650" and is aligned to unlockingly engage the actuation tab 25712" that is formed on the distal end of the closure lock 25702" when the surgical staple cartridge 25600" has been operably installed in the elongate channel 25310" and the camming assembly 25650" is in its unfired beginning position within the cartridge 25600".

Returning to FIG. 201, in one example, the unlocking feature 25660" has a tapered nose portion 25662" that is configured to operably interact with the actuation tab 25712" so that the when the tapered nose portion 25662" is brought into engagement with the actuation tab 25712", the closure lock 25702" is moved upward against a downward biasing force established by the lower spring 25720". When the closure lock 25702" is pivoted upward into the unlocked position, the anvil locking tab 25710" on the closure lock 25702" is no longer in blocking alignment with the lock lug 25414" on the anvil mounting portion 24410".

FIG. 198 illustrates an initial insertion of an unfired compatible surgical staple cartridge 25600" into the channel 25310". As can be seen in FIG. 198, the tapered nose portion 25662" of the camming assembly 25650" has not yet interacted with the actuator tab portion 25712" on the closure lock 25702". The closure lock 25702" remains biased downward to a locked position wherein the anvil locking tab 25710" of the closure lock 25702" is in blocking alignment with the lock lug 25414" on the anvil mounting portion 25410" of the anvil 25400". As the surgical staple cartridge 25600" is further advanced proximally into a seated position within the channel 25310", the tapered nose portion 25662" on the camming assembly 25650" contacts the actuation tab 25712" and biases the closure lock 25702" upward to an unlocked position wherein the anvil locking tab 25710" is no longer aligned with the anvil lock lug 25414". When in that position, the user may close the anvil 25400" by distally advancing the end effector closure tube to apply closing motions to the anvil 25400". Thus, in this embodiment, the closure locking system 25700" is actuated by the camming assembly 25650", but only when the camming assembly 25650" is in an unfired beginning position. Once the surgical staple cartridge 25600" has been removed from the channel 25310", the lower spring 25720" on the closure lock 25702" will bias the closure lock 25702" downwardly back into its locked position wherein the anvil locking tab 25710" is in blocking alignment with the lock lug 25414" on the anvil 25400".

FIG. 202 illustrates insertion of a staple cartridge 25600X" that has a camming assembly therein that is not in a proximal-most unfired position. Because the camming assembly is not in its unfired, beginning position, the tapered nose portion is absent to bias the closure lock 25702" upward into the unlocked position. The closure lock 25702' remains in the locked position wherein the anvil locking tab 25710" thereof is in blocking alignment with the anvil lock lug 25414" on the anvil 25400". Should the user unwittingly attempt to close the anvil 25400", the anvil lock lug 25414" will contact the anvil locking tab 25710" on the closure lock 25702" and prevent the anvil 25400" from pivoting to the closed position.

FIGS. 203-207 illustrate an alternative cartridge nose assembly 25800 that may be employed with any of the cartridges and channel arrangements disclosed herein to provide another mechanism for ensuring that a surgical staple cartridge that is inserted into the end effector channel is compatible with the end effector and to provide the user with another visual indicator that the cartridge has been fired. For example, the cartridge nose assembly 25800 may be employed with the cartridge 25600 and the channel 25310 of the end effector 25300 (FIG. 188). In the illustrated arrangement, cartridge nose assembly 25800 comprises a nose assembly body 25802 that is movably coupled to a distal end 25606 of the cartridge body 25602. As can be seen in FIGS. 205 and 206, the distal end portion 25606 of the cartridge body 25602 comprises a distally extending tapered portion 25605 that is adapted to be received within complementary shaped nose notch 25804 in the nose assembly body 25802. In addition, the nose assembly body 25802 is configured with axial alignment features (not shown) that may be slidably supported in axial grooves 25607 provided in the distal end portion 25606 of the cartridge body 25602.

As can be seen in FIGS. 207 and 208, a nose retainer latch arm 25810 extends proximally from an upper portion of the nose assembly body 25802 into a latch cavity 25680 formed in the cartridge body 25602. The nose assembly body 25802 is axially movable from a locked position shown in FIGS. 205 and 207 to an unlocked position shown in FIGS. 206 and 208. When the nose assembly body 25802 is in the unlocked position, a retention latch 25812 that is formed on a proximal end of the retainer latch arm 25810 engages a retention lug 25682 that is formed on the distal end portion 25606 of the cartridge body 25602 to retain the cartridge nose assembly 25800 on the distal end 25606 of the cartridge body 25602.

Referring now to FIGS. 205 and 206, the nose assembly body 25802 further comprises proximally extending nose tab portions 25820 that are sized to frictionally engage corresponding distal extending channel ledges 25317 formed on a distal end 25315 of the channel 25310 to retain the nose assembly 25800 in the proximally forward "locked position". As can be seen in FIGS. 207 and 208, the nose assembly body 25802 may further include an integral spring arm 25830 that is configured to interact with a spring lug 25684 that is formed on the distally extending tapered portion 25605 of the cartridge body 25602. The spring arm 25830 applies a distal biasing force BF to the cartridge nose assembly 25800 to increase the frictional force between the nose tab portions 25820 and the channel ledges 25317 to retain the cartridge nose assembly 25800 in the locked position.

In operation, the cartridge nose assembly 25800 is in the locked position when the cartridge 25600 is in its unfired state and is ready to be installed in the channel 25310. To install the unfired cartridge 25600 into the end effector 25300, the cartridge body 25602 is placed in the channel 25310 and then advanced proximally therein to engage the channel ledges 25317 with the nose tab portions 25820 as shown in FIGS. 205 and 206. As discussed above, when the cartridge 25600 is unfired, the camming assembly 25650 is in its proximal-most beginning position. During the firing process, the camming assembly 25650 is driven in the cartridge body 25602 to its distal-most position therein. When the camming assembly 25650 reaches its distal-most position, a central body portion 25651 of the camming assembly 25650 contacts the cartridge nose assembly 25800 with a sufficient amount of force to overcome the frictional forces FF retaining the cartridge nose assembly 25800 in the locked position and moves the cartridge nose assembly 25800 axially into the unlocked position. In the alternative, the user may disengage the cartridge nose assembly 25800 by pulling it distally to the unlocked position. Once the cartridge nose assembly 25800 is moved to the unlocked position, the cartridge 25600 may be removed from the elongate channel 25310. In addition, the distally extending cartridge nose assembly 25800 may provide the user with a visual indication that the cartridge has been fired (spent).

FIGS. 209 and 210 illustrate a portion of a surgical end effector 26300 that employs a firing member 26120 that may be configured to be distally advanced by a rotary powered firing system or an axial powered (non-rotary powered) firing system. In particular, the firing member 26120 may be employed in connection with any of the various end effector arrangements and firing drive system configurations disclosed herein, as well as in connection with those end effector and firing drive system configurations described in the various references incorporated by reference herein.

As can be seen in FIGS. 209 and 210, the firing member 26120 comprises a firing member body 26122 that includes a firing member lockout system 26140 that comprises a firing member lockout 26142 that is pivotally attached to the firing member body 26122. The firing member lockout 26142 comprises a lockout body 26144 that comprises a pair of legs 26146 that straddle the firing member body 26122 and are pivotally attached thereto. The lockout body 26144 further includes a sled latch 26148 that is configured for contact with a camming sled or camming assembly 26650 that is operably supported in a staple cartridge (not shown). FIG. 209 illustrates the firing member 26120 in a proximal-most starting position. As can be seen in FIGS. 209 and 210, a firing lockout hole 26315 is provided through a bottom portion 26312 of an elongate channel 26310 of the end effector 26300. A lockout spring 26150 is mounted in the elongate channel 26310 and is configured to bias the firing member lockout 26142 downward such that, if a fresh unfired staple cartridge has not been properly loaded into the elongate channel 26310, a distal edge 26149 of the lockout body 26144 engages an angled distal edge 26317 of the firing lockout hole 26315. When in that position, should the user inadvertently attempt to distally advance the firing member 26120, the firing member lockout 26142 prevents the distal advancement of the firing member 26120 as shown in FIG. 210.

A fresh, unfired surgical staple cartridge contains a camming assembly 26650 that is located in a starting or unfired position that is proximal to the lines of staple drivers that are supported in the cartridge body. As used herein, the terms "fresh, unfired" means that the staple cartridge has all of its intended staples or fasteners in their respective unfired positions and the camming assembly is in a proximal unfired starting position. When a fresh, unfired surgical staple cartridge has been properly seated within the elongate channel 26310, a proximally extending unlocking portion 26653 on the camming assembly 26650 engages the sled latch 26148 on the firing member lockout 26142 to pivot the firing member lockout 26142 into an unlocked position wherein the firing member lockout 26142 does not extend into the firing lockout hole 26315 in the elongate channel 26310. FIG. 209 illustrates a camming assembly 26650 in the starting position and the firing member 26120 is free to be advanced distally by actuating the firing drive system.

At the completion of the firing process, the camming assembly 26650 may remain at the distal end of the staple cartridge (i.e., in a "fired" "position") while the firing member 26120 is retracted back to its starting position wherein the anvil may be opened and the spent cartridge removed from the channel 26310. Thus, once a surgical staple cartridge has been spent (e.g., completely fired) the camming assembly 26650 is not returned to its starting position. As such, if the spent cartridge were to be inadvertently re-installed in the end effector 26300, the camming assembly 26650 is not in a starting position wherein the camming assembly 26650 can unlock the firing member lockout 26142. Thus, the firing member lockout system 26140 may also be referred to herein as a "spent cartridge lockout system".

FIGS. 211-214 illustrate an anvil 26400 that is configured to be pivotally supported on the channel 26310 or a similar channel of the various types disclosed herein. In FIGS. 211-213, the channel has been omitted for clarity. In the illustrated arrangement, the anvil 26400 includes a cartridge verification system 26440 that may be configured to prevent firing of an incompatible cartridge that has been otherwise seated in the cartridge. The anvil 26400 and cartridge verification system 26440 may be used in connection with a surgical end effector 26300 that employs a firing member 26120 that is equipped with an onboard firing member lockout system 26140 that is configured to prevent the distal advancement of the firing member 26120 unless the firing member lockout 26142 has been moved to an unlocked position through interaction with a corresponding camming assembly located in the surgical staple cartridge. The cartridge verification system 26440 may also be used in connection with surgical end effectors that employ an axially advanced (non-rotary) firing member that is otherwise equipped with a firing member lockout system that is similar to the firing member lockout system 26140.

FIG. 214 illustrates a portion of a surgical staple cartridge 26600 that is compatible with the surgical end effector 26300. In at least one arrangement, the surgical staple cartridge 26600 comprises an elongate cartridge body 26602 that is sized to be removably seated in the elongate channel of the end effector 26300. The cartridge body 26602 includes a cartridge slot 26608 that extends from a proximal end portion 26604 to a distal end portion of the cartridge body 26602. The cartridge body 26602 further comprises a cartridge deck surface 26610 that confronts a staple-forming undersurface 26404 of the anvil 26400 when the cartridge 26600 is seated in the channel and the anvil 26400 is pivoted to a closed position. Although not shown in FIG. 214, the surgical staple cartridge 26600 may have a plurality of (usually three) lines of surgical staple pockets on each side of the cartridge slot 26608 that open through the cartridge deck surface 26610. Each staple pocket may have a staple driver (not shown) associated therewith that supports a surgical staple or fastener (not shown) thereon. In at least one example, the cartridge body 26602 is molded from a polymer material with the staple pockets molded or machined therein. In one arrangement, the staple pockets also open through a bottom of the cartridge body 26602 to facilitate installation of the drivers and fasteners into their respective pockets. Once the drivers and fasteners are inserted into their respective staple pockets, a cartridge pan 26620 is attached to the bottom of the cartridge body 26602. When installed, the cartridge pan 26620 may, among other things, prevent the drivers and fasteners from falling out of the bottom of the cartridge body 26602 during handling and installation of the cartridge 26600 into the elongate channel 26310.

In the illustrated arrangement, the cartridge 26600 operably supports a camming assembly 26650 therein. The camming assembly 26650 comprises a central body portion 26652 and a series of spaced cam members 26654 that are configured to move axially within corresponding cam slots 26609 formed on each side of the cartridge slot 26608 in the cartridge body 26602. The cam slots 26609 are aligned with corresponding lines of drivers in the cartridge body 26602 to facilitate camming contact with a corresponding cam member 26654 as the camming assembly 26650 is driven through the staple cartridge 26600 from a beginning position within the proximal end portion 26604 of the cartridge body 26602 to an ending position within the distal end portion of the cartridge body 26602. The central body portion 26652 includes the proximally extending unlocking portion 26653 that is configured to engage the sled latch 26148 on the firing member lock 26142 when the cartridge 26600 has been properly loaded into the channel 26310. As can be seen in FIG. 214, when the camming assembly 26650 is in its proximal-most starting position wherein the unlocking portion 26653 can move the firing member lockout 26142 to the unlocked position, each of the cam members 26654 may protrude proximally out of their respective cam slots 26609.

Referring now to FIGS. 211 and 215, in the illustrated arrangement, the cartridge verification system 26440 comprises a cartridge verification member or shuttle member 26442 that is attached to an underside of an anvil mounting portion 26410 of the anvil 26400. The cartridge verification member 26442 may be of one-piece construction and include a pair of downwardly extending shuttle legs 26444 that are bifurcated by a firing member slot 26447 (FIG. 215) to facilitate passage of the firing member 26120 therebetween. In other arrangements, the cartridge verification member 26442 may be of two-piece construction which consists of two separate downwardly extending shuttle legs 26444 that are separated from each other by a space 26448 that is configured to accommodate passage of the firing member body 26122 therethrough. In either case, the shuttle member 26442 may be fabricated from a compliant polymer or rubber material and be attached to the underside of the anvil mounting portion 26410 by appropriate adhesive of fastener arrangements.

In the illustrated example, each shuttle leg 26444 includes a distally protruding sled actuator arm 26446. Returning to FIG. 214, the cartridge body 26602 includes two proximally protruding verification features or cartridge key portions 26630 that are configured to unlockingly engage the sled actuator arm 26446 on a corresponding shuttle leg 26444 when the cartridge 26600 is operably seated in the channel 26310. As will be discussed further below, if the verification features 26630 are not present to contact the corresponding sled actuator arm 26446, the sled actuator arms 26446 would otherwise contact the protruding cam members 26654 and push or urge the camming assembly 26650 distally into a position wherein the unlocking portion 26653 on the camming assembly 26650 is no longer in unlocking engagement with the sled latch 26148 on the firing member lock 26142.

Interaction between the cartridge verification system 26440 and cartridge 26600 may be understood from reference to FIGS. 211-216. FIG. 211 illustrates initial installation of a compatible surgical staple cartridge 26600 into the end effector 26300. Although the channel has been omitted from the drawings, the anvil 26400 is shown in a fully open position. In the illustrated example, the anvil 26400 is movably journaled on the channel such that upon application of an initial closure motion thereto from a closure member arrangement of many of the various closure systems described herein, the anvil 26400 pivots to a partially closed position or intermediate position shown in FIG. 212. When in that position, each sled actuator arm 26446 is confrontingly aligned with the corresponding verification feature 26630 on the cartridge body 26602. Further application of the closure motion to the anvil 26400 may also cause the anvil 26400 to translate distally into a closed position. When the anvil 26400 moves distally, the verification features 26630 block the distal movement of the corresponding compliant sled actuator arms 26446 to prevent the sled actuator arm 26446 from contacting the proximally protruding cam members 26654. Thus, the camming assembly 26650 remains in its starting position wherein the unlocking portion 26653 on the camming assembly 26650 remains in unlocking engagement with the sled latch 26148 on the firing member lock 26142. Thus, the firing member 26120 is free to move distally through the cartridge 26600 upon actuation of the firing drive system.

FIG. 216 illustrates a cartridge 26600X that may be very similar to cartridge 26600 but is "incompatible" with the surgical end effector 26300. For example, the cartridge 26600X lacks the verification features or key portions 26630 of the cartridge 26600. In addition, to lacking the verification features or keys 26630, the cartridge 26600X may also differ from the cartridge 26600 in the numbers, sizes, locations, etc. of the fasteners contained therein, notwithstanding the fact that the cartridge 26600X may have a camming assembly 26650 that is identical in construction and use as the camming assembly 26650 employed in cartridges 26600.

FIGS. 217-219 illustrate insertion of an incompatible cartridge 26600X into the surgical end effector 26300. FIG. 217 illustrates initial installation of an incompatible surgical staple cartridge 26600X into the end effector 26300. Although the channel has been omitted from the drawings, the anvil 26400 is shown in a fully open position. FIG. 218 illustrates the anvil 26400 in an intermediate position upon application of an initial closure motion thereto. When in that position, each sled actuator arm 26446 is confrontingly aligned with corresponding cam members 26654 that protrude proximally out of their respective cam slots 26609. Further application of the closure motion to the anvil 26400 may cause the anvil 26400 to translate distally into a final closed position. When the anvil 26400 moves distally, the sled actuator arms 26446 contact the proximally protruding cam members 26654 and move the camming assembly 26650 distally to a point wherein the unlocking portion 26653 thereon is no longer in engagement with the sled latch 26148 on the firing member lock 26142. Thus, the firing member lockout 26142 remains in locking engagement with the elongate channel 26310 of the end effector 26300 to prevent the distal advancement of the firing member 26120 upon actuation of the firing drive system.

FIGS. 220-222 illustrate another cartridge verification system 26440' that may be employed with an end effector 26300' that employs a firing member 20500 that is axially advanced by a firing member beam 1900 in the various manners discussed herein. As was discussed above, the firing member 20500 comprises a firing member body 20502 that is configured to axially pass through vertically aligned slots in the anvil (not shown), a staple cartridge 26600', and the elongate channel 26310'. A lower foot assembly 20506 that comprises a pair of laterally extending lower flanges extends from a bottom end of the firing member body 20502 to slidably engage corresponding channel ledges that are formed on each side of the channel slot. An upper foot that comprises two laterally extending anvil tabs 20507 may be formed on an upper end of the firing member body 20502 and is configured to slidably engage anvil ledges (not shown) that are formed on each side of the anvil slot. In at least one arrangement, the firing member 20500 further includes a pair of central tabs (not shown) that extend laterally from each side of the firing member body 20502.

The firing member body 20502 is also configured with a proximally extending spring tail 20512 that may be configured to operably interface with a firing member lockout spring (not shown) that is mounted in the elongate channel 26310' and is configured to bias the firing member 20500 downward in the elongate channel 26310' into a locked position. When in the locked position, the firing member foot 20506 and/or the central tabs are misaligned with corresponding passages in the channel 20310' and as such, should the user attempt to distally advance the firing member 20500 when in that locked out state, the firing member 20500 would not move distally due to such misalignment. That is, the foot 20506 and/or central tabs contact portions of the elongate channel 20310' to thereby prevent the distal advancement of the firing member 20500. In one arrangement, a sled latch 20514 is formed on the firing member body 20502 and is configured to be engaged by a proximally extending unlocking portion 26653' on a camming assembly 26650' that is operably supported in a proximal-most unfired or starting position within a compatible cartridge 26600' that has been operably seated in the channel 26310'. When a fresh, unfired staple cartridge 26600' with the camming assembly 26650' thereof in its unfired position has been operably installed in the elongate channel 26310', the unlocking portion 26653' on the camming assembly 26650' engages the sled latch 20514 on the firing member body 20502 and moves the firing member 20500 upward into an unlocked position wherein the lower foot assembly 20506 and/or the central tabs are aligned with their respective passages in the channel 26310' to permit the firing member 20500 to axially advance therein. As the user distally advances the firing member 20500 into the cartridge 26600', the firing member 20500 also drives the camming assembly 20650' therein which cams the drivers upward to drive the staples or fasteners supported thereon into forming contact with the underside of the anvil. The tissue cutting member 20504 on the firing member 20500 then cuts through the stapled tissue. Once the firing member 20500 has been driven to its distal-most position corresponding to the ending position of the camming assembly 26650', the firing member 20500 is retracted back to its proximal-most position, leaving the camming assembly 26650' in the distal end of the cartridge 26600'. When the firing member 20500 returns to its proximal-most beginning position, the lock spring once again biases the firing member 20500 back into its locked position. Thus, should the user inadvertently try to reuse the spent cartridge, the camming assembly 26650' is not in its starting position which is required to unlock the firing member 20500. Thus, this firing member lockout arrangement may also be referred to herein as a "spent cartridge lockout arrangement".

In the arrangement depicted in FIGS. 220 and 221, the cartridge verification system 26440' comprises an axially movable, cartridge verification member or seating shuttle 26442' that is supported within the channel 26310' for axial movement from a distal-most cartridge engagement position to a proximal verification location within the channel 26310'. A shuttle spring 26449' is mounted within the channel 26310' and serves to bias the cartridge verification member or seating shuttle 26442' into the distal-most cartridge engagement position. As can be seen in FIGS. 220 and 221, the cartridge verification member or shuttle 26442' further includes a pair of distally protruding sled actuator arms 26446'. The sled actuator arms 26446' are positioned to contact corresponding cam members on a camming assembly of a non-compliant cartridge as will be discussed below.

FIG. 222 illustrates a proximal end portion 26604' of the surgical staple cartridge 26600' that is compatible with the surgical end effector 26300'. In at least one arrangement, the surgical staple cartridge 26600' comprises an elongate cartridge body 26602' that is sized to be removably seated in the elongate channel 26310'. The cartridge body 26602' includes a cartridge slot 26608' that extends from the proximal end portion 26604' to a distal end portion of the cartridge body 26602'. The cartridge body 26602' further comprises a cartridge deck surface 26610' that confronts a staple-forming undersurface of the anvil when the cartridge 26600' is seated in the channel 26310' and the anvil is pivoted to a closed position. Although not shown in FIG. 222, the surgical staple cartridge 26600' may have a plurality of (usually three) lines of surgical staple pockets on each side of the cartridge slot 26608' that open through the cartridge deck surface 26610'. Each staple pocket may have a staple driver (not shown) associated therewith that supports a surgical staple or fastener (not shown) thereon. In at least one example, the cartridge body 26602' is molded from a polymer material with the staple pockets molded or machined therein. In one arrangement, the staple pockets also open through a bottom of the cartridge body 26602' to facilitate installation of the drivers and fasteners into their respective pockets. Once the drivers and fasteners are inserted into their respective staple pockets, a cartridge pan 26620' is attached to the bottom of the cartridge body 26602'. When installed, the cartridge pan 26620' may, among other things, prevent the drivers and fasteners from falling out of the bottom of the cartridge body 26602' during handling and installation of the cartridge 26600' into the elongate channel 26310'.

In the illustrated arrangement, cartridge 26600' operably supports a camming assembly 26650' therein. The camming assembly 26650' comprises a central body portion 26652' and a series of spaced cam members 26654' that are configured to move axially within corresponding cam slots 26609' formed on each side of the cartridge slot 26608' in the cartridge body 26602'. The cam slots 26609' are aligned with corresponding lines of drivers in the cartridge body 26602' to facilitate camming contact with a corresponding cam member 26654' as the camming assembly 26650' is driven through the staple cartridge 26600' from a beginning position within the proximal end portion 26604' of the cartridge body 26602' to an ending position within the distal end portion of the cartridge body 26602'. The central body portion 26652' includes the proximally extending unlocking portion 26653' that is configured to engage the sled latch 20514 on the firing member 20500 when the cartridge 26600' has been properly loaded into the channel 26310'.

The compatible cartridge 26600' further includes proximally protruding verification features or key formations 26630' that are configured to engage the sled actuator arms 26446' when the cartridge 26600' is operably seated in the channel 26310'. In the illustrated arrangement, the cartridge body 26602' additional has two side verification features or cartridge key formations 26632' that are also configured to engage the cartridge verification member or shuttle 26442'. As will be discussed further below, if the verification formations 26630', 26632' are not present to contact the corresponding sled actuator arm 26446' and the cartridge verification member or shuttle 26442', the sled actuator arms 26446' would otherwise contact the protruding cam members 26654' and push or urge the camming assembly 26650' distally into a position wherein the unlocking portion 26653' on the camming assembly 26650' is no longer in unlocking engagement with the sled latch 20514 on the firing member 20500.

Turning now to FIGS. 223-225, in the illustrated arrangement, the verification features or key formations 26630', 26632' each have an angled lower alignment surface 26634' thereon that facilitate initial insertion of the cartridge 26600' into the channel 26310' at a first position angle FPA wherein the angled lower alignment surfaces 26634' avoid abutting contact with the sled actuator arms 26446'. The surfaces 26634' may be referred to herein as secondary surfaces. Once the user has positioned the surgical staple cartridge 26600' in the first installation position, the cartridge 26600' is then pivoted downward into the channel 26310' into position 2 wherein vertical abutment surfaces 26636' (secondary surfaces) on the verification features or cartridge key formations 26630', 26632' abut the corresponding vertical abutment surfaces 26641' and 26647' (primary surfaces) on the cartridge verification member or shuttle 26442'. The user may then advance the cartridge 26600' proximally into position 3 within the elongate channel 26310'.

FIG. 226 illustrates insertion of an incompatible cartridge 26600X' into the surgical end effector 26300'. In this example, the incompatible cartridge 26600X' lacks the verification features or cartridge key formations 26630', 26632' that were provided on the compatible cartridge 26600' to engage the cartridge verification member or shuttle 26442'. Thus, as the cartridge 26600X' is seated in the channel 26310', the sled actuator arms 26446' contact the protruding cam members 26654' and push or urge the camming assembly 26650' distally into a position wherein the unlocking portion 26653' on the camming assembly 26650' is not in unlocking engagement with the sled latch 20514 on the firing member 20500. Thus, the firing member 20500 remains locked in position and the user would be unable to distally advance the firing member 20500 into the incompatible cartridge 26600X'.

FIGS. 227 and 228 illustrate insertion of the incompatible cartridge 26600X' into the end effector 26300' wherein the incompatible cartridge 26600X' has been initially inserted too far proximally into the channel 26310' such that the distal end of the firing member 20500 has contacted and pushed the camming assembly 26650' or "sled" too far distally within the cartridge 26600X' so as to be in the appropriate position to unlockingly engage the sled latch 20514 portion of the firing member 20500 after the cartridge 26600X' has ultimately been seated in the channel 26310' in a proper position. Likewise, when the incompatible cartridge 26600X' is initially inserted in a diagonal position 1 as was described above an then moved to positions 2 and 3, the firing member 20500 may bump the camming assembly 26650' or sled distally out of the firing member unlocking position such that once properly seated, the camming assembly 26650' would fail to unlock the firing member 20500. See FIGS. 229 and 230.

FIGS. 231-233 illustrate another cartridge verification system 26440" that may be employed with an end effector 26300" that employs a firing member 20500 that is axially advanced by a firing member beam 1900 in the various manners discussed herein. As was discussed above, the firing member 20500 comprises a firing member body 20502 that is configured to axially pass through vertically aligned slots in the anvil (not shown), a staple cartridge, and the elongate channel 26310". A lower foot assembly (not shown) that comprises a pair of laterally extending lower flanges extends from a bottom end of the firing member body 20502 to slidably engage corresponding channel ledges that are formed on each side of the channel slot. An upper foot 20507 that comprises two laterally extending anvil tabs 20509 may be formed on an upper end of the firing member body 20502 and is configured to slidably engage anvil ledges (not shown) that are formed on each side of the anvil slot. In at least one arrangement, the firing member 20500 further includes a pair of central tabs 20510 that extend laterally from each side of the firing member body 20502.

The firing member body 20502 is also configured with a proximally extending spring tail (not shown) that may be configured to operably interface with a firing member lockout spring (not shown) that is mounted in the elongate channel 26310" and is configured to bias the firing member 20500 downward in the elongate channel 26310' into a locked position. When in the locked position, the firing member foot and/or the central tabs 20510 are misaligned with corresponding passages in the channel 20310" and as such, should the user attempt to distally advance the firing member 20500 when in this locked out state, the firing member 20500 would not move distally due to such misalignment. That is, the foot and/or central tabs 20510 contact portions of the elongate channel 26310" to thereby prevent the distal advancement of the firing member 20500. In one arrangement, a sled latch 20514 is formed on the firing member body 20502 and is configured to be engaged by a proximally extending unlocking portion on a camming assembly that is operably supported in a proximal-most starting position within a compatible cartridge that has been operably seated in the channel 26310".

When a fresh, unfired compatible staple cartridge with the camming assembly thereof in its starting (unfired) position has been operably installed in the elongate channel 26310", an unlocking portion on the camming assembly engages the sled latch 20514 on the firing member body 20502 and moves the firing member 20500 upward into an unlocked position wherein the lower foot assembly and/or the central tabs 20510 are aligned with their respective passages in the channel 26310" to permit the firing member 20500 to axially advance therein. As the user distally advances the firing member 20500 into the cartridge, the firing member 20500 also drives the camming assembly therein which cams the drivers upward to drive the staples or fasteners supported thereon into forming contact with the underside of the anvil. A tissue cutting member 20504 on the firing member 20500 then cuts through the stapled tissue. Once the firing member 20500 has been driven to its distal-most position corresponding to the ending position of the camming assembly, the firing member 20500 is retracted back to its proximal-most position, leaving the camming assembly in the distal end (fired position) of the cartridge. When the firing member 20500 returns to its proximal-most beginning position, the lock spring once again biases the firing member 20500 back into its locked position. Thus, should the user inadvertently try to reuse the spent cartridge, the camming assembly is not in its starting position which is required to unlock the firing member 20500. Such firing member locking system may also be referred to herein as a "spent cartridge lockout system".

In the arrangement depicted in FIGS. 231-233, the cartridge verification system 26440" comprises an axially movable, cartridge verification shuttle 26442" that is supported within the channel 26310" for axial movement from a distal-most cartridge engagement position to a proximal verification location within the channel 26310". A shuttle spring 26449" is mounted within the channel 26310" and serves to bias the cartridge verification shuttle 26442" into the distal-most cartridge engagement position. As can be seen in FIGS. 231 and 232, the cartridge verification shuttle 26442" further includes distally extending shuttle base members 26644" and pair of laterally movable shuttle drive arms 26450". Each shuttle drive arm 26450" has a drive latch feature 26452" thereon that has an angled proximal drive surface 26454" and an angled distal drive surface 26456" that converge together to form a point 26548". The shuttle drive arms 26450" are biased laterally inward into a driving position by the shuttle spring 26449". When the shuttle drive arms 26450" are in the driving position, the angled proximal drive surfaces 26454" are in driving engagement with the central tabs 20510 on the firing member 20500 as shown in FIGS. 231 and 232. When the shuttle drive arms 26450" are in that position, distal advancement of the firing member 20500 will cause the seating shuttle 26442" to move distally therewith.

FIG. 233 illustrates a proximal end portion 26604" of a surgical staple cartridge 26600" that is compatible with the surgical end effector 26300" and seated within the channel 26310". In at least one arrangement, the surgical staple cartridge 26600" comprises an elongate cartridge body 26602" that is sized to be removably seated in the elongate channel 26310". The cartridge body 26602" includes a cartridge slot 26608" that extends from the proximal end portion 26604" to a distal end portion of the cartridge body 26602". The cartridge 26600" operably supports a camming assembly 26650" therein. The camming assembly 26650" comprises a central body portion 26652" and a series of spaced cam members 26654" that are configured to move axially within corresponding cam slots 26609" formed on each side of the cartridge slot 26608" in the cartridge body 26602". The cam slots 26609" are aligned with corresponding lines of drivers in the cartridge body 26602" to facilitate camming contact with a corresponding cam member 26654" as the camming assembly 26650" is driven through the staple cartridge 26600" from a beginning position within the proximal end portion 26604" of the cartridge body 26602" to an ending position within the distal end portion of the cartridge body 26602". The central body portion 26652" includes the proximally extending unlocking portion 26653" that is configured to engage the sled latch 20514 on the firing member 20500 when the cartridge 26600" has been properly loaded into the channel 26310".

The compatible cartridge 26600" further includes proximally protruding unlocking features or cartridge key formations 26630" that are configured to engage the shuttle drive arms 26450" when the cartridge 26600" is operably seated in the channel 26310". As can be seen in FIG. 233, during the distal advancement of the firing member 20500, the verification shuttle 26442" is driven distally until each shuttle drive arm 26450" contacts a corresponding cartridge key formation 26630" which causes the shuttle drive arms 26450" to bias laterally outward. As the firing member 20500 continues to move distally, the drive latch features 26452" on the shuttle drive arms 26450" disengage from the corresponding central tabs 20510 on the firing member body 20502 to permit the firing member 20500 to move distally without driving the verification shuttle 26442" distally. Thus, in such case, the verification shuttle 26442" has not moved sufficiently distally so as to move the camming assembly 26650" out of unlocking engagement with the sled latch 20514 on the firing member 20500. Therefore, the firing member 20500 may be driven distally through the compatible cartridge 26600" to drive the fasteners therefrom and to cut the tissue that has been clamped in the end effector 26300". When the firing member 20500 is retracted back into its starting position, a tapered surface 20511 on each central tab 20510 contacts the angled distal drive surface 26456" on the corresponding drive latch feature 26452" to bias the shuttle arms 26450" laterally to permit the central tabs 20510 to reengage the angled proximal drive surfaces 26454" so that the verification shuttle 26442" can once again be driven distally with the firing member 20500.

FIGS. 231 and 232 illustrate an incompatible cartridge 26600X" loaded into the surgical end effector 26300". As can be seen in those Figures, the incompatible cartridge 26600X" lacks the proximally protruding unlocking features or cartridge key formations 26630" that are provided on the compatible cartridge 26600". Thus, when the firing member 20500 is distally advanced, the cartridge verification shuttle 26442" also moves distally with the firing member 20500. As the cartridge verification shuttle 26442" moves distally, the distal ends 26645" of the distally extending shuttle base members 26644" contact the camming assembly 26650" and move the camming assembly 26650" out of unlocking engagement with the sled latch 20514 on the firing member 20500. When the unlocking portion 26653" of the camming assembly 26650" disengages the sled latch 20514, the firing member body 20502 will drop into locking engagement with the elongate channel 26310" thereby preventing further distal advancement of the firing member 20500.

As can be further seen in FIGS. 232 and 233, in the illustrated arrangement, a lateral stiffener member 26470" protrudes laterally outward from each shuttle arm 26450". When the firing member 20500 and the verification shuttle 26442" are located in their respective proximal-most starting positions, each lateral stiffener member 26470" is laterally aligned with a corresponding channel notch 26472" provided in each channel sidewall 26314" to provide clearance for the shuttle arms 26450" to move laterally when a compatible cartridge 26600" has been properly loaded into the end effector 26300". However, when an incompatible cartridge 26600X" has been loaded into the end effector 26300" and the user begins to advance the firing member 20500 as well as the verification shuttle 26442" distally, the lateral stiffener members 26470" are no longer aligned with the channel notches 26472" in the channel sidewalls 26314" as can be seen in FIG. 232. In such instance, the lateral stiffener members 26470" prevent the shuttle arms 26450" from biasing laterally outward out of engagement with the central tabs 20510 that extend laterally from each side of the firing member body 20502.

The cartridge verification systems described herein may address various problems that may, from time-to-time, be encountered when using an end effector that is capable of initially accepting a variety of cartridges wherein some of the cartridges are not otherwise particularly compatible with the end effector. For example, a cartridge may operably fit into the channel of the end effector, but the cartridge may lack proper fastener configurations that are compatible with the forming pockets on the end effector anvil. The incompatible cartridge may not have the proper numbers and forms of staples, etc. The cartridge may not have a camming assembly that is compatible with the firing member lockout arrangement employed by the end effector. Some cartridges may have an appropriate camming assembly, but the camming assembly may at some point have moved to a marginal unlocking position wherein the camming assembly may or may not unlockingly engage the firing member lockout arrangement. At least some of the cartridge verification systems may address that issue. The cartridge verification systems disclosed herein may also provide the ability to differentiate between an old obsolete cartridge and a newer more appropriate cartridge that has, for example, features that are better paired to the end effector components. The cartridge verification systems may also ensure that a cartridge is properly seated in the end effector channel and minimize any misalignment of the cartridge in the channel wherein the proximal end of the cartridge is positioned relative to the firing member in an undesirable position wherein the central tabs on the firing member may get under the cartridge pan rather than on top of it as desired. Such misalignment may result in the damage and bending of the cartridge pan which could lead to premature locking of the firing member.

FIGS. 234-239 illustrate another cartridge verification system 27440 that may be employed with an end effector 27300 that employs a firing member 20500 (described above) that is axially advanced by a firing member beam 1900 in the various manners discussed herein. In the illustrated arrangement, the cartridge verification system 27440 comprises an axially movable cartridge verification member or shuttle 27442 that is supported within a channel 27310 of the end effector 27300 for axial movement from a distalmost cartridge engagement position to a proximal verification location within the channel 27310. The cartridge verification member or shuttle 27442 may be fabricated from spring steel and include an elongate body 27444 that has a blocking hook 27446 that is formed on a distal end 27445 of the elongate body 27444. See FIG. 235. The cartridge verification member or shuttle 27442 further includes an actuator portion 27448 that is formed on a proximal end 27447 of the elongate body 27444.

Still referring to FIG. 235, the cartridge verification member or shuttle 27442 is configured to axially move within a shuttle track 27360 that is formed in a channel bottom 27312 of the channel 27310. As can be seen in FIG. 235, the shuttle track 27360 comprises a curved transverse portion 27362 that extends transversely relative to a channel slot 27313 that is centrally disposed in the channel bottom 27312 to accommodate axial passage of the firing member 20500 therethrough. The transverse curved portion 27362 of the shuttle track 27360 terminates in a ramped track portion 27364 that is located on another side of the channel slot 27313. As can be seen in FIG. 235, the ramped track portion 27364 has an angled bottom surface 27366. A proximal end 27370 of the shuttle track 27360 abuts an axial spring cavity 27380 that is configured to support a shuttle spring 27382 that is journaled on a spring retainer pin 27449 that protrudes proximally from the actuator portion 27448 of the cartridge verification member or shuttle 27442. The shuttle spring 27382 serves to bias the verification shuttle 27442 into a distal-most, locked position wherein the cartridge verification member or shuttle 27442 blocks distal advancement of a camming assembly 27650 and the firing member 20500.

FIG. 234 illustrates a proximal end portion 27604 of a surgical staple cartridge 27600 that is compatible with the surgical end effector 27300. In at least one arrangement, the surgical staple cartridge 27600 comprises an elongate cartridge body 27602 that is sized to be removably seated in the elongate channel 27310. The cartridge body 27602 includes a cartridge slot 27608 that extends from the proximal end portion 27604 to a distal end portion of the cartridge body 27602. The cartridge body 27602 further comprises a cartridge deck surface 27610 that confronts a staple-forming undersurface of the anvil when the cartridge 27600 is seated in the channel 27310 and the anvil is pivoted to a closed position. Although not shown in FIG. 234, the surgical staple cartridge 27600 may have a plurality of (usually three) lines of surgical staple pockets on each side of the cartridge slot 27608 that open through the cartridge deck surface 27610. Each staple pocket may have a staple driver (not shown) associated therewith that supports a surgical staple or fastener (not shown) thereon. In at least one example, the cartridge body 27602 is molded from a polymer material with the staple pockets molded or machined therein. In one arrangement, the staple pockets also open through a bottom of the cartridge body 27602 to facilitate installation of the drivers and fasteners into their respective pockets. Once the drivers and fasteners are inserted into their respective staple pockets, a cartridge pan 27620 is attached to the bottom of the cartridge body 27602. When installed, the cartridge pan 27620 may, among other things, prevent the drivers and fasteners from falling out of the bottom of the cartridge body 27602 during handling and installation of the cartridge 27600 into the elongate channel 27310.

In the illustrated arrangement, cartridge 27600 operably supports a camming assembly 27650 therein. The camming assembly 27650 comprises a central body portion 27652 and a series of spaced cam members 27654 that are configured to move axially within corresponding cam slots 27609 formed on each side of the cartridge slot 27608 in the cartridge body 27602. The cam slots 27609 are aligned with corresponding lines of drivers in the cartridge body 27602 to facilitate camming contact with a corresponding cam member 27654 as the camming assembly 27650 is driven through the staple cartridge 27600 from a beginning position within the proximal end portion 27604 of the cartridge body 27602 to an ending position within the distal end portion of the cartridge body 27602. The central body portion 27652 includes a proximally extending unlocking portion 27653 that is configured to engage the sled latch 20514 on the firing member 20500 when the cartridge 27600 has been properly loaded into the channel 27310.

The compatible cartridge 27600 further includes a proximally protruding verification feature or cartridge key formation 27630 that is configured to engage the sled actuator 27448 when the cartridge 27600 is operably seated in the channel 27310. The verification feature 27630 biases the cartridge verification member or shuttle 27442 into the proximal-most, unlocked position wherein the camming assembly 27650 and the firing member 20500 may be distally displaced through the cartridge 27600. When the cartridge verification member or shuttle 27442 is in the unlocked position, the blocking hook 27446 that is formed on the distal end 27445 of the elongate body 27444 of the cartridge verification member or shuttle 27442 is retracted into the curved transverse portion 27362 of the shuttle track 27360 and does not extend across the channel slot 27313 in the channel bottom 27312. When the blocking hook 27446 is not extending across the channel slot 27313, the firing member 20500 and the camming assembly 27650 can be advanced into the cartridge 27310".

FIGS. 238 and 239 illustrate the surgical end effector 27300 with an incompatible cartridge 27600X installed therein. In this example, the incompatible cartridge 27600X lacks the verification feature or cartridge key formation 27630 that was provided on the compatible cartridge 27600 to engage the actuator portion 27448 of the cartridge verification member or shuttle 27442. Thus, the shuttle spring 27382 has biased the cartridge verification member or shuttle 27442 distally into its locked position wherein the blocking hook 27446 that is formed on the distal end 27445 of the elongate body 27444 of the cartridge verification member or shuttle 27442 extends transversely across the channel slot 27313 and into the ramped track portion 27364. As the blocking hook 27446 enters the ramped track portion 27364, the angled bottom surface 27366 causes the blocking hook 27446 to move upward into a position wherein the blocking hook 27446 blocks the distal advancement of the camming assembly 27650 and the firing member 20500. Thus, when in that position, should the user unwittingly attempt to distally advance the firing member 20500, the blocking hook 27446 will block the distal advancement of the camming assembly 27650 and the firing member 20500.

In at least one arrangement as shown in FIG. 239, the portion of the blocking hook 27446 that transversely spans the channel slot 27313 may be reinforced with an additional reinforcement block portion 27450 that is attached thereto. That is the portion of the blocking hook 27446 that is reinforced has a cross-sectional thickness that is greater than a cross-sectional thickness of the remaining body portions of the cartridge verification member or shuttle 26442. Alternative arrangements are contemplated for use with those end effectors disclosed herein that employ an axially movable closure member for moving the anvil to a closed position such as, for example, an end effector closure tube. In such end effector arrangements, for example, the end effector closure tube may be configured to bias the verification shuttle to the locked, blocking position when the closure member is actuated to close the anvil. The cartridge verification system 27440 may also be effectively employed with surgical end effectors that have rotary powered firing member arrangements with firing member lockout systems of the types disclosed herein.

FIGS. 240-243 illustrate an alternative surgical staple cartridge 28600 that may be employed in connection with various end effector arrangements disclosed herein. In the illustrated arrangement, the surgical staple cartridge 28600 comprises an elongate cartridge body 28602 that is sized to be removably seated in the elongate channel of the end effector. As can be seen in FIG. 241, the cartridge body 28602 includes a cartridge slot 28608 that extends from a proximal end portion 28604 of the cartridge body 28602 to a distal end portion of the cartridge body 28602. The cartridge body 28602 further comprises a cartridge deck surface 28610 that confronts a staple-forming undersurface of the anvil when the cartridge 28600 is seated in the channel and the anvil is pivoted to a closed position. Although not shown in FIG. 241, the surgical staple cartridge 28600 may have a plurality of (usually three) lines of surgical staple pockets on each side of the cartridge slot 28608 that open through the cartridge deck surface 28610. Each staple pocket may have a staple driver (not shown) associated therewith that supports a surgical staple or fastener (not shown) thereon. In at least one example, the cartridge body 28602 is molded from a polymer material with the staple pockets molded or machined therein. In one arrangement, the staple pockets also open through a bottom of the cartridge body 28602 to facilitate installation of the drivers and fasteners into their respective pockets. Once the drivers and fasteners are inserted into their respective staple pockets, a cartridge pan 28620 is attached to the bottom of the cartridge body 28602. When installed, the cartridge pan 28620 may, among other things, prevent the drivers and fasteners from falling out of the bottom of the cartridge body 28602 during handling and installation of the cartridge 28600 into the elongate channel.

In the illustrated arrangement, cartridge 28600 operably supports a camming assembly 28650 therein. The camming assembly 28650 comprises a central body portion 28652 and a series of spaced cam members 28654, 28654' that are configured to move axially within corresponding cam slots 28609 formed on each side of the cartridge slot 28608 in the cartridge body 28602. The cam slots 28609 are aligned with corresponding lines of drivers in the cartridge body 28602 to facilitate camming contact with a corresponding cam member 28654, 28654' as the camming assembly 28650 is driven through the staple cartridge 28600 from a beginning position within the proximal end portion 28604 of the cartridge body 28602 to an ending position within the distal end portion of the cartridge body 28602.

Still referring to FIG. 241, the cartridge 28600 is equipped with a camming assembly locking system 28440 that is configured to retain the camming assembly 28650 in its starting position unless the cartridge 28600 has been loaded into a compatible end effector. In the illustrated arrangement for example, the camming assembly locking system 28440 comprises a laterally displaceable lock feature 28442 that comprises an actuator portion 28444 and a locking tab 28446. As can be seen in FIG. 241, the locking tab 28446 is configured to be received within a lock cavity 28655 provided in a corresponding cam member 28654' when the camming assembly 28650 is in a locked position. See FIGS. 240 and 241. The actuator portion 28444 is configured to be contacted by an actuator lug or other portion of the end effector anvil when the anvil is moved to a closed position. For example, an actuator lug 28411 may be formed on an anvil mounting portion of any of the various anvils disclosed herein and be configured to laterally bias the actuator portion 28444 laterally into an unlocked position when the anvil is moved to a closed position. When the actuator portion 28444 is in an unlocked position, the locking tab 28446 is moved laterally out of the lock cavity 28655 in the cam member 28654' and the cam assembly 28650 may then be distally advanced through the cartridge 28600 when the firing drive system is activated as described herein. See FIGS. 242 and 243.

In various instances, a surgical stapling instrument comprises a cartridge jaw configured to receive a replaceable staple cartridge. The stapling instrument further comprises a staple firing system configured to eject, or fire, staples from the staple cartridge and an anvil comprising forming surfaces, or pockets, configured to deform the staples. The staple firing system comprises a tissue cutting knife which is moved from a proximal end of the staple cartridge toward a distal end during a staple firing stroke. During the staple firing stroke, the tissue cutting knife abuts and pushes a sled in the staple cartridge which drives the staples toward and against the anvil. As the staples are deformed against the anvil, the staples are implanted in the tissue in longitudinal rows and the tissue cutting knife incises the tissue between two of the longitudinal staple rows. After the staple firing stroke has been completed, and/or after a sufficient length of the staple firing stroke has been completed, the tissue cutting knife is retracted proximally. However, the cartridge sled is not retracted proximally with the tissue cutting knife. Instead, the cartridge sled is left behind at the distal-most position in which it was pushed by the tissue cutting knife. After a staple cartridge has been fired, or at least partially fired, it is removed from the cartridge jaw and then replaced with another replaceable staple cartridge, if desired. At such point, the stapling instrument can be re-used to continue stapling and incising the patient tissue. In some instances, however, a previously-fired staple cartridge can be accidentally loaded into the cartridge jaw. If the tissue cutting knife were to be advanced distally within such a previously-fired staple cartridge, the stapling instrument would cut the patient tissue without stapling it. The stapling instrument would similarly cut the patient tissue without stapling it if the tissue cutting knife were advanced distally through a staple firing stroke without a staple cartridge positioned in the cartridge jaw at all. To this end, the stapling instrument comprises one or more lockouts which prevents this from happening, as discussed in greater detail below.

The disclosures of U.S. Patent Application Publication No. 2004/0232200, entitled Surgical stapling instrument having a spent cartridge lockout, filed on May 20, 2003, U.S. Patent Application Publication No. 2004/0232199, entitled Surgical stapling instrument having a firing lockout for an unclosed anvil, U.S. Patent Application Publication No. 2004/0232197, entitled Surgical stapling instrument incorporating an e-beam firing mechanism, filed on May 20, 2003, U.S. Patent Application Publication No. 2004/0232196, entitled Surgical stapling instrument having separate distinct closing and firing systems, filed on May 20, 2003, U.S. Patent Application Publication No. 2004/0232195, entitled SURGICAL STAPLING INSTRUMENT HAVING A SINGLE LOCKOUT MECHANISM FOR PREVENTION OF FIRING, filed on May 20, 3003, and U.S. Patent Application Publication No. 2018/0085123, entitled Articulating surgical stapling instrument incorporating a two-piece e-beam firing mechanism, filed on Aug. 17, 2017 are incorporated by reference in their entireties.

Referring to FIG. 244, a surgical stapling instrument 30000 comprises a cartridge jaw, or channel, 30010 and a staple cartridge 30020 seated in the cartridge jaw 30010. The staple cartridge 30020 comprises a cartridge body 30022, staple cavities defined in the cartridge body 30022, and staples removably stored in the staple cavities. The staple cartridge 30020 further comprises a sled 30030 and staple drivers which are driven by the sled 30030 to eject the staples from the staple cavities as the sled 30030 is advanced distally during a staple firing stroke. The stapling instrument 30000 further comprises a firing member 30040 which is configured to engage the sled 30030 and push the sled 30030 distally, as discussed in greater detail below.

Further to the above, the firing member 30040 comprises a cutting portion 30042 including a tissue knife 30044. The cutting portion 30042 further comprises a distal nose 30043 which is configured to sit on a shoulder 30033 defined on the sled 30030 when the sled 30030 is in its unfired position in the staple cartridge 30020 and the firing member 30040 is moved distally from its unfired position illustrated in FIG. 244. Once the distal nose 30043 is on the sled shoulder 30033, the firing member 30040 can be advanced distally to perform the staple firing stroke. Notably, the cutting portion 30042 further comprises a first camming member 30046 configured to engage a cam surface of the channel 30010 and a second camming member 30048 configured to engage a cam surface on the anvil of the stapling instrument 30000 which co-operate to position the anvil and the staple cartridge 30020 relative to one another. That said, embodiments are envisioned without one or both of the camming members 30046 and 30048.

Referring to FIG. 245, the firing member 30040 is biased toward the channel 30010 by a spring and, if the sled 30030 is not in its unfired position when the firing member 30040 is advanced distally to start the staple firing stroke, the distal nose 30043 of the cutting portion 30042 will miss, or not land on, the shoulder 30033 and the cutting portion 30042 will dive downwardly toward the channel 30010 instead. The cutting portion 30042 comprises lockout pins 30045 extending laterally therefrom which enter a lockout window, or recess, 30012 defined in the channel 30010 when the distal nose 30043 does not land on the shoulder 30033 of the sled 30030. In such instances, the firing member 30040 is permitted to travel distally within the lockout window 30012; however, the distal end of the lockout window 30012 comprises a lockout shoulder 30015 which is contacted by the lockout pins 30045 to stop the distal advancement of the firing member 30040. In such instances, as a result, the firing member 30040 is locked out and prevented from performing its staple firing stroke. Had the sled 30030 been its unfired position, however, the interaction between the distal nose 30043 of the cutting portion 30042 and the shoulder 30033 of the sled 30030 would have prevented the firing member 30040 from diving into the lockout window 30012 and the staple firing stroke could have been performed.

Further to the above, the firing member 30040 would dive into the lockout window 30012 if the firing member 30040 were advanced distally without a staple cartridge positioned in and/or a staple cartridge properly seated in the cartridge channel 30010. In view of the above, the surgical instrument 30000 comprises a lockout which prevents the staple firing stroke if the staple cartridge in the surgical instrument 30000 is missing, improperly seated, and/or has been at least partially spent. That said, various instances can arise where a staple cartridge has not been fired, i.e., all of its staples are still positioned in their staple cavities, and, yet, the distal nose 30043 of the cutting portion 30042 can miss the shoulder 30033 of the sled 30030 owing to various manufacturing tolerances, for instance. Such instances would cause the firing member 30040 to be locked out unnecessarily and require a clinician to replace the staple cartridge with another staple cartridge. Such instances may not happen that often, but if they do they are inconvenient to the clinician.

A surgical instrument 30100 is illustrated in FIG. 246 and includes an improvement which can reduce the possibility of the distal nose 30043 of the cutting portion 30042 missing the shoulder 30033 of the sled 30030. The surgical instrument 30100 is similar to the surgical instrument 30000 in many respects but includes a staple cartridge 30120 instead of the staple cartridge 30020. The staple cartridge 30120 comprises a cartridge body 30122, staple cavities defined in the cartridge body 30122, and staples removably stored in the staple cavities. Referring to FIG. 247, the staple cartridge 30120 further comprises a sled 30030 which, similar to the above, is movable distally from an unfired position during a staple firing stroke if the distal nose 30043 of the cutting portion 30042 catches the shoulder 30033 of the sled 30030. If not, referring to FIG. 248, the cutting portion 30042 is pushed into the lockout window 30012 defined in the cartridge channel 30010 when the firing member 30040 is advanced distally.

Referring to FIGS. 249 and 250, the cartridge body 30122 comprises proximal ramps 30126 configured to lift the firing member 30040 upwardly when the firing member 30040 is advanced distally. More specifically, the lockout pins 30045 extending laterally from the firing member 30040 contact ramp surfaces 30127 defined on the proximal ramps 30126 which guide the cutting portion 30042 away from the lockout window 30012 when the firing member 30040 is advanced distally. They do so, further to the above, against the biasing force of the spring pushing the firing member 30040 toward the cartridge channel 30010. The lifting of the firing member 30040 in this manner increases the probability that the nose 30043 of the firing member 30040 will land on the shoulder 30033 of the sled 30030—even if the sled 30030 has been accidentally pushed slightly distally from its unfired position. Thus, the possibility of an unfired staple cartridge becoming unintentionally locked out is reduced. If the staple cartridge 30120 has been at least partially fired, however, the nose 30043 will miss the shoulder 30033 and the lockout pins 30045 will fall through a window 30125 defined between the proximal ramps 30126 and into the lockout window 30012. Thus, as above, the surgical instrument 30100 will be locked out if an at least partially spent staple cartridge 30120 is seated in the cartridge channel 30010. Moreover, as above, the surgical instrument 30100 will be locked out if a staple cartridge is missing from the cartridge channel 30010 and the staple firing stroke is initiated as the firing member 30040 will immediately enter the lockout window 30012 owing to the absence of the proximal ramps 30126.

Notably, further to the above, the ramps 30126 are positioned proximally with respect to the shoulder 30033 of the sled 30030. As such, the firing member 30040 must consecutively pass the missing cartridge/improper cartridge lockout provided by the ramps 30126 and the spent cartridge lockout provided by the sled 30030 as the firing member 30040 is moved distally to perform the staple firing stroke. Moreover, the ramps 30126 lift the firing member 30040 to a proper height to be supported by the sled 30030. Ultimately, the ramps 30126 of the cartridge body 30122 and the shoulder 30033 of the sled 30030 work together to defeat the lockouts of the stapling instrument 30100.

A staple cartridge 30220 is illustrated in FIG. 251 in accordance with at least one alternative embodiment. The staple cartridge 30220 comprises a cartridge body 30222 which is similar to the cartridge body 30122 in many respects. That said, the cartridge body 30222 comprises proximal ramps 30226 which extend further proximally than the proximal ramps 30126. As such, the firing member 30040 will be lifted earlier in its staple firing stroke when a staple cartridge 30220 is used. In various instances, the staple cartridge 30220 can include a larger drop window 30225 than the drop window 30125. Moreover, the proximal ramps 30226 comprise ramp surfaces 30227 which are shorter than the ramp surfaces 30127. In such instances, the firing member 30040 will not be lifted as high when a staple cartridge 30220 is used as compared to when a staple cartridge 30120 is used. In any event, such parameters can be used to hone an appropriate lifting motion for the firing member 30040.

As discussed above, the lockout pins 30045 of the firing member 30040 are configured to contact the ramps 30226 which lift the firing member 30040 such that the firing member 30040 can land on the shoulder 30033 of the sled 30030 if the sled 30030 is properly positioned in the staple cartridge 30220. That said, alternative embodiments are envisioned in which ramps can lift any suitable portion of a staple firing member onto the shoulder 30033 of the sled 30030. For instance, the firing member 30040 can comprise laminate bars attached to the cutting portion 30042 which contact the ramps 30226 and cause the firing member 30040 to be lifted upwardly when the staple firing stroke is initiated.

Referring again to FIG. 251, the staple cartridge 30220 comprises a pan 30024 at least partially extending under the cartridge body 30222. The pan 30024 is configured to prevent the staple drivers and/or staples within the cartridge body 30222 from falling out of the bottom of the cartridge body 30222. The pan 30024 comprises latches 30021 engaged with slots defined in the cartridge body 30222. The pan 30024 further comprises windows 30029 defined therein which, in co-operation with projections extending from the cartridge body 30222, align the pan 30024 with the cartridge body 30222. In addition to or in lieu of the above, the lifts ramps 30226, for example, can extend from the pan 30024.

A surgical stapling instrument 30300 is illustrated in FIG. 252. The stapling instrument 30300 is similar to the stapling instrument 30200 in many respects. That said, the stapling instrument 30300 comprises a staple cartridge 30320 instead of the staple cartridge 30220. The staple cartridge 30320 comprises a cartridge body 30322, staple cavities defined in the cartridge body 30322, and staples removably stored in the staple cavities. The cartridge body 30322 further comprises a longitudinal slot 30023 defined therein which is configured to receive the firing member 30040 and, in addition, a proximal ramp 30327 extending in front of the longitudinal slot 30023 which lofts the firing member 30040 onto the sled 30030 if the sled 30030 is in, or at least nearly in, its unfired position, as illustrated in FIG. 253. If the sled 30030 has been at least partially advanced through its staple firing stroke, the shoulder 30033 will not catch the nose 30043 of the firing member 30040 and the cutting portion 30042 will fall through a window defined between ramp supports 30326 and into the lockout window 30012.

Referring to FIGS. 254 and 256, the ramp 30327 also comprises a gate configured to pivot out of the way of the firing member 30040 when a sufficient pushing force is applied to the firing member 30040. The ramp 30327 comprises a first end rotatably mounted to one of the ramp supports 30326 and a second end releasably attached to the other ramp support 30326. Referring to FIGS. 255 and 257, the second end of the ramp 30327 is configured to release from its ramp support 30326 after the firing member 30040 has been lofted upwardly such that, once the ramp 30327 gives way, the nose 30043 of the firing member 30040 falls on the shoulder 30033 of the sled 30030—if the sled 30030 is in its unfired position, or at least close to its unfired position. At such point, the ramp 30327 no longer impedes the distal movement of the firing member 30040 and the firing member 30040 can be advanced distally through the longitudinal slot 30023. The ramp 30327 remains displaced to the side throughout the staple firing stroke and after the firing member 30040 has been retracted back into its unfired position. As such, the displaced ramp 30327 cannot lift the firing member 30040 if the firing member 30040 were to be advanced distally once again. In such instances, the lockout pins 30045 of the cutting portion 30042 would be pushed into the lockout window 30012 by the spring acting against the firing member 30040 if the firing member 30040 were advanced distally before the spent staple cartridge 30320 is replaced. Thus, the ramp 30327 acts as a spent cartridge lockout. In at least one alternative embodiment, the ramp 30327 is configured to break away from the cartridge body 30322 to release the firing member 30040.

Moreover, further to the above, the lockout arrangement of the stapling instrument 30300 also acts as an improper/incompatible cartridge lockout. If an improper, or incompatible, staple cartridge not having the ramp 30327, or another suitably configured ramp, were to be seated in the cartridge channel 30010, the firing member 30040 would not be lofted onto a sled of the improper staple cartridge and, instead, the lockout pins 30045 would be forced into the lockout window 30012 thereby locking out the staple firing system. In such instances, the firing member 30040 can be retracted back into its unfired position and the improper/incompatible staple cartridge can be replaced with a proper/compatible staple cartridge. The accidental swapping of an improper staple cartridge for a proper staple cartridge can happen in an operating room where certain staple cartridges are meant to be only used with certain stapling instruments, among other instances.

As discussed above, the ramp 30327 extends behind the sled 30030. As a result, the ramp 30327 can protect the sled 30030 from being bumped distally accidentally. In various instances, the staple cartridge 30320 is loaded into the stapling instrument 30300 by inserting the proximal end of the staple cartridge 30320 into the cartridge channel 30010 first and then seating the staple cartridge 30320 in the cartridge channel 30010. As such, the possibility exits that the sled 30030 will contact the cartridge channel 30010, for example, and be pushed distally within the staple cartridge 30320 from its proximal unfired position. In such instances, the sled 30030 may no longer be positioned to defeat the staple firing lockout of the stapling instrument 30300 when the staple firing stroke is initiated and, thus, the stapling firing lockout will treat this staple cartridge 30320 as being spent and it must be replaced to use the stapling instrument 30300. The ramp 30327 can prevent this as it extends proximally behind the sled 30030 and can prevent the sled 30030 from being bumped distally within the staple cartridge 30320 when the staple cartridge 30320 is being installed.

As discussed above, the sled 30030, when properly positioned in the staple cartridge, defeats the staple firing lockout of the stapling instrument such that the staple firing stroke can be completed. In use, the firing member 30040 is advanced distally, at least partially, to assess whether or not the sled 30030 is properly positioned and that the staple firing lockout has been defeated. More specifically, the firing member 30040 is advanced distally until the firing member 30040 is supported by the sled 30030 to perform the staple firing stroke—if the sled 30030 is properly positioned in the staple cartridge 30320—or contact the lockout shoulder 30015 if the sled 30030 is not properly positioned in the staple cartridge 30320 or the staple cartridge 30320 is missing from the cartridge channel 30010. If the firing member 30040 contacts the lockout shoulder 30015, the firing member 30040 may need to be retracted to be able to insert an unspent staple cartridge 30320 into the cartridge channel 30010 and/or retracted to start another staple firing stroke. With this in mind, the surgical instrument 30400 of FIGS. 258 and 259 is configured to limit the travel of a firing member such that the firing member can be stopped before it reaches the lockout shoulder 30015 if the staple cartridge is missing from the cartridge channel, as discussed in greater detail below.

The firing member 30440 of the surgical instrument 30400, further to the above, is similar to the firing member 30040 in many respects but comprises a cutting member 30442 including secondary lockout pins 30449 extending laterally therefrom. If the staple cartridge 30320 is not positioned in the cartridge channel 30410 of the stapling instrument 30400, the cutting member 30442 will immediately enter the lockout window 30012 when the firing member 30440 is advanced distally and the secondary lockout pins 30449 will quickly contact a secondary lockout shoulder 30419 in the lockout window 30012. Thus, if a staple cartridge 30320 is not present in the cartridge channel 30410, the firing member 30440 will not have to travel distally until it contacts the lockout shoulder 30015. In such instances, the distance in which the firing member 30440 needs to be retracted is at least reduced. In certain instances, the secondary lockout shoulder 30419 is positioned such that the cutting member 30442 does not need to be retracted at all. In such instances, as a result, an unspent staple cartridge 30320 can be inserted into the channel 30410 and the staple firing stroke can be completed without having to retract the firing member 30440.

Further to the above, the interaction between the lockout pins 30449 and the lockout shoulder 30419 provides a missing cartridge lockout. If the staple cartridge 30320 is seated in the cartridge channel 30410, the cutting member 30442 engages the ramp 30327 of the staple cartridge 30320 which lifts the lockout pins 30449 over the lockout shoulder 30419. Stated another way, the presence of the staple cartridge 30320 in the cartridge channel 30010 defeats the secondary staple firing lockout. That said, the sled 30030 of the staple cartridge 30320 must be properly positioned in the staple cartridge 30320 in order for the staple firing stroke to be completed as the nose 30043 of the cutting member 30442 must still land on the shoulder 30033 of the sled 30030 in order for the lockout pins 30045 to be lifted over the lockout shoulder 30015, as described above. Stated another way, the presence of the sled 30030 in the staple cartridge 30320 in its unfired position defeats the primary firing lockout and the presence of the staple cartridge 30320 in the cartridge channel 30410 defeats the secondary firing lockout. Thus, the stapling instrument 30400 comprises a primary missing cartridge lockout and a secondary missing cartridge lockout, where the primary missing cartridge lockout also serves as a spent cartridge lockout.

A surgical stapling instrument 30500 is illustrated in FIG. 260. The stapling instrument 30500 is similar to the stapling instrument 30000 in many respects. Among other things, the stapling instrument 30500 comprises a cartridge channel 30510, a staple cartridge 30520 removably positionable in the cartridge channel 30510, a firing member 30040, and a staple firing lockout 30514. The staple firing lockout 30514 comprises a resilient metal spring, for example, mounted in the cartridge channel 30510. That said, the staple firing lockout 30514 can be comprised of any suitable material. The staple firing lockout 30514 comprises a base mounted in the cartridge channel 30510 and flexible lock arms 30516 extending from the base. Each flexible lock arm 30516 moves independently of the other and comprises a lock window 30515 defined therein which is configured to receive and releasably capture a lockout pin 30045 extending from the firing member 30040. The flexible lock arms 30516 are configured such that they extend inwardly toward and/or against the side of the firing member 30040 and are, thus, biased to capture the lockout pins 30045. When one or both of the lockout pins 30045 are captured in a lock window 30515, the staple firing member 30040 is prevented from being advanced distally through a staple firing stroke.

Further to the above, the staple cartridge 30520 comprises a cartridge body 30522, staple cavities defined in the cartridge body 30522, and staples removable stored in the staple cavities. The staple cartridge 30520 further comprises a pan 30024 attached to the cartridge body 30522 and a sled configured to travel distally within the staple cartridge 30520 to eject the staples from the staple cavities during a staple firing stroke. Similar to the above, the firing member 30040 is configured to push the sled distally to perform the staple firing stroke once the firing member 30040 has been unlocked. To this end, referring to FIGS. 260 and 263, the cartridge body 30522 comprises projections, or keys, 30526 extending proximally therefrom which are configured to engage the lock arms 30516 when the staple cartridge 30520 is seated in the cartridge channel 30510. Notably, the ends of the lock arms 30516 flare outwardly such that, when the projections 30526 contact the lock arms 30516, the lock arms 30516 aren't trapped between the projections 30526 and the firing member 30040. As a result, the projections 30526 flex the lock arms 30516 laterally outwardly such that the lockout pins 30045 extending from the firing member 30040 are no longer positioned in the lockout windows 30515 of the firing lockout 30514 when the staple cartridge 30520 is seated in the cartridge channel 30510. Thus, the act of seating the staple cartridge 30520 in the cartridge channel 30510 unlocks the stapling instrument 30500.

If a staple cartridge 30520 is not seated in the cartridge channel 30510, as discussed above, the firing member 30040 remains locked by the firing lockout 30514 and the stapling instrument 30500 cannot be used to staple the patient's tissue. If a staple cartridge is seated in the cartridge channel 30510 that does not have the projections, or keys, 30526, such as the staple cartridge 30020, for example, it will not unlock the firing lockout 30514, as illustrated in FIGS. 261 and 262, and, as a result, the stapling instrument 30500 cannot be used to staple the patient's tissue. As depicted in FIGS. 261 and 262, the proximal end of the cartridge body 30022 does not engage, and/or sufficiently displace, the lock arms 30516. Thus, in this instance, the staple cartridge 30020 would be an improper staple cartridge as it does not unlock the staple firing drive of the stapling instrument 30500 and, correspondingly, the staple cartridge 30520 would be a proper staple cartridge as it can unlock the staple firing drive of the stapling instrument 30500. As such, the firing lockout 30514 is both a missing cartridge lockout and an improper cartridge lockout. The stapling instrument 30500 can further comprise a spent cartridge lockout. In the event that an improper staple cartridge is seated in the stapling instrument 30500 and the stapling instrument 30500 cannot be fired, the improper staple cartridge can be removed and a proper staple cartridge, i.e., a staple cartridge 30520, can be seated in the stapling instrument 30500 to unlock the staple firing drive.

As discussed above in connection with the stapling instrument 30000, referring again to FIG. 245, the lockout pins 30045 of the firing member 30040 engage the lock shoulder 30015 if the sled 30030 is not in its proper position in the staple cartridge 30020. As also discussed above, the firing member 30040 of the stapling instrument 30000 is advanced distally before engaging the lock shoulder 30015 and, thus, has time to accelerate before contacting the lock shoulder 30015. As such, the firing member 30040 of the stapling instrument 30000 can impact the lock shoulder 30015 with significant speed and energy. As such, the lock shoulder 30015 is robustly designed to absorb this impact; however, there exists a possibility that the firing member 30040 can plow or blow through the lock shoulder 30015 thereby unintentionally defeating the staple firing lockout of the stapling instrument 30000. The lockout 30514 of FIGS. 260 and 261 can reduce, if not eliminate, these potential problems. For instance, the lock windows 30515 of the firing lockout 30514 are sized and configured to prevent little, if any, proximal and distal translation of the staple firing member 30040 while the lock arms 30516 are engaged with the lockout pins 30045 and, thus, the staple firing member 30040 has little, if any, time to accelerate before being stopped by the distal ends of the lock windows 30515. Moreover, once the lockout pins 30045 engage the distal ends of the lock windows 30515, the lock arms 30516 are placed in tension and, as a result, are capable of handling significant loads before failing, if they fail at all.

As discussed above, both lock arms 30516 are disengaged from the firing member 30040 by the cartridge body 30522 when the staple cartridge 30520 is seated in the stapling instrument 30500. That said, alternative embodiments are envisioned in which a first component of a staple cartridge unlocks a first lock arm 30516 and a second component of the staple cartridge unlocks a second lock arm 30516 when the staple cartridge is seated in the stapling instrument 30500. For instance, a cartridge body of the staple cartridge can unlock the first lock arm 30516 and a sled of the staple cartridge can unlock the second lock arm 30516.

A surgical stapling instrument 30600 is illustrated in FIG. 264 and a surgical stapling instrument 30700 is illustrated in FIG. 265. The stapling instruments 30600 and 30700 are similar to the stapling instrument 30500 in many respects. Referring to FIG. 264, the stapling instrument 30600 comprises a cartridge channel 30610, a staple cartridge 30620 removably positionable in the cartridge channel 30610, and a staple firing lockout 30614 mounted to the cartridge channel 30610 which prevents the firing member 30040 from being advanced through a staple firing stroke unless the staple cartridge 30620 is seated in the cartridge channel 30610. Similarly, referring to FIG. 265, the stapling instrument 30700 comprises a cartridge channel 30710, a staple cartridge 30720 removably positionable in the cartridge channel 30710, and a staple firing lockout 30714 mounted to the cartridge channel 30710 which prevents the firing member 30040 from being advanced through a staple firing stroke unless the staple cartridge 30720 is seated in the cartridge channel 30710. Notably, however, seating the staple cartridge 30720 in the stapling instrument 30600 does not unlock the staple firing system of the stapling instrument 30600 and, likewise, seating the staple cartridge 30620 in the stapling instrument 30700 does not unlock the staple firing system of the stapling instrument 30700. Thus, the stapling instruments 30600 and 30700 can be used in the same operating room at the same time without the possibility of being used with the wrong staple cartridge, despite the fact that the staple cartridges 30620 and 30720 may be confusingly similar.

Referring to FIG. 266, further to the above, the staple cartridge 30620 further comprises a cartridge body 30622 including a proximal end 30626 that is angled such that the center of the cartridge body 30622, i.e., the portion closest to the longitudinal slot 30023, extends further proximally than the lateral sides of the cartridge body 30622. The staple cartridge 30620 further comprises a sled 30630, which is similar to the sled 30030 in many respects, that comprises a proximal end 30636 having a profile that matches, or at least substantially matches, the profile of the proximal end 30626 of the cartridge body 30622. Referring again to FIG. 264, the firing lockout 30614 is similar to the firing lockout 30514. Among other things, the firing lockout 30614 comprises lock arms 30616 which releasingly hold the firing member 30040 in its unfired position until the lock arms 30616 are displaced laterally by the proximal end of the cartridge body 30622 and/or the proximal end of the sled 30630 to release the lockout pins 30045 from lock windows defined in the lock arms 30616. If the staple cartridge 30620 is removed from the cartridge channel 30610, the lock arms 30616 resiliently return to their locked position.

Referring to FIG. 267, further to the above, the staple cartridge 30700 further comprises a cartridge body 30722 including a proximal end 30726 that is angled such that the laterals sides of the cartridge body 30722, i.e., the portions furthest away from the longitudinal slot 30023, extend further proximally than the center of the cartridge body 30722. The staple cartridge 30720 further comprises a sled 30730, which is similar to the sled 30030 in many respects, that comprises a proximal end 30736 having a profile that matches, or at least substantially matches, the profile of the proximal end 30726 of the cartridge body 30722. Referring again to FIG. 265, the firing lockout 30714 is similar to the firing lockout 30514. Among other things, the firing lockout 30714 comprises lock arms 30716 which releasingly hold the firing member 30040 in its unfired position until the lock arms 30716 are displaced laterally by the proximal end of the cartridge body 30722 and/or the proximal end of the sled 30730 to release the lockout pins 30045 from lock windows defined in the lock arms 30716. If the staple cartridge 30720 is removed from the cartridge channel 30710, the lock arms 30716 resiliently return to their locked position.

Notably, further to the above, the proximal end of the staple cartridge 30620 would not displace, or at least sufficiently displace, the lock arms 30716 of the firing lockout 30714 to disengage the firing lockout 30714 from the firing member 30040 if the staple cartridge 30620 were to be seated in the stapling instrument 30700. Moreover, the proximal end of the staple cartridge 30720 would not displace, or at least sufficiently displace, the lock arms 30616 of the firing lockout 30614 to disengage the firing lockout 30614 from the firing member 30040 if the staple cartridge 30720 were to be seated in the stapling instrument 30600. Thus, the staple cartridges 30620 and 30720 each comprise unique keying features which unlock their respective, or proper, stapling instruments.

In various instances, further to the above, the cartridge body and/or sled of a staple cartridge, or staple cartridge type, can comprise one or more unique keying features which can only unlock its respective stapling instrument. In certain instances, the pan extending under the cartridge body can comprise a proximal feature, or key, configured to unlock the staple firing drive of its stapling instrument. Referring to FIG. 268, a cartridge pan 30824, which is similar to the pan 30024 in many respects, comprises a proximal projection, or key, 30826 configured to unlock the staple firing drive of a stapling instrument. The projection 30826 is comprised of folded sheet metal to form a tubular structure, for example. The tubular structure is strengthened by a nested interconnection including a tab 30827 and a slot 30828.

A surgical stapling instrument 30900 is illustrated in FIGS. 269 and 271 and a surgical stapling instrument 31000 is illustrated in FIG. 272. The stapling instruments 30900 and 31000 are similar to the stapling instrument 30500 in many respects. Referring to FIG. 269, the stapling instrument 30900 comprises a cartridge channel 30910, a staple cartridge 30920 removably positionable in the cartridge channel 30910, and a staple firing lockout 30914 mounted to the cartridge channel 30910 which prevents the firing member 30040 from being advanced through a staple firing stroke unless the staple cartridge 30920 is seated in the cartridge channel 30910. Similarly, referring to FIG. 272, the stapling instrument 31000 comprises a cartridge channel, a staple cartridge 31020 removably positionable in the cartridge channel, and a staple firing lockout 31014 mounted to the cartridge channel which prevents the firing member 30040 from being advanced through a staple firing stroke unless the staple cartridge 31020 is seated in the cartridge channel.

Notably, the staple firing lockout 30914 comprises only one lock arm 30916 which extends alongside the right side of the firing member 30040. That said, the one lock arm 30916 comprises a lock window defined therein which is configured to capture and suitably hold a lockout pin 30045 of the firing member 30040 to hold the firing member 30040 in its unfired position, as illustrated in FIG. 271, until the staple cartridge 30920 is seated in the cartridge channel 30910, as illustrated in FIG. 269. More specifically, the cartridge body 30922 of the staple cartridge 30920 comprises a proximal projection, or key, 30926 extending from the right side of the cartridge body 30922 that engages the lock arm 30916 and flexes the lock arm 30916 laterally outwardly when the staple cartridge 30920 is seated in the cartridge channel 30910. Notably, the cartridge body 30922 does not comprise a projection, or key, 30926 extending from the left side of the cartridge body 30922.

Also, notably, the staple firing lockout 31014 comprises only one lock arm 31016 which extends alongside the left side of the firing member 30040. That said, the one lock arm 31016 comprises a lock window defined therein which is configured to capture and suitably hold a lockout pin 30045 of the firing member 30040 to hold the firing member 30040 in its unfired position, as illustrated in FIG. 272, until the staple cartridge 31020 is seated in the cartridge channel of the stapling instrument 31000. More specifically, the cartridge body 31022 of the staple cartridge 31020 comprises a proximal projection, or key, 31026 extending from the left side of the cartridge body 31022 that engages the lock arm 31016 and flexes the lock arm 31016 laterally outwardly when the staple cartridge 31020 is seated in the stapling instrument 31000. Notably, the cartridge body 31022 does not comprise a projection, or key, 31026 extending from the right side of the cartridge body 31022.

Owing to the asymmetry of the cartridge bodies 30922 and 31022 and the corresponding asymmetry of the staple firing lockouts 30914 and 31014, seating the staple cartridge 31020 in the stapling instrument 30900 does not unlock the staple firing system of the stapling instrument 30900 and, likewise, seating the staple cartridge 30920 in the stapling instrument 31000 does not unlock the staple firing system of the stapling instrument 31000. Thus, the stapling instruments 30900 and 31000 can be used in the same operating room at the same time without the possibility of being used with the wrong staple cartridge despite the fact that the staple cartridges 30920 and 31020 may be confusingly similar. In some instances, the staple pattern produced by the staple cartridge 30920 is different than the staple pattern produced by the staple cartridge 30120 and, as a result, the anvil of the stapling instrument 30900 will have a different forming pocket arrangement than the anvil of the stapling instrument 31000. In such instances, the asymmetrical key/firing lockout arrangements disclosed herein can prevent a mismatch between the arrangement of the staple cavities and the arrangement of the staple forming pockets.

Referring to FIGS. 273 and 274, a staple cartridge 31120 comprises a cartridge body 31122 including parallel longitudinal rows of staple cavities while a staple cartridge 31220 comprises a cartridge body 31222 including rows of staple cavities oriented in transverse directions. Similar to the above, referring to FIG. 273, the proximal end of the cartridge body 31122 comprises keys 31126 extending from the left side of the cartridge body 31122—but not the right, or opposite, side of the cartridge body 31122—and the proximal end of the cartridge body 31222, referring to FIG. 274, comprises keys 31226 extending from the right side of the cartridge body 31222—but not the left side of the cartridge body 31222. The staple cartridge 31120 (FIG. 273) is used with a first stapling instrument having parallel longitudinal rows of anvil staple forming pockets and a left-side staple firing lockout, such as the firing lockout 31014 (FIG. 272), for example. The staple cartridge 31220 (FIG. 274) is used with a second stapling instrument having longitudinal rows of transverse staple forming pockets and a right-side staple firing lockout, such as the firing lockout 30914 (FIG. 271), for example. The staple cartridge 31220 does not unlock the first stapling instrument and, similarly, the staple cartridge 31120 does not unlock the second stapling instrument. As such, the keys 31126 of the staple cartridge 31120 cannot unlock a stapling instrument having staple forming pockets which extend in transverse directions and, correspondingly, the keys 31226 of the staple cartridge 31220 cannot unlock a stapling instrument having staple forming pockets which extend in parallel longitudinal rows.

Notably, the staple cartridge 31120 and the staple cartridge 31220 are substantially the same length and have substantially the same shape. Moreover, the staple cartridges 31120 and 31220 are both configured to produce staple lines in the patient tissue which are approximately 60 mm in length. However, the staple cartridges 31120 and 31220 could both be configured to produce staple lines which are approximately 30 mm in length or 45 mm in length, for example. Moreover, it is entirely possible that the cartridge body 31122 and the cartridge body 31222 have the same color. In various instances, a commercial supplier may color-code the cartridge bodies of the staple cartridges that they sell to indicate the size of the staples stored therein. For instance, the cartridge bodies containing unformed staples having an approximately 4 mm unformed height are green, for example. The cartridge bodies containing unformed staples having an approximately 2.5 mm unformed height could be white, for example. Thus, it is entirely possible that the staple cartridges 31120 and 31220 have the same color. As such, it is possible that a clinician could grab one staple cartridge when they intended to grab the other and install the staple cartridge in the wrong stapling instrument. The improvements disclosed herein account for such possibilities and lockout the stapling instrument in such instances.

A surgical instrument 30800 is illustrated in FIGS. 275-279. Referring primarily to FIGS. 277 and 278, the surgical instrument 30800 comprises a cartridge channel 30810, a staple cartridge 30820 removably positioned in the cartridge channel 30810, a firing member 30040, and a lockout 30814 mounted to the cartridge channel 30810. The lockout 30814 comprises a leaf spring 30816 including a proximal end anchored in an aperture defined in the cartridge channel 30810 and a distal end which is movable relative to the fixed proximal end. Referring primarily to FIGS. 277 and 279, the lockout 30814 further comprises a lockout box 30815 configured to capture one of the lockout pins 30045 extending from the cutting portion 30042 of the firing member 30040 and hold the firing member 30040 in an unfired position when the staple cartridge 30820 is not seated in the cartridge channel 30810. The lockout box 30815 comprises a distal wall configured to prevent the firing member 30040 from being advanced distally, a proximal wall configured to prevent the firing member 30040 from being retracted proximally, and a bottom wall connecting the proximal wall and the distal wall of the lockout box 30815. The top of the lockout box 30815, however, is open but could be closed.

The staple cartridge 30820 comprises a cartridge body 30822, a sled, and a pan 30824 attached to and extending under the cartridge body 30822. Further to the above, the pan 30824 comprises a proximal projection 30826 configured to engage the leaf spring 30816 of the lockout 30814 when the staple cartridge 30820 is seated in the cartridge channel 30810, as illustrated in FIGS. 276 and 278. When the projection 30826 contacts the leaf spring 30816, the leaf spring 30816 flexes laterally such that the lockout pin 30045 is no longer captured in the lockout box 30815 of the lockout 30814. At such point, the firing member 30040 has been unlocked and the firing member 30040 can be advanced distally to perform a staple firing stroke. Referring primarily to FIG. 278, the distal, or free, end of the leaf spring 30816 extends into a window 30819 defined in the cartridge channel 30810. The window 30819 provides clearance for the leaf spring 30816 when the leaf spring 30816 is flexed by the staple cartridge 30820. Also, a bottom sidewall of the window 30819 supports the distal end of the leaf spring 30816 such that the distal end is at least simply supported. In any event, the lockout 30814 provides a missing cartridge lockout and an improper cartridge lockout for staple cartridges, such as the staple cartridge 30020, that do not have an appropriate key for unlocking the stapling instrument 30800.

As discussed above, the lockout 30814 is moved from a locked position (FIGS. 276 and 153) to an unlocked position (FIG. 278) when the staple cartridge 30820 is seated in the cartridge channel 30810 of the stapling instrument 30800. This deflection is seen in FIG. 279 which illustrates the lockout 30814 in its locked position in solid and its unlocked position in phantom. In instances where an improper or incompatible staple cartridge, i.e., a staple cartridge not having a suitable key, is seated in the cartridge channel 30810, the leaf spring 30816 will not be deflected, or at least suitably deflected, to unlock the firing member 30040. Notably, the lockout 30814 further comprises a tab 30817 extending from the leaf spring 30816 such that the tab 30817 moves laterally with the leaf spring 30816 when the lockout 30814 is deflected. When the lockout 30814 is in its locked position, as illustrated in FIG. 277, the tab 30817 prevents the anvil of the surgical instrument 30800, i.e., the anvil 30050, from being moved into a closed, or fully-clamped, position, as described in greater detail below.

The anvil 30050 is rotatably coupled to the cartridge channel 30810 about pivot pins 30051 mounted in apertures defined in the cartridge channel 30810. When the anvil 30050 is rotated toward the cartridge channel 30810 by a closure system of the surgical instrument 30800, and the staple cartridge 30820 is not seated in the cartridge channel 30810, a bottom surface 30057 of the anvil 30050 contacts the tab 30817 and the anvil 30050 is blocked from being moved into its closed or fully-clamped position. When the staple cartridge 30820 is seated in the cartridge channel 30810, however, the tab 30817 is displaced laterally such that, when the anvil 30050 is closed, the anvil 30050 does not contact the tab 30817 and the anvil 30050 can be moved into its closed or fully-clamped position. Thus, the lockout 30814 also comprises an anvil closure lockout as the lockout 30814 prevents the anvil 30050 from being closed when the staple cartridge 30820 is not seated in the cartridge channel 30810. In such instances, the clinician will become quickly aware that an improper staple cartridge is positioned in the cartridge channel 30810 and/or that a staple cartridge is missing altogether as they won't be able to close the anvil 30050. Because the anvil 30050 can't be closed onto the tissue, the staple firing stroke of the stapling instrument 30800 would also be prevented in such instances. In alternative embodiments where the staple cartridge jaw is rotatable instead of the anvil, such a lockout could be used to prevent the staple cartridge jaw from being rotated into a closed or fully-clamped position if an improper staple cartridge is positioned in the staple cartridge jaw or a staple cartridge is missing from the cartridge jaw altogether.

As discussed above, the lockout 30814 is configured to resist the closure of the anvil 30050. To this end, further to the above, the proximal end of the lockout 30814 is fixedly supported in the cartridge channel 30810 and the distal end of the lockout 30814 is simply supported by the sidewalls of the window 30819. This is the case when the lockout 30814 is in both of its locked (FIG. 277) and unlocked (FIG. 278) configurations. As such, the lockout 30814 can act as a beam supported at both ends and is well-suited to withstand the clamping load applied by the anvil 30050. Similarly, the tab 30817 extending from the lockout 30814 is also supported by the cartridge channel 30810. More specifically, the tab 30817 is slidably supported in a slot 30818 defined in the cartridge channel 30810 when the lockout 30814 is in both of its locked (FIG. 277) and unlocked (FIG. 278) configurations. As such, the lockout 30814 can act as a beam supported at both ends and an intermediate position and is well-suited to withstand the clamping load applied by the anvil 30050. That said, any suitable support arrangement could be used.

As discussed above, the lockout 30814 is configured to prevent the anvil 30050 of the stapling instrument 30800 from being moved into a closed, or fully-clamped, position when the staple cartridge 30820 is not seated in the cartridge channel 30810. That said, the lockout 30814 is configured to prevent the anvil 30050 from being substantially closed at all when the staple cartridge 30820 is not seated in the cartridge channel 30810. In such instances, the anvil 30050 can be moved slightly toward the cartridge channel 30810; however, the anvil 30050 is noticeably open when the anvil 30050 contacts the tab 30817 of the lockout 30814. In various alternative embodiments, the anvil 30050 is prevented from moving at all until the staple cartridge 30820 is seated in the cartridge channel 30810. In either event, the stapling instrument 30800 is not insertable into a patient through a trocar when the anvil 30050 is locked out. More specifically, a trocar comprises an inner passageway, or cannula, that is sized and configured to closely receive a surgical instrument therein and, when the anvil 30050 is locked out as described above, the distance between the anvil 30050 and the cartridge channel 30810 is too large for the stapling instrument 30800 to fit through the inner passageway. As a result, in such instances, the clinician using the stapling instrument 30800 will become aware that an improper staple cartridge is positioned in the stapling instrument 30800 before the stapling instrument 30800 is inserted into the patient.

A staple cartridge 31520 is illustrated in FIG. 279A. The staple cartridge 31520 comprises a cartridge body 31522 and a pan 31524 attached to the cartridge body 31522. The pan 31524 comprises lock arms 31521 engaged with lateral channels defined in the cartridge body 31522 which hold the pan 31524 to the cartridge body 31522. The pan 31524 is comprised of stamped metal, such as stainless steel, for example. The pan 31524 comprises two lateral sides—one on each side of the longitudinal slot 30023. Each lateral side of the pan 31524 extends along a lateral side of the cartridge body 31522 and under a portion of the cartridge body 31522. Each lateral side of the pan 31524 further comprises a proximal end 31527 that wraps around the proximal end of the cartridge body 31522. The proximal ends 31527 extend orthogonally, or at least substantially orthogonally, to the lateral sides of the pan 31524. Each proximal end 31527 comprises a tab which is folded to form a proximally-extending key 31526. Similar to the above, the keys 31526 are configured to unlock a staple firing system of a stapling instrument when the staple cartridge 31520 is seated in the stapling instrument.

Further to the above, each key 31526 comprises a rounded proximal end created by folding over the tabs outwardly such that the ends of the tab are brought back into contact with the proximal end 31527. As a result, the keys 31526 are sturdy and deflection of the keys 31526 is prevented, or at least substantially reduced. As such, the keys 31526 will reliably deflect the firing system locks to unlock the firing system when the staple cartridge 31520 is seated in the stapling instrument. Each proximal end 31527 further comprises one or more retention teeth 31529 which extend into slots 31528 defined in the proximal end 31527. The slots 31528 facilitate the folding of the proximal ends 31527 and also prevent, or at least limit, movement and/or deflection within the keys 31526. The teeth 31529 bite into the proximal end 31527 and hold the key 31526 in its folded configuration.

A staple cartridge 31620 is illustrated in FIG. 279B. The staple cartridge 31620 comprises a cartridge body 31522 and a pan 31624 attached to the cartridge body 31522. The pan 31624 comprises lock arms 31621 engaged with lateral channels defined in the cartridge body 31522 which hold the pan 31624 to the cartridge body 31522. The pan 31624 is comprised of stamped metal, such as stainless steel, for example. The pan 31624 comprises two lateral sides—one on each side of the longitudinal slot 30023. Each lateral side of the pan 31624 extends along a lateral side of the cartridge body 31522 and under a portion of the cartridge body 31522. Each lateral side of the pan 31624 further comprises a proximal end that wraps downwardly around the proximal end of the cartridge body 31522. The proximal ends extend orthogonally, or at least substantially orthogonally, to the lateral sides of the pan 31624. Each proximal end comprises a tab which is folded to form a proximally-extending key 31626. Similar to the above, the keys 31626 are configured to unlock a staple firing system of a stapling instrument when the staple cartridge 31620 is seated in the stapling instrument.

Further to the above, each key 31626 comprises a laterally-facing U-shaped channel. More specifically, each key 31626 comprises an inner base 31627, a laterally-extending top side 31628 extending from the inner base 31627, and a laterally-extending bottom side 31629 extending from the opposite side of the inner base 31627. The U-shaped configuration of the keys 31626 prevents the keys 31626 from buckling under a longitudinal load and/or deflecting under a laterally-directed torque. Notably, the keys 31626 are folded from tabs extending from the pan 31624 in such a manner so as to create clearance gaps 31625 under the keys 31626. The clearance gaps 31625 are sized and configured to permit the locking pins of a firing member to pass under the keys 31626 during a staple firing stroke of the firing member.

A staple cartridge 31720 is illustrated in FIG. 279C. The staple cartridge 31720 comprises a cartridge body 31522 and a pan 31724 attached to the cartridge body 31522. The pan 31724 comprises lock arms 31721 and 31721' engaged with lateral channels defined in the cartridge body 31522 which hold the pan 31724 to the cartridge body 31522. The pan 31724 is comprised of stamped metal, such as stainless steel, for example. The pan 31724 comprises two lateral sides—one on each side of the longitudinal slot 30023. Each lateral side of the pan 31724 extends along a lateral side of the cartridge body 31522 and under a portion of the cartridge body 31522. One lateral side of the pan 31724 further comprises a proximal end 31727 that wraps downwardly around the proximal end of the cartridge body 31522. The proximal end 31727 extends orthogonally, or at least substantially orthogonally, to the lateral side of the pan 31724. The proximal end 31727 comprises a tab which is folded to form a proximally-extending key 31726. Similar to the above, the key 31726 is configured to unlock a staple firing system of a stapling instrument when the staple cartridge 31720 is seated in the stapling instrument.

Further to the above, the lateral side of the pan 31724 comprises an arcuate or circular cut-out and the proximal end 31727 comprises an arcuate or circular projection 31723 that is bent around the side of the cartridge body 31522 into the circular cut-out. The projection 31723 is closely received in the cut-out such that the proximal end 31727 of the pan 31724 is greatly stiffened or strengthened by this arrangement. The key 31726 comprises an L-shaped tab bent proximally from the pan 31724. The key 31726 comprises a shoulder 31728 bent upwardly from the proximal end 31727 to create this L-shaped configuration. The shoulder 31728 comprises at least one notch, or strain relief, 31729 configured to facilitate the bending of the key 31726. The L-shaped configuration of the key 31726 prevents the key 31726 from buckling under a longitudinal load and/or deflecting under a laterally-directed torque. Notably, the key 31726 is folded from a tab extending from the pan 31724 in such a manner so as to create a clearance gap 31725 under the key 31726. The clearance gap 31725 is sized and configured to permit the locking pin of a firing member to pass under the key 31726 during a staple firing stroke of the firing member.

A staple cartridge 31920 is illustrated in FIG. 279E. The staple cartridge 31920 comprises a cartridge body 31522 and a pan 31924 attached to the cartridge body 31522. The pan 31924 comprises lock arms 31921 engaged with lateral channels defined in the cartridge body 31522 which hold the pan 31924 to the cartridge body 31522. The pan 31924 is comprised of stamped metal, such as stainless steel, for example. The pan 31924 comprises two lateral sides—one on each side of the longitudinal slot 30023. Each lateral side of the pan 31924 extends along a lateral side of the cartridge body 31522 and under a portion of the cartridge body 31522. One lateral side of the pan 31924 further comprises a proximal end 31927 that wraps around the proximal end of the cartridge body 31522. The proximal end 31927 extends orthogonally, or at least substantially orthogonally, to the lateral side of the pan 31924. The proximal end 31927 comprises a tab which is folded to form a proximally-extending key 31926. Similar to the above, the key 31926 is configured to unlock a staple firing system of a stapling instrument when the staple cartridge 31920 is seated in the stapling instrument.

Further to the above, the key 31926 comprises an L-shaped tab bent proximally from the pan 31924. The key 31926 comprises a shoulder 31928 bent upwardly from the proximal end 31927 to create this L-shaped configuration. The L-shaped configuration of the key 31926 prevents the key 31926 from buckling under a longitudinal load and/or deflecting under a laterally-directed torque. Moreover, a free edge of the shoulder 31928 is welded, soldered, and/or brazed to the proximal end 31927 in order to strengthen the key 31926. That said, any suitable number of welds 31929 can be used to secure or strengthen the key 31926. Notably, the key 31926 is folded from a tab extending from the pan 31924 in such a manner so as to create a clearance gap 31925 under the key 31926. The clearance gap 31925 is sized and configured to permit the locking pin of a firing member to pass under the key 31926 during a staple firing stroke of the firing member.

A staple cartridge 31820 is illustrated in FIG. 279D. The staple cartridge 31820 comprises a cartridge body 31522 and a pan 31824 attached to the cartridge body 31522. The pan 31824 comprises lock arms 31821 engaged with lateral channels defined in the cartridge body 31522 which hold the pan 31824 to the cartridge body 31522. The pan 31824 is comprised of stamped metal, such as stainless steel, for example. The pan 31824 comprises two lateral sides—one on each side of the longitudinal slot 30023. Each lateral side of the pan 31824 extends along a lateral side of the cartridge body 31522 and under a portion of the cartridge body 31522. One lateral side of the pan 31824 further comprises a proximal end 31827 that wraps around the proximal end of the cartridge body 31522. The proximal end 31827 extends orthogonally, or at least substantially orthogonally, to the lateral side of the pan 31824. The proximal end 31827 comprises a tab which is folded to form a proximally-extending key 31826. Similar to the above, the key 31826 is configured to unlock a staple firing system of a stapling instrument when the staple cartridge 31820 is seated in the stapling instrument.

Further to the above, the key 31826 comprises a rounded proximal end created by folding over the tab outwardly such that the end of the tab is brought back into contact with the proximal end 31827. As a result, the key 31826 is sturdy and deflection of the key 31826 is prevented, or at least substantially reduced. As such, the key 31826 will reliably deflect the firing system locks to unlock the firing system when the staple cartridge 31820 is seated in the stapling instrument. The proximal end 31827 further comprises one or more retention teeth 31829 which extend into slots 31828 defined in the proximal end 31827. The slots 31828 facilitate the folding of the proximal end 31827 and also prevent, or at least limit, movement and/or deflection within the key 31826. The teeth 31829 bite into the proximal end 31827 and hold the key 31826 in its folded configuration. Notably, the key 31826 is folded from a tab extending from the pan 31824 in such a manner so as to create a clearance gap 31825 under the key 31826. The clearance gap 31825 is sized and configured to permit the locking pin of a firing member to pass under the key 31826 during a staple firing stroke of the firing member.

Many of the lockouts disclosed herein are defeated when a compatible or proper staple cartridge is seated in the stapling instrument. When seated, a staple cartridge is locked into position within the stapling instrument. In such instances, there is little, if any, relative movement possible between the staple cartridge and the stapling instrument until the staple cartridge is uninstalled from the stapling instrument.

In various instances, a surgical stapling assembly comprises a shaft and an end effector extending distally from the shaft including a first jaw and a second jaw rotatable relative to the first jaw. The surgical stapling assembly may comprise a lockout member configured to prevent the inadvertent firing of the surgical stapling assembly and/or the clamping of the surgical stapling assembly until a lockout key unlocks the lockout member. The lockout key may be a part of a staple cartridge configured to be installed in one of the first jaw and the second jaw, for example. Particularly, the lockout key may be a part of a sled of the staple cartridge such that the staple cartridge can unlock the lockout member when the sled is in its unfired position indicating that the staple cartridge is unspent when the staple cartridge is installed within the surgical stapling assembly. In at least one instance, further action may be required to unlock the lockout with the lockout key. For example, an end effector may be required to attain a fully clamped configuration before the lockout key can unlock the lockout member. One example of a lockout can be found in U.S. Patent Application Publication No. 2016/0249921 entitled SURGICAL APPARATUS WITH CONDUCTOR STRAIN RELIEF, now U.S. Pat. No. 10,085,749, the entire disclosure of which is hereby incorporated by reference herein.

In at least one instance, surgical stapling assemblies, such as the one described above, may be used with a surgical robot. The surgical stapling assemblies can be configured to be attached to robotic systems and operated by way of robotic arms of the robotic systems. These robotic systems allow for surgeons to be outside of a sterile field within which the patient is present. In at least one instance, a technician and/or another surgeon, for example, may be located within the bounds of the sterile field to monitor the interface between the tools and the patient. This technician and/or surgeon may attach and detach instruments to the robotic arms during a surgical procedure. In some instances, it may be advantageous to be able to actively bypass the lockout member of a surgical stapling assembly. Providing this ability can enable a surgeon or technician to manually defeat a lockout means of a staple cartridge when the lockout means, for whatever reason, cannot be automatically defeated. Providing this ability may also enable a surgeon to test the operability of the lockout member to ensure that the lockout member is functional prior to using the surgical stapling assembly. In an instance where a surgeon wants to manually override the lockout member to fire a staple cartridge, a surgeon or clinician may know that the installed staple cartridge is a proper unfired staple cartridge and may want to fire the staple cartridge regardless of the fact that the lockout member was not actually defeated. In at least one instance, the clinician may want remove that lockout member from the firing sequence and prevent it from being a part of the firing stroke. Moreover, providing direct access to the lockout member within the end effector itself for manual unlocking can provide an advantage with or without a system that automatically defeats the lockout member. Direct access to the lockout member within the end effector can eliminate additional components that otherwise may be present in a system utilizing an unlocking mechanism to unlock the lockout member that is further upstream of the lockout member. Using an unlocking mechanism further upstream to the lockout member within the shaft of the surgical instrument, for example, can introduce additional components that might jam or fail during the application of an unlocking actuation.

FIGS. 280-284 depict a surgical stapling assembly 41000 configured to clamp, staple, and cut the tissue of a patient. The surgical stapling assembly 41000 is configured to be attached to, detached from, and operated by a surgical robot and/or a surgical instrument handle. The surgical stapling assembly 41000 comprises a shaft 41100, a first jaw 41200 pivotably supported within the shaft 41100, and a second jaw 41300 attached to the shaft 41100. The first jaw 41200 is movable between an unclamped configuration and a clamped configuration to clamp and unclamp tissue positioned between the first jaw 41200 and the second jaw 41300. The surgical stapling assembly 41000 further comprises a staple cartridge 41230 comprising a plurality of staples removably stored therein. The staple cartridge 41230 is configured to be installed into the first jaw 41200 and replaced with other staple cartridges. The surgical stapling assembly 41000 further comprises a firing member 41400 extending through the shaft 41100 that is configured to move the first jaw 41200 relative to the second jaw 41300 between the unclamped configuration and the clamped configuration, deploy staples from the staple cartridge 41230, and cut tissue during a firing stroke with a knife, or blade, 41422. The firing member 41400 is configured to be actuated by a drive system of a surgical robot and/or a surgical instrument handle. Embodiments are envisioned where the firing member 41400 is driven with a rotary drive shaft. Embodiments are also envisioned where the jaw configured to receive the staple cartridge is fixed to the shaft and the jaw containing the anvil is movable between a clamped configuration and an unclamped configuration.

The surgical stapling assembly 41000 further comprises a lockout 41500 (FIG. 284) configured to prevent the firing member 41400 from moving distally past a specific position unless a proper unspent staple cartridge is installed within the first jaw 41200 and the first jaw 41200 is in a fully clamped configuration. In at least one instance, the firing member 41400 is permitted to move a first distance between a home position and the specific position regardless of the condition of the lockout 41500 to permit clamping and unclamping of tissue, as discussed in greater detail below. The lockout 41500 is biased toward a locked configuration where the firing member 41400 is prevented from moving distally beyond the specific position. The lockout 41500 is movable into an unlocked configuration where the firing member 41400 is permitted to move distally beyond the specific position to deploy staples from the staple cartridge 41230. Discussed in greater detail below, the surgical stapling assembly 41000 further comprises a direct access orifice defined therein configured to allow a clinician to manually, or artificially, unlock the lockout 41500, i.e., move the lockout 41500 into the unlocked configuration.

The first jaw 41200 comprises a channel 41210 configured to receive the staple cartridge 41230 therein. The staple cartridge 41230 is configured to be installed within the channel 41210 and readily replaced with another staple cartridge. The staple cartridge 41230 further comprises a sled 41235 movable between an unfired position and a fired position to eject the staples from the staple cartridge 41230 as the sled 41235 is pushed distally through a cartridge body 41232 of the staple cartridge 41230 by the firing member 41400. The second jaw 41300 comprises an anvil 41320 comprising a staple-forming surface 41310 configured to form the staples ejected from the staple cartridge 41230.

The first jaw 41200 is movable relative to the second jaw 41300 between an unclamped configuration and a clamped configuration by the firing member 41400. Embodiments are envisioned where the second jaw 41300 is movable relative to the first jaw 41200. To clamp tissue, the firing member 41400 is moved distally a first distance from a home position to cam the first jaw 41200 into a clamped configuration. Referring to FIG. 283, the firing member 41400 comprises anvil-camming portions 41423 configured to engage a ramp 41332 of an anvil channel 41330 defined within the second jaw 41300 and channel-camming portions 41424 configured to engage a ramp 41222 of a bottom surface 41220 of the first jaw 41200. The anvil-camming portions 41423 and the channel-camming portions 41424 extend laterally from a distal portion 41420 of the firing member 41400 and are configured to control the distance between the first jaw 41200 and the second jaw 41300 as the distal portion 41420 of the firing member moves through its firing stroke. During the first distance discussed above, the anvil-camming portions 41423 and the channel-camming portions 41424 engage the first and second jaws 41200, 41300 and cam the first jaw 41200 into a clamped configuration. Further distal movement of the distal portion 41420 of the firing member 41400 holds the first and second jaws 41200, 41300 relative to each other during the firing stroke and pushes the sled 41235 distally to eject staples stored within the staple cartridge 41230.

The surgical stapling assembly 41000 further comprises a lockout 41500 configured to prevent the firing member from being advanced distally beyond the first distance unless a proper unspent staple cartridge is installed within the first jaw 41200 and the first jaw 41200 is fully clamped. The lockout 41500 comprises a lockout member 41510 pivotably supported within the shaft 41100 and movable between an unlocked configuration (FIG. 281) where the firing member 41400 is permitted to move beyond the first distance to complete the firing stroke and a locked configuration (FIG. 282) where the firing member 41400 is prevented from moving beyond the first distance. The lockout member 41510 is biased into the locked configuration by a spring 41520. A proper unspent staple cartridge installed within the channel 41210 can overcome the bias provided by the spring 41520 when the first jaw 41200 is moved into the clamped configuration.

To unlock the lockout 41500, the first jaw 41200 must be moved into its clamped configuration to present the sled 41235 to engage and unlock the lockout member 41510. The sled 41235 cannot defeat the lockout 41500 when the first jaw 41200 is not in its clamped configuration. Embodiments are envisioned where the cartridge jaw is not pivotable but, rather, the anvil jaw is pivotable. In such embodiments, mere insertion of the staple cartridge presents the sled 41235 to defeat the lockout 41500. In such embodiments, the lockout 41500 can be defeated prior to the application of any clamping motions to the anvil jaw.

To unlock the lockout 41500, as discussed above, a proper unspent staple cartridge must be installed in the first jaw 41200 of the surgical stapling assembly 41000. The staple cartridge 41230 comprises a sled 41235 comprising a lockout key 41237 extending proximally therefrom. The lockout key 41237 is configured to move the lockout member 41510 into the unlocked configuration when the sled 41235 is in an unfired position and the first jaw 41200 is moved into the clamped configuration. To unlock the lockout, the lockout key 41237 pivots the lockout member 41510 into the unlocked configuration by moving a lockout ledge, or leg, 41511 of the lockout member 41510 away from a lockout notch 41412 defined in a firing shaft, or bar, 41410 of the firing member 41400 which would otherwise prevent distal movement of the firing member 41400 beyond an initial distance used for clamping when the first jaw 41200 is moved into the clamped configuration. The lockout member 41510 comprises a pair of arms 41512 extending distally from the lockout ledge 41511 which are configured to straddle the firing member 41400 as the firing member 41400 moves through its firing stroke.

FIG. 281 illustrates the lockout key 41237 engaged with distal ends 41516 of the arms 41512 on a distal end 41515 of the lockout member 41510. As illustrated in FIG. 281, the lockout member 41510 has pivoted relative to the shaft 41100 about nubs 41513 (FIG. 284) of the lockout member 41510 into the unlocked configuration. When the lockout member 41510 is in the unlocked configuration, the lockout notch 41412 of the firing shaft 41410 will clear the lockout ledge 41511 of the lockout member 41510 thereby permitting the firing member 41400 to move distally through the staple cartridge 41230. Referring to FIG. 282, if the lockout key 41237 is not present upon clamping the first jaw 41200 into the clamped configuration, the lockout member 41510 remains biased in the locked configuration by way of the spring 41520 (FIG. 283) pushing against the tabs 41514 (FIG. 284) of the lockout member 41510 where the lockout ledge 41511 engages the notch 41412 of the firing shaft 41410 to block distal movement of the firing member 41400 beyond the initial distance used for clamping.

As discussed above, the surgical stapling assembly 41000 further comprises a direct access orifice 41425 defined therein configured to allow a clinician to artificially move the lockout member 41510 into the unlocked configuration. The orifice 41425 can be positioned in any suitable component such that a tool 41590 can access the lockout member 41510 through the orifice 41425 to move the lockout member 41510 into the unlocked configuration. The orifice 41425 is defined in the channel-camming portions 41424 of the distal portion 41420 of the firing member 41400. The orifice 41425 may comprise access slits defined in the channel-camming portions 41424, for example. In at least one instance, the orifice 41425 is defined in the shaft 41100 and/or a component thereof. Nonetheless, the lockout member 41510 is directly accessible through the orifice 41425. The tool 41590 comprises a hook portion 41591 configured to be inserted through the orifice 41425 and an opening 41517 defined between the arms 41512 of the lockout member 41510 to hook, or latch, onto an upper side of the ledge 41511 to pull the ledge 41511 and thus pivot the lockout member 41510 into the unlocked configuration overcoming the spring bias which encourages the lockout member 41510 into the locked configuration. The orifice 41425 can be configured such that commonly-avoidable tools, such as a screwdriver, for example, do not fit within the orifice, or exterior access aperture, 41425. Portions of the lockout member 41510 are illustrated in phantom in the unlocked configuration where tool 41590 has positioned the lockout member 41510 into the unlocked configuration. Arms 41512' and ledge 41511' are phantom versions of the arms 41512 and ledge 41511 of the lockout member 41510 illustrated in the unlocked configuration.

Once the lockout member 41510 is manually, or artificially, defeated to move the lockout 41500 into the unlocked configuration, the firing member 41400 is permitted to move distally past an unfired location and into the staple cartridge 41230. The unfired location is defined as the position after clamping but before firing. Once the firing member 41400 is advanced distally past its unfired position, the tool 41590 can be disengaged from the lockout member 41510 and removed from the orifice 41425 to allow the lockout 41500 to resume normal operation. For instance, the lockout member 41510 will pivot into the locked configuration when the firing member 41400 returns to the unfired location after having at least partially fired a staple cartridge. During the firing stroke, the lockout member 41510 is accessible with the tool 41590 through a secondary access aperture 41160 defined between a proximal end of the channel 41210 and a distal end of the shaft 41100. That said, the lockout member 41510 will remain defeated during the staple firing stroke. In at least one instance, the direct access orifice is positioned within the shaft 41100, for example, and can provide access to the lockout member 41510 during the firing stroke of the firing member 41400. In at least one instance, the secondary access aperture 41160 comprises the primary lockout access aperture.

The lockout 41500 can be positioned in any suitable location. In at least one instance, the lockout 41500 may be positioned proximal to the distal portion 41420 of the firing member 41400 when the firing member 41400 is in its proximal most position (such as the position illustrated in FIG. 283). In such an instance, the access aperture may be defined in a shaft housing, or frame, of the surgical stapling assembly 41000. In at least one instance, the access aperture is defined in the channel 41210.

In at least one instance, the tool 41590 can be inserted through the direct access aperture 41425 to unlock the lockout 41500 prior to the insertion of the staple cartridge 41230 into the channel 41210. Moving the lockout 41500 to its unlocked configuration prior to the insertion of a staple cartridge can aid the staple cartridge installation by preventing the lockout 41500 from engaging the staple cartridge during installation. Some lockouts disable improper staple cartridges by bumping a sled of the staple cartridge from its unfired, firable position to an unfired, unfirable position which can cause the staple cartridge to become instantly spent. Moreover, such lockouts may bump a sled of a proper staple cartridge during installation of the proper staple cartridge. Unlocking the lockout 41500 prior to installation of the staple cartridge can ensure that the proper staple cartridge is not disabled accidentally during installation.

FIGS. 285 and 286 depict a surgical stapling assembly 42000 for use in clamping, stapling, and cutting the tissue of a patient. The surgical stapling assembly 42000 is similar to other stapling assemblies described herein in many respects. The surgical stapling assembly 42000 comprises a firing assembly 42100 and a cartridge channel 42200 configured to receive a staple cartridge therein. The firing assembly 42100 is configured to push a sled of a proper unspent staple cartridge installed within the cartridge channel 42200 to deploy the staples of the staple cartridge and cut the stapled tissue. The surgical stapling assembly 42000 further comprises a lockout 42300 configured to prevent the firing assembly 42100 from being advanced through an improper staple cartridge. The lockout 42300 comprises a spring 42310 which biases the lockout 42300 toward a locked configuration. The lockout 42300 is configured to be pushed proximally by a proper unspent staple cartridge to unlock the firing assembly 42100. Notably, the lockout 42300 is configured such that lockout 42300 does not accidentally push the sled of the proper staple cartridge into a position which would induce a lockout condition for the firing assembly 42100. The lockout 42300 can employ any suitable lockout method. The firing assembly 42100 is similar to other firing assemblies described herein.

The surgical stapling assembly 42000 further comprises a direct access cutout, or aperture, 42210 defined in the bottom of the cartridge channel 42200 at a proximal end of a longitudinal slot 42230 defined in the cartridge channel 42200. The firing assembly 42100 is movable through the slot 42230 of the cartridge channel 42200 during a staple firing stroke. The direct access cutout 42210 allows for a tool to be inserted within the surgical stapling assembly 42000 to access the lockout 42300 directly. The tool can be inserted through the direct access cutout 42210 to move the lockout 42300 into an unlocked configuration (FIG. 286). Unlocking the lockout 42300 in this manner can be referred to as artificially unlocking the lockout 42300 because an unspent staple cartridge has not automatically unlocked the lockout 42300 for whatever reason. The direct access cutout 42210 comprises a proximal end 42211 and a distal end 42213 comprising a wider cutout portion than the proximal end 42211. The wider cutout portion of the distal end 42213 can aid in the proper insertion of the tool into the channel 42200. For example, the tool can comprise a lock-engaging portion that fits in the distal end 42213 but not the proximal end 42211 thereby eliminating the possibility of mis-inserting the tool in the proximal end 42211. Moreover, the lockout 42300, and its position relative to other components of the surgical stapling assembly 42000, is also directly visible through the direct access cutout 42210. Nonetheless, a tool can be inserted through the cutout 42210 to pull and/or push the lockout 42300 proximally to overcome the spring bias and move the lockout 42300 into the unlocked configuration. The tool can also be removed and disengaged from the lockout 42300 such that the lockout 42300 can resume normal operation. Moreover, providing the ability to manually move the lockout 42300 may allow a clinician to move the lockout 42300 away from its locked position before installing a staple cartridge into the cartridge channel 42200 to prevent the lockout 42300 from moving a sled of the staple cartridge that is being installed into the cartridge channel 42200 prematurely.

FIGS. 287 and 288 depict a surgical stapling assembly 43000 comprising a firing assembly 43100, a frame 43400 that supports the firing assembly 43100 therein, a cartridge channel 43300 pivotably attached to the frame 43400, and a lockout key mechanism 43500 configured to defeat a lockout of the surgical stapling assembly 43000. The surgical stapling assembly 43000 can comprise any suitable lockout; however, a diving knife lockout where the firing assembly 43100 falls into a locking recess in the absence of a proper unspent staple cartridge being positioned in the cartridge channel 43300 is described below.

The firing assembly 43100 comprises a firing shaft 43110 and a firing member 43120 attached to the distal end of the firing shaft 43110. Although a linear firing shaft is illustrated, the firing assembly 43100 may be configured with a rotary drive shaft. The firing shaft 43110 is configured to be actuated by a firing driver of a surgical instrument handle and/or a surgical robot, for example. Any suitable drive mechanism may be used. The firing member 43120 comprises anvil-camming pins 43122 and channel camming pins 43123 extending laterally therefrom. The pins 43122, 43123 are configured to control the clamping pressure on the tissue captured within the surgical stapling assembly 43000 during a firing stroke. The firing member 43120 further comprises a cutting edge 43121 configured to cut the clamped tissue. The firing member 43120 further comprises a ledge, or distal nose, 43124 configured to engage and/or rest on top of a sled of an unfired proper staple cartridge such that the firing member 43120 does not fall into the lockout recess.

The firing assembly 43100 further comprises an extension 43111 configured to be biased downwardly toward the channel 43300 by a spring member mounted within the frame 43400. Discussed in greater detail below, the downward bias of the extension 43111 encourages the firing assembly 43100 toward its locked out condition. The downward bias is overcome when an unspent proper staple cartridge is installed within the cartridge channel 43300.

The lockout key mechanism 43500 comprises a spring 43530, a wedge 43520 slidably supported within the frame 43400, and a lifter spring 43510 comprising a proximal end 43511 mounted to the frame 43400. The wedge 43520 comprises a ramp 43521 on which a distal end 43512 of the lifter spring 43510 rests. When a staple cartridge is inserted into the cartridge channel 43300, the staple cartridge 43200 pushes the wedge 43520 proximally. Proximal movement of the wedge 43520 causes the lifter spring 43510 to lift the firing member 43120 to defeat a first stage of the lockout. The lifter spring 43510 comprises a notch 43513 defined on the distal end 43512 configured to engage lifter pins 43125 extending laterally from the firing member 43120 when the lifter spring 43510 is lifted by the wedge 43520 of the staple cartridge 43200.

Once the first stage of the lockout has been overcome, the firing assembly 43100 is advanced distally to assess the second stage of the lockout. This second stage of the lockout is defeated when the sled of the staple cartridge 43200 is in its proximal unfired position. Similar to the above, the firing shaft 43110 can be lifted onto the sled by the staple cartridge 43200 as the firing shaft 43110 is advanced distally.

To cause the nose 43124 of the firing member 43120 to land on an unfired sled of the staple cartridge 43200 to defeat the second stage of the lockout and prevent the firing member 43120 from falling into the lockout recess, a cartridge body key 43211 is provided on a proximal end 43201 of the cartridge body 43210. Referring now to FIG. 288, as the staple cartridge 43200 is installed in the cartridge channel 43300, the cartridge body key 43211 pushes the wedge 43520 proximally and overcomes the spring bias provided by the spring 43530. As the wedge 43520 is pushed proximally, the wedge 43520 lifts the lifter spring 43510. At this point, the notch 43513 can grab the lifter pins 43125 and lift the firing assembly 43100. Lifting the firing assembly 43100 in this manner can be referred to as defeating the first stage of the lockout. Notably, a staple cartridge without the proper cartridge lockout key may be able to be installed in the cartridge channel 43300 but will not be able to lift the firing assembly 43100. Once the staple cartridge 43200 is installed in the cartridge channel 43300 and the firing assembly 43100 is lifted, the firing assembly 43100 can be advanced distally such that the notch 43513 can hold the firing assembly 43100 at the proper height and for the proper distance so that the nose 43124 can land on the unfired sled in the staple cartridge 43200 thereby avoiding the lockout recess. Landing the nose 43124 on the unfired sled can be referred to as defeating the second stage of the lockout. If the sled in the staple cartridge 43200 is not in its unfired position, the firing assembly 43100 will fall into the lockout recess and not be able to be advanced distally beyond its locked configuration. In at least one instance, the cartridge body key 43211 extends proximally from a cartridge body pan 43220 of the staple cartridge 43200.

FIG. 289 depicts a first staple cartridge 43610 comprising a proximal end 43611 and a lockout key 43613 extending from the proximal end 43611. The lockout key 43613 comprises a first profile. FIG. 289 depicts a second staple cartridge 43620 comprising a proximal end 43621 and a lockout key 43623 extending from the proximal end 43621. The lockout key 43623 comprises a second profile that is different than the first profile of the lockout key 43613. The first staple cartridge 43610 is configured to unlock only the stapling instruments it is compatible with and the second staple cartridge 43620 is configured to unlock only the stapling instruments it is compatible with.

Referring back to the lockout key mechanism 43500 in FIGS. 287 and 288, cartridges using different key profiles can be used to ensure that the firing member is lifted at the appropriate location and with the appropriate height. Lifting the firing member at different locations, referring to FIG. 289, causes different lift timings of the firing member. This can be used to ensure that an improper staple cartridge can not unlock a non-compatible instrument. FIGS. 290 and 291 contain graphs illustrating the different lift timings 43610', 43620' and displacements 43610", 43620" provided by the cartridges 43610, 43620. The staple cartridge 43610 is configured to lift the firing member earlier than the staple cartridge 43620. In a compatible surgical instrument, the first staple cartridge 43610 will cause a wedge, for example, such as the wedge described herein, to lift the firing member at the appropriate time and location such that the firing member will land on an unfired sled of the first staple cartridge 43610 so as to defeat the lockout and enable the firing member to be advanced distally to perform a staple firing stroke. In an incompatible surgical instrument, the first staple cartridge 43610 will cause a wedge, for example, to lift the firing member at the incorrect time and location causing the firing member to fall before reaching the sled or causing the firing member to bump the sled distally before being lifted onto the sled. Both situations involving installing an incompatible cartridge and instrument will cause the firing member to enter a locked out condition upon an attempt to move the firing member through a firing stroke. The second staple cartridge 43620 works in a similar manner. That said, the second staple cartridge 43620 cannot unlock an instrument compatible with the first staple cartridge 43610, and vice versa.

FIGS. 292 and 293 depict a system 44000 comprising a first cartridge 44100 (FIG. 292) and a second cartridge 44200 (FIG. 293). The first staple cartridge 44100 comprises a cartridge body 44110 comprising a proximal end 44111, a distal end 44112, and a plurality of staple cavities 44114 arranged in rows extending between the proximal end 44111 and the distal end 44112. The first staple cartridge 44100 further comprises a cartridge pan 44130 configured to hold staples in the cartridge body 44110, and a sled 44120 configured to deploy the staples from the cartridge body 44110. The cartridge body 44110 further comprises a longitudinal slot 44113 defined therein configured to receive a firing member of a surgical stapling assembly. The longitudinal slot 44113 defines a first lateral side and a second lateral side labeled "A" and "B" respectively. The cartridge body 44110 further comprises a lockout key 44116 extending from a proximal face 44115 of the first lateral side "A" of the cartridge body 44110.

The second staple cartridge 44200 comprises a cartridge body 44210 comprising a proximal end 44211, a distal end 44212, and a plurality of staple cavities 44214 arranged in rows extending between the proximal end 44211 and the distal end 44212. The second staple cartridge 44200 further comprises a cartridge pan 44230 configured to hold staples in the cartridge body 44210, and a sled 44220 configured to deploy the staples from the cartridge body 44210. The cartridge body 44210 further comprises a longitudinal slot 44213 defined therein configured to receive a firing member of a surgical stapling assembly. The longitudinal slot 44213 defines a first lateral side and a second lateral side labeled "A" and "B" respectively. The cartridge body 44210 further comprises a lockout key 44216 extending from a proximal face 44215 of the second lateral side "B" of the cartridge body 44210.

The staple cavities 44114 comprise three rows on each side of the longitudinal slot 44113. Each row defines a row axis with which each staple cavity in that row is aligned. In other words, the proximal end and the distal end of each cavity in a single row is aligned with the row axis of that row. The staple cavities 44214 comprise three rows on each side of the longitudinal slot 44213. Each row defines a row axis with which each staple cavity in that row is transversely aligned. Each side of the staple cartridge 44200 comprises an outer row of staple cavities 44214, an inner row of staple cavities 44214, and a middle row of staple cavities 44214 positioned between the outer row of staple cavities 44214 and the inner row of staple cavities 44214. The staple cavities 44214 of the middle row define cavity axes that are transverse to cavity axes defined by the staple cavities 44214 in the inner row and the staple cavities 44214 in the outer row.

The system 44000 provides a way to prevent an improper staple cartridge from being used with a surgical stapling assembly by providing the lockout keys of each cartridge on different sides of the staple cartridge. Providing the lockout keys on different sides of the staple cartridge prevents the use of a stapling assembly comprising corresponding staple-forming pockets for the first staple cartridge 44100 with the second staple cartridge 44200 and the use of a stapling assembly comprising corresponding staple-forming pockets for the second staple cartridge 44200 with the first staple cartridge 44100. Thus, the first staple cartridge 44100 will not be able to unlock a firing lockout of a surgical stapling assembly meant for the second staple cartridge 44200 and the second staple cartridge 44200 will not be able to unlock a firing lockout of a surgical stapling assembly meant for the first staple cartridge 44100. This prevents improper cartridge installation which may result in deploying staples against an anvil with non-corresponding staple-forming pockets.

FIGS. 294-303 depict a surgical stapling assembly 45000 configured to clamp, staple, and cut the tissue of a patient. The surgical stapling assembly 45000 can be used with a surgical robot and/or a surgical instrument handle. The surgical stapling assembly 45000 comprises a first jaw 45200, a second jaw 45400 movable relative to the first jaw 45200 between an unclamped configuration and a clamped configuration, and a firing assembly 45500. The surgical stapling assembly 45000 further comprises a replaceable staple cartridge 45300 comprising a plurality of staples removably stored therein which are configured to be deployed by the firing assembly 45500. The first jaw 45200 comprises a channel 45210 configured to receive the replaceable staple cartridge 45300. The second jaw 45400 comprises an anvil 45410 comprising a staple-forming surface 45415 configured to form the staples deployed from the staple cartridge 45300. The first jaw 45200 further comprises pin apertures 45212 (FIG. 295) in which pivot pins 45413 of the second jaw 45400 are received to permit the second jaw 45400 to pivot relative to the first jaw 45200. Embodiments are envisioned where the fixed jaw comprises the anvil and the movable jaw comprises the channel and the staple cartridge.

To clamp tissue with the surgical stapling assembly 45000, the second jaw 45400 comprises a camming surface 45412 formed on a proximal end 45411 thereof which is configured to be engaged by a closure member. The closure member comprises a closure tube, for example, but can comprise any other suitable configuration. The closure member is configured to cam the second jaw 45400 from the unclamped configuration to the clamped configuration toward the channel 45210 by engaging and sliding along the camming surface 45412. To unclamp the surgical stapling assembly 45000, the closure member is retracted proximally. A spring may be provided to bias the second jaw 45400 into the unclamped configuration as the closure member disengages the camming surface 45412.

To staple and cut tissue with the surgical stapling assembly 45000, a proper unspent staple cartridge must be installed within the surgical stapling assembly 45000. When a proper unspent staple cartridge is installed within the channel 45210, the firing assembly 45500 can be actuated through the staple cartridge 45300 to push a sled 45340 of the staple cartridge 45300 distally from an unfired position to a fired position to deploy the staples stored within the staple cartridge 45300 during a staple firing stroke. As the firing assembly 45500 is moved through the staple firing stroke, a cutting edge 45523 of the firing assembly cuts the tissue clamped between the first jaw 45200 and the second jaw 45400. In at least one instance, the cutting edge 45523 trails behind the staple deployment to prevent tissue from being cut before the tissue is stapled.

Referring primarily to FIGS. 296-299, the firing assembly 45500 comprises a firing member 45520 comprising the cutting edge 45523, anvil-camming portions 45521 and channel-camming portions 45522 configured to control the distance between the first jaw 45200 and the second jaw 45400 during the staple firing stroke, and laterally-extending portions 45525 positioned between the anvil-camming portions 45521 and the channel-camming portions 45522 configured to fall into a lockout as discussed in greater detail below. The firing member 45520 further comprises a tail 45526 extending proximally therefrom which is configured to interface with a spring 45240 mounted in the shaft as discussed in greater detail below.

To prevent the firing assembly 45500 from being advanced through an improper and/or spent staple cartridge, the surgical stapling assembly 45000 further comprises a lockout system. The surgical stapling assembly 45000 comprises a diving-knife lockout such as those disclosed herein where the firing assembly 45500 falls into a lockout pocket if a proper unspent staple cartridge is not installed within the surgical stapling assembly 45000. A proper unspent staple cartridge, such as the staple cartridge 45300, is configured to prevent the firing assembly 45500 from falling into the lockout pocket by lifting the firing assembly 45500 when the staple cartridge 45300 is unspent. In such instances, a distal end of the firing assembly will land on an unfired sled of the staple cartridge 45300. The firing assembly 45500 may then be advanced through the staple cartridge 45300.

The staple cartridge 45300 includes a lockout key 45330 to lift the firing assembly 45500 to the proper height and proper distance to get the firing assembly 45500 to land on an unfired sled and defeat the lockout of the surgical stapling assembly 45000. The staple cartridge 45300 further comprises a cartridge body 45310 comprising a proximal end 45301 comprising a proximal face 45313 and a longitudinal slot 45311 configured to receive the firing assembly 45500 during the staple firing stroke. The lockout key 45330 extends proximally from the proximal face 45313 of the cartridge body 45310 and comprises a pair of protrusions defining a proximal longitudinal slot portion 45333 of the longitudinal slot 45311. The proximal longitudinal slot portion 45333 is configured to straddle the firing member 45520 when the staple cartridge 45300 is installed in the channel 45210. Each protrusion of the lockout key 45330 comprises a ramped surface, or portion, 45331 and a non-ramped portion, or surface, 45332. The staple cartridge 45300 further comprises a pan 45320 configured to hold the staples within the cartridge body 45310. The pan 45320 is configured to clip onto a deck 45312 of the cartridge body 45310. The pan 45320 may be removably affixed to the cartridge body 45310 by a series of hooks 45321 that are formed on the sidewalls of the cartridge pan 45320 and configured to hookingly engage corresponding portions of the cartridge body 45310. In at least one instance, the pan can comprise the lockout key.

The firing assembly 45500 comprises a firing shaft 45510 configured to transfer firing motions to the firing member 45520. The firing member 45520 is attached to a distal end 45513 of the firing shaft 45510. The firing member 45520 is biased downwardly by the spring 45420 mounted in the shaft. More specifically, the spring 45420 pushes the tail 45526 of the firing member 45520 downwardly to bias the firing member 45520 unless the firing member 45520 is lifted upwardly away from the firing lockout. To lift the firing assembly 45500, the surgical stapling assembly 45000 comprises a floating pin 45600 positioned behind the firing member 45520 of the firing assembly 45500. The floating pin 45600 is supported within a slot, or channel, 45213 defined in the sides of the staple cartridge channel 45210. The floating pin 45600 is configured to move vertically within the slot 45213 by the ramped surfaces 45331. More specifically, the floating pin 45600 is pushed upwardly by the lockout key 45330 into the staple cartridge channel 45210 which, in turn, contacts the bottom edge of the firing member 45520 and pushes the firing member 45520 upwardly. Thus, the floating pin 45600 keeps the firing member 45520 from diving into the firing lockout when the staple cartridge 45300 is seated in the staple cartridge channel 45210. As such, the lockout key 45330 overcomes the downward spring bias applied to the firing member 45520 by the spring 45240.

Once the staple cartridge 45300 is fully installed and the firing assembly 45500 is lifted to the position illustrated in FIG. 298, the firing assembly 45500 can then be advanced distally toward the sled 45340 of the staple cartridge 45300. Thus, with the proper lockout key, the first stage of the lockout is defeated. If the sled 45340 is in its unfired position, a distal nose, or shelf, 45524 of the firing member 45520 will land on a corresponding platform 45341 of the sled 45340 and avoid the lockout discussed above. Landing the distal nose 45524 of the firing member 45520 on the platform 45341 of the sled 45340 when the sled 45340 is in its unfired position defeats a second stage of the lockout. As the firing assembly 45500 is advanced distally, the bottom surface 45511 rides over the floating pin 45600 and the height of the firing assembly 45500 is governed by the engagement between the floating pin 45600, the bottom surface 45511 of the firing shaft 45510, and the lockout key 45600.

Because the height of the firing assembly 45500 is governed by the engagement between the floating pin 45600, the bottom surface 45511 of the firing shaft 45510, and the lockout key 45600, the firing shaft 45510 is configured such that the firing assembly 45500 may still fall into the lockout when the sled 45340 of the staple cartridge 45300 is not in its unfired position. Referring to FIGS. 300 and 301, the bottom surface 45511 comprises a notch 45515 defined proximal to the distal end 45513 of the firing shaft 45510. The notch 45515 is configured such that the firing shaft 45510 will fall into the lockout if the sled 45340 is not present in its unfired position. FIG. 300 illustrates the staple cartridge 45300 installed within the channel 45210; however, the sled 45340 is not present in its unfired position. Thus, turning to FIG. 301, the firing shaft 45510 is not sufficiently lifted upwardly by the floating pin 45600 to lift the firing shaft 45510 out of the lockout. Instead, the firing shaft 45510 is pulled down by the spring 45240 as the firing assembly 45500 is advanced distally owing to the floating pin 45600 fitting in the notch 45515. To perform a staple firing stroke, the improper cartridge must be removed and replaced with a proper unfired staple cartridge.

If a staple cartridge is installed in the surgical stapling assembly that does not have a proper lockout key, the floating pin 45600 will remain in its lower most position illustrated in FIG. 296. If an attempt is made to advance the firing assembly 45500 distally, the firing assembly 45500 will be unable to overcome the first stage of the lockout.

FIG. 304 depicts the staple cartridge 45300 discussed above. FIG. 305 depicts a second staple cartridge 45900 comprising a cartridge body 45910 and a pan 45920 configured to hold a plurality of staples in the staple cartridge 45900. The cartridge body 45910 further comprises a lockout key 45930 extending proximally from a proximal face 45913 of the cartridge body 45910. As can be seen from FIGS. 304 and 305, the staple cartridge 45300 and the second staple cartridge 45900 comprise similar features; however, they comprise lockout keys having different configurations. The lockout key 45330 of the staple cartridge 45300 comprises a first length 45338 and a first height 45339 while the lockout key 45930 of the second staple cartridge 45900 comprises a second length 45938 and a second height 45939 which are different than the first length 45338 and the first height 45339, respectively. The staple cartridges 45300, 45900 are part of a system in which the staple cartridge 45300 can only unlock a first instrument but not a second instrument while the second staple cartridge 45900 can only unlock the second instrument and not the first instrument. The lockout key 45930 comprises a ramped surface 45931 and a flat surface 45932 which have different dimensions than the surfaces 45331, 45332 of the lockout key 45330. The lockout key 45330 of the staple cartridge 45300 is shown in phantom lines in FIG. 305 for comparison purposes.

Differing lockout key configurations between similar looking cartridges, for example, can prevent a clinician from inserting and using an incompatible cartridge in a second instrument. In this instance, the lockout keys 45330, 45930 will cause a firing assembly of an instrument to lift to different heights and at different times during the firing stroke of the firing assembly. Referring back to the floating pin 45600, if the second staple cartridge 45900 is installed in the surgical stapling assembly 45000, the firing assembly 45500 will be lifted by the floating pin 45600 at a height which is less than a height at which the firing assembly 45500 will be lifted by the floating pin 45600 if the staple cartridge 45300 is installed. This will cause the firing assembly 45500 to not be able to land on the sled platform of the second staple cartridge and, instead, will become locked out. This will prevent the use of an improper staple cartridge within a stapling instrument.

The instrument with which the second staple cartridge 45900 may be used can comprise a similar floating pin system as discussed above; however, this floating pin may be located in a different position relative to the second staple cartridge 45900 such that the lockout key 45930 can lift the firing member of this instrument to the appropriate height and at the appropriate time to land on the sled of the second staple cartridge 45900 to bypass the lockout of the instrument. In at least one instance, the lockout keys described herein comprise cartridge body fins, for example.

Various aspects of the subject matter described herein are set out in the following examples.

Example 1—A method for controlling a powered surgical stapler that includes an end effector with jaws that are movable between an open and a closed position and a firing member that is movable between a starting position and an ending position within the end effector. The method comprises installing a surgical staple cartridge in one of the jaws of the end effector, generating a first rotary control motion, converting the first rotary control motion to a first axial motion, converting the first axial motion to a pivoting closure motion, applying the pivoting closure motion to one of the jaws to pivot the jaw to the closed position, generating a second rotary control motion, applying the second rotary control motion to the firing member, and preventing axial movement of the firing member from the starting position to the ending position unless the surgical staple cartridge is in ready to fire condition.

Example 2—The method of Example 1, wherein preventing axial movement comprises engaging a firing member lockout system in a locked position to prevent axial movement of the firing member prior to installing, and maintaining the firing member lockout system in the locked position unless a camming assembly in the installed surgical staple cartridge unlockingly engages the firing member lockout system when the surgical staple cartridge is installed in the end effector.

Example 3—The method of Examples 1 or 2, further comprising preventing the jaw configured to receive the pivoting closure motion from moving to the closed position unless the installed surgical staple cartridge is compatible with the end effector.

Example 4—The method of Example 3, wherein preventing the jaw configured to receive the pivoting closure motion from moving to the closed position comprises engaging a closure lockout system in a locked open position to prevent the jaw configured to receive the pivoting closure motion from pivoting in response thereto, and maintaining the closure lockout system in the locked open position unless an unlocking feature is present on the installed surgical staple cartridge to unlockingly engage the closure lockout system when the surgical staple cartridge is installed in the end effector.

Example 5—The method of Examples 1, 2, 3, or 4, wherein the surgical staple cartridge includes an axially movable camming assembly that is configured to be axially moved through the surgical staple cartridge upon generating a second rotary control motion.

Example 6—The method of Example 5, wherein the end effector includes an onboard rotary firing drive shaft that rotatably interfaces with the firing member and wherein the camming assembly is configured to rotatably interface with the onboard rotary firing drive shaft.

Example 7—The method of Examples 5 or 6, wherein the camming assembly includes a movable cutting member that is movable from a deployed position to a stored position.

Example 8—The method of Example 7, further comprising moving the cutting member to the stored position when the firing member has reached the ending position.

Example 9—The method of Examples 1, 2, 3, 4, 5, 6, 7, or 8, wherein generating a first rotary control motion in a first rotary direction is discontinued after applying the pivoting closure motion to one of the jaws to pivot the jaw to the closed position.

Example 10—The method of Examples 1, 2, 3, 4, 5, 6, 7, 8, or 9, wherein generating a first rotary control motion in a first rotary direction is maintained during the application of the second rotary control motion to the firing member.

Example 11—A method for controlling a powered surgical stapler that includes an end effector with jaws that are movable between an open and a closed position by a closure member that is axially movable through the end effector and a firing member that is axially movable between a starting position and an ending position within the end effector. The method comprises installing a surgical staple cartridge in one of the jaws of the end effector, applying a first rotary control motion to the closure member to cause the closure member to apply a closure motion to the jaws to move the jaws to a closed position, applying a second rotary control motion to the firing member, and preventing axial movement of the firing member from the starting position to the ending position unless the surgical staple cartridge is in ready to fire condition.

Example 12—The method of Example 11, wherein preventing axial movement comprises engaging a firing member lockout system in a locked position to prevent axial movement of the firing member prior to installing, and maintaining the firing member lockout system in the locked position unless a camming assembly in the installed surgical staple cartridge unlockingly engages the firing member lockout system when the surgical staple cartridge is installed in the end effector.

Example 13—The method of Examples 11 or 12, wherein applying a first rotary control motion is maintained during applying the second rotary control motion to the firing member.

Example 14—The method of Examples 11, 12, or 13, wherein applying a first rotary control motion is periodically maintained during applying the second rotary control motion to the firing member while the firing member moves from the starting to ending position within the end effector.

Example 15—The method of Examples 11, 12, 13, or 14, wherein applying a first rotary control motion to the closure member to cause the closure member to apply a closure motion to the jaws to move the jaws to a closed position comprises energizing a closure motor to apply a rotary closure motion to a rotary closure shaft that rotatably interfaces with the closure member and wherein applying a second rotary control motion to the firing member comprises energizing a firing motor to apply a rotary firing motion to a firing drive shaft that rotatably interfaces with the firing member.

Example 16—The method of Example 15, further comprising discontinuing energizing the closure motor after the closure member has moved the jaws to a closed position, monitoring an amount of current drawn by the firing motor while the firing member is moved from the starting position to the ending position, and re-energizing the closure motor to apply rotary closure motions to the closure member when the amount of current drawn by the firing motor exceeds a predetermined threshold.

Example 17—A method for controlling a powered surgical stapler that includes an end effector with jaws that are movable between an open and a closed position. The method comprises installing a surgical staple cartridge in one of the jaws of the end effector. The surgical staple cartridge includes an onboard firing member that is movable between a starting position and an ending position within the staple cartridge. The method further comprises generating a first rotary control motion, converting the first rotary control motion to a first axial motion in a first axial direction, converting the first axial motion in the first axial direction to a pivoting closure motion, applying the pivoting closure motion to one of the jaws to pivot the jaw to the closed position, generating a second rotary control motion, applying the second rotary control motion to the onboard firing member, and preventing axial movement of the onboard firing member from the starting position to the ending position unless the surgical staple cartridge is in ready to fire condition.

Example 18—The method of Example 17, wherein preventing axial movement comprises maintaining an onboard firing member lockout system in a locked position unless an onboard camming assembly in the installed surgical staple cartridge is in unlocking engagement with the onboard firing member lockout system when the surgical staple cartridge is installed in the end effector.

Example 19—The method of Examples 17 or 18, further comprising preventing the jaw configured to receive the pivoting closure motion from moving to the closed position unless the installed surgical staple cartridge is compatible with the end effector.

Example 20—The method of Example 19, wherein preventing the jaw configured to receive the pivoting closure motion from moving to the closed position comprises engaging a closure lockout system in a locked open position to prevent the jaw configured to receive the pivoting closure motion from pivoting in response thereto, and maintaining the closure lockout system in the locked open position unless an unlocking feature is present on the installed surgical staple cartridge to unlockingly engage the closure lockout system when the surgical staple cartridge is installed in the end effector.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical stapling device, comprising:
    a surgical end effector, comprising:
        a cartridge jaw defining a vertically extending end effector central plane; and
        an anvil comprising:
            an anvil mounting tab, wherein said anvil mounting tab is positioned only on one lateral side of the vertically extending end effector central plane such that said anvil is pivotally coupled to said cartridge jaw only on the one lateral side of the vertically extending end effector central plane for selective pivotal motion relative to said cartridge jaw between a closed position and an open position, wherein said anvil mounting tab is pivotally coupled to said cartridge jaw about a pivot axis that is transverse to the vertically extending end effector central plane; and
            an anvil tail protruding proximally from said anvil mounting tab;
    a firing member, wherein said firing member is axially movable within said surgical end effector between a starting position and an ending position;
    a rotary firing shaft operably interfacing with said firing member to apply rotary firing motions thereto to drive said firing member between the starting position and the ending position;
    a closure linkage operably coupled to said anvil tail, wherein said closure linkage is configured to apply opening motions and closing motions to said anvil tail; and
    a rotary closure shaft operably interfacing with said closure linkage to apply rotary closure motions to said closure linkage, wherein said rotary closure shaft is independently rotatable relative to said rotary firing shaft.

2. The surgical stapling device of claim 1, wherein said closure linkage is positioned only on the one lateral side of the vertically extending end effector central plane.

3. The surgical stapling device of claim 2, wherein said rotary firing shaft is positioned on another lateral side of the vertically extending end effector central plane.

4. The surgical stapling device of claim 1, wherein said closure linkage is pivotally coupled to a proximal end of said anvil tail.

5. The surgical stapling device of claim 4, wherein said closure linkage is pivotally coupled to said proximal end of said anvil tail on the one lateral side of the vertically extending end effector central plane and on another lateral side of the vertically extending end effector central plane.

6. The surgical stapling device of claim 5, further comprising a closure shuttle operably interfacing with said closure linkage and threadably interfacing with said rotary closure shaft.

7. The surgical stapling device of claim 6, wherein said rotary firing shaft is concentric with said rotary closure shaft.

8. The surgical stapling device of claim 1, wherein said rotary firing shaft comprises a flexible rotary firing shaft, and wherein said rotary closure shaft comprises a flexible rotary closure shaft.

9. The surgical stapling device of claim 1, wherein said cartridge jaw comprises a channel configured to removably support a replaceable surgical staple cartridge therein.

10. The surgical stapling device of claim 9, wherein said firing member comprises anvil engagement features and channel engagement features.

11. A surgical instrument, comprising:
a first jaw defining a vertically extending central plane;
a second jaw comprising a mounting tab located only on one lateral side of the vertically extending central plane, wherein said mounting tab is pivotally coupled to said first jaw only on the one lateral side of the vertically extending central plane, wherein said second jaw is pivotally coupled to said first jaw about a pivot axis that is transverse to the vertically extending central plane;
a firing member supported within said first jaw for movement between a starting position and an ending position within said first jaw;
a firing drive member operably interfacing with said firing member; and
a closure drive member operably interfacing with the second jaw, wherein at least a portion of said closure drive member and at least a portion of said firing drive member are operably supported within said first jaw on opposite lateral sides of the vertically extending central plane.

12. The surgical instrument of claim 11, wherein said firing drive member comprises a rotary firing drive shaft.

13. The surgical instrument of claim 11, wherein said closure drive member comprises a rotary closure drive shaft.

14. The surgical instrument of claim 11, wherein said firing drive member comprises a rotary firing drive shaft, and wherein said closure drive member comprises a rotary closure drive shaft.

15. The surgical instrument of claim 11, wherein said second jaw further comprises a second jaw tail that protrudes proximally from said mounting tab, and wherein said closure drive member comprises a closure linkage assembly operably coupled to said second jaw tail.

16. The surgical instrument of claim 11, wherein said first jaw comprises a channel configured to operably support a replaceable surgical staple cartridge therein, wherein said second jaw comprises an anvil, and wherein said firing member comprises a tissue cutting member.

17. A surgical instrument, comprising:
a first jaw defining a vertically extending central plane;
a second jaw comprising:
a mounting tab located only on one lateral side of the vertically extending central plane, wherein said mounting tab is pivotally coupled to said first jaw only on the one lateral side of the vertically extending central plane; and
a second jaw tail protruding proximally from the mounting tab;
a closure linkage coupled to said second jaw tail on the one lateral side of the vertically extending central plane and on another lateral side of the vertically extending central plane;
a rotary closure drive shaft centrally disposed along the vertically extending central plane; and
a closure shuttle threaded onto said rotary closure drive shaft and configured to move axially upon rotation of said rotary closure drive shaft, wherein said closure shuttle is configured to operably interface with said closure linkage on both sides of the vertically extending central plane.

18. The surgical instrument of claim 17, wherein said second jaw is pivotally coupled to said first jaw about a pivot axis that is transverse to the vertically extending central plane.

* * * * *